(12) United States Patent
Bylock

(10) Patent No.: US 9,248,187 B2
(45) Date of Patent: *Feb. 2, 2016

(54) OXADIAZOLE INHIBITORS OF LEUKOTRIENE PRODUCTION FOR COMBINATION THERAPY

(71) Applicant: Lars Anders Bylock, Wiesbaden (DE)

(72) Inventor: Lars Anders Bylock, Wiesbaden (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 359 days.

This patent is subject to a terminal disclaimer.

(21) Appl. No.: 13/755,351

(22) Filed: Jan. 31, 2013

(65) Prior Publication Data

US 2013/0195879 A1   Aug. 1, 2013

Related U.S. Application Data

(60) Provisional application No. 61/593,638, filed on Feb. 1, 2012.

(51) Int. Cl.
| | |
|---|---|
| A61K 39/00 | (2006.01) |
| A61K 45/06 | (2006.01) |
| A61K 31/497 | (2006.01) |
| A61K 31/506 | (2006.01) |
| A61K 31/5377 | (2006.01) |
| A61K 31/541 | (2006.01) |
| A61K 31/366 | (2006.01) |
| C07D 413/14 | (2006.01) |
| C07D 413/10 | (2006.01) |
| C07D 417/14 | (2006.01) |
| C07D 498/04 | (2006.01) |
| A61K 31/4245 | (2006.01) |

(52) U.S. Cl.
CPC .............. *A61K 45/06* (2013.01); *A61K 31/366* (2013.01); *A61K 31/4245* (2013.01); *A61K 31/497* (2013.01); *A61K 31/506* (2013.01); *A61K 31/5377* (2013.01); *A61K 31/541* (2013.01); *C07D 413/10* (2013.01); *C07D 413/14* (2013.01); *C07D 417/14* (2013.01); *C07D 498/04* (2013.01)

(58) Field of Classification Search
CPC . A61K 45/06; A61K 31/4245; A61K 31/541; A61K 31/366; A61K 31/5377; A61K 31/506; A61K 31/497; C07D 498/04; C07D 413/14; C07D 417/14
USPC ............... 424/139.1; 514/275, 252.19, 230.5, 514/227.8, 210.2, 213.01, 255.05, 236.2
See application file for complete search history.

(56) References Cited

U.S. PATENT DOCUMENTS

| | | | |
|---|---|---|---|
| 6,911,444 | B2 | 6/2005 | Lacrampe et al. |
| 7,319,108 | B2 | 1/2008 | Schwink et al. |
| 8,575,201 | B2 | 11/2013 | Bartolozzi et al. |
| 8,580,829 | B2 | 11/2013 | Bartolozzi et al. |
| 2007/0105866 | A1 | 5/2007 | Hutchinson et al. |
| 2009/0192171 | A1 | 7/2009 | Hutchinson et al. |
| 2010/0197591 | A1 | 8/2010 | Aspnes et al. |
| 2011/0206652 | A1 | 8/2011 | Kayser et al. |
| 2011/0206783 | A1 | 8/2011 | Burgey et al. |
| 2012/0214787 | A1 | 8/2012 | Bartolozzi et al. |
| 2012/0220561 | A1 | 8/2012 | Bartolozzi et al. |
| 2012/0245162 | A1 | 9/2012 | Bartolozzi et al. |
| 2012/0295896 | A1 | 11/2012 | Bartolozzi et al. |

FOREIGN PATENT DOCUMENTS

| | | |
|---|---|---|
| JP | 05112564 B1 | 1/2013 |
| WO | 2006044602 A2 | 4/2006 |
| WO | 2007056228 A2 | 5/2007 |
| WO | 2007120574 A2 | 10/2007 |
| WO | 2008030369 A1 | 3/2008 |
| WO | 2008128335 A1 | 10/2008 |
| WO | 2008156721 A1 | 12/2008 |
| WO | 2009048547 A1 | 4/2009 |
| WO | 2011143466 A1 | 11/2011 |
| WO | 2012024150 A1 | 2/2012 |
| WO | 2012040137 A1 | 3/2012 |

OTHER PUBLICATIONS

Anonymous: Thomson Reuters Integrity. (2013) XP-002692486; Drugs and Biologics Search Results 42 pgs http://integrity.thomsonpharma.com/integrity/xmlxsl/pk__prod-list.
Chabner, Bruce A. et al. "Antineoplastic Agents" Chemotherapy of Neoplastic Diseases, Goodman & Gilmans, The Pharmacological Basis of Therapeutics, (2006) 11th edition, pp. 1315-1403.
International Search Report for PCT/US2011/047356 mailed on Oct. 28, 2011.
International Search Report for PCT/US2011/048743 mailed on Nov. 2, 2011.
International Search Report for PCT/US2011/052252 mailed on Nov. 2, 2011.
International Search Report for PCT/US2011/052254 mailed on Nov. 16, 2011.
International Search Report for PCT/US2013/051871 mailed on Mar. 7, 2013.
Machine Translation of JP05112564 (May 7, 1993).
Poupaert, Jacques H. "Drug Design: Basic Principles and Applications" Encyclopedia of Pharmaceutical Technology, 3rd Edition, (2007) pp. 1362-1369.

*Primary Examiner* — Jason Sims
*Assistant Examiner* — Ibrahim D Bori
(74) *Attorney, Agent, or Firm* — Michael P. Morris; Usha R. Patel

(57) ABSTRACT

The present invention relates to combination therapy using compound of formula (I):

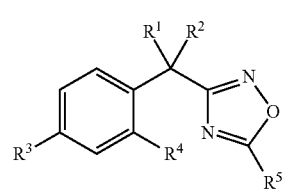

or pharmaceutically acceptable salts thereof, wherein $R^1$-$R^5$ are as defined herein and an additional pharmaceutically active agent. The invention also relates to pharmaceutical compositions comprising these combinations, and methods of using these combinations in the treatment of various diseases and disorders.

17 Claims, 1 Drawing Sheet

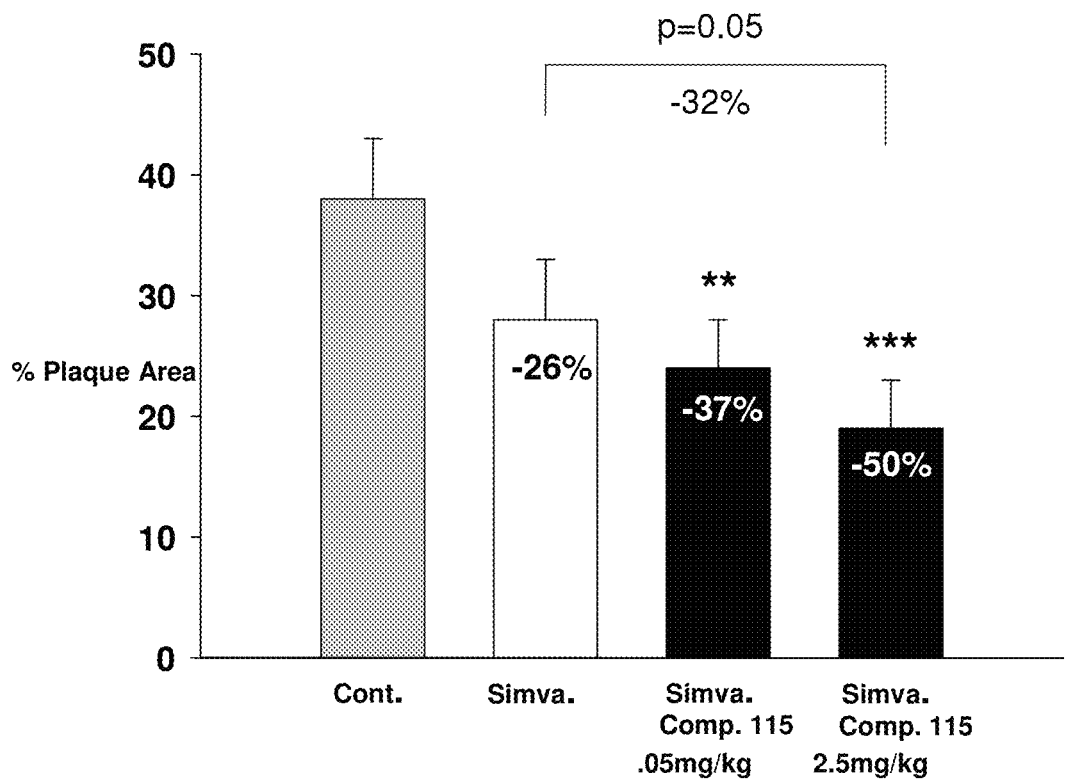
Effect of exemplary compound of formula I, i.e. compound 115, on atherosclerotic plaque in the descending aorta (mean ± SEM) (p<0.01, *p<0.001 vs Cont.)

OXADIAZOLE INHIBITORS OF LEUKOTRIENE PRODUCTION FOR COMBINATION THERAPY

FIELD OF THE INVENTION

This invention relates to combination therapy using oxadiazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to combination therapy using pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to ApoE$^{-/-}$xCD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Curr. Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

BRIEF DESCRIPTION OF FIGURE

FIG. 1: Effect of exemplary compound of Formula I, i.e. compound 115, on atherosclerotic plaque in the descending aorta (mean±SEM) (p<0.01, *p<0.001 vs Cont.)

DETAILED DESCRIPTION OF THE INVENTION

In its first broadest embodiment, the present invention relates to a compound of formula I:

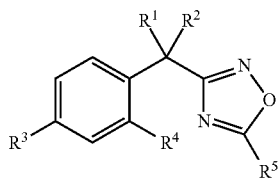

wherein:
$R^1$ and $R^2$ are each independently hydrogen, $C_{1-7}$ alkyl or $C_{3-10}$ carbocycle, with the proviso that both $R^1$ and $R^2$ are not hydrogen;
$R^3$ is a 5-11 membered heteroaryl ring containing one to three heteroatoms selected from nitrogen, oxygen and sulfur, wherein the heteroaryl ring is optionally independently substituted with one to three groups selected from $C_{1-5}$ alkyl optionally substituted with one to three halogen atoms, $C_{1-5}$ alkoxy, $C_{1-3}$ hydroxy, halogen, hydroxy, —O-benzyl, oxo, cyano, amino, —NH—$C_{3-6}$ carbocycle, $C_{1-6}$ alkylamino and $C_{1-3}$ dialkylamino;
$R^4$ is hydrogen, $C_{1-3}$ alkyl, halogen or nitrile;
$R^5$ is $C_{1-6}$ alkyl, $C_{3-10}$ carbocycle, 3-11 membered heterocycle, aryl, 5-11 membered heteroaryl, —C(O)—$R^6$, hydroxy or —$NR^7R^8$, wherein each $R^5$ is optionally independently substituted with one to three groups selected from $R^9$, $R^{10}$ and $R^{11}$;
$R^6$ is $C_{3-8}$ heterocycle or —NH-5-6 membered heterocycle, each optionally independently substituted with one to three groups selected from $R^9$, $R^{10}$ and $R^{11}$;
$R^7$ and $R^8$ are each independently hydrogen, 5-6 membered heterocycle optionally substituted with $C_{1-6}$ alkyl, $C_{3-10}$ carbocycle optionally substituted with hydroxy or $C_{1-6}$ alkyl;
$R^9$, $R^{10}$ and $R^{11}$ are independently selected from
(a) —H,
(b) —OH,
(c) halogen,
(d) —CN,
(e) —$CF_3$,
(f) $C_{1-6}$alkyl optionally substituted with one to three —OH, —N($R^{12}$)($R^{13}$), 3-6 membered heterocycle, $C_{1-6}$alkoxy, $C_{1-6}$alkoxy-O—$C_{1-6}$alkyl, —$CO_2R^{12}$, —C(O)N($R^{12}$)($R^{13}$) or —S(O)$_n C_{1-6}$alkyl,
(g) $C_{1-6}$alkoxy,
(h) —N($R^{12}$)($R^{13}$),
(i) —S(O)$_n C_{1-6}$alkyl,
(j) —$CO_2R^{12}$,
(k) —C(O)N($R^{12}$)($R^{13}$),
(l) —S(O)$_2$N($R^{12}$)($R^{13}$),
(m) a 3-10 membered heterocyclic group optionally substituted with one to three $C_{1-6}$ alkyl groups,
(n') oxo,
(o) —C(O)—$C_{1-3}$ alkyl;
$R^{12}$ and $R^{13}$ are each independently selected from —H, —$C_{1-6}$alkyl, C(O)$C_{1-6}$alkyl, and a 3-6 membered heterocyclic group, each of which is optionally independently substituted with one to three $C_{1-6}$alkyl groups, —OH, $C_{1-6}$alkoxy, —C(O)N($R^{14}$)($R^{15}$), —S(O)$_n C_{1-6}$alkyl, CN, a 3-6 membered heterocyclic group, —O$C_{1-6}$alkyl, $CF_3$, or;
$R^{12}$ and $R^{13}$ taken together with the nitrogen ring to which they are attached form a heterocyclyl ring optionally substituted with one to three —OH, CN, —O$C_{1-6}$alkyl or oxo;
$R^{14}$ and $R^{15}$ are each independently selected from —H and —$C_{1-6}$alkyl;
n is 0, 1 or 2;
or a pharmaceutically acceptable salt thereof.

In a second embodiment, the present invention relates to a compound as described in the broadest embodiment above, wherein:
$R^1$ and $R^2$ are each independently hydrogen, methyl, ethyl, propyl, isopropyl, butyl, isobutyl, tert. butyl, pentyl, hexyl, cyclopropyl, cyclobutyl, cyclopentyl or cylohexyl, with the proviso that both $R^1$ and $R^2$ are not hydrogen;
$R^3$ is pyridinyl, pyrimidinyl, pyrazinyl, pyridazinyl, pyrrolyl, imidazolyl, thienyl, furanyl or thiazolyl, wherein each heteroaryl ring is optionally independently substituted with one to three groups selected from $C_{1-3}$ alkyl optionally substituted with one to three halogen atoms, $C_{1-3}$ alkoxy, $C_{1-3}$ hydroxy, halogen, hydroxy, —O-benzyl, oxo, cyano, amino, —NH—$C_{3-6}$ carbocycle, $C_{1-6}$ alkylamino and $C_{1-3}$ dialkylamino;
or
$R^3$ is pyridooxazinyl, dihydro-pyridooxazinyl, dihydropyrrolopyridinyl, pyrrolopyridinyl or pyrrolopyrazinyl, wherein each heteroaryl ring is optionally independently substituted with one to three groups selected from $C_{1-3}$ alkyl optionally substituted with one to three halogen atoms, $C_{1-3}$ alkoxy, $C_{1-3}$ hydroxy, halogen, hydroxy, —O-benzyl, oxo, cyano, amino, —NH—$C_{3-6}$ carbocycle, $C_{1-3}$ alkylamino and $C_{1-3}$ dialkylamino;
$R^4$ is hydrogen, methyl or fluoro;
$R^5$ is methyl, ethyl, propyl, isopropyl, butyl, isobutyl, tert-butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, azetidinyl, pyrrolidinyl, tetrahydropyranyl, pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, —C(O)—$R^6$, hydroxy or —$NR^7R^8$, wherein each $R^5$ is optionally independently substituted with one to three groups selected from $R^9$, $R^{10}$ and $R^{11}$;
$R^6$ is piperidinyl, piperazinyl, tetrahydropyranyl, morpholinyl, thiomorpholinyl or —NH-piperadinyl each optionally independently substituted with one to three groups selected from $R^9$, $R^{10}$ and $R^{11}$;
$R^7$ and $R^8$ are each independently hydrogen, 5-6 membered heterocycle optionally substituted with methyl, $C_{3-6}$ carbocycle optionally substituted with hydroxy, or $C_{1-5}$ alkyl;
$R^9$, $R^{10}$ and $R^{11}$ are independently selected from
(a) —H,
(b) —OH,
(c) halogen,
(d) —CN,
(e) —$CF_3$, (f) $C_{1-6}$alkyl optionally substituted with one to three —OH, —N($R^{12}$)($R^{13}$), 3-6 membered heterocycle, $C_{1-6}$alkoxy, $C_{1-6}$alkoxy-O—$C_{1-6}$alkyl, —$CO_2R^{12}$, —C(O)N($R^{12}$)($R^{13}$) or —S(O)$_n C_{1-6}$alkyl, (g) $C_{1-6}$alkoxy,
(h) —N($R^{12}$)($R^{13}$),
(i) —S(O)$_n C_{1-6}$alkyl,
(j) —$CO_2R^{12}$,
(k) —C(O)N($R^{12}$)($R^{13}$),
(l) —S(O)$_2$N($R^{12}$)($R^{13}$),
(m) a 3-8 membered heterocyclic group optionally substituted with one to three $C_{1-6}$ alkyl groups,
(n') oxo,
(o) —C(O)—$C_{1-3}$ alkyl;

$R^{12}$ and $R^{13}$ are each independently selected from —H, —$C_{1-6}$alkyl, C(O)$C_{1-6}$alkyl, and a 3-6 membered heterocyclic group, each of which is optionally independently substituted with one to three $C_{1-6}$alkyl groups, —OH, $C_{1-6}$alkoxy, —C(O)N($R^{14}$)($R^{15}$), —S(O)$_n C_{1-6}$alkyl, CN, a 3-6 membered heterocyclic group, —O$C_{1-6}$alkyl, $CF_3$; or, $R^{12}$ and $R^{13}$ taken together with the nitrogen ring to which they are attached can form a heterocyclyl ring optionally substituted with one to three —OH, CN, —O$C_{1-6}$alkyl or oxo;

$R^{14}$ and $R^{15}$ are each independently selected from —H and —$C_{1-4}$alkyl;

n is 1 or 2;

or a pharmaceutically acceptable salt thereof.

In a third embodiment, the present invention relates to a compound as described in any of the preceding embodiments above, wherein:

$R^1$ and $R^2$ are each independently hydrogen, methyl, ethyl, propyl, isopropyl, tert-butyl, cyclopropyl or cyclobutyl, with the proviso that both $R^1$ and $R^2$ are not hydrogen;

or a pharmaceutically acceptable salt thereof.

In a fourth embodiment there is provided a compound of formula (I) as described in any of the preceding embodiments above, wherein:

$R^3$ is pyridinyl, pyrazinyl, pyridazinyl or pyrimidinyl, wherein each heteroaryl ring is optionally independently substituted with one to two groups selected from $C_{1-3}$ alkyl optionally substituted with one to three halogen atoms, $C_{1-3}$ alkoxy, $C_{1-3}$ hydroxy, halogen, hydroxy, —O-benzyl, oxo, cyano, amino, —NH—$C_{3-6}$-carbocycle, $C_{1-5}$ alkylamino and $C_{1-3}$ dialkylamino; or $R^3$ is pyridooxazinyl, dihydro-pyridooxazinyl, dihydro-pyrrolopyridinyl, pyrrolopyridinyl or pyrrolopyrazinyl;

or a pharmaceutically acceptable salt thereof.

In a fifth embodiment there is provided a compound as described in any of the preceding embodiments above, wherein:

$R^5$ is methyl, ethyl, propyl, isopropyl, butyl, pentyl, hexyl, cyclopropyl, cyclobutyl, cyclopentyl, cyclohexyl, phenyl, azetidinyl, piperidinyl, piperazinyl, morpholinyl, tetrahydropyranyl, thiazolyl, oxazolyl, isoxazolyl, pyrazolyl, imidazolyl, pyridinyl, pyrimidinyl, pyrazinyl, pyridazinyl, quinolinyl, isoquinolinyl, —C(O)-piperizinyl, —C(O)-piperidinyl, —C(O)-morpholinyl, —C(O)—NH-piperidinyl, hydroxy or —NR$^7$R$^8$, wherein each $R^5$ is optionally independently substituted with one to three groups selected from $R^9$, $R^{10}$ and $R^{11}$;

$R^7$ and $R^8$ are each independently hydrogen, 5-6 membered heterocycle optionally substituted with methyl, $C_{3-6}$ carbocycle optionally substituted with hydroxy or $C_1$-$C_5$ alkyl;

$R^9$, $R^{10}$ and $R^{11}$ are independently selected from
(a) —H,
(b) —OH,
(c) halogen,
(d) —CN,
(e) —$CF_3$,
(f) $C_{1-6}$alkyl optionally substituted with one to three —OH, —N($R^{12}$)($R^{13}$), morpholinyl, piperazinyl, $C_{1-6}$alkoxy, $C_{1-3}$alkoxy-O—$C_{1-3}$alkyl, —$CO_2R^{12}$ or —C(O)N($R^{12}$)($R^{13}$),
(g) $C_{1-3}$alkoxy,
(h) —N($R^{12}$)($R^{13}$),
(i) —S(O)$_n C_{1-6}$alkyl,
(j) —$CO_2R^{12}$,
(k) —C(O)N($R^{12}$)($R^{13}$),
(l) —S(O)$_2$N($R^{12}$)($R^{13}$),
(m) morpholinyl, piperazinyl, piperidinyl or oxetanyl each optionally substituted with a methyl group,
(n') oxo,
(o) —C(O)—$CH_3$;

$R^{12}$ and $R^{13}$ are each independently selected from —H and —$C_{1-6}$alkyl, wherein the alkyl group is optionally substituted with one to three —OH, $C_{1-6}$alkoxy, —C(O)N($R^{14}$)($R^{15}$) or —S(O)$_n C_{1-6}$alkyl;

$R^{14}$ and $R^{15}$ are each independently selected from —H and —$C_{1-4}$alkyl; n is 2;

or a pharmaceutically acceptable salt thereof.

In a sixth embodiment there is provided a compound of formula (I) as described in the second embodiment above, wherein:

$R^1$ and $R^2$ are each independently hydrogen, methyl, ethyl, propyl, isopropyl, tert-butyl, cyclopropyl or cyclobutyl, with the proviso that both $R^1$ and $R^2$ are not hydrogen;

$R^3$ is pyridinyl, pyrazinyl, pyridazinyl or pyrimidinyl, wherein each heteroaryl ring is optionally independently substituted with one to two groups selected from methyl, methoxy, —$CH_2$OH, trifluoromethyl, bromo, chloro, fluoro, hydroxy, —O-benzyl, oxo, cyano, amino, —NH—$C_{3-6}$-carbocycle, $C_{1-4}$ alkylamino and $C_{1-3}$ dialkylamino; or $R^3$ is pyridooxazinyl, dihydro-pyridooxazinyl, dihydro-pyrrolopyridinyl, pyrrolopyridinyl or pyrrolopyrazinyl;

$R^4$ is hydrogen;

$R^5$ is methyl, ethyl, propyl, isopropyl, butyl, pentyl, cyclopropyl, cyclobutyl, cyclopentyl, cyclohexyl, phenyl, azetidinyl, piperidinyl, piperazinyl, morpholinyl, tetrahydropyranyl, thiazolyl, oxazolyl, isoxazolyl, pyrazolyl, imidazolyl, pyridinyl, pyrimidinyl, pyrazinyl, pyridazinyl, quinolinyl, isoquinolinyl, —C(O)-piperazinyl, —C(O)-morpholinyl, —C(O)—NH-piperidinyl, hydroxy or —NR$^7$R$^8$, wherein each $R^5$ is optionally independently substituted with one to three groups selected from $R^9$, $R^{10}$ and $R^{11}$;

$R^7$ and $R^8$ are each independently hydrogen, piperidinyl optionally substituted with a methyl group, cyclohexyl optionally substituted with a hydroxy group, methyl or ethyl;

$R^9$, $R^{10}$ and $R^{11}$ are independently selected from
(a) —H,
(b) —OH,
(c) halogen,
(d) —CN,
(e) —$CF_3$,
(f) $C_{1-6}$alkyl optionally substituted with one to three —OH, —N($R^{12}$)($R^{13}$), morpholinyl, piperazinyl, $C_{1-3}$alkoxy, $C_{1-3}$alkoxy-O—$C_{1-3}$alkyl, —$CO_2$H or —C(O)N($R^{12}$)($R^{13}$),
(g) $C_{1-3}$alkoxy,
(h) —N($R^{12}$)($R^{13}$),
(i) —S(O)$_2 C_{1-2}$alkyl,
(j) —$CO_2R^{12}$,
(k) —C(O)N($R^{12}$)($R^{13}$),
(l) —S(O)$_2$N($R^{12}$)($R^{13}$), (m) morpholinyl, piperazinyl, or oxetanyl each optionally substituted with a methyl group, (n') oxo, (o) —C(O)—CH$_3$;

R$^{12}$ and R$^{13}$ are each independently selected from —H and —C$_{1-6}$alkyl, wherein the alkyl group is optionally independently substituted with one to three —OH, C$_{1-6}$alkoxy, —C(O)N(R$^{14}$)(R$^{15}$), or —S(O)$_2$C$_{1-6}$alkyl;

R$^{14}$ and R$^{15}$ are each independently selected from —H and —C$_{1-4}$alkyl;

or a pharmaceutically acceptable salt thereof.

In a seventh embodiment there is provided a compound as described in the embodiment immediately above, wherein:

R$^1$ is methyl,

R$^2$ is selected from methyl, ethyl, isopropyl, tert-butyl, cyclopropyl and cyclobutyl;

or a pharmaceutically acceptable salt thereof.

In an eighth embodiment there is provided a compound as described in the sixth embodiment above, wherein:

R$^3$ is selected from

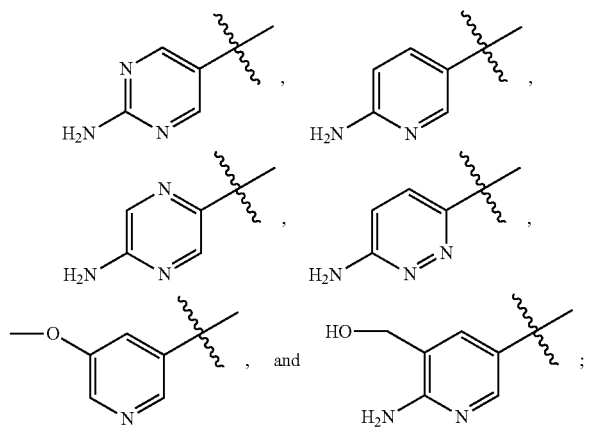

or a pharmaceutically acceptable salt thereof.

In a ninth embodiment there is provided a compound as described in the sixth embodiment above, wherein:

R$^5$ is pyrazolyl optionally independently substituted with one to three groups selected from R$^9$, R$^{10}$ and R$^{11}$;

or a pharmaceutically acceptable salt thereof.

In a tenth embodiment there is provided a compound as described in the sixth embodiment above, wherein:

R$^1$ is methyl,

R$^2$ is selected from methyl, ethyl, isopropyl, tert-butyl, cyclopropyl and cyclobutyl;

R$^3$ is selected from

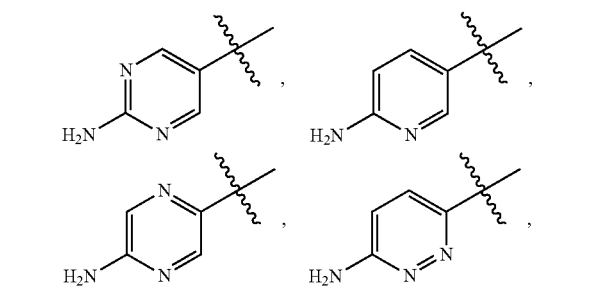

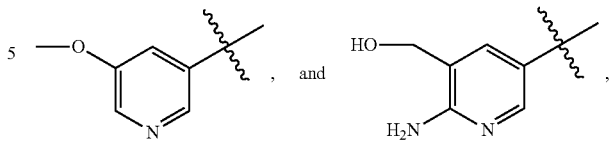

R$^4$ is hydrogen,

R$^5$ is selected from

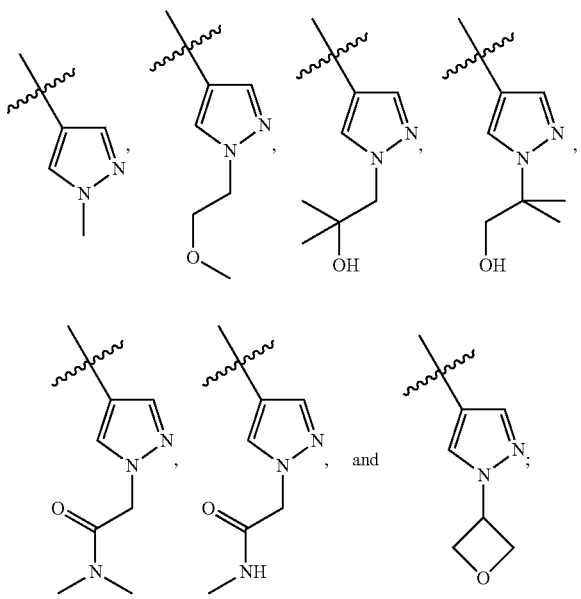

or a pharmaceutically acceptable salt thereof.

In an eleventh embodiment there is provided a compound as described in the tenth embodiment above, wherein:

R$^2$ is cyclopropyl or cyclobutyl;

or a pharmaceutically acceptable salt thereof.

In a twelfth embodiment there is provided a compound as described in the tenth embodiment above, wherein:

R$^2$ is selected from methyl, ethyl, isopropyl and tert-butyl;

or a pharmaceutically acceptable salt thereof.

In a thirteenth embodiment there is provided a compound as described in the sixth embodiment above, wherein:

R$^3$ is selected from

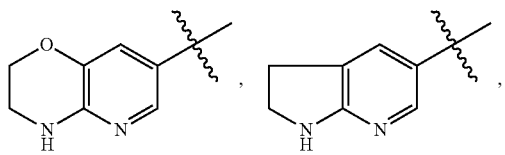

-continued

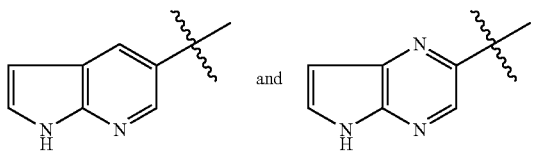

or a pharmaceutically acceptable salt thereof.

In a fourteenth embodiment there is provided a compound as described in the sixth embodiment above, wherein:

$R^3$ is selected from

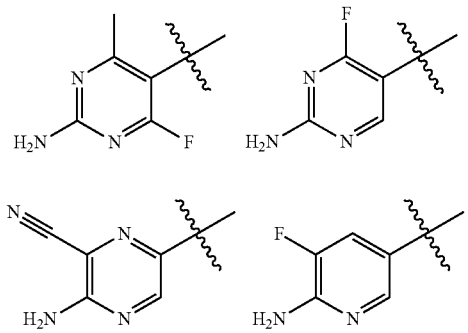

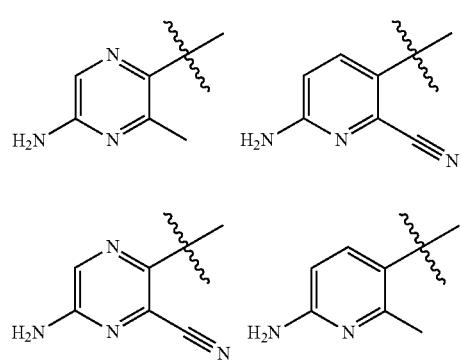

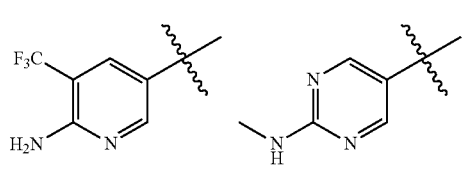

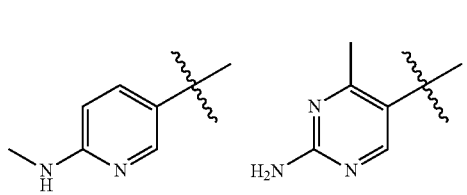

or a pharmaceutically acceptable salt thereof.

In a fifteenth embodiment there is provided a compound as described in the tenth embodiment above, wherein:

$R^1$ is methyl,
$R^2$ is cyclopropyl;
$R^3$ is selected from

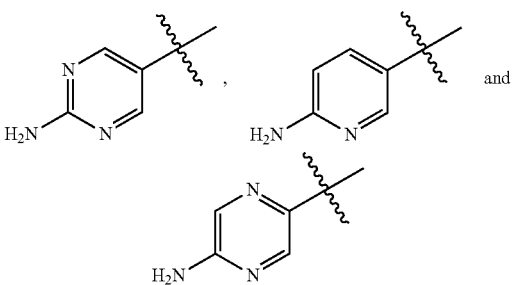

$R^4$ is hydrogen,
$R^5$ is selected from

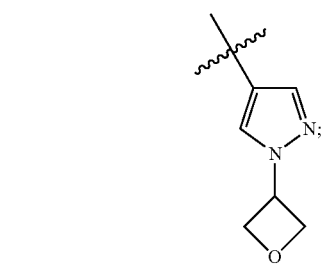

or a pharmaceutically acceptable salt thereof.

In a sixteenth embodiment there is provided a compound of formula I, wherein
$R^1$ is methyl,
$R^2$ is cyclopropyl;
$R^3$ is selected from

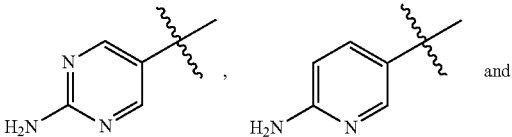

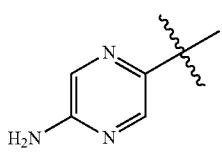

R⁴ is hydrogen,
R⁵ is selected from

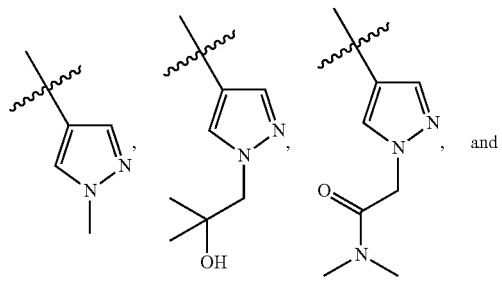

and

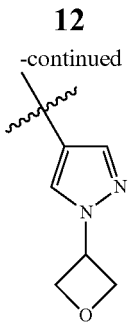

or a pharmaceutically acceptable salt thereof.

The following are representative compounds of the invention which can be made by the general synthetic schemes, the examples, and known methods in the art.

TABLE 1

| Example | Structure | Name |
|---|---|---|
| 1 | 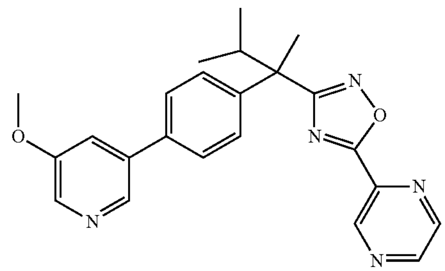 [SMILES: COc1cncc(-c2ccc(C(C)(c3noc(-c4cnccn4)n3)C(C)C)cc2)c1] | 2-(3-{2-[4-(5-methoxypyridin-3-yl)phenyl]-3-methylbutan-2-yl}-1,2,4-oxadiazol-5-yl)pyrazine |
| 2 | 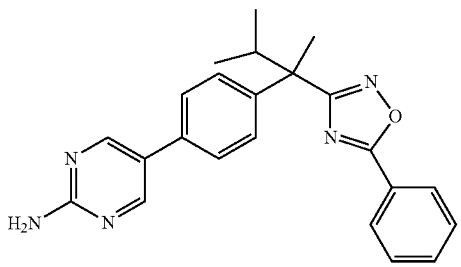 [SMILES: CC(C)C(C)(c1ccc(-c2cnc(N)nc2)cc1)c1noc(-c2ccccc2)n1] | 5-{4-[3-methyl-2-(5-phenyl-1,2,4-oxadiazol-3-yl)butan-2-yl]phenyl}pyrimidin-2-amine |
| 3 | 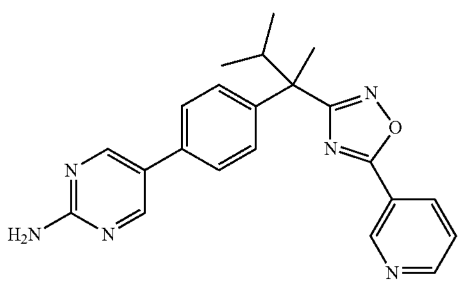 [SMILES: CC(C)C(C)(c1ccc(-c2cnc(N)nc2)cc1)c1noc(-c2cccnc2)n1] | 5-(4-{3-methyl-2-[5-(pyridin-3-yl)-1,2,4-oxadiazol-3-yl]butan-2-yl}phenyl)pyrimidin-2-amine |
| 4 | 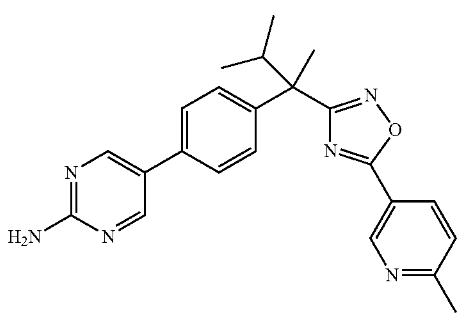 [SMILES: Cc1ccc(-c2nc(C(C)(c3ccc(-c4cnc(N)nc4)cc3)C(C)C)no2)cn1] | 5-(4-{3-methyl-2-[5-(6-methylpyridin-3-yl)-1,2,4-oxadiazol-3-yl]butan-2-yl}phenyl)pyrimidin-2-amine |

TABLE 1-continued

| Example | Structure | Name |
|---|---|---|
| 5 | 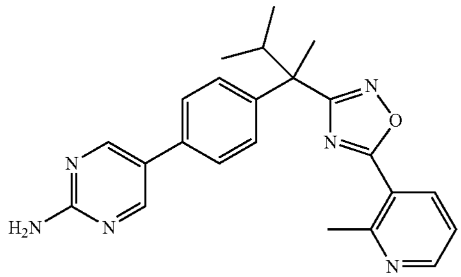 [SMILES: Cc1ncccc1-c1nc(C(C)(c2ccc(-c3cnc(N)nc3)cc2)C(C)C)no1] | 5-(4-{3-methyl-2-[5-(2-methylpyridin-3-yl)-1,2,4-oxadiazol-3-yl]butan-2-yl}phenyl)pyrimidin-2-amine |
| 6 | 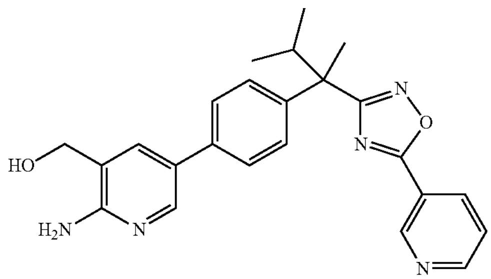 [SMILES: CC(C)C(C)(c1ccc(-c2cnc(N)c(CO)c2)cc1)c1noc(-c2cccnc2)n1] | [2-amino-5-(4-{3-methyl-2-[5-(pyridin-3-yl)-1,2,4-oxadiazol-3-yl]butan-2-yl}phenyl)pyridin-3-yl]methanol |
| 7 | 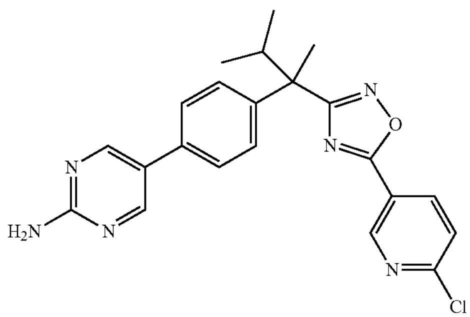 [SMILES: CC(C)C(C)(c1ccc(-c2cnc(N)nc2)cc1)c1noc(-c2ccc(Cl)nc2)n1] | 5-(4-{2-[5-(6-chloropyridin-3-yl)-1,2,4-oxadiazol-3-yl]-3-methylbutan-2-yl}phenyl)pyrimidin-2-amine |
| 8 | 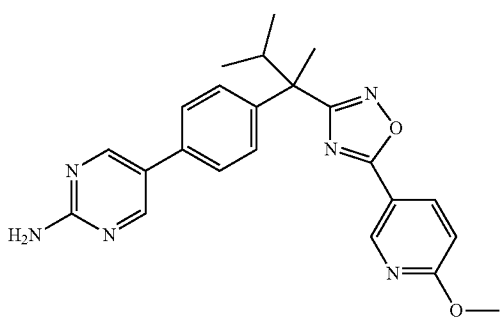 [SMILES: COc1ccc(-c2nc(C(C)(c3ccc(-c4cnc(N)nc4)cc3)C(C)C)no2)cn1] | 5-(4-{2-[5-(6-methoxypyridin-3-yl)-1,2,4-oxadiazol-3-yl]-3-methylbutan-2-yl}phenyl)pyrimidin-2-amine |
| 9 | 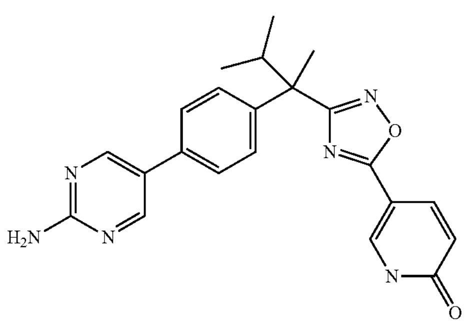 [SMILES: CC(C)C(C)(c1ccc(-c2cnc(N)nc2)cc1)c1noc(-c2ccc(=O)[nH]c2)n1] | 5-(3-{2-[4-(2-aminopyrimidin-5-yl)phenyl]-3-methylbutan-2-yl}-1,2,4-oxadiazol-5-yl)pyridin-2(1H)-one |

TABLE 1-continued

| Example | Structure | Name |
|---|---|---|
| 10 | 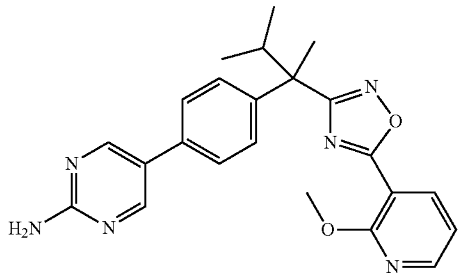 [SMILES: COc1ncccc1-c1nc(C(C)(c2ccc(-c3cnc(N)nc3)cc2)C(C)C)no1] | 5-(4-{2-[5-(2-methoxypyridin-3-yl)-1,2,4-oxadiazol-3-yl]-3-methylbutan-2-yl}phenyl)pyrimidin-2-amine |
| 11 | 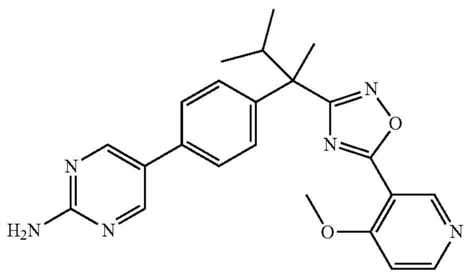 [SMILES: COc1ccncc1-c1nc(C(C)(c2ccc(-c3cnc(N)nc3)cc2)C(C)C)no1] | 5-(4-{2-[5-(4-methoxypyridin-3-yl)-1,2,4-oxadiazol-3-yl]-3-methylbutan-2-yl}phenyl)pyrimidin-2-amine |
| 12 | 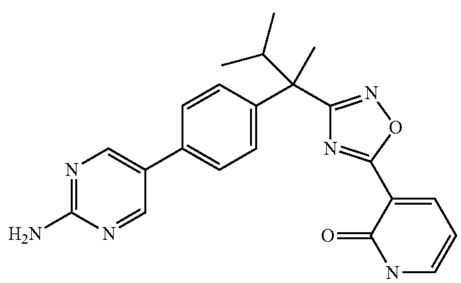 [SMILES: CC(C)C(C)(c1ccc(-c2cnc(N)nc2)cc1)c1noc(-c2ccc[nH]c2=O)n1] | 3-(3-{2-[4-(2-aminopyrimidin-5-yl)phenyl]-3-methylbutan-2-yl}-1,2,4-oxadiazol-5-yl)pyridin-2(1H)-one |
| 13 | 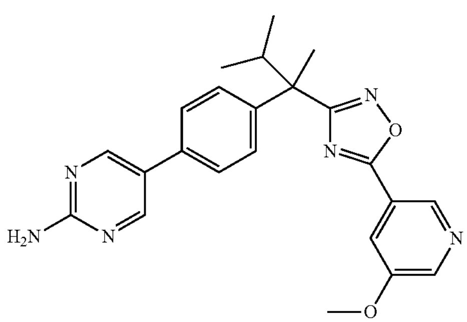 [SMILES: COc1cncc(-c2nc(C(C)(c3ccc(-c4cnc(N)nc4)cc3)C(C)C)no2)c1] | 5-(4-{2-[5-(5-methoxypyridin-3-yl)-1,2,4-oxadiazol-3-yl]-3-methylbutan-2-yl}phenyl)pyrimidin-2-amine |
| 14 | 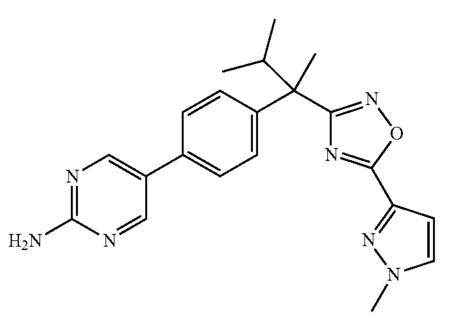 [SMILES: CC(C)C(C)(c1ccc(-c2cnc(N)nc2)cc1)c1noc(-c2ccn(C)n2)n1] | 5-(4-{3-methyl-2-[5-(1-methyl-1H-pyrazol-3-yl)-1,2,4-oxadiazol-3-yl]butan-2-yl}phenyl)pyrimidin-2-amine |

TABLE 1-continued

| Example | Structure | Name |
|---|---|---|
| 15 | 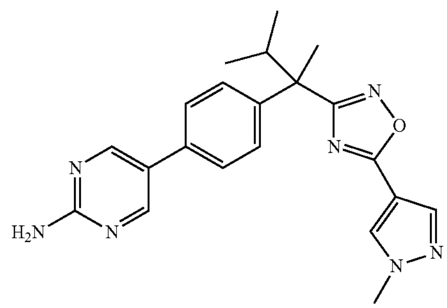 [SMILES: CC(C)C(C)(c1ccc(-c2cnc(N)nc2)cc1)c1noc(-c2cnn(C)c2)n1] | 5-(4-{3-methyl-2-[5-(1-methyl-1H-pyrazol-4-yl)-1,2,4-oxadiazol-3-yl]butan-2-yl}1phenyl)pyrimidin-2-amine |
| 16 | 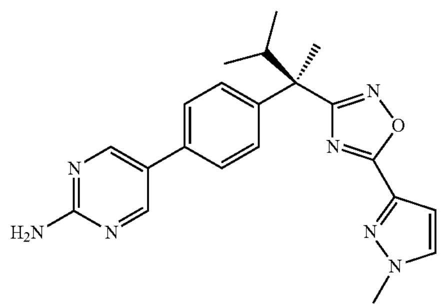 [SMILES: CC(C)[C@](C)(c1ccc(-c2cnc(N)nc2)cc1)c1noc(-c2ccn(C)n2)n1] | 5-(4-{(2R)-3-methyl-2-[5-(1-methyl-1H-pyrazol-3-yl)-1,2,4-oxadiazol-3-yl]butan-2-yl}phenyl)pyrimidin-2-amine |
| 17 | 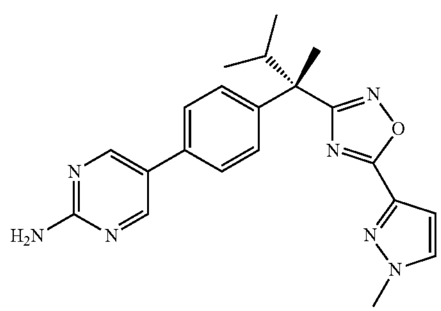 [SMILES: CC(C)[C@@](C)(c1ccc(-c2cnc(N)nc2)cc1)c1noc(-c2ccn(C)n2)n1] | 5-(4-{(2S)-3-methyl-2-[5-(1-methyl-1H-pyrazol-3-yl)-1,2,4-oxadiazol-3-yl]butan-2-yl}phenyl)pyrimidin-2-amine |
| 18 | 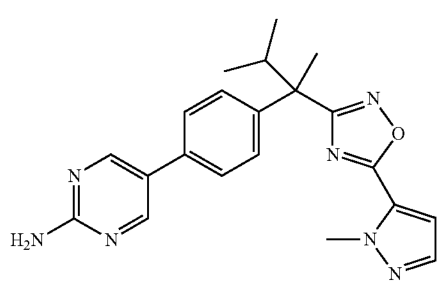 [SMILES: CC(C)C(C)(c1ccc(-c2cnc(N)nc2)cc1)c1noc(-c2ccnn2C)n1] | 5-(4-{3-methyl-2-[5-(1-methyl-1H-pyrazol-5-yl)-1,2,4-oxadiazol-3-yl]butan-2-yl}phenyl)pyrimidin-2-amine |
| 19 | 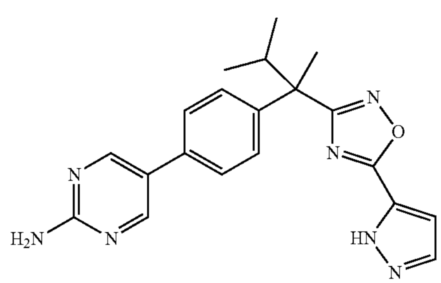 [SMILES: CC(C)C(C)(c1ccc(-c2cnc(N)nc2)cc1)c1noc(-c2ccn[nH]2)n1] | 5-(4-{3-methyl-2-[5-(1H-pyrazol-5-yl)-1,2,4-oxadiazol-3-yl]butan-2-yl}phenyl)pyrimidin-2-amine |

TABLE 1-continued

| Example | Structure | Name |
|---|---|---|
| 20 | 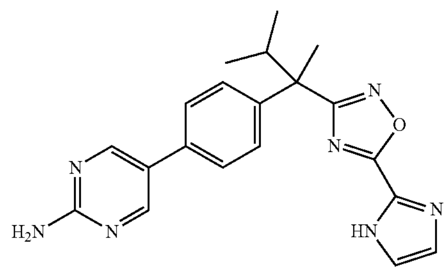 [SMILES: CC(C)C(C)(c1ccc(-c2cnc(N)nc2)cc1)c1noc(-c2ncc[nH]2)n1] | 5-(4-{2-[5-(1H-imidazol-2-yl)-1,2,4-oxadiazol-3-yl]-3-methylbutan-2-yl}phenyl)pyrimidin-2-amine |
| 21 | 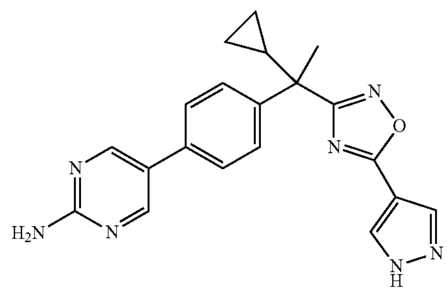 [SMILES: CC(c1ccc(-c2cnc(N)nc2)cc1)(c1noc(-c2cn[nH]c2)n1)C1CC1] | 5-(4-{1-cyclopropyl-1-[5-(1H-pyrazol-4-yl)-1,2,4-oxadiazol-3-yl]ethyl}phenyl)pyrimidin-2-amine |
| 22 | 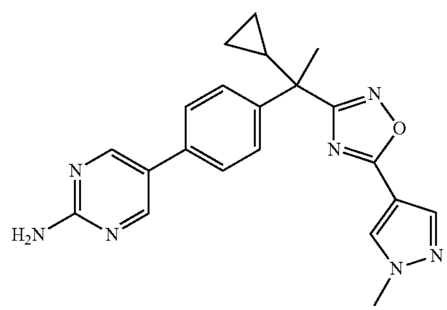 [SMILES: Cn1cc(-c2nc(C(C)(c3ccc(-c4cnc(N)nc4)cc3)C3CC3)no2)cn1] | 5-(4-{1-cyclopropyl-1-[5-(1-methyl-1H-pyrazol-4-yl)-1,2,4-oxadiazol-3-yl]ethyl}phenyl)pyrimidin-2-amine |
| 23 | 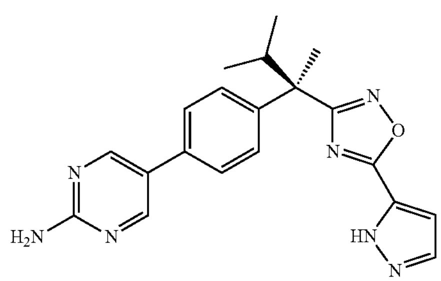 [SMILES: CC(C)[C@](C)(c1ccc(-c2cnc(N)nc2)cc1)c1noc(-c2ccn[nH]2)n1] | 5-(4-{(2R)-3-methyl-2-[5-(1H-pyrazol-5-yl)-1,2,4-oxadiazol-3-yl]butan-2-yl}phenyl)pyrimidin-2-amine |
| 24 | 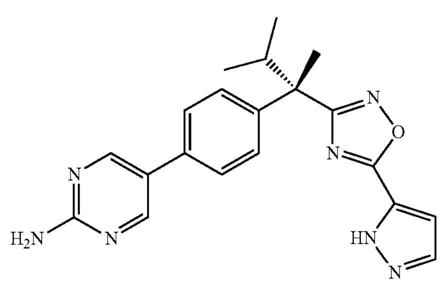 [SMILES: CC(C)[C@@](C)(c1ccc(-c2cnc(N)nc2)cc1)c1noc(-c2ccn[nH]2)n1] | 5-(4-{(2S)-3-methyl-2-[5-(1H-pyrazol-5-yl)-1,2,4-oxadiazol-3-yl]butan-2-yl}phenyl)pyrimidin-2-amine |

TABLE 1-continued

| Example | Structure | Name |
|---|---|---|
| 25 | 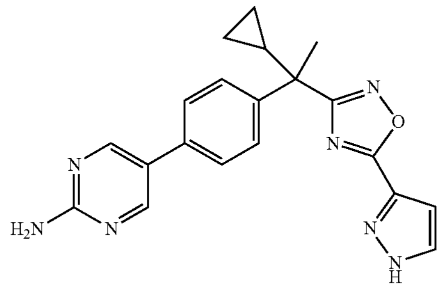 [SMILES: CC(c1ccc(-c2cnc(N)nc2)cc1)(c1noc(-c2cc[nH]n2)n1)C1CC1] | 5-(4-{1-cyclopropyl-1-[5-(1H-pyrazol-3-yl)-1,2,4-oxadiazol-3-yl]ethyl}phenyl)pyrimidin-2-amine |
| 26 | 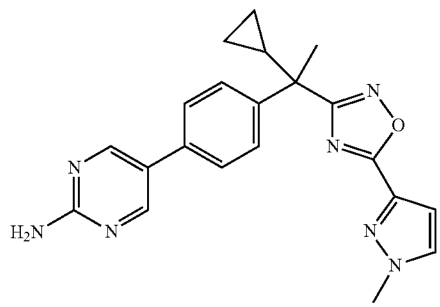 [SMILES: Cn1ccc(-c2nc(C(C)(c3ccc(-c4cnc(N)nc4)cc3)C3CC3)no2)n1] | 5-(4-{1-cyclopropyl-1-[5-(1-methyl-1H-pyrazol-3-yl)-1,2,4-oxadiazol-3-yl]ethyl}phenyl)pyrimidin-2-amine |
| 27 | 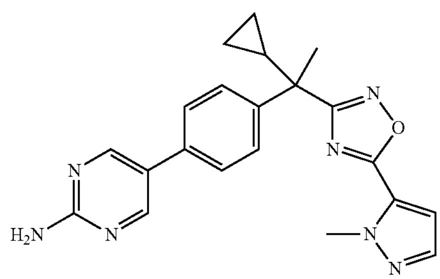 [SMILES: Cn1nccc1-c1nc(C(C)(c2ccc(-c3cnc(N)nc3)cc2)C2CC2)no1] | 5-(4-{1-cyclopropyl-1-[5-(1-methyl-1H-pyrazol-5-yl)-1,2,4-oxadiazol-3-yl]ethyl}phenyl)pyrimidin-2-amine |
| 28 | 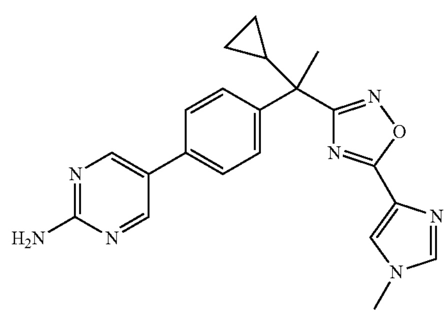 [SMILES: Cn1cnc(-c2nc(C(C)(c3ccc(-c4cnc(N)nc4)cc3)C3CC3)no2)c1] | 5-(4-{1-cyclopropyl-1-[5-(1-methyl-1H-imidazol-4-yl)-1,2,4-oxadiazol-3-yl]ethyl}phenyl)pyrimidin-2-amine |
| 29 | 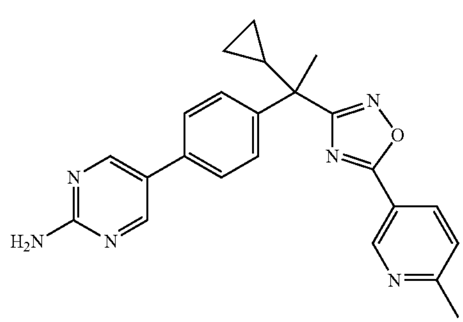 [SMILES: Cc1ccc(-c2nc(C(C)(c3ccc(-c4cnc(N)nc4)cc3)C3CC3)no2)cn1] | 5-(4-{1-cyclopropyl-1-[5-(6-methylpyridin-3-yl)-1,2,4-oxadiazol-3-yl]ethyl}phenyl)pyrimidin-2-amine |

TABLE 1-continued

| Example | Structure | Name |
|---|---|---|
| 30 | 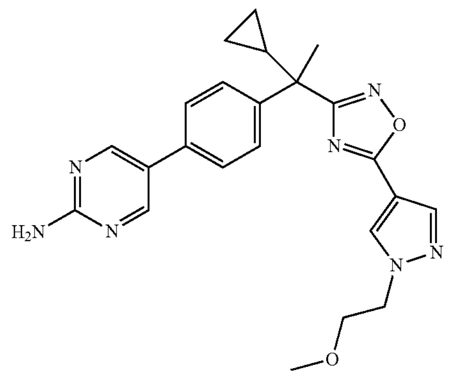 [SMILES: COCCn1cc(-c2nc(C(C)(c3ccc(-c4cnc(N)nc4)cc3)C3CC3)no2)cn1] | 5-[4-(1-cyclopropyl-1-{5-[1-(2-methoxyethyl)-1H-pyrazol-4-yl]-1,2,4-oxadiazol-3-yl}ethyl)phenyl]pyrimidin-2-amine |
| 31 | 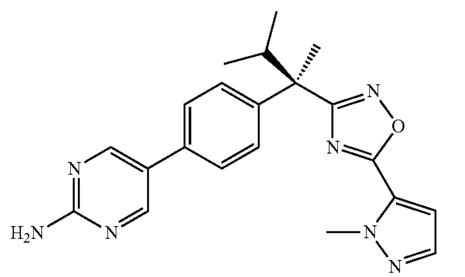 [SMILES: CC(C)[C@](C)(c1ccc(-c2cnc(N)nc2)cc1)c1noc(-c2ccnn2C)n1] | 5-(4-{(2R)-3-methyl-2-[5-(1-methyl-1H-pyrazol-5-yl)-1,2,4-oxadiazol-3-yl]butan-2-yl}phenyl)pyrimidin-2-amine |
| 32 | 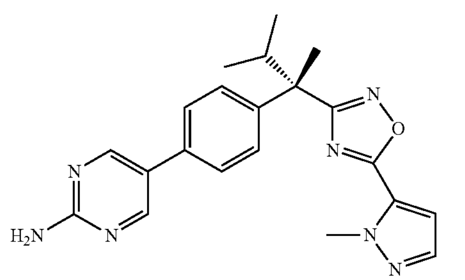 [SMILES: CC(C)[C@@](C)(c1ccc(-c2cnc(N)nc2)cc1)c1noc(-c2ccnn2C)n1] | 5-(4-{(2S)-3-methyl-2-[5-(1-methyl-1H-pyrazol-5-yl)-1,2,4-oxadiazol-3-yl]butan-2-yl}phenyl)pyrimidin-2-amine |
| 33 | 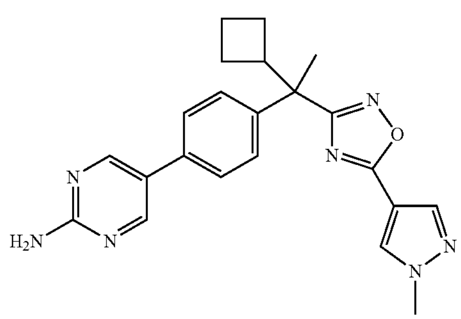 [SMILES: Cn1cc(-c2nc(C(C)(c3ccc(-c4cnc(N)nc4)cc3)C3CCC3)no2)cn1] | 5-(4-{1-cyclobutyl-1-[5-(1-methyl-1H-pyrazol-4-yl)-1,2,4-oxadiazol-3-yl]ethyl}phenyl)pyrimidin-2-amine |
| 34 | 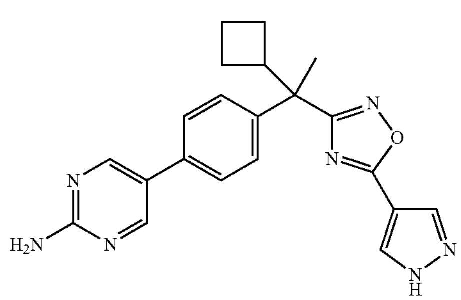 [SMILES: CC(c1ccc(-c2cnc(N)nc2)cc1)(c1noc(-c2cn[nH]c2)n1)C1CCC1] | 5-(4-{1-cyclobutyl-1-[5-(1H-pyrazol-4-yl)-1,2,4-oxadiazol-3-yl]ethyl}phenyl)pyrimidin-2-amine |

TABLE 1-continued

| Example | Structure | Name |
|---|---|---|
| 35 | 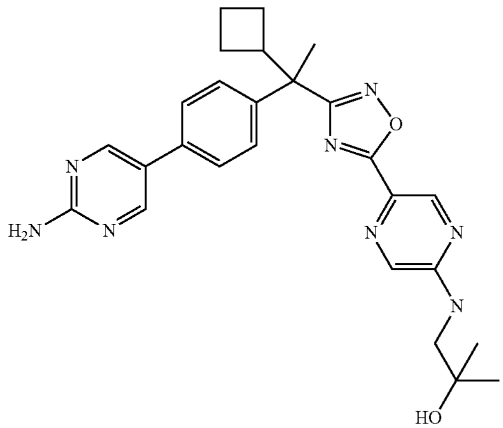 [SMILES: CC(C)(O)CNc1cnc(-c2nc(C(C)(c3ccc(-c4cnc(N)nc4)cc3)C3CCC3)no2)cn1] | 1-{[5-(3-{1-[4-(2-aminopyrimidin-5-yl)phenyl]-1-cyclobutylethyl}-1,2,4-oxadiazol-5-yl)pyrazin-2-yl]amino}-2-methylpropan-2-ol |
| 36 | 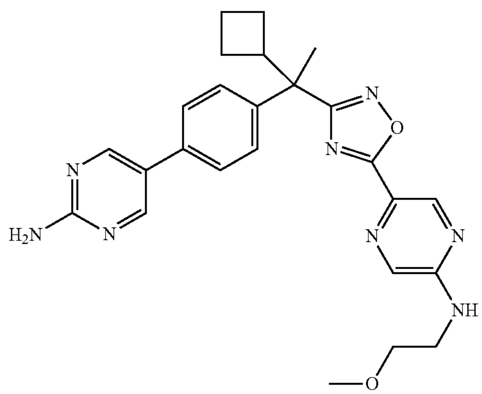 [SMILES: COCCNc1cnc(-c2nc(C(C)(c3ccc(-c4cnc(N)nc4)cc3)C3CCC3)no2)cn1] | 5-{4-[1-cyclobutyl-1-(5-{5-[(2-methoxyethyl)amino]pyrazin-2-yl}-1,2,4-oxadiazol-3-yl)ethyl]phenyl}pyrimidin-2-amine |
| 37 | 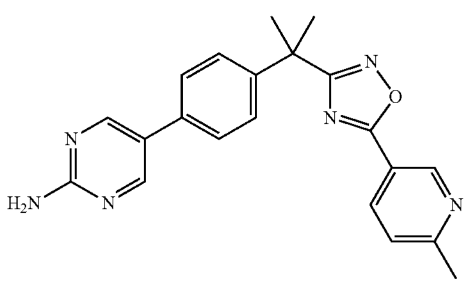 [SMILES: Cc1ccc(-c2nc(C(C)(C)c3ccc(-c4cnc(N)nc4)cc3)no2)cn1] | 5-(4-{2-[5-(6-methylpyridin-3-yl)-1,2,4-oxadiazol-3-yl]propan-2-yl}phenyl)pyrimidin-2-amine |
| 38 | 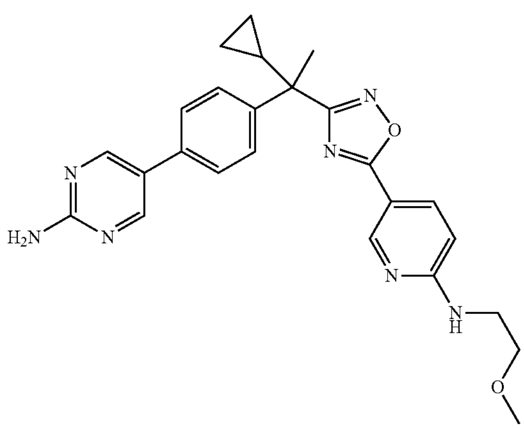 [SMILES: COCCNc1ccc(-c2nc(C(C)(c3ccc(-c4cnc(N)nc4)cc3)C3CC3)no2)cn1] | 5-{4-[1-cyclopropyl-1-(5-{6-[(2-methoxyethyl)amino]pyridin-3-yl}-1,2,4-oxadiazol-3-yl)ethyl]phenyl}pyrimidin-2-amine |

TABLE 1-continued

| Example | Structure | Name |
|---|---|---|
| 39 | 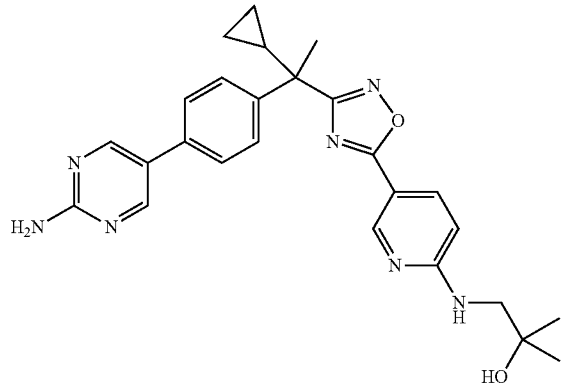 [SMILES: CC(C)(O)CNc1ccc(-c2nc(C(C)(c3ccc(-c4cnc(N)nc4)cc3)C3CC3)no2)cn1] | 1-{[5-(3-{1-[4-(2-aminopyrimidin-5-yl)phenyl]-1-cyclopropylethyl}-1,2,4-oxadiazol-5-yl)pyridin-2-yl]amino}-2-methylpropan-2-ol |
| 40 | 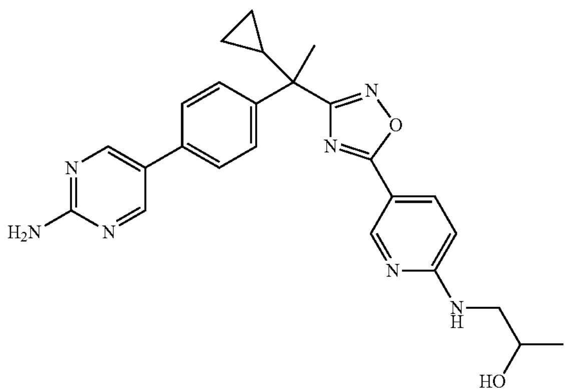 [SMILES: CC(O)CNc1ccc(-c2nc(C(C)(c3ccc(-c4cnc(N)nc4)cc3)C3CC3)no2)cn1] | 1-{[5-(3-{1-[4-(2-aminopyrimidin-5-yl)phenyl]-1-cyclopropylethyl}-1,2,4-oxadiazol-5-yl)pyridin-2-yl]amino}propan-2-ol |
| 41 | 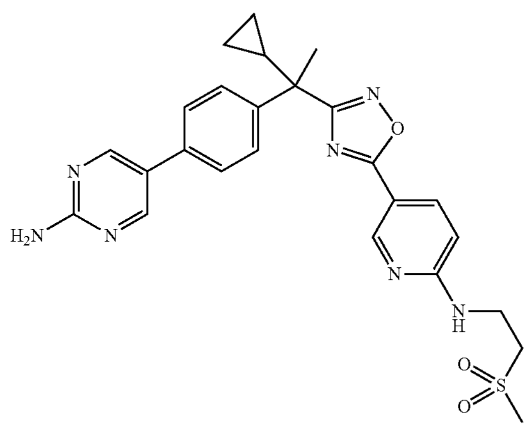 [SMILES: CC(c1ccc(-c2cnc(N)nc2)cc1)(c1noc(-c2ccc(NCCS(C)(=O)=O)nc2)n1)C1CC1] | 5-(4-{1-cyclopropyl-1-[5-(6-{[2-(methylsulfonyl)ethyl]amino}pyridin-3-yl)-1,2,4-oxadiazol-3-yl]ethyl}phenyl)pyrimidin-2-amine |
| 42 | 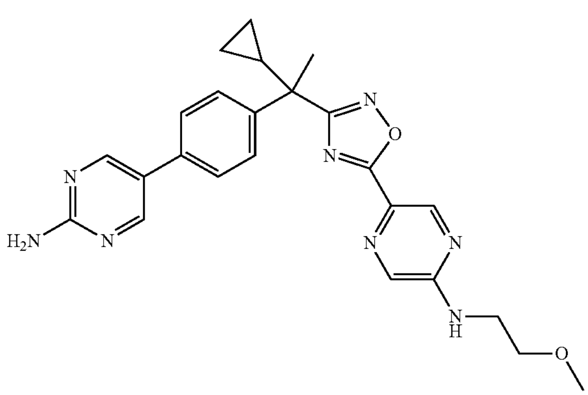 [SMILES: COCCNc1cnc(-c2nc(C(C)(c3ccc(-c4cnc(N)nc4)cc3)C3CC3)no2)cn1] | 5-{4-[1-cyclopropyl-1-(5-{5-[(2-methoxyethyl)amino]pyrazin-2-yl}-1,2,4-oxadiazol-3-yl)ethyl]phenyl}pyrimidin-2-amine |

TABLE 1-continued

| Example | Structure | Name |
|---|---|---|
| 43 | 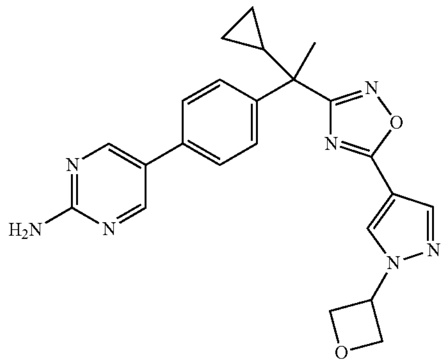 [SMILES: CC(c1ccc(-c2cnc(N)nc2)cc1)(c1noc(-c2cnn(C3COC3)c2)n1)C1CC1] | 5-[4-(1-cyclopropyl-1-{5-[1-(oxetan-3-yl)-1H-pyrazol-4-yl]-1,2,4-oxadiazol-3-yl}ethyl)phenyl]pyrimidin-2-amine |
| 44 | 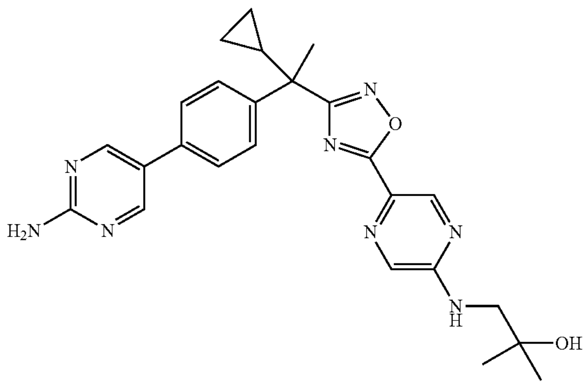 [SMILES: CC(C)(O)CNc1cnc(-c2nc(C(C)(c3ccc(-c4cnc(N)nc4)cc3)C3CC3)no2)cn1] | 1-{[5-(3-{1-[4-(2-aminopyrimidin-5-yl)phenyl]-1-cyclopropylethyl}-1,2,4-oxadiazol-5-yl)pyrazin-2-yl]amino}-2-methylpropan-2-ol |
| 45 | 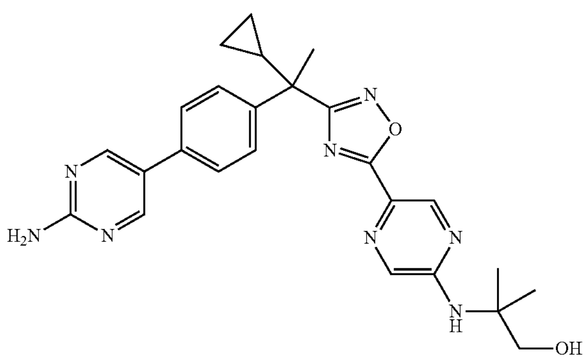 [SMILES: CC(C)(CO)Nc1cnc(-c2nc(C(C)(c3ccc(-c4cnc(N)nc4)cc3)C3CC3)no2)cn1] | 2-{[5-(3-{1-[4-(2-aminopyrimidin-5-yl)phenyl]-1-cyclopropylethyl}-1,2,4-oxadiazol-5-yl)pyrazin-2-yl]amino}-2-methylpropan-1-ol |
| 46 | 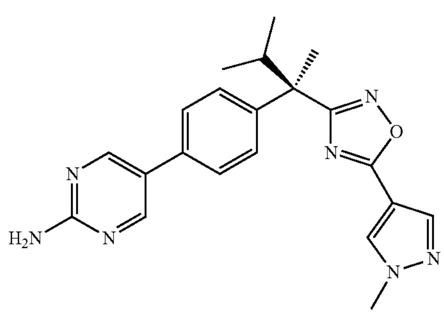 [SMILES: CC(C)[C@](C)(c1ccc(-c2cnc(N)nc2)cc1)c1noc(-c2cnn(C)c2)n1] | 5-(4-{(2R)-3-methyl-2-[5-(1-methyl-1H-pyrazol-4-yl)-1,2,4-oxadiazol-3-yl]butan-2-yl}phenyl)pyrimidin-2-amine |

TABLE 1-continued

| Example | Structure | Name |
|---|---|---|
| 47 | 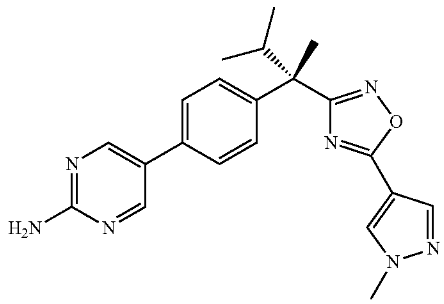 [SMILES: CC(C)[C@@](C)(c1ccc(-c2cnc(N)nc2)cc1)c1noc(-c2cnn(C)c2)n1] | 5-(4-{(2S)-3-methyl-2-[5-(1-methyl-1H-pyrazol-4-yl)-1,2,4-oxadiazol-3-yl]butan-2-yl}phenyl)pyrimidin-2-amine |
| 48 | 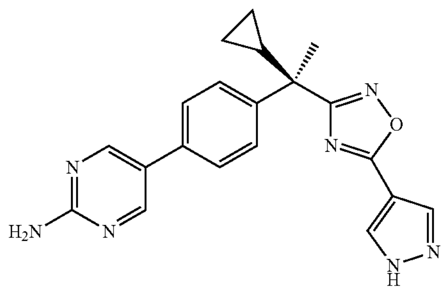 [SMILES: C[C@@](c1ccc(-c2cnc(N)nc2)cc1)(c1noc(-c2cn[nH]c2)n1)C1CC1] | 5-(4-{(1R)-1-cyclopropyl-1-[5-(1H-pyrazol-4-yl)-1,2,4-oxadiazol-3-yl]ethyl}phenyl)pyrimidin-2-amine |
| 49 | 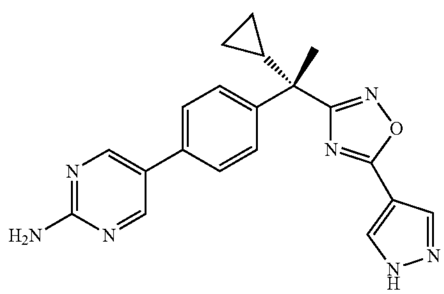 [SMILES: C[C@](c1ccc(-c2cnc(N)nc2)cc1)(c1noc(-c2cn[nH]c2)n1)C1CC1] | 5-(4-{(1S)-1-cyclopropyl-1-[5-(1H-pyrazol-4-yl)-1,2,4-oxadiazol-3-yl]ethyl}phenyl)pyrimidin-2-amine |
| 50 | 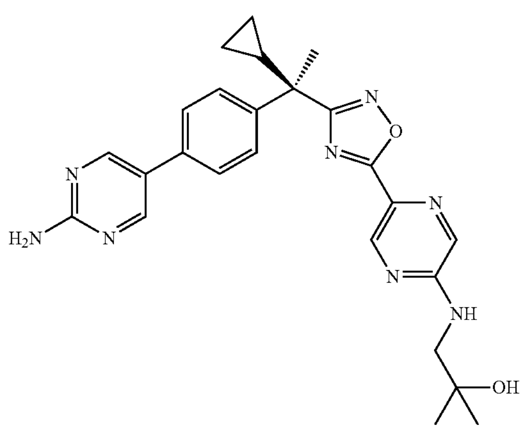 [SMILES: CC(C)(O)CNc1cnc(-c2nc([C@@](C)(c3ccc(-c4cnc(N)nc4)cc3)C3CC3)no2)cn1] | 1-{[5-(3-{(1R)-1-[4-(2-aminopyrimidin-5-yl)phenyl]-1-cyclopropylethyl}-1,2,4-oxadiazol-5-yl)pyrazin-2-yl]amino}-2-methylpropan-2-ol |

TABLE 1-continued

| Example | Structure | Name |
|---|---|---|
| 51 | 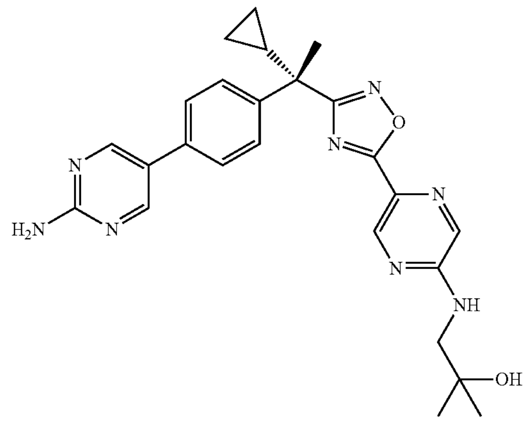 [SMILES: CC(C)(O)CNc1cnc(-c2nc([C@](C)(c3ccc(-c4cnc(N)nc4)cc3)C3CC3)no2)cn1] | 1-{[5-(3-{(1S)-1-[4-(2-aminopyrimidin-5-yl)phenyl]-1-cyclopropylethyl}-1,2,4-oxadiazol-5-yl)pyrazin-2-yl]amino}-2-methylpropan-2-ol |
| 52 | 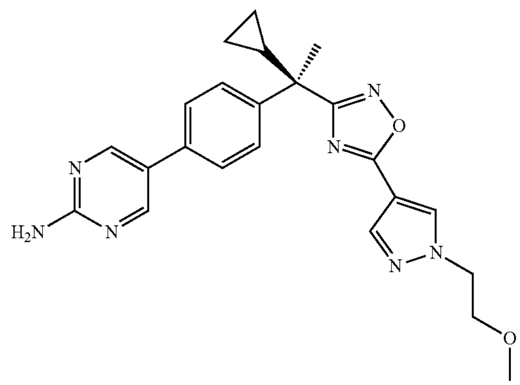 [SMILES: COCCn1cc(-c2nc([C@@](C)(c3ccc(-c4cnc(N)nc4)cc3)C3CC3)no2)cn1] | 5-{4-[(1R)-1-cyclopropyl-1-{5-[1-(2-methoxyethyl)-1H-pyrazol-4-yl]-1,2,4-oxadiazol-3-yl}ethyl]phenyl}pyrimidin-2-amine |
| 53 | 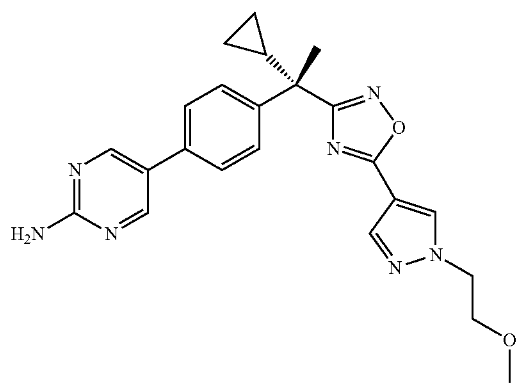 [SMILES: COCCn1cc(-c2nc([C@](C)(c3ccc(-c4cnc(N)nc4)cc3)C3CC3)no2)cn1] | 5-{4-[(1S)-1-cyclopropyl-1-{5-[1-(2-methoxyethyl)-1H-pyrazol-4-yl]-1,2,4-oxadiazol-3-yl}ethyl]phenyl}pyrimidin-2-amine |
| 54 | 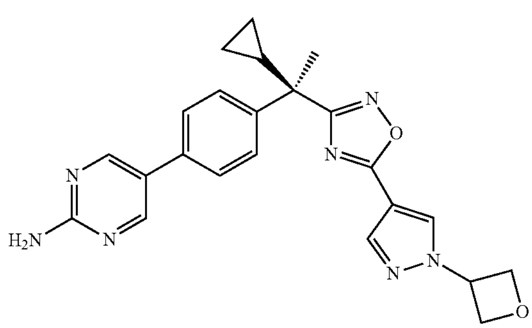 [SMILES: C[C@@](c1ccc(-c2cnc(N)nc2)cc1)(c1noc(-c2cnn(C3COC3)c2)n1)C1CC1] | 5-{4-[(1R)-1-cyclopropyl-1-{5-[1-(oxetan-3-yl)-1H-pyrazol-4-yl]-1,2,4-oxadiazol-3-yl}ethyl]phenyl}pyrimidin-2-amine |

TABLE 1-continued

| Example | Structure | Name |
|---|---|---|
| 55 | 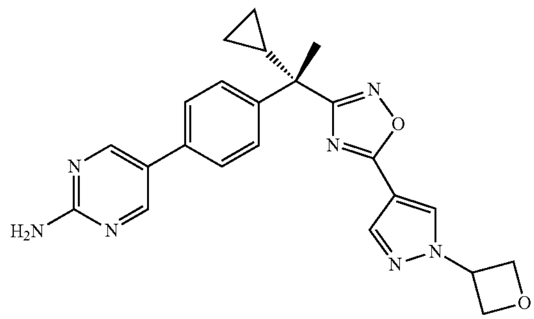 [SMILES: C[C@](c1ccc(-c2cnc(N)nc2)cc1)(c1noc(-c2cnn(C3COC3)c2)n1)C1CC1] | 5-{4-[(1S)-1-cyclopropyl-1-{5-[1-(oxetan-3-yl)-1H-pyrazol-4-yl]-1,2,4-oxadiazol-3-yl}ethyl]phenyl}pyrimidin-2-amine |
| 56 | 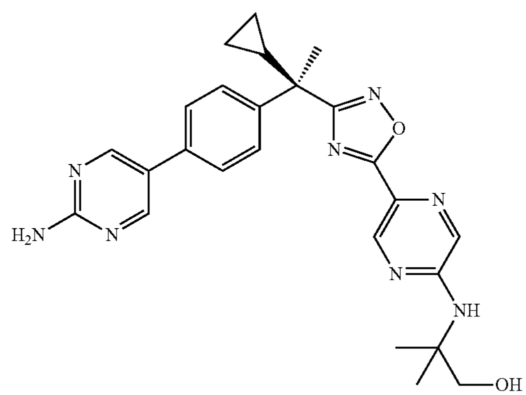 [SMILES: CC(C)(CO)Nc1cnc(-c2nc([C@@](C)(c3ccc(-c4cnc(N)nc4)cc3)C3CC3)no2)cn1] | 2-{[5-(3-{(1R)-1-[4-(2-aminopyrimidin-5-yl)phenyl]-1-cyclopropylethyl}-1,2,4-oxadiazol-5-yl)pyrazin-2-yl]amino}-2-methylpropan-1-ol |
| 57 | 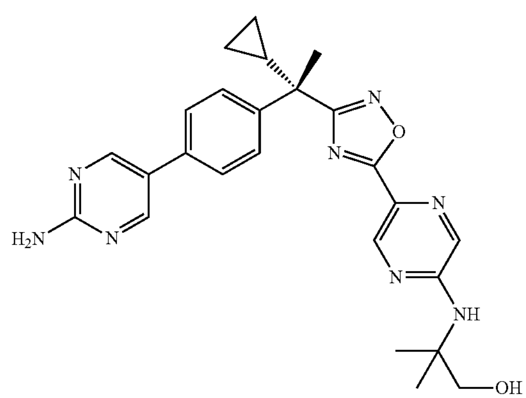 [SMILES: CC(C)(CO)Nc1cnc(-c2nc([C@](C)(c3ccc(-c4cnc(N)nc4)cc3)C3CC3)no2)cn1] | 2-{[5-(3-{(1S)-1-[4-(2-aminopyrimidin-5-yl)phenyl]-1-cyclopropylethyl}-1,2,4-oxadiazol-5-yl)pyrazin-2-yl]amino}-2-methylpropan-1-ol |
| 58 | 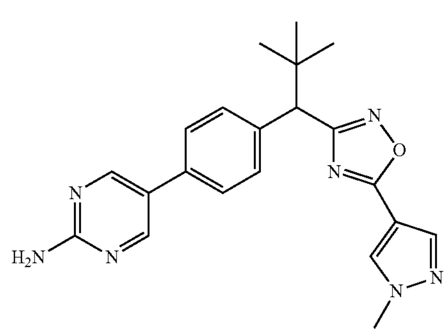 [SMILES: Cn1cc(-c2nc(C(c3ccc(-c4cnc(N)nc4)cc3)C(C)(C)C)no2)cn1] | 5-(4-{2,2-dimethyl-1-[5-(1-methyl-1H-pyrazol-4-yl)-1,2,4-oxadiazol-3-yl]propyl}phenyl)pyrimidin-2-amine |

TABLE 1-continued

| Example | Structure | Name |
|---|---|---|
| 59 | 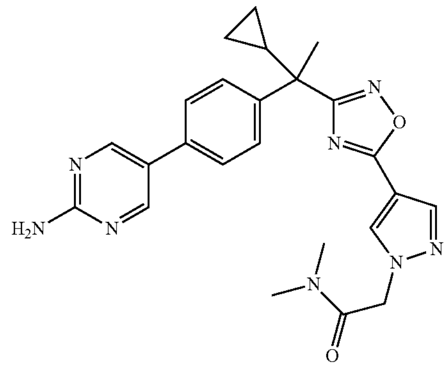 [SMILES: CN(C)C(=O)Cn1cc(-c2nc(C(C)(c3ccc(-c4cnc(N)nc4)cc3)C3CC3)no2)cn1] | 2-[4-(3-{1-[4-(2-aminopyrimidin-5-yl)phenyl]-1-cyclopropylethyl}-1,2,4-oxadiazol-5-yl)-1H-pyrazol-1-yl]-N,N-dimethylacetamide |
| 60 | 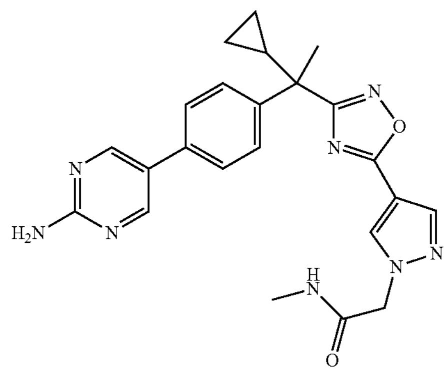 [SMILES: CNC(=O)Cn1cc(-c2nc(C(C)(c3ccc(-c4cnc(N)nc4)cc3)C3CC3)no2)cn1] | 2-[4-(3-{1-[4-(2-aminopyrimidin-5-yl)phenyl]-1-cyclopropylethyl}-1,2,4-oxadiazol-5-yl)-1H-pyrazol-1-yl]-N-methylacetamide |
| 61 | 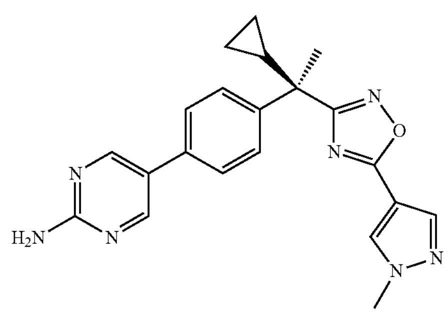 [SMILES: Cn1cc(-c2nc([C@@](C)(c3ccc(-c4cnc(N)nc4)cc3)C3CC3)no2)cn1] | 5-(4-{(1R)-1-cyclopropyl-1-[5-(1-methyl-1H-pyrazol-4-yl)-1,2,4-oxadiazol-3-yl]ethyl}phenyl)pyrimidin-2-amine |
| 62 | 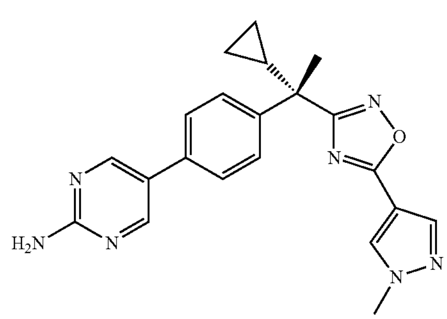 [SMILES: Cn1cc(-c2nc([C@](C)(c3ccc(-c4cnc(N)nc4)cc3)C3CC3)no2)cn1] | 5-(4-{(1S)-1-cyclopropyl-1-[5-(1-methyl-1H-pyrazol-4-yl)-1,2,4-oxadiazol-3-yl]ethyl}phenyl)pyrimidin-2-amine |

TABLE 1-continued

| Example | Structure | Name |
|---|---|---|
| 63 | 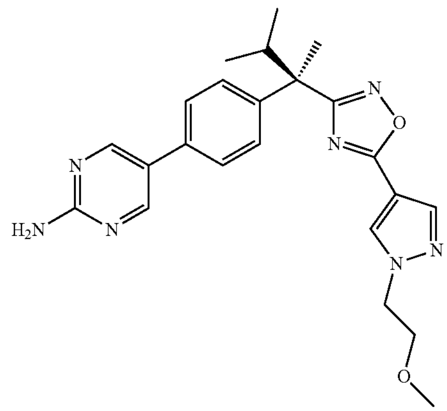 [SMILES: COCCn1cc(-c2nc([C@@](C)(c3ccc(-c4cnc(N)nc4)cc3)C(C)C)no2)cn1] | 5-{4-[(2R)-2-{5-[1-(2-methoxyethyl)-1H-pyrazol-4-yl]-1,2,4-oxadiazol-3-yl}-3-methylbutan-2-yl]phenyl}pyrimidin-2-amine |
| 64 | 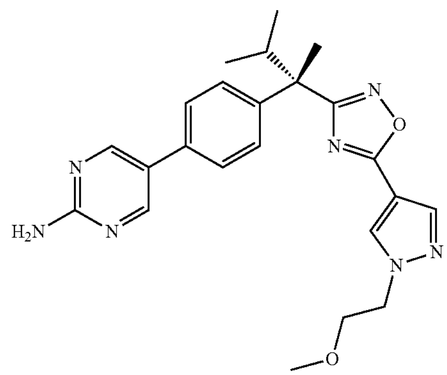 [SMILES: COCCn1cc(-c2nc([C@](C)(c3ccc(-c4cnc(N)nc4)cc3)C(C)C)no2)cn1] | 5-{4-[(2S)-2-{5-[1-(2-methoxyethyl)-1H-pyrazol-4-yl]-1,2,4-oxadiazol-3-yl}-3-methylbutan-2-yl]phenyl}pyrimidin-2-amine |
| 65 | 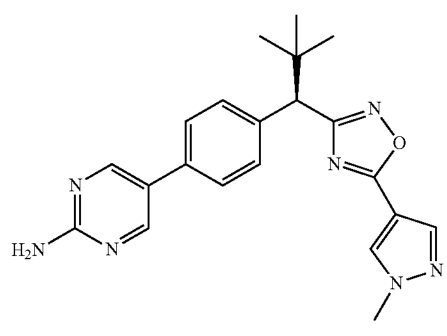 [SMILES: Cn1cc(-c2nc([C@@H](c3ccc(-c4cnc(N)nc4)cc3)C(C)(C)C)no2)cn1] | 5-(4-{(1R)-2,2-dimethyl-1-[5-(1-methyl-1H-pyrazol-4-yl)-1,2,4-oxadiazol-3-yl]propyl}phenyl)pyrimidin-2-amine |
| 66 | 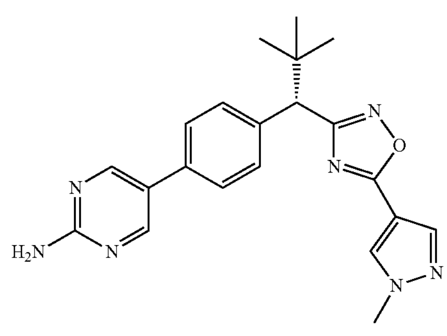 [SMILES: Cn1cc(-c2nc([C@H](c3ccc(-c4cnc(N)nc4)cc3)C(C)(C)C)no2)cn1] | 5-(4-{(1S)-2,2-dimethyl-1-[5-(1-methyl-1H-pyrazol-4-yl)-1,2,4-oxadiazol-3-yl]propyl}phenyl)pyrimidin-2-amine |

TABLE 1-continued
| Example | Structure | Name |
|---|---|---|
| 67 | 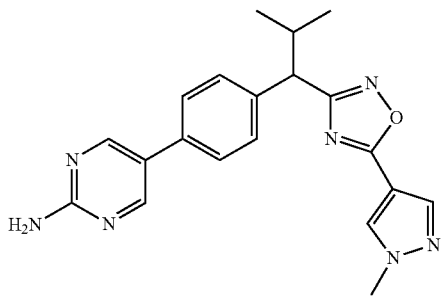 [SMILES: CC(C)C(c1ccc(-c2cnc(N)nc2)cc1)c1noc(-c2cnn(C)c2)n1] | 5-(4-{2-methyl-1-[5-(1-methyl-1H-pyrazol-4-yl)-1,2,4-oxadiazol-3-yl]propyl}phenyl)pyrimidin-2-amine |
| 68 | 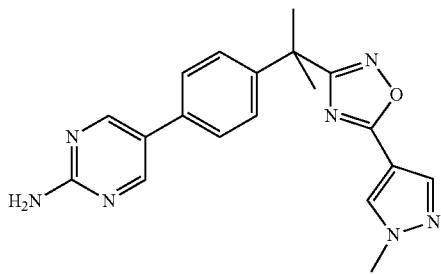 [SMILES: Cn1cc(-c2nc(C(C)(C)c3ccc(-c4cnc(N)nc4)cc3)no2)cn1] | 5-(4-{2-[5-(1-methyl-1H-pyrazol-4-yl)-1,2,4-oxadiazol-3-yl]propan-2-yl}phenyl)pyrimidin-2-amine |
| 69 | 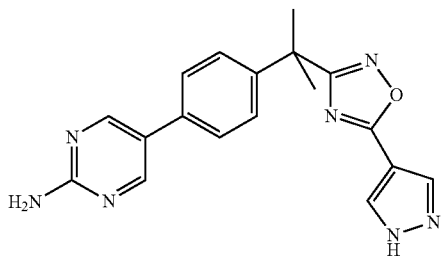 [SMILES: CC(C)(c1ccc(-c2cnc(N)nc2)cc1)c1noc(-c2cn[nH]c2)n1] | 5-(4-{2-[5-(1H-pyrazol-4-yl)-1,2,4-oxadiazol-3-yl]propan-2-yl}phenyl)pyrimidin-2-amine |
| 70 | 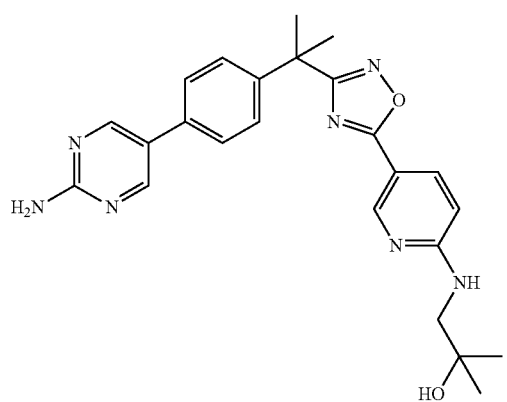 | 1-{[5-(3-{2-[4-(2-aminopyrimidin-5-yl)phenyl]propan-2-yl}-1,2,4-oxadiazol-5-yl)pyridin-2-yl]amino}-2-methylpropan-2-ol |

TABLE 1-continued

| Example | Structure | Name |
|---|---|---|
| 71 | 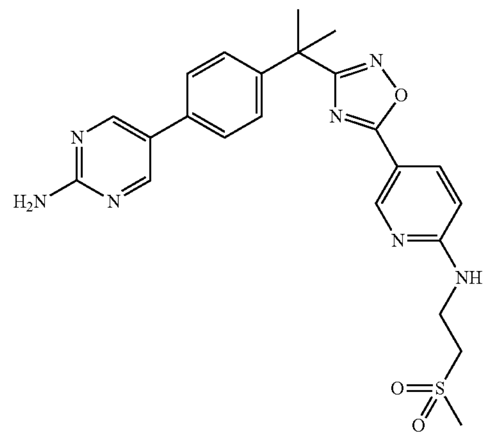 [SMILES: CC(C)(c1ccc(-c2cnc(N)nc2)cc1)c1noc(-c2ccc(NCCS(C)(=O)=O)nc2)n1] | 5-(4-{2-[5-(6-{[2-(methylsulfonyl)ethyl]amino}pyridin-3-yl)-1,2,4-oxadiazol-3-yl]propan-2-yl}phenyl)pyrimidin-2-amine |
| 72 | 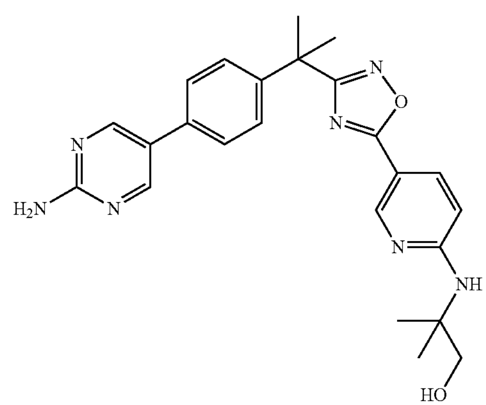 [SMILES: CC(C)(CO)Nc1ccc(-c2nc(C(C)(C)c3ccc(-c4cnc(N)nc4)cc3)no2)cn1] | 2-{[5-(3-{2-[4-(2-aminopyrimidin-5-yl)phenyl]propan-2-yl}-1,2,4-oxadiazol-5-yl)pyridin-2-yl]amino}-2-methylpropan-1-ol |
| 73 | 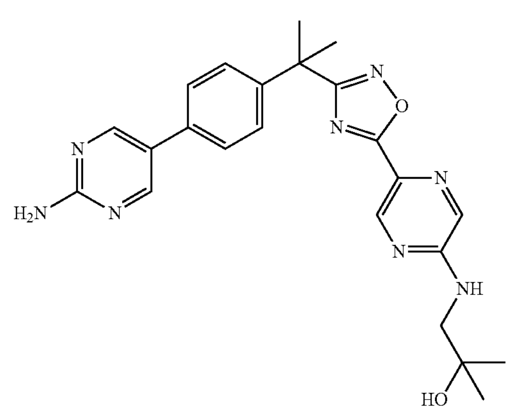 [SMILES: CC(C)(O)CNc1cnc(-c2nc(C(C)(C)c3ccc(-c4cnc(N)nc4)cc3)no2)cn1] | 1-{[5-(3-{2-[4-(2-aminopyrimidin-5-yl)phenyl]propan-2-yl}-1,2,4-oxadiazol-5-yl)pyrazin-2-yl]amino}-2-methylpropan-2-ol |

TABLE 1-continued

| Example | Structure | Name |
|---|---|---|
| 74 | 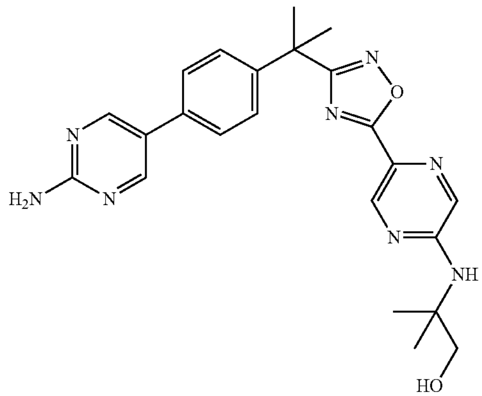 [SMILES: CC(C)(CO)Nc1cnc(-c2nc(C(C)(C)c3ccc(-c4cnc(N)nc4)cc3)no2)cn1] | 2-{[5-(3-{2-[4-(2-aminopyrimidin-5-yl)phenyl]propan-2-yl}-1,2,4-oxadiazol-5-yl)pyrazin-2-yl]amino}-2-methylpropan-1-ol |
| 75 | 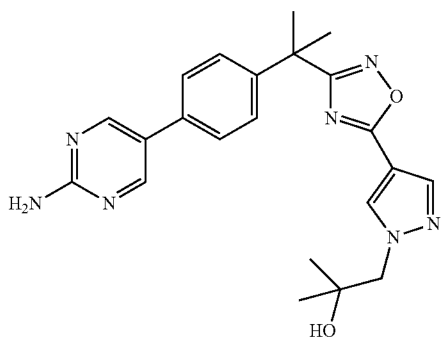 [SMILES: CC(C)(O)Cn1cc(-c2nc(C(C)(C)c3ccc(-c4cnc(N)nc4)cc3)no2)cn1] | 1-[4-(3-{2-[4-(2-aminopyrimidin-5-yl)phenyl]propan-2-yl}-1,2,4-oxadiazol-5-yl)-1H-pyrazol-1-yl]-2-methylpropan-2-ol |
| 76 | 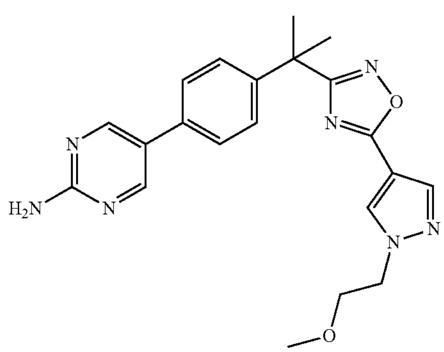 [SMILES: COCCn1cc(-c2nc(C(C)(C)c3ccc(-c4cnc(N)nc4)cc3)no2)cn1] | 5-[4-(2-{5-[1-(2-methoxyethyl)-1H-pyrazol-4-yl]-1,2,4-oxadiazol-3-yl}propan-2-yl)phenyl]pyrimidin-2-amine |
| 77 | 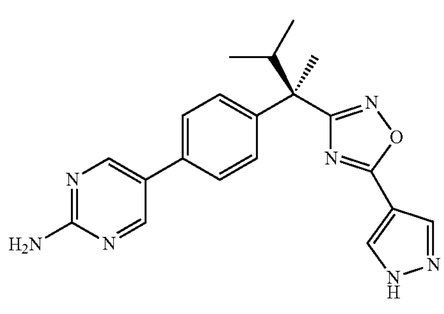 [SMILES: CC(C)[C@](C)(c1ccc(-c2cnc(N)nc2)cc1)c1noc(-c2cn[nH]c2)n1] | 5-(4-{(2R)-3-methyl-2-[5-(1H-pyrazol-4-yl)-1,2,4-oxadiazol-3-yl]butan-2-yl}phenyl)pyrimidin-2-amine |

TABLE 1-continued

| Example | Structure | Name |
|---|---|---|
| 78 | 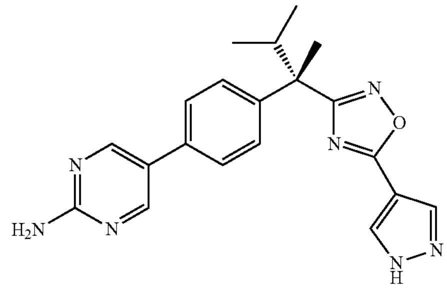 [SMILES: CC(C)[C@@](C)(c1ccc(-c2cnc(N)nc2)cc1)c1noc(-c2cn[nH]c2)n1] | 5-(4-{(2S)-3-methyl-2-[5-(1H-pyrazol-4-yl)-1,2,4-oxadiazol-3-yl]butan-2-yl}phenyl)pyrimidin-2-amine |
| 79 | 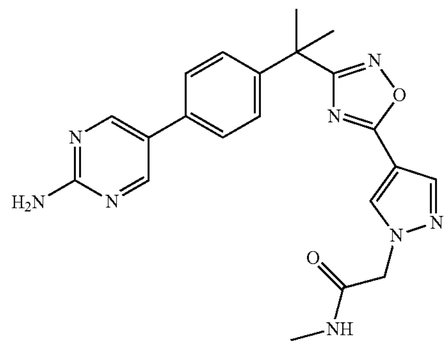 [SMILES: CNC(=O)Cn1cc(-c2nc(C(C)(C)c3ccc(-c4cnc(N)nc4)cc3)no2)cn1] | 2-[4-(3-{2-[4-(2-aminopyrimidin-5-yl)phenyl]propan-2-yl}-1,2,4-oxadiazol-5-yl)-1H-pyrazol-1-yl]-N-methylacetamide |
| 80 | 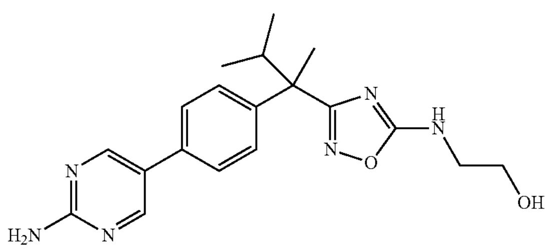 [SMILES: CC(C)C(C)(c1ccc(-c2cnc(N)nc2)cc1)c1noc(NCCO)n1] | 2-[(3-{2-[4-(2-aminopyrimidin-5-yl)phenyl]-3-methylbutan-2-yl}-1,2,4-oxadiazol-5-yl)amino]ethanol |
| 81 | 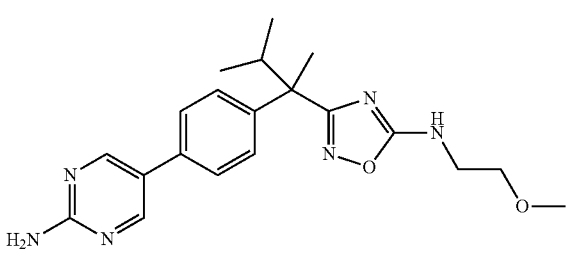 [SMILES: COCCNc1nc(C(C)(c2ccc(-c3cnc(N)nc3)cc2)C(C)C)no1] | 5-[4-(2-{5-[(2-methoxyethyl)amino]-1,2,4-oxadiazol-3-yl}-3-methylbutan-2-yl)phenyl]pyrimidin-2-amine |
| 82 | 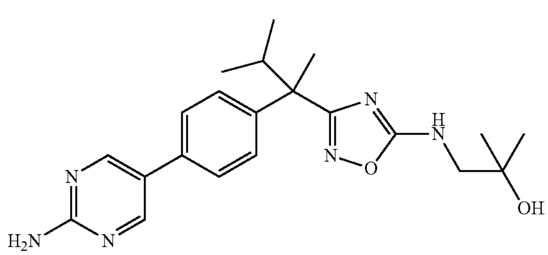 [SMILES: CC(C)C(C)(c1ccc(-c2cnc(N)nc2)cc1)c1noc(NCC(C)(C)O)n1] | 1-[(3-{2-[4-(2-aminopyrimidin-5-yl)phenyl]-3-methylbutan-2-yl}-1,2,4-oxadiazol-5-yl)amino]-2-methylpropan-2-ol |

TABLE 1-continued

| Example | Structure | Name |
|---|---|---|
| 83 | 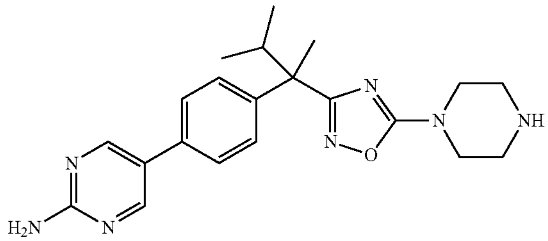 [SMILES: CC(C)C(C)(c1ccc(-c2cnc(N)nc2)cc1)c1noc(N2CCNCC2)n1] | 5-(4-{3-methyl-2-[5-(piperazin-1-yl)-1,2,4-oxadiazol-3-yl]butan-2-yl}phenyl)pyrimidin-2-amine |
| 84 | 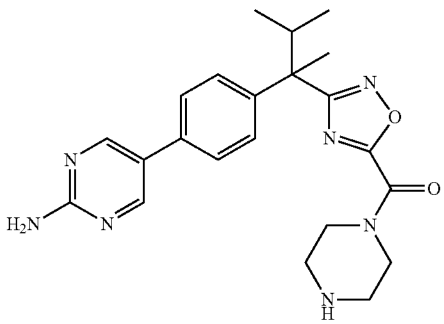 [SMILES: CC(C)C(C)(c1ccc(-c2cnc(N)nc2)cc1)c1noc(C(=O)N2CCNCC2)n1] | (3-{2-[4-(2-aminopyrimidin-5-yl)phenyl]-3-methylbutan-2-yl}-1,2,4-oxadiazol-5-yl)(piperazin-1-yl)methanone |
| 85 | 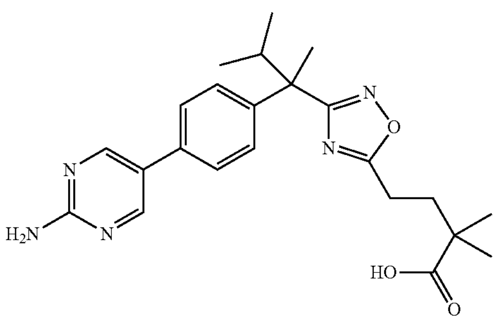 [SMILES: CC(C)C(C)(c1ccc(-c2cnc(N)nc2)cc1)c1noc(CCC(C)(C)C(=O)O)n1] | 4-(3-{2-[4-(2-aminopyrimidin-5-yl)phenyl]-3-methylbutan-2-yl}-1,2,4-oxadiazol-5-yl)-2,2-dimethylbutanoic acid |
| 86 | 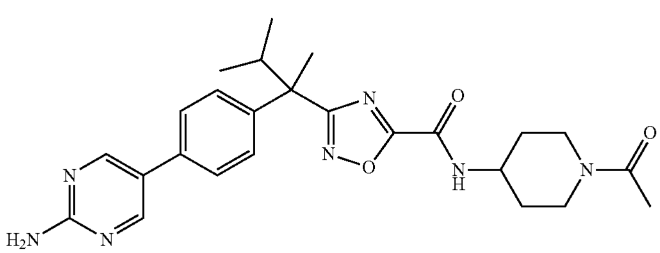 [SMILES: CC(=O)N1CCC(NC(=O)c2nc(C(C)(c3ccc(-c4cnc(N)nc4)cc3)C(C)C)no2)CC1] | N-(1-acetylpiperidin-4-yl)-3-{2-[4-(2-aminopyrimidin-5-yl)phenyl]-3-methylbutan-2-yl}-1,2,4-oxadiazole-5-carboxamide |
| 87 | 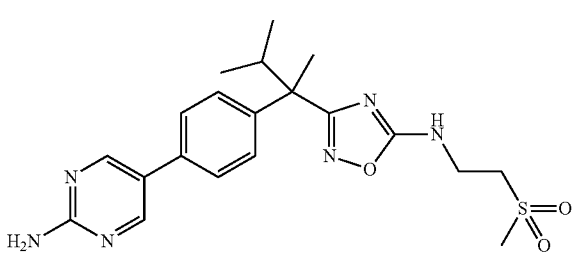 [SMILES: CC(C)C(C)(c1ccc(-c2cnc(N)nc2)cc1)c1noc(NCCS(C)(=O)=O)n1] | 5-{4-[3-methyl-2-(5-{[2-(methylsulfonyl)ethyl]amino}-1,2,4-oxadiazol-3-yl)butan-2-yl]phenyl}pyrimidin-2-amine |

TABLE 1-continued

| Example | Structure | Name |
|---|---|---|
| 88 | 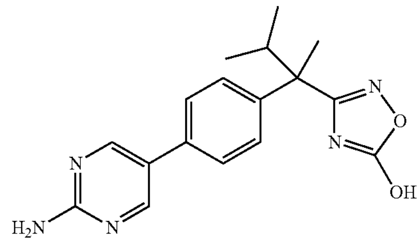 [SMILES: CC(C)C(C)(c1ccc(-c2cnc(N)nc2)cc1)c1noc(O)n1] | 3-{2-[4-(2-aminopyrimidin-5-yl)phenyl]-3-methylbutan-2-yl}-1,2,4-oxadiazol-5-ol |
| 89 | 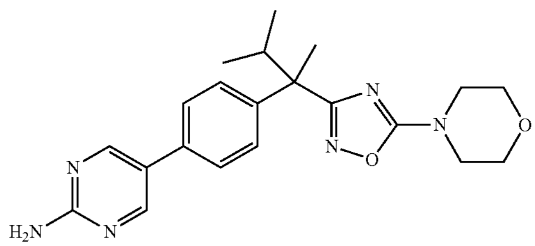 [SMILES: CC(C)C(C)(c1ccc(-c2cnc(N)nc2)cc1)c1noc(N2CCOCC2)n1] | 5-(4-{3-methyl-2-[5-(morpholin-4-yl)-1,2,4-oxadiazol-3-yl]butan-2-yl}phenyl)pyrimidin-2-amine |
| 90 | 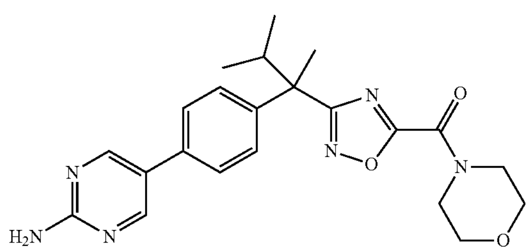 [SMILES: CC(C)C(C)(c1ccc(-c2cnc(N)nc2)cc1)c1noc(C(=O)N2CCOCC2)n1] | (3-{2-[4-(2-aminopyrimidin-5-yl)phenyl]-3-methylbutan-2-yl}-1,2,4-oxadiazol-5-yl)(morpholin-4-yl)methanone |
| 91 | 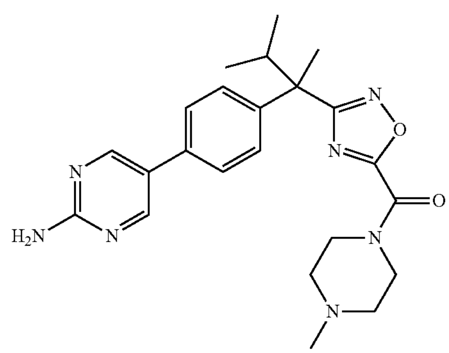 [SMILES: CC(C)C(C)(c1ccc(-c2cnc(N)nc2)cc1)c1noc(C(=O)N2CCN(C)CC2)n1] | (3-{2-[4-(2-aminopyrimidin-5-yl)phenyl]-3-methylbutan-2-yl}-1,2,4-oxadiazol-5-yl)(4-methylpiperazin-1-yl)methanone |
| 92 | 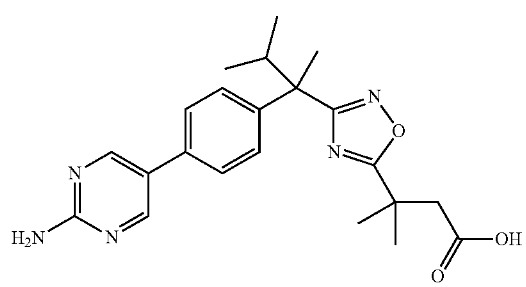 [SMILES: CC(C)C(C)(c1ccc(-c2cnc(N)nc2)cc1)c1noc(C(C)(C)CC(=O)O)n1] | 3-(3-{2-[4-(2-aminopyrimidin-5-yl)phenyl]-3-methylbutan-2-yl}-1,2,4-oxadiazol-5-yl)-3-methylbutanoic acid |

TABLE 1-continued

| Example | Structure | Name |
|---|---|---|
| 93 | 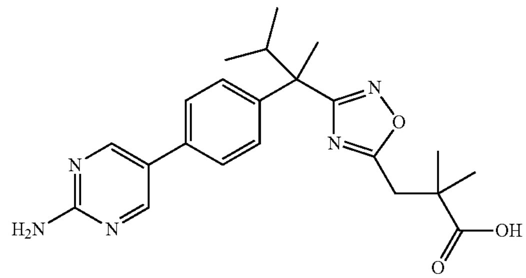 [SMILES: CC(C)C(C)(c1ccc(-c2cnc(N)nc2)cc1)c1noc(CC(C)(C)C(=O)O)n1] | 3-(3-{2-[4-(2-aminopyrimidin-5-yl)phenyl]-3-methylbutan-2-yl}-1,2,4-oxadiazol-5-yl)-2,2-dimethylpropanoic acid |
| 94 | 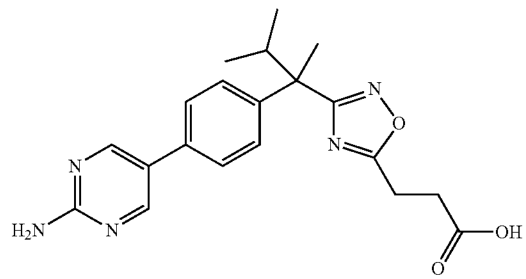 [SMILES: CC(C)C(C)(c1ccc(-c2cnc(N)nc2)cc1)c1noc(CCC(=O)O)n1] | 3-(3-{2-[4-(2-aminopyrimidin-5-yl)phenyl]-3-methylbutan-2-yl}-1,2,4-oxadiazol-5-yl)propanoic acid |
| 95 | 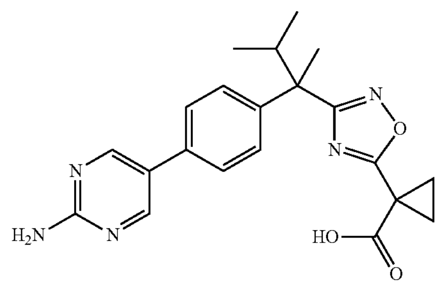 [SMILES: CC(C)C(C)(c1ccc(-c2cnc(N)nc2)cc1)c1noc(C2(C(=O)O)CC2)n1] | 1-(3-{2-[4-(2-aminopyrimidin-5-yl)phenyl]-3-methylbutan-2-yl}-1,2,4-oxadiazol-5-yl)cyclopropanecarboxylic acid |
| 96 | 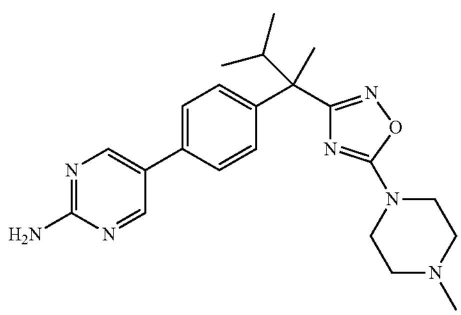 [SMILES: CC(C)C(C)(c1ccc(-c2cnc(N)nc2)cc1)c1noc(N2CCN(C)CC2)n1] | 5-(4-{3-methyl-2-[5-(4-methylpiperazin-1-yl)-1,2,4-oxadiazol-3-yl]butan-2-yl}phenyl)pyrimidin-2-amine |
| 97 | 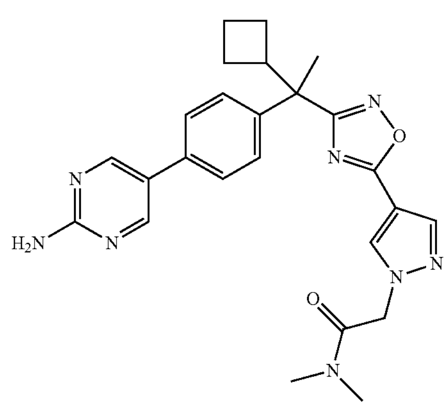 [SMILES: CN(C)C(=O)Cn1cc(-c2nc(C(C)(c3ccc(-c4cnc(N)nc4)cc3)C3CCC3)no2)cn1] | 2-[4-(3-{1-[4-(2-aminopyrimidin-5-yl)phenyl]-1-cyclobutylethyl}-1,2,4-oxadiazol-5-yl)-1H-pyrazol-1-yl]-N,N-dimethylacetamide |

TABLE 1-continued

| Example | Structure | Name |
|---|---|---|
| 98 | 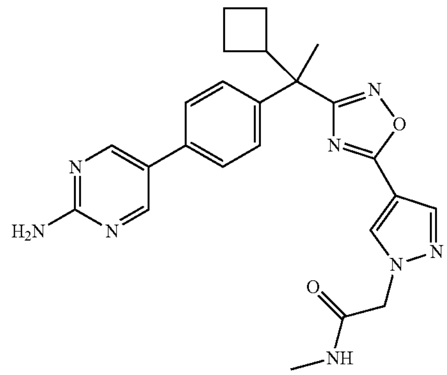 [SMILES: CNC(=O)Cn1cc(-c2nc(C(C)(c3ccc(-c4cnc(N)nc4)cc3)C3CCC3)no2)cn1] | 2-[4-(3-{1-[4-(2-aminopyrimidin-5-yl)phenyl]-1-cyclobutylethyl}-1,2,4-oxadiazol-5-yl)-1H-pyrazol-1-yl]-N-methylacetamide |
| 99 | 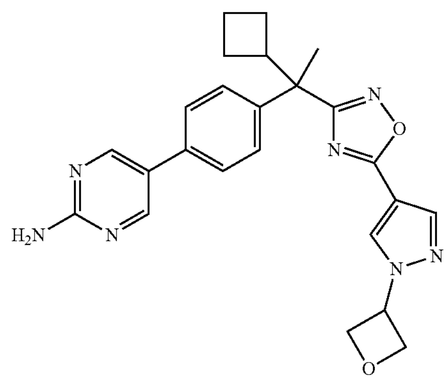 [SMILES: CC(c1ccc(-c2cnc(N)nc2)cc1)(c1noc(-c2cnn(C3COC3)c2)n1)C1CCC1] | 5-[4-(1-cyclobutyl-1-{5-[1-(oxetan-3-yl)-1H-pyrazol-4-yl]-1,2,4-oxadiazol-3-yl}ethyl)phenyl]pyrimidin-2-amine |
| 100 | 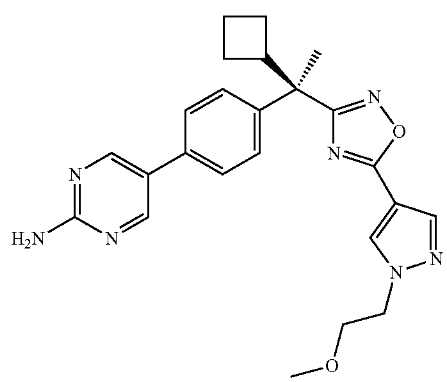 [SMILES: COCCn1cc(-c2nc([C@@](C)(c3ccc(-c4cnc(N)nc4)cc3)C3CCC3)no2)cn1] | 5-{4-[(1R)-1-cyclobutyl-1-{5-[1-(2-methoxyethyl)-1H-pyrazol-4-yl]-1,2,4-oxadiazol-3-yl}ethyl]phenyl}pyrimidin-2-amine |
| 101 | 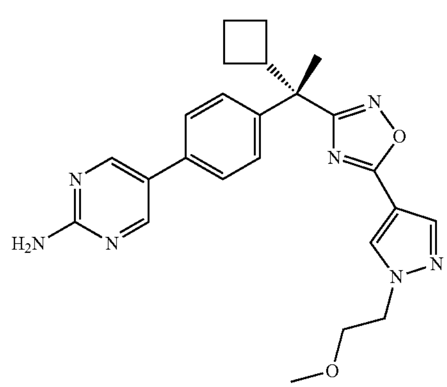 [SMILES: COCCn1cc(-c2nc([C@](C)(c3ccc(-c4cnc(N)nc4)cc3)C3CCC3)no2)cn1] | 5-{4-[(1S)-1-cyclobutyl-1-{5-[1-(2-methoxyethyl)-1H-pyrazol-4-yl]-1,2,4-oxadiazol-3-yl}ethyl]phenyl}pyrimidin-2-amine |

TABLE 1-continued

| Example | Structure | Name |
|---|---|---|
| 102 | 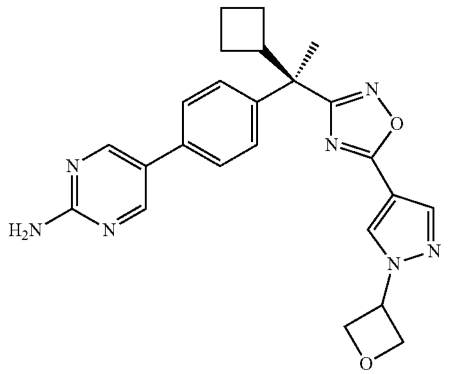 [SMILES: C[C@@](c1ccc(-c2cnc(N)nc2)cc1)(c1noc(-c2cnn(C3COC3)c2)n1)C1CCC1] | 5-{4-[(1R)-1-cyclobutyl-1-{5-[1-(oxetan-3-yl)-1H-pyrazol-4-yl]-1,2,4-oxadiazol-3-yl}ethyl]phenyl}pyrimidin-2-amine |
| 103 | 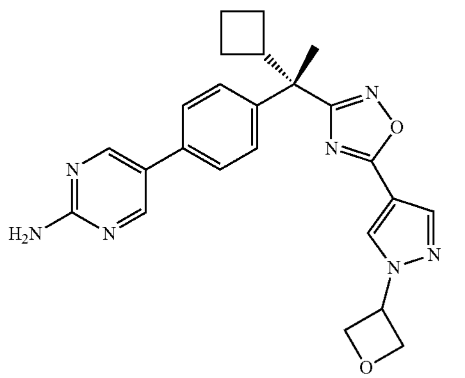 [SMILES: C[C@](c1ccc(-c2cnc(N)nc2)cc1)(c1noc(-c2cnn(C3COC3)c2)n1)C1CCC1] | 5-{4-[(1S)-1-cyclobutyl-1-{5-[1-(oxetan-3-yl)-1H-pyrazol-4-yl]-1,2,4-oxadiazol-3-yl}ethyl]phenyl}pyrimidin-2-amine |
| 104 | 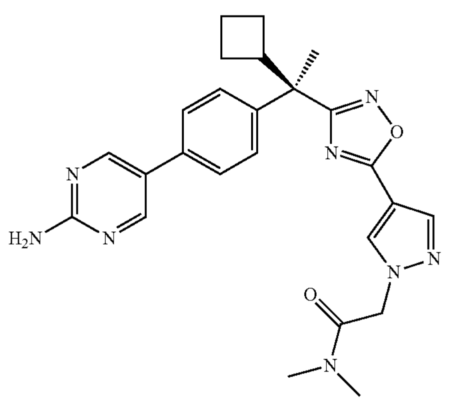 [SMILES: CN(C)C(=O)Cn1cc(-c2nc([C@@](C)(c3ccc(-c4cnc(N)nc4)cc3)C3CCC3)no2)cn1] | 2-[4-(3-{(1R)-1-[4-(2-aminopyrimidin-5-yl)phenyl]-1-cyclobutylethyl}-1,2,4-oxadiazol-5-yl)-1H-pyrazol-1-yl]-N,N-dimethylacetamide |
| 105 | 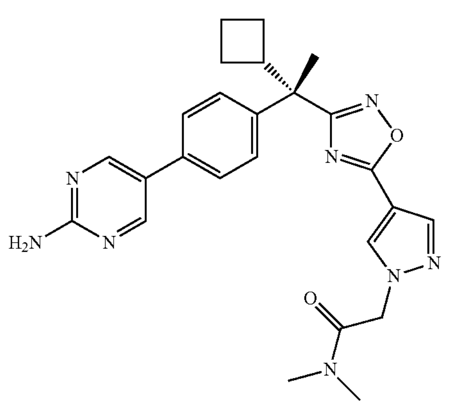 [SMILES: CN(C)C(=O)Cn1cc(-c2nc([C@](C)(c3ccc(-c4cnc(N)nc4)cc3)C3CCC3)no2)cn1] | 2-[4-(3-{(1S)-1-[4-(2-aminopyrimidin-5-yl)phenyl]-1-cyclobutylethyl}-1,2,4-oxadiazol-5-yl)-1H-pyrazol-1-yl]-N,N-dimethylacetamide |

TABLE 1-continued

| Example | Structure | Name |
|---|---|---|
| 106 | 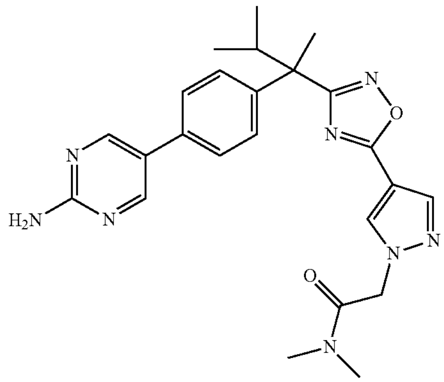 [SMILES: CC(C)C(C)(c1ccc(-c2cnc(N)nc2)cc1)c1noc(-c2cnn(CC(=O)N(C)C)c2)n1] | 2-[4-(3-{2-[4-(2-aminopyrimidin-5-yl)phenyl]-3-methylbutan-2-yl}-1,2,4-oxadiazol-5-yl)-1H-pyrazol-1-yl]-N,N-dimethylacetamide |
| 107 | 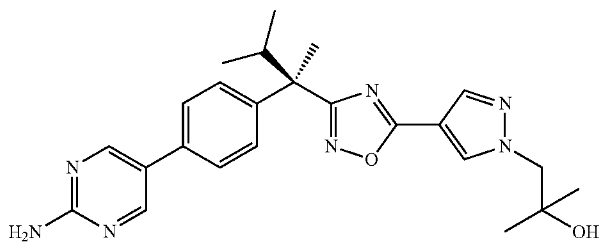 | 1-[4-(3-{(2R)-2-[4-(2-aminopyrimidin-5-yl)phenyl]-3-methylbutan-2-yl}-1,2,4-oxadiazol-5-yl)-1H-pyrazol-1-yl]-2-methylpropan-2-ol |
| 108 | 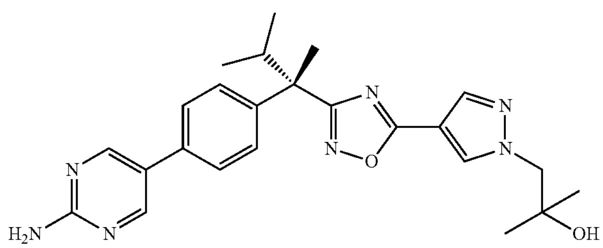 [SMILES: CC(C)[C@@](C)(c1ccc(-c2cnc(N)nc2)cc1)c1noc(-c2cnn(CC(C)(C)O)c2)n1] | 1-[4-(3-{(2S)-2-[4-(2-aminopyrimidin-5-yl)phenyl]-3-methylbutan-2-yl}-1,2,4-oxadiazol-5-yl)-1H-pyrazol-1-yl]-2-methylpropan-2-ol |
| 109 | 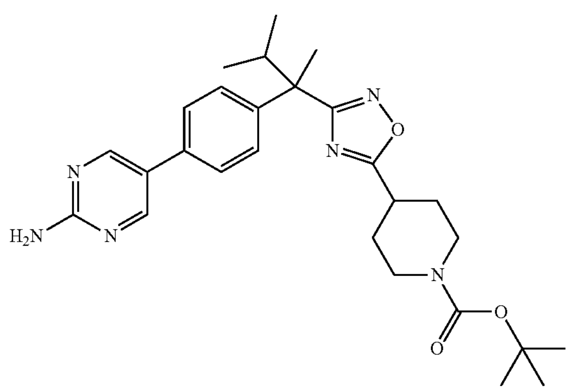 [SMILES: CC(C)C(C)(c1ccc(-c2cnc(N)nc2)cc1)c1noc(C2CCN(C(=O)OC(C)(C)C)CC2)n1] | tert-butyl 4-(3-{2-[4-(2-aminopyrimidin-5-yl)phenyl]-3-methylbutan-2-yl}-1,2,4-oxadiazol-5-yl)piperidine-1-carboxylate |
| 110 | 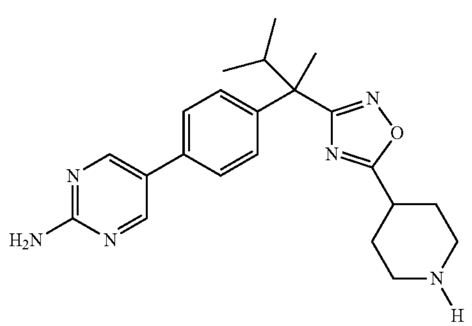 [SMILES: CC(C)C(C)(c1ccc(-c2cnc(N)nc2)cc1)c1noc(C2CCNCC2)n1] | 5-(4-{3-methyl-2-[5-(piperidin-4-yl)-1,2,4-oxadiazol-3-yl]butan-2-yl}phenyl)pyrimidin-2-amine |

TABLE 1-continued

| Example | Structure | Name |
| --- | --- | --- |
| 111 | 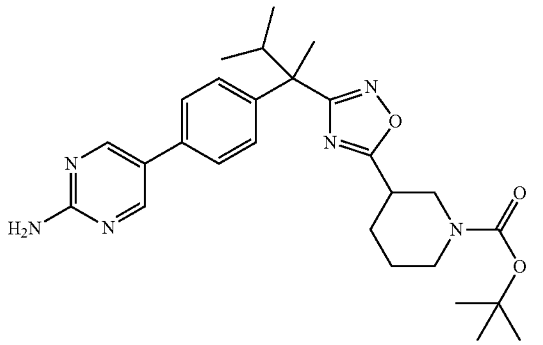 [SMILES: CC(C)C(C)(c1ccc(-c2cnc(N)nc2)cc1)c1noc(C2CCCN(C(=O)OC(C)(C)C)C2)n1] | tert-butyl 3-(3-{2-[4-(2-aminopyrimidin-5-yl)phenyl]-3-methylbutan-2-yl}-1,2,4-oxadiazol-5-yl)piperidine-1-carboxylate |
| 112 | 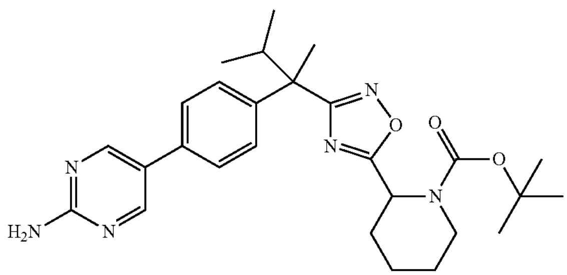 [SMILES: CC(C)C(C)(c1ccc(-c2cnc(N)nc2)cc1)c1noc(C2CCCCN2C(=O)OC(C)(C)C)n1] | tert-butyl 2-(3-{2-[4-(2-aminopyrimidin-5-yl)phenyl]-3-methylbutan-2-yl}-1,2,4-oxadiazol-5-yl)piperidine-1-carboxylate |
| 113 | 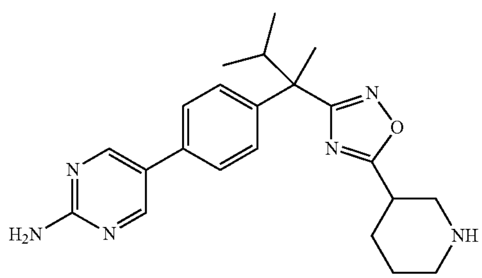 [SMILES: CC(C)C(C)(c1ccc(-c2cnc(N)nc2)cc1)c1noc(C2CCCNC2)n1] | 5-(4-{3-methyl-2-[5-(piperidin-3-yl)-1,2,4-oxadiazol-3-yl]butan-2-yl}phenyl)pyrimidin-2-amine |
| 114 | 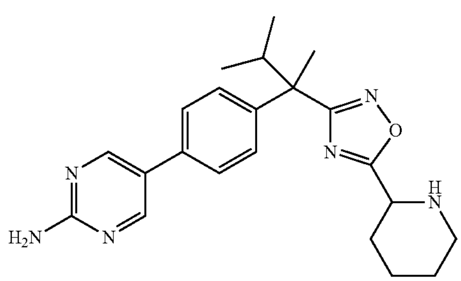 [SMILES: CC(C)C(C)(c1ccc(-c2cnc(N)nc2)cc1)c1noc(C2CCCCN2)n1] | 5-(4-{3-methyl-2-[5-(piperidin-2-yl)-1,2,4-oxadiazol-3-yl]butan-2-yl}phenyl)pyrimidin-2-amine |
| 115 | 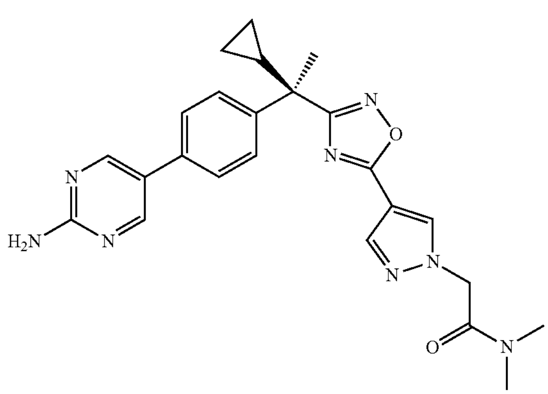 [SMILES: CN(C)C(=O)Cn1cc(-c2nc([C@@](C)(c3ccc(-c4cnc(N)nc4)cc3)C3CC3)no2)cn1] | 2-[4-(3-{(1R)-1-[4-(2-aminopyrimidin-5-yl)phenyl]-1-cyclopropylethyl}-1,2,4-oxadiazol-5-yl)-1H-pyrazol-1-yl]-N,N-dimethylacetamide |

TABLE 1-continued

| Example | Structure | Name |
|---|---|---|
| 116 | 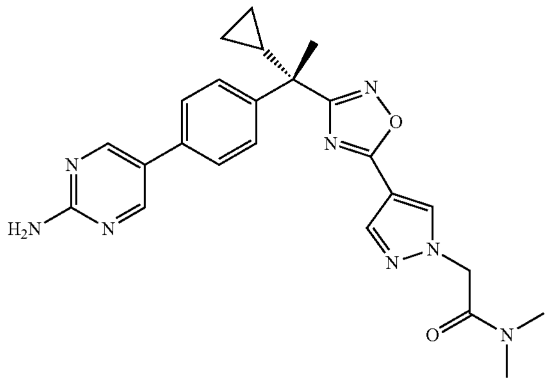 [SMILES: CN(C)C(=O)Cn1cc(-c2nc([C@](C)(c3ccc(-c4cnc(N)nc4)cc3)C3CC3)no2)cn1] | 2-[4-(3-{(1S)-1-[4-(2-aminopyrimidin-5-yl)phenyl]-1-cyclopropylethyl}-1,2,4-oxadiazol-5-yl)-1H-pyrazol-1-yl]-N,N-dimethylacetamide |
| 117 | 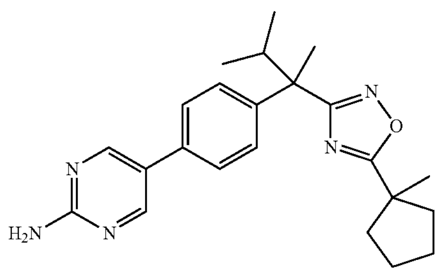 [SMILES: CC(C)C(C)(c1ccc(-c2cnc(N)nc2)cc1)c1noc(C2(C)CCCC2)n1] | 5-(4-{3-methyl-2-[5-(1-methylcyclopentyl)-1,2,4-oxadiazol-3-yl]butan-2-yl}phenyl)pyrimidin-2-amine |
| 118 | 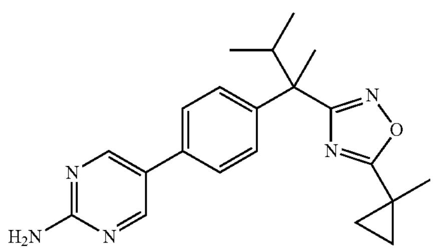 [SMILES: CC(C)C(C)(c1ccc(-c2cnc(N)nc2)cc1)c1noc(C2(C)CC2)n1] | 5-(4-{3-methyl-2-[5-(1-methylcyclopropyl)-1,2,4-oxadiazol-3-yl]butan-2-yl}phenyl)pyrimidin-2-amine |
| 119 | 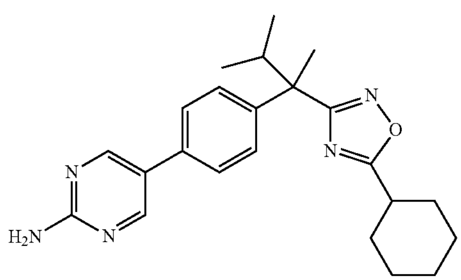 [SMILES: CC(C)C(C)(c1ccc(-c2cnc(N)nc2)cc1)c1noc(C2CCCCC2)n1] | 5-{4-[2-(5-cyclohexyl-1,2,4-oxadiazol-3-yl)-3-methylbutan-2-yl]phenyl}pyrimidin-2-amine |
| 120 | 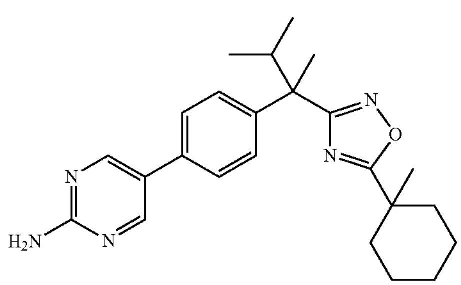 [SMILES: CC(C)C(C)(c1ccc(-c2cnc(N)nc2)cc1)c1noc(C2(C)CCCCC2)n1] | 5-(4-{3-methyl-2-[5-(1-methylcyclohexyl)-1,2,4-oxadiazol-3-yl]butan-2-yl}phenyl)pyrimidin-2-amine |

TABLE 1-continued

| Example | Structure | Name |
|---|---|---|
| 121 | 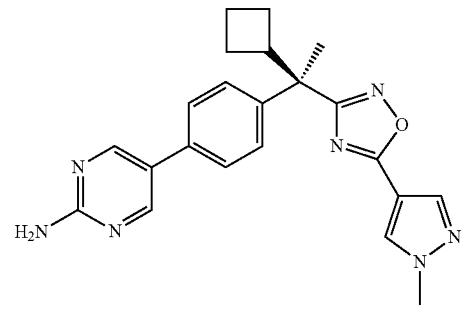 [SMILES: Cn1cc(-c2nc([C@@](C)(c3ccc(-c4cnc(N)nc4)cc3)C3CCC3)no2)cn1] | 5-(4-{(1R)-1-cyclobutyl-1-[5-(1-methyl-1H-pyrazol-4-yl)-1,2,4-oxadiazol-3-yl]ethyl}phenyl)pyrimidin-2-amine |
| 122 | 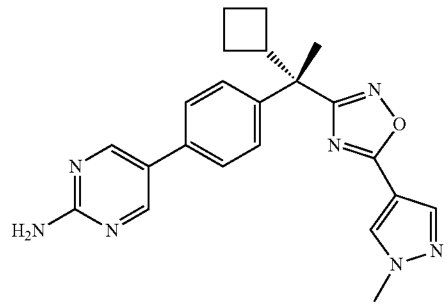 [SMILES: Cn1cc(-c2nc([C@](C)(c3ccc(-c4cnc(N)nc4)cc3)C3CCC3)no2)cn1] | 5-(4-{(1S)-1-cyclobutyl-1-[5-(1-methyl-1H-pyrazol-4-yl)-1,2,4-oxadiazol-3-yl]ethyl}phenyl)pyrimidin-2-amine |
| 123 | 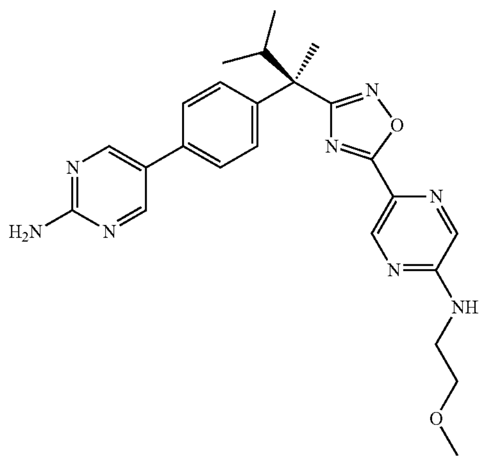 [SMILES: COCCNc1cnc(-c2nc([C@@](C)(c3ccc(-c4cnc(N)nc4)cc3)C(C)C)no2)cn1] | 5-{4-[(2R)-2-(5-{5-[(2-methoxyethyl)amino]pyrazin-2-yl}-1,2,4-oxadiazol-3-yl)-3-methylbutan-2-yl]phenyl}pyrimidin-2-amine |
| 124 | 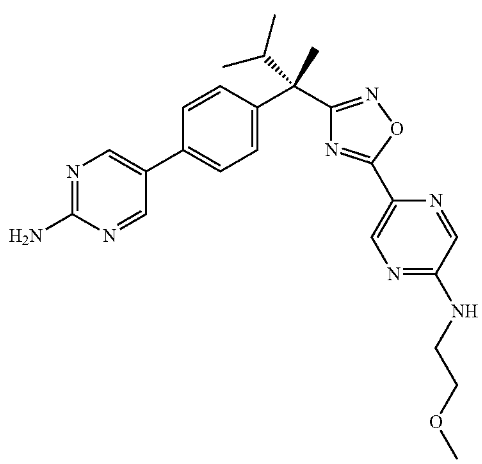 [SMILES: COCCNc1cnc(-c2nc([C@](C)(c3ccc(-c4cnc(N)nc4)cc3)C(C)C)no2)cn1] | 5-{4-[(2S)-2-(5-{5-[(2-methoxyethyl)amino]pyrazin-2-yl}-1,2,4-oxadiazol-3-yl)-3-methylbutan-2-yl]phenyl}pyrimidin-2-amine |

TABLE 1-continued

| Example | Structure | Name |
|---|---|---|
| 125 | 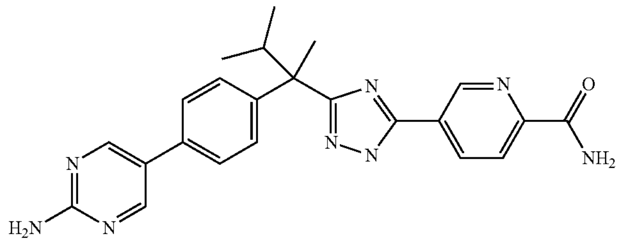 [SMILES: CC(C)C(C)(c1ccc(-c2cnc(N)nc2)cc1)c1n[nH]c(-c2ccc(C(N)=O)nc2)n1] | 5-(3-{2-[4-(2-aminopyrimidin-5-yl)phenyl]-3-methylbutan-2-yl}-1,2,4-oxadiazol-5-yl)pyridine-2-carboxamide |
| 126 | 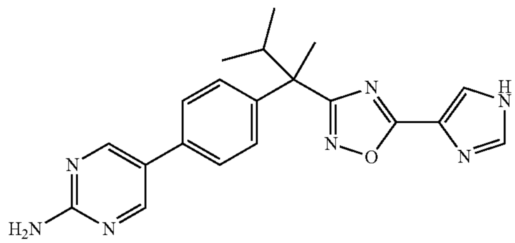 [SMILES: CC(C)C(C)(c1ccc(-c2cnc(N)nc2)cc1)c1noc(-c2c[nH]cn2)n1] | 5-(4-{2-[5-(1H-imidazol-4-yl)-1,2,4-oxadiazol-3-yl]-3-methylbutan-2-yl}phenyl)pyrimidin-2-amine |
| 127 | 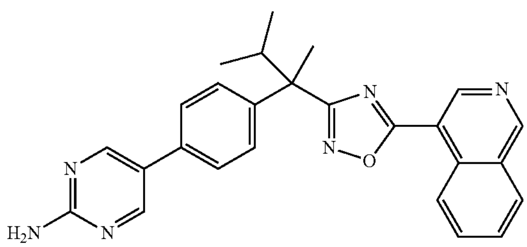 [SMILES: CC(C)C(C)(c1ccc(-c2cnc(N)nc2)cc1)c1noc(-c2cncc3ccccc23)n1] | 5-(4-{2-[5-(isoquinolin-4-yl)-1,2,4-oxadiazol-3-yl]-3-methylbutan-2-yl}phenyl)pyrimidin-2-amine |
| 128 | 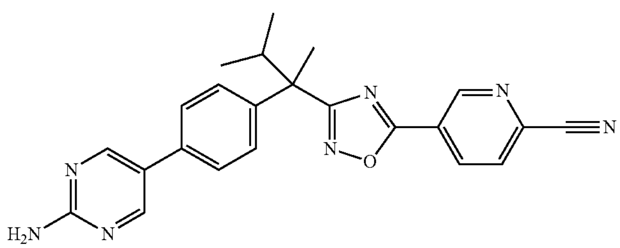 [SMILES: CC(C)C(C)(c1ccc(-c2cnc(N)nc2)cc1)c1noc(-c2ccc(C#N)nc2)n1] | 5-(3-{2-[4-(2-aminopyrimidin-5-yl)phenyl]-3-methylbutan-2-yl}-1,2,4-oxadiazol-5-yl)pyridine-2-carbonitrile |
| 129 | 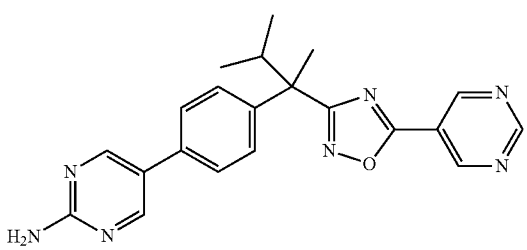 [SMILES: CC(C)C(C)(c1ccc(-c2cnc(N)nc2)cc1)c1noc(-c2cncnc2)n1] | 5-(4-{3-methyl-2-[5-(pyrimidin-5-yl)-1,2,4-oxadiazol-3-yl]butan-2-yl}phenyl)pyrimidin-2-amine |
| 130 | 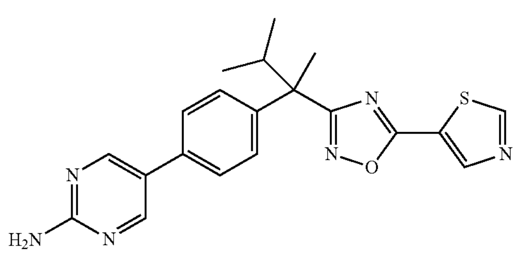 | 5-(4-{3-methyl-2-[5-(1,3-thiazol-5-yl)-1,2,4-oxadiazol-3-yl]butan-2-yl}phenyl)pyrimidin-2-amine |

TABLE 1-continued

| Example | Structure | Name |
|---|---|---|
| 131 | 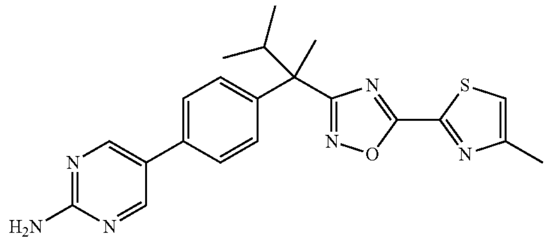 [SMILES: Cc1csc(-c2nc(C(C)(c3ccc(-c4cnc(N)nc4)cc3)C(C)C)no2)n1] | 5-(4-{3-methyl-2-[5-(4-methyl-1,3-thiazol-2-yl)-1,2,4-oxadiazol-3-yl]butan-2-yl}phenyl)pyrimidin-2-amine |
| 132 | 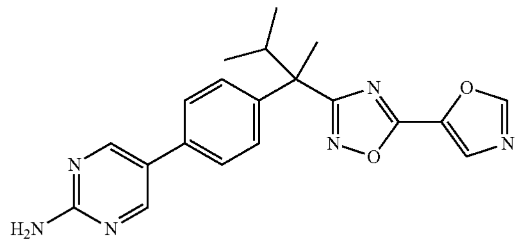 [SMILES: CC(C)C(C)(c1ccc(-c2cnc(N)nc2)cc1)c1noc(-c2cnco2)n1] | 5-(4-{3-methyl-2-[5-(1,3-oxazol-5-yl)-1,2,4-oxadiazol-3-yl]butan-2-yl}phenyl)pyrimidin-2-amine |
| 133 | 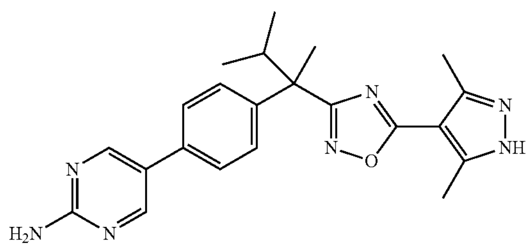 [SMILES: Cc1n[nH]c(C)c1-c1nc(C(C)(c2ccc(-c3cnc(N)nc3)cc2)C(C)C)no1] | 5-(4-{2-[5-(3,5-dimethyl-1H-pyrazol-4-yl)-1,2,4-oxadiazol-3-yl]-3-methylbutan-2-yl}phenyl)pyrimidin-2-amine |
| 134 | 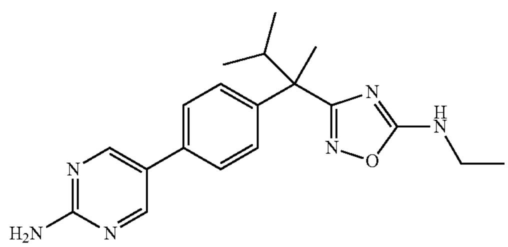 [SMILES: CCNc1nc(C(C)(c2ccc(-c3cnc(N)nc3)cc2)C(C)C)no1] | 5-(4-{2-[5-(ethylamino)-1,2,4-oxadiazol-3-yl]-3-methylbutan-2-yl}phenyl)pyrimidin-2-amine |
| 135 | 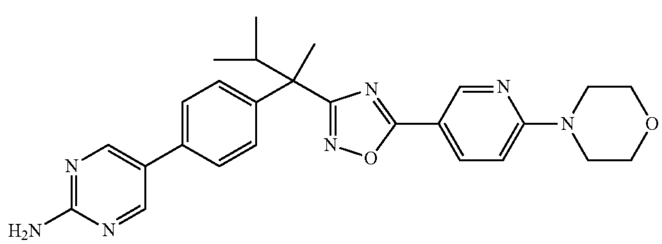 [SMILES: CC(C)C(C)(c1ccc(-c2cnc(N)nc2)cc1)c1noc(-c2ccc(N3CCOCC3)nc2)n1] | 5-[4-(3-methyl-2-{5-[6-(morpholin-4-yl)pyridin-3-yl]-1,2,4-oxadiazol-3-yl}butan-2-yl)phenyl]pyrimidin-2-amine |
| 136 | 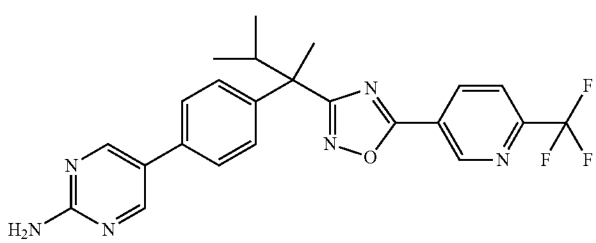 [SMILES: CC(C)C(C)(c1ccc(-c2cnc(N)nc2)cc1)c1noc(-c2ccc(C(F)(F)F)nc2)n1] | 5-[4-(3-methyl-2-{5-[6-(trifluoromethyl)pyridin-3-yl]-1,2,4-oxadiazol-3-yl}butan-2-yl)phenyl]pyrimidin-2-amine |

TABLE 1-continued

| Example | Structure | Name |
|---|---|---|
| 137 | 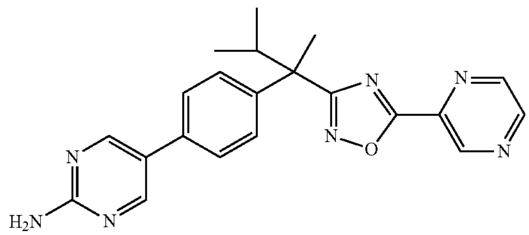 [SMILES: CC(C)C(C)(c1ccc(-c2cnc(N)nc2)cc1)c1noc(-c2cnccn2)n1] | 5-(4-{3-methyl-2-[5-(pyrazin-2-yl)-1,2,4-oxadiazol-3-yl]butan-2-yl}phenyl)pyrimidin-2-amine |
| 138 | 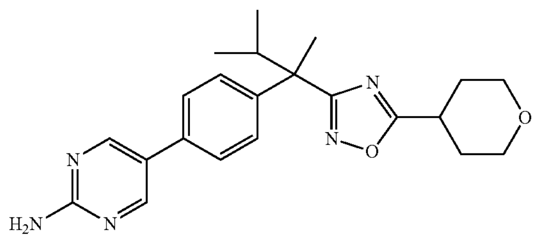 [SMILES: CC(C)C(C)(c1ccc(-c2cnc(N)nc2)cc1)c1noc(C2CCOCC2)n1] | 5-(4-{3-methyl-2-[5-(tetrahydro-2H-pyran-4-yl)-1,2,4-oxadiazol-3-yl]butan-2-yl}phenyl)pyrimidin-2-amine |
| 139 | 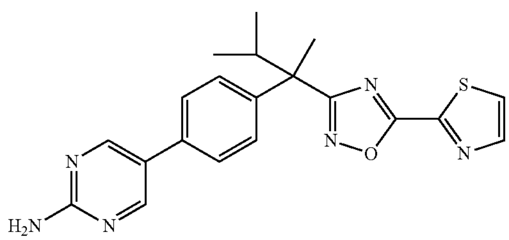 [SMILES: CC(C)C(C)(c1ccc(-c2cnc(N)nc2)cc1)c1noc(-c2nccs2)n1] | 5-(4-{3-methyl-2-[5-(1,3-thiazol-2-yl)-1,2,4-oxadiazol-3-yl]butan-2-yl}phenyl)pyrimidin-2-amine |
| 140 | 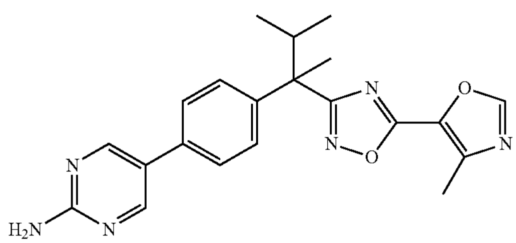 [SMILES: Cc1ncoc1-c1nc(C(C)(c2ccc(-c3cnc(N)nc3)cc2)C(C)C)no1] | 5-(4-{3-methyl-2-[5-(4-methyl-1,3-oxazol-5-yl)-1,2,4-oxadiazol-3-yl]butan-2-yl}phenyl)pyrimidin-2-amine |
| 141 | 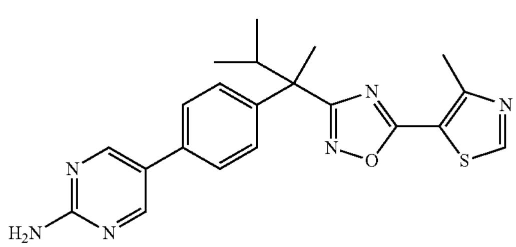 [SMILES: Cc1ncsc1-c1nc(C(C)(c2ccc(-c3cnc(N)nc3)cc2)C(C)C)no1] | 5-(4-{3-methyl-2-[5-(4-methyl-1,3-thiazol-5-yl)-1,2,4-oxadiazol-3-yl]butan-2-yl}phenyl)pyrimidin-2-amine |
| 142 | 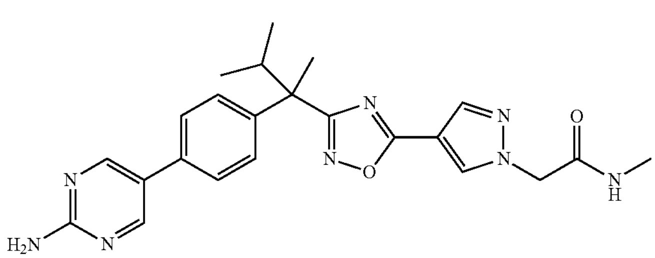 [SMILES: CNC(=O)Cn1cc(-c2nc(C(C)(c3ccc(-c4cnc(N)nc4)cc3)C(C)C)no2)cn1] | 2-[4-(3-{2-[4-(2-aminopyrimidin-5-yl)phenyl]-3-methylbutan-2-yl}-1,2,4-oxadiazol-5-yl)-1H-pyrazol-1-yl]-N-methylacetamide |

TABLE 1-continued

| Example | Structure | Name |
|---|---|---|
| 143 | 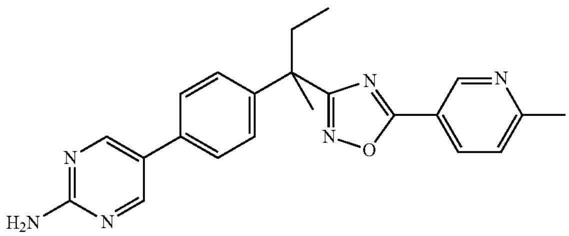 [SMILES: CCC(C)(c1ccc(-c2cnc(N)nc2)cc1)c1noc(-c2ccc(C)nc2)n1] | 5-(4-{2-[5-(6-methylpyridin-3-yl)-1,2,4-oxadiazol-3-yl]butan-2-yl}phenyl)pyrimidin-2-amine |
| 144 | 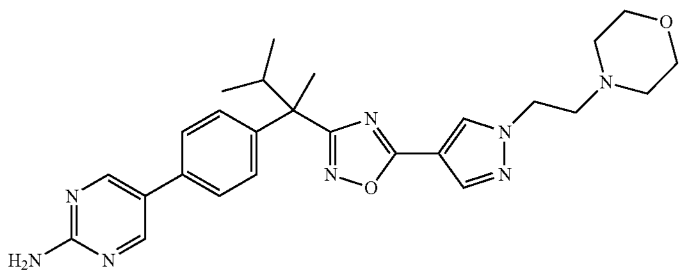 [SMILES: CC(C)C(C)(c1ccc(-c2cnc(N)nc2)cc1)c1noc(-c2cnn(CCN3CCOCC3)c2)n1] | 5-{4-[3-methyl-2-(5-{1-[2-(morpholin-4-yl)ethyl]-1H-pyrazol-4-yl}-1,2,4-oxadiazol-3-yl)butan-2-yl]phenyl}pyrimidin-2-amine |
| 145 | 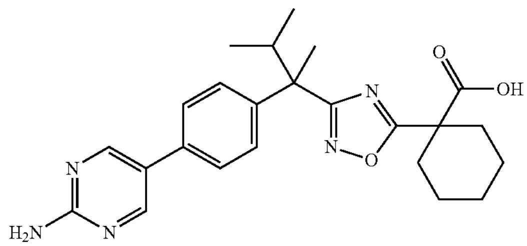 [SMILES: CC(C)C(C)(c1ccc(-c2cnc(N)nc2)cc1)c1noc(C2(C(=O)O)CCCCC2)n1] | 1-(3-{2-[4-(2-aminopyrimidin-5-yl)phenyl]-3-methylbutan-2-yl}-1,2,4-oxadiazol-5-yl)cyclohexanecarboxylic acid |
| 146 | 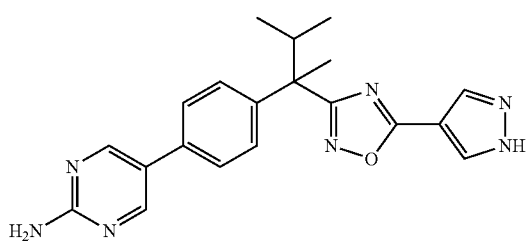 [SMILES: CC(C)C(C)(c1ccc(-c2cnc(N)nc2)cc1)c1noc(-c2cn[nH]c2)n1] | 5-(4-{3-methyl-2-[5-(1H-pyrazol-4-yl)-1,2,4-oxadiazol-3-yl]butan-2-yl}phenyl)pyrimidin-2-amine |
| 147 | 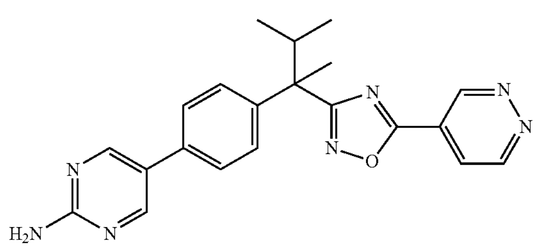 [SMILES: CC(C)C(C)(c1ccc(-c2cnc(N)nc2)cc1)c1noc(-c2ccnnc2)n1] | 5-(4-{3-methyl-2-[5-(pyridazin-4-yl)-1,2,4-oxadiazol-3-yl]butan-2-yl}phenyl)pyrimidin-2-amine |
| 148 | 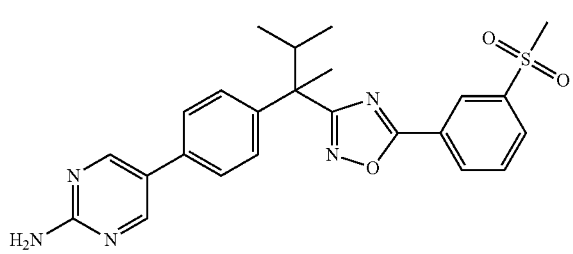 [SMILES: CC(C)C(C)(c1ccc(-c2cnc(N)nc2)cc1)c1noc(-c2cccc(S(C)(=O)=O)c2)n1] | 5-[4-(3-methyl-2-{5-[3-(methylsulfonyl)phenyl]-1,2,4-oxadiazol-3-yl}butan-2-yl)phenyl]pyrimidin-2-amine |

TABLE 1-continued

| Example | Structure | Name |
|---|---|---|
| 149 | 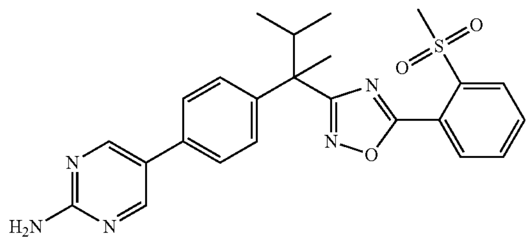 [SMILES: CC(C)C(C)(c1ccc(-c2cnc(N)nc2)cc1)c1noc(-c2ccccc2S(C)(=O)=O)n1] | 5-[4-(3-methyl-2-{5-[2-(methylsulfonyl)phenyl]-1,2,4-oxadiazol-3-yl}butan-2-yl)phenyl]pyrimidin-2-amine |
| 150 | 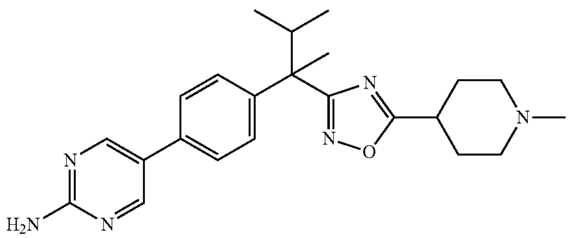 [SMILES: CC(C)C(C)(c1ccc(-c2cnc(N)nc2)cc1)c1noc(C2CCN(C)CC2)n1] | 5-(4-{3-methyl-2-[5-(1-methylpiperidin-4-yl)-1,2,4-oxadiazol-3-yl]butan-2-yl}phenyl)pyrimidin-2-amine |
| 151 | 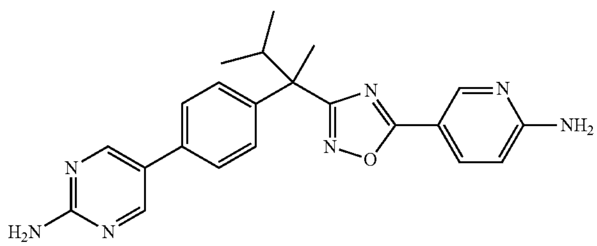 [SMILES: CC(C)C(C)(c1ccc(-c2cnc(N)nc2)cc1)c1noc(-c2ccc(N)nc2)n1] | 5-(4-{2-[5-(6-aminopyridin-3-yl)-1,2,4-oxadiazol-3-yl]-3-methylbutan-2-yl}phenyl)pyrimidin-2-amine |
| 152 | 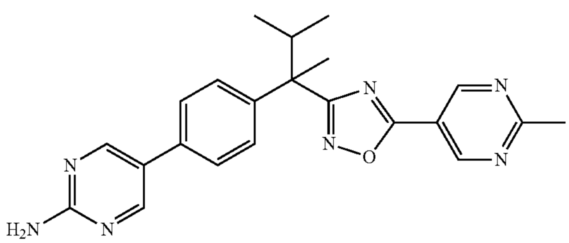 [SMILES: Cc1ncc(-c2nc(C(C)(c3ccc(-c4cnc(N)nc4)cc3)C(C)C)no2)cn1] | 5-(4-{3-methyl-2-[5-(2-methylpyrimidin-5-yl)-1,2,4-oxadiazol-3-yl]butan-2-yl}phenyl)pyrimidin-2-amine |
| 153 | 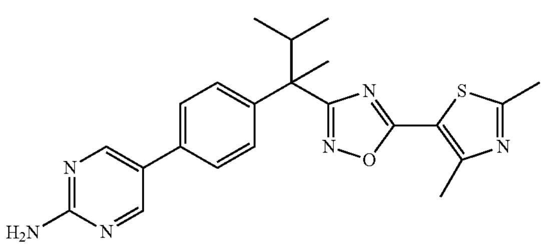 [SMILES: Cc1nc(C)c(-c2nc(C(C)(c3ccc(-c4cnc(N)nc4)cc3)C(C)C)no2)s1] | 5-(4-{2-[5-(2,4-dimethyl-1,3-thiazol-5-yl)-1,2,4-oxadiazol-3-yl]-3-methylbutan-2-yl}phenyl)pyrimidin-2-amine |
| 154 | 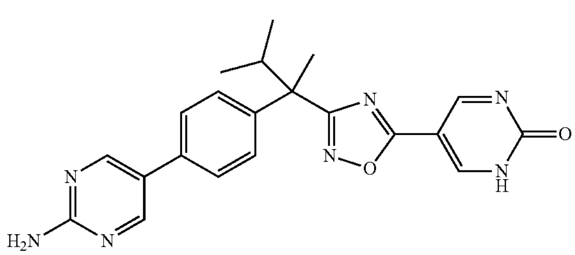 [SMILES: CC(C)C(C)(c1ccc(-c2cnc(N)nc2)cc1)c1noc(-c2cnc(=O)[nH]c2)n1] | 5-(3-{2-[4-(2-aminopyrimidin-5-yl)phenyl]-3-methylbutan-2-yl}-1,2,4-oxadiazol-5-yl)pyrimidin-2(1H)-one |

TABLE 1-continued

| Example | Structure | Name |
|---|---|---|
| 155 | 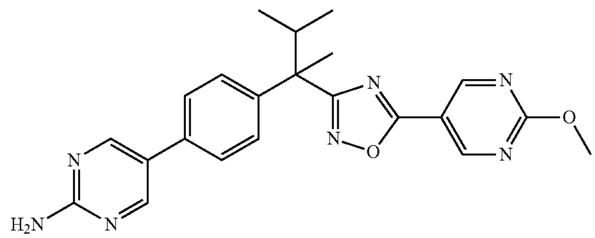 [SMILES: COc1ncc(-c2nc(C(C)(c3ccc(-c4cnc(N)nc4)cc3)C(C)C)no2)cn1] | 5-(4-{2-[5-(2-methoxypyrimidin-5-yl)-1,2,4-oxadiazol-3-yl]-3-methylbutan-2-yl}phenyl)pyrimidin-2-amine |
| 156 | 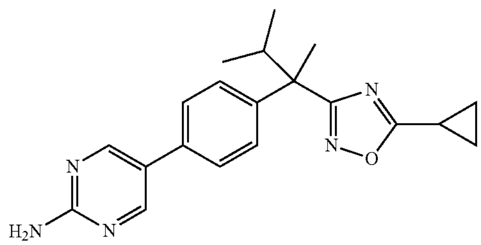 [SMILES: CC(C)C(C)(c1ccc(-c2cnc(N)nc2)cc1)c1noc(C2CC2)n1] | 5-{4-[2-(5-cyclopropyl-1,2,4-oxadiazol-3-yl)-3-methylbutan-2-yl]phenyl}pyrimidin-2-amine |
| 157 | 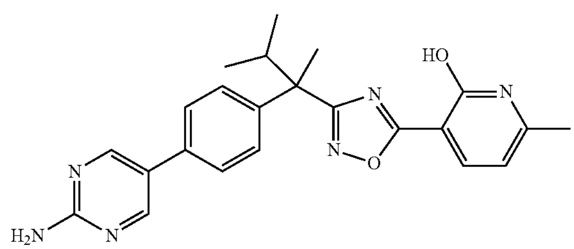 [SMILES: Cc1ccc(-c2nc(C(C)(c3ccc(-c4cnc(N)nc4)cc3)C(C)C)no2)c(O)n1] | 3-(3-{2-[4-(2-aminopyrimidin-5-yl)phenyl]-3-methylbutan-2-yl}-1,2,4-oxadiazol-5-yl)-6-methylpyridin-2-ol |
| 158 | 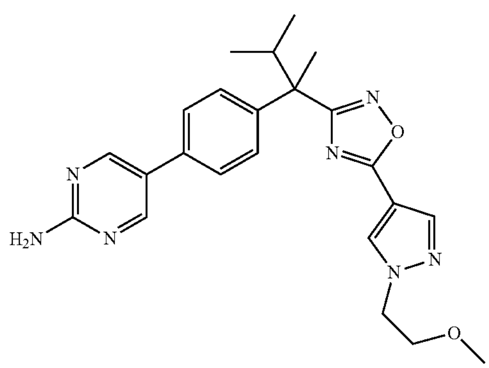 [SMILES: COCCn1cc(-c2nc(C(C)(c3ccc(-c4cnc(N)nc4)cc3)C(C)C)no2)cn1] | 5-[4-(2-{5-[1-(2-methoxyethyl)-1H-pyrazol-4-yl]-1,2,4-oxadiazol-3-yl}-3-methylbutan-2-yl)phenyl]pyrimidin-2-amine |
| 159 | 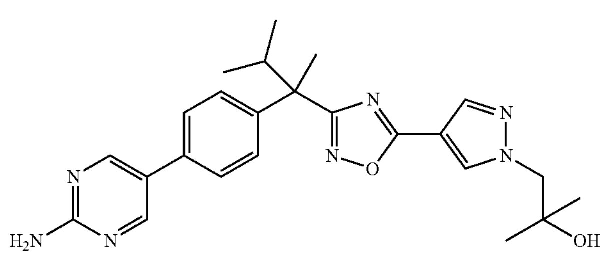 [SMILES: CC(C)C(C)(c1ccc(-c2cnc(N)nc2)cc1)c1noc(-c2cnn(CC(C)(C)O)c2)n1] | 1-[4-(3-{2-[4-(2-aminopyrimidin-5-yl)phenyl]-3-methylbutan-2-yl}-1,2,4-oxadiazol-5-yl)-1H-pyrazol-1-yl]-2-methylpropan-2-ol |

TABLE 1-continued

| Example | Structure | Name |
|---|---|---|
| 160 | 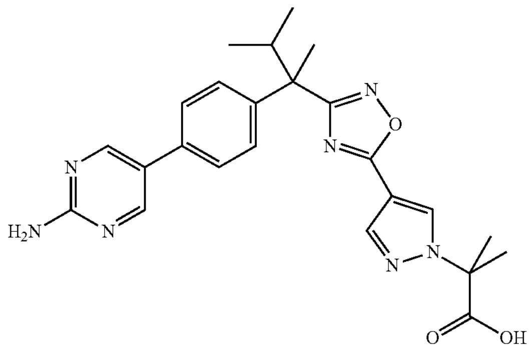 [SMILES: CC(C)C(C)(c1ccc(-c2cnc(N)nc2)cc1)c1noc(-c2cnn(C(C)(C)C(=O)O)c2)n1] | 2-[4-(3-{2-[4-(2-aminopyrimidin-5-yl)phenyl]-3-methylbutan-2-yl}-1,2,4-oxadiazol-5-yl)-1H-pyrazol-1-yl]-2-methylpropanoic acid |
| 161 | 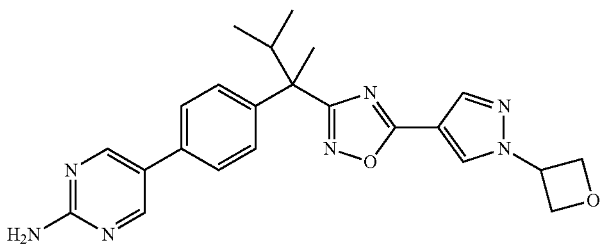 [SMILES: CC(C)C(C)(c1ccc(-c2cnc(N)nc2)cc1)c1noc(-c2cnn(C3COC3)c2)n1] | 5-[4-(3-methyl-2-{5-[1-(oxetan-3-yl)-1H-pyrazol-4-yl]-1,2,4-oxadiazol-3-yl}butan-2-yl)phenyl]pyrimidin-2-amine |
| 162 | 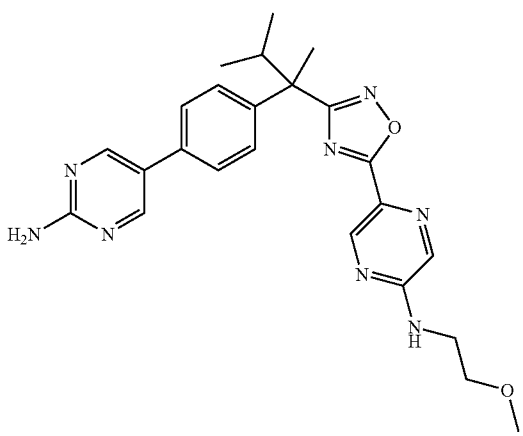 [SMILES: COCCNc1cnc(-c2nc(C(C)(c3ccc(-c4cnc(N)nc4)cc3)C(C)C)no2)cn1] | 5-{4-[2-(5-{5-[(2-methoxyethyl)amino]pyrazin-2-yl}-1,2,4-oxadiazol-3-yl)-3-methylbutan-2-yl]phenyl}pyrimidin-2-amine |
| 163 | 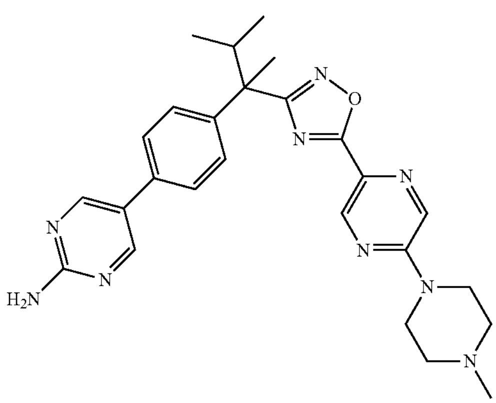 [SMILES: CC(C)C(C)(c1ccc(-c2cnc(N)nc2)cc1)c1noc(-c2cnc(N3CCN(C)CC3)cn2)n1] | 5-[4-(3-methyl-2-{5-[5-(4-methylpiperazin-1-yl)pyrazin-2-yl]-1,2,4-oxadiazol-3-yl}butan-2-yl)phenyl]pyrimidin-2-amine |

TABLE 1-continued

| Example | Structure | Name |
|---|---|---|
| 164 | 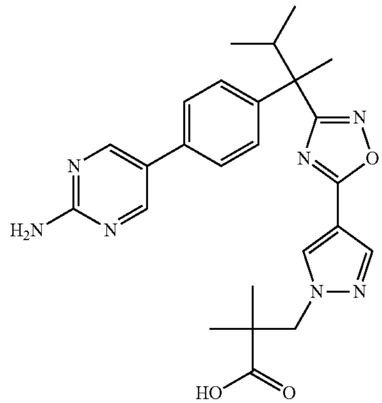 [SMILES: CC(C)C(C)(c1ccc(-c2cnc(N)nc2)cc1)c1noc(-c2cnn(CC(C)(C)C(=O)O)c2)n1] | 3-[4-(3-{2-[4-(2-aminopyrimidin-5-yl)phenyl]-3-methylbutan-2-yl}-1,2,4-oxadiazol-5-yl)-1H-pyrazol-1-yl]-2,2-dimethylpropanoic acid |
| 165 | 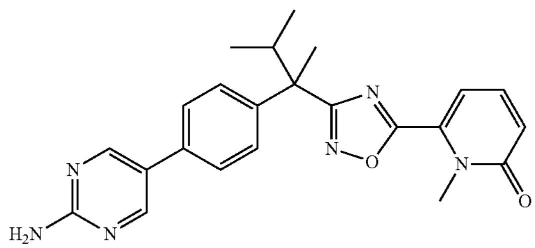 [SMILES: CC(C)C(C)(c1ccc(-c2cnc(N)nc2)cc1)c1noc(-c2cccc(=O)n2C)n1] | 6-(3-{2-[4-(2-aminopyrimidin-5-yl)phenyl]-3-methylbutan-2-yl}-1,2,4-oxadiazol-5-yl)-1-methylpyridin-2(1H)-one |
| 166 | 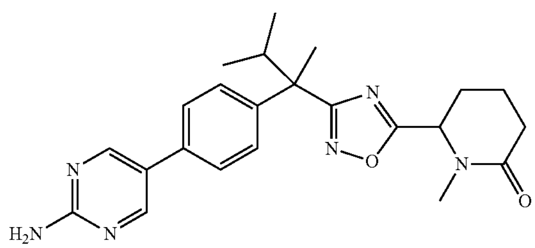 [SMILES: CC(C)C(C)(c1ccc(-c2cnc(N)nc2)cc1)c1noc(C2CCCC(=O)N2C)n1] | 6-(3-{2-[4-(2-aminopyrimidin-5-yl)phenyl]-3-methylbutan-2-yl}-1,2,4-oxadiazol-5-yl)-1-methylpiperidin-2-one |
| 167 | 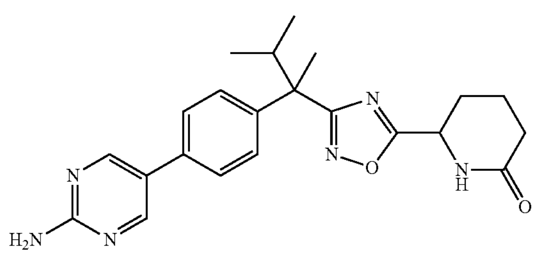 [SMILES: CC(C)C(C)(c1ccc(-c2cnc(N)nc2)cc1)c1noc(C2CCCC(=O)N2)n1] | 6-(3-{2-[4-(2-aminopyrimidin-5-yl)phenyl]-3-methylbutan-2-yl}-1,2,4-oxadiazol-5-yl)piperidin-2-one |
| 168 | 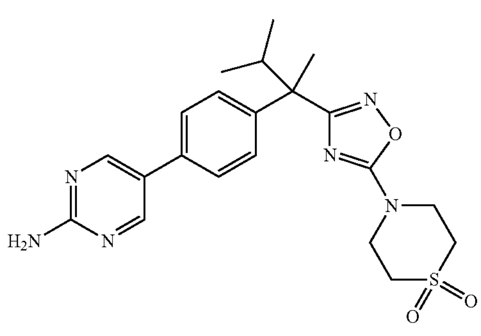 [SMILES: CC(C)C(C)(c1ccc(-c2cnc(N)nc2)cc1)c1noc(N2CCS(=O)(=O)CC2)n1] | 5-(4-{1-[5-(1,1-Dioxo-l1ambda6-thiomorpholin-4-yl)-[1,2,4]oxadiazol-3-yl]-1,2-dimethyl-propyl}-phenyl)-pyrimidin-2-ylamine |

TABLE 1-continued

| Example | Structure | Name |
|---|---|---|
| 169 | 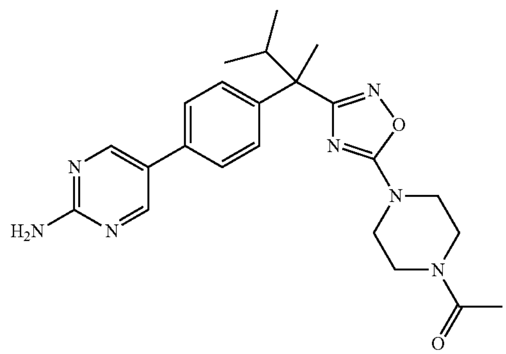 [SMILES: CC(=O)N1CCN(c2nc(C(C)(c3ccc(-c4cnc(N)nc4)cc3)C(C)C)no2)CC1] | 1-[4-(3-{1-[4-(2-Amino-pyrimidin-5-yl)-phenyl]-1,2-dimethyl-propyl}-[1,2,4]oxadiazol-5-yl)-piperazin-1-yl]-ethanone |
| 170 | 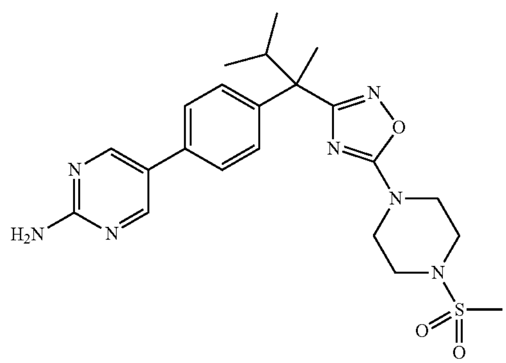 [SMILES: CC(C)C(C)(c1ccc(-c2cnc(N)nc2)cc1)c1noc(N2CCN(S(C)(=O)=O)CC2)n1] | 5-(4-{1-[5-(4-Methanesulfonyl-piperazin-1-yl)-[1,2,4]oxadiazol-3-yl]-1,2-dimethyl-propyl}-phenyl)-pyrimidin-2-ylamine |
| 171 | 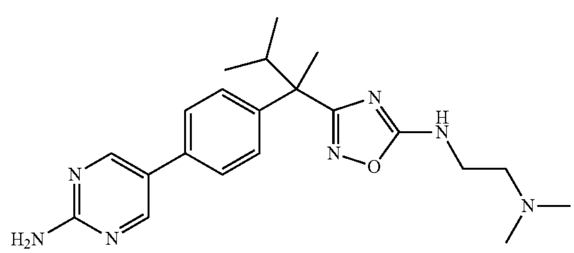 [SMILES: CC(C)C(C)(c1ccc(-c2cnc(N)nc2)cc1)c1noc(NCCN(C)C)n1] | N-(3-{1-[4-(2-Amino-pyrimidin-5-yl)-phenyl]-1,2-dimethyl-propyl}-[1,2,4]oxadiazol-5-yl)-N',N'-dimethyl-ethane-1,2-diamine |
| 172 | 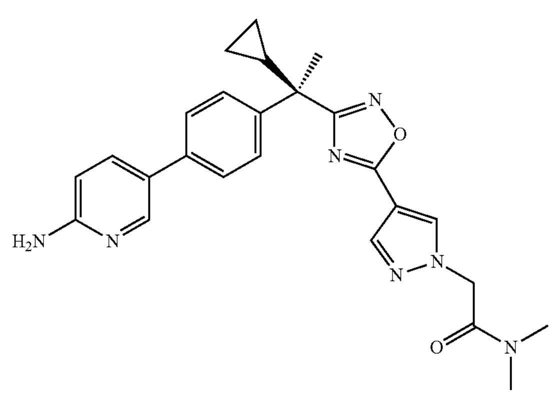 [SMILES: CN(C)C(=O)Cn1cc(-c2nc([C@@](C)(c3ccc(-c4ccc(N)nc4)cc3)C3CC3)no2)cn1] | 2-[4-(3-{(R)-1-[4-(6-Amino-pyridin-3-yl)-phenyl]-1-cyclopropyl-ethyl}-[1,2,4]oxadiazol-5-yl)-pyrazol-1-yl]-N,N-dimethyl-acetamide |

| Example | Structure | Name |
|---|---|---|
| 173 | 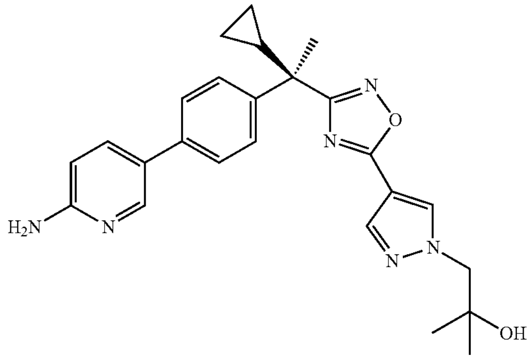 [SMILES: CC(C)(O)Cn1cc(-c2nc([C@@](C)(c3ccc(-c4ccc(N)nc4)cc3)C3CC3)no2)cn1] | 1-[4-(3-{(R)-1-[4-(6-Amino-pyridin-3-yl)-phenyl]-1-cyclopropyl-ethyl}-[1,2,4]oxadiazol-5-yl)-pyrazol-1-yl]-2-methyl-propan-2-ol |
| 174 | 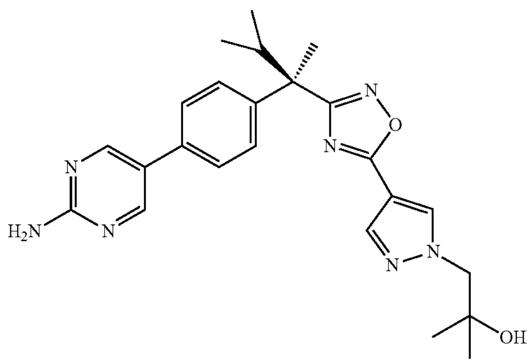 [SMILES: CC(C)[C@](C)(c1ccc(-c2cnc(N)nc2)cc1)c1noc(-c2cnn(CC(C)(C)O)c2)n1] | 1-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-2-methyl-propan-2-ol |
| 175 | 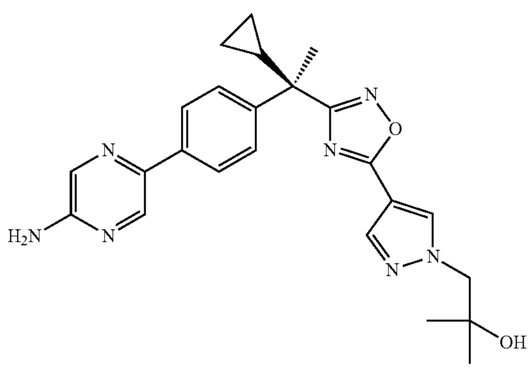 [SMILES: CC(C)(O)Cn1cc(-c2nc([C@@](C)(c3ccc(-c4cnc(N)cn4)cc3)C3CC3)no2)cn1] | 1-[4-(3-{(R)-1-[4-(5-Amino-pyrazin-2-yl)-phenyl]-1-cyclopropyl-ethyl}-[1,2,4]oxadiazol-5-yl)-pyrazol-1-yl]-2-methyl-propan-2-ol |
| 176 | 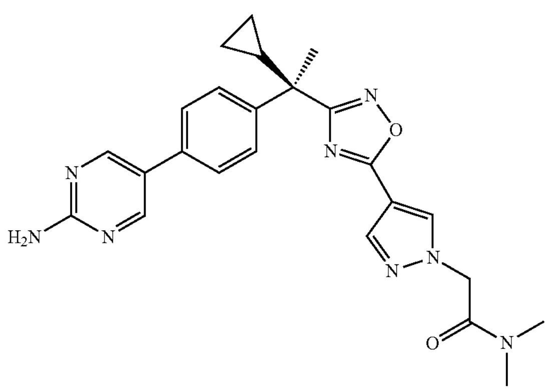 [SMILES: CN(C)C(=O)Cn1cc(-c2nc([C@@](C)(c3ccc(-c4cnc(N)nc4)cc3)C3CC3)no2)cn1] | 2-[4-(3-{(R)-1-[4-(5-Amino-pyrazin-2-yl)-phenyl]-1-cyclopropyl-ethyl}-[1,2,4]oxadiazol-5-yl)-pyrazol-1-yl]-N,N-dimethyl-acetamide |

TABLE 1-continued

| Example | Structure | Name |
|---|---|---|
| 177 | 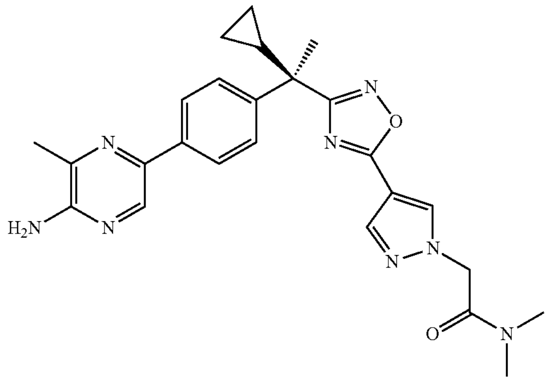 [SMILES: Cc1nc(-c2ccc([C@](C)(c3noc(-c4cnn(CC(=O)N(C)C)c4)n3)C3CC3)cc2)cnc1N] | 2-[4-(3-{(R)-1-[4-(5-Amino-6-methyl-pyrazin-2-yl)-phenyl]-1-cyclopropyl-ethyl}-[1,2,4]oxadiazol-5-yl)-pyrazol-1-yl]-N,N-dimethyl-acetamide |
| 178 | 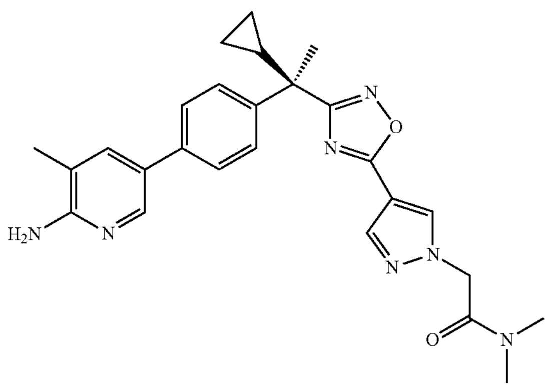 | 2-[4-(3-{(R)-1-[4-(6-Amino-5-methyl-pyridin-3-yl)-phenyl]-1-cyclopropyl-ethyl}-[1,2,4]oxadiazol-5-yl)-pyrazol-1-yl]-N,N-dimethyl-acetamide |
| 179 | 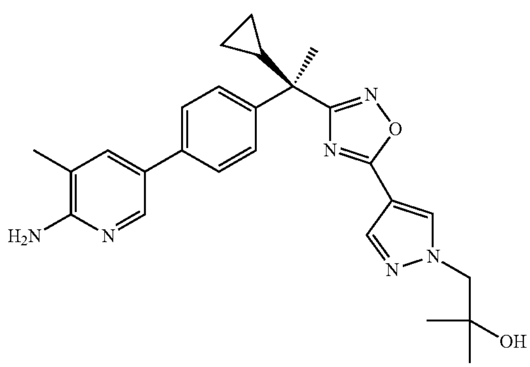 [SMILES: Cc1cc(-c2ccc([C@](C)(c3noc(-c4cnn(CC(C)(C)O)c4)n3)C3CC3)cc2)cnc1N] | 1-[4-(3-{(R)-1-[4-(6-Amino-5-methyl-pyridin-3-yl)-phenyl]-1-cyclopropyl-ethyl}-[1,2,4]oxadiazol-5-yl)-pyrazol-1-yl]-2-methyl-propan-2-ol |
| 180 | 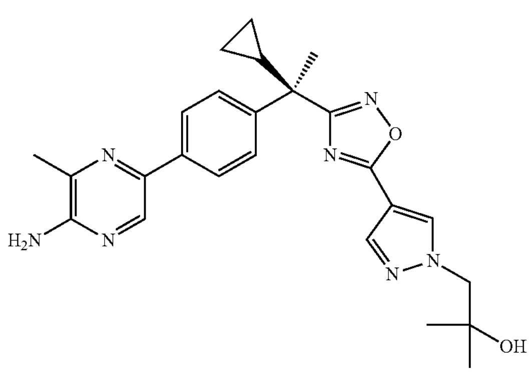 [SMILES: Cc1nc(-c2ccc([C@](C)(c3noc(-c4cnn(CC(C)(C)O)c4)n3)C3CC3)cc2)cnc1N] | 1-[4-(3-{(R)-1-[4-(5-Amino-6-methyl-pyrazin-2-yl)-phenyl]-1-cyclopropyl-ethyl}-[1,2,4]oxadiazol-5-yl)-pyrazol-1-yl]-2-methyl-propan-2-ol |

TABLE 1-continued

| Example | Structure | Name |
|---|---|---|
| 181 | 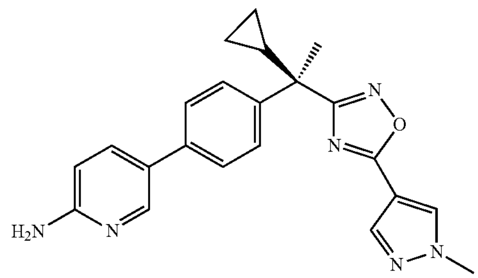 [SMILES: Cn1cc(-c2nc([C@@](C)(c3ccc(-c4ccc(N)nc4)cc3)C3CC3)no2)cn1] | 5-(4-{(R)-1-Cyclopropyl-1-[5-(1-methyl-1H-pyrazol-4-yl)-[1,2,4]oxadiazol-3-yl]-ethyl}-phenyl)-pyridin-2-ylamine |
| 182 | 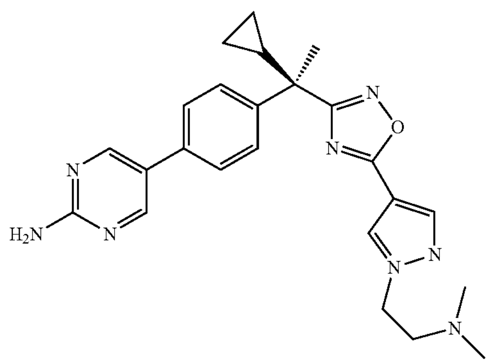 | 5-[4-((R)-1-Cyclopropyl-1-{5-[1-(2-dimethylamino-ethyl)-1H-pyrazol-4-yl]-[1,2,4]oxadiazol-3-yl}-ethyl)-phenyl]-pyrimidin-2-ylamine |
| 183 | 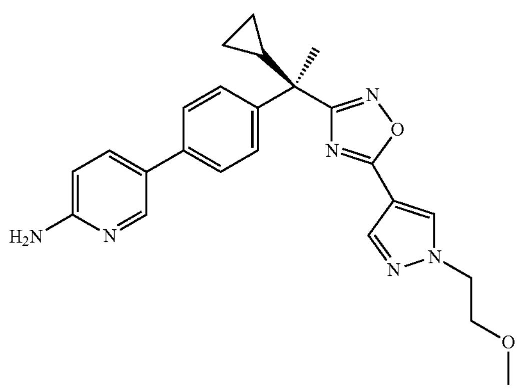 [SMILES: COCCn1cc(-c2nc([C@@](C)(c3ccc(-c4ccc(N)nc4)cc3)C3CC3)no2)cn1] | 5-[4-((R)-1-Cyclopropyl-1-{5-[1-(2-methoxy-ethyl)-1H-pyrazol-4-yl]-[1,2,4]oxadiazol-3-yl}-ethyl)-phenyl]-pyridin-2-ylamine |
| 184 | 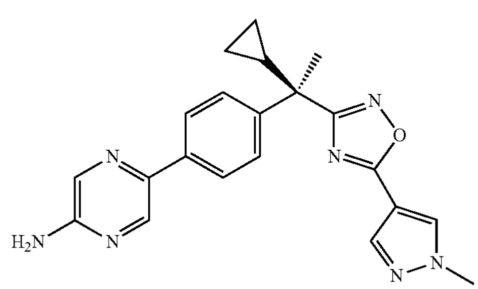 [SMILES: Cn1cc(-c2nc([C@@](C)(c3ccc(-c4cnc(N)cn4)cc3)C3CC3)no2)cn1] | 5-(4-{(R)-1-Cyclopropyl-1-[5-(1-methyl-1H-pyrazol-4-yl)-[1,2,4]oxadiazol-3-yl]-ethyl}-phenyl)-pyrazin-2-ylamine |
| 185 | 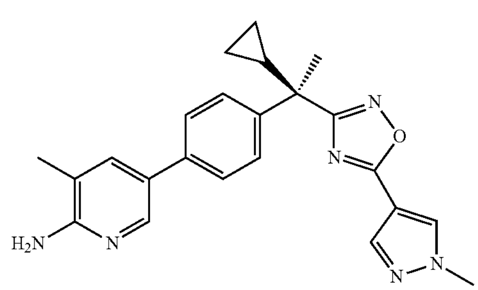 [SMILES: Cc1cc(-c2ccc([C@](C)(c3noc(-c4cnn(C)c4)n3)C3CC3)cc2)cnc1N] | 5-(4-{(R)-1-Cyclopropyl-1-[5-(1-methyl-1H-pyrazol-4-yl)-[1,2,4]oxadiazol-3-yl]-ethyl}-phenyl)-3-methyl-pyridin-2-ylamine |

TABLE 1-continued

| Example | Structure | Name |
|---|---|---|
| 186 | 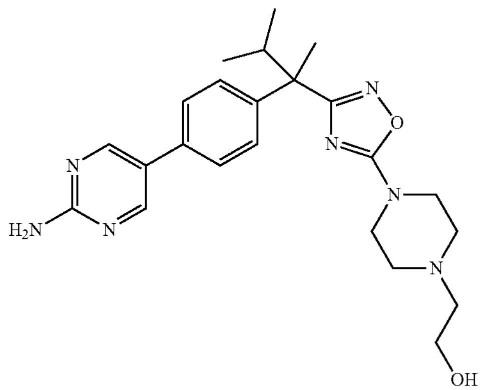 [SMILES: CC(C)C(C)(c1ccc(-c2cnc(N)nc2)cc1)c1noc(N2CCN(CCO)CC2)n1] | 2-[4-(3-{1-[4-(2-Amino-pyrimidin-5-yl)-phenyl]-1,2-dimethyl-propyl}-[1,2,4]oxadiazol-5-yl)-piperazin-1-yl]-ethanol |
| 187 | 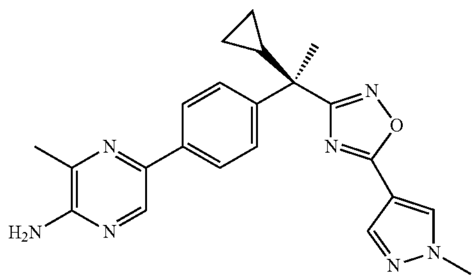 [SMILES: Cc1nc(-c2ccc([C@](C)(c3noc(-c4cnn(C)c4)n3)C3CC3)cc2)cnc1N] | 5-(4-{(R)-1-Cyclopropyl-1-[5-(1-methyl-1H-pyrazol-4-yl)-[1,2,4]oxadiazol-3-yl]-ethyl}-phenyl)-3-methyl-pyrazin-2-ylamine |
| 188 | 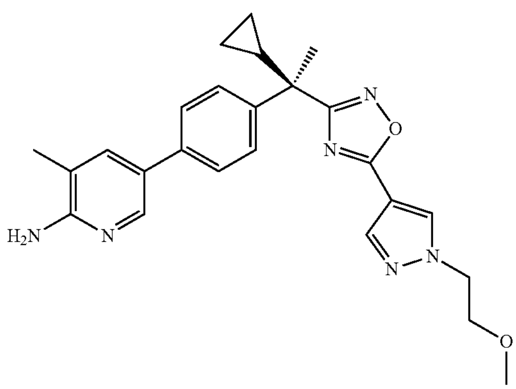 [SMILES: COCCn1cc(-c2nc([C@@](C)(c3ccc(-c4cnc(N)c(C)c4)cc3)C3CC3)no2)cn1] | 5-[4-((R)-1-Cyclopropyl-1-{5-[1-(2-methoxy-ethyl)-1H-pyrazol-4-yl]-[1,2,4]oxadiazol-3-yl}-ethyl)-phenyl]-3-methyl-pyridin-2-ylamine |
| 189 | 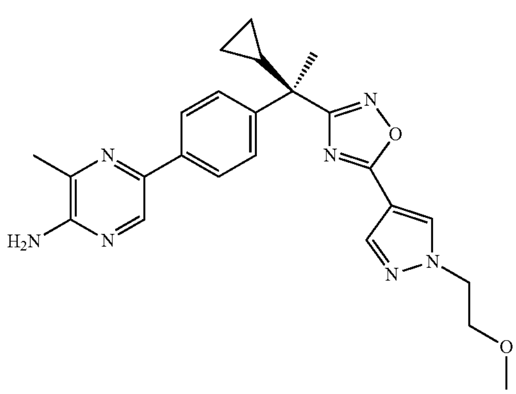 [SMILES: COCCn1cc(-c2nc([C@@](C)(c3ccc(-c4cnc(N)c(C)n4)cc3)C3CC3)no2)cn1] | 5-[4-((R)-1-Cyclopropyl-1-{5-[1-(2-methoxy-ethyl)-1H-pyrazol-4-yl]-[1,2,4]oxadiazol-3-yl}-ethyl)-phenyl]-3-methyl-pyrazin-2-ylamine |

TABLE 1-continued

| Example | Structure | Name |
|---|---|---|
| 190 | 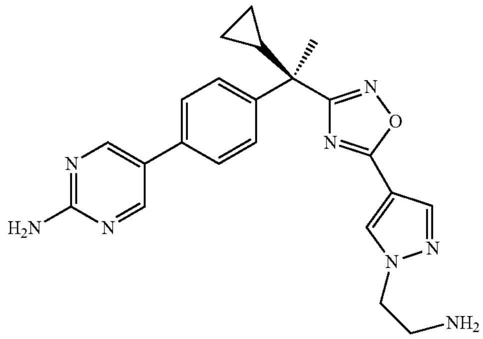 [SMILES: C[C@@](c1ccc(-c2cnc(N)nc2)cc1)(c1noc(-c2cnn(CCN)c2)n1)C1CC1] | 5-[4-((R)-1-{5-[1-(2-Amino-ethyl)-1H-pyrazol-4-yl]-[1,2,4]oxadiazol-3-yl}-1-cyclopropyl-ethyl)-phenyl]-pyrimidin-2-ylamine |
| 191 | 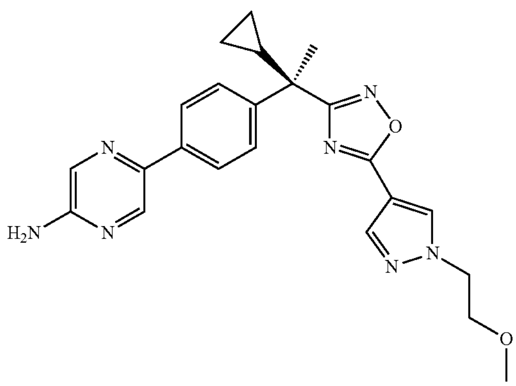 [SMILES: COCCn1cc(-c2nc([C@@](C)(c3ccc(-c4cnc(N)cn4)cc3)C3CC3)no2)cn1] | 5-[4-((R)-1-Cyclopropyl-1-{5-[1-(2-methoxy-ethyl)-1H-pyrazol-4-yl]-[1,2,4]oxadiazol-3-yl}-ethyl)-phenyl]-pyrazin-2-ylamine |
| 192 | 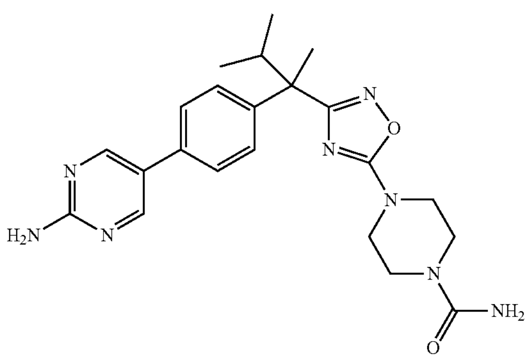 [SMILES: CC(C)C(C)(c1ccc(-c2cnc(N)nc2)cc1)c1noc(N2CCN(C(N)=O)CC2)n1] | 4-(3-{1-[4-(2-Amino-pyrimidin-5-yl)-phenyl]-1,2-dimethyl-propyl}-[1,2,4]oxadiazol-5-yl)-piperazine-1-carboxylic acid amide |
| 193 | 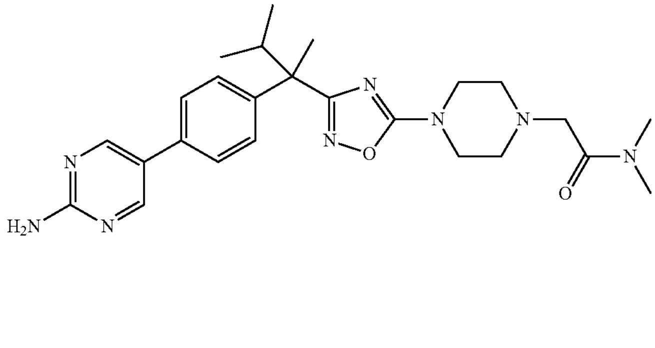 [SMILES: CC(C)C(C)(c1ccc(-c2cnc(N)nc2)cc1)c1noc(N2CCN(CC(=O)N(C)C)CC2)n1] | 2-[4-(3-{1-[4-(2-Amino-pyrimidin-5-yl)-phenyl]-1,2-dimethyl-propyl}-[1,2,4]oxadiazol-5-yl)-piperazin-1-yl]-N,N-dimethyl-acetamide |

TABLE 1-continued

| Example | Structure | Name |
|---|---|---|
| 194 | 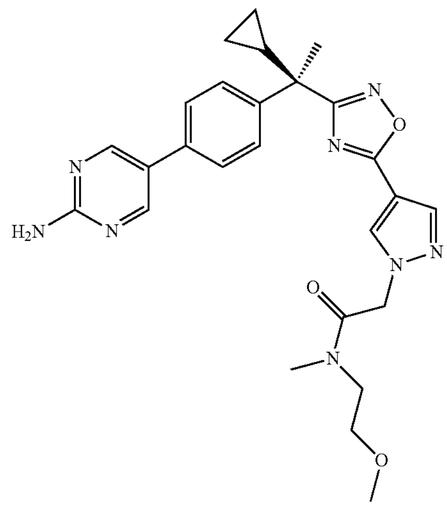 [SMILES: COCCN(C)C(=O)Cn1cc(-c2nc([C@@](C)(c3ccc(-c4cnc(N)nc4)cc3)C3CC3)no2)cn1] | 2-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-N-(2-methoxy-ethyl)-N-methyl-acetamide |
| 195 | 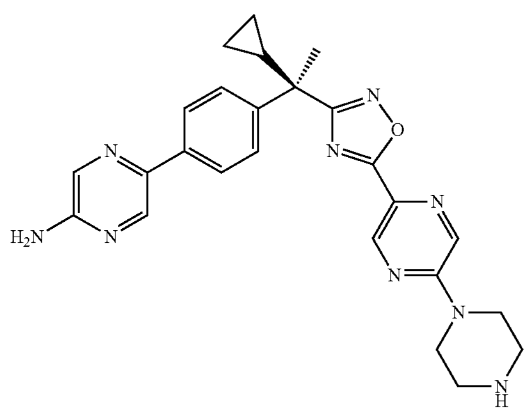 [SMILES: C[C@@](c1ccc(-c2cnc(N)cn2)cc1)(c1noc(-c2cnc(N3CCNCC3)cn2)n1)C1CC1] | 5-(4-{(R)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyrazin-2-ylamine |
| 196 | 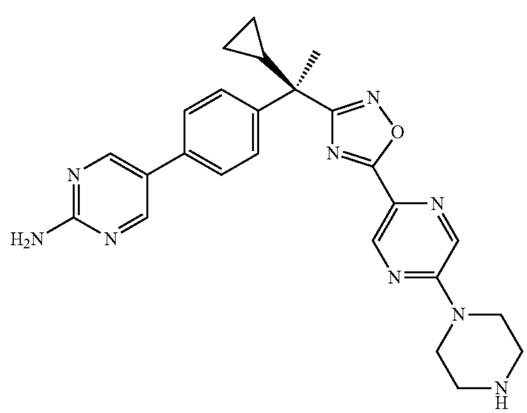 [SMILES: C[C@@](c1ccc(-c2cnc(N)nc2)cc1)(c1noc(-c2cnc(N3CCNCC3)cn2)n1)C1CC1] | 5-(4-{(R)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyrimidin-2-ylamine |

TABLE 1-continued

| Example | Structure | Name |
|---|---|---|
| 197 | 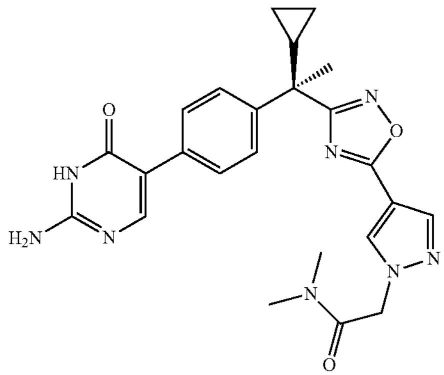 [SMILES: CN(C)C(=O)Cn1cc(-c2nc([C@@](C)(c3ccc(-c4cnc(N)[nH]c4=O)cc3)C3CC3)no2)cn1] | 2-[4-(3-{(R)-1-[4-(2-Amino-6-oxo-1,6-dihydro-pyrimidin-5-yl)-phenyl]-1-cyclopropyl-ethyl}-[1,2,4]oxadiazol-5-yl)-pyrazol-1-yl]-N,N-dimethyl-acetamide |
| 198 | 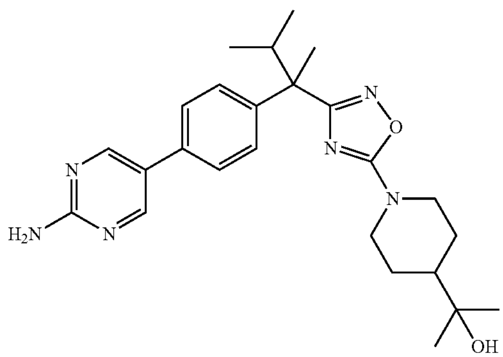 [SMILES: CC(C)C(C)(c1ccc(-c2cnc(N)nc2)cc1)c1noc(N2CCC(C(C)(C)O)CC2)n1] | 2-[1-(3-{1-[4-(2-Amino-pyrimidin-5-yl)-phenyl]-1,2-dimethyl-propyl}-[1,2,4]oxadiazol-5-yl)-piperidin-4-yl]-propan-2-ol |
| 199 | 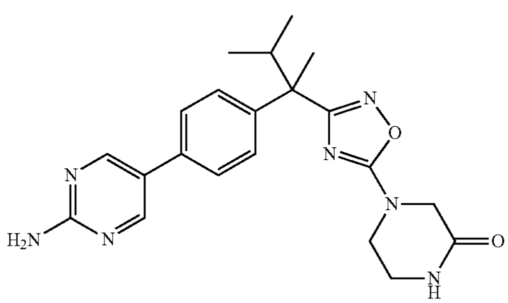 [SMILES: CC(C)C(C)(c1ccc(-c2cnc(N)nc2)cc1)c1noc(N2CCNC(=O)C2)n1] | 4-(3-{1-[4-(2-Amino-pyrimidin-5-yl)-phenyl]-1,2-dimethyl-propyl}-[1,2,4]oxadiazol-5-yl)-piperazin-2-one |
| 200 | 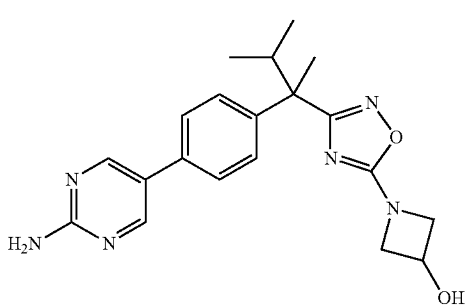 [SMILES: CC(C)C(C)(c1ccc(-c2cnc(N)nc2)cc1)c1noc(N2CC(O)C2)n1] | 1-(3-{1-[4-(2-Amino-pyrimidin-5-yl)-phenyl]-1,2-dimethyl-propyl}-[1,2,4]oxadiazol-5-yl)-azetidin-3-ol |

TABLE 1-continued

| Example | Structure | Name |
|---|---|---|
| 201 | 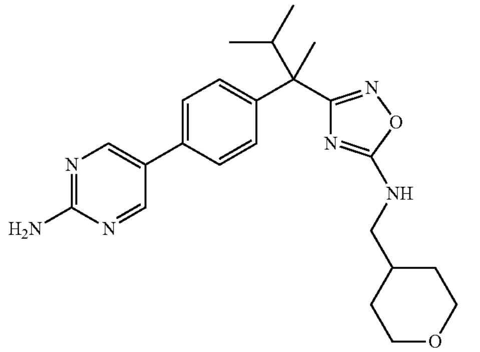 [SMILES: CC(C)C(C)(c1ccc(-c2cnc(N)nc2)cc1)c1noc(NCC2CCOCC2)n1] | 5-[4-(1,2-Dimethyl-1-{5-[(tetrahydro-pyran-4-ylmethyl)-amino]-[1,2,4]oxadiazol-3-yl}-propyl)-phenyl]-pyrimidin-2-ylamine |
| 202 | 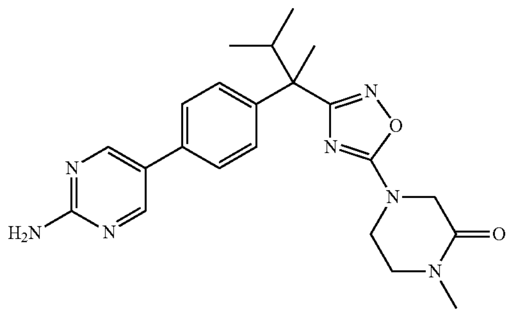 [SMILES: CC(C)C(C)(c1ccc(-c2cnc(N)nc2)cc1)c1noc(N2CCN(C)C(=O)C2)n1] | 4-(3-{1-[4-(2-Amino-pyrimidin-5-yl)-phenyl]-1,2-dimethyl-propyl}-[1,2,4]oxadiazol-5-yl)-1-methyl-piperazin-2-one |
| 203 | 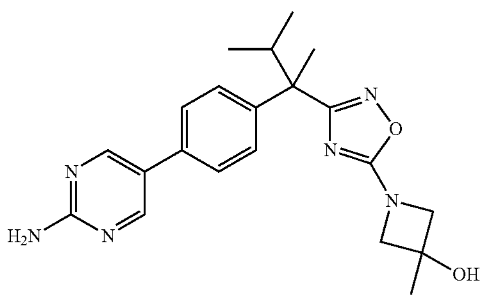 [SMILES: CC(C)C(C)(c1ccc(-c2cnc(N)nc2)cc1)c1noc(N2CC(C)(O)C2)n1] | 1-(3-{1-[4-(2-Amino-pyrimidin-5-yl)-phenyl]-1,2-dimethyl-propyl}-[1,2,4]oxadiazol-5-yl)-3-methyl-azetidin-3-ol |
| 204 | 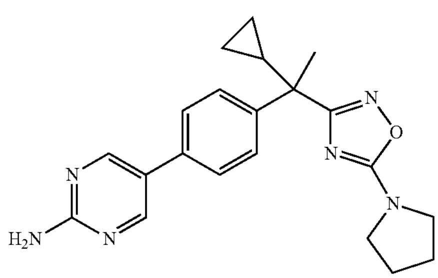 [SMILES: CC(c1ccc(-c2cnc(N)nc2)cc1)(c1noc(N2CCCC2)n1)C1CC1] | 5-{4-[1-Cyclopropyl-1-(5-pyrrolidin-1-yl-[1,2,4]oxadiazol-3-yl)-ethyl]-phenyl}-pyrimidin-2-ylamine |
| 205 | 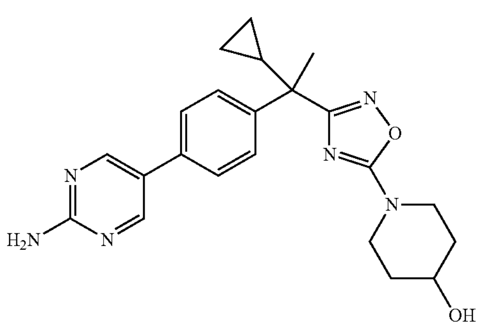 [SMILES: CC(c1ccc(-c2cnc(N)nc2)cc1)(c1noc(N2CCC(O)CC2)n1)C1CC1] | 1-(3-{1-[4-(2-Amino-pyrimidin-5-yl)-phenyl]-1-cyclopropyl-ethyl}-[1,2,4]oxadiazol-5-yl)-piperidin-4-ol |

TABLE 1-continued

| Example | Structure | Name |
|---|---|---|
| 206 | 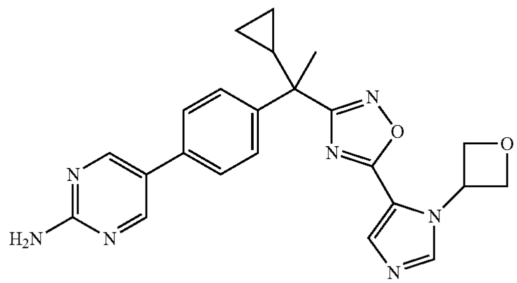 [SMILES: CC(c1ccc(-c2cnc(N)nc2)cc1)(c1noc(-c2cncn2C2COC2)n1)C1CC1] | 5-(4-{1-Cyclopropyl-1-[5-(3-oxetan-3-yl-3H-imidazol-4-yl)-[1,2,4]oxadiazol-3-yl]-ethyl}-phenyl)-pyrimidin-2-ylamine |
| 207 | 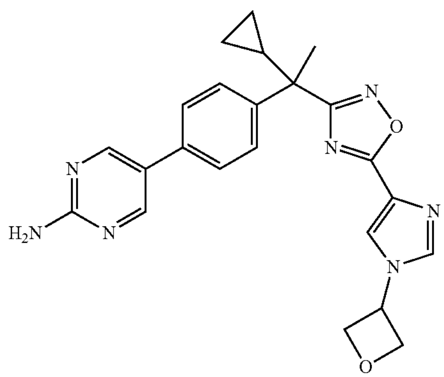 [SMILES: CC(c1ccc(-c2cnc(N)nc2)cc1)(c1noc(-c2cn(C3COC3)cn2)n1)C1CC1] | 5-(4-{1-Cyclopropyl-1-[5-(1-oxetan-3-yl-1H-imidazol-4-yl)-[1,2,4]oxadiazol-3-yl]-ethyl}-phenyl)-pyrimidin-2-ylamine |
| 208 | 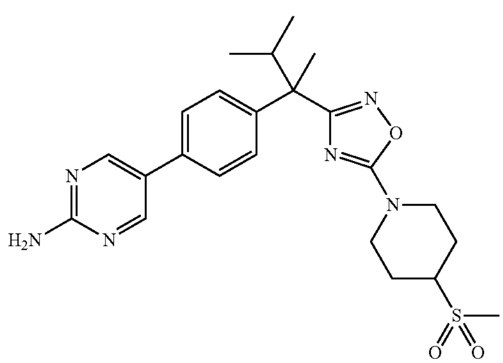 [SMILES: CC(C)C(C)(c1ccc(-c2cnc(N)nc2)cc1)c1noc(N2CCC(S(C)(=O)=O)CC2)n1] | 5-(4-{1-[5-(4-Methanesulfonyl-piperidin-1-yl)-[1,2,4]oxadiazol-3-yl]-1,2-dimethyl-propyl}-phenyl)-pyrimidin-2-ylamine |
| 209 | 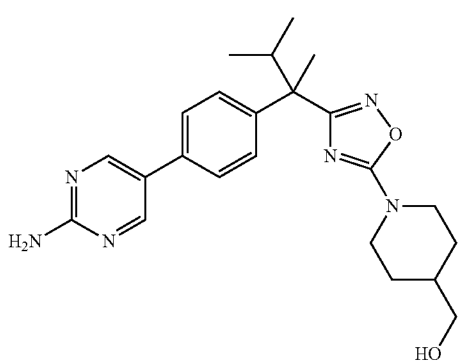 [SMILES: CC(C)C(C)(c1ccc(-c2cnc(N)nc2)cc1)c1noc(N2CCC(CO)CC2)n1] | [1-(3-{1-[4-(2-Amino-pyrimidin-5-yl)-phenyl]-1,2-dimethyl-propyl}-[1,2,4]oxadiazol-5-yl)-piperidin-4-yl]-methanol |

TABLE 1-continued

| Example | Structure | Name |
|---|---|---|
| 210 | 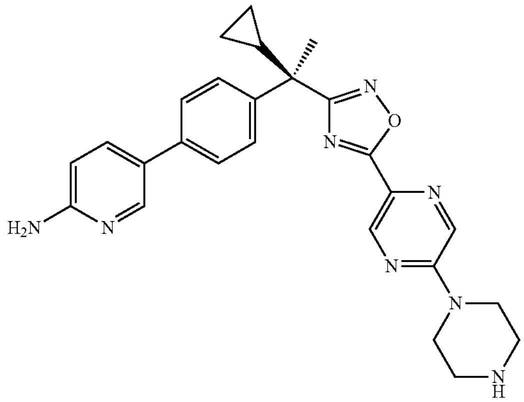 [SMILES: C[C@@](c1ccc(-c2ccc(N)nc2)cc1)(c1noc(-c2cnc(N3CCNCC3)cn2)n1)C1CC1] | 5-(4-{(R)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyridin-2-ylamine |
| 211 | 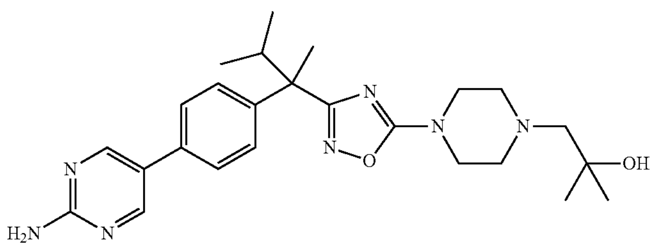 [SMILES: CC(C)C(C)(c1ccc(-c2cnc(N)nc2)cc1)c1noc(N2CCN(CC(C)(C)O)CC2)n1] | 1-[4-(3-{1-[4-(2-Amino-pyrimidin-5-yl)-phenyl]-1,2-dimethyl-propyl}-[1,2,4]oxadiazol-5-yl)-piperazin-1-yl]-2-methyl-propan-2-ol |
| 212 | 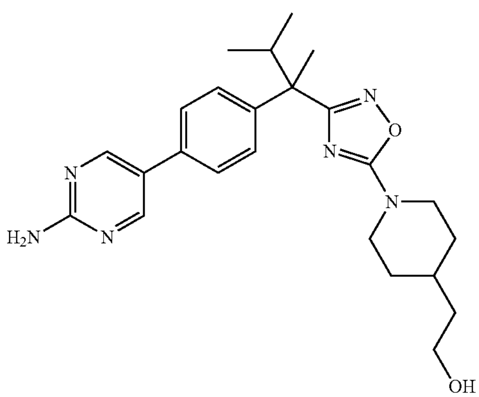 [SMILES: CC(C)C(C)(c1ccc(-c2cnc(N)nc2)cc1)c1noc(N2CCC(CCO)CC2)n1] | 2-[1-(3-{1-[4-(2-Amino-pyrimidin-5-yl)-phenyl]-1,2-dimethyl-propyl}-[1,2,4]oxadiazol-5-yl)-piperidin-4-yl]-ethanol |
| 213 | 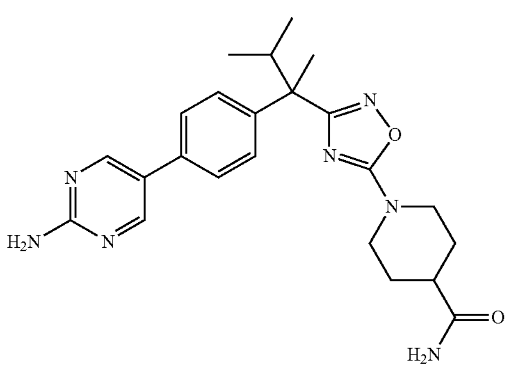 [SMILES: CC(C)C(C)(c1ccc(-c2cnc(N)nc2)cc1)c1noc(N2CCC(C(N)=O)CC2)n1] | 1-(3-{1-[4-(2-Amino-pyrimidin-5-yl)-phenyl]-1,2-dimethyl-propyl}-[1,2,4]oxadiazol-5-yl)-piperidine-4-carboxylic acid amide |

TABLE 1-continued

| Example | Structure | Name |
|---|---|---|
| 214 | 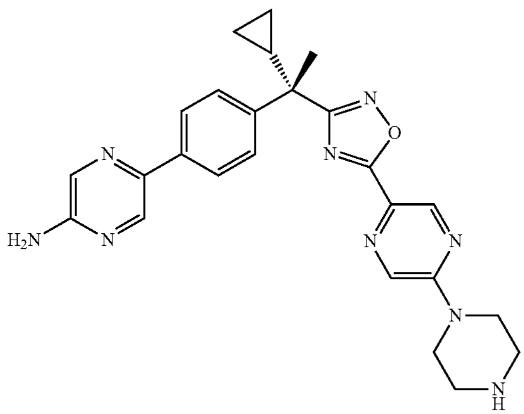 [SMILES: C[C@](c1ccc(-c2cnc(N)cn2)cc1)(c1noc(-c2cnc(N3CCNCC3)cn2)n1)C1CC1] | 5-(4-{(S)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyrazin-2-ylamine |
| 215 | 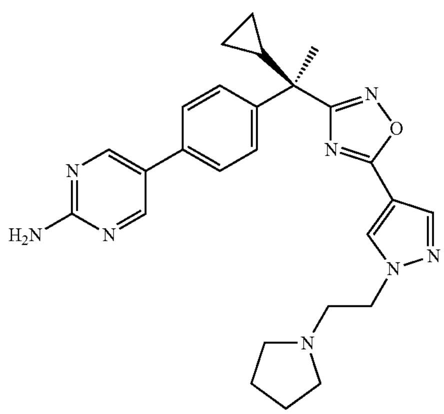 [SMILES: C[C@@](c1ccc(-c2cnc(N)nc2)cc1)(c1noc(-c2cnn(CCN3CCCC3)c2)n1)C1CC1] | 5-[4-((R)-1-Cyclopropyl-1-{5-[1-(2-pyrrolidin-1-yl-ethyl)-1H-pyrazol-4-yl]-[1,2,4]oxadiazol-3-yl}-ethyl)-phenyl]-pyrimidin-2-ylamine |
| 216 | 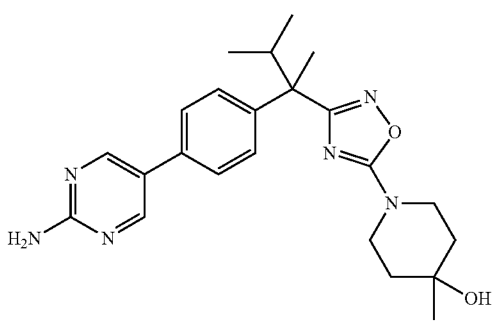 [SMILES: CC(C)C(C)(c1ccc(-c2cnc(N)nc2)cc1)c1noc(N2CCC(C)(O)CC2)n1] | 1-(3-{1-[4-(2-Amino-pyrimidin-5-yl)-phenyl]-1,2-dimethyl-propyl}-[1,2,4]oxadiazol-5-yl)-4-methyl-piperidin-4-ol |
| 217 | 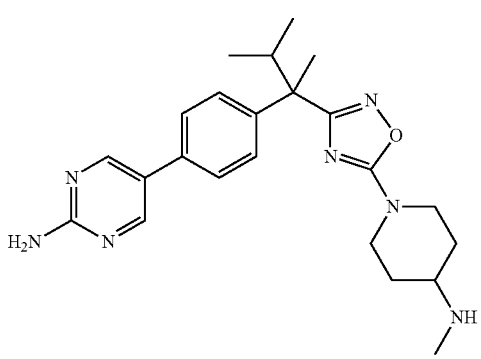 [SMILES: CNC1CCN(c2nc(C(C)(c3ccc(-c4cnc(N)nc4)cc3)C(C)C)no2)CC1] | 5-(4-{1,2-Dimethyl-1-[5-(4-methylamino-piperidin-1-yl)-[1,2,4]oxadiazol-3-yl]-propyl}-phenyl)-pyrimidin-2-ylamine |

TABLE 1-continued

| Example | Structure | Name |
|---|---|---|
| 218 | 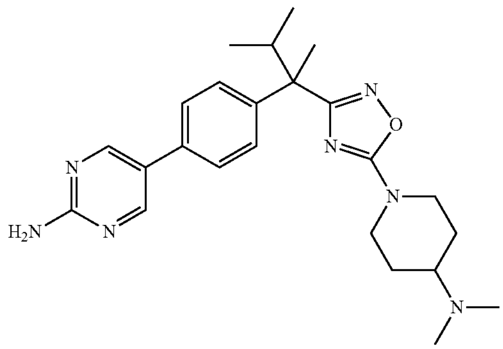 [SMILES: CC(C)C(C)(c1ccc(-c2cnc(N)nc2)cc1)c1noc(N2CCC(N(C)C)CC2)n1] | 5-(4-{1-[5-(4-Dimethylamino-piperidin-1-yl)-[1,2,4]oxadiazol-3-yl]-1,2-dimethyl-propyl}-phenyl)-pyrimidin-2-ylamine |
| 219 | 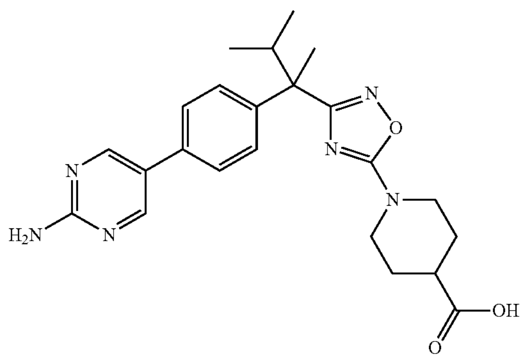 [SMILES: CC(C)C(C)(c1ccc(-c2cnc(N)nc2)cc1)c1noc(N2CCC(C(=O)O)CC2)n1] | 1-(3-{1-[4-(2-Amino-pyrimidin-5-yl)-phenyl]-1,2-dimethyl-propyl}-[1,2,4]oxadiazol-5-yl)-piperidine-4-carboxylic acid |
| 220 | 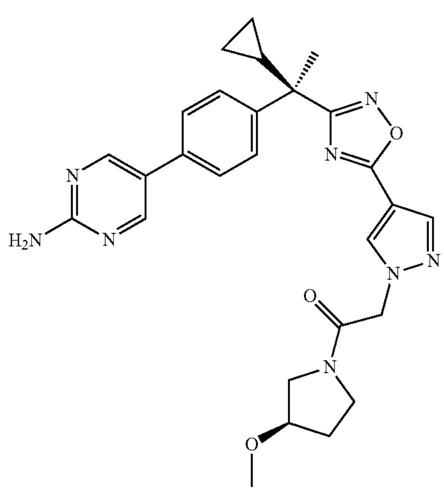 [SMILES: CO[C@@H]1CCN(C(=O)Cn2cc(-c3nc([C@@](C)(c4ccc(-c5cnc(N)nc5)cc4)C4CC4)no3)cn2)C1] | 2-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-1-((R)-3-methoxy-pyrrolidin-1-yl)-ethanone |

TABLE 1-continued

| Example | Structure | Name |
|---|---|---|
| 221 | 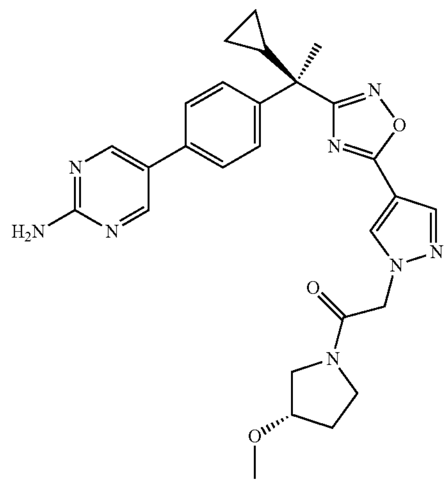 [SMILES: CO[C@H]1CCN(C(=O)Cn2cc(-c3nc([C@@](C)(c4ccc(-c5cnc(N)nc5)cc4)C4CC4)no3)cn2)C1] | 2-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-1-((S)-3-methoxy-pyrrolidin-1-yl)-ethanone |
| 222 | 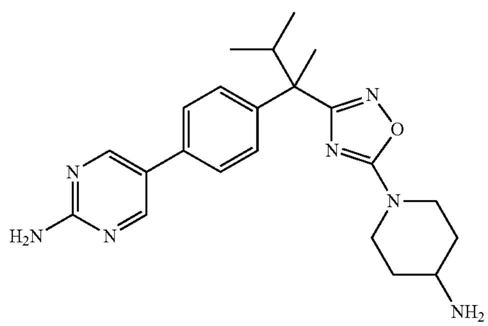 [SMILES: CC(C)C(C)(c1ccc(-c2cnc(N)nc2)cc1)c1noc(N2CCC(N)CC2)n1] | 5-(4-{1-[5-(4-Amino-piperidin-1-yl)-[1,2,4]oxadiazol-3-yl]-1,2-dimethyl-propyl}-phenyl)-pyrimidin-2-ylamine |
| 223 | 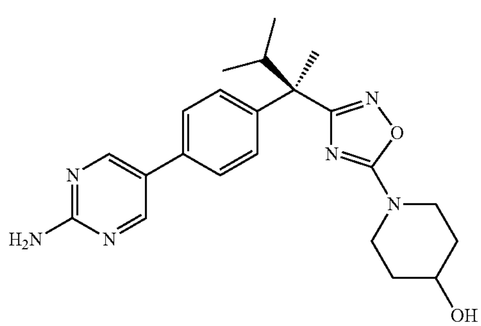 [SMILES: CC(C)[C@](C)(c1ccc(-c2cnc(N)nc2)cc1)c1noc(N2CCC(O)CC2)n1] | 1-(3-{(R)-1-[4-(2-Amino-pyrimidin-5-yl)-phenyl]-1,2-dimethyl-propyl}-[1,2,4]oxadiazol-5-yl)-piperidin-4-ol |
| 224 | 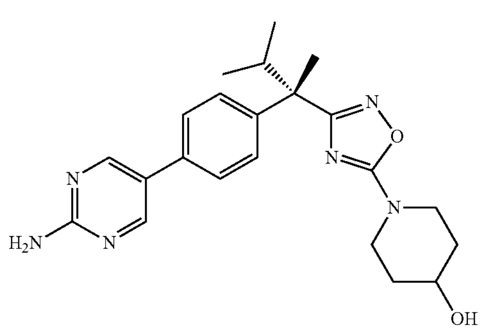 [SMILES: CC(C)[C@@](C)(c1ccc(-c2cnc(N)nc2)cc1)c1noc(N2CCC(O)CC2)n1] | 1-(3-{(S)-1-[4-(2-Amino-pyrimidin-5-yl)-phenyl]-1,2-dimethyl-propyl}-[1,2,4]oxadiazol-5-yl)-piperidin-4-ol |

TABLE 1-continued

| Example | Structure | Name |
|---|---|---|
| 225 | 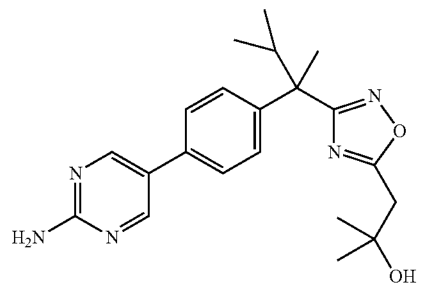 [SMILES: CC(C)C(C)(c1ccc(-c2cnc(N)nc2)cc1)c1noc(CC(C)(C)O)n1] | 1-(3-{1-[4-(2-Amino-pyrimidin-5-yl)-phenyl]-1,2-dimethyl-propyl}-[1,2,4]oxadiazol-5-yl)-2-methyl-propan-2-ol |
| 226 | 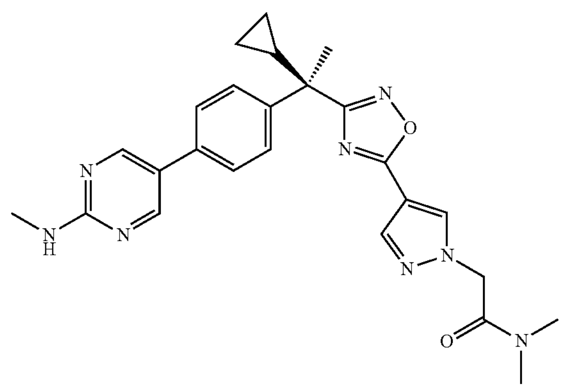 | 2-[4-(3-{(R)-1-Cyclopropyl-1-[4-(2-methylamino-pyrimidin-5-yl)-phenyl]-ethyl}-[1,2,4]oxadiazol-5-yl)-pyrazol-1-yl]-N,N-dimethyl-acetamide |
| 227 | 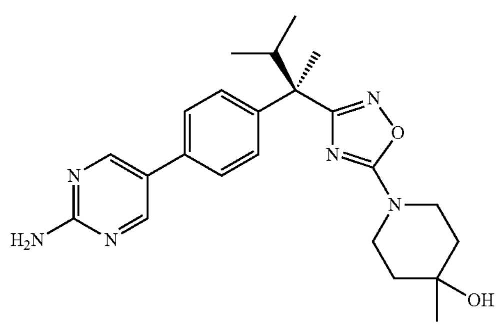 [SMILES: CC(C)[C@](C)(c1ccc(-c2cnc(N)nc2)cc1)c1noc(N2CCC(C)(O)CC2)n1] | 1-(3-{(R)-1-[4-(2-Amino-pyrimidin-5-yl)-phenyl]-1,2-dimethyl-propyl}-[1,2,4]oxadiazol-5-yl)-4-methyl-piperidin-4-ol |
| 228 | 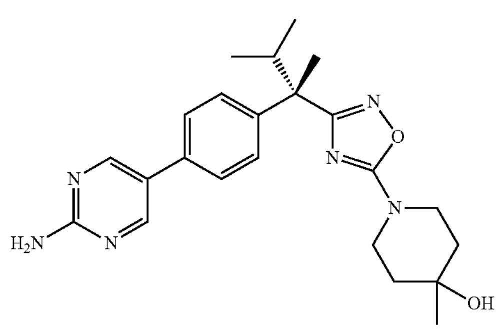 [SMILES: CC(C)[C@@](C)(c1ccc(-c2cnc(N)nc2)cc1)c1noc(N2CCC(C)(O)CC2)n1] | 1-(3-{(S)-1-[4-(2-Amino-pyrimidin-5-yl)-phenyl]-1,2-dimethyl-propyl}-[1,2,4]oxadiazol-5-yl)-4-methyl-piperidin-4-ol |

TABLE 1-continued

| Example | Structure | Name |
|---|---|---|
| 229 | 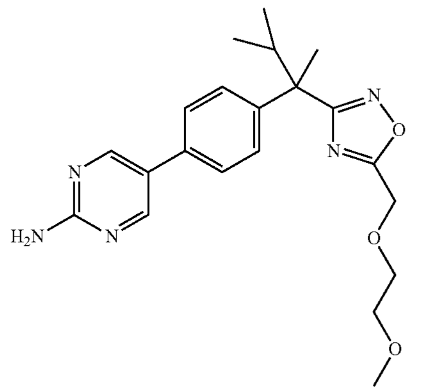 [SMILES: COCCOCc1nc(C(C)(c2ccc(-c3cnc(N)nc3)cc2)C(C)C)no1] | 5-(4-{1-[5-(2-Methoxy-ethoxymethyl)-[1,2,4]oxadiazol-3-yl]-1,2-dimethyl-propyl}-phenyl)-pyrimidin-2-ylamine |
| 230 | 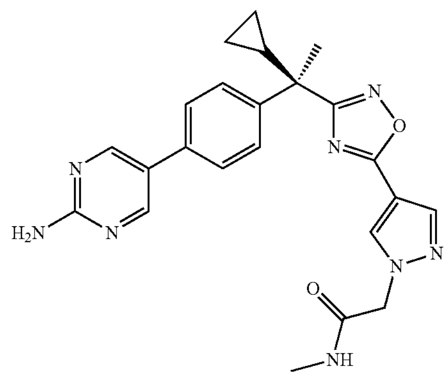 [SMILES: CNC(=O)Cn1cc(-c2nc([C@@](C)(c3ccc(-c4cnc(N)nc4)cc3)C3CC3)no2)cn1] | 2-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-N-methyl-acetamide |
| 231 | 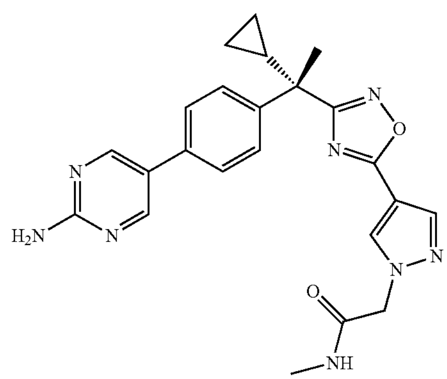 [SMILES: CNC(=O)Cn1cc(-c2nc([C@](C)(c3ccc(-c4cnc(N)nc4)cc3)C3CC3)no2)cn1] | 2-[4-(3-{(S)-1-[4-(2-Amino-pyrimidin-5-yl)-phenyl]-1-cyclopropyl-ethyl}-[1,2,4]oxadiazol-5-yl)-pyrazol-1-yl]-N-methyl-acetamide |
| 232 | 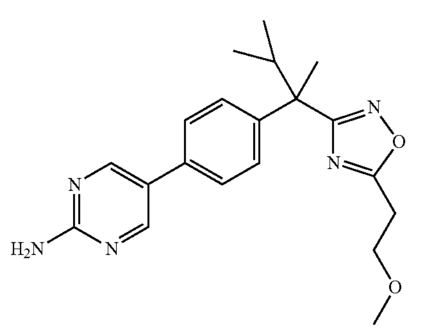 [SMILES: COCCc1nc(C(C)(c2ccc(-c3cnc(N)nc3)cc2)C(C)C)no1] | 5-(4-{1-[5-(2-Methoxy-ethyl)-[1,2,4]oxadiazol-3-yl]-1,2-dimethyl-propyl}-phenyl)-pyrimidin-2-ylamine |

TABLE 1-continued

| Example | Structure | Name |
|---|---|---|
| 233 | 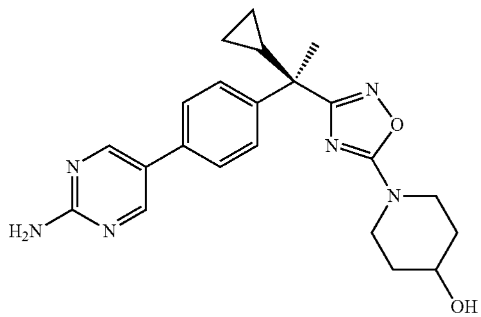 [SMILES: C[C@@](c1ccc(-c2cnc(N)nc2)cc1)(c1noc(N2CCC(O)CC2)n1)C1CC1] | 1-(3-{(R)-1-[4-(2-Amino-pyrimidin-5-yl)-phenyl]-1-cyclopropyl-ethyl}-[1,2,4]oxadiazol-5-yl)-piperidin-4-ol |
| 234 | 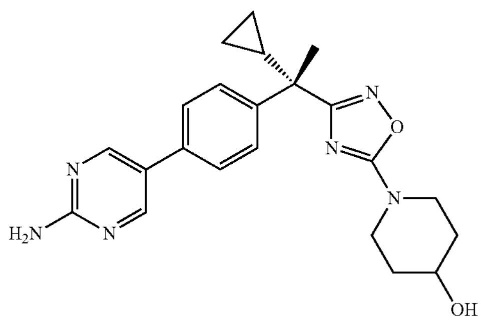 [SMILES: C[C@](c1ccc(-c2cnc(N)nc2)cc1)(c1noc(N2CCC(O)CC2)n1)C1CC1] | 1-(3-{(S)-1-[4-(2-Amino-pyrimidin-5-yl)-phenyl]-1-cyclopropyl-ethyl}-[1,2,4]oxadiazol-5-yl)-piperidin-4-ol |
| 235 | 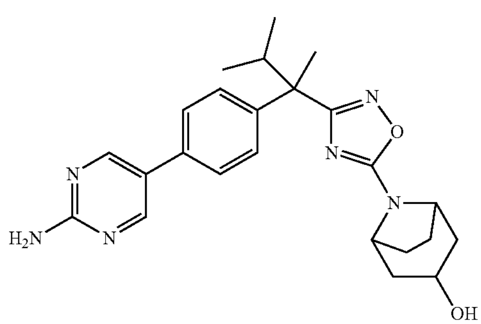 [SMILES: CC(C)C(C)(c1ccc(-c2cnc(N)nc2)cc1)c1noc(N2C3CCC2CC(O)C3)n1] | 8-(3-{1-[4-(2-Amino-pyrimidin-5-yl)-phenyl]-1,2-dimethyl-propyl}-[1,2,4]oxadiazol-5-yl)-8-aza-bicyclo[3.2.1]octan-3-ol |
| 236 | 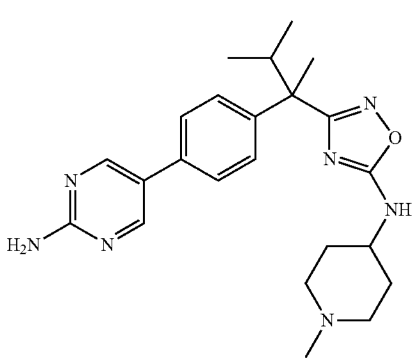 [SMILES: CC(C)C(C)(c1ccc(-c2cnc(N)nc2)cc1)c1noc(NC2CCN(C)CC2)n1] | 5-(4-{1,2-Dimethyl-1-[5-(1-methyl-piperidin-4-ylamino)-[1,2,4]oxadiazol-3-yl]-propyl}-phenyl)-pyrimidin-2-ylamine |

TABLE 1-continued

| Example | Structure | Name |
|---|---|---|
| 237 | 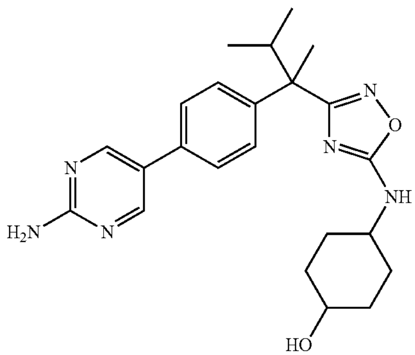 [SMILES: CC(C)C(C)(c1ccc(-c2cnc(N)nc2)cc1)c1noc(NC2CCC(O)CC2)n1] | 4-(3-{1-[4-(2-Amino-pyrimidin-5-yl)-phenyl]-1,2-dimethyl-propyl}-[1,2,4]oxadiazol-5-ylamino)-cyclohexanol |
| 238 | 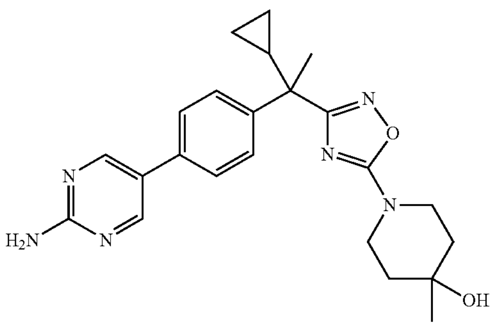 [SMILES: CC1(O)CCN(c2nc(C(C)(c3ccc(-c4cnc(N)nc4)cc3)C3CC3)no2)CC1] | 1-(3-{1-[4-(2-Amino-pyrimidin-5-yl)-phenyl]-1-cyclopropyl-ethyl}-[1,2,4]oxadiazol-5-yl)-4-methyl-piperidin-4-ol |
| 239 | 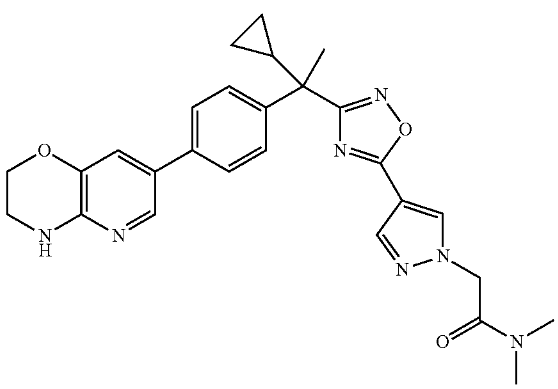 [SMILES: CN(C)C(=O)Cn1cc(-c2nc(C(C)(c3ccc(-c4cnc5c(c4)OCCN5)cc3)C3CC3)no2)cn1] | 2-[4-(3-{1-Cyclopropyl-1-[4-(3,4-dihydro-2H-pyrido[3,2-b][1,4]oxazin-7-yl)-phenyl]-ethyl}-[1,2,4]oxadiazol-5-yl)-pyrazol-1-yl]-N,N-dimethyl-acetamide |
| 240 | 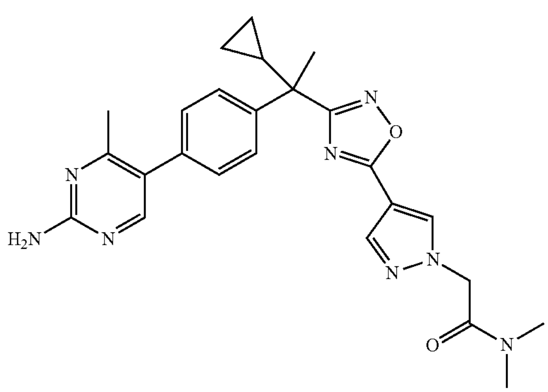 [SMILES: Cc1nc(N)ncc1-c1ccc(C(C)(c2noc(-c3cnn(CC(=O)N(C)C)c3)n2)C2CC2)cc1] | 2-[4-(3-{1-[4-(2-Amino-4-methyl-pyrimidin-5-yl)-phenyl]-1-cyclopropyl-ethyl}-[1,2,4]oxadiazol-5-yl)-pyrazol-1-yl]-N,N-dimethyl-acetamide |

TABLE 1-continued

| Example | Structure | Name |
|---|---|---|
| 241 | 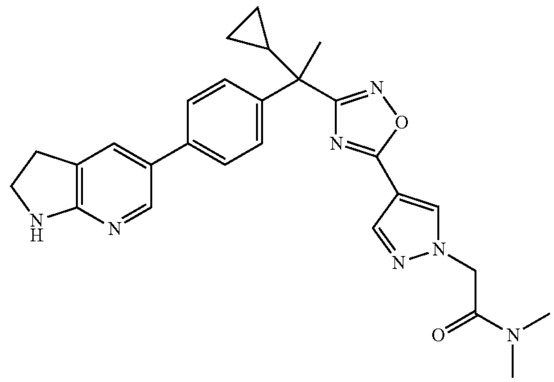 [SMILES: CN(C)C(=O)Cn1cc(-c2nc(C(C)(c3ccc(-c4cnc5c(c4)CCN5)cc3)C3CC3)no2)cn1] | 2-[4-(3-{1-Cyclopropyl-1-[4-(2,3-dihydro-1H-pyrrolo[2,3-b]pyridin-5-yl)-phenyl]-ethyl}-[1,2,4]oxadiazol-5-yl)-pyrazol-1-yl]-N,N-dimethyl-acetamide |
| 242 | 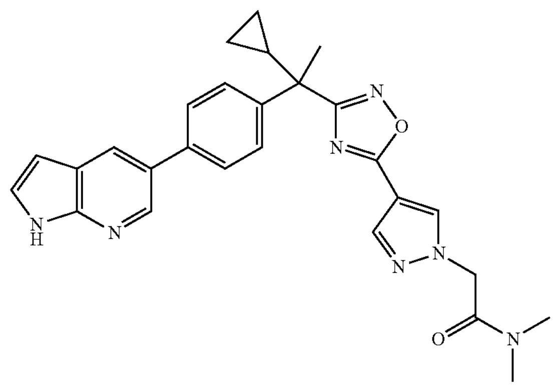 [SMILES: CN(C)C(=O)Cn1cc(-c2nc(C(C)(c3ccc(-c4cnc5[nH]ccc5c4)cc3)C3CC3)no2)cn1] | 2-[4-(3-{1-Cyclopropyl-1-[4-(1H-pyrrolo[2,3-b]pyridin-5-yl)-phenyl]-ethyl}-[1,2,4]oxadiazol-5-yl)-pyrazol-1-yl]-N,N-dimethyl-acetamide |
| 243 | 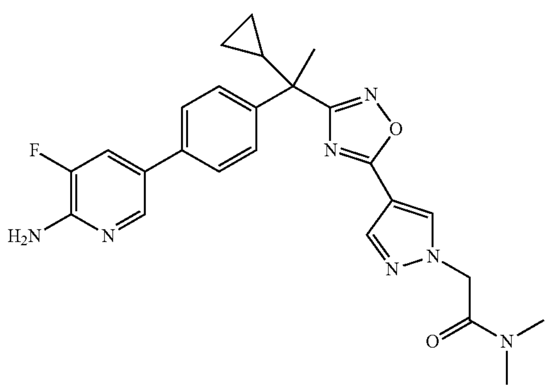 [SMILES: CN(C)C(=O)Cn1cc(-c2nc(C(C)(c3ccc(-c4cnc(N)c(F)c4)cc3)C3CC3)no2)cn1] | 2-[4-(3-{1-[4-(6-Amino-5-fluoro-pyridin-3-yl)-phenyl]-1-cyclopropyl-ethyl}-[1,2,4]oxadiazol-5-yl)-pyrazol-1-yl]-N,N-dimethyl-acetamide |
| 244 | 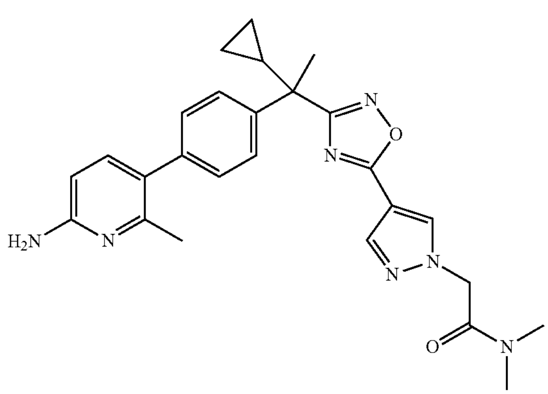 [SMILES: Cc1nc(N)ccc1-c1ccc(C(C)(c2noc(-c3cnn(CC(=O)N(C)C)c3)n2)C2CC2)cc1] | 2-[4-(3-{1-[4-(6-Amino-2-methyl-pyridin-3-yl)-phenyl]-1-cyclopropyl-ethyl}-[1,2,4]oxadiazol-5-yl)-pyrazol-1-yl]-N,N-dimethyl-acetamide |

TABLE 1-continued

| Example | Structure | Name |
|---|---|---|
| 245 | 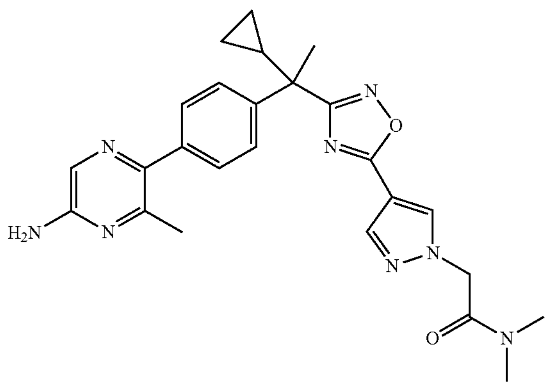 [SMILES: Cc1nc(N)cnc1-c1ccc(C(C)(c2noc(-c3cnn(CC(=O)N(C)C)c3)n2)C2CC2)cc1] | 2-[4-(3-{1-[4-(5-Amino-3-methyl-pyrazin-2-yl)-phenyl]-1-cyclopropyl-ethyl}-[1,2,4]oxadiazol-5-yl)-pyrazol-1-yl]-N,N-dimethyl-acetamide |
| 246 | 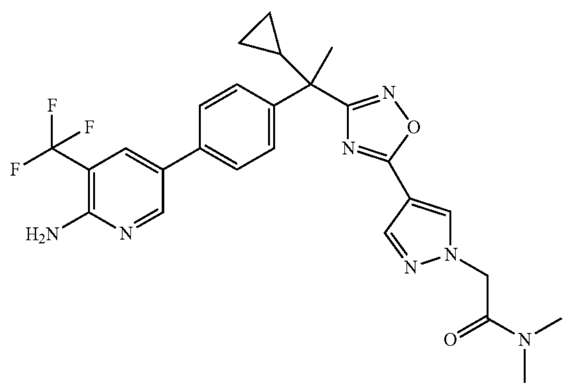 [SMILES: CN(C)C(=O)Cn1cc(-c2nc(C(C)(c3ccc(-c4cnc(N)c(C(F)(F)F)c4)cc3)C3CC3)no2)cn1] | 2-[4-(3-{1-[4-(6-Amino-5-trifluoromethyl-pyridin-3-yl)-phenyl]-1-cyclopropyl-ethyl}-[1,2,4]oxadiazol-5-yl)-pyrazol-1-yl]-N,N-dimethyl-acetamide |
| 247 | 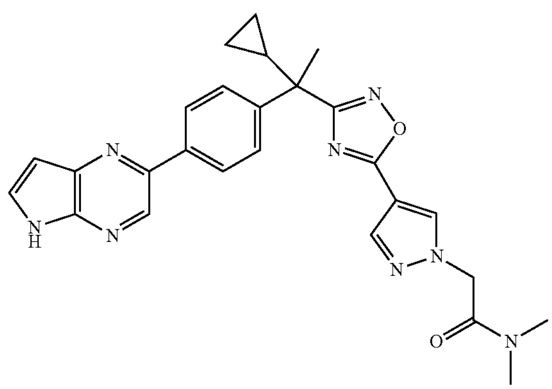 [SMILES: CN(C)C(=O)Cn1cc(-c2nc(C(C)(c3ccc(-c4cnc5[nH]ccc5n4)cc3)C3CC3)no2)cn1] | 2-[4-(3-{1-Cyclopropyl-1-[4-(5H-pyrrolo[2,3-b]pyrazin-2-yl)-phenyl]-ethyl}-[1,2,4]oxadiazol-5-yl)-pyrazol-1-yl]-N,N-dimethyl-acetamide |
| 248 | 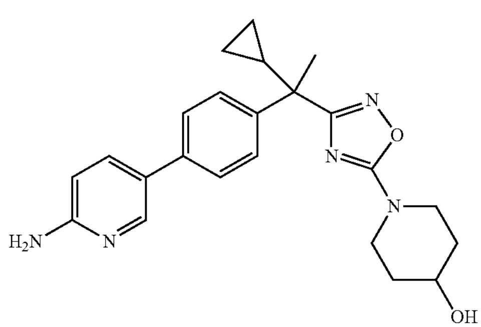 [SMILES: CC(c1ccc(-c2ccc(N)nc2)cc1)(c1noc(N2CCC(O)CC2)n1)C1CC1] | 1-(3-{1-[4-(6-Amino-pyridin-3-yl)-phenyl]-1-cyclopropyl-ethyl}-[1,2,4]oxadiazol-5-yl)-piperidin-4-ol |

TABLE 1-continued

| Example | Structure | Name |
|---|---|---|
| 249 | 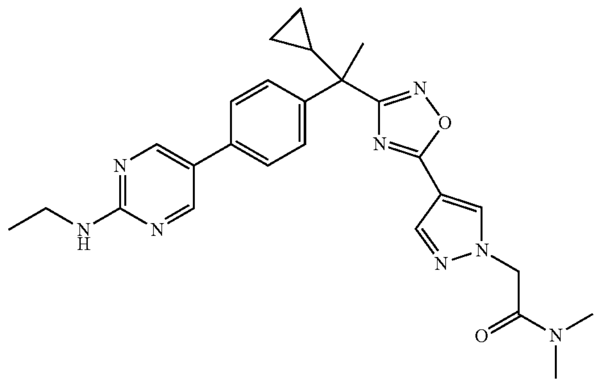 [SMILES: CCNc1ncc(-c2ccc(C(C)(c3noc(-c4cnn(CC(=O)N(C)C)c4)n3)C3CC3)cc2)cn1] | 2-[4-(3-{1-Cyclopropyl-1-[4-(2-ethylamino-pyrimidin-5-yl)-phenyl]-ethyl}-[1,2,4]oxadiazol-5-yl)-pyrazol-1-yl]-N,N-dimethyl-acetamide |
| 250 | 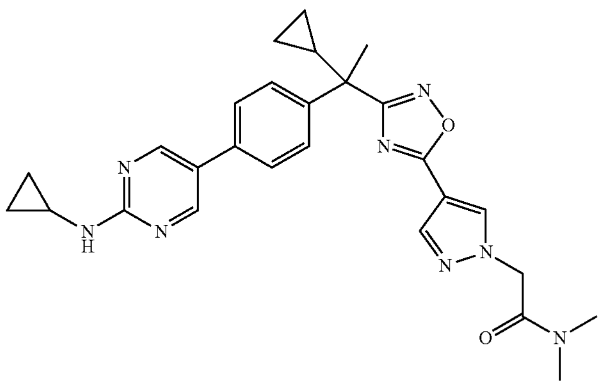 [SMILES: CN(C)C(=O)Cn1cc(-c2nc(C(C)(c3ccc(-c4cnc(NC5CC5)nc4)cc3)C3CC3)no2)cn1] | 2-[4-(3-{1-Cyclopropyl-1-[4-(2-cyclopropylamino-pyrimidin-5-yl)-phenyl]-ethyl}-[1,2,4]oxadiazol-5-yl)-pyrazol-1-yl]-N,N-dimethyl-acetamide |
| 251 | 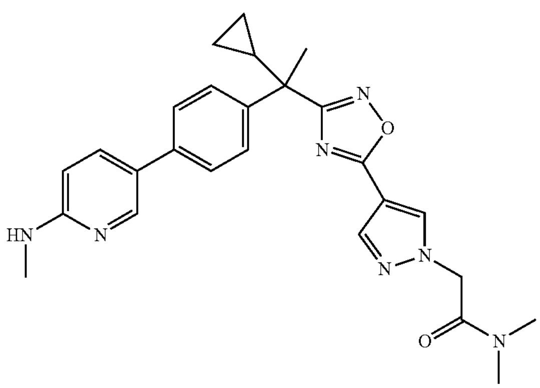 [SMILES: CNc1ccc(-c2ccc(C(C)(c3noc(-c4cnn(CC(=O)N(C)C)c4)n3)C3CC3)cc2)cn1] | 2-[4-(3-{1-Cyclopropyl-1-[4-(6-methylamino-pyridin-3-yl)-phenyl]-ethyl}-[1,2,4]oxadiazol-5-yl)-pyrazol-1-yl]-N,N-dimethyl-acetamide |
| 252 | 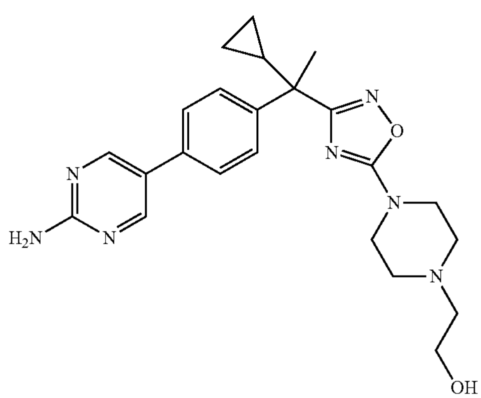 [SMILES: CC(c1ccc(-c2cnc(N)nc2)cc1)(c1noc(N2CCN(CCO)CC2)n1)C1CC1] | 2-[4-(3-{1-[4-(2-Amino-pyrimidin-5-yl)-phenyl]-1-cyclopropyl-ethyl}-[1,2,4]oxadiazol-5-yl)-piperazin-1-yl]-ethanol |

TABLE 1-continued

| Example | Structure | Name |
|---|---|---|
| 253 | 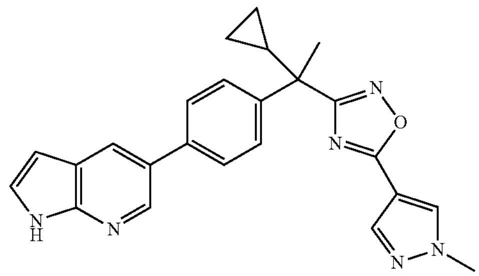 | 5-(4-{1-Cyclopropyl-1-[5-(1-methyl-1H-pyrazol-4-yl)-[1,2,4]oxadiazol-3-yl]-ethyl}-phenyl)-1H-pyrrolo[2,3-b]pyridine |
| 254 | 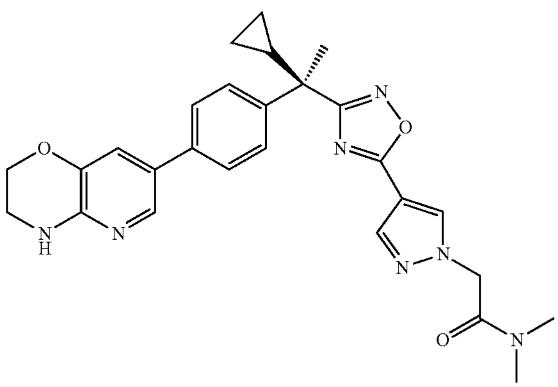 [SMILES: CN(C)C(=O)Cn1cc(-c2nc([C@@](C)(c3ccc(-c4cnc5c(c4)OCCN5)cc3)C3CC3)no2)cn1] | 2-[4-(3-{(R)-1-Cyclopropyl-1-[4-(3,4-dihydro-2H-pyrido[3,2-b][1,4]oxazin-7-yl)-phenyl]-ethyl}-[1,2,4]oxadiazol-5-yl)-pyrazol-1-yl]-N,N-dimethyl-acetamide |
| 255 | 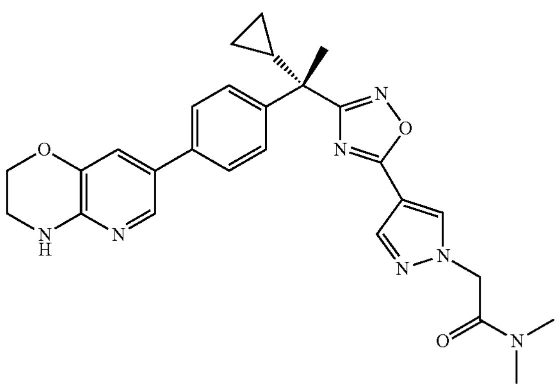 [SMILES: CN(C)C(=O)Cn1cc(-c2nc([C@](C)(c3ccc(-c4cnc5c(c4)OCCN5)cc3)C3CC3)no2)cn1] | 2-[4-(3-{(S)-1-Cyclopropyl-1-[4-(3,4-dihydro-2H-pyrido[3,2-b][1,4]oxazin-7-yl)-phenyl]-ethyl}-[1,2,4]oxadiazol-5-yl)-pyrazol-1-yl]-N,N-dimethyl-acetamide |
| 256 | 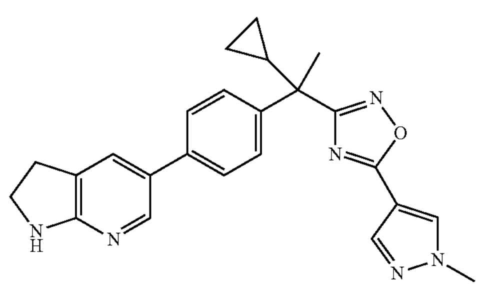 [SMILES: Cn1cc(-c2nc(C(C)(c3ccc(-c4cnc5c(c4)CCN5)cc3)C3CC3)no2)cn1] | 5-(4-{1-Cyclopropyl-1-[5-(1-methyl-1H-pyrazol-4-yl)-[1,2,4]oxadiazol-3-yl]-ethyl}-phenyl)-2,3-dihydro-1H-pyrrolo[2,3-b]pyridine |

TABLE 1-continued

| Example | Structure | Name |
|---|---|---|
| 257 | 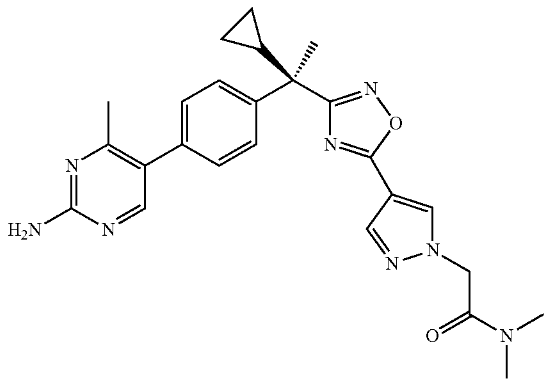 [SMILES: Cc1nc(N)ncc1-c1ccc([C@](C)(c2noc(-c3cnn(CC(=O)N(C)C)c3)n2)C2CC2)cc1] | 2-[4-(3-{(R)-1-[4-(2-Amino-4-methyl-pyrimidin-5-yl)-phenyl]-1-cyclopropyl-ethyl}-[1,2,4]oxadiazol-5-yl)-pyrazol-1-yl]-N,N-dimethyl-acetamide |
| 258 | 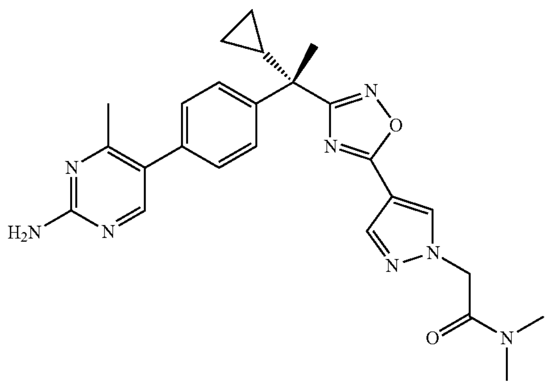 | 2-[4-(3-{(S)-1-[4-(2-Amino-4-methyl-pyrimidin-5-yl)-phenyl]-1-cyclopropyl-ethyl}-[1,2,4]oxadiazol-5-yl)-pyrazol-1-yl]-N,N-dimethyl-acetamide |
| 259 | 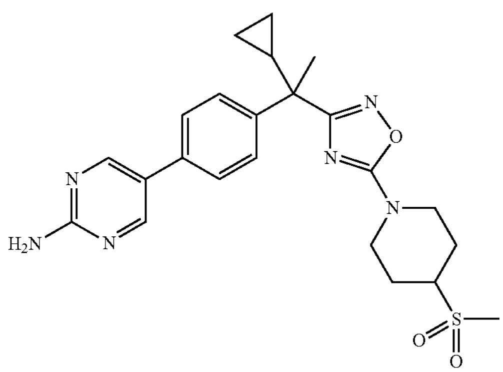 [SMILES: CC(c1ccc(-c2cnc(N)nc2)cc1)(c1noc(N2CCC(S(C)(=O)=O)CC2)n1)C1CC1] | 5-(4-{1-Cyclopropyl-1-[5-(4-methanesulfonyl-piperidin-1-yl)-[1,2,4]oxadiazol-3-yl]-ethyl}-phenyl)-pyrimidin-2-ylamine |
| 260 | 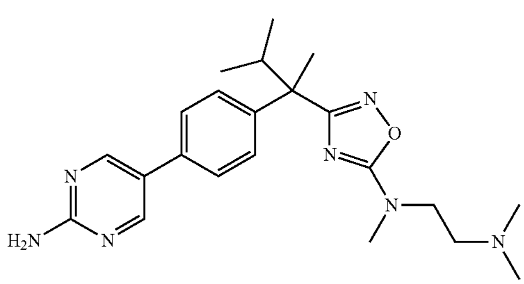 [SMILES: CC(C)C(C)(c1ccc(-c2cnc(N)nc2)cc1)c1noc(N(C)CCN(C)C)n1] | N-(3-{1-[4-(2-Amino-pyrimidin-5-yl)-phenyl]-1,2-dimethyl-propyl}-[1,2,4]oxadiazol-5-yl)-N',N',N'-trimethyl-ethane-1,2-diamine |

| Example | Structure | Name |
|---|---|---|
| 261 | 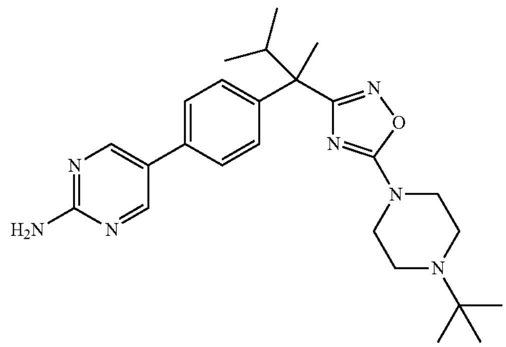 [SMILES: CC(C)C(C)(c1ccc(-c2cnc(N)nc2)cc1)c1noc(N2CCN(C(C)(C)C)CC2)n1] | 5-(4-{1-[5-(4-tert-Butyl-piperazin-1-yl)-[1,2,4]oxadiazol-3-yl]-1,2-dimethyl-propyl}-phenyl)-pyrimidin-2-ylamine |
| 262 | 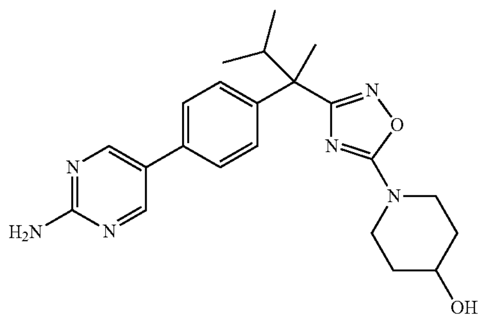 [SMILES: CC(C)C(C)(c1ccc(-c2cnc(N)nc2)cc1)c1noc(N2CCC(O)CC2)n1] | 1-(3-{1-[4-(2-Amino-pyrimidin-5-yl)-phenyl]-1,2-dimethyl-propyl}-[1,2,4]oxadiazol-5-yl)-piperidin-4-ol |
| 263 | 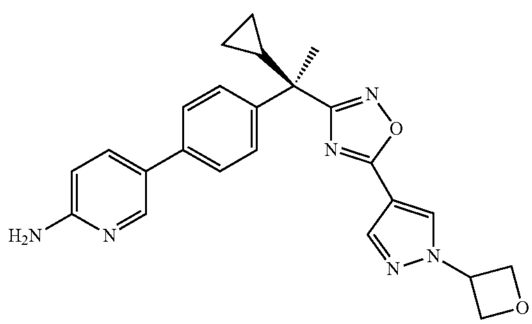 [SMILES: C[C@@](c1ccc(-c2ccc(N)nc2)cc1)(c1noc(-c2cnn(C3COC3)c2)n1)C1CC1] | 5-(4-{(R)-1-Cyclopropyl-1-[5-(1-oxetan-3-yl-1H-pyrazol-4-yl)-[1,2,4]oxadiazol-3-yl]-ethyl}-phenyl)-pyridin-2-ylamine |
| 264 | 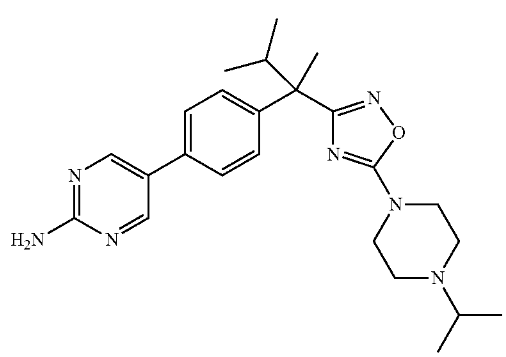 [SMILES: CC(C)N1CCN(c2nc(C(C)(c3ccc(-c4cnc(N)nc4)cc3)C(C)C)no2)CC1] | 5-(4-{1-[5-(4-Isopropyl-piperazin-1-yl)-[1,2,4]oxadiazol-3-yl]-1,2-dimethyl-propyl}-phenyl)-pyrimidin-2-ylamine |

TABLE 1-continued

| Example | Structure | Name |
|---|---|---|
| 265 | 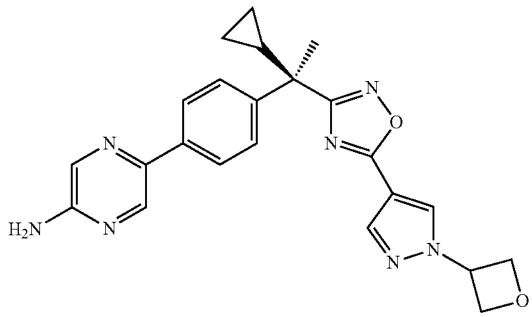 [SMILES: C[C@@](c1ccc(-c2cnc(N)cn2)cc1)(c1noc(-c2cnn(C3COC3)c2)n1)C1CC1] | 5-(4-{(R)-1-Cyclopropyl-1-[5-(1-oxetan-3-yl-1H-pyrazol-4-yl)-[1,2,4]oxadiazol-3-yl]-ethyl}-phenyl)-pyrazin-2-ylamine; compound with trifluoro-acetic acid |
| 266 | 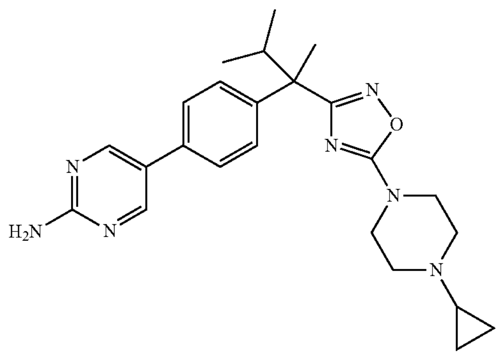 [SMILES: CC(C)C(C)(c1ccc(-c2cnc(N)nc2)cc1)c1noc(N2CCN(C3CC3)CC2)n1] | 5-(4-{1-[5-(4-Cyclopropyl-piperazin-1-yl)-[1,2,4]oxadiazol-3-yl]-1,2-dimethyl-propyl}-phenyl)-pyrimidin-2-ylamine |
| 267 | 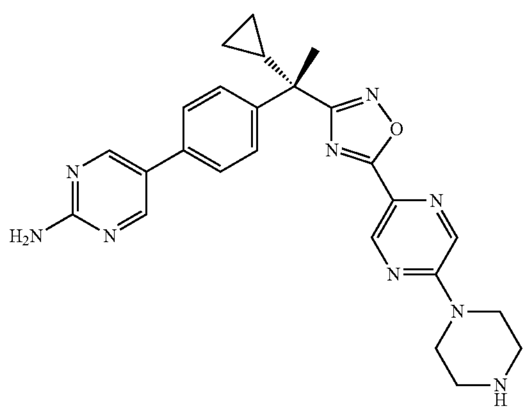 [SMILES: C[C@](c1ccc(-c2cnc(N)nc2)cc1)(c1noc(-c2cnc(N3CCNCC3)cn2)n1)C1CC1] | 5-(4-{(S)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyrimidin-2-ylamine |
| 268 | 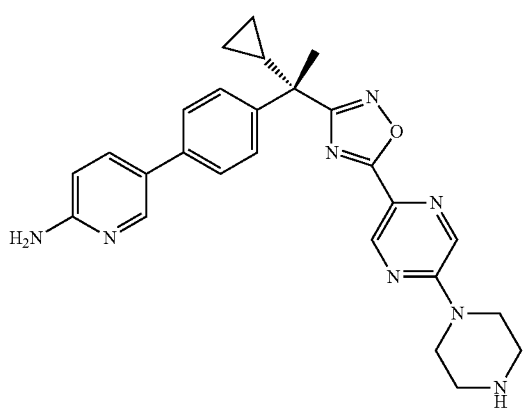 | 5-(4-{(S)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyridin-2-ylamine |

TABLE 1-continued

| Example | Structure | Name |
|---|---|---|
| 269 | 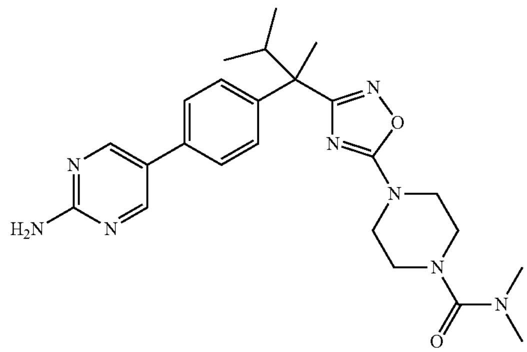 [SMILES: CC(C)C(C)(c1ccc(-c2cnc(N)nc2)cc1)c1noc(N2CCN(C(=O)N(C)C)CC2)n1] | 4-(3-{1-[4-(2-Amino-pyrimidin-5-yl)-phenyl]-1,2-dimethyl-propyl}-[1,2,4]oxadiazol-5-yl)-piperazine-1-carboxylic acid dimethylamide |
| 270 | 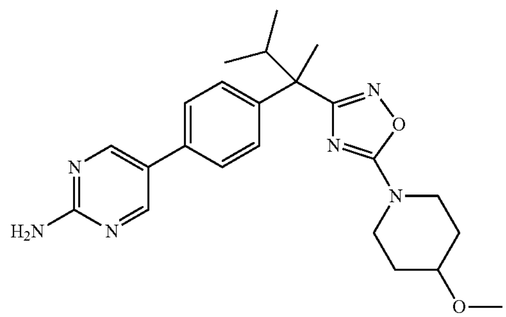 [SMILES: COC1CCN(c2nc(C(C)(c3ccc(-c4cnc(N)nc4)cc3)C(C)C)no2)CC1] | 5-(4-{1-[5-(4-Methoxy-piperidin-1-yl)-[1,2,4]oxadiazol-3-yl]-1,2-dimethyl-propyl}-phenyl)-pyrimidin-2-ylamine |
| 271 | 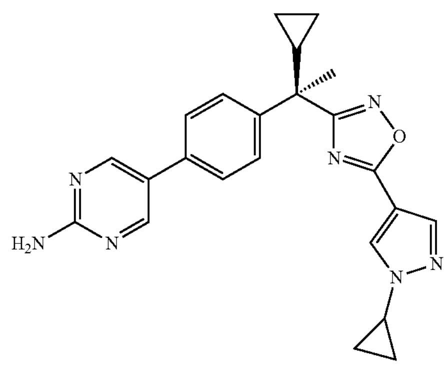 [SMILES: C[C@@](c1ccc(-c2cnc(N)nc2)cc1)(c1noc(-c2cnn(C3CC3)c2)n1)C1CC1] | 5-(4-{(R)-1-Cyclopropyl-1-[5-(1-cyclopropyl-1H-pyrazol-4-yl)-[1,2,4]oxadiazol-3-yl]-ethyl}-phenyl)-pyrimidin-2-ylamine |
| 272 | 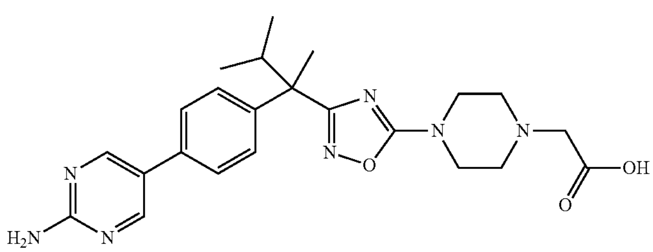 | [4-(3-{1-[4-(2-Amino-pyrimidin-5-yl)-phenyl]-1,2-dimethyl-propyl}-[1,2,4]oxadiazol-5-yl)-piperazin-1-yl]-acetic acid |
| 273 | 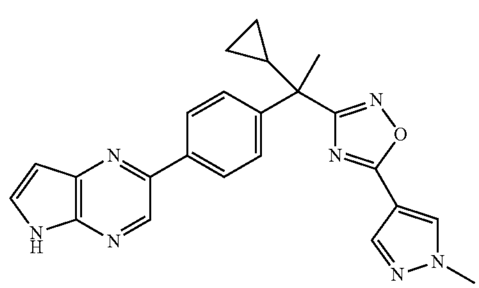 [SMILES: Cn1cc(-c2nc(C(C)(c3ccc(-c4cnc5[nH]ccc5n4)cc3)C3CC3)no2)cn1] | 2-(4-{1-Cyclopropyl-1-[5-(1-methyl-1H-pyrazol-4-yl)-[1,2,4]oxadiazol-3-yl]-ethyl}-phenyl)-5H-pyrrolo[2,3-b]pyrazine |

TABLE 1-continued

| Example | Structure | Name |
|---|---|---|
| 274 | 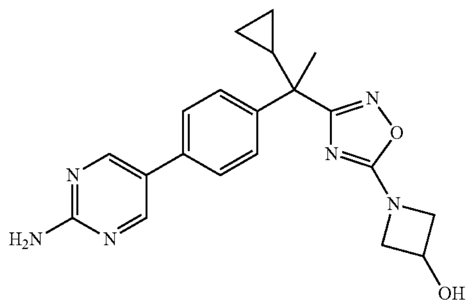 [SMILES: CC(c1ccc(-c2cnc(N)nc2)cc1)(c1noc(N2CC(O)C2)n1)C1CC1] | 1-(3-{1-[4-(2-Amino-pyrimidin-5-yl)-phenyl]-1-cyclopropyl-ethyl}-[1,2,4]oxadiazol-5-yl)-azetidin-3-ol |
| 275 | 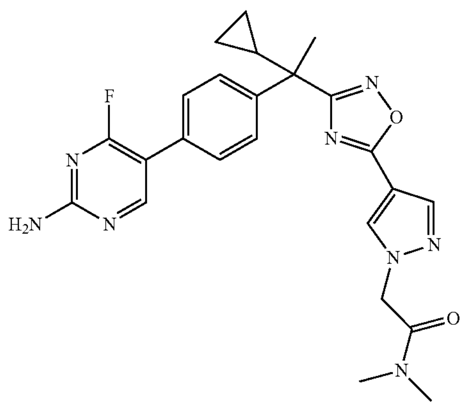 [SMILES: CN(C)C(=O)Cn1cc(-c2nc(C(C)(c3ccc(-c4cnc(N)nc4F)cc3)C3CC3)no2)cn1] | 2-[4-(3-{1-[4-(2-Amino-4-fluoro-pyrimidin-5-yl)-phenyl]-1-cyclopropyl-ethyl}-[1,2,4]oxadiazol-5-yl)-pyrazol-1-yl]-N,N-dimethyl-acetamide |
| 276 | 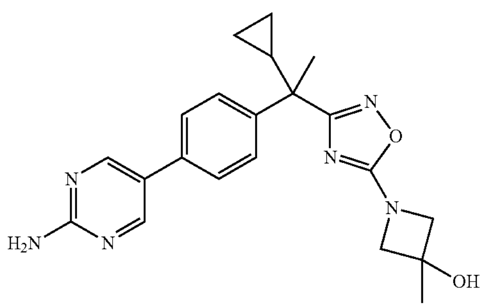 [SMILES: CC1(O)CN(c2nc(C(C)(c3ccc(-c4cnc(N)nc4)cc3)C3CC3)no2)C1] | 1-(3-{1-[4-(2-Amino-pyrimidin-5-yl)-phenyl]-1-cyclopropyl-ethyl}-[1,2,4]oxadiazol-5-yl)-3-methyl-azetidin-3-ol |
| 277 | 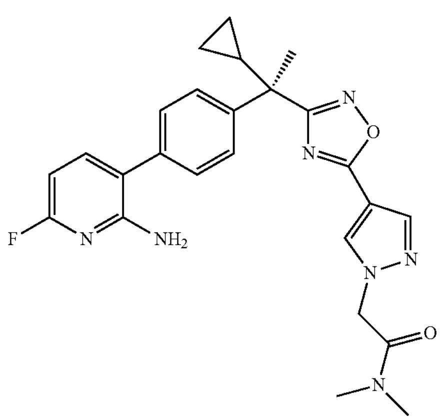 [SMILES: CN(C)C(=O)Cn1cc(-c2nc([C@@](C)(c3ccc(-c4ccc(F)nc4N)cc3)C3CC3)no2)cn1] | 2-[4-(3-{1-[4-(2-Amino-6-fluoro-pyridin-3-yl)-phenyl]-1-cyclopropyl-ethyl}-[1,2,4]oxadiazol-5-yl)-pyrazol-1-yl]-N,N-dimethyl-acetamide |

TABLE 1-continued

| Example | Structure | Name |
|---|---|---|
| 278 | 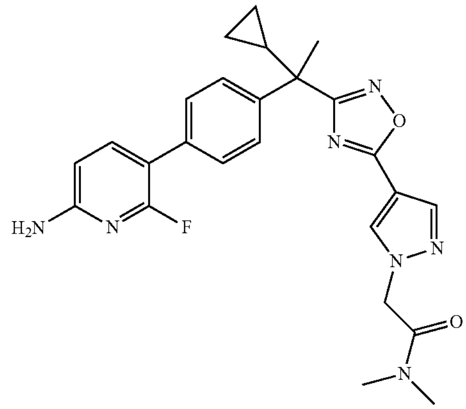 [SMILES: CN(C)C(=O)Cn1cc(-c2nc(C(C)(c3ccc(-c4ccc(N)nc4F)cc3)C3CC3)no2)cn1] | 2-[4-(3-{1-[4-(6-Amino-2-fluoro-pyridin-3-yl)-phenyl]-1-cyclopropyl-ethyl}-[1,2,4]oxadiazol-5-yl)-pyrazol-1-yl]-N,N-dimethyl-acetamide idin-3-yl)-phenyl]-1-cyclopropyl-ethyl}-[1,2,4]oxadiazol-5-yl)-pyrazol-1-yl]-N,N-dimethyl-acetamide |
| 279 | 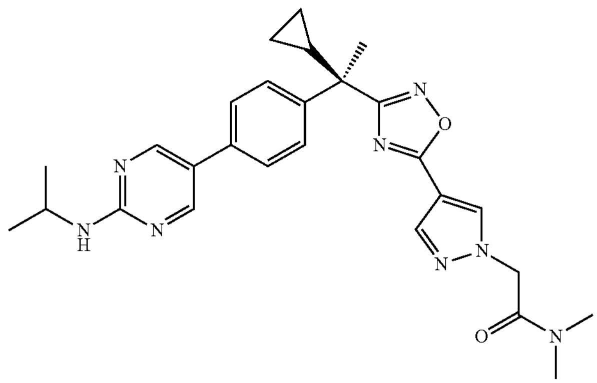 [SMILES: CC(C)Nc1ncc(-c2ccc([C@](C)(c3noc(-c4cnn(CC(=O)N(C)C)c4)n3)C3CC3)cc2)cn1] | 2-[4-(3-{(R)-1-Cyclopropyl-1-[4-(2-isopropylamino-pyrimidin-5-yl)-phenyl]-ethyl}-[1,2,4]oxadiazol-5-yl)-pyrazol-1-yl]-N,N-dimethyl-acetamide |
| 280 | 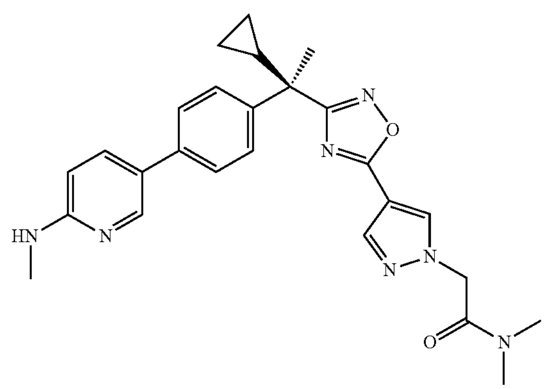 [SMILES: CNc1ccc(-c2ccc([C@](C)(c3noc(-c4cnn(CC(=O)N(C)C)c4)n3)C3CC3)cc2)cn1] | 2-[4-(3-{(R)-1-Cyclopropyl-1-[4-(6-methylamino-pyridin-3-yl)-phenyl]-ethyl}-[1,2,4]oxadiazol-5-yl)-pyrazol-1-yl]-N,N-dimethyl-acetamide |
| 281 | 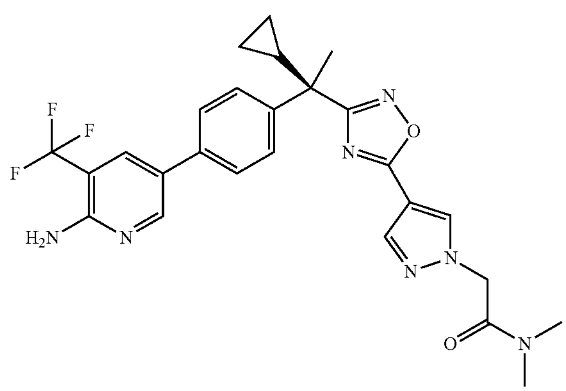 [SMILES: CN(C)C(=O)Cn1cc(-c2nc([C@@](C)(c3ccc(-c4cnc(N)c(C(F)(F)F)c4)cc3)C3CC3)no2)cn1] | 2-[4-(3-{(R)-1-[4-(6-Amino-5-trifluoromethyl-pyridin-3-yl)-phenyl]-1-cyclopropyl-ethyl}-[1,2,4]oxadiazol-5-yl)-pyrazol-1-yl]-N,N-dimethyl-acetamide |

| Example | Structure | Name |
|---|---|---|
| 282 | 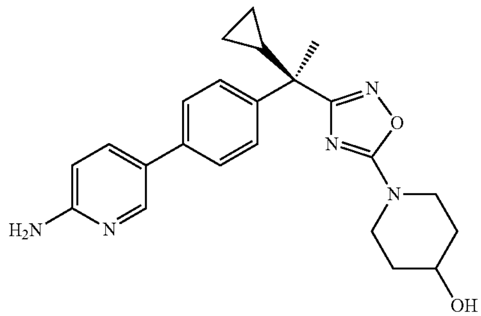 [SMILES: C[C@@](c1ccc(-c2ccc(N)nc2)cc1)(c1noc(N2CCC(O)CC2)n1)C1CC1] | 1-(3-{(R)-1-[4-(6-Amino-pyridin-3-yl)-phenyl]-1-cyclopropyl-ethyl}-[1,2,4]oxadiazol-5-yl)-piperidin-4-ol |
| 283 | 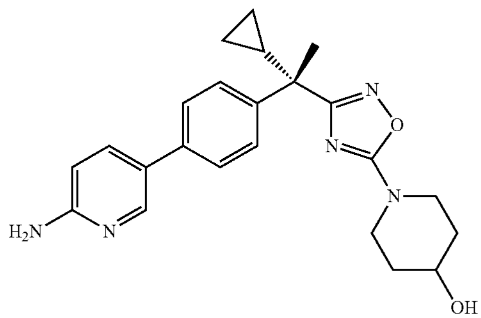 [SMILES: C[C@](c1ccc(-c2ccc(N)nc2)cc1)(c1noc(N2CCC(O)CC2)n1)C1CC1] | 1-(3-{(S)-1-[4-(6-Amino-pyridin-3-yl)-phenyl]-1-cyclopropyl-ethyl}-[1,2,4]oxadiazol-5-yl)-piperidin-4-ol |
| 284 | 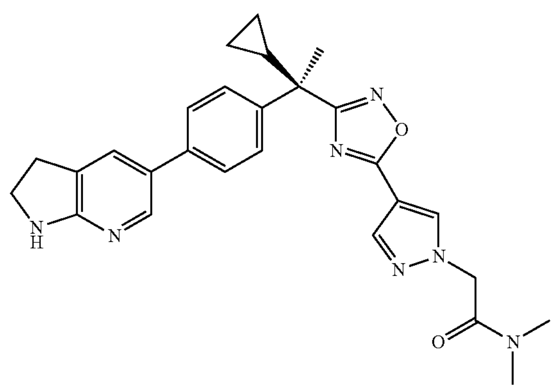 [SMILES: CN(C)C(=O)Cn1cc(-c2nc([C@@](C)(c3ccc(-c4cnc5c(c4)CCN5)cc3)C3CC3)no2)cn1] | 2-[4-(3-{(R)-1-Cyclopropyl-1-[4-(2,3-dihydro-1H-pyrrolo[2,3-b]pyridin-5-yl)-phenyl]-ethyl}-[1,2,4]oxadiazol-5-yl)-pyrazol-1-yl]-N,N-dimethyl-acetamide |
| 285 | 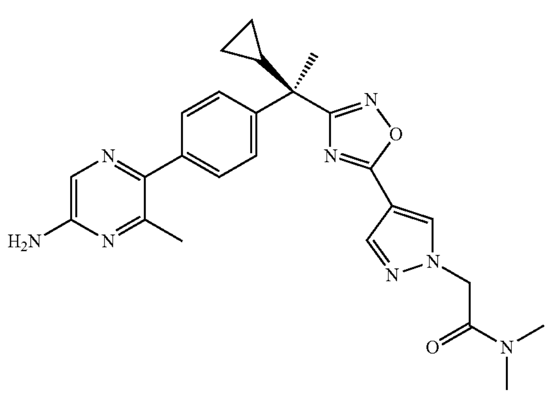 [SMILES: Cc1nc(N)cnc1-c1ccc([C@](C)(c2noc(-c3cnn(CC(=O)N(C)C)c3)n2)C2CC2)cc1] | 2-[4-(3-{(R)-1-[4-(5-Amino-3-methyl-pyrazin-2-yl)-phenyl]-1-cyclopropyl-ethyl}-[1,2,4]oxadiazol-5-yl)-pyrazol-1-yl]-N,N-dimethyl-acetamide |

TABLE 1-continued

| Example | Structure | Name |
|---|---|---|
| 286 | 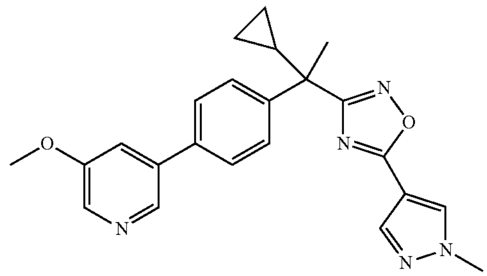 | 3-(4-{1-Cyclopropyl-1-[5-(1-methyl-1H-pyrazol-4-yl)-[1,2,4]oxadiazol-3-yl]-ethyl}-phenyl)-5-methoxy-pyridine |
| 287 | 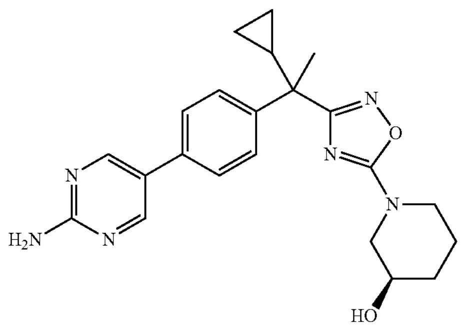 [SMILES: CC(c1ccc(-c2cnc(N)nc2)cc1)(c1noc(N2CCC[C@@H](O)C2)n1)C1CC1] | (R)-1-(3-{1-[4-(2-Amino-pyrimidin-5-yl)-phenyl]-1-cyclopropyl-ethyl}-[1,2,4]oxadiazol-5-yl)-piperidin-3-ol |
| 288 | 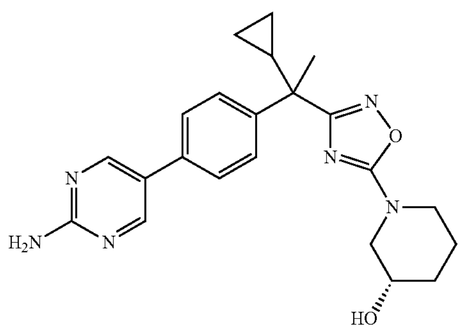 [SMILES: CC(c1ccc(-c2cnc(N)nc2)cc1)(c1noc(N2CCC[C@H](O)C2)n1)C1CC1] | (S)-1-(3-{1-[4-(2-Amino-pyrimidin-5-yl)-phenyl]-1-cyclopropyl-ethyl}-[1,2,4]oxadiazol-5-yl)-piperidin-3-ol |
| 289 | 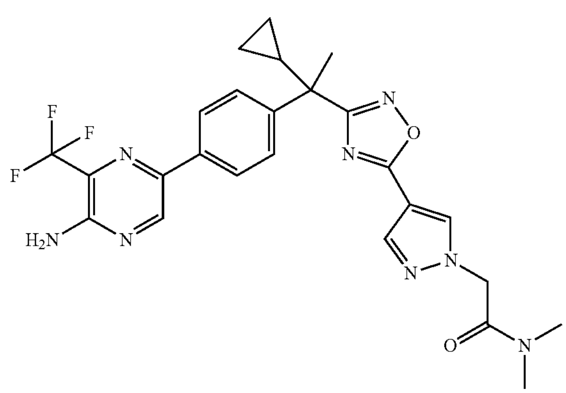 [SMILES: CN(C)C(=O)Cn1cc(-c2nc(C(C)(c3ccc(-c4cnc(N)c(C(F)(F)F)n4)cc3)C3CC3)no2)cn1] | 2-[4-(3-{1-[4-(5-Amino-6-trifluoromethyl-pyrazin-2-yl)-phenyl]-1-cyclopropyl-ethyl}-[1,2,4]oxadiazol-5-yl)-pyrazol-1-yl]-N,N-dimethyl-acetamide |
| 290 | 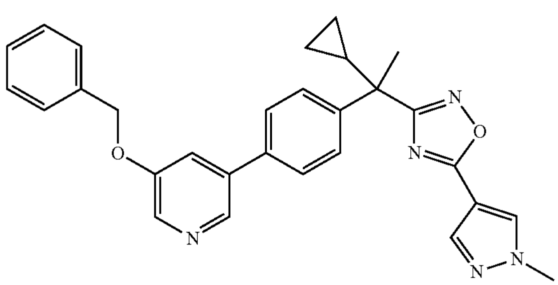 [SMILES: Cn1cc(-c2nc(C(C)(c3ccc(-c4cncc(OCc5ccccc5)c4)cc3)C3CC3)no2)cn1] | 3-Benzyloxy-5-(4-{1-cyclopropyl-1-[5-(1-methyl-1H-pyrazol-4-yl)-[1,2,4]oxadiazol-3-yl]-ethyl}-phenyl)-pyridine |

TABLE 1-continued

| Example | Structure | Name |
| --- | --- | --- |
| 291 | 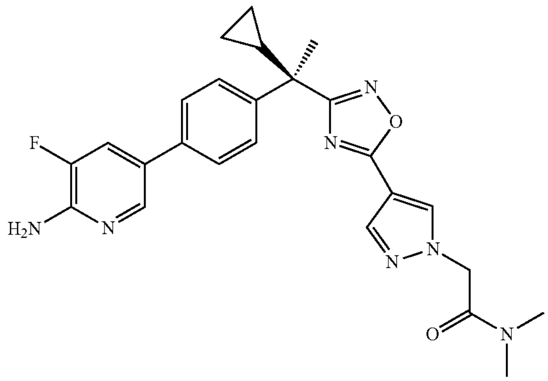 [SMILES: CN(C)C(=O)Cn1cc(-c2nc([C@@](C)(c3ccc(-c4cnc(N)c(F)c4)cc3)C3CC3)no2)cn1] | 2-[4-(3-{(R)-1-[4-(6-Amino-5-fluoro-pyridin-3-yl)-phenyl]-1-cyclopropyl-ethyl}-[1,2,4]oxadiazol-5-yl)-pyrazol-1-yl]-N,N-dimethyl-acetamide |
| 292 | 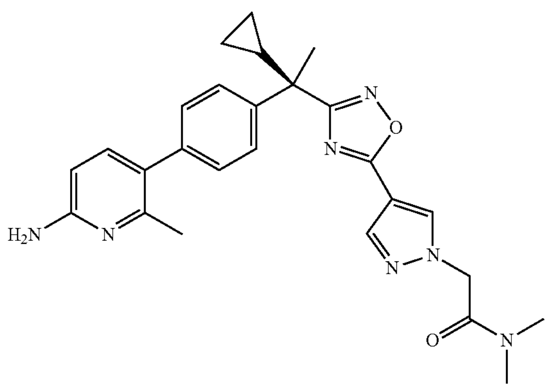 [SMILES: Cc1nc(N)ccc1-c1ccc([C@](C)(c2noc(-c3cnn(CC(=O)N(C)C)c3)n2)C2CC2)cc1] | 2-[4-(3-{(R)-1-[4-(6-Amino-2-methyl-pyridin-3-yl)-phenyl]-1-cyclopropyl-ethyl}-[1,2,4]oxadiazol-5-yl)-pyrazol-1-yl]-N,N-dimethyl-acetamide |
| 293 | 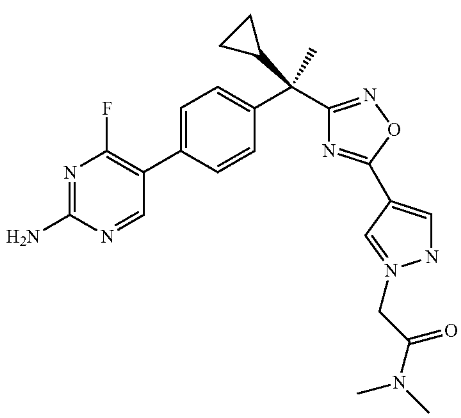 | 2-[4-(3-{(R)-1-[4-(2-Amino-4-fluoro-pyrimidin-5-yl)-phenyl]-1-cyclopropyl-ethyl}-[1,2,4]oxadiazol-5-yl)-pyrazol-1-yl]-N,N-dimethyl-acetamide |
| 294 | 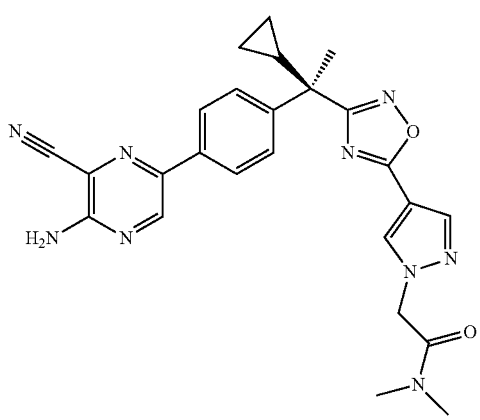 [SMILES: CN(C)C(=O)Cn1cc(-c2nc([C@@](C)(c3ccc(-c4cnc(N)c(C#N)n4)cc3)C3CC3)no2)cn1] | 2-[4-(3-{(R)-1-[4-(5-Amino-6-cyano-pyrazin-2-yl)-phenyl]-1-cyclopropyl-ethyl}-[1,2,4]oxadiazol-5-yl)-pyrazol-1-yl]-N,N-dimethyl-acetamide |

TABLE 1-continued

| Example | Structure | Name |
|---|---|---|
| 295 | 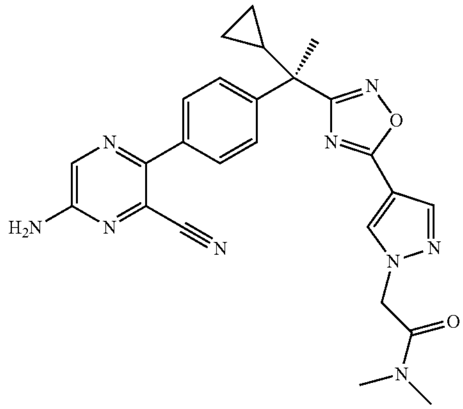 [SMILES: CN(C)C(=O)Cn1cc(-c2nc([C@@](C)(c3ccc(-c4ncc(N)nc4C#N)cc3)C3CC3)no2)cn1] | 2-[4-(3-{1-[4-(5-Amino-3-cyano-pyrazin-2-yl)-phenyl]-1-cyclopropyl-ethyl}-[1,2,4]oxadiazol-5-yl)-pyrazol-1-yl]-N,N-dimethyl-acetamide |
| 296 | 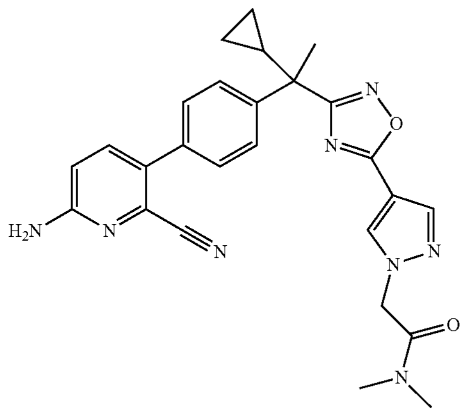 [SMILES: CN(C)C(=O)Cn1cc(-c2nc(C(C)(c3ccc(-c4ccc(N)nc4C#N)cc3)C3CC3)no2)cn1] | 2-[4-(3-{1-[4-(6-Amino-2-cyano-pyridin-3-yl)-phenyl]-1-cyclopropyl-ethyl}-[1,2,4]oxadiazol-5-yl)-pyrazol-1-yl]-N,N-dimethyl-acetamide |
| 297 | 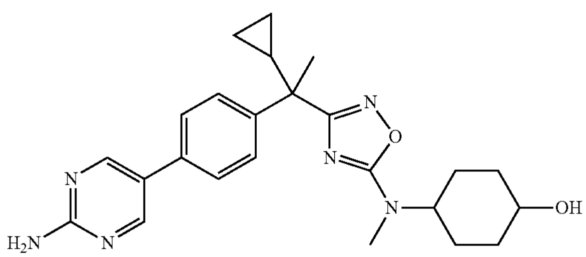 [SMILES: CN(c1nc(C(C)(c2ccc(-c3cnc(N)nc3)cc2)C2CC2)no1)C1CCC(O)CC1] | 4-[(3-{1-[4-(2-Amino-pyrimidin-5-yl)-phenyl]-1-cyclopropyl-ethyl}-[1,2,4]oxadiazol-5-yl)-methyl-amino]-cyclohexanol |
| 298 | 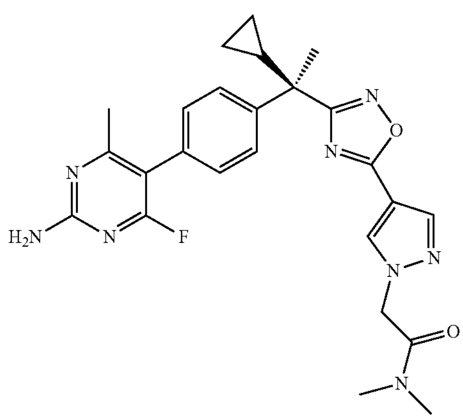 [SMILES: Cc1nc(N)nc(F)c1-c1ccc([C@](C)(c2noc(-c3cnn(CC(=O)N(C)C)c3)n2)C2CC2)cc1] | 2-[4-(3-{(R)-1-[4-(2-Amino-4-fluoro-6-methyl-pyrimidin-5-yl)-phenyl]-1-cyclopropyl-ethyl}-[1,2,4]oxadiazol-5-yl)-pyrazol-1-yl]-N,N-dimethyl-acetamide |

In one embodiment, the invention relates to any of the compounds depicted in Table 1 above or pharmaceutically acceptable salts thereof.

Representative compounds of the invention show activity in the FLAP binding assay, described in the assessment of biological properties section, as shown in Table 2.

TABLE 2

| Example | FLAP binding IC$_{50}$ (nM) | Human Whole Blood IC$_{50}$ (nM) |
|---|---|---|
| 1 | 57 | |
| 2 | 5.1 | 680 |
| 3 | 1.7 | 94 |
| 4 | 1.6 | 310 |
| 5 | 1.6 | 150 |
| 6 | 1.1 | 70 |
| 7 | 3.1 | 560 |
| 8 | 3.8 | 530 |
| 9 | 2.9 | 210 |
| 10 | 4.3 | |
| 11 | 1.9 | 89 |
| 12 | 3.3 | 290 |
| 13 | 3.6 | 460 |
| 14 | 4.6 | 140 |
| 15 | 2.0 | 46 |
| 16 | 2.5 | 110 |
| 17 | 24 | 510 |
| 18 | 3.3 | 320 |
| 19 | 5.8 | 260 |
| 20 | 10 | 3200 |
| 21 | 5.5 | 87 |
| 22 | 4.2 | 46 |
| 23 | 6.9 | 170 |
| 24 | 19 | 410 |
| 25 | 6.0 | 170 |
| 26 | 9.1 | 160 |
| 27 | 12 | 330 |
| 28 | 26 | 320 |
| 29 | 5.3 | 190 |
| 30 | 5.0 | 60 |
| 31 | 1.6 | 200 |
| 32 | 18 | 2500 |
| 33 | 6.6 | 210 |
| 34 | 3.7 | 160 |
| 35 | 3.2 | 360 |
| 36 | 3.2 | 170 |
| 37 | 7.4 | 250 |
| 38 | 2.2 | 97 |
| 39 | 2.1 | 110 |
| 40 | 2.3 | 100 |
| 41 | 2.2 | 170 |
| 42 | 1.5 | 25 |
| 43 | 2.5 | 30 |
| 44 | 2.2 | 150 |
| 45 | 3.1 | 140 |
| 46 | 1.6 | 33 |
| 47 | 7.7 | 360 |
| 48 | 6.8 | 190 |
| 49 | 19 | 680 |
| 50 | 1.3 | 95 |
| 51 | 3.9 | 140 |
| 52 | 2.4 | 26 |
| 53 | 27 | 450 |
| 54 | 2.6 | 27 |
| 55 | 11 | 200 |
| 56 | 2.4 | 79 |
| 57 | 6.8 | 150 |
| 58 | 11 | 190 |
| 59 | 1.1 | 76 |
| 60 | 4.0 | 140 |
| 61 | 1.3 | 15 |
| 62 | 18 | 350 |
| 63 | 1.1 | 14 |
| 64 | 16 | 410 |
| 65 | 75 | 1500 |
| 66 | 11 | 330 |
| 67 | 6.2 | 190 |
| 68 | 6.7 | 93 |
| 69 | 7.7 | 120 |
| 70 | 7.1 | 590 |
| 71 | 17 | 900 |
| 72 | 12 | 440 |
| 73 | 28 | 990 |
| 74 | 17 | 640 |
| 75 | 23 | 260 |
| 76 | 35 | 270 |
| 77 | 1.7 | 36 |
| 78 | 1.3 | 240 |
| 79 | 150 | 2200 |
| 80 | 23 | 350 |
| 81 | 11 | 180 |
| 82 | 13 | 220 |
| 83 | 26 | 1100 |
| 84 | 120 | 1700 |
| 85 | 48 | >5000 |
| 86 | 190 | >5000 |
| 87 | 41 | 970 |
| 88 | 51% inh@1000 nM | >5000 |
| 89 | 13 | 270 |
| 90 | 63 | 1500 |
| 91 | 54 | 1300 |
| 92 | 110 | >5000 |
| 93 | 240 | >5000 |
| 94 | 350 | >5000 |
| 95 | 130 | >5000 |
| 96 | 7.5 | 150 |
| 97 | 8.8 | 170 |
| 98 | 12 | 570 |
| 99 | 3.9 | 200 |
| 100 | 2.3 | 110 |
| 101 | 280 | >5000 |
| 102 | 1.6 | 51 |
| 103 | 130 | 2700 |
| 104 | 6.1 | 130 |
| 105 | 490 | >5000 |
| 106 | 4.8 | 76 |
| 107 | 0.86 | 17 |
| 108 | 8.7 | 320 |
| 109 | 46 | 1500 |
| 110 | 190 | 2800 |
| 111 | 15 | 2900 |
| 112 | 190 | >5000 |
| 113 | 66 | 3100 |
| 114 | 21 | 1100 |
| 115 | 1.9 | 58 |
| 116 | 150 | 2000 |
| 117 | 31 | 1200 |
| 118 | 9.9 | 820 |
| 119 | 9.2 | 900 |
| 120 | 40 | 2100 |
| 121 | 2.6 | 91 |
| 122 | 140 | 3200 |
| 123 | 1.7 | 42 |
| 124 | 2.3 | 31 |
| 125 | 1.5 | 290 |
| 126 | 4.6 | 260 |
| 127 | 2.9 | 650 |
| 128 | 1.6 | 240 |
| 129 | 2 | 180 |
| 130 | 1.4 | 180 |
| 131 | 8.7 | |
| 132 | 2.8 | 330 |
| 133 | 1.6 | 190 |
| 134 | 8.3 | 190 |
| 135 | 1.4 | 250 |
| 136 | 5.4 | 320 |
| 137 | 2.8 | 77 |
| 138 | 15 | 760 |
| 139 | 4.4 | |
| 140 | 4.1 | 710 |
| 141 | 1.5 | 530 |
| 142 | 1.1 | 59 |
| 143 | 4.1 | 360 |
| 144 | 3.1 | 26 |
| 145 | 17 | 2500 |
| 146 | 1.3 | 46 |
| 147 | 2.7 | 86 |
| 148 | 14 | 610 |
| 149 | 58 | |
| 150 | 330 | 1800 |
| 151 | 2.3 | 100 |
| 152 | 3.3 | 270 |
| 153 | 4.6 | 180 |
| 154 | 3.3 | |

TABLE 2-continued

| Example | FLAP binding IC$_{50}$ (nM) | Human Whole Blood IC$_{50}$ (nM) |
|---|---|---|
| 155 | 1.9 | 81 |
| 156 | 15 | |
| 157 | 3.3 | 760 |
| 158 | 3.4 | 55 |
| 159 | 4.6 | 83 |
| 160 | 9.0 | >5000 |
| 161 | 2.0 | 36 |
| 162 | 2.3 | 41 |
| 163 | 0.74 | 30 |
| 164 | 1.4 | 2700 |
| 165 | 2.1 | 89 |
| 166 | 26 | 2400 |
| 167 | 46 | 4300 |
| 168 | 21 | 390 |
| 169 | 14 | 370 |
| 170 | 14 | 310 |
| 171 | 220 | 1900 |
| 172 | 1.1 | 66 |
| 173 | 2.4 | 31 |
| 174 | 1.2 | 19 |
| 175 | 2.2 | 39 |
| 176 | 1.2 | 73 |
| 177 | 8.9 | 66 |
| 178 | 2.2 | 180 |
| 179 | 4.6 | 49 |
| 180 | 2.9 | 29 |
| 181 | 3.3 | 51 |
| 182 | 3.1 | 14 |
| 183 | 5.5 | 39 |
| 184 | 2.0 | 23 |
| 185 | 1.9 | 28 |
| 186 | 20 | 150 |
| 187 | 17 | 23 |
| 188 | 48 | 51 |
| 189 | 13 | 49 |
| 190 | 5.9 | 230 |
| 191 | 5.9 | 17 |
| 192 | 23 | 740 |
| 193 | 18 | 230 |
| 194 | 6.0 | 96 |
| 195 | 4.6 | 280 |
| 196 | 2.2 | 180 |
| 197 | 16 | >5000 |
| 198 | 7.5 | 280 |
| 199 | 32 | 690 |
| 200 | 15 | 250 |
| 201 | 13 | 200 |
| 202 | 46 | 350 |
| 203 | 15 | 130 |
| 204 | 13 | 150 |
| 205 | 11 | 68 |
| 206 | 23 | 310 |
| 207 | 92 | 700 |
| 208 | 13 | 250 |
| 209 | 8.2 | 100 |
| 210 | 4.4 | 190 |
| 211 | 12 | 230 |
| 212 | 12 | 86 |
| 213 | 14 | 330 |
| 214 | 12 | 450 |
| 215 | 3.6 | 28 |
| 216 | 7.7 | 34 |
| 217 | 90 | 1200 |
| 218 | 130 | 920 |
| 219 | 39 | >5000 |
| 220 | 8.5 | 210 |
| 221 | 6.2 | 150 |
| 222 | 130 | 1700 |
| 223 | 7.3 | 55 |
| 224 | 80 | 760 |
| 225 | 16 | 350 |
| 226 | 2.0 | 30 |
| 227 | 3.1 | 21 |
| 228 | 54 | 550 |
| 229 | 99 | 550 |
| 230 | 3.8 | 160 |
| 231 | 120 | 700 |
| 232 | 37 | 370 |
| 233 | 5.2 | 37 |
| 234 | 230 | 1000 |
| 235 | 29 | 780 |
| 236 | 89 | 1300 |
| 237 | 26 | 470 |
| 238 | 5.0 | 29 |
| 239 | 4.1 | 290 |
| 240 | 15 | 190 |
| 241 | 3.4 | 170 |
| 242 | 5.7 | 310 |
| 243 | 12 | 170 |
| 244 | 25 | 270 |
| 245 | 28 | 310 |
| 246 | 19 | 430 |
| 247 | 5.9 | 300 |
| 248 | 10 | 80 |
| 249 | 370 | >5000 |
| 250 | 470 | >5000 |
| 251 | 9.1 | 130 |
| 252 | 15 | 220 |
| 253 | 3.8 | 120 |
| 254 | 2.8 | 210 |
| 255 | 15 | 1800 |
| 256 | 4.5 | 51 |
| 257 | 7.3 | 150 |
| 258 | 430 | 2300 |
| 259 | 16 | 270 |
| 260 | 94 | 900 |
| 261 | 11 | 190 |
| 262 | 11 | 84 |
| 263 | 3.5 | 21 |
| 264 | 11 | 120 |
| 265 | 5.1 | 22 |
| 266 | 16 | 170 |
| 267 | 12 | 390 |
| 268 | 9.3 | 600 |
| 269 | 24 | 230 |
| 270 | 9.8 | 96 |
| 271 | 4.9 | 51 |
| 272 | 280 | >5000 |
| 273 | 6.1 | 56 |
| 274 | 40 | 200 |
| 275 | 11 | 220 |
| 276 | 28 | 260 |
| 277 | 64 | >5000 |
| 278 | 5.0 | 150 |
| 279 | 76 | >5000 |
| 280 | 3.0 | 35 |
| 281 | 5.0 | 160 |
| 282 | 6.5 | 44 |
| 283 | 16 | 920 |
| 284 | 4.7 | 200 |
| 285 | 7.0 | 190 |
| 286 | 16 | 2100 |
| 287 | 7.0 | 150 |
| 288 | 2.5 | 200 |
| 289 | 22 | 1000 |
| 290 | 22 | 2000 |
| 291 | 4.5 | 89 |
| 292 | 8.5 | 150 |
| 293 | 3.5 | 110 |
| 294 | 7.0 | 200 |
| 295 | 7.5 | 150 |
| 296 | 12 | 230 |
| 297 | 8.5 | 79 |
| 298 | 10 | 130 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term $C_{1-3}$ hydroxy also means —$C_{1-3}$alkyl-hydroxy or —$C_{1-3}$alkyl-OH.

The term "$C_{3-10}$ carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl(decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" or "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl, pyridooxazinyl, dihydro-pyridooxazinyl, dihydro-pyrrolopyridinyl, pyrrolopyridinyl, pyrrolopyrazinyl, and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4 \text{ alkyl})_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all Schemes, unless specified otherwise, $R^1$, $R^2$, $R^3$, $R^4$ and $R^5$ in the Formulas below shall have the meaning of $R^1$, $R^2$, $R^3$, $R^4$ and $R^5$ in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, recrystallization and/or preparative HPLC.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

The compounds of Formula (I) may be synthesized according to Scheme 1:

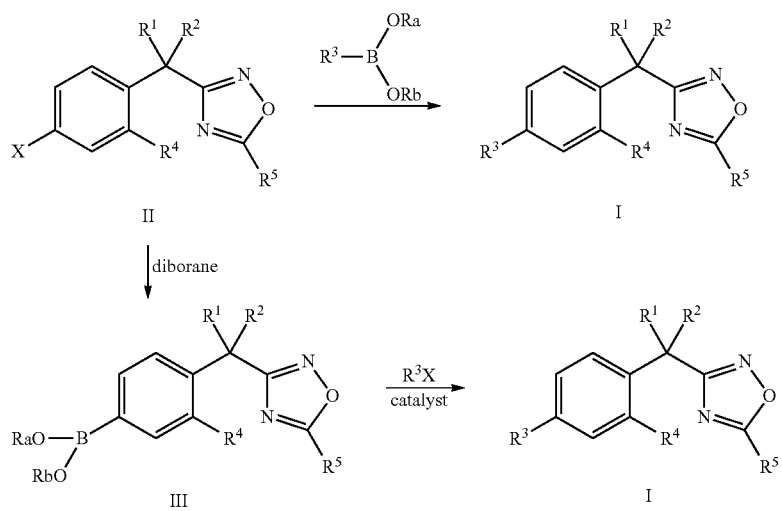

As illustrated in scheme 1, reaction of a compound of formula II with a boronic acid or the corresponding boronic acid ester shown in the above scheme, in a suitable solvent, in the presence of a suitable catalyst, provides a compound of formula (I). Ra and Rb are hydrogen or Ra and Rb together with the oxygen atoms to which they are attached form a 5-6 membered ring optionally substituted with 2-4 methyl groups.

Alternatively, reaction of a compound of formula II with a diborane, under standard reaction conditions, provides a compound of formula III. Coupling the intermediate of formula III with a halide or triflate $R^3X$, in a suitable solvent, in the presence of a suitable catalyst, provides a compound of formula (I). X is chloro, bromo, triflate, or iodo.

The compounds of Formula (I) may be prepared according to Scheme 2:

Scheme 2

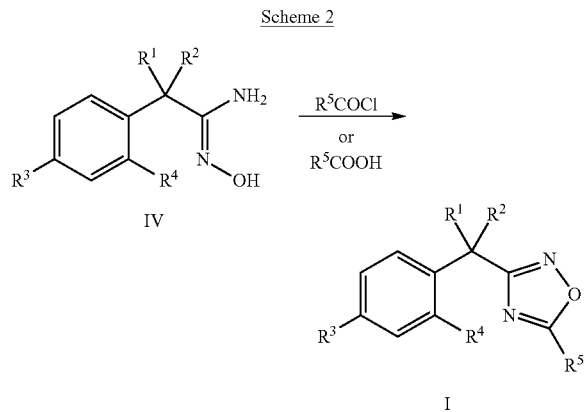

As illustrated in scheme 2, reaction of a compound of formula IV with an acid chloride $R^5COCl$, in a suitable solvent, in the presence of a suitable base, provides a compound of formula (I).

Alternatively, reaction of a compound of formula IV with an acid $R^5COOH$, in a suitable solvent, in the presence of carbonyl diimidazole, or other suitable amide coupling reagent, provides a compound of formula (I).

The intermediate of formula II may be synthesized as outlined in Scheme 3:

Scheme 3

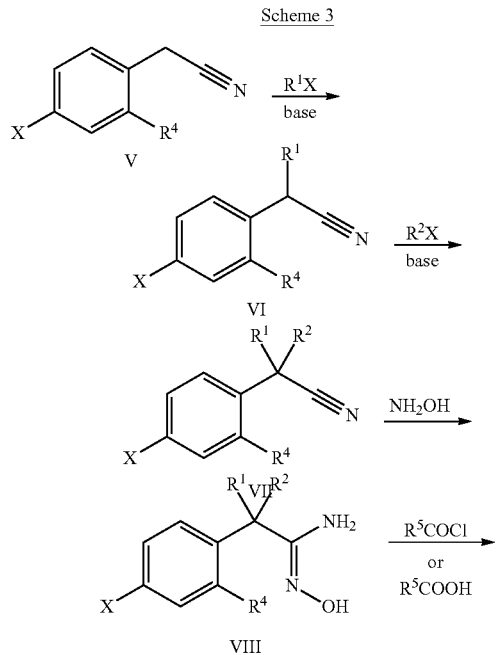

-continued

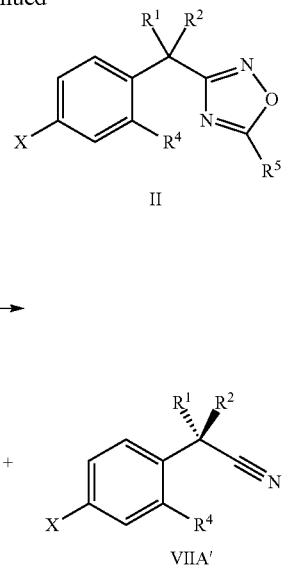

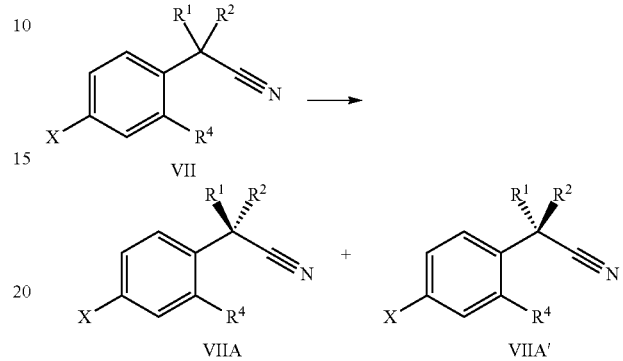

As illustrated in scheme 3, reaction of a nitrile of formula V with a halide $R^1X$, in a suitable solvent, in the presence of a suitable base such as sodium hydride or potassium t-butoxide, provides a substituted nitrile of formula VI. Further reaction of the intermediate of formula VI with a halide $R^2X$, in a suitable solvent, in the presence of a suitable base, provides the corresponding disubstituted nitrile of formula VII. X is chloro, bromo, or iodo. Reaction of the compound of formula VII with hydroxylamine, under standard reaction conditions, provides a compound of formula VIII. Reaction of the compound of formula VIII with an acid chloride $R^5COCl$, in a suitable solvent, in the presence of a suitable base, provides a compound of formula II. Alternatively, reaction of a compound of formula VIII with an acid $R^5COOH$, in a suitable solvent, in the presence of carbonyl diimidazole, or other suitable amide coupling reagent, provides a compound of formula II.

Alternatively, reaction of a compound of formula VIII with a reagent such as carbonyldiimidazole provides a compound of formula II wherein $R^5$ is —OH. Further transformation of this —OH may be carried out by procedures known in the art, to provide additional compounds of formula II.

Nitrile intermediate of formula VII may also be resolved via resolution techniques, known to one skilled in the art, to provide the enantiomers VIIA and VIIA'. Each of these enantiomers may be further converted to a compound of formula I by the reaction sequence shown above in scheme 3.

The intermediate of formula II may also be synthesized as shown in Scheme 4:

Scheme 4

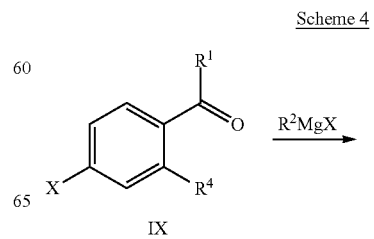

-continued

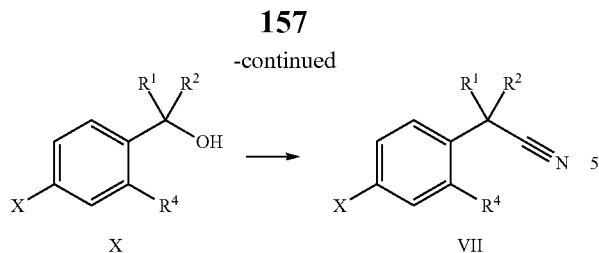

As shown in scheme 4, reaction of a carbonyl compound of formula IX with a grignard reagent R²MgX, in a suitable solvent, provides a hydroxy compound of formula X. Conversion of the hydroxyl group in compound of formula X to a cyano group, using standard procedures, provides a compound of formula VII. The compound of formula VII is converted to the intermediate of formula II by the reactions shown in scheme 3. X in R²MgX is chloro, bromo or iodo.

The intermediate of formula IV may be synthesized according to Scheme 5:

Scheme 5

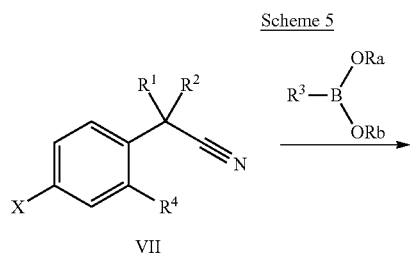

-continued

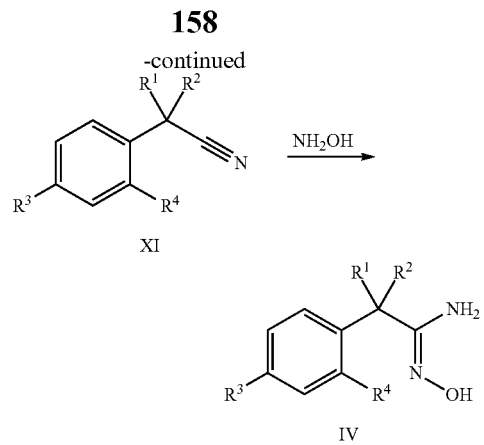

As illustrated above in scheme 5, reaction of a nitrile of formula VII with a boronic acid or the corresponding boronic acid ester shown in the above scheme, in a suitable solvent, in the presence of a suitable catalyst, provides a compound of formula XI. Ra and Rb are hydrogen or Ra and Rb together with the oxygen atoms to which they are attached form a 5-6 membered ring optionally substituted with 2-4 methyl groups. Reaction of a compound of formula XI with hydroxylamine, under standard reaction conditions, provides a compound of formula IV.

The nitrile intermediate of formula VII may be synthesized according to Scheme 6:

Scheme 6

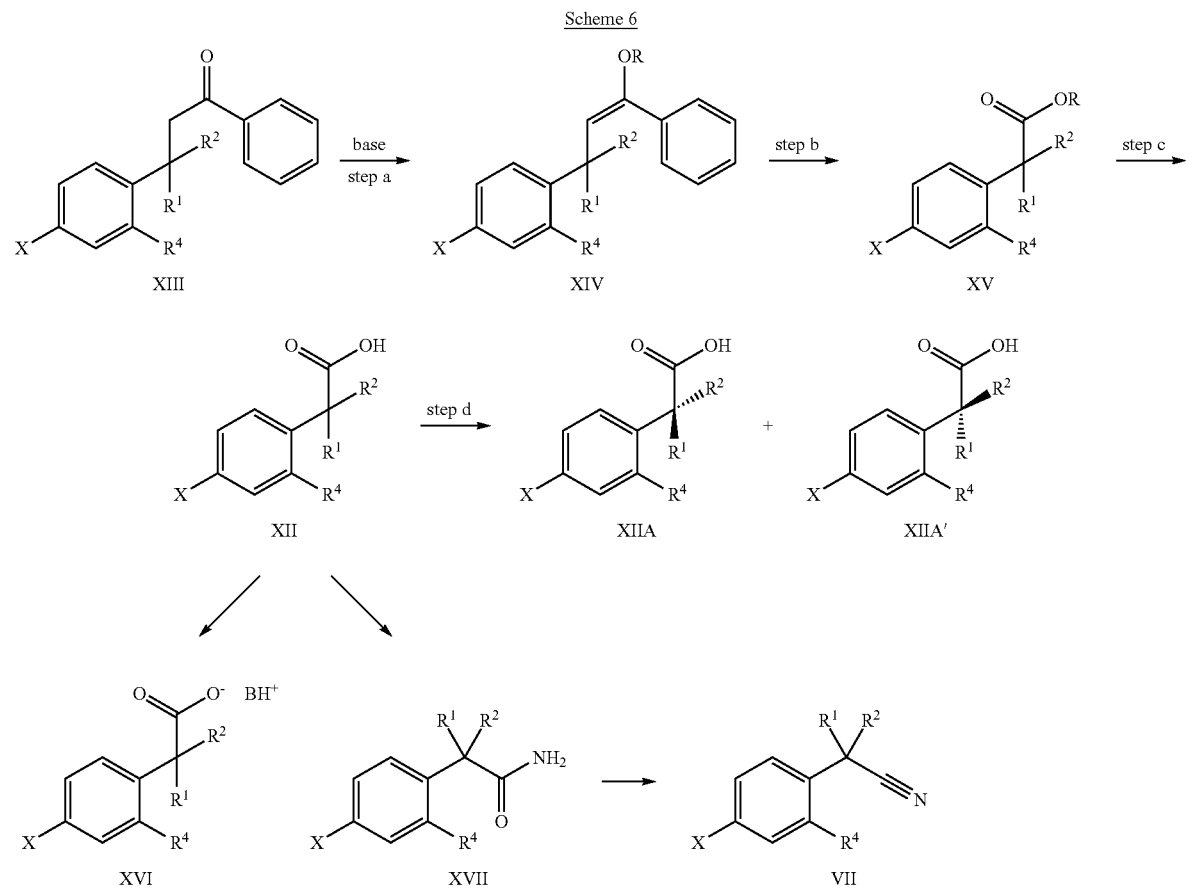

As illustrated in scheme 6, reaction of a ketone of formula XIII with methylating agent in the presence of a suitable base, in a suitable solvent, provides an enolether of formula XIV. Reaction of the enolether XIV with an oxidizing agent such as ozone, under suitable conditions, provides an ester of formula XV. Hydrolysis of the ester of formula XV, in a suitable solvent, in the presence of a suitable base, provides an acid of formula XII. This racemic acid may be resolved to provide the enantiomers XIIA and XIIA'. Alternatively, the acid XII may be reacted with an organic base such as a primary or secondary amine, in a suitable solvent, to provide the corresponding salt.

Reaction of a carboxylic acid of XII with a reagent such as ammonia, in a suitable solvent, provides an amide of formula XVII. Reaction of the amide of formula XVII with a suitable dehydrating agent, in a suitable solvent, provides a nitrile of formula VII. Non-limiting examples of bases useful in step (a) include potassium t-butoxide, sodium t-butoxide, lithium t-butoxide, sodium hydride, potassium hydride, lithium hydride, sodium hexamethyldisilazide, potassium hexamethyldisilazide, lithium hexamethyldisilazide, sodium methoxide, potassium methoxide, lithium methoxide, sodium ethoxide, potassium ethoxide, lithium ethoxide, LDA, n-butyllithium, sec-butyllithium or t-butyllithium. Non-limiting examples of solvents useful for step (a) include dimethylformamide, dichloromethane, ethyl acetate, hexane, heptane, acetonitrile, methyl tert-butyl ether, isopropyl acetate, toluene, and cyclopropylmethyl ether. Non-limiting examples of alkylating agents useful in step (a) include dimethyl sulfate, dimethyl carbonate, bromomethane, methyl trifluoromethanesulfonate and iodomethane. Non-limiting examples of silylating agents useful in step (a) include trimethylchlorosilane, tert-butyldimethylchlorosilane, triphenylchlorosilane, and triisopropylchlorosilane, triethylchlorosilane.

Non-limiting examples of solvents useful in step (b) include dimethylformamide, dichloromethane, ethyl acetate, hexane, heptane, acetonitrile, methyl tert-butyl ether, isopropyl acetate, toluene, and cyclopropylmethyl ether. Non-limiting examples of bases useful in step (b) include 1,8-diazabicycloundec-7-ene (DBU), triethylamine, pyridine, 4-methylmorpholine, diisopropylethylamine and dimethylamine. Non-limiting examples of dehydrating agents useful in step (b) include acetic anhydride, methanesulfonyl chloride, trifluoroacetic anhydride, toluenesulfonyl chloride, sodium hypochlorite, calcium hypochlorite and tert-butyl hypochlorite.

Non-limiting examples of bases useful in step (c) include potassium hydroxide, sodium hydroxide, lithium hydroxide and cesium hydroxide. Non-limiting examples of solvents useful in step (c) include methanol, methanol-water mixture, dimethylformamide, dichloromethane, ethyl acetate, hexane, heptane, acetonitrile, methyl tert-butyl ether, isopropyl acetate, toluene, and cyclopropylmethyl ether.

The resolution of the racemic acid of formula XII described in optional step d) can be carried out using methods known in the art including, for example, fractional crystallization and chiral chromatography.

In one embodiment, the invention relates to a process of making intermediate acids XII, XII A or XIIA' according to scheme 6 above. In another embodiment the invention relates to an intermediate acid of formula XII, XIIA or XIIA'

Compounds of formula I as well as intermediates prepared by the above methods may be further converted to additional intermediates or compounds of formula I by methods known in the art and exemplified in the Synthetic Examples section below.

SYNTHETIC EXAMPLES

The following are representative compounds of the invention which can be made by the general synthetic schemes, the examples, and known methods in the art.

LCMS retention time and observed m/z data for the compounds below is obtained by one of the following methods:

LC-MS Method A

| Column | Agilent Zorbax Eclipse XDB-C8 |
| --- | --- |
| | 5 μm 4.6 × 150 mm |
| | Ambient temperatur |
| Mobile phase | A = Formic acid (aq) 0.1% |
| | B = Formic acid (acetonitrile) 0.1% |
| Flow rate | 1.5 ml/min |
| Injection volume | 7uL |
| Detector | 200-600 nm |

| Time (mins) | % B |
| --- | --- |
| 0 | 1 |
| 2 | 20 |
| 7 | 95 |
| 9 | 95 |
| 9.3 | 1 |
| 10 | 1 |

LC-MS Method B

| Column | Agilent Zorbax C18 SB |
| --- | --- |
| | 3.5 μm, 4.6 × 30 mm |
| | Ambient temperature |
| Mobile phase | A = Formic acid (aq) 0.1% |
| | B = Formic acid (acetonitrile) 0.1% |
| Flow rate | 2.5 ml/min |
| Injection volume | 7 μL |
| Detector | 200-600 nm |

| Time (mins) | % B |
| --- | --- |
| 0 | 5 |
| 1.7 | 95 |
| 2 | 95 |
| 2.1 | 5 |
| 2.3 | 5 |

LC-MS Method C

| Column | Agilent SB-C18 |
| --- | --- |
| | 1.8 μm, 3 × 50 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 μL |
| Detector | 220 and 254 nm |

| Time (mins) | % B |
| --- | --- |
| 0 | 5 |
| 3.8 | 90 |
| 4.5 | 100 |

LC-MS Method D

| Column | Agilent SB-C18 |
|---|---|
| | 1.8 µm, 3 × 50 mm column |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 µL |
| Detector | 220 and 254 nm |

| Gradient | Time (mins) | % B |
|---|---|---|
| | 0 | 12 |
| | 0.25 | 30 |
| | 0.3 | 40 |
| | 1.19 | 95 |
| | 1.75 | 100 |

LC-MS Method E

| Column | Agilent SB-AQ |
|---|---|
| | 1.8 µm, 3 × 50 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 µL |
| Detector | 220 and 254 nm |

| Gradient | Time (mins) | % B |
|---|---|---|
| | 0 | 5 |
| | 0.25 | 50 |
| | 0.3 | 70 |
| | 1.3 | 90 |
| | 1.7 | 100 |

LC-MS Method F

| Column | Waters Atlantis dC18 100 × 2.1 mm, |
|---|---|
| | 3 µm column |
| | 40° C. |
| Mobile phase | A - 0.1% Formic acid (water) |
| | B - 0.1% Formic acid (acetonitrile) |
| Flow rate | 0.6 ml/min |
| Injection volume | 3 µL |
| Detector | 215 nm (nominal) |

| Gradient | Time (mins) | % B |
|---|---|---|
| | 0 | 5 |
| | 5 | 100 |
| | 5.4 | 100 |
| | 5.42 | 5 |

Synthetic Methods

The compounds of the invention may be prepared by the methods described below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization and/or reverse phase HPLC. HPLC purification methods used anywhere from 0-100% acetonitrile in water and may contain 0.1% formic acid, 0.1% TFA or 0.2% ammonium hydroxide and used one of the following columns:

a) Waters Sunfire OBD C18 5 µM 30×150 mm column
b) Waters XBridge OBD C18 5 µM 30×150 mm column
c) Waters ODB C8 5 µM 19×150 mm column.
d) Waters Atlantis ODB C18 5 µM 19×50 mm column.
e) Waters Atlantis T3 OBD 5 µM 30×100 mm column
f) Phenomenex Gemini Axia C18 5 µM 30×100 mm column
g) Waters SunFire C18 Prep OBD Sum 19×100 mm
h) Waters XBridge Prep C18 5 um 19×100 mm Starting materials and reagents are either commercially available or may be prepared by one skilled in the art using methods described in the chemical literature.

Synthesis of Nitrile Intermediates

Synthesis of 2-(4-bromo-phenyl)-2,3-dimethylbutyronitrile

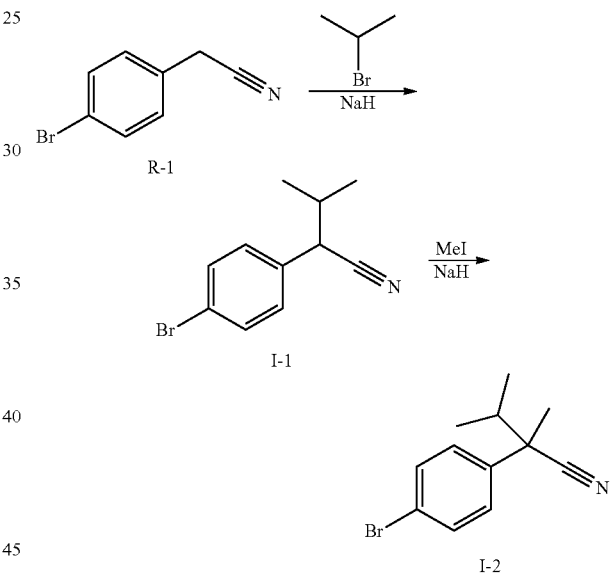

To a solution of R-1 (20.0 g, 0.102 mol) in DMF (300 mL) at 0° C. is added NaH (60% in oil suspension, 4.28 g, 0.107 mol) slowly. The mixture is then stirred for a further 15 minutes and 2-bromopropane (9.60 mL, 0.107 mol) is added. The reaction mixture is allowed to warm to room temperature, stirring continued for 2 hours and then concentrated in vacuo. The residue is partitioned between $CH_2Cl_2$ and brine. The combined organics are dried with $Na_2SO_4$, filtered and concentrated in vacuo. The residue is purified by flash chromatography ($SiO_2$, 0-15% EtOAc in heptane) to give I-1 (21.3 g); m/z 238.3, 240.2 [M/M+2H]

I-1 (21.3 g, 89.6 mmol) is dissolved in DMF (300 mL). The mixture is cooled to 0° C. and NaH (60% in oil suspension, 3.76 g, 94.1 mmol) is added slowly. The mixture is then stirred for a further 15 minutes and methyl iodide (5.9 mL, 94.1 mmol) is added. The reaction mixture is stirred at 0° C. to room temperature for 2 hours and then concentrated in vacuo. The residue is partitioned between methylene chloride and brine. The combined organics are dried with $Na_2SO_4$, filtered and concentrated in vacuo. The residue is purified by flash chromatography (SiO$_2$, 0-15% EtOAc in heptane) to give the title intermediate (21.7 g); m/z 252.3, 254.3 [M/M+2H].

The following intermediates are synthesized in similar fashion from the appropriate reagents:

| Intermediate | Structure |
|---|---|
| I-3 | 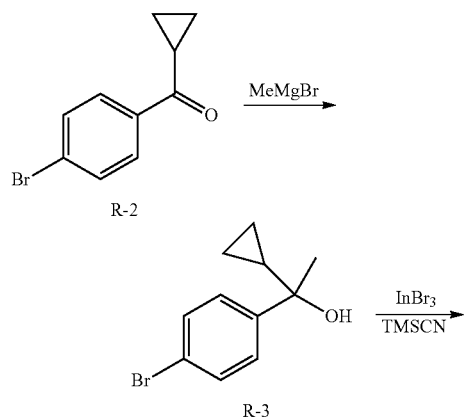 |

Synthesis of 2-(4-bromo-phenyl)-2-cyclopropylpropionitrile

To a solution of R-2 (5.00 g, 22 mmol) in THF (30 mL) is added a solution of MeMgBr (1.0M in butyl ether, 27.0 mL). The solution is stirred for 30 min then treated with saturated aqueous NaHCO$_3$. The mixture is partioned between CH$_2$Cl$_2$ and brine then organics are collected, dried with MgSO$_4$, filtered, and concentrated to give R-3 (5.35 g). To a solution of R-3 (5.35 g, 22.2 mmol) in CH$_2$Cl$_2$ (100 mL) is added TMSCN (5.9 mL, 44 mmol) and InBr$_3$ (790 mg, 2.22 mmol). The reaction is stirred overnight then poured into 20% aqueous Na$_2$CO$_3$. The mixture is extracted with CH$_2$Cl$_2$, dried with MgSO$_4$, filtered, and concentrated in vacuo. The residue is purified by flash chromatography (SiO$_2$, 0-15% EtOAc in heptane) to give the title intermediate (3.82 g); $^1$H-NMR, 400 MHz, DMSO-d6 ppm: 7.65 (2H) (d: J=12 Hz); 7.52 (2H) (d: J=12 Hz); 1.69 (3H) (s); 1.41 (1H) (m); 0.68 (1H) (m); 0.58 (2H) (m); 0.41 (1H) (m).

The following intermediates are synthesized in similar fashion from the appropriate reagents:

| Intermediate | Structure | m/z [M + H] |
|---|---|---|
| I-5 | 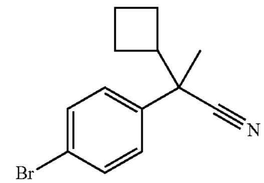 | 265.2 |

2-(4-Bromo-Phenyl)-2-Cyclopropylpropionitrile can Also be Prepared in the Following Manner To a solution of R-2 (309 g, 1.37 mol) in THF (3.0 L) is added dropwise MeMgBr (3M in Et$_2$O 1.37 L, 4.12 mol) at −78° C. The mixture is stirred at −78° C. for 10 min and then at room temperature for 2 h. The reaction mixture is quenched with saturated aqueous NH$_4$Cl and extracted with EtOAc. The combined organic layers are washed with brine, dried over anhydrous Na$_2$SO$_4$ and concentrated to afford the crude compound R-3 (330 g) which is used in the next step without further purification.

To a solution of R-3 (330 g, 1.37 mol) in CH$_2$Cl$_2$ (2.4 L) is added dropwise BF$_3$.EtO$_2$ (198 g, 1.37 mol) at −78° C. The mixture is stirred at the same temperature for 30 min. TMSCN (272 g, 2.74 mol) is added drop-wise at −78° C. After addition, the reaction is allowed to stir at room temperature for 2 h. The reaction mixture is quenched with chilled water and the organic layer is separated. The aqueous phase is extracted with CH$_2$Cl$_2$. The organic layer is washed with brine, dried over anhydrous Na$_2$SO$_4$ and concentrated. The residue is purified by chromatography on silica gel with petroleum ether/EtOAc (50:1) to give the title intermediate (160 g).

Preparation of (R)-2-(4-bromo-phenyl)-2-cyclopropylpropionitrile (I-6) and (S)-2-(4-bromo-phenyl)-2-cyclopropylpropionitrile (I-7)

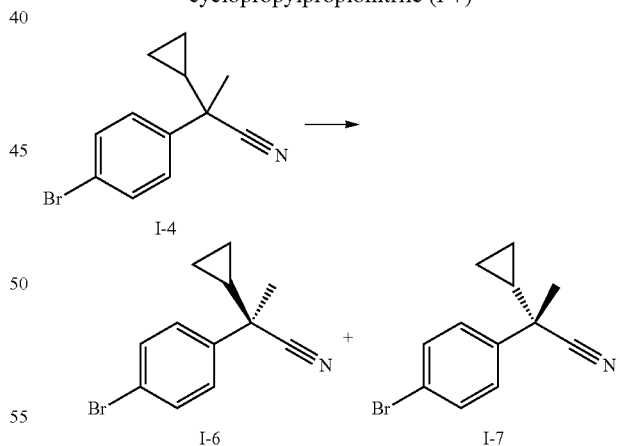

Enantiomers I-6 and I-7 are prepared by resolution of I-4 (150 g) on a ChiralPak AY-H 300×20 mm SFC column (eluting 85:15 SF CO$_2$:ethanol, 80 mL/min flow rate). The faster eluting isomer is determined to be I-7; $^1$H-NMR, 400 MHz, CDCl3-d6 ppm: 7.54-7.50 (2H) (m); 7.41-7.37 (2H) (m); 1.73 (3H) (s); 1.26-1.19 (1H) (m); 0.74-0.50 (4H) (m); the slower eluting isomer is I-6; $^1$H-NMR, 400 MHz, CDCl3-d6 ppm: 7.54-7.50 (2H) (m); 7.41-7.37 (2H) (m); 1.73 (3H) (s); 1.26-1.19 (1H) (m); 0.74-0.50 (4H) (m).

Synthesis of 2-(4-bromo-phenyl)-3,3-dimethylbutyronitrile

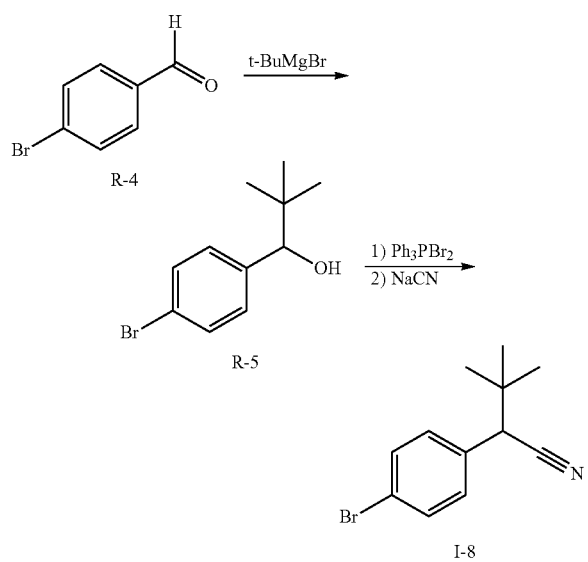

To a solution of t-BuMgBr (110 mL, 1.0 M in THF) is added a solution of R-4 (10 g, 54 mmol) in THF (50 mL). The solution is stirred for 10 min then treated with saturated aqueous NaHCO$_3$. The mixture is partioned between methylene chloride and brine, the organics are collected, dried with MgSO$_4$, filtered, and concentrated. Purification of the crude by flash chromatography (SiO$_2$, Heptane to 15% EtOAc in Heptane) gives a yellow solid that is further purified by slurrying in heptane to give after filtration R-5 (4.67 g). To a solution of R-5 (4.63 g, 19.0 mmol) in CH$_3$CN (100 mL) is added imidazole (3.89 g, 57.1 mmol) followed by Ph$_3$PBr$_2$ (24.1 g, 57.1 mmol). The mixture is heated at 40° C. for 6 h then cooled to 23° C. and partioned between EtOAc and saturated aqueous NaHCO$_3$. The organics are collected, washed with water, dried with MgSO$_4$, filtered, and concentrated in vacuo. The residue is slurried in heptane and resulting solid is filtered. The filtrate is collected and volatiles are removed in vacuo. The residue is dissolved in DMSO (100 mL) and treated with NaCN (1.11 g, 22.7 mmol). The mixture is heated at 140° C. for 3 h then cooled to 23° C. The mixture is partioned between Et$_2$O and water. The organics are washed with water, dried with MgSO$_4$, filtered, and concentrated. Purification of the crude by flash chromatography (SiO$_2$, Hep to 15% EtOAc in Hep) yields the title intermediate (2.37 g) $^1$H-NMR, 400 MHz, CDCl$_3$ ppm: 7.59 (2H) (d: J=12 Hz); 7.33 (2H) (d: J=12 Hz); 4.26 (1H) (brs); 1.35 (9H) (s).

Synthesis of Carboxamidine Intermediates

Synthesis of 2-(4-bromo-phenyl)-N-hydroxy-2,3-dimethylbutyramidine

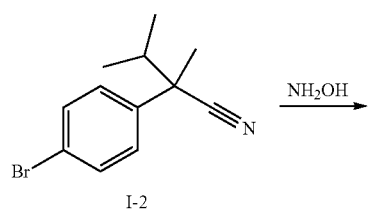

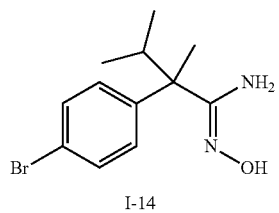

A solution of I-2 (10.0 g, 40 mmol) in EtOH (50 mL) is treated with 50% aqueous hydroxylamine (50 mL). The reaction is heated at 80° C. overnight then concentrated in vacuo. The solid is filtered and washed with water then heptane. The solid is collected and triturated with EtOAc then filtered, collected, and dried to afford the title intermediate (10.4 g); m/z 285.4; 287.2 [M/M+2H]

The following intermediates are synthesized in similar fashion from the appropriate reagents:

| Intermediate | Structure | m/z [M/M + 2H] |
|---|---|---|
| I-15 | 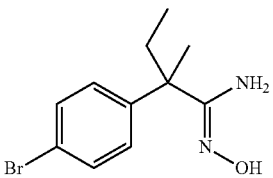 | Not available |
| I-16 | 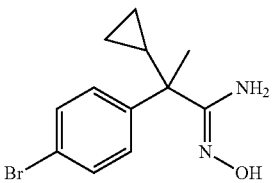 [SMILES: CC(/C(N)=N/O)(c1ccc(Br)cc1)C1CC1] | 283.0/285.0 |
| I-17 | 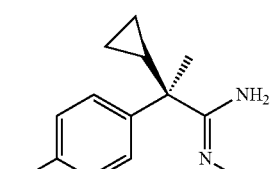 | 283.1/285.0 |
| I-19 | 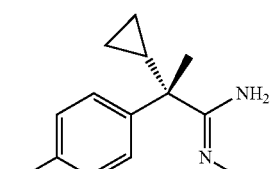 | 283.1/285.0 |

Synthesis of 2-[4-(2-aminopyrimidin-5-yl)phenyl]-N-hydroxy-2,3-dimethyl Butanimidamide

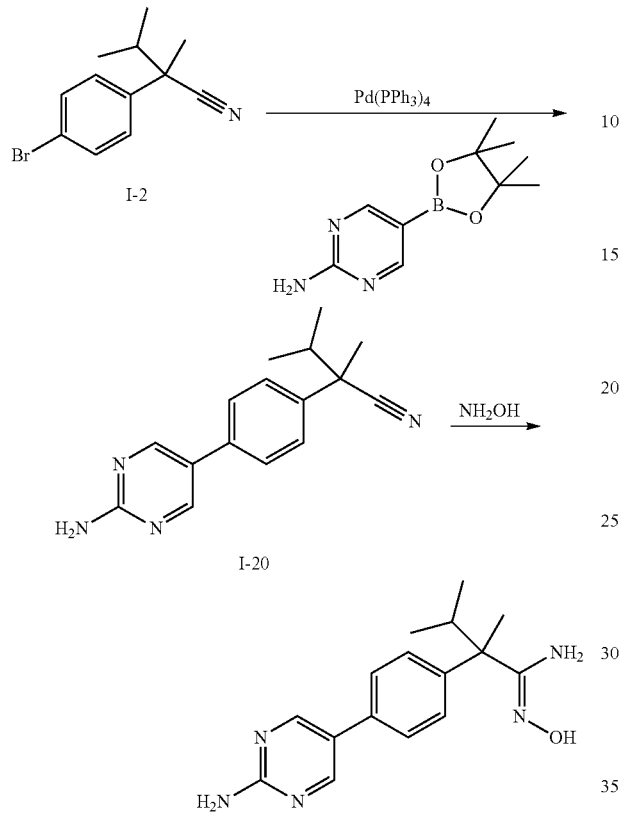

A solution of I-2 (2.00 g, 7.93 mmol), 2-aminopyrimidine-5-boronic acid pinacol ester (2.63 g, 11.9 mmol), and tetrakis(triphenylphosphine)palladium(0) (459 mg, 0.397 mmol) in THF (20 mL) and saturated aqueous $Na_2CO_3$ (10 mL) is heated at 80° C. for 3 h. The mixture is cooled to 23° C. then pardoned between EtOAc and brine. The organics are collected, dried with $MgSO_4$, filtered, and concentrated to give a residue that is purified by flash chromatography ($SiO_2$, $CH_2Cl_2$ to 3% MeOH in $CH_2Cl_2$) to afford I-20 (m/z 267.5 [M+H]).

The following intermediates were synthesized in similar fashion from the appropriate reagents:

| Intermediate | Structure | m/z [M + H] |
|---|---|---|
| I-20A | | 264.0 |
| I-20B | 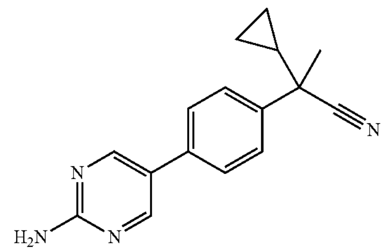 [SMILES: CC(C#N)(c1ccc(-c2cnc(N)nc2)cc1)C1CC1] | 265.1 |
| I-20C | 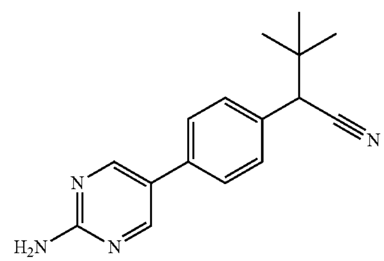 [SMILES: CC(C)(C)C(C#N)c1ccc(-c2cnc(N)nc2)cc1] | 267.0 |
| I-20D | 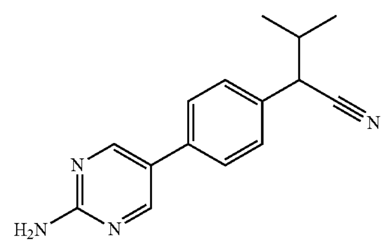 [SMILES: CC(C)C(C#N)c1ccc(-c2cnc(N)nc2)cc1] | 253.1 |
| I-20E | 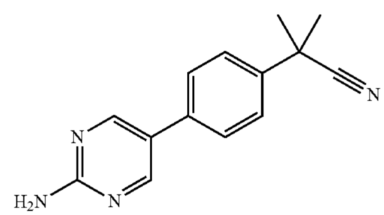 [SMILES: CC(C)(C#N)c1ccc(-c2cnc(N)nc2)cc1] | Not available |
| I-20F | 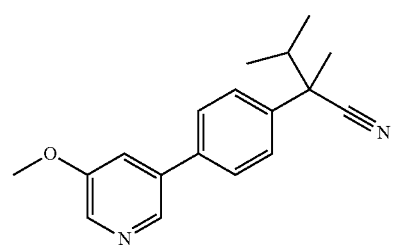 [SMILES: COc1cncc(-c2ccc(C(C)(C#N)C(C)C)cc2)c1] | 281.7 |

I-20 is dissolved in EtOH (30 mL) and treated with 50% aqueous hydroxylamine (12 mL). The reaction is heated at 80° C. for 48 h then cooled to 23° C. and filtered through Celite. The filtrate is partioned between EtOAc and water. The organics are collected, dried with $MgSO_4$, filtered, and concentrated in vacuo. Purification of the crude by flash chromatography ($SiO_2$, $CH_2Cl_2$ to 10% MeOH in $CH_2Cl_2$) provides the title intermediate (1.56 g); m/z: 300.4 [M+H]

The following intermediates were synthesized in similar fashion from the appropriate reagents:

| Intermediate | Structure | m/z [M + H] |
|---|---|---|
| I-22 | 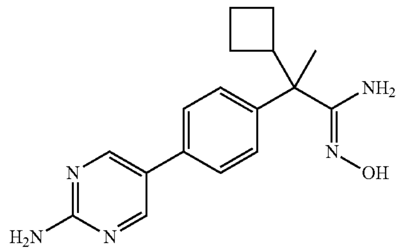 [SMILES: CC(/C(N)=N/O)(c1ccc(-c2cnc(N)nc2)cc1)C1CCC1] | 312.4 |
| I-23 | 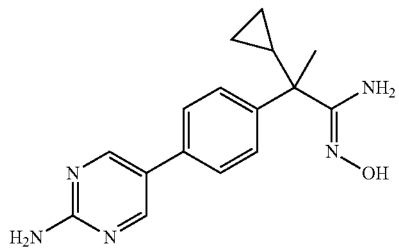 [SMILES: CC(/C(N)=N/O)(c1ccc(-c2cnc(N)nc2)cc1)C1CC1] | 298.4 |
| I-24 | 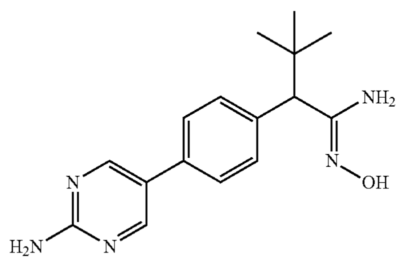 [SMILES: CC(C)(C)C(/C(N)=N/O)c1ccc(-c2cnc(N)nc2)cc1] | Not available |
| I-25 | 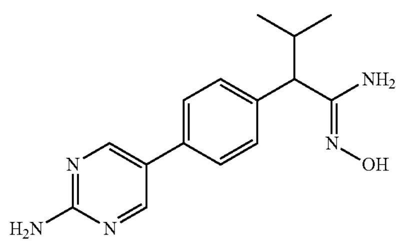 [SMILES: CC(C)C(/C(N)=N/O)c1ccc(-c2cnc(N)nc2)cc1] | 286.2 |
| I-26 | 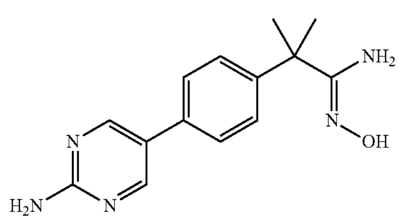 [SMILES: CC(C)(/C(N)=N/O)c1ccc(-c2cnc(N)nc2)cc1] | 272.1 |
| I-27 | 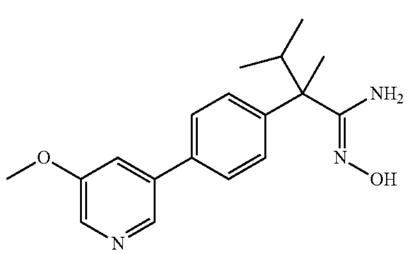 [SMILES: COc1cncc(-c2ccc(C(C)(/C(N)=N/O)C(C)C)cc2)c1] | Not available |

Synthesis of: (R)-2-[4-(2-amino-pyrimidin-5-yl)-phenyl]-2-cyclopropyl-N-hydroxy-propionamidine

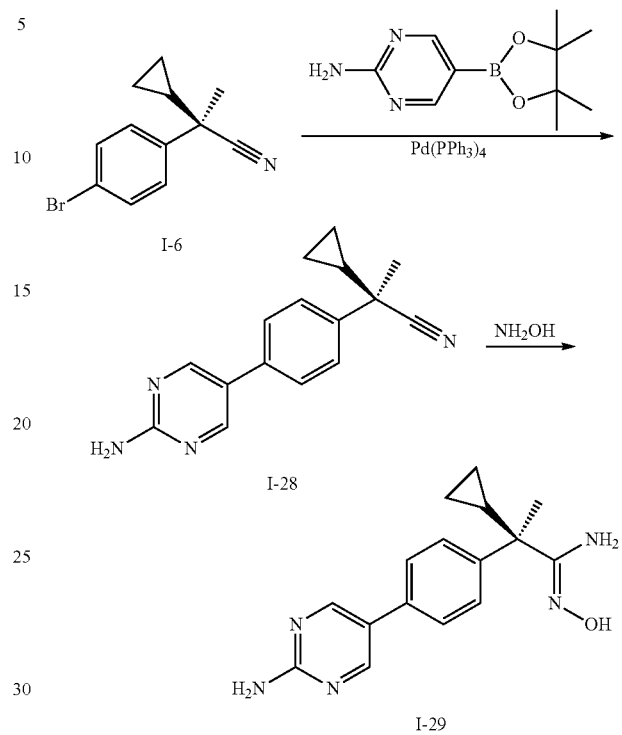

To a mixture of I-6 (18.5 g, 0.074 mol) in THF (300 mL) are added 5-(4,4,5,5-tetramethyl-[1,3,2]dioxaborolan-2-yl)-pyrimidin-2-ylamine (19.6 g, 0.089 mol), tetrakis(triphenylphosphine)palladium (0) (8.5 g, 0.007 mol) and 2M Na$_2$CO$_3$ (74 mL, 0.148 mol). The mixture is heated to 80° C. for 24 hours. The solution is cooled down to room temperature and is extracted with EtOAc and water. The combined organic layer is dried with MgSO$_4$ and is filtered. The filtrate is concentrated and the residue is re-suspended in CH$_2$Cl$_2$. The solid that precipitated out from the solution is collected by filtration. The solid is dried and is confirmed to be I-28 (14.8 g); m/z 265.4 [M+H].

A suspension of I-28 (14.8 g, 0.056 mol), KOH (15.7 g, 0.28 mol), and hydroxylamine solution in H$_2$O (50% by weight) (34 mL, 0.56 mol) is stirred at 85° C. for 48 hours. The mixture is cooled and the solid is filtered and is dried to afford the title intermediate (12.5 g); m/z 298.4 [M+H].

Synthesis of (R)-2-Cyclopropyl-N-hydroxy-2-[4-(2-methylamino-pyrimidin-5-yl)-phenyl]-propionamidine

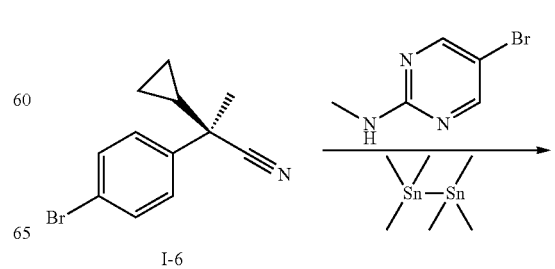

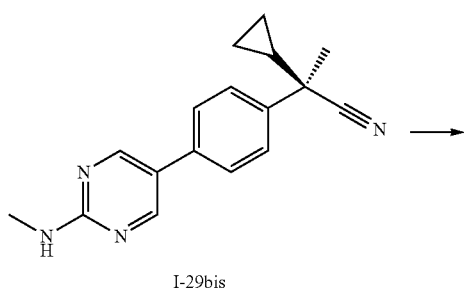

I-29bis

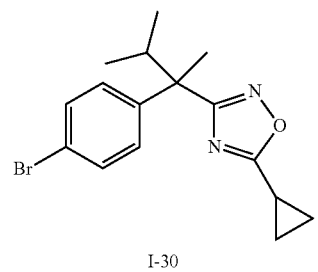

I-30

A mixture of I-14 (150 mg, 0.53 mmol) and cyclopropyl-carbonyl chloride (60 mg, 0.58 mmol) in pyridine (2 mL) is stirred at room temperature for 15 minutes before heating at 110° C. for 18 h. The reaction mixture is concentrated in vacuo, then partitioned between $CH_2Cl_2$ and saturated aqueous $NaHCO_3$. The organics are dried with $Na_2SO_4$, filtered and concentrated in vacuo to give the title intermediate (167 mg); m/z 336.0 [M+H].

The following intermediates are synthesized in similar fashion from the appropriate reagents:

In a 5 ml microwave reaction vessel are combined 5-bromo-2-(methylamino)pyrimidine (451 mg, 2.39 mmol) and hexamethyldistannane (0.456 ml, 2.19 mmol) in toluene (5 ml). The mixture is degassed using argon after which tetrakis(triphenylphosphine) palladium (0) (115 mg, 0.10 mmol) is added. The reaction is degassed once more, capped and warmed to 115° C. for 1 h. Upon cooling to ambient temperature, I-6 (500 mg, 1.99 mmol) is introduced along with tetrakis(triphenylphosphine) palladium (0) (115 mg, 0.10 mmol). The vessel is capped and warmed to 115° C. over night. After this time the reaction is cooled and concentrated. The resulting solid is purified via flash chromatography (silica gel, 0-100% EtOAc/heptanes) to afford I-29bis (134 mg); m/z 279.4 [M+H].

To a suspension of I-29bis (134 mg, 0.481 mmol) in EtOH (3.2 ml) is added hydroxylamine solution in $H_2O$ (50% by weight) (1.18 mL, 19.24 mmol) is stirred at 85° C. for 72 hours. The mixture is cooled and concentrated, and diluted with water and ethyl acetate. White solid is filtered and is dried, organic is purified by flash chromatography and combined with solid to afford the title intermediate, (110 mg); m/z 312.4 [M+H].

| Intermediate | Structure |
|---|---|
| I-31 | 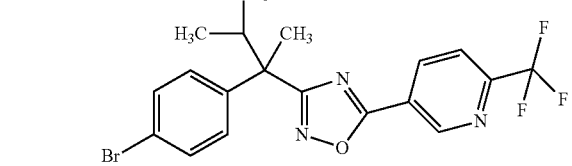 |
| I-32 | 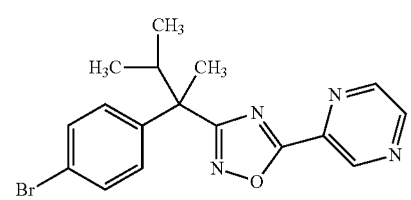 [SMILES: CC(C)C(C)(c1ccc(Br)cc1)c1noc(-c2cnccn2)n1] |
| I-33 | 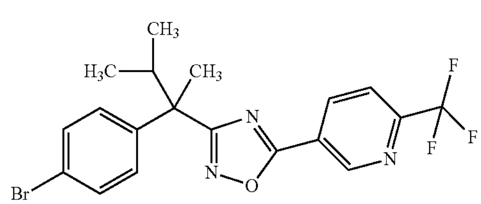 [SMILES: CC(C)C(C)(c1ccc(Br)cc1)c1noc(-c2ccc(C(F)(F)F)nc2)n1] |

Synthesis of Aryl Bromide Intermediates

Synthesis of 3-[2-(4-bromophenyl)-3-methylbutan-2-yl]-5-cyclopropyl-1,2,4-oxadiazole

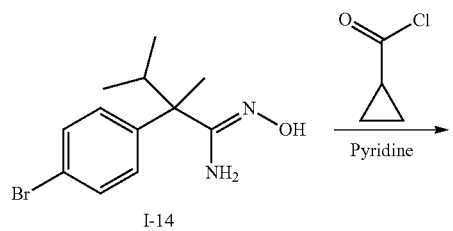

I-14

| Intermediate | Structure |
|---|---|
| I-34 | 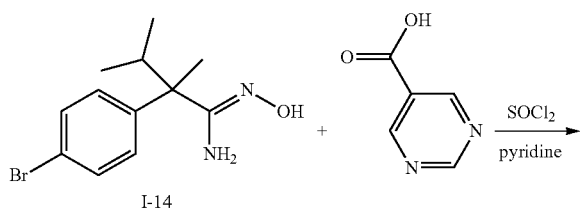 |

Synthesis of 5-{3-[2-(4-bromophenyl)-3-methylbutan-2-yl]-1,2,4-oxadiazol-5-yl}pyrimidine To a solution of pyrimidine-5-carboxylic acid (200 mg, 0.70 mmol) in pyridine (1.0 mL) is added thionyl chloride (61 μL, 0.84 mmol). The mixture is stirred at room temperature for 15 minutes before I-14 (91 mg, 0.74 mmol) is added. The resulting mixture is heated at 110° C. for 18 h then concentrated in vacuo. The residue is partitioned between EtOAc and saturated aqueous NaHCO$_3$, washed with brine, dried with Na$_2$SO$_4$, filtered, and concentrated in vacuo to give the title compound (236 mg); m/z 373.0, 375.0 [M, M+2H]

The following intermediates were synthesized in similar fashion from the appropriate reagents:

| Intermediate | Structure | m/z |
|---|---|---|
| I-36 | 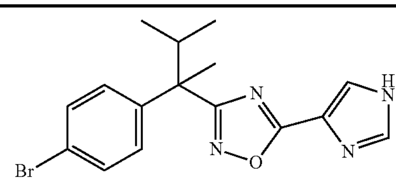 | 361.0/363.0 [M/M + 2H] |
| I-37 | 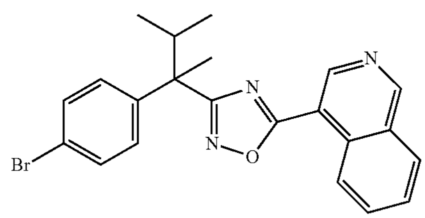 [SMILES: CC(C)C(C)(c1ccc(Br)cc1)c1noc(-c2cncc3ccccc23)n1] | 422.0/424.0 [M/M + 2H] |
| I-38 | 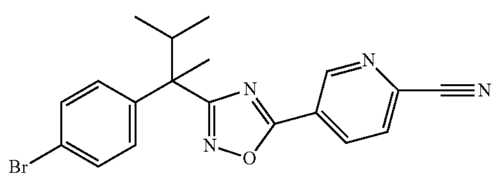 [SMILES: CC(C)C(C)(c1ccc(Br)cc1)c1noc(-c2ccc(C#N)nc2)n1] | 397.0/399.0 [M/M + 2H] |
| I-39 | 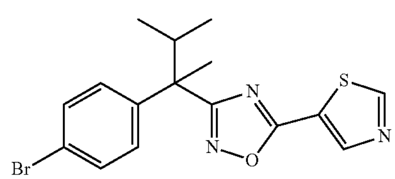 | 380.0 [M + 2H] |
| I-40 | 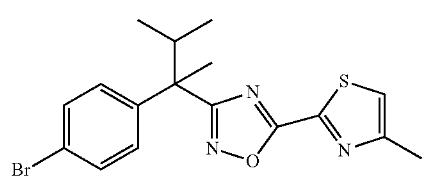 [SMILES: Cc1csc(-c2nc(C(C)(c3ccc(Br)cc3)C(C)C)no2)n1] | 392.0/394.0 [M/M + 2H] |

-continued

| Intermediate | Structure | m/z |
|---|---|---|
| I-41 | 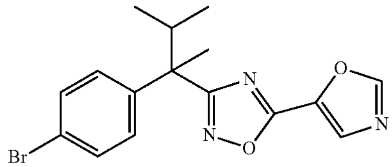 [SMILES: CC(C)C(C)(c1ccc(Br)cc1)c1noc(-c2cnco2)n1] | 362.0/364.0 [M/M + 2H] |
| I-42 | 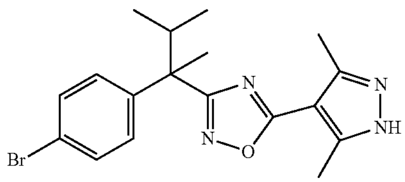 [SMILES: Cc1n[nH]c(C)c1-c1nc(C(C)(c2ccc(Br)cc2)C(C)C)no1] | 389.0/391.0 [M/M + 2H] |
| I-43 | 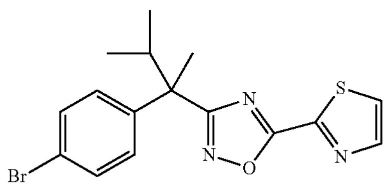 [SMILES: CC(C)C(C)(c1ccc(Br)cc1)c1noc(-c2nccs2)n1] | Not available |
| I-44 | 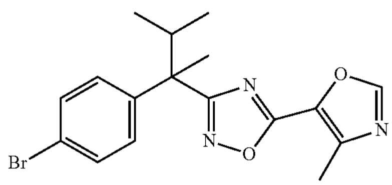 [SMILES: Cc1ncoc1-c1nc(C(C)(c2ccc(Br)cc2)C(C)C)no1] | Not available |
| I-45 | 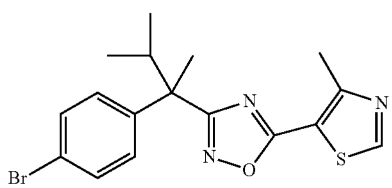 [SMILES: Cc1ncsc1-c1nc(C(C)(c2ccc(Br)cc2)C(C)C)no1] | Not available |
| I-46 | 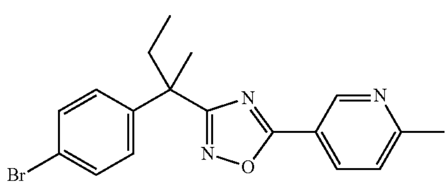 [SMILES: CCC(C)(c1ccc(Br)cc1)c1noc(-c2ccc(C)nc2)n1] | 372.0/374.0 [M/M + 2H] |
| I-47 | 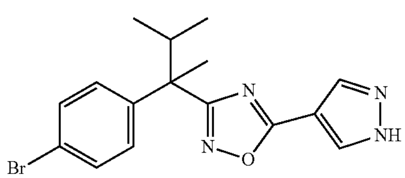 [SMILES: CC(C)C(C)(c1ccc(Br)cc1)c1noc(-c2cn[nH]c2)n1] | 361.0/363.0 [M/M + 2H] |
| I-48 | 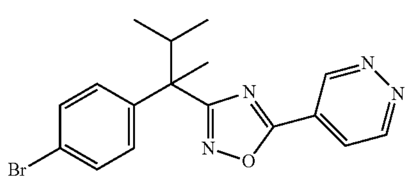 [SMILES: CC(C)C(C)(c1ccc(Br)cc1)c1noc(-c2ccnnc2)n1] | 374.0 [M + H] |

-continued

| Intermediate | Structure | m/z |
|---|---|---|
| I-49 | 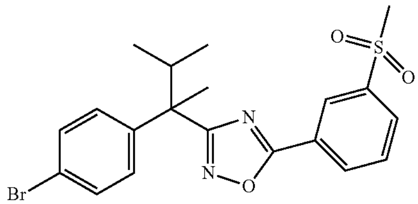 [SMILES: CC(C)C(C)(c1ccc(Br)cc1)c1noc(-c2cccc(S(C)(=O)=O)c2)n1] | 450.0 [M + H] |
| I-50 | 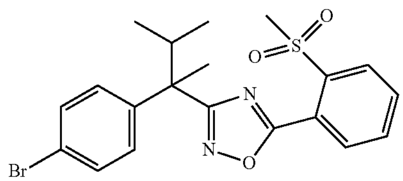 [SMILES: CC(C)C(C)(c1ccc(Br)cc1)c1noc(-c2ccccc2S(C)(=O)=O)n1] | Not available |
| I-51 | 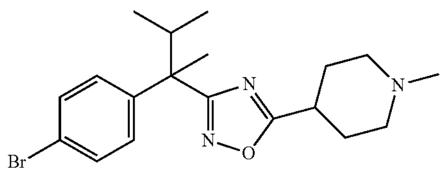 [SMILES: CC(C)C(C)(c1ccc(Br)cc1)c1noc(C2CCN(C)CC2)n1] | 393.0 [M + H] |
| I-52 | 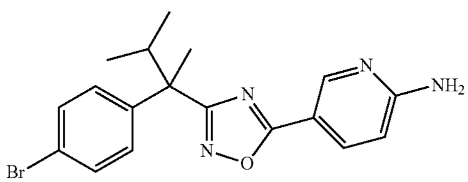 [SMILES: CC(C)C(C)(c1ccc(Br)cc1)c1noc(-c2ccc(N)nc2)n1] | 388.0 [M + H] |
| I-53 | 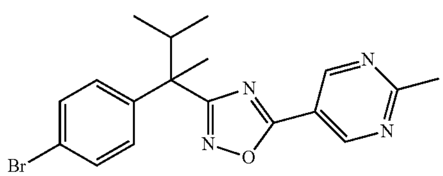 [SMILES: Cc1ncc(-c2nc(C(C)(c3ccc(Br)cc3)C(C)C)no2)cn1] | 388.0 [M + H] |
| I-54 | 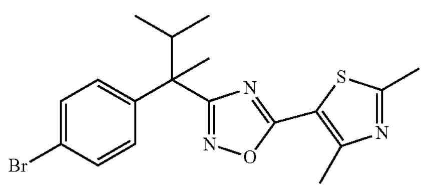 [SMILES: Cc1nc(C)c(-c2nc(C(C)(c3ccc(Br)cc3)C(C)C)no2)s1] | 407.0 [M + H] |
| I-55 | 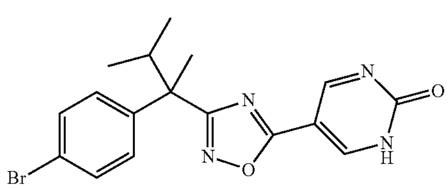 [SMILES: CC(C)C(C)(c1ccc(Br)cc1)c1noc(-c2cnc(=O)[nH]c2)n1] | 390.0 [M + H] |
| I-56 | 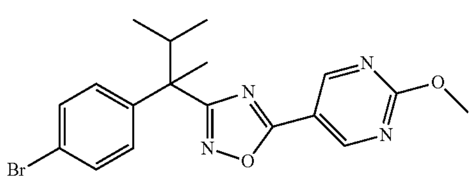 [SMILES: COc1ncc(-c2nc(C(C)(c3ccc(Br)cc3)C(C)C)no2)cn1] | 404.0 [M + H] |

| Intermediate | Structure | m/z |
|---|---|---|
| I-57 | 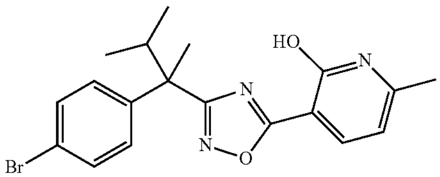 [SMILES: Cc1ccc(-c2nc(C(C)(c3ccc(Br)cc3)C(C)C)no2)c(O)n1] | 403.0 [M + H] |
| I-58 | 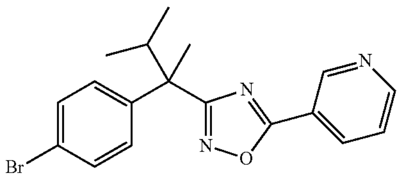 [SMILES: CC(C)C(C)(c1ccc(Br)cc1)c1noc(-c2cccnc2)n1] | 372.4/374.5 [M/M + 2H] |

Synthesis of 3-[1-(4-bromo-phenyl)-1-cyclopropyl-ethyl]-5-(1H-pyrazol-4-yl)-[1,2,4]oxadiazole

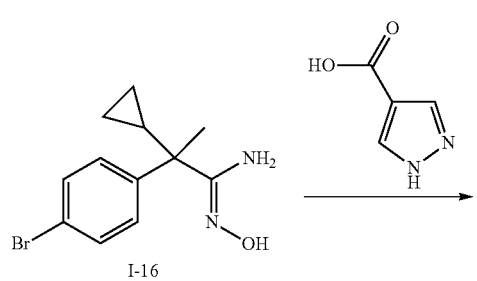

| Intermediate | Structure | m/z |
|---|---|---|
| I-60 | 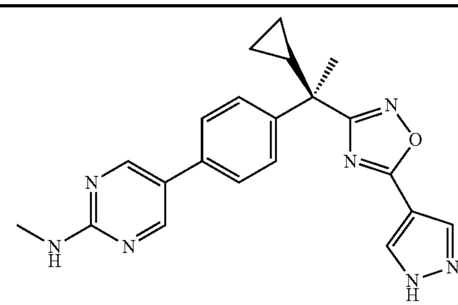 | 388.4 [M + H] |

Synthesis of 3-[(R)-1-(4-bromo-phenyl)-1-cyclopropyl-ethyl]-5-(1H-pyrazol-4-yl)-[1,2,4]oxadiazole

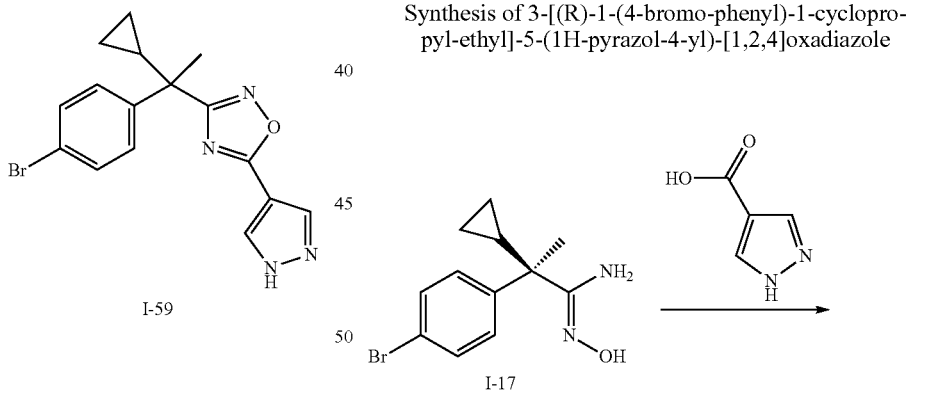

1,1'-Carbonyldiimidazole (4.9 g, 30.7 mmol) is added to a mixture of 1H-pyrazole-4-carboxylic acid (3.4 g, 30.7 mmol) in 1,4-dioxane (150 ml). The mixture is stirred at 50° C. for 30 minutes, I-16 is added and the reaction mixture is heated at 85° C. for 48 hours. The reaction mixture is cooled to room temperature, poored into a solution of saturated NaHCO$_3$ and extracted with EtOAc. The organic layers are dried over MgSO4, filtered and concentrated to afford the crude product that is purified via flash chromatography (SiO$_2$, 0-6% MeOH/CH$_2$Cl$_2$) to afford the title intermediate (6.9 g); m/z 359,361 [M, M+2H].

The following intermediates are synthesized in similar fashion from the appropriate reagents:

To a sealed tube is added 1H-pyrazole-4-carboxylic acid (484 mg, 4.2 mmol) in 1,4-dioxane (8 ml), followed by the addition of 1,1'-carbonyldiimidazole (679 mg, 4.2 mmol). The reaction mixture is stirred at 55° C. for 30 minutes. Then I-17 (1.1 g, 4.0 mmol) in 1,4-dioxane (5 ml) is added to the above mixture. The reaction mixture is stirred at 120° C. for 18 hours. The reaction mixture is concentrated in vacuo. The residue is diluted with EtOAc, washed with water, brine, dried under anhy. Na$_2$SO$_4$, filtered and concentrated. The residue is purified by flash chromatography (SiO$_2$, 0-5% MeOH/CH$_2$Cl$_2$) to afford the title intermediate (1.3 g); m/z 359.0, 361.0 [M, M+2H].

Synthesis of 2-(4-{3-[1-(4-bromo-phenyl)-1-cyclopropyl-ethyl]-[1,2,4]oxadiazol-5-yl}-pyrazol-1-yl)-N,N-dimethyl-acetamide

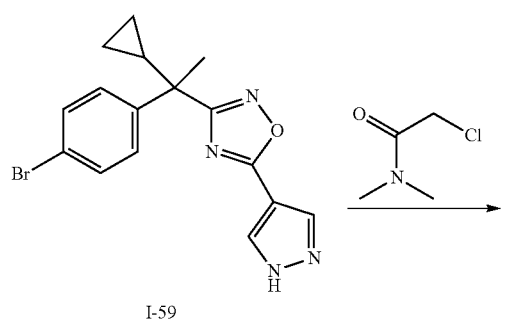

To a solution of I-59 (6.9 g, 19 mmol) in DMF (80 mL) are added K$_2$CO$_3$ (5.3 g, 38 mmol) and 2-chloro-N,N-dimethylacetamide (2.9 g, 28 mmol) at room temperature. The mixture is stirred at the same temperature for 24 hours. Water (200 mL) is added and the mixture is extracted with EtOAc (300 mL). The combined organic layer is dried with MgSO$_4$ and filtered. The filtrate is concentrated and the remaining residue was purified via silica gel flash column chromatography with 8% MeOH in CH$_2$Cl$_2$ as the eluent to afford the title intermediate (8.3 g); m/z 444.2, 446.2 [M, M+2].

The following intermediates are synthesized in similar fashion from the appropriate reagents:

| Intermediate | Structure | m/z [M/M + 2H] |
|---|---|---|
| I-63 | 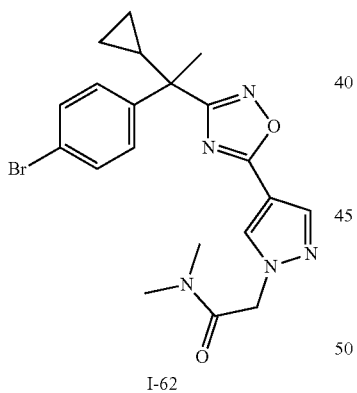 | 444.2/446.2 |
| I-64[a] | 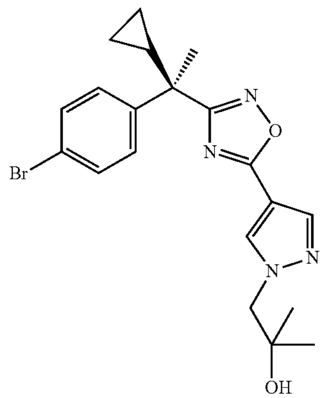 [SMILES: CC(C)(O)Cn1cc(-c2nc([C@@](C)(c3ccc(Br)cc3)C3CC3)no2)cn1] | 431.2/433.2 |
| I-65[b] | 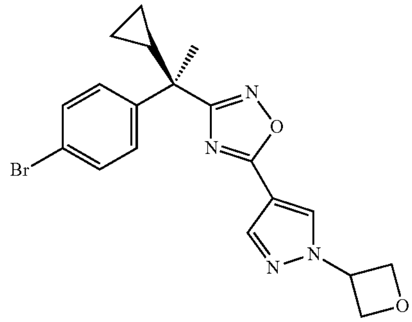 [SMILES: C[C@@](c1ccc(Br)cc1)(c1noc(-c2cnn(C3COC3)c2)n1)C1CC1] | 415.1/417.1 |

[a]The reaction mixtures is stirred at 80° C. for 48 hours

[b]The reaction is run starting from the corresponding iodide and the mixture is stirred at 80° C. overnight

183
Synthesis of 3-[(R)-1-(4-bromo-phenyl)-1-cyclopropyl-ethyl]-5-(1-methyl-1H-pyrazol-4-yl)-[1,2,4]oxadiazole

184
Synthesis of 2-[4-(3-{1-cyclopropyl-1-[4-(4,4,5,5-tetramethyl-[1,3,2]dioxaborolan-2-yl)-phenyl]-ethyl}-[1,2,4]oxadiazol-5-yl)-pyrazol-1-yl]-N,N-dimethyl-acetamide

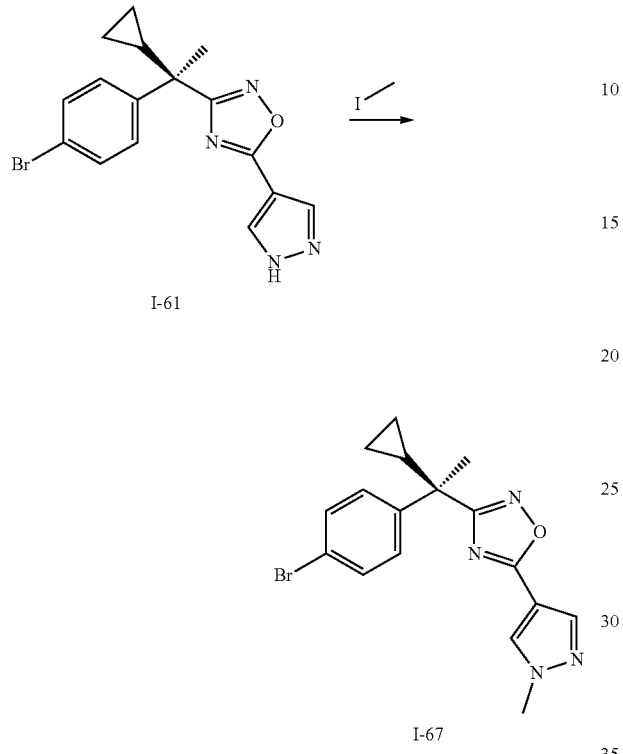

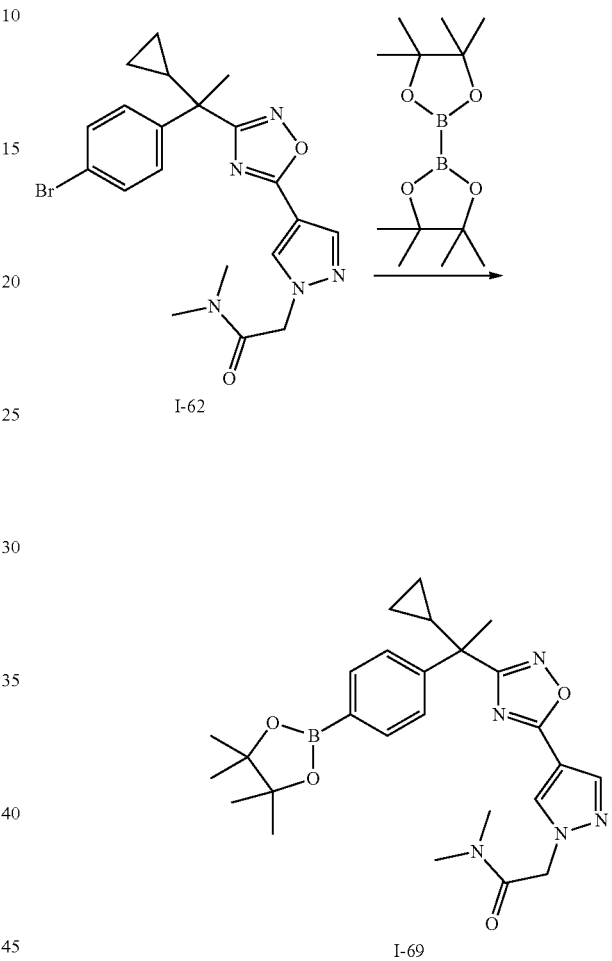

To a vial is added I-61 (550 mg, 1.531 mmol), iodomethane (0.191 mL, 3.062 mmol) and K₂CO₃ (423 mg, 3.062 mmol) in 6 ml of DMF. The reaction mixture is stirred at room temperature for 2 hrs, then poured into water and brine, and extracted with EtOAc (4×25 ml). The combined organic fractions are dried with sodium sulfate, filtered, and concentrated in vacuo to afford the title intermediate (516 mgs); m/z 374.0, 376.0 [M/M+2]

The following intermediates are synthesized in similar fashion from the appropriate reagents:

| Intermediate | Structure | m/z [M/M + 2H] |
|---|---|---|
| I-68 | 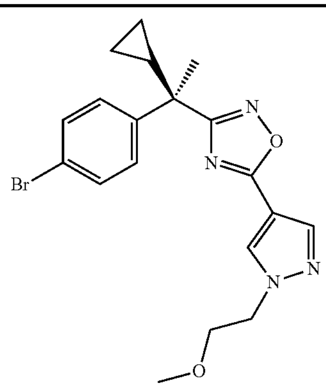 | 417.2/419.2 |

To a solution of I-62 (2.6 g, 5.9 mmol) in 1,4-dioxane (20 mL) in a pressure vial are added bis(pinacolato)diboron (2.2 g, 8.8 mmol), KOAc (2.3 g, 23 mmol) and tetrakis(triphenylphosphine)palladium (0) (481 mg, 0.6 mmol). The reaction mixture is stirred under Ar at 100° C. for 4 hours. The mixture is cooled down and is concentrated in vacuo. The residue is diluted with EtOAc (100 mL) and is passed through a plug of Celite and is rinsed thoroughly with EtOAc (20 mL). The filtrate is dried with magnesium sulfate and is filtered to afford the title intermediate (1.9 g); m/z 492.3 (M+H)

The following intermediates were synthesized in similar fashion from the appropriate reagents:

| Intermediate | Structure | m/z [M + H] |
|---|---|---|
| I-70<sup>a</sup> | 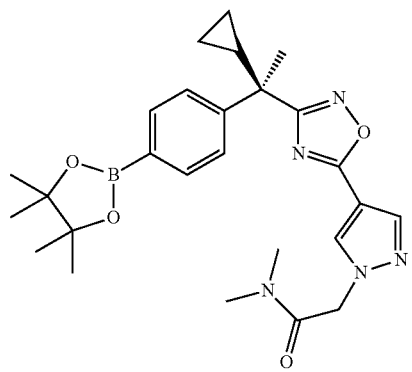 [SMILES: CN(C)C(=O)Cn1cc(-c2nc([C@@](C)(c3ccc(B4OC(C)(C)C(C)(C)O4)cc3)C3CC3)no2)cn1] | 492.4 |
| I-71<sup>a</sup> | 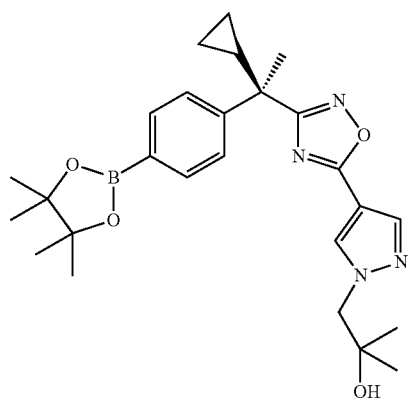 [SMILES: CC(C)(O)Cn1cc(-c2nc([C@@](C)(c3ccc(B4OC(C)(C)C(C)(C)O4)cc3)C3CC3)no2)cn1] | 479.5 |
| I-72<sup>a</sup> | 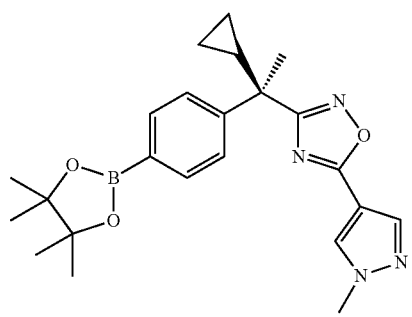 [SMILES: Cn1cc(-c2nc([C@@](C)(c3ccc(B4OC(C)(C)C(C)(C)O4)cc3)C3CC3)no2)cn1] | 421.5 |

-continued

| Intermediate | Structure | m/z [M + H] |
|---|---|---|
| I-73[b] | 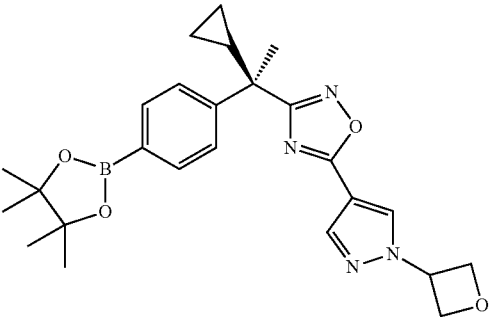 [SMILES: CC1(C)OB(c2ccc([C@](C)(c3noc(-c4cnn(C5COC5)c4)n3)C3CC3)cc2)OC1(C)C] | 463.3 |
| I-74[b] | 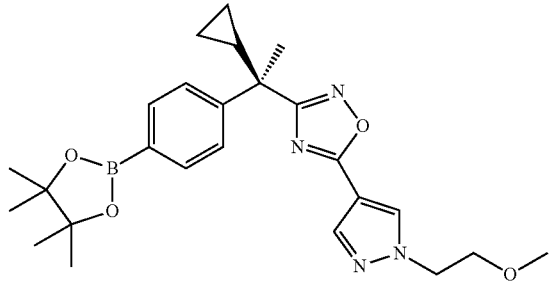 | 465.3 |
| I-75[b] | 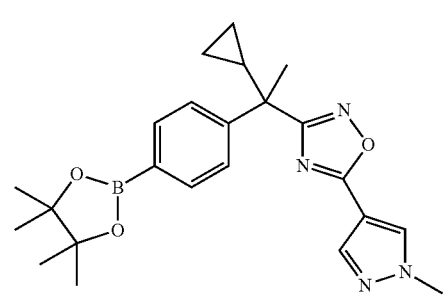 | 421.3 |

[a]1,1'-bis(diphenylphosphino) ferrocenedichloropalladium(II) dichloromethane is used instead
[b]1,1'-bis(diphenylphosphino) ferrocenedichloropalladium(II) dichloromethane is used instead and the reaction mixture is stirred at 100° C. overnight Synthesis of Boc-Piperidine Intermediates Synthesis of 5'-(3-{1-[4-(2-amino-pyrimidin-5-yl)-phenyl]-1-cyclopropyl-ethyl}-[1,2,4]oxadiazol-5-yl)-2,3,5,6-tetrahydro-[1,2']bipyrazinyl-4-carboxylic Acid tert-butyl Ester

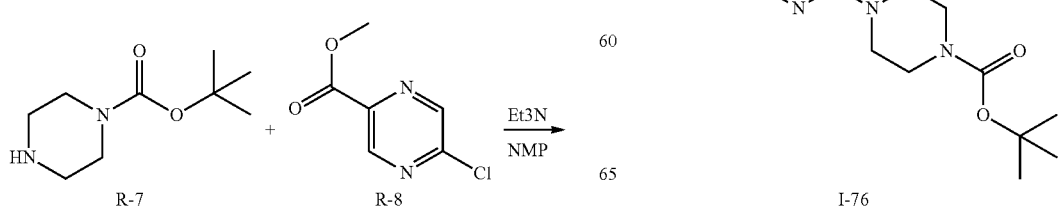

-continued

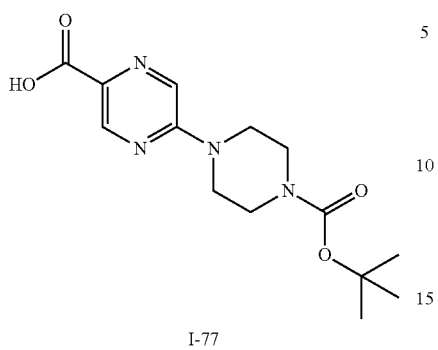

I-77

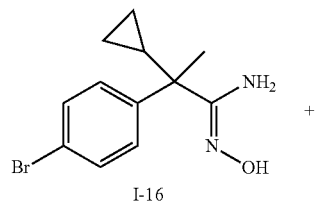

I-16

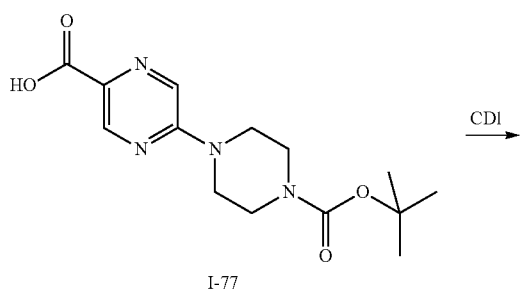

I-77

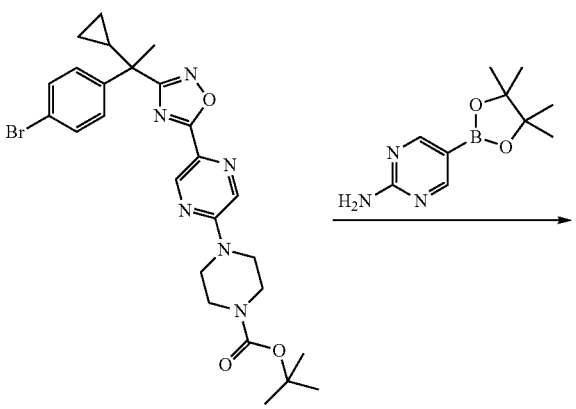

I-78

-continued

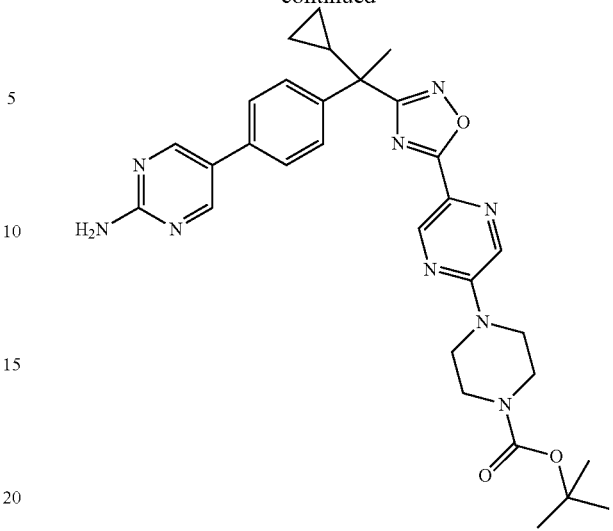

I-79

A 250 ml RB flask is charged with R-7 (5.4 g, 28.99 mmol) in 100 mL of NMP. R-8 (5.00 g, 28.99 mmol) is added followed by triethylamine (4.85 ml, 34.79 mmol). The reaction is heated to 60° C. under nitrogen overnight. The reaction is cooled to room temperature, poured into ice water and the precipitated I-76 (8.60 g) is isolated by filtration; m/z 323.4 [M+H]

To a stirred suspension of I-76 (8.60 g, 26.68 mmol) in ethanol (250 ml) is added 5M NaOH (26.68 ml, 133.39 mmol) at room temperature. The mixture becomes homogenous before a persisting precipitate forms and becomes a solid mass. Water (200 ml) is added and the mixture is stirred for 4 h after which time the reaction appears complete. The light brown sludge is poured into a beaker and treated with water. AcOH is added to reach acidic pH and the product is extracted into DCM (2×). The combined organics are dried over anhydrous $MgSO_4$, filtered and concentrated to give the product as a solid which is suspended in heptanes. The solid is collected via filtration and washed with heptanes to give I-77 (7.90 g); m/z 309.4 [M+H].

To a suspension of I-77 (3.0 g, 9.71 mmol) in THF (40 ml) is added 1,1'-carbonyldiimidazole (1.6 g, 9.71 mmol) at room temperature. The mixture is stirred at 50° C. for 30 minutes. After this time I-16 (2.5 g, 8.83 mmol) is added and the resulting mixture is heated at 80° C. for 3 hours. The mixture is cooled down and treated with AcOH (8 ml). The mixture is warmed to 80° C. and stirred over night. Upon cooling to room temperature, the reaction is concentrated and diluted with water. The product is extracted into DCM (2×). The combined organics are washed with brine and dried over anhydrous $MgSO_4$. The mixture is filtered and concentrated. The remaining crude is purified via flash chromatography (silica gel, 0-5% MeOH/DCM) to afford I-78 (2.2 g). In a microwave reaction vessel is added I-78 (0.50 g, 0.90 mmol) in 15 ml of DMF, followed by the addition of 2-aminopyrimidine-5-boronic acid pinacol ester (0.30 g, 1.35 mmol), tetrakis(triphenylphosphine)palladium(0) (105 mg, 0.09 mmol) and aq. $Na_2CO_3$ (2.0M, 1.8 ml). The reaction mixture is stirred at 85° C. for 16 hours. After this time the reaction mixture is poured into brine and extracted with EtOAc (3×). The combined organic fractions are dried over anhydrous $MgSO_4$, filtered, then concentrated in vacuo to give the crude material. Purification via flash chromatography (silica gel, 0-5% MeOH/DCM) affords the title intermediate (150 mg); m/z 570.4 [M+H]

The following intermediates are synthesized in similar fashion from the appropriate reagents:

| Intermediate | Structure | m/z [M + H] |
|---|---|---|
| I-80 | 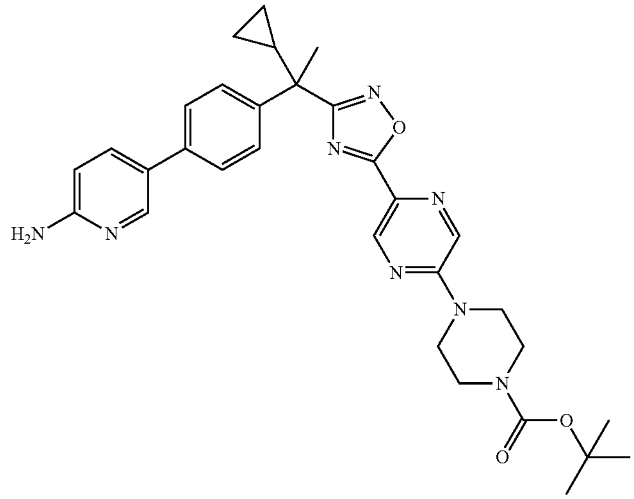 [SMILES: CC(C)(C)OC(=O)N1CCN(c2cnc(-c3nc(C(C)(c4ccc(-c5ccc(N)nc5)cc4)C4CC4)no3)cn2)CC1] | 569.4 |
| I-81 | 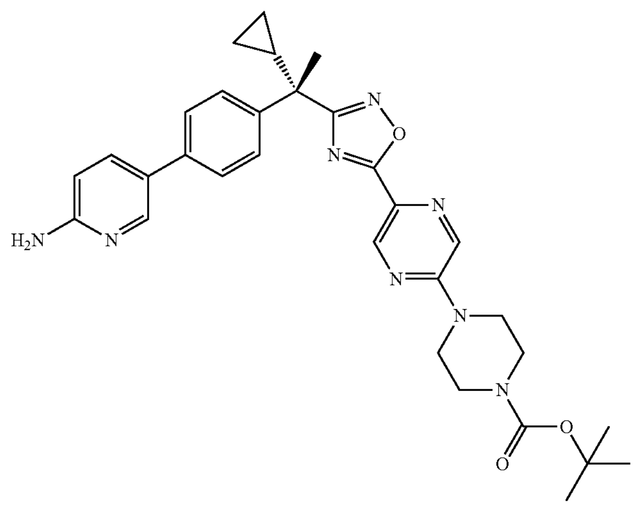 | 569.4 |
| I-82 | 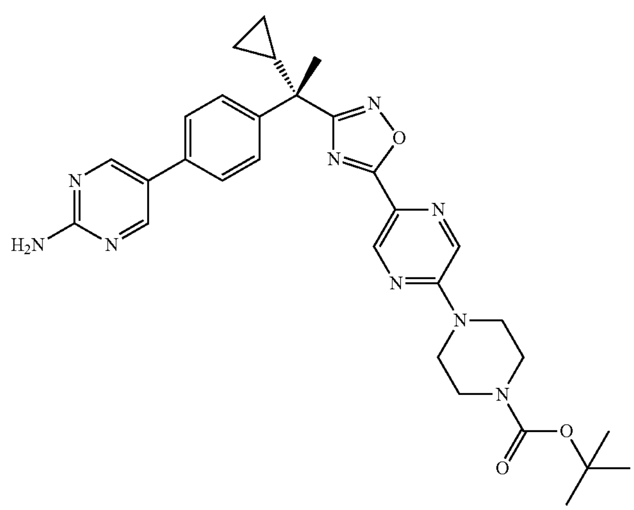 [SMILES: CC(C)(C)OC(=O)N1CCN(c2cnc(-c3nc([C@](C)(c4ccc(-c5cnc(N)nc5)cc4)C4CC4)no3)cn2)CC1] | 570.4 |

| Intermediate | Structure | m/z [M + H] |
|---|---|---|
| I-83 | 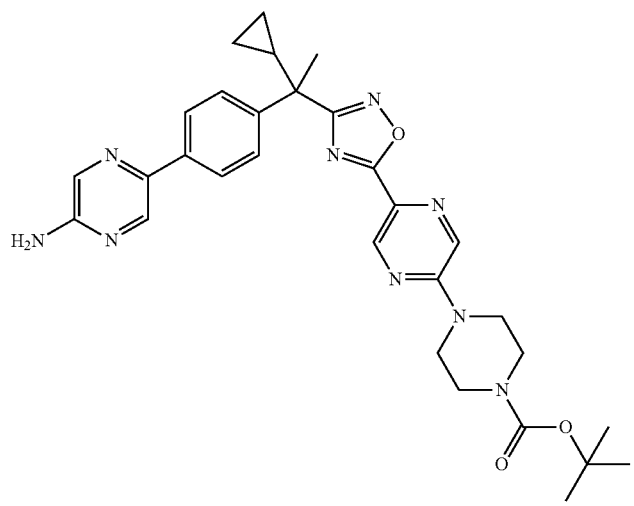 | 570.4 |
Synthesis of 5'-(3-{(S)-1-[4-(5-amino-pyrazin-2-yl)-phenyl]-1-cyclopropyl-ethyl}-[1,2,4]oxadiazol-5-yl)-2,3,5,6-tetrahydro-[1,2']bipyrazinyl-4-carboxylic Acid tert-butyl Ester
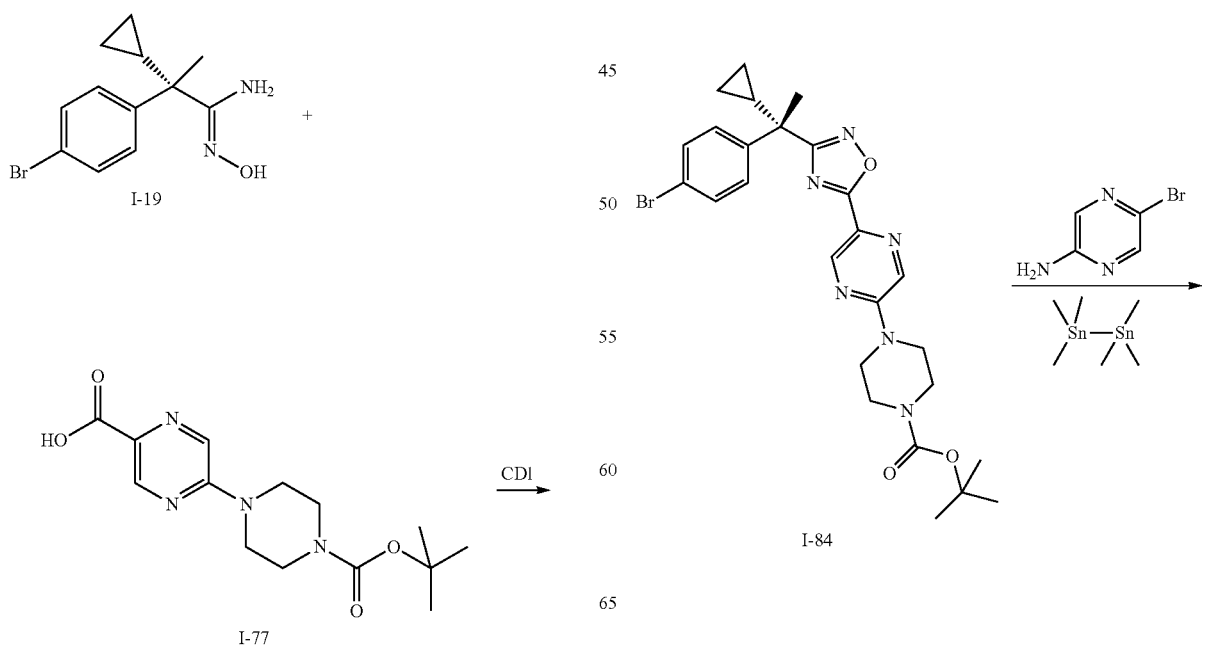

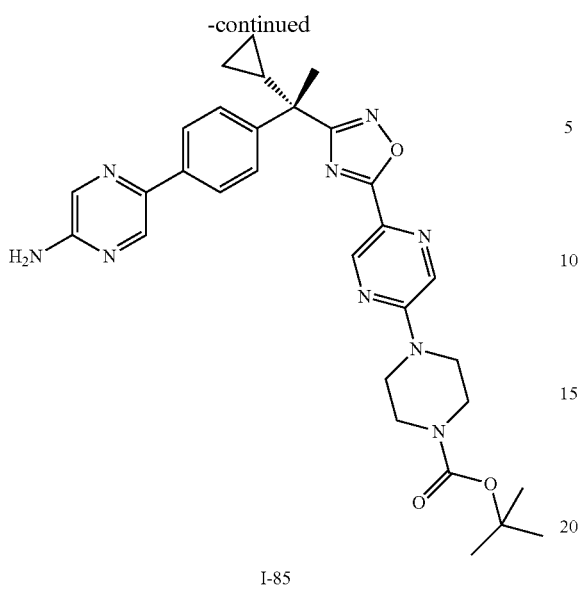

I-85

To a suspension of I-77 (1.0 g, 3.53 mmol) in THF (20 ml) is added 1,1'-carbonyldiimidazole (0.63 g, 3.88 mmol) at room temperature. The mixture is stirred at 50° C. for 30 minutes. After this time I-19 (1.2 g, 3.88 mmol) is added as a THF solution (15 ml) and the resulting mixture is heated at 80° C. for 3 hours. The mixture is cooled and treated with AcOH (8 ml) then warmed to 80° C. and stirred over night. After this time the reaction is cooled to room temperature, concentrated and diluted with water. Extracted the product into DCM (2×). The combined organics are washed with brine and dried (MgSO$_4$). Filtered and concentrated. The remaining crude is purified via flash chromatography (silica gel, 0-5% MeOH/DCM) to afford I-84 (1.2 g).

In a 5 ml microwave reaction vessel are combined 5-amino-2-bromopyrazine (60 mg, 0.34 mmol) and hexamethyldistannane (120 mg, 0.38 mmol) in toluene (2 ml). The mixture is degassed using argon after which tetrakis(triphenylphosphine) palladium (0) (40 mg, 0.03 mmol) is added. The reaction is degassed once more, capped and warmed to 115° C. for 1 h. Upon cooling to ambient temperature, I-84 (270 mg, 0.48 mmol) is introduced along with tetrakis(triphenylphosphine) palladium (0) (30 mg, 0.05 mmol). The vessel is capped and warmed to 115° C. over night. After this time the reaction is cooled and concentrated. The crude is suspended in DCM/MeOH, treated with silica gel and concentrated. The resulting solid is purified via flash chromatography (silica gel, 0-10% MeOH/DCM) to afford the title intermediate (100 mg).

Synthesis of 4-fluoro-pyrimidin-2-ylamine

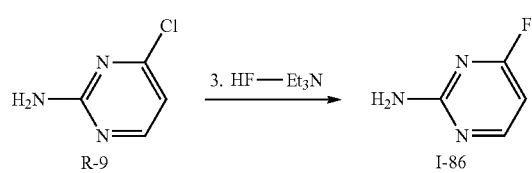

To a suspension of R-9 (100 mg, 0.77 mmol) in CH$_3$CN (10 mL) is added HF in Et$_3$N (0.26 mL, 1.5 mmol) at room temperature. The solution is heated to 80° C. for 48 hours. The solution is cooled down and water (10 mL) is added. The solution is extracted with EtOAc (20 mL) and H$_2$O (5 mL). The combined organic layer is dried with MgSO$_4$ and is filtered. The filtrate is concentrated to afford I-86 (25 mg); m/z 113.9 [M+H].

The following intermediates are synthesized in similar fashion from the appropriate reagents:

| Intermediate | Structure | m/z [M + H] |
|---|---|---|
| I-86bis | 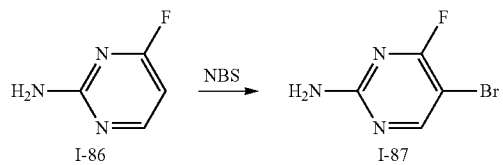 | 127.9 |

Synthesis of 5-bromo-4-fluoro-pyrimidin-2-ylamine

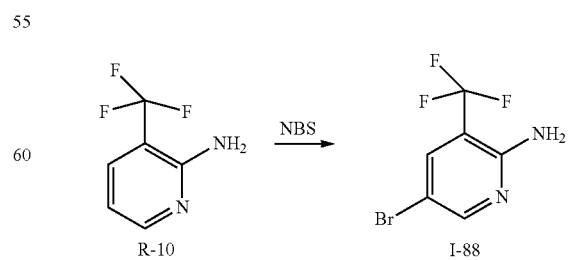

To a solution of I-86 (280 mg, 2.5 mmol) in CH$_3$CN (20 mL) is added N-bromosuccinimide (881 mg, 4.9 mmol) at room temperature. The solution is stirred at the same temperature for 12 hours. The solid that precipitates out from the solution is collected and is dried to afford the title intermediate (250 mg); m/z 191.9, 193.9 [M, M+2H]

The following intermediates are synthesized in similar fashion from the appropriate reagents:

| Intermediate | Structure | m/z [M/M + 2 + H] |
|---|---|---|
| I-87bis | 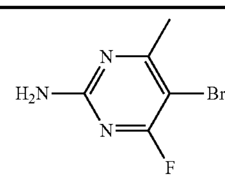 | 205.9/207.9 |

Synthesis of 5-bromo-3-trifluoromethyl-pyridin-2-ylamine

To a stirred solution of R-10 (2.70 g, 16.66 mmol) in DMF (15 ml) is added N-bromosuccinimide (3.00 g, 16.85 mmol)

as a DMF solution (15 ml, dropwise). After 4 h the reaction is poured onto ice. The resulting precipitate is collected via filtration to give the product as an off-white solid. Dissolved into DCM and washed with brine. The layers are separated and the organic phase is dried (MgSO$_4$), filtered and concentrated to give the title intermediate (3.8 g); m/z 241.2/243.2 [M/M+2H].

Synthesis of 5-bromo-3-fluoro-pyridin-2-ylamine

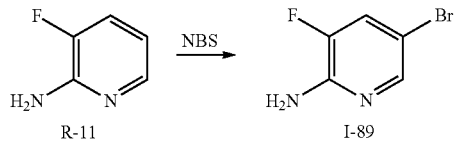

To a round bottom flask is added R-11 (500 mg, 4.46 mmol) in CH$_3$CN (120 ml) at 0° C., followed by the addition of N-bromosuccinimide (397 mg, 2.23 mmol). The reaction mixture is stirred (protected from light) vigorously for 15 minutes, then at room temperature for 1 hour. The additional portion of N-bromosuccinimide (397 mg, 2.23 mmol) is added at 0° C., then the reaction mixture is stirred at room temperature for 2 hours. The reaction mixture is concentrated in vacuo. The residue is dissolved in EtOAc, washed with sat Na$_2$S$_2$O$_3$ (20 ml), brine, dried over anhy. Na$_2$SO$_4$, filtered and concentrated. The residue is purified by flash chromatography (SiO$_2$, 0-20% EtOAc/heptane) to afford the title intermediate (772 mg); m/z 190.89/192.86 [M/M+2H].

The following intermediates are synthesized in similar fashion from the appropriate reagents:

| Intermediate | Structure | m/z [M/M + 2H] |
|---|---|---|
| I-90 | 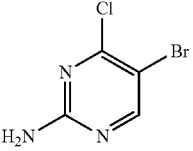 | 207.9/209.9 |

Synthesis of (5-bromo-pyrimidin-2-yl)-tert-butyl-amine

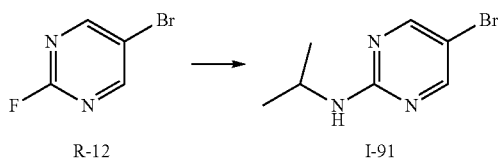

To a vial is added R-12 (200 mg, 1.13 mmol) in DMF (5 ml), followed by the addition of K$_2$CO$_3$ (312 mg, 2.26 mmol) and isopropylamine (134 mg, 2.27 mmol). The reaction mixture is stirred at 70° C. for 3 hours. The reaction mixture is concentrated in vacuo. The residue is dissolved in EtOAc, washed with water, brine, dried under anhy. Na$_2$SO$_4$, filtered and concentrated to afford the title intermediate (221 mg); m/z 216.0/218.0 [M/M+2H].

The following intermediates are synthesized in similar fashion from the appropriate reagents:

| Intermediate | Structure | m/z [M/M + 2H] |
|---|---|---|
| I-92 | 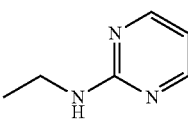 | 202.2/204.2 |
| I-93 | 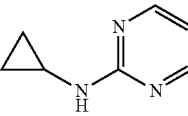 | 213.93/215.93 |

Synthesis of 3-Benzyloxy-5-bromo-pyridine

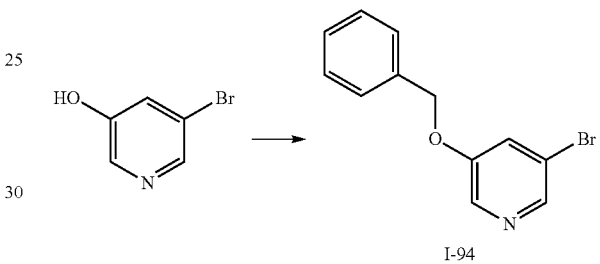

To a vial is added 3-bromo-5-hydroxypyridine (200 mg, 1.15 mmol), benzyl alcohol (137 mg, 1.27 mmol) and triphenylphosphine (332 mg, 1.27 mmol) in THF (5 ml) at 0° C., followed by the addition of diisopropyl azodicarboxylate (256 mg, 1.27 mmol). The reaction mixture is stirred at room temperature for 18 hours. The reaction mixture is concentrated in vacuo. The residue is diluted with EtOAc, washed with sat NaHCO$_3$, water, brine, dried under anhy. Na$_2$SO$_4$, filtered and concentrated. The residue is purified by flash chromatography (SiO$_2$, 0-5% MeOH/CH$_2$Cl$_2$) to afford title compound (97 mg); m/z 264.0, 266.0 [M, M+2H]

Synthesis of 5-Bromo-3-trifluoromethyl-pyrazin-2-ylamine

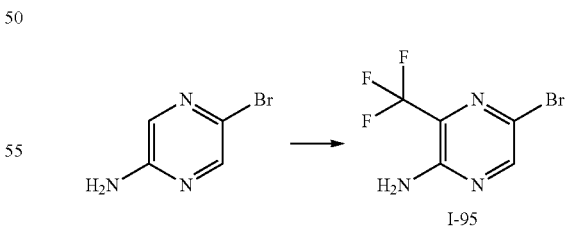

To a solution of 2-amino-5-bromopyrazine (174 mg, 1 mmol) in DMSO (3 ml) stifling under Ar is added ferrocene (56 mg, 0.3 mmol) and degassed for 5 minutes with Ar. 2 ml of 1N H$_2$SO$_4$ in DMSO is added, followed by CF$_3$I (0.276 ml, 3 mmol) in DMSO (2 ml), giving a slight yellow solution. 0.2 ml of 30% H$_2$O$_2$ is added slowly, causing the reaction to go from yellow to dark green in color. The reaction was heated to 50° C. for 2 hours under Ar. After cooling to room temperature, the reaction mixture is poured into brine, and product is extracted with EtOAc (4×20 ml). The combined organic fractions are dried with magnesium sulfate, filtered, then concentrated in vacuo. The crude material was purified by flash chromatography (SiO$_2$, Biotage SNAP 10 g, 0-50% EtOAc/hept) which yields 70 mg of title compound; m/z 242.0, 244.0 (M, M+2H)

Synthesis of 4-benzyloxy-5-bromo-pyrimidin-2-ylamine

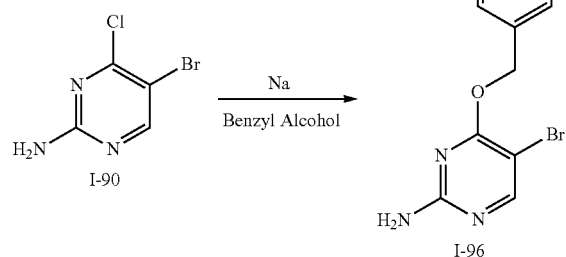

A 20 ml microwave reaction vessel is charged with benzyl alcohol (7.0 ml) and sodium (145 mg, 6.33 mmol). The vessel is capped and stirred at ambient temperature until the sodium is consumed. After this time, I-90 (1.10 g, 5.28 mmol) is added and the reaction is warmed to 130° C. for 2 h. Upon cooling to room temperature the reaction mixture is concentrated to low volume. The remaining residue is diluted with water. The water is decanted and the remaining oil is treated with methanol. The precipitated solid is collected via filtration and washed with methanol to give the title intermediate (0.86 g); m/z 282.0 [M+H].

Synthesis of (5-bromo-pyridin-2-yl)-methyl-amine

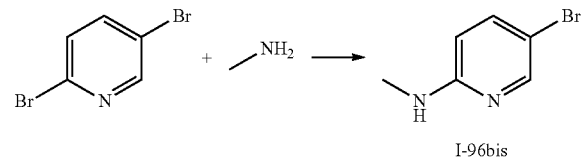

A 20 ml microwave reaction vessel is charged with 2,5-Dibromo-pyridine (2.00 g, 8.44 mmol) and treated with methylamine (10.45 ml of a 33% solution in ethanol, 84.43 mmol) and warmed to 80° C. for 3 days. After this time the reaction is concentrated and the remaining solid is treated with 1M HCl (50 ml) and DCM. The layers are separated and the aqueous phase is basified using 1N NaOH (to pH~11). The product was extracted into DCM (2×) and the combined organics were dried (MgSO4), filtered and concentrated to give the desired product I-96bis (1.20 g). 1H-NMR (400 MHz, DMSO-d6): 2.75 ppm (d, 3H), 6.44 ppm (d, 1H), 6.72 ppm (bs, 1H), 7.51 ppm (dd, 1H), 8.05 ppm (s, 1H)

Synthesis of 2-[4-(3-{(R)-1-[4-(2-Amino-4-benzyloxy-pyrimidin-5-yl)-phenyl]-1-cyclo propyl-ethyl}-[1,2,4]oxadiazol-5-yl)-pyrazol-1-yl]-N,N-dimethyl-acetamide

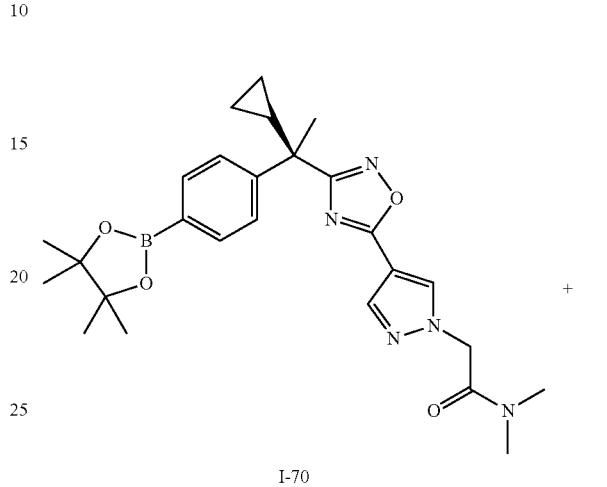

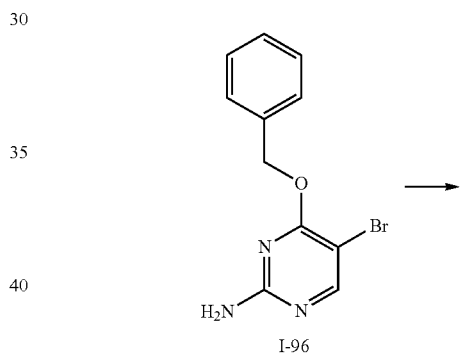

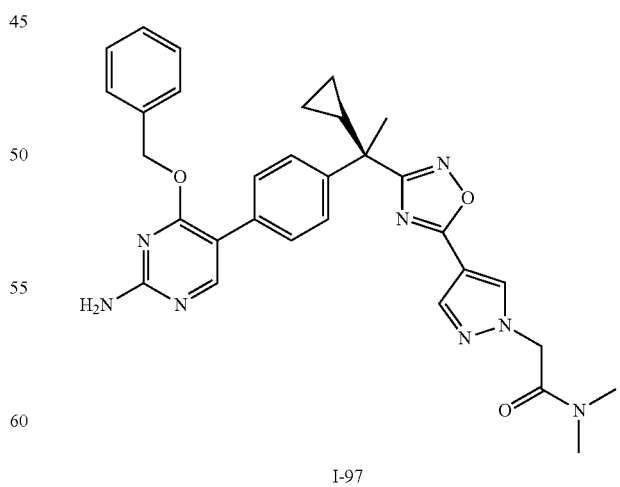

I-97 is prepared following Method 26 (using Palladium tetrakis, 2M Na$_2$CO$_3$, and DMF at 85° C. for 16 h); m/z 565.0 [M+H].

Synthesis of 2-{2-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-ethyl}-isoindole-1,3-dione

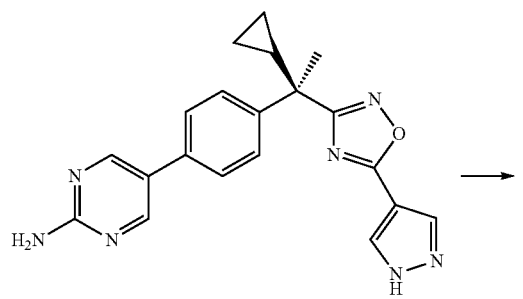

Example 48

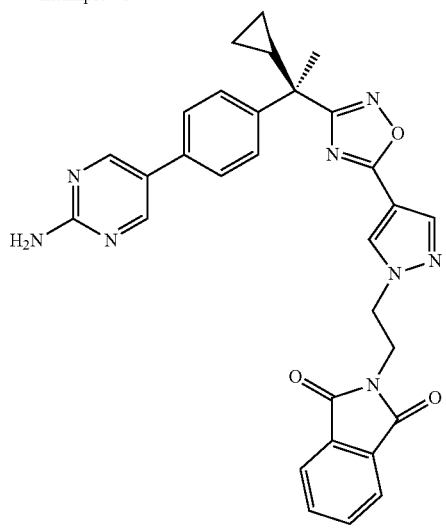

I-98

Example 48 (100 mg, 0.266 mmol) is treated with DMF (2.5 mL), 2-(2-Bromo-ethyl)-isoindole-1,3-dione (101 mg, 0.399 mmol), and Cs$_2$CO$_3$ (83.0 mg, 0.599 mmol) and the reaction is stirred overnight. The resulting mixture is diluted with water and ethyl acetate and the phases separated. The organic phase is washed with water and brine, dried over Na$_2$SO$_4$, filtered, and concentrated in vacuo. The resulting residue is purified by flash chromatography over silica eluting 0-10% methanol/CH$_2$Cl$_2$ to give I-98 (120 mg).

Synthesis of Final Compounds

Method 1

Synthesis of 2-(3-{2-[4-(5-methoxypyridin-3-yl)phenyl]-3-methylbutan-2-yl}-1,2,4-oxadiazol-5-yl)pyrazine (Example 1, Table 1)

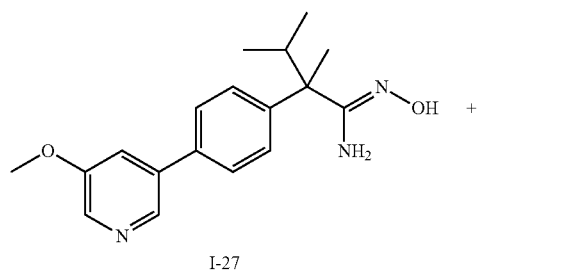

I-27

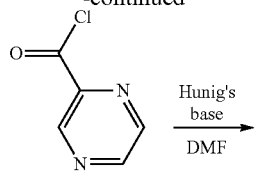

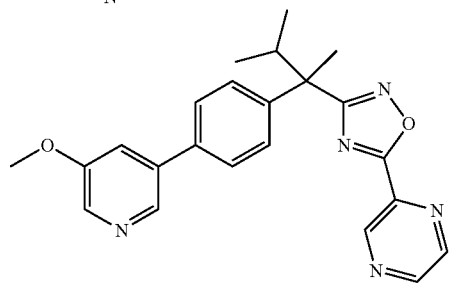

Example 1

To a solution of I-27 (200 mg, 0.64 mmol) in DMF (5 mL) is added Hunig's base (0.3 mL, 1.6 mmol) followed by pyrazine-2-carbonyl chloride (110 mg, 0.80 mmol). The reaction mixture is heated at 120° C. for 2 h then volatiles are removed in vacuo. The residue is purified by flash chromatography (SiO$_2$, heptane to 60% EtOAc in heptane) to give the title compound (165 mg).

The following compounds were synthesized in similar fashion from the appropriate intermediates:
Examples 2-5, table 1
Example 7, table 1
Examples 117-118, table 1
Example 120, table 1

Method 2

Synthesis of [2-amino-5-(4-{3-methyl-2-[5-(pyridin-3-yl)-1,2,4-oxadiazol-3-yl]butan-2-yl}phenyl)pyridin-3-yl]methanol (Example 6, Table 1)

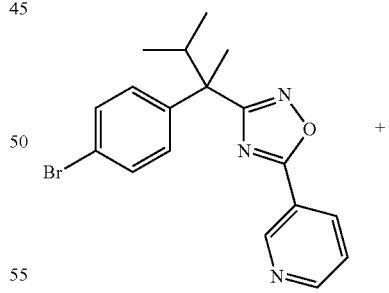

I-58

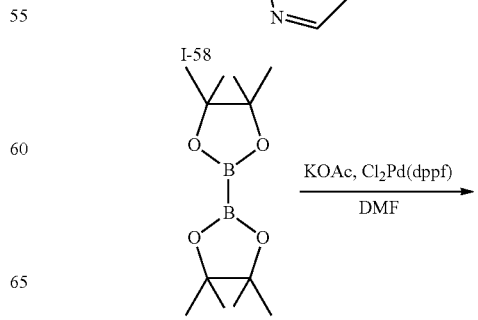

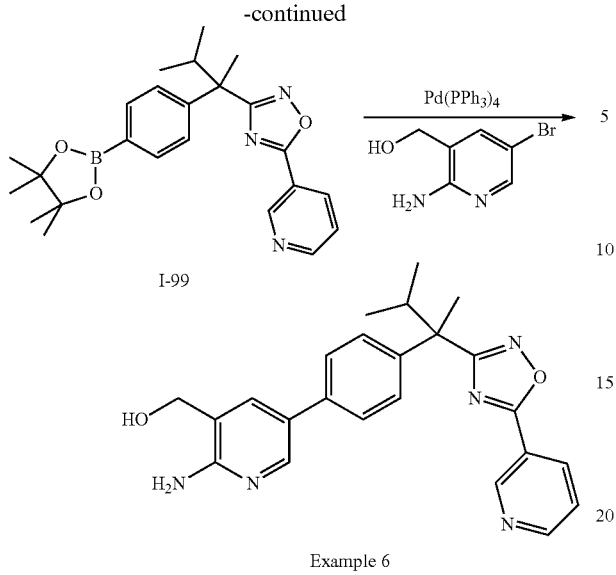

I-99

Example 6

I-58 (0.450 g, 1.21 mmol) is suspended in 1,4-dioxane (3.0 mL). Bis(pinacolato)diborane (0.364 g, 1.43 mmol), potassium acetate (0.500 g, 5.09 mmol) and 1,1'-bis(diphenylphosphino)ferrocenedichloropalladium(II) dichloromethane complex (0.100 g, 0.122 mmol) is added. This reaction mixture is de-gassed and heated under argon at 100° C. for 4 h. The mixture is cooled to room temperature then diluted with EtOAc and washed with water. The organics are collected and concentrated in vacuo to afford a residue that is purified by flash chromatography (SiO$_2$, hexane to 30% EtOAc in hexane) to give I-99 (0.362 g); m/z 420.61 [M+1]

I-99 (0.100 g, 0.238 mmol) is dissolved in DMF (2.0 mL) and treated with 2-amino-5-bormo-3(hydroxymethyl)pyridine (0.051 g, 0.25 mmol), tetrakis(triiphenylphosphine)palladium(0) (0.029 g, 0.025 mmol), and aqueous Na$_2$CO$_3$ (2.0 M, 1.0 mL, 1.0 mmol). This reaction mixture is de-gassed and heated under argon at 100° C. for 4 h. The mixture is cooled to room temperature then diluted with EtOAc and washed with water. The organics are collected and concentrated in vacuo to afford a residue that is purified by flash chromatography (SiO$_2$, 0-10% MeOH in CH$_2$Cl$_2$) to give the title compound (0.025 g).

Method 3

Synthesis of 5-(4-{2-[5-(6-methoxypyridin-3-yl)-1,2,4-oxadiazol-3-yl]-3-methylbutan-2-yl}phenyl)pyrimidin-2-amine (Example 8, Table 1)

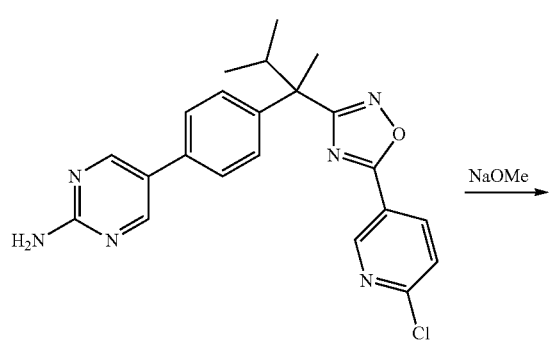

Example 7

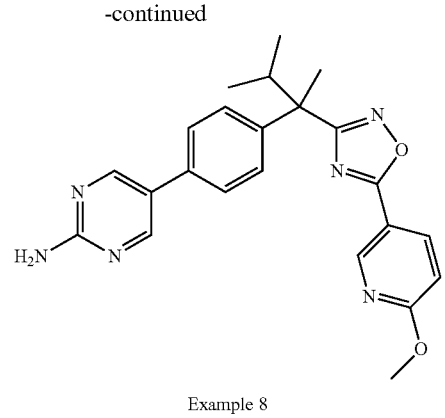

Example 8

Example 7 (35 mg, 0.083 mmol) is dissolved in MeOH (2.0 mL). A 25% (w/w) NaOMe solution in MeOH (50 µL) is added. The reaction mixture is heated at 70° C. for 6 h then volatiles are removed in vacuo. The residue is purified by flash chromatography (SiO$_2$, 0-10% MeOH in CH$_2$Cl$_2$) to give the title compound (26 mg).

The following compounds are synthesized in similar fashion from the appropriate intermediates:

Example 9, table 1

Method 4

Synthesis of 3-(3-{2-[4-(2-aminopyrimidin-5-yl)phenyl]-3-methylbutan-2-yl}-1,2,4-oxadiazol-5-yl)pyridin-2(1H)-one (Example 12, Table 1)

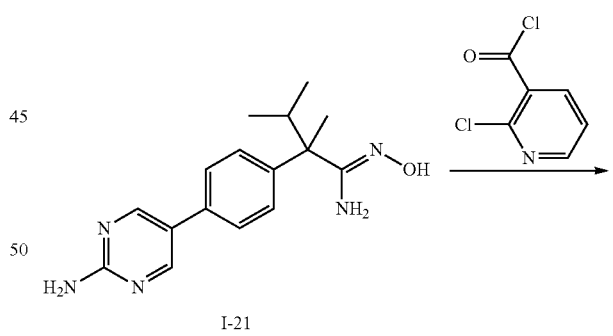

I-21

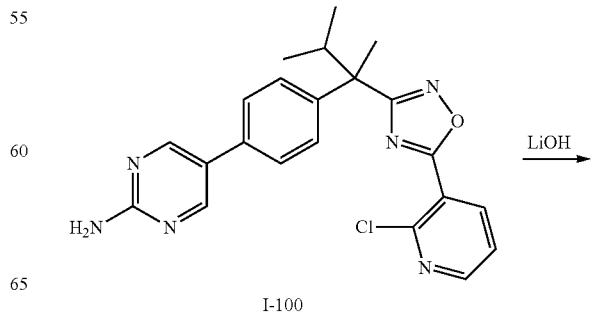

I-100

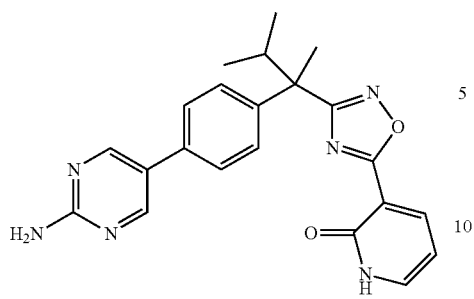

Example 12

I-21 (100 mg, 0.255 mmol) is dissolved in 1-methyl-2-pyrrolidinone (1 mL). Ethyl-diisopropylamine (0.3 mL, 1.6 mmol) is added followed by 2 chloro-nicotinyl chloride (62 mg, 0.35 mmol). The reaction mixture is heated at 120° C. for 1 h then cooled to room temperature and pardoned between $CH_2Cl_2$ and water. The organics are collected and volatiles are removed in vacuo. The residue is purified by flash chromatography ($SiO_2$, 0-100% ethyl acetate in heptane) to afford I-100 (78 mg); m/z 421.48 [M+1] I-100 (35 mg, 0.083 mmol) is dissolved in 1,4-dioxane (2.0 mL). A 10% (w/w) aqueous LiOH solution (50 µL) is added. The reaction mixture is heated at 70° C. for 2 h. The solvent is removed in vacuo and the residue is suspended in water (2.0 mL). The precipitate is collected by filtration, washed with water, and air-dried. The solid is further purified by flash chromatography ($SiO_2$, 0-10% MeOH in $CH_2Cl_2$) to give the title compound (28 mg).

The following compounds are synthesized in similar fashion from the appropriate intermediates:
Example 1, Table 1

Method 5

Synthesis of 5-(4-{2-[5-(4-methoxypyridin-3-yl)-1,2,4-oxadiazol-3-yl]-3-methylbutan-2-yl}phenyl)pyrimidin-2-amine (Example 11, Table 1)

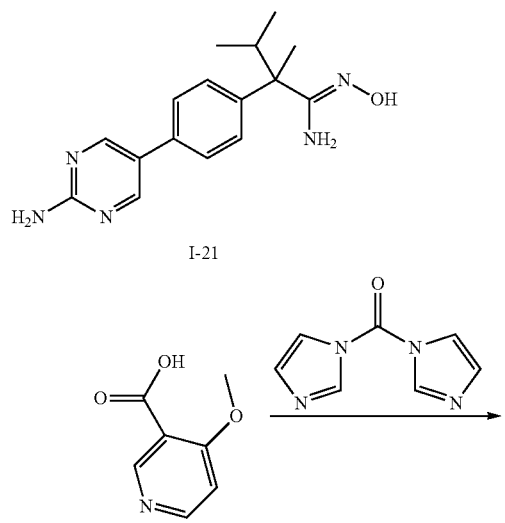

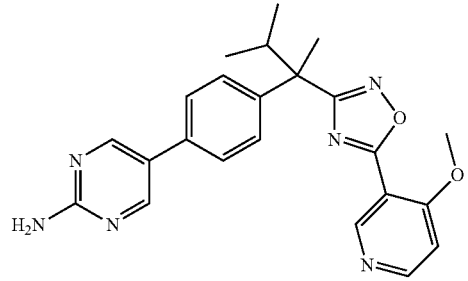

Example 11

4-Methoxy-nicotinic acid (54 mg, 0.35 mmol) is dissolved in 1-methyl-2-pyrrolidinone (1 mL) and carbonyldiimidazole (57 mg, 0.35 mmol) is added. The mixture is stirred for 15 minutes then I-21 (100 mg, 0.255 mmol) is added. This reaction mixture is heated at 120° C. for 1 h then cooled to room temperature and diluted with water. The solid is collected by filtration and purified by flash chromatography ($SiO_2$, 0-100% EtOAc in heptane) to give the title compound (19 mg).

The following compounds were synthesized in similar fashion from the appropriate intermediates:
Examples 13-15, table 1
Examples 18-22, table 1
Examples 25-29, table 1
Examples 33-34, table 1
Example 37, table 1
Example 58, table 1
Examples 67-69, table 1
Example 119, table 1

Synthesis of 5-(4-{(R)-1-cyclopropyl-1-[5-(1H-pyrazol-4-yl)-[1,2,4]oxadiazol-3-yl]-ethyl}-phenyl)-pyrimidin-2-ylamine (Example 48, Table 1)

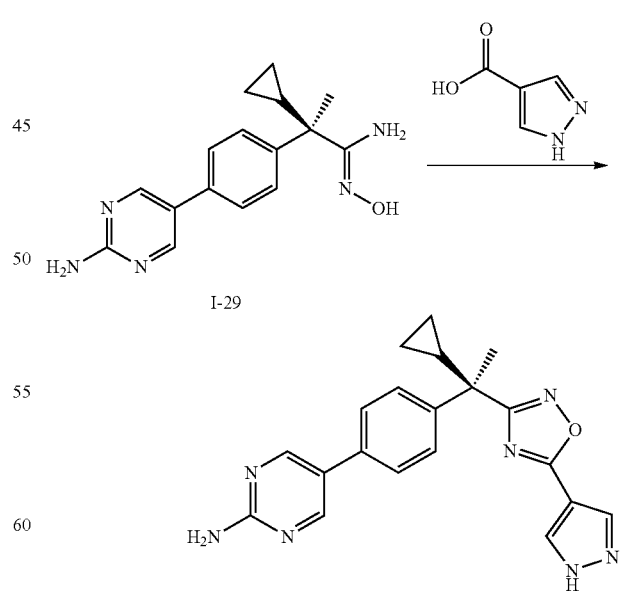

Example 48

To a suspension of 1H-pyrazole-4-carboxylic acid (7.1 g, 0.063 mol) in THF (200 mL) is added 1,1'-carbonyldiimidazole (10.2 g, 0.063 mol) at room temperature. The mixture is stirred at 50° C. for 30 minutes. A suspension of I-29 (12.5 g, 0.042 mol) in THF (100 mL) is added to the above mixture and the resulting mixture is heated under reflux for 24 hours. The mixture is cooled down and the solid is collected by means of filtration. The solid is then suspended in AcOH (150 mL) at room temperature. The mixture is heated to 90° C. for 2 hours. The solution is cooled down and is concentrated under vacuum. The residue is dissolved in EtOAc (100 mL) and the solution is washed with $H_2O$ (200 mL) and saturated $NaHCO_3$ solution (200 mL). The organic layer is concentrated to afford the title compound (14.7 g, 0.040 mol).

Method 6

Synthesis of 4-(3-{1-[4-(2-Amino-pyrimidin-5-yl)-phenyl]-1,2-dimethyl-propyl}-1,2,4-oxadiazol-5-yl)-piperidine-1-carboxylic Acid tert-butyl Ester (Example 109, Table 1) and 5-(4-{3-methyl-2-[5-(piperidin-4-yl)-1,2,4-oxadiazol-3-yl]butan-2-yl}phenyl)pyrimidin-2-amine (Example 110, Table 1)

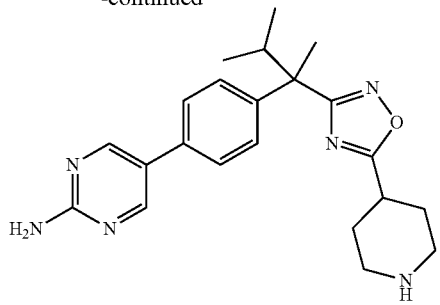

Example 110

To a suspension of N-Boc-isonipocotic acid (115 mg, 0.50 mmol) in THF (1 mL) is added carbonyldiimidazole (81 mg, 0.50 mmol). The mixture is heated at 55° C. for 20 min then treated with I-21 (100 mg, 0.33 mmol). The reaction mixture is heated at 55° C. for 17 h then heated in microwave at 150° C. for 20 min. The mixture is cooled to room temperature then directly purified by flash chromatography ($SiO_2$, 15-100% EtOAc in heptane) to give Example 109 (89 mg).

Example 109 (83 mg, 0.17 mmol) is dissolved in $CH_2Cl_2$ (1 mL) and treated with a solution of HCl in 1,4-dioxane (4.0 M, 0.4 mL). The mixture is stirred at room temperature for 3.5 h then resulting solid is filtered, washed with $CH_2Cl_2$, collected, and dried to afford the title compound (63 mg).

The following compounds are synthesized in similar fashion from the appropriate intermediates:

Examples 111-114, table 1

Method 7

Synthesis of 5-(4-{3-methyl-2-[5-(1H-pyrazol-4-yl)-1,2,4-oxadiazol-3-yl]butan-2-yl}phenyl)pyrimidin-2-amine (Example 146, table 1)

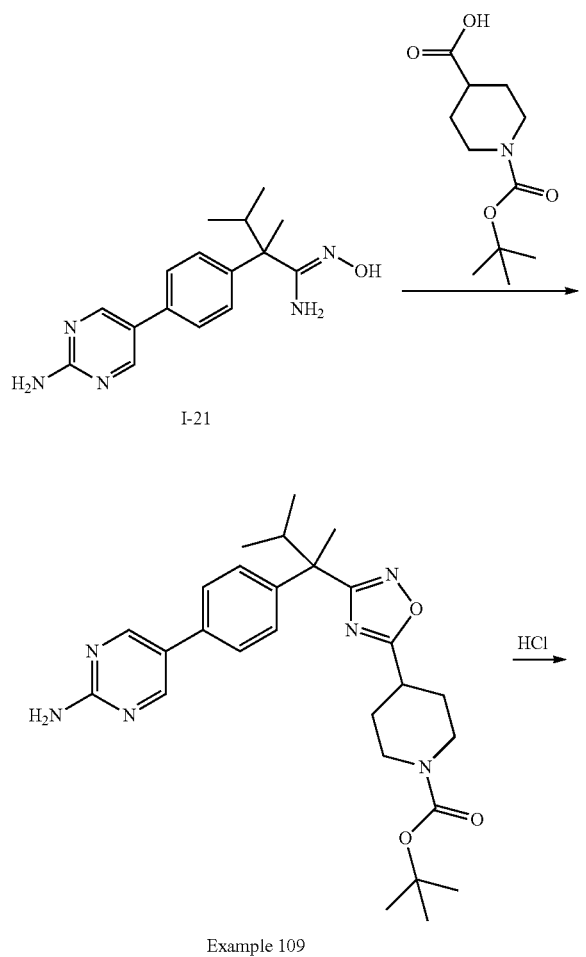

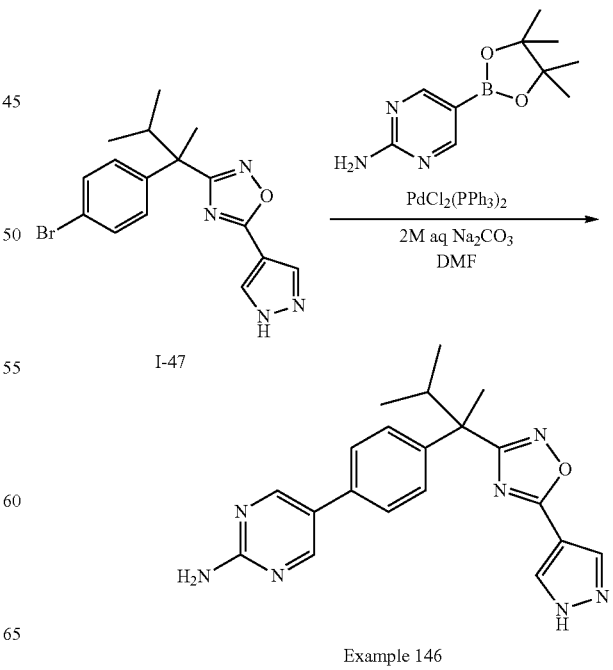

A mixture of I-47 (70 mg, 0.19 mmol), 2-aminopyrimidine-5-boronic acid pinacol ester (51 mg, 0.23 mmol) and 2M aqueous Na$_2$CO$_3$ (0.2 mL) in DMF (1 mL) is degassed under N$_2$ for 5 minutes. To this mixture is added PdCl$_2$(PPh$_3$)$_2$ (14 mg, 0.02 mmol). The mixture is stirred at 80° C. for 18 h then partitioned between EtOAc and water. The organics are washed with water, dried with Na$_2$SO$_4$, filtered, and concentrated in vacuo. The residue is purified by preparative HPLC to give the title compound (13 mg).

The following compounds are synthesized in similar fashion from the appropriate intermediates:

Examples 125, table 1—upon reaction of I-38 with -aminopyrimidine-5-boronic acid, PdCl$_2$dppf (0.05 eq) and dppf (0.05 eq) only Example 125 is formed instead of Example 128

Example 126-133, table 1
Example 139, table 1
Example 143, table 1
Examples 146-157, table 1

Method 8

Synthesis of 5-[4-(3-methyl-2-{5-[6-(trifluoromethyl)pyridin-3-yl]-1,2,4-oxadiazol-3-yl}butan-2-yl)phenyl]pyrimidin-2-amine (Example 136, table 1)

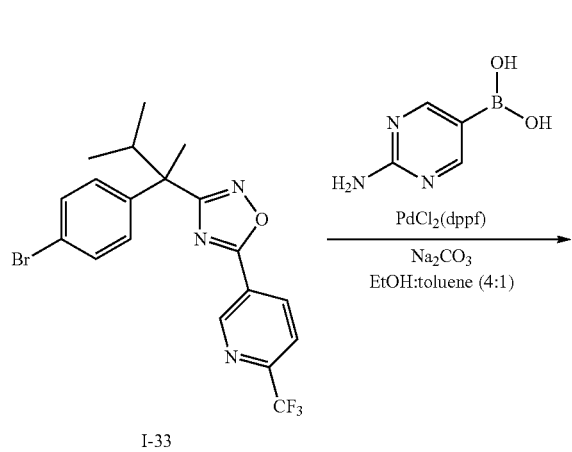

I-33

Example 136

To a suspension of I-33 (156 mg, 0.35 mmol), 2-aminopyrimidine-5-boronic acid (58 mg, 0.42 mmol) and 2M aqueous Na$_2$CO$_3$ (0.53 mL) in ethanol:toluene (4:1, 2 ml) in a pressure tube is added [1,1'-bis(diphenylphosphino)-ferrocene] dichloro palladium (II) (25 mg, 0.030 mmol) and 1,1'-bis (diphenylphosphino)ferrocene (15 mg, 0.02 mmol). The reaction mixture is stirred at 90° C. for 2 h. The reaction mixture is filtered through a pad of Celite, washed with EtOAc and CH$_2$Cl$_2$. The collected filtrate is concentrated in vacuo. Purification by preparative HPLC gives the title compound (72 mg).

The following compounds are synthesized in similar fashion from the appropriate intermediates:

Example 135-138, table 1

Examples 140-141, table 1

Method 9

Synthesis of 2-[4-(3-{1-[4-(2-aminopyrimidin-5-yl)phenyl]-1-cyclopropylethyl}-1,2,4-oxadiazol-5-yl)-1H-pyrazol-1-yl]-N,N-dimethylacetamide (Example 59, table 1)

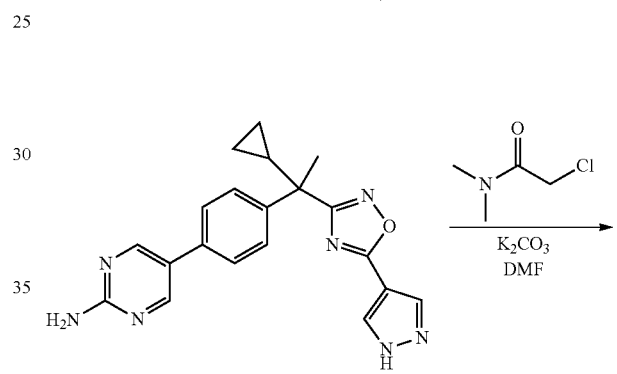

Example 21

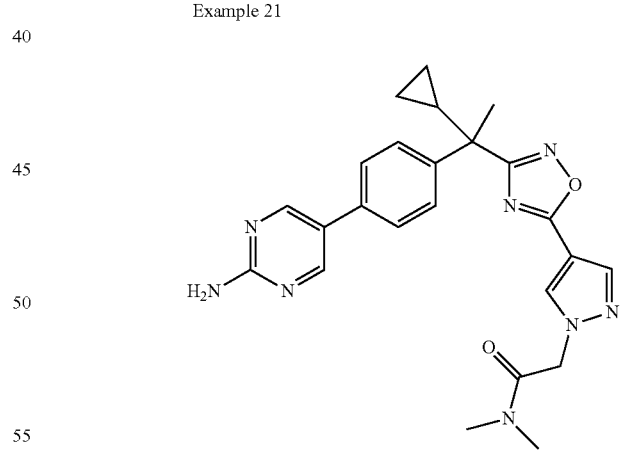

Example 59

To a solution of example 21 (350 mg, 0.94 mmol) in DMF (1 mL) is added K$_2$CO$_3$ (260 mg, 1.9 mmol) and 2-chloro-N,N-dimethylacetamide (0.19 mL, 1.9 mmol). The reaction mixture is stirred for 20 h at room temperature then directly purified by preparative HPLC (10-60% CH$_3$CN in water containing 0.1% TFA) to give the title compound (200 mg).

The following intermediates are synthesized in similar fashion from the appropriate reagents:

| Intermediate | Structure | m/z [M + H] |
|---|---|---|
| I-100bis[a] | 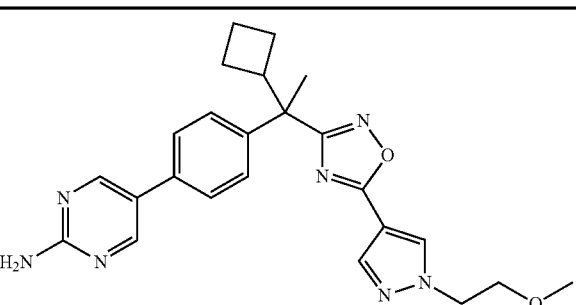 | 446.4 |

[a]The reaction mixture is heated at 50° C.

The following compounds are synthesized in similar fashion from the appropriate intermediates:
Example 30, table 1
Example 43, table 1
Example 60, table 1 Example 75-76, table 1
Example 79, table 1
Examples 97-99, table 1
Example 106, table 1
Example 271, table 1—the reaction is performed at 130° C. for 48 hours starting from the corresponding bromide Synthesis of 2-[4-(3-{(R)-1-[4-(2-amino-pyrimidin-5-yl)-phenyl]-1-cyclopropyl-ethyl}-[1,2,4]oxadiazol-5-yl)-pyrazol-1-yl]-N,N-dimethyl-acetamide (Example 115, Table 1)

To a solution of Example 48 (14.7 g, 0.040 mol) in DMF (150 mL) are added 2-chloro-N,N-dimethylacetamide (6.1 mL, 0.059 mol) and K$_2$CO$_3$ (10.9 g, 0.079 mol) at room temperature. The mixture is stirred at the same temperature for 2 hours. Water (100 mL) is added and the mixture is extracted with EtOAc (200 mL). The combined organic layer is dried with MgSO$_4$ (20 g) and is filtered. The filtrate is concentrated and the remaining solid is re-suspended in small amount of acetonitrile (30 mL) for 10 minutes. The solid is collected by filtration and is washed with cold acetonitrile. The resulting solid is dried under vacuum and is confirmed to be the title compound (10 g).

The title compound is further purified, if desired, by recrystallization from ethanol, methanol or THF. Alternatively, the title compound is converted to its hydrochloride salt by dissolving the free base in ethanol or isopropyl alcohol followed by addition of aqueous hydrochloric acid to the solution.

Method 10

Synthesis of 2-[(3-{2-[4-(2-aminopyrimidin-5-yl)phenyl]-3-methylbutan-2-yl}-1,2,4-oxadiazol-5-yl)amino]ethanol (Example 80, Table 1)

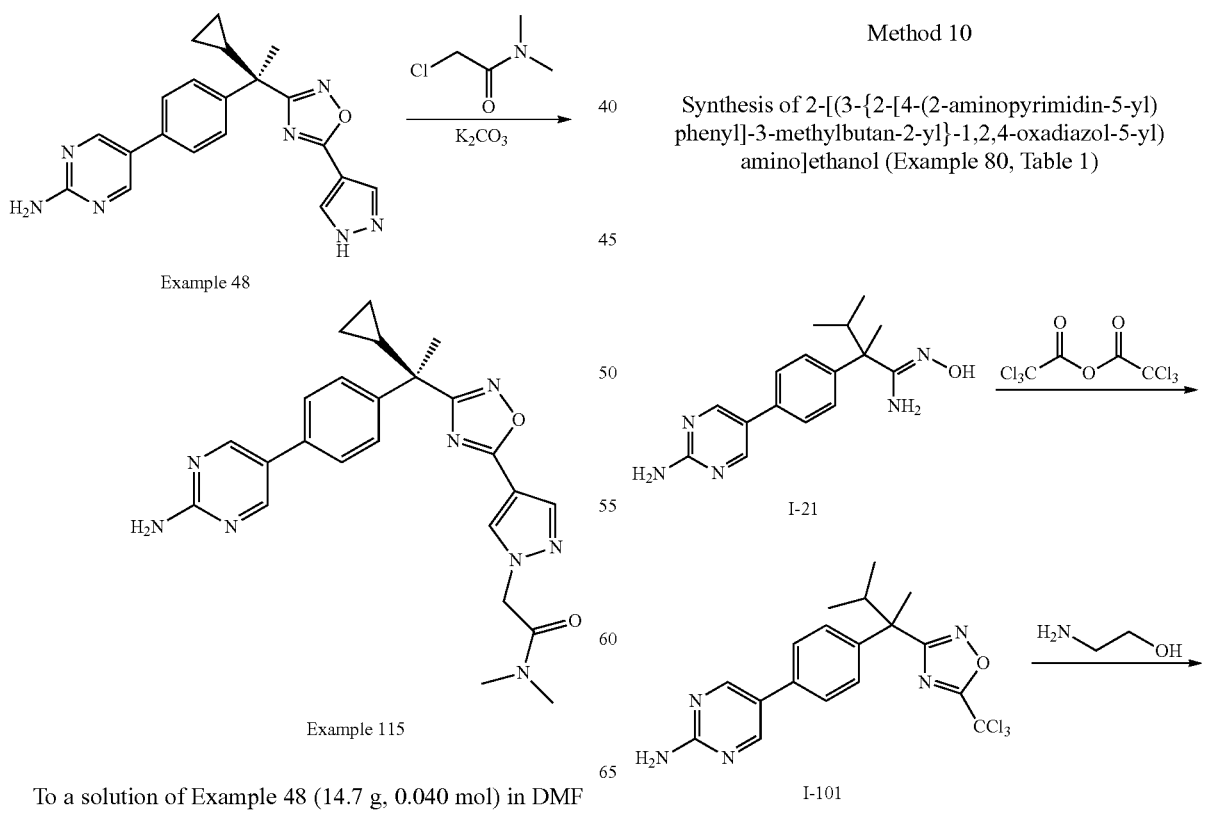

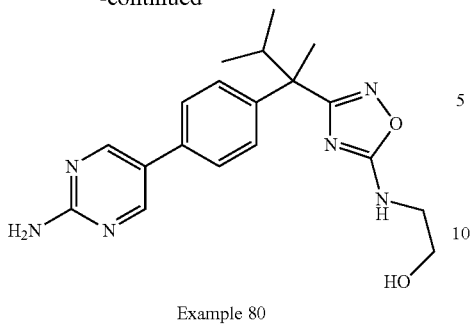

Example 80

To a solution of I-21 (900 mg, 3.0 mmol) in toluene (35 mL) is added trichloroacetic anhydride (0.69 mL, 3.6 mmol). The reaction mixture is heated at reflux for 2.5 h then cooled to room temperature. The mixture is diluted with EtOAc, washed with saturated aqueous NaHCO$_3$, dried with Na$_2$SO$_4$, filtered and concentrated to afford I-101 (1.25 g); m/z 426.31/428.22 [M/M+2H].

To a solution of I-101 (80 mg, 0.19 mmol) and KOH (19 mg, 0.28 mmol) in DMSO (1 mL) is added ethanolamine (20 μL, 0.28 mmol). The reaction mixture is stirred at room temperature for 1 h then treated with water. The mixture is extracted with EtOAc, washed with brine, dried with Na$_2$SO$_4$, filtered, and concentrated. The residue is purified by flash chromatography (SiO$_2$, 0-10% MeOH in CH$_2$Cl$_2$) to yield the title compound (45 mg).

The following compounds are synthesized in similar fashion from the appropriate intermediates:

Examples 81-83, table 1

Example 84, table 1—side product isolated from the reaction performed to form Example 83

Example 86, table 1—the intended amine derivative is not isolated and the amide side product is the only one that is isolated Example 87, table 1

Examples 89, table 1

Example 90, table 1—side product isolated from the reaction performed to form Example 89

Example 91, table 1—the intended amine derivative is not isolated and the amide side product is the only one that is isolated Example 134, table 1

Example 171, table 1

Method 11

Synthesis of 1-{[5-(3-{1-[4-(2-aminopyrimidin-5-yl)phenyl]-1-cyclopropylethyl}-1,2,4-oxadiazol-5-yl)pyrazin-2-yl]amino}-2-methylpropan-2-ol (Example 44, Table 1)

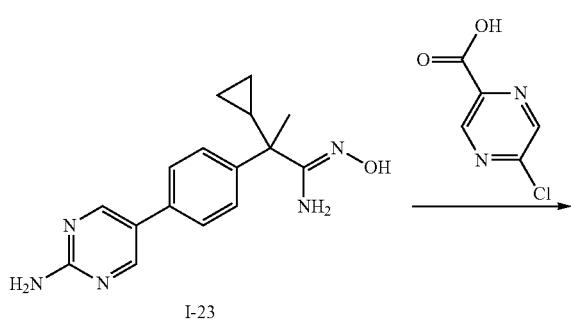

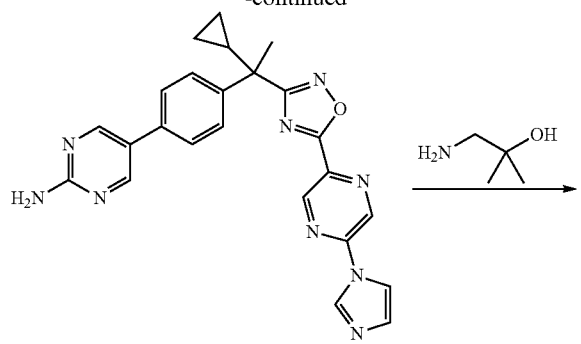

I-102

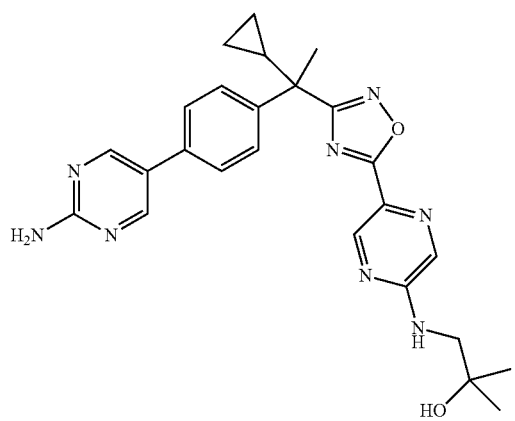

Example 44

To a solution of 5-chloro-pyrazine-2-carboxylic acid (490 mg, 3.1 mmol) in NMP (3 mL) is added carbonyldiimidazole (500 mg, 3.1 mmol). The mixture is stirred at 50° C. for 0.5 h then treated with I-23 (830 mg, 2.8 mmol) and heated at 110° C. for 2 h. The mixture is cooled to room temperature, treated with water, and stirred for 18 h. The resulting solid is filtered, dried, and collected to give I-102 (1.0 g). 1H NMR (DMSO-d6) δ ppm 9.40 (1H, s), 9.20 (1H, s), 8.75 (1H, s), 8.55 (2H, s), 8.10 (1H, s), 7.60 (2H, d), 7.40 (2H, d), 7.20 (1H, s), 6.75 (2H, s), 1.65-1.75 (1H, m), 1.55 (3H, s), 0.3-0.75 (4H, m).

I-102 (300 mg, 0.66 mmol) is dissolved in 1-amino-2-methyl-propan-2-ol (1.5 mL) and heated at 80° C. for 4 h. The mixture is cooled to room temperature and treated with water. The resulting solid is filtered, collected, and further purified by recrystallization from CH$_3$CN to give the title compound (155 mg).

The following compounds are synthesized in similar fashion from the appropriate intermediates:

Example 42, table 1

Example 45, table 1

Examples 35-36, table 1

Examples 73-74, table 1

Examples 162-163, table 1

215
Method 12

Synthesis of 5-{4-[1-cyclopropyl-1-(5-{6-[(2-methoxyethyl)amino]pyridin-3-yl}-1,2,4-oxadiazol-3-yl)ethyl]phenyl}pyrimidin-2-amine
(Example 38, Table 1)

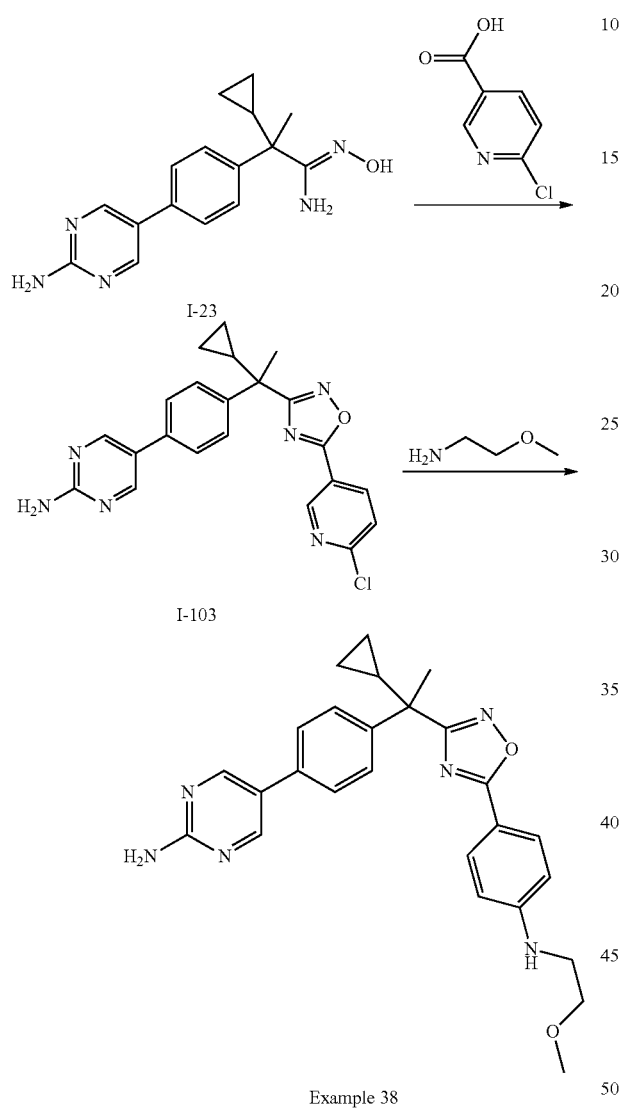

Example 38

To a solution of 6-chloronicotinic acid (500 mg, 3.2 mmol) in NMP (7 mL) is added carbonyldiimidazole (520 mg, 2.9 mmol). The mixture is stirred at room temperature for 1 h then treated with I-23 (860 mg, 2.8 mmol) and heated at 130° C. for 2 h. The mixture is cooled to room temperature and treated with water. The resulting solid is filtered, dried, and collected to give I-103 (350 mg); m/z 419.33 [M+H]

I-103 (150 mg, 0.36 mmol) is dissolved in 2-methoxyethylamine (0.5 mL) and heated at 80° C. for 2 h. The mixture is cooled to room temperature and treated with water to afford a residue. The water is decanted and the residue is purified by preparative HPLC (10-60% CH$_3$CN in water containing 0.1% TFA) to give the title compound (98 mg).

The following compounds are synthesized in similar fashion from the appropriate intermediates:

216

Example 39-41, table 1
Examples 70-72, table 1

Method 13

Synthesis of 1-[4-(3-{2-[4-(2-aminopyrimidin-5-yl)phenyl]-3-methylbutan-2-yl}-1,2,4-oxadiazol-5-yl)-1H-pyrazol-1-yl]-2-methylpropan-2-ol
(Example 159, Table 1)

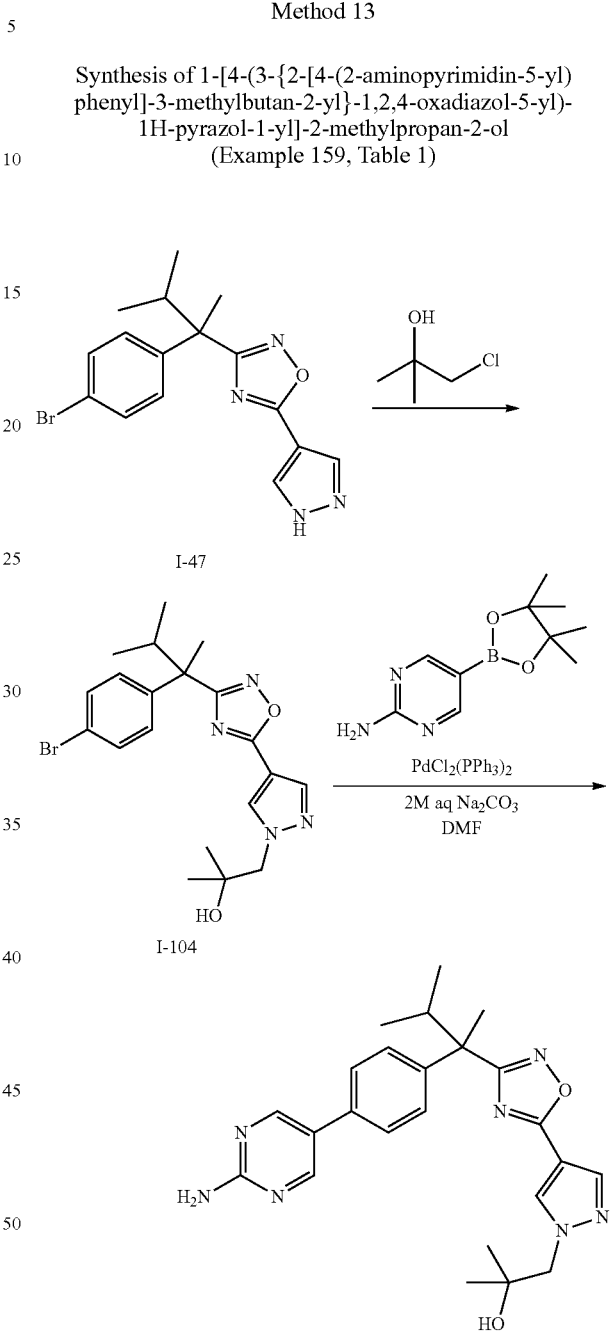

Example 159

To a suspension of I-47 (336 mg, 0.93 mmol) and potassium carbonate (154 mg, 1.12 mmol) in DMF (6 mL) is added 1-chloro-2-methyl-propan-2-ol (100 µL, 0.98 mmol). The reaction mixture is stirred at 80° C. for 16 h then concentrated in vacuo. The residue is extracted with CH$_2$Cl$_2$, washed with saturated aqueous NH$_4$Cl, dried with Na$_2$SO$_4$, filtered and concentrated in vacuo to afford I-104 (365 mg); m/z 434 [M+H].

The following intermediates are synthesized in similar fashion from the appropriate reagents:

| Intermediate | Structure | m/z [M/M + 2H] |
|---|---|---|
| I-104A | 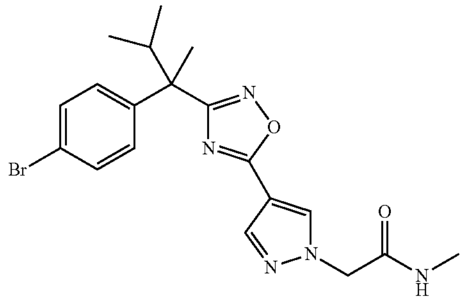 [SMILES: CNC(=O)Cn1cc(-c2nc(C(C)(c3ccc(Br)cc3)C(C)C)no2)cn1] | 432.0/434.0 |
| I-104B | 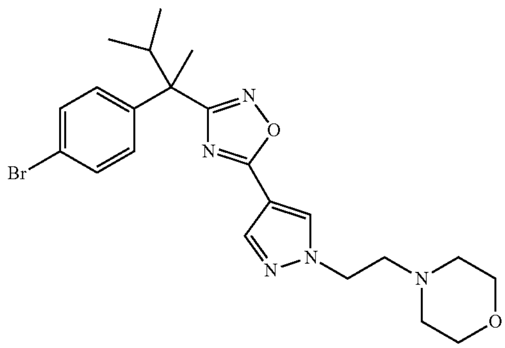 [SMILES: CC(C)C(C)(c1ccc(Br)cc1)c1noc(-c2cnn(CCN3CCOCC3)c2)n1] | 474.0/476.0 |
| I-104C | 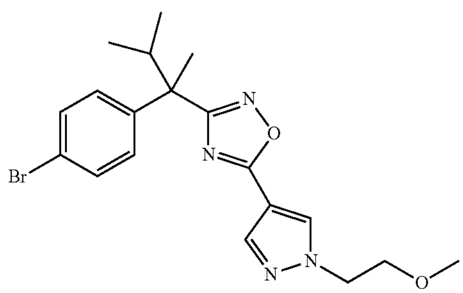 [SMILES: COCCn1cc(-c2nc(C(C)(c3ccc(Br)cc3)C(C)C)no2)cn1] | 419.0/421.0 |
| I-104D | 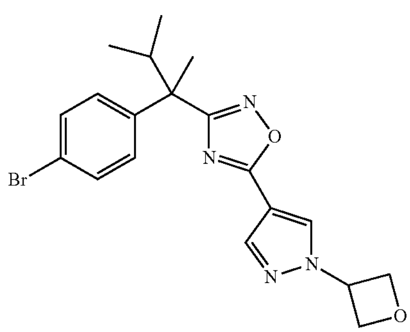 [SMILES: CC(C)C(C)(c1ccc(Br)cc1)c1noc(-c2cnn(C3COC3)c2)n1] | 417.0/419.0 |

A mixture of I-104 (365 mg, 0.84 mmol), 2-aminopyrimidine-5-boronic acid pinacol ester (279 mg, 1.26 mmol) and 2M aqueous Na₂CO₃ (0.85 mL) in DMF (4 mL) is degassed under N₂ for 5 minutes. To this mixture is added bis(triphenylphosphine)palladium(II)chloride (59 mg, 0.08 mmol). The mixture is stirred at 80° C. for 18 h then concentrated in vacuo. The residue is extracted with CH₂Cl₂, washed with saturated aqueous NaHCO₃, dried with Na₂SO₄, filtered, and concentrated in vacuo. The residue is purified by flash chromatography (SiO₂, 0-5% MeOH in CH₂Cl₂) to give the title compound (268 mg).

The following compounds are synthesized in similar fashion from the appropriate intermediates:
Example 142, table 1
Example 144, table 1
Example 158, table 1
Example 161, table 1

Method 14

Synthesis of 1-(3-{2-[4-(2-aminopyrimidin-5-yl)phenyl]-3-methylbutan-2-yl}-1,2,4-oxadiazol-5-yl)cyclopropanecarboxylic Acid (Example 95, Table 1)

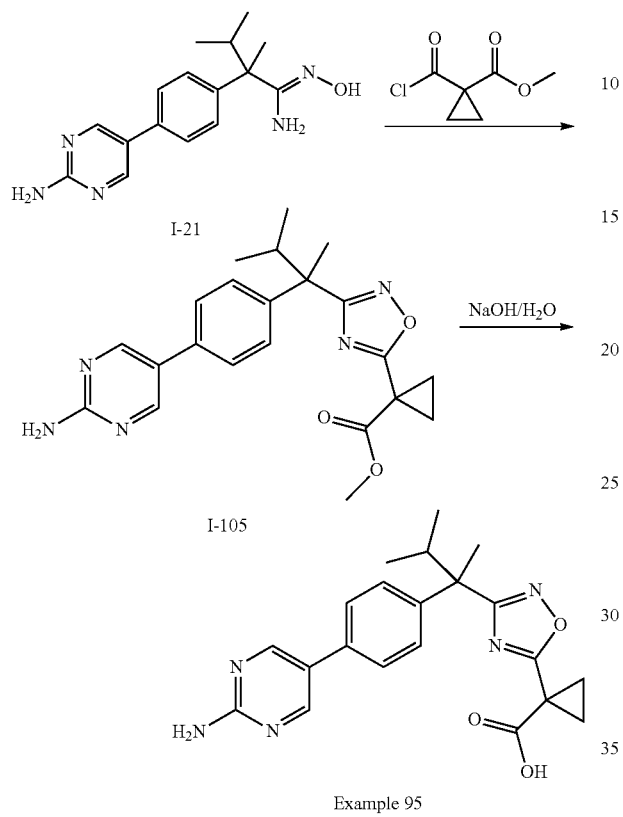

To a solution I-21 (189 mg, 0.63 mmol) in DMF (1 mL) is added a solution of 1-chlorocarbonyl-1-cyclopropanecarboxylic acid methyl ester (113 mg, 0.69 mmol) in DMF (1 mL). The reaction mixture is stirred at room temperature for 15 min then heated at 120° C. for 2 h. The mixture is cooled then treated with water and extracted with EtOAc, washed with brine, dried with $Na_2SO_4$, filtered, and concentrated in vacuo. The residue is purified by flash chromatography ($SiO_2$, 0-10% MeOH in $CH_2Cl_2$) to give I-105 (30 mg); m/z 408 [M+H].

To a solution of I-105 (30 mg, 0.074 mmol) in MeOH (0.5 mL) is added an aqueous solution of NaOH (4.0M, 90 μL). The reaction mixture is stirred at room temperature for 1 h then concentrated in vacuo. The residue is pardoned between EtOAc and water then the aqueous layer was acidified to pH~4 with 1 M aqueous HCl. The aqueous mixture is extracted with EtOAc and concentrated in vacuo to afford a residue that is purified by preparative HPLC to afford the title compound (20 mg).

Method 15

Synthesis of 1-(3-{2-[4-(2-aminopyrimidin-5-yl)phenyl]-3-methylbutan-2-yl}-1,2,4-oxadiazol-5-yl)cyclohexanecarboxylic Acid (Example 145, Table 1)

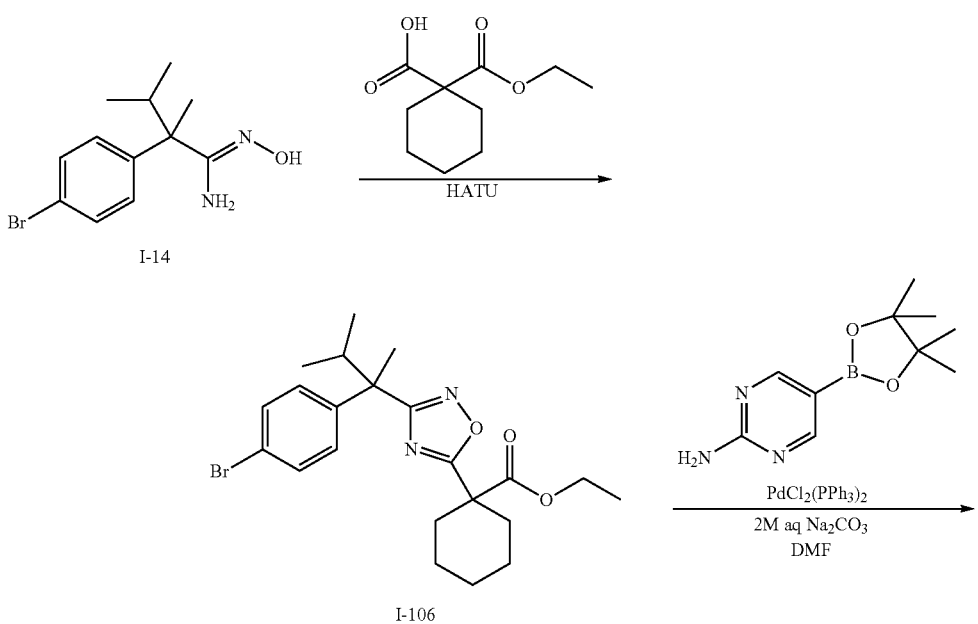

-continued

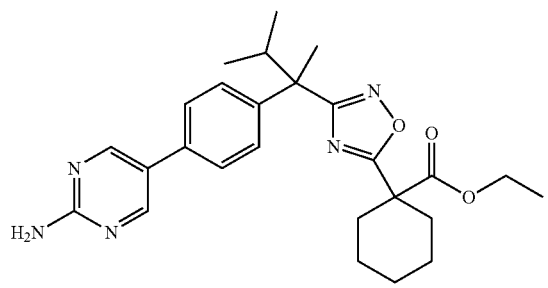

I-107

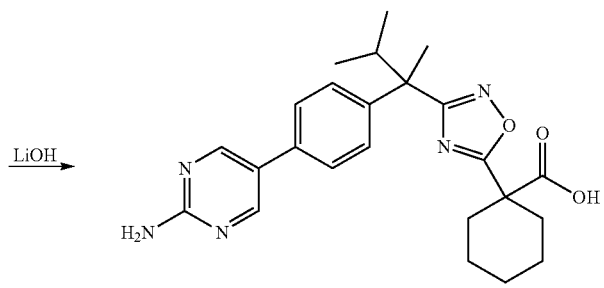

Example 145

A mixture of cyclohexane-1,1-dicarboxylic acid monoethyl ester (142 mg, 0.50 mmol), HATU (199 mg, 0.52 mmol) and triethylamine (80 μL, 0.55 mmol) in DMF (2.5 mL) is stirred for 5 min then I-14 (100 mg, 0.50 mmol) is added. The mixture is stirred at room temperature for 2 h then at 90° C. for 18 h then concentrated in vacuo. The resultant residue is partitioned between 1 M aqueous HCl and EtOAc. The organics are washed with brine, dried over MgSO₄, filtered and concentrated in vacuo. The residue is purified by flash chromatography (SiO₂, 15% EtOAc in cyclohexane) to give I-106 (251 mg); m/z 449/451 [M/M+2H].

A mixture of I-106 (223 mg, 0.50 mmol), 2-aminopyrimidine-5-boronic acid pinacol ester (121 mg, 0.55 mmol) and 2M aqueous Na₂CO₃ (1.9 mL) in DMF (5 mL) is degassed under N₂ for 5 minutes. To this mixture is added bis(triphenylphosphine)palladium(II)chloride (35 mg, 0.05 mmol). The mixture is stirred at 80° C. for 1 h then concentrated in vacuo. The residue is extracted with EtOAc, washed with saturated aqueous NaHCO₃, dried with Na₂SO₄, filtered, and concentrated in vacuo. The residue is purified by flash chromatography (SiO₂, 0-20% EtOAc in cyclohexane) to give I-107 (182 mg); m/z 464 [M+H].

To a solution of I-107 (175 mg, 0.38 mmol) in 1:1 THF: water (3 mL) is added LiOH—H₂O (17 mg, 0.40 mmol). The reaction mixture is stirred at room temperature for 2 d then THF is removed in vacuo. The aqueous mixture is washed with EtOAc then acidified with saturated aqueous NH₄Cl. The aqueous mixture is extracted with EtOAc, washed with brine, dried with MgSO₄, filtered, and concentrated in vacuo. The resultant solid is triturated with Et₂O then filtered, collected and dried to yield the title compound (88 mg).

Method 16

Synthesis of 3-[4-(3-{2-[4-(2-aminopyrimidin-5-yl)phenyl]-3-methylbutan-2-yl}-1,2,4-oxadiazol-5-yl)-1H-pyrazol-1-yl]-2,2-dimethylpropanoic Acid (Example 164, Table 1)

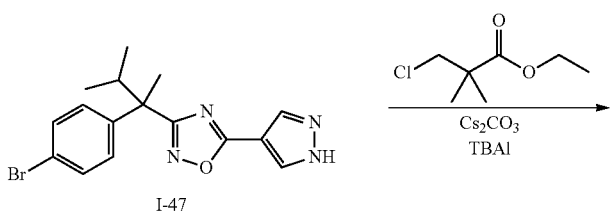

I-47

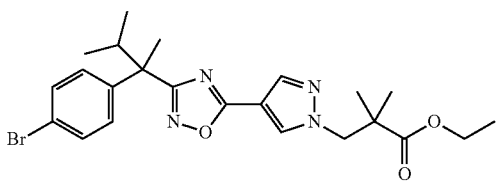

I-108

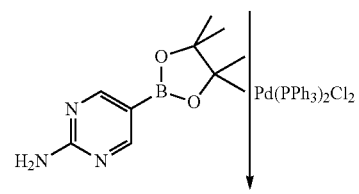

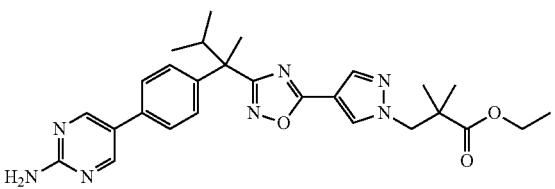

Example 164

I-109

To a mixture of I-47 (407 mg, 1.13 mmol) and 3-chloro-2,2-dimethyl propionic acid ethyl ester (557 mg, 3.38 mmol) in DMF (8 mL) is added $Cs_2CO_3$ (734 mg, 2.25 mmol) and tetrabutylammonium iodide (832 mg, 2.25 mmol). The mixture is stirred at 80° C. for 36 h then concentrated in vacuo. The residue is partitioned between $CH_2Cl_2$ and saturated aqueous $NaHCO_3$. The organics are dried with $Na_2SO_4$, filtered and concentrated in vacuo. The residue is purified by flash chromatography ($SiO_2$, 10% EtOAc in cyclohexane) to give I-108 (299 mg); m/z 489/491 [M/M+2H].

The following intermediate is synthesized in similar fashion from the appropriate reagents:

| Intermediate | Structure | m/z [M + 2H] |
|---|---|---|
| I-108bis[a] | 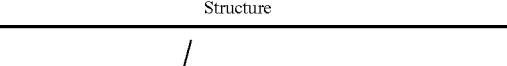 | 463.0 |

[a]The reaction is run at 80° C. for 8 hours using $K_2CO_3$ in DMF

A mixture of I-108 (290 mg, 0.46 mmol), 2-aminopyrimidine-5-boronic acid pinacol ester (307 mg, 1.39 mmol) and 2M aqueous $Na_2CO_3$ (0.46 mL) in DMF (6 mL) is degassed under $N_2$ for 5 minutes. To this mixture is added bis(triphenylphosphine)palladium(II)chloride (65 mg, 0.09 mmol). The mixture is stirred at 80° C. for 3 h then concentrated in vacuo. The residue is extracted with EtOAc, washed with saturated aqueous $NaHCO_3$, dried with $Na_2SO_4$, filtered, and concentrated in vacuo. The residue is purified by flash chromatography ($SiO_2$, 0-1% MeOH in $CH_2Cl_2$) to give I-109 (171 mg); m/z 504.90 [M+H].

The following intermediate is synthesized in similar fashion from the appropriate reagents:

| Intermediate | Structure | m/z [M + H] |
|---|---|---|
| I-109bis[a] | 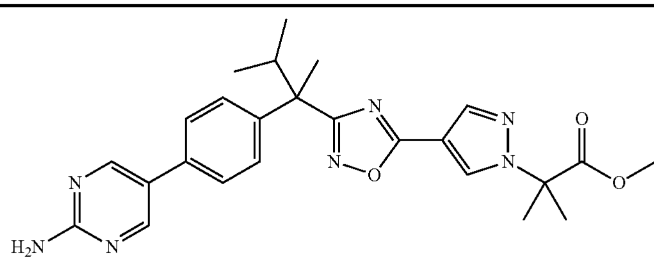 | 476.0 |

A mixture of I-109 (171 mg, 0.282 mmol), $LiOH \cdot H_2O$ (12 mg, 0.286 mmol), methanol (2.5 mL), THF (2.5 mL) and water (1.3 mL) is heated at 40° C. for 8 h then concentrated in vacuo. The residue is purified by preparative HPLC to give the title compound (33 mg).

The following compound is synthesized in similar fashion from the appropriate intermediates:

Example 160, table 1

Method 17

Synthesis of 6-(3-{2-[4-(2-aminopyrimidin-5-yl)phenyl]-3-methylbutan-2-yl}-1,2,4-oxadiazol-5-yl)-1-methylpyridin-2(1H)-one (Example 165, Table 1)

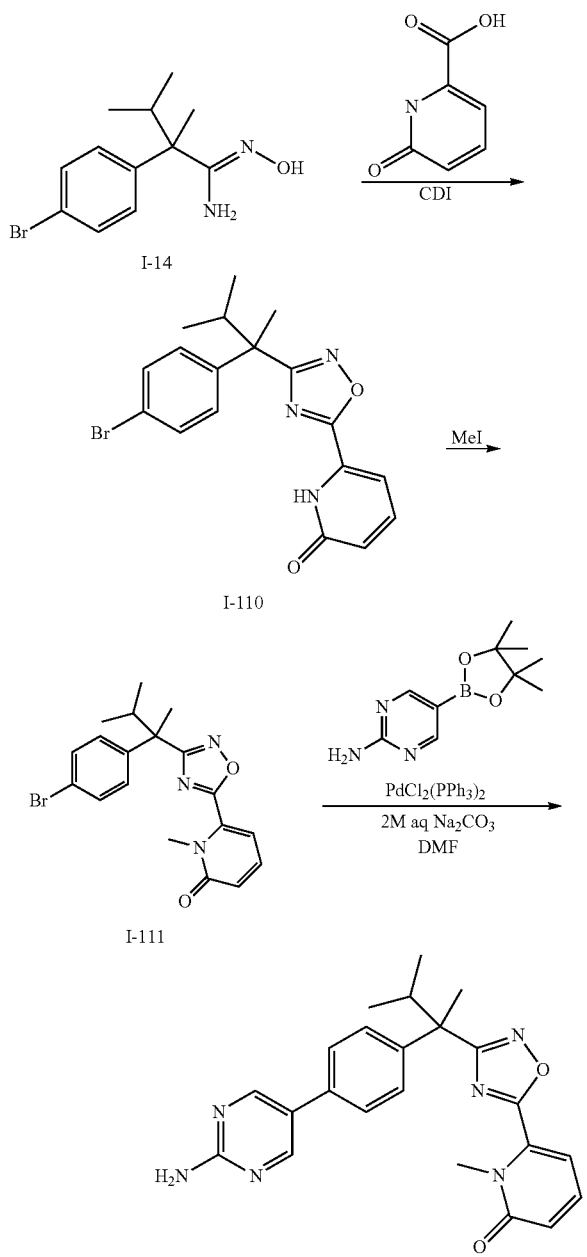

To a solution of 2-carboxylic acid-6-oxo-pyridine (161 mg, 1.16 mmol) in DMF (3 mL) is added carbonyldiimidazole (188 mg, 1.16 mmol). The mixture is stirred for 20 min at 50° C. then treated with I-14 (300 mg, 1.05 mmol) and stirred at 110° C. for 3 h. The mixture is concentrated in vacuo and the residue is extracted with EtOAc, washed with saturated aqueous NaHCO₃, dried with MgSO₄, filtered, and concentrated. The residue is purified by flash chromatography (SiO₂, 2% MeOH in CH₂Cl₂) to give I-110 (223 mg); m/z 389.95 [M+1].

The following intermediates are synthesized in similar fashion from the appropriate reagents:

| Intermediate | Structure | m/z [M/M + 2H] |
|---|---|---|
| I-110bis | 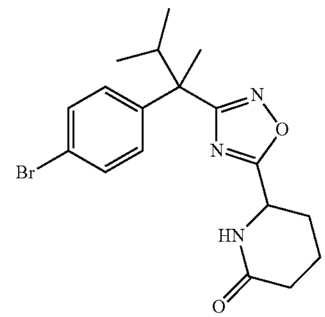 [SMILES: CC(C)C(C)(c1ccc(Br)cc1)c1noc(C2CCCC(=O)N2)n1] | 392.0/394.0 |

To a solution of I-110 (223 mg, 0.41 mmol) in THF (3 mL) is added K₂CO₃ (68 mg, 0.49 mmol) and MeI (30 μL, 0.49 mmol). The mixture is stirred at 40° C. for 20 h and is treated with additional MeI (30 μL, 0.49 mmol) at 3 h and 15 h. The mixture is treated with saturated aqueous ammonia and MeOH then volatiles are removed in vacuo. The residue is extracted with EtOAc, washed with saturated aqueous NaHCO₃, water, brine, dried with MgSO₄, filtered, and concentrated. Purification of the crude by flash chromatography (SiO₂, 0-10% EtOAc in cyclohexane) yields I-111 (80 mg); m/z 403.85 [M+1].

The following intermediates are synthesized in similar fashion from the appropriate reagents:

| Intermediate | Structure | m/z [M/M + 2H] |
|---|---|---|
| I-111bis | 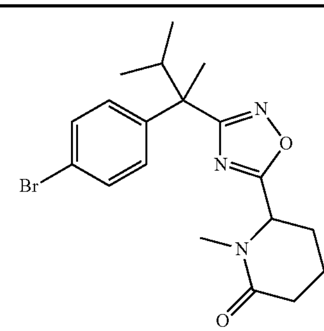 | 406.0/408.0 |

A mixture of I-111 (80 mg, 0.19 mmol), 2-aminopyrimidine-5-boronic acid pinacol ester (124 mg, 0.56 mmol) and 2M aqueous Na₂CO₃ (0.20 mL) in DMF (2 mL) is degassed under N₂ for 5 minutes. To this mixture is added PdCl₂(PPh₃)₂ (26 mg, 0.094 mmol). The mixture is stirred at 80° C. for 3 h then concentrated in vacuo. The residue is extracted with EtOAc, washed with saturated aqueous NaHCO₃, dried with Na₂SO₄, filtered, and concentrated in vacuo. The residue is purified by flash chromatography (SiO₂, 0-1% MeOH in CH₂Cl₂) to give the title compound (30 mg).

The following compounds are synthesized in similar fashion from the appropriate intermediates:

Example 166-167, table 1—the reaction is run starting from a mixture of I-110bis and I-111bis. Silica gel column chromatography affords Example 166 and 167.

Method 18

Synthesis of 2-[4-(3-{(1R)-1-[4-(2-aminopyrimidin-5-yl)phenyl]-1-cyclopropylethyl}-1,2,4-oxadiazol-5-yl)-1H-pyrazol-1-yl]-N,N-dimethylacetamide (Example 115) and 2-[4-(3-{(1S)-1-[4-(2-aminopyrimidin-5-yl)phenyl]-1-cyclopropylethyl}-1,2,4-oxadiazol-5-yl)-1H-pyrazol-1-yl]-N,N-dimethylacetamide (Example 116, Table 1)

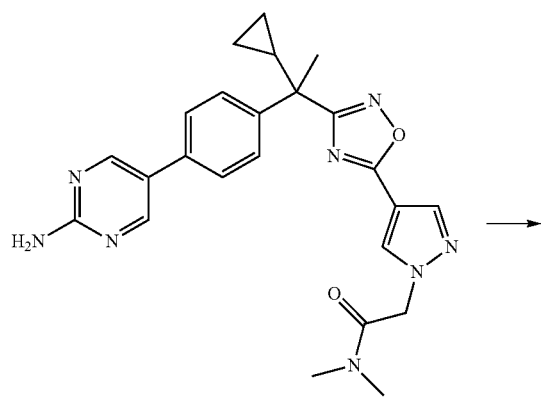

Example 59

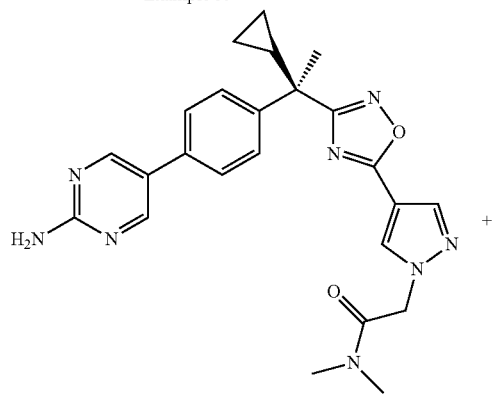

Example 115

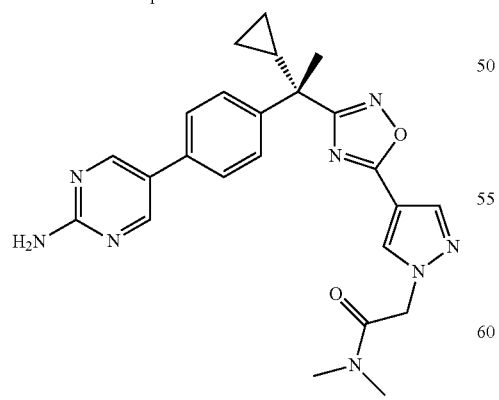

Example 116

Enantiomers 115 and 116 are prepared by resolution of example 59 (100 mg) on a Chiralpak® AD-H (available form Chiral Technologies, Inc., Exton, Pa.) semi-preparative (250× 20 mm) HPLC column (eluting with 95% EtOH in heptane containing 0.1% diethylamine). The faster eluting enantiomer 115 having a retention time of ~35 min and the slower eluting enantiomer 116 having a retention time of ~73 min. The eluants are concentrated to provide Example 115 (32 mg) and Example 116 (27 mg).

The following compounds are synthesized in similar fashion from the appropriate intermediates:

Examples 23-24, table 1

Examples 31-32, table 1—eluting with 70% EtOH with 0.1% diethylamine/heptane

Examples 61-62, table 1

Examples 65-66, table 1

Examples 77-78, table 1

Examples 102-103, table 1

Example 104-105, table 1—95% EtOH in heptanes +0.05% diethylamine at 8 ml/min 40° C.

Examples 107-108, table 1

Example 115-116, table 1—95% EtOH in heptanes +0.05% diethylamine at 55 ml/min

Examples 121-122, table 1—95% EtOH in heptanes +0.4% diethylamine at 55 ml/min

Examples 123-124, table 1

Example 227-228, table 1

Example 230-231, table 1

Example 233-234, table 1

Example 254-255, table 1

Example 257-258, table 1

Example 282-283, table 1

Method 19

Preparation of 5-(4-{(2R)-3-methyl-2-[5-(1-methyl-1H-pyrazol-4-yl)-1,2,4-oxadiazol-3-yl]butan-2-yl}phenyl)pyrimidin-2-amine (Example 46) and 5-(4-{(2S)-3-methyl-2-[5-(1-methyl-1H-pyrazol-4-yl)-1,2,4-oxadiazol-3-yl]butan-2-yl}phenyl)pyrimidin-2-amine (Example 47, Table 1)

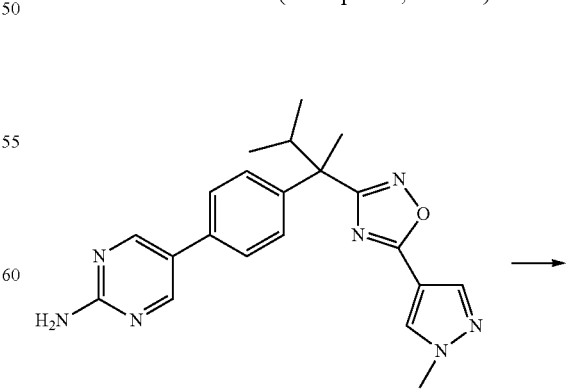

Example 15

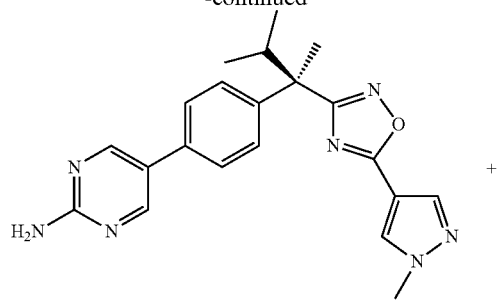

Example 46

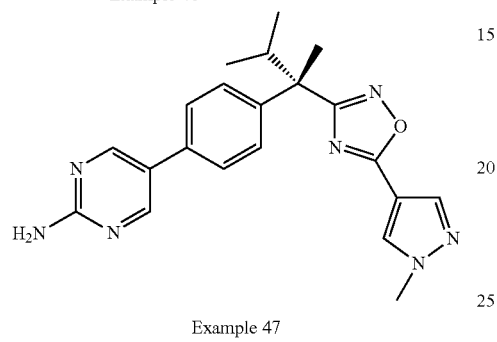

Example 47

Enantiomers 46 and 47 are prepared by resolution of example 15 (50 mg) on a Chiralpak® AD-H (available form Chiral Technologies, Inc., Exton, Pa.) semi-preparative (250× 30 mm) HPLC column (eluting with 70% MeOH in CO₂) at 250 bar. The faster eluting enantiomer 46 having a retention time of ~5 min (Chiralpak® AD-H analytical HPLC column 4.6×100 mm) and the slower eluting enantiomer 47 having a retention time of ~13 min. The eluants are concentrated to provide Example 46 (12 mg) and Example 47 (15 mg).

The following compounds are resolved in similar fashion:
Examples 16-17, table 1
Examples 48-49, table 1

Method 20

Preparation of 2-{[5-(3-{(1R)-1-[4-(2-aminopyrimidin-5-yl)phenyl]-1-cyclopropylethyl}-1,2,4-oxadiazol-5-yl)pyrazin-2-yl]amino}-2-methylpropan-1-ol (Example 56, Table 1) and 2-{[5-(3-{(1S)-1-[4-(2-aminopyrimidin-5-yl)phenyl]-1-cyclopropylethyl}-1,2,4-oxadiazol-5-yl)pyrazin-2-yl]amino}-2-methylpropan-1-ol (Example 57, Table 1)

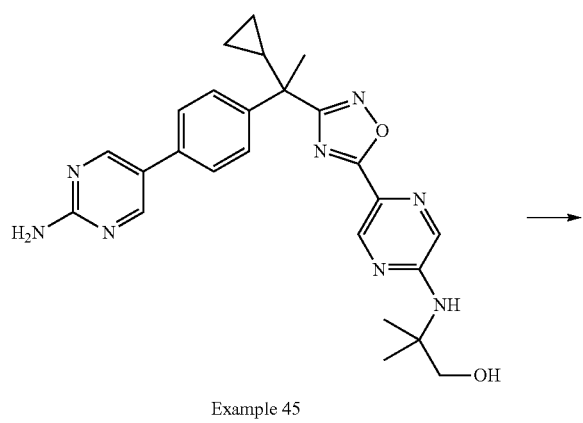

Example 45

→

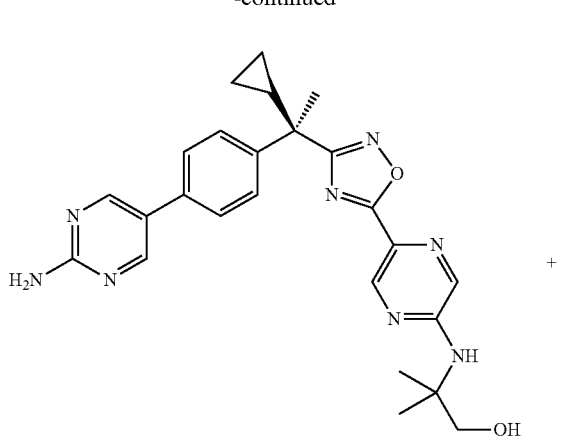

Example 56

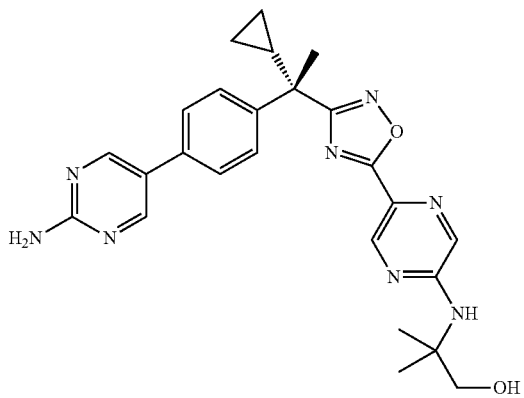

Example 57

Enantiomers 56 and 57 are prepared by resolution of Example 45 (89 mg) on a RegisPak (available form Chiral Technologies, Inc., Exton, Pa.) semi-preparative (250×30 mm) HPLC column (eluting with 70% MeOH in CO₂) at 250 bar. The faster eluting enantiomer 56 having a retention time of ~5 min (Chiralpak® AD-H analytical HPLC column 4.6×100 mm) and the slower eluting enantiomer 57 having a retention time of ~13 min. The eluants were concentrated to provide Example 56 (12 mg) and Example 57 (15 mg).

The following compounds are resolved in similar fashion:
Examples 50-51, table 1—eluting with 55% MeOH in CO₂
Examples 52-53, table 1—eluting with 45% of 3/1/0.1 MeOH/isopropanol/isopropylamine in CO₂
Examples 54-55, table 1—eluting with 55% EtOH in CO₂
Examples 56-57, table 1—eluting with 45% 1/1 methanol/isopropanol
Example 100-101, table 1—eluting with 40% co-solvent of 1:1 methanol:isopropanol with 0.5% isopropylamine at 150 bar
Example 63-64, table 1

Method 21

Synthesis of 5-(4-{3-methyl-2-[5-(4-methylpiperazin-1-yl)-1,2,4-oxadiazol-3-yl]butan-2-yl}phenyl)pyrimidin-2-amine (Example 96, Table 1)

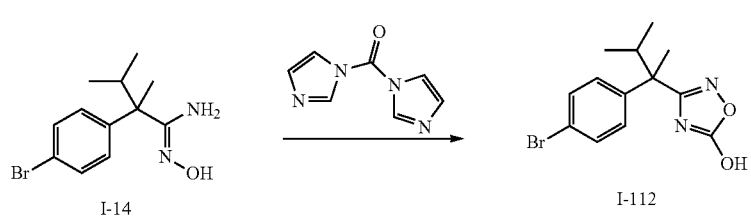

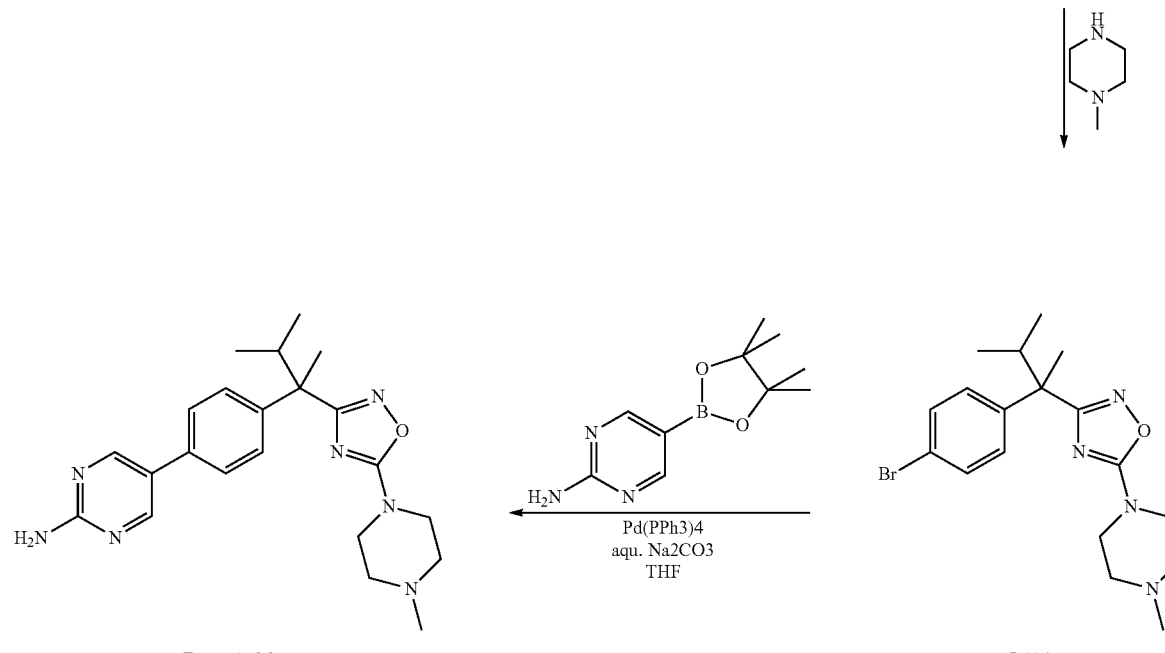

Example 96

I-114

To a mixture of I-14 (1.029 g, 3.61 mmol) and carbonyldiimidazole (702 mg, 7.33 mmol) is added acetonitrile (20 mL). The reaction mixture is heated at 75° C. for 18 hours. After this time, the reaction mixture is concentrated in vacuo and purified by flash chromatography (SiO2, 12-100% EtOAc in heptane) to give I-112 (373 mg); m/z 311.2/313.2 [M/M+2H].

To a solution of I-112 (163 mg, 0.523 mmol) in pyridine (0.5 mL) is added POCl₃ (0.479 mL, 5.23 mmol). The reaction mixture is heated at 90° C. for 18 hours. The reaction mixture is cooled to room temperature and carefully poured into ice water and then extracted with EtOAc twice. The organics are combined and washed with brine, dried over Na₂SO₄, filtered and concentrated in vacuo. The residue is purified by flash chromatography (SiO2, 12-100% EtOAc in heptane) to give I-113 (59 mg); 1H-NMR (DMSO-d6) δ ppm 7.50 (2H, d), 7.35 (2H, d), 2.62 (1H, m), 1.60 (3H, s), 0.83 (3H, d), 0.6 (3H, d).

To a solution of I-113 (44 mg, 0.133 mmol) in DMSO (1 mL) is added 1-methylpiperazine (0.148 mL, 1.33 mmol) and the reaction mixture is stirred at room temperature for 1.5 hours. The reaction mixture is quenched with water and extracted with EtOAc twice. The organics are combined and washed with water then brine, dried over Na₂SO₄, filtered and concentrated in vacuo. The residue is purified by flash chromatography (SiO₂, 10-100% MeOH in CH₂Cl₂) to give I-114 (45 mg); m/z 393.0/395.0 [M/M+2H].

The following intermediates are synthesized in similar fashion from the appropriate reagents:

| Intermediate | Structure | m/z [M/M + 2H] |
|---|---|---|
| I-115[b] | 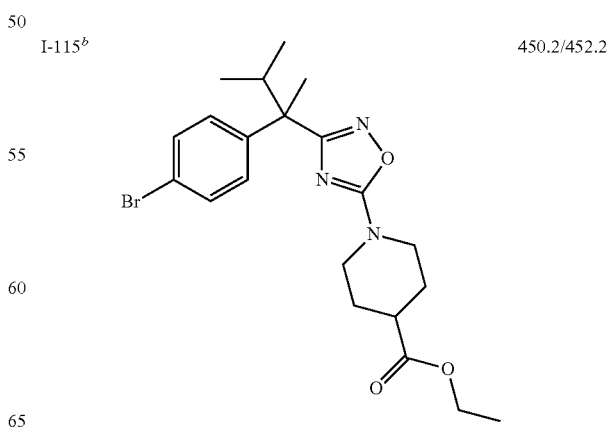 | 450.2/452.2 |

| Intermediate | Structure | m/z [M/M + 2H] |
|---|---|---|
| I-116[a] | 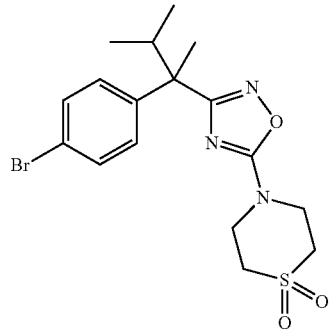 [SMILES: CC(C)C(C)(c1ccc(Br)cc1)c1noc(N2CCS(=O)(=O)CC2)n1] | 428.2/430.2 |
| I-117[a] | 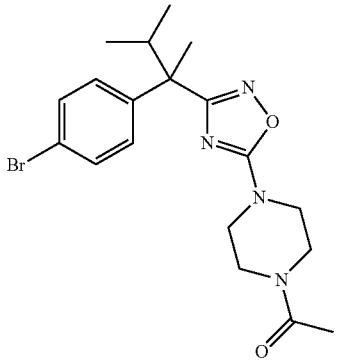 [SMILES: CC(=O)N1CCN(c2nc(C(C)(c3ccc(Br)cc3)C(C)C)no2)CC1] | 421.2/423.2 |
| I-118[b] | 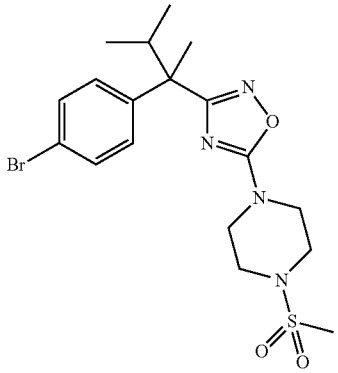 [SMILES: CC(C)C(C)(c1ccc(Br)cc1)c1noc(N2CCN(S(C)(=O)=O)CC2)n1] | 457.2/459.2 |
| I-119[a] | 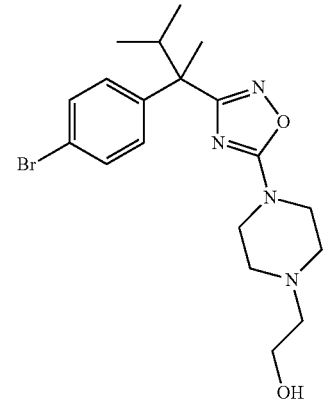 [SMILES: CC(C)C(C)(c1ccc(Br)cc1)c1noc(N2CCN(CCO)CC2)n1] | 423.2/425.2 |
| I-120[b] | 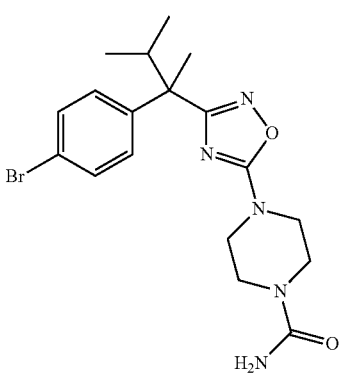 [SMILES: CC(C)C(C)(c1ccc(Br)cc1)c1noc(N2CCN(C(N)=O)CC2)n1] | 422.2/424.2 |
| I-121[b] | 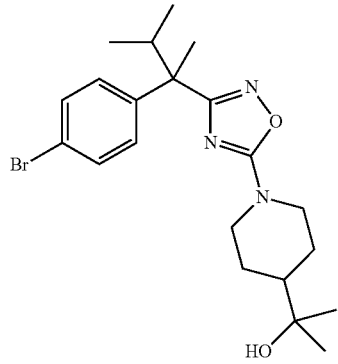 [SMILES: CC(C)C(C)(c1ccc(Br)cc1)c1noc(N2CCC(C(C)(C)O)CC2)n1] | 436.4/438.4 |
| I-122[b] | 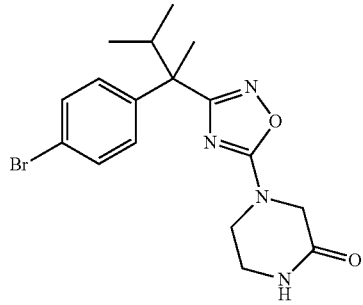 [SMILES: CC(C)C(C)(c1ccc(Br)cc1)c1noc(N2CCNC(=O)C2)n1] | 393.2/395.4 |
| I-123[b] | 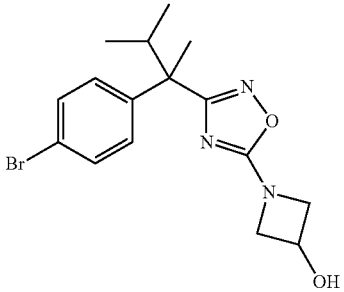 [SMILES: CC(C)C(C)(c1ccc(Br)cc1)c1noc(N2CC(O)C2)n1] | 366.2/368.2 |

| Intermediate | Structure | m/z [M/M + 2H] |
|---|---|---|
| I-124[b] | 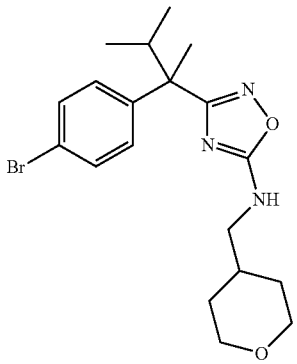 [SMILES: CC(C)C(C)(c1ccc(Br)cc1)c1noc(NCC2CCOCC2)n1] | 408.4/410.4 |
| I-125[b] | 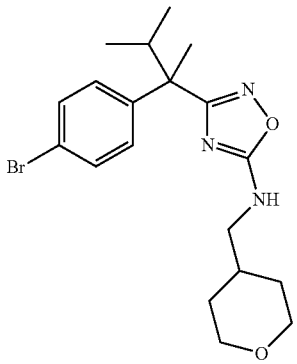 [SMILES: CC(C)C(C)(c1ccc(Br)cc1)c1noc(NCC2CCOCC2)n1] | 407.1/409.1 |
| I-126[b] | 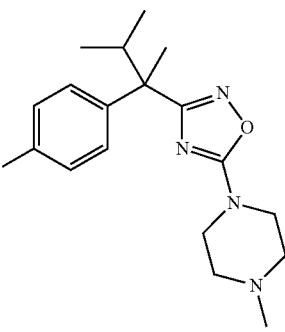 | 456.2/458.2 |
| I-127[b] | 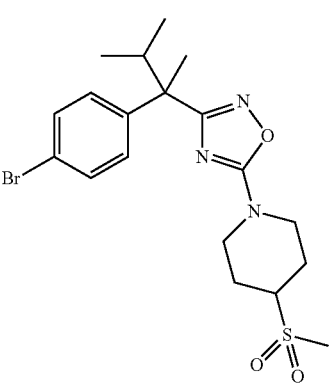 [SMILES: CC(C)C(C)(c1ccc(Br)cc1)c1noc(N2CCC(S(C)(=O)=O)CC2)n1] | 408.2/410.2 |
| I-128[b] | 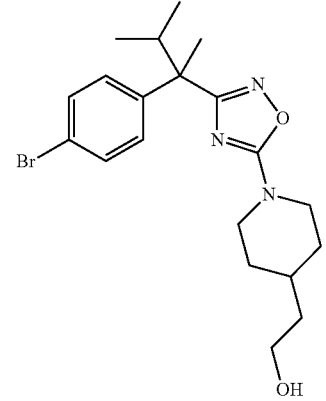 [SMILES: CC(C)C(C)(c1ccc(Br)cc1)c1noc(N2CCC(CCO)CC2)n1] | 422.3/424.2 |
| I-129[b] | 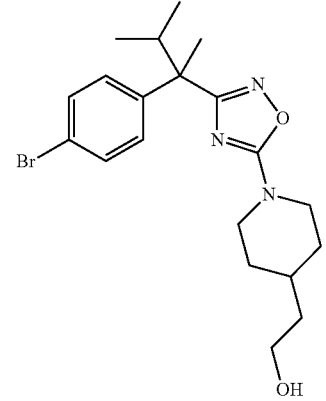 [SMILES: CC(C)C(C)(c1ccc(Br)cc1)c1noc(N2CCC(CCO)CC2)n1] | 421.2/423.2 |
| I-130[b] | 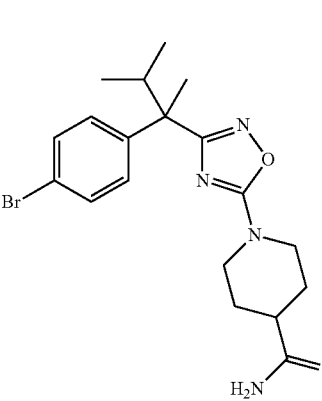 | 421.2/423.2 |
| I-131[b] | 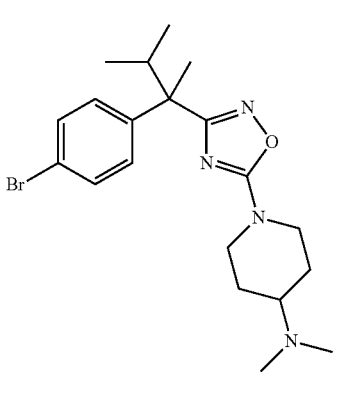 | 407.4/409.4 |

-continued
| Intermediate | Structure | m/z [M/M + 2H] |
|---|---|---|
| I-132[b] | 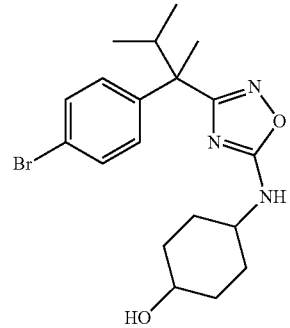 [SMILES: CC(C)C(C)(c1ccc(Br)cc1)c1noc(NC2CCC(O)CC2)n1] | 408.2/410.1 |
| I-133[b] | 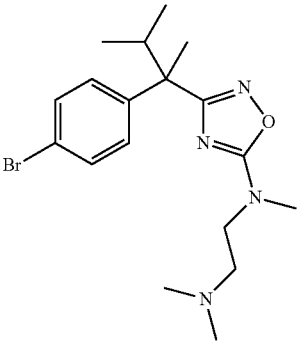 [SMILES: CC(C)C(C)(c1ccc(Br)cc1)c1noc(N(C)CCN(C)C)n1] | 395.4/397.4 |
| I-134[b] | 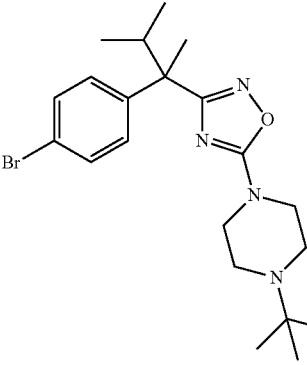 | 435.4/437.4 |
| I-135[b] | 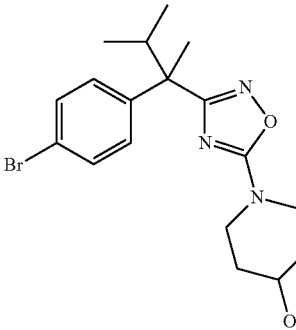 | 394.4/396.2 |
-continued
| Intermediate | Structure | m/z [M/M + 2H] |
|---|---|---|
| I-136[b] | 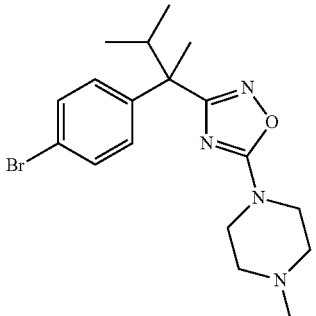 | 421.4/423.4 |
| I-137[c] | 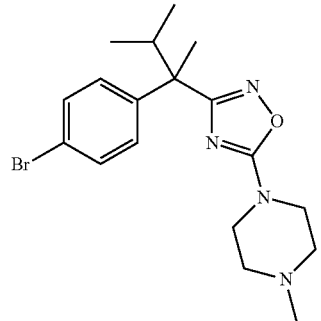 | 419.4/421.2 |
| I-138[b] | 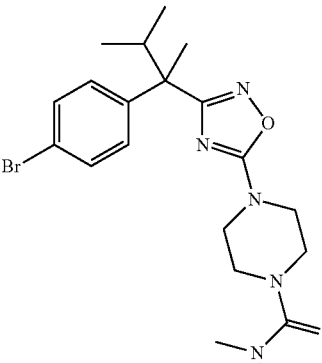 | 450.4/452.4 |
| I-139[b] | 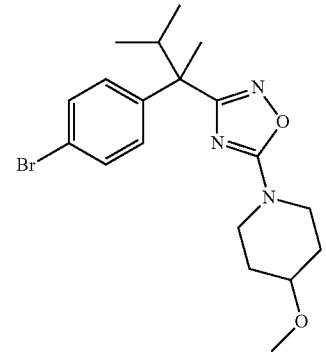 [SMILES: COC1CCN(c2nc(C(C)(c3ccc(Br)cc3)C(C)C)no2)CC1] | 408.2/410.2 |

| Intermediate | Structure | m/z [M/M + 2H] |
|---|---|---|
| I-140 | (structure) | 420.4/422.4 |
| I-140bis | (structure) | 507.3/509.3 |
| I-140tris | (structure) | 493.3/495.3 |

[a] 1.2 equ. of amine and 1.2 equ. of diisopropylethylamine are used.
[b] 1.2 equ. of amine (either as free base or hydrochloride salt) and 2.5 equ. of diisopropylethylamine are used.
[c] 1.2 equ. of amine as di-hydrochloride salt and 5 equ. of diisopropylethylamine are used.

The mixture of I-114 (45.000 mg, 0.114 mmol), 2-aminopyrimidine-5-boronic acid pinacol ester (30.286 mg, 0.137 mmol) and tetrakis(triphenylphosphine)palladium (0) (13.173 mg, 0.011 mmol) in a vial is evacuated and back filled with Ar 3 times. Then THF (1 mL) and sat. $Na_2CO_3$ aqueous solution are added and the mixture is heated to 65° C. for 18 hours. After this time, the reaction mixture is quenched with water and extracted with EtOAc twice. The organics are combined and washed with brine, dried over $Na_2SO_4$, filtered and concentrated in vacuo. The residue is purified by flash chromatography (SiO2, 12-100% EtOAc in heptane) to give Example 96 (12 mg).

The following intermediates are synthesized in similar fashion from the appropriate reagents:

| Intermediate | Structure | m/z [M + H] |
|---|---|---|
| I-141[a] | (structure) | 522.4 |

| Intermediate | Structure | m/z [M + H] |
|---|---|---|
| I-142[a] | 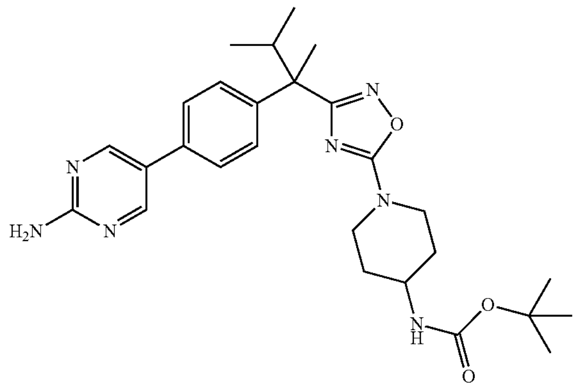 [SMILES: CC(C)C(C)(c1ccc(-c2cnc(N)nc2)cc1)c1noc(N2CCC(NC(=O)OC(C)(C)C)CC2)n1] | 508.4 |
| I-143[a] | 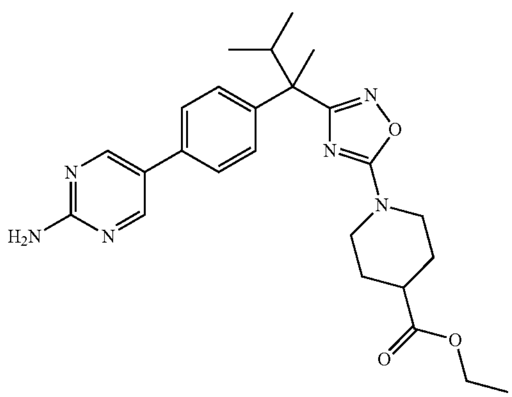 [SMILES: CCOC(=O)C1CCN(c2nc(C(C)(c3ccc(-c4cnc(N)nc4)cc3)C(C)C)no2)CC1] | 465.4 |

[a]The reaction has been performed in the microwave oven at 110° C. for 45 minutes.

The following compounds are synthesized in similar fashion from the appropriate intermediates:

Examples 168, table 1

Example 169, table 1—the last step has been performed in the microwave oven at 110° C. for one hour Example 170, table 1—the last step has been performed in the microwave oven at 110° C. for 45 minutes Examples 186, table 1—the last step has been performed in the microwave oven at 110° C. for 45 minutes Examples 192, table 1

Examples 198-202, table 1—the last step has been performed in the microwave oven at 110° C. for 45 minutes Examples 208-209, table 1—the last step has been performed in the microwave oven at 110° C. for 45 minutes Examples 212-213, table 1—the last step has been performed in the microwave oven at 110° C. for 45 minutes Examples 218, table 1—the last step has been performed in the microwave oven at 110° C. for 45 minutes Example 235, table 1—the last step has been performed in the microwave oven at 100° C. for two hours Examples 236-237, table 1—the last step has been performed in the microwave oven at 110° C. for 45 minutes Examples 260, table 1

Examples 261-262, table 1—the last step has been performed in the microwave oven at 110° C. for 45 minutes Examples 264, table 1—the last step has been performed in the microwave oven at 110° C. for 45 minutes Examples 266, table 1—the last step has been performed in the microwave oven at 110° C. for 45 minutes Examples 269-270, table 1—the last step has been performed in the microwave oven at 110° C. for 45 minutes Method 22

Synthesis of 4-(3-{2-[4-(2-aminopyrimidin-5-yl)phenyl]-3-methylbutan-2-yl}-1,2,4-oxadiazol-5-yl)-2,2-dimethylbutanoic Acid (Example 85, Table 1)

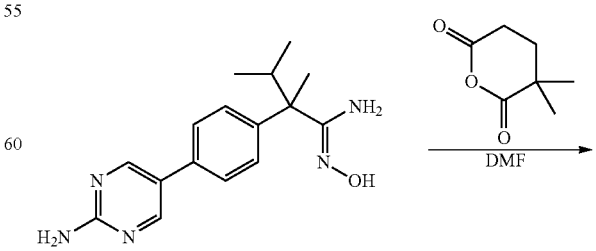

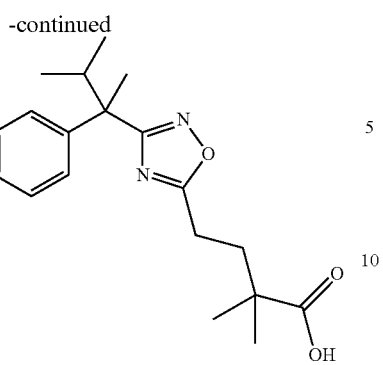

Example 85

To a solution of I-21 (100 mg, 0.334 mmol) in DMF (1 mL) is added 2,2-dimethylglutaric anhydride (52 mg, 0.367 mmol). The reaction mixture is heated to 120° C. for 2.5 hours. After this time, the reaction mixture is quenched with water and extracted with EtOAc twice. The organics are combined and washed with water then brine, dried over $Na_2SO_4$, filtered and concentrated in vacuo. The residue is purified by flash chromatography (SiO2, 10-100% MeOH in $CH_2Cl_2$) then triturated in hot MeOH to give Example 85 (40 mg).

The following compounds are synthesized in similar fashion from the appropriate intermediates:
Example 92-94, Table 1

Method 23

Synthesis of: 5-(4-{(R)-1-Cyclopropyl-1-[5-(3,4,5,6-tetrahydro-2H-[1,2']bipyrazinyl-5'-yl)-[1,2,4]oxadiazol-3-yl]-ethyl}-phenyl)-pyrazin-2-ylamine (Example 195, Table 1)

Step 1

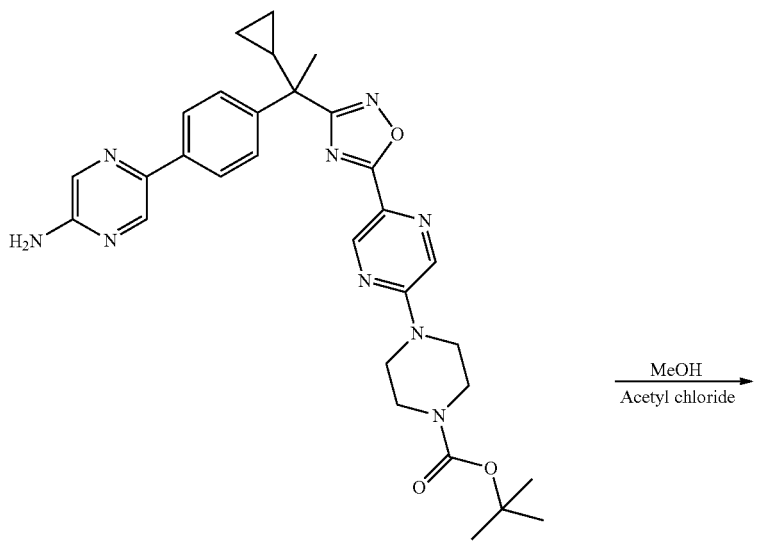

I-83

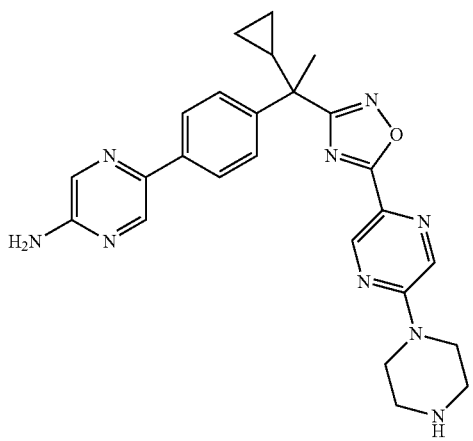

I-143bis

To cold (0° C.) methanol (20 ml) is added 1 ml of acetyl chloride (dropwise). Upon complete addition, I-83 (350 mg, 0.61 mmol) is added as a methanol solution (5 ml). Allow to gradually warm to RT and stir over night. After this time the reaction is basified using 7N ammonia and concentrated to dryness. The remaining residue is purified via flash chromatography (silica gel, 0-10% MeOH/DCM) to give I-135.

The following intermediates are synthesized in similar fashion from the appropriate reagents:

| Intermediate | Structure | m/z [M + H] |
|---|---|---|
| I-143tris | 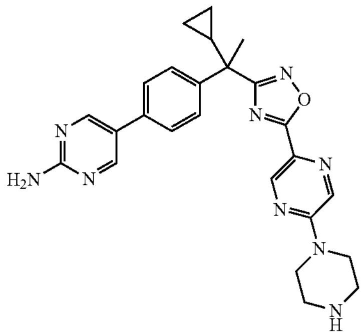 [SMILES: CC(c1ccc(-c2cnc(N)nc2)cc1)(c1noc(-c2cnc(N3CCNCC3)cn2)n1)C1CC1] | Not available |
| I-143quadris | 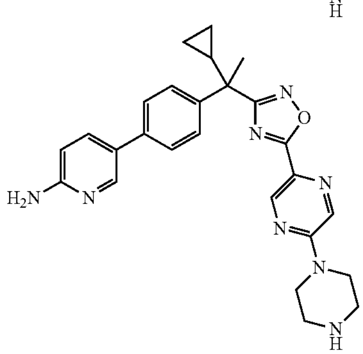 | 469.4 |

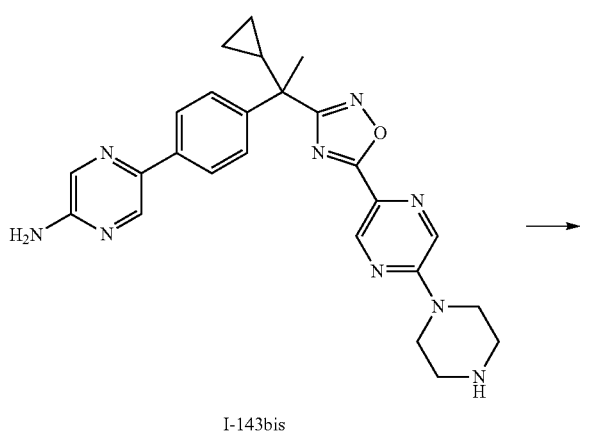

The following compounds are synthesized in a similar fashion from the appropriate intermediates:
Example 214, Table 1—the crude is purified via flash chromatography (silica gel, 0-100% MeOH/DCM)
Example 267, Table 1
Example 268, Table 1—the crude is concentrated to dryness and purified the crude via flash chromatography (silica gel, 0-10% MeOH/DCM, with 0.5% NH4OH)

Step 2

I-143bis

-continued

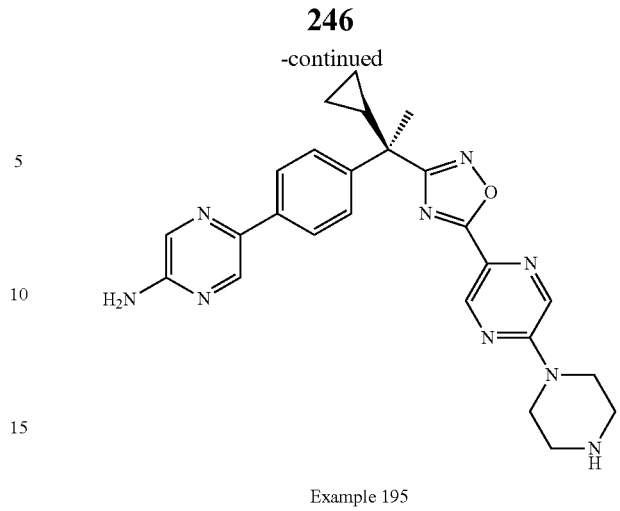

Example 195

Chiral resolution of I-135 was performed using a ChiralPak® AD-H column (3.0×25.0 cm, available from Chiral Technologies, West Chester Pa.). Eluting with methanol/IPA (1:3) with 1% isopropylamine at 150 bar afforded Example 195 (6 mg).

The following compounds are synthesized in a similar fashion from the appropriate intermediates:
Example 196, Table 1—the chiral resolution is performed at 125 psi
Example 210, Table 1—the chiral resolution is performed at 125 psi, with no ispropylamine in the eluent Method 24

Synthesis of 1-(3-{1-[4-(2-Amino-pyrimidin-5-yl)-phenyl]-1,2-dimethyl-propyl}-[1,2,4]oxadiazol-5-yl)-2-methyl-propan-2-ol (Example 225, Table 1)

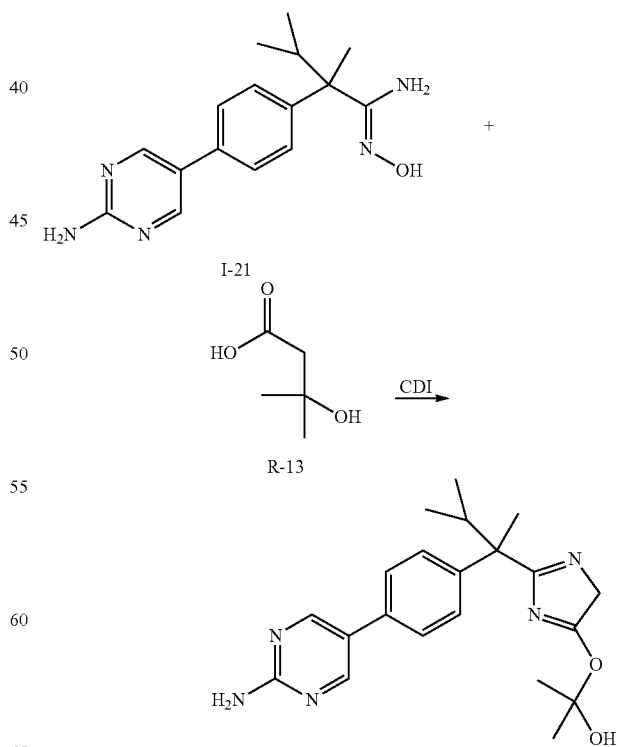

Example 225

To a suspension of R-13 (118 mg, 1.0 mmol) in THF 10 ml) is added 1,1′-carbonyldiimidazole (162 mg, 1.0 mmol) at room temperature. The mixture is stirred at 50° C. for 30 minutes. After this time I-21 (200 mg, 0.67 mmol) is added and the resulting mixture is heated under reflux for 3 hours. After this time the reaction is cooled to RT, treated with HOAc (1 ml) and warmed to 80° C. After stifling for 3 days the mixture is cooled to RT and concentrated. The remaining residue is purified via flash chromatography (silica gel, 0-8% MeOH/DCM) to afford the title compound (80 mg).

The following compounds are synthesized in a similar fashion from the appropriate intermediates:

Example 229, Table 1—no AcOH is added in the reaction mixture

Example 232, Table 1—no AcOH is added in the reaction mixture

Method 25

Synthesis of 5-(4-{1-Cyclopropyl-1-[5-(3-oxetan-3-yl-3H-imidazol-4-yl)-[1,2,4]oxadiazol-3-yl]-ethyl}-phenyl)-pyrimidin-2-ylamine
(Example 206, Table 1)

Synthesis of 5-(4-{1-Cyclopropyl-1-[5-(1-oxetan-3-yl-1H-imidazol-4-yl)-[1,2,4]oxadiazol-3-yl]-ethyl}-phenyl)-pyrimidin-2-ylamine
(Example 207, Table 1)

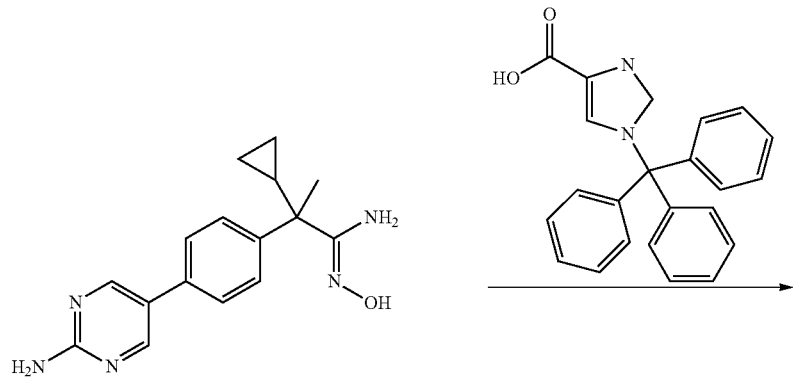

I-23

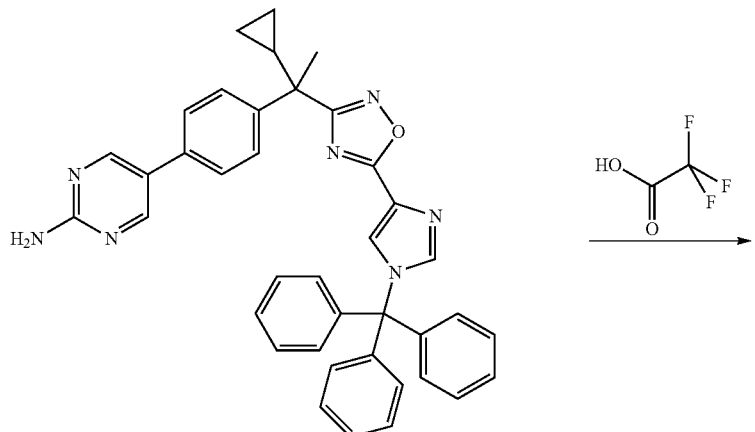

I-144

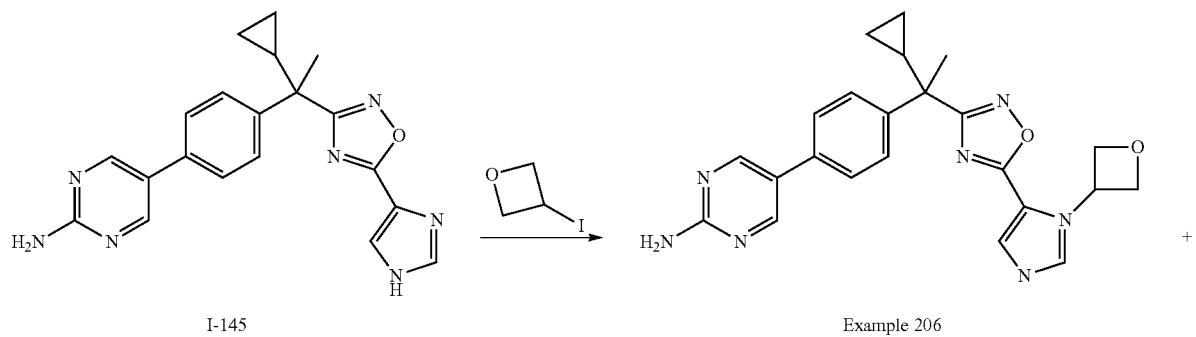

I-145                                                                 Example 206

-continued

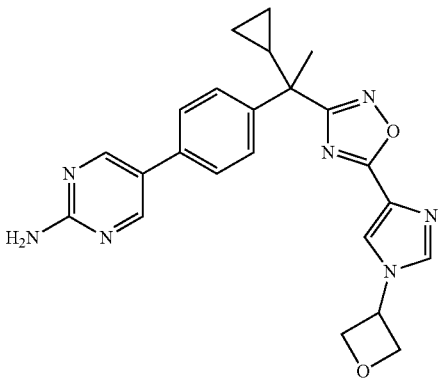

Example 207

To a suspension of 1-trityl-1H-imidazole-4-carboxylic acid (893 mg, 2.5 mmol) in THF (10 mL) is added 1,1'-carbonyldiimidazole (409 mg, 2.5 mmol) at room temperature. The mixture is stirred at 50° C. for 30 minutes. A suspension of I-23 (500 mg, 1.7 mmol) in THF (5 mL) is added to the above mixture and the resulting mixture is heated at 130° C. in a microwave reactor for 2 hours. The mixture is cooled down and is concentrated under vacuum. The residue is extracted with $H_2O$ (10 mL) and EtOAc (20 mL). The combined organic layer is dried with $MgSO_4$ and is filtered. The filtrate is concentrated and the residue is purified by silica gel flash column chromatography with 10% MeOH in $CH_2Cl_2$ as the eluent to afford I-144 (150 mg); m/z 374 [M-trityl group].

To a solution of I-144 (80 mg, 0.13 mmol) in $CH_2Cl_2$ (10 mL) is added TFA (0.015 mL, 0.19 mmol) at room temperature. The solution is stirred at the same temperature for 24 hours. The solution is concentrated under vacuum to afford I-145 (48 mg); m/z 374 [M+H].

To a round bottom flask is added I-145 (100 mg, 0.27 mmol), 3-iodooxetane (98 mg, 0.54 mmol) and $K_2CO_3$ (111 mg, 0.8 mmol) in DMF (10 mL). The reaction mixture is stirred at 80° C. for 12 hours. The reaction is cooled down and water (10 mL) is added. The solution is extracted with EtOAc (20 mL) and $H_2O$ (10 mL). The combined organic layer is dried with $MgSO_4$ and is filtered. The filtrate is concentrated and the residue is purified by silica gel flash column chromatography with 10% MeOH in TBME as the eluent to afford the title compounds (Example 206: 8 mg; Example 207: 10 mg).

Method 26

Synthesis of 2-[4-(3-{1-[4-(2-Amino-4-fluoro-pyrimidin-5-yl)-phenyl]-1-cyclopropyl-ethyl}-[1,2,4]oxadiazol-5-yl)-pyrazol-1-yl]-N,N-dimethyl-acetamide (Example 275, Table 1)

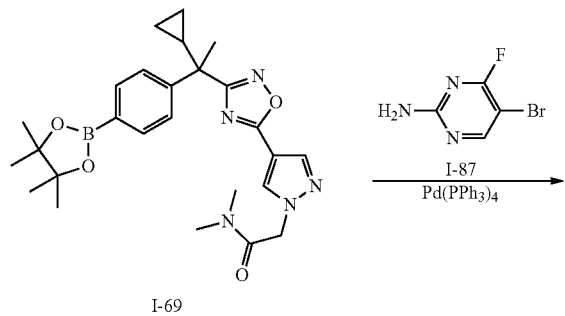

-continued

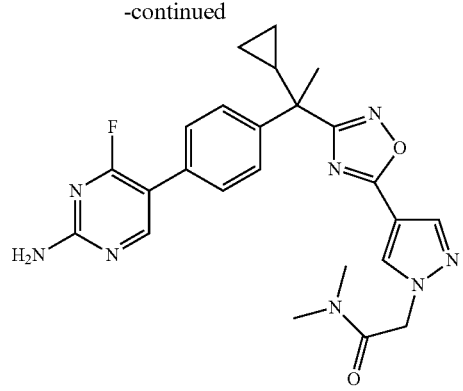

Example 275

To a solution of I-69 (300 mg, 0.6 mmol) in DMF (10 mL) are added I-87 (140 mg, 0.7 mmol), tetrakis(triphenylphosphine)palladium (0) (70 mg, 0.06 mmol) and 2M $Na_2CO_3$ (1.5 mL, 3.0 mmol). The mixture is heated to 100° C. for 1 hour in a microwave reactor. The mixture is cooled down and is extracted with $H_2O$ (20 mL) and EtOAc (30 mL). The combined organic layer is dried with $MgSO_4$ and is filtered. The filtrate is concentrated and the residue is purified by silica gel flash column chromatography with 10% MeOH in $CH_2Cl_2$ as the eluent to afford the title compound (200 mg).

The following compounds are synthesized in a similar fashion from the appropriate intermediates:

Example 175, Table 1—the reaction is run at 120° C.
Example 176-180, Table 1—the reaction is run at 120° C.
Example 184-185, Table 1—the reaction is run at 120° C.
Example 187-189, Table 1—the reaction is run at 120° C.
Example 191, Table 1—the reaction is run at 120° C.
Example 239-243, Table 1—the reaction is run for 6 hours at 100° C. in an oil bath
Example 244-246, Table 1
Example 247, Table 1—the reaction is run for 6 hours at 100° C. in an oil bath
Example 249-250, Table 1—the reaction is run for 6 hours at 100° C. in an oil bath
Example 251, Table 1—the reaction is run at 85° C. overnight
Example 253, Table 1—the reaction is run for 6 hours at 100° C. in an oil bath
Example 256, Table 1—the reaction is run for 6 hours at 100° C. in an oil bath Example 265, Table 1—the reaction is run for 6 hours at 100° C. in an oil bath
Example 273, Table 1—the reaction is run for 6 hours at 100° C. in an oil bath
Example 275, Table 1
Example 279, Table 1
Example 280-281, Table 1—the reaction is run for 48 hours at 80° C.
Example 284-286, Table 1
Example 289-291, Table 1
Example 292, Table 1—the reaction is run for 16 hours at 85° C.
Example 293-294, Table 1
Example 298, Table 1

Method 27

2-[4-(3-{(R)-1-[4-(6-Amino-pyridin-3-yl)-phenyl]-1-cyclopropyl-ethyl}-[1,2,4]oxadiazol-5-yl)-pyrazol-1-yl]-N,N-dimethyl-acetamide (Example 172, Table 1)

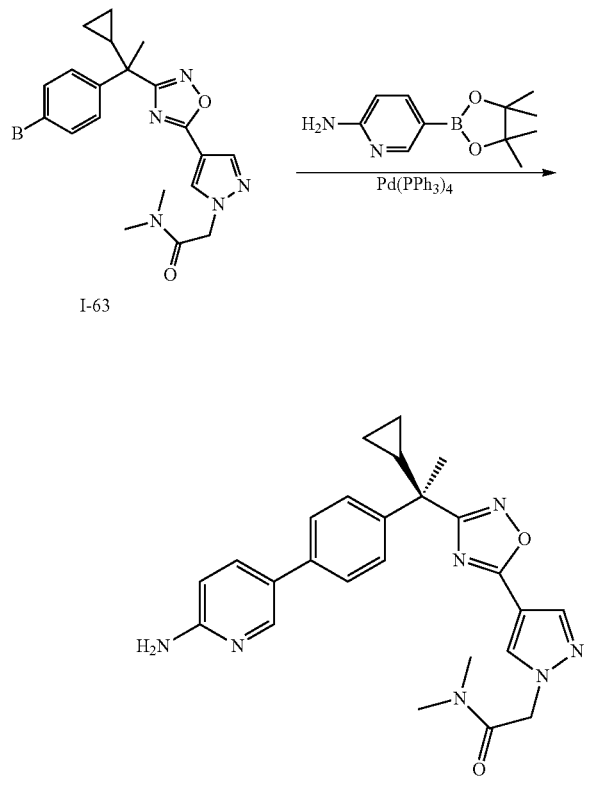

To a microwave vial is added I-63 (100 mg, 0.225 mmol) in DMF (2 ml), followed by the addition of 2-aminopyridine-5-boronic acid pinacol ester (55 mg, 0.25 mmol), tetrakis(triphenylphosphine)palladium(0) (26 mg, 0.023 mmol) and 2 M aq. $Na_2CO_3$ (0.4 ml, 0.8 mmol). The reaction mixture is stirred in microwave reactor at 120° C. for 1 hour. The residue is diluted with EtOAc, washed with water, brine, dried under anhy. $Na_2SO_4$, filtered and concentrated. The residue is purified by flash chromatography ($SiO_2$, 0-5% MeOH/$CH_2Cl_2$) to afford the title compound (39 mg).

The following compounds are synthesized in a similar fashion from the appropriate intermediates:

Example 173-174, Table 1
Example 181, Table 1
Example 183, Table 1
Example 263, Table 1—the reaction is run at 80° C. overnight

Method 28

Synthesis of 5-(4-{1,2-Dimethyl-1-[5-(4-methylamino-piperidin-1-yl)-[1,2,4]oxadiazol-3-yl]-propyl}-phenyl)-pyrimidin-2-ylamine (Example 217, Table 1)

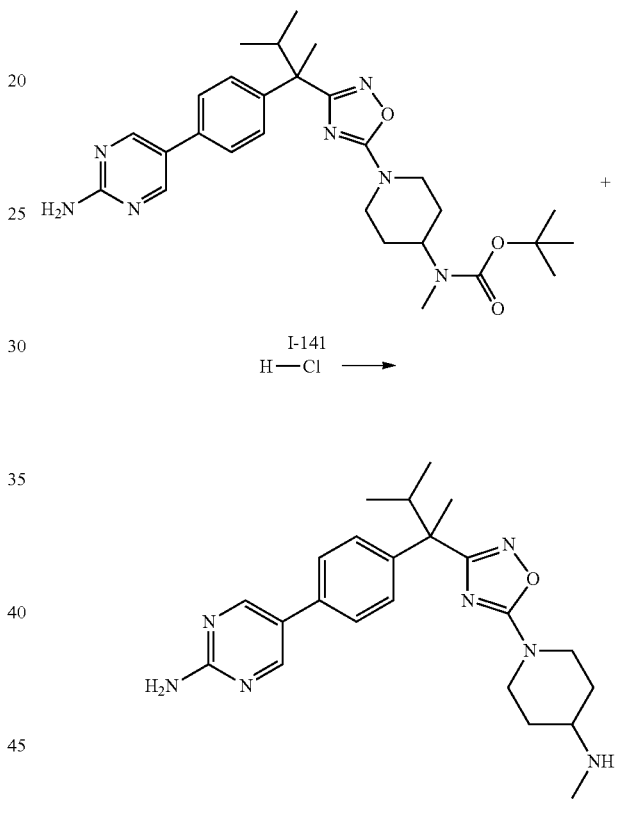

I-141 (138 mg, 0.265 mmol) is dissolved in DCM (2 mL) and 4N HCl in 1,4-dioxane (0.663 mL, 2.65 mmol) is added and the reaction mixture is stirred at room temperature for 3 hours. After this time, the reaction mixture is concentrated in vacuo and the residue is dissolved in MeOH and passed through a PL-$HCO_3$ MP-resin column to free base the product. The filtrate is concentrated in vacuo and the crude is purified by preparative TLC using 10% MeOH/DCM as solvent mixtures to afford the title compound (71 mg); m/z 422.4 [M+1].

The following compounds are synthesized in a similar fashion from the appropriate intermediates:

Example 222, Table 1

Method 29

Synthesis of 2-[4-(3-{1-[4-(2-Amino-pyrimidin-5-yl)-phenyl]-1,2-dimethyl-propyl}-[1,2,4]oxadiazol-5-yl)-piperazin-1-yl]-N,N-dimethyl-acetamide (Example 193, Table 1)

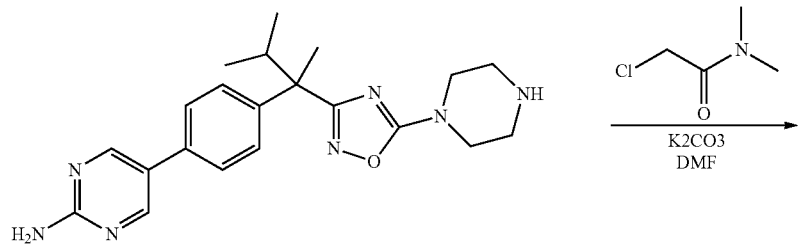

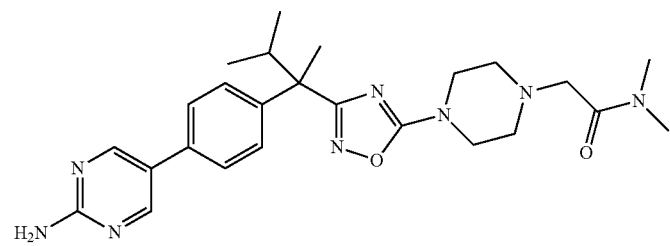

Example 193

Synthesis of 2-[4-(3-{1-[4-(2-Amino-pyrimidin-5-yl)-phenyl]-1,2-dimethyl-propyl}-[1,2,4]oxadiazol-5-yl)-piperazin-1-yl]-N,N-dimethyl-acetamide Synthesis is performed in similar conditions used in Method 9 using the appropriate reagents.

The following intermediates are synthesized in similar fashion from the appropriate reagents:

| Intermediate | Structure | m/z [M + H] |
|---|---|---|
| I-146 | 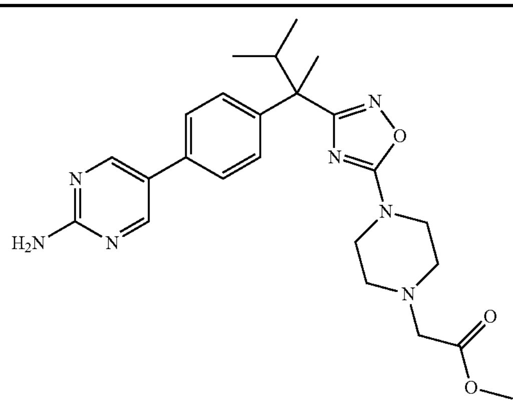 | 466.0 |

The following compounds are synthesized in a similar fashion from the appropriate intermediates:

Example 211, Table 1

Method 30

Synthesis of 1-(3-{1-[4-(2-Amino-pyrimidin-5-yl)-phenyl]-1,2-dimethyl-propyl}-[1,2,4]oxadiazol-5-yl)-piperidine-4-carboxylic Acid (Example 219, Table 1)

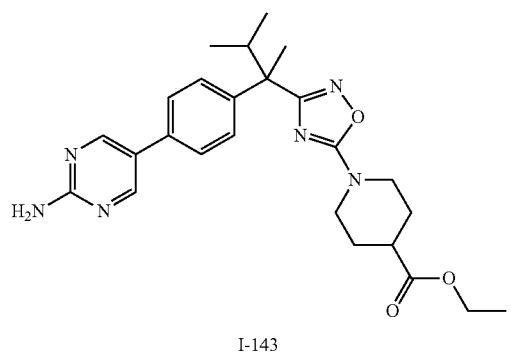

I-143

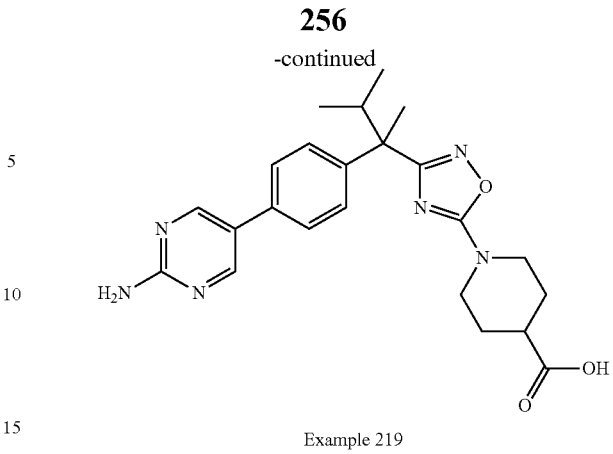

Example 219

Synthesis is similar to conditions used in Method 14 Step 2 using the appropriate reagents; m/z 437.4 [M+1]. Compound is purified by trituration from hot MeOH.

The following compounds are synthesized in a similar fashion from the appropriate intermediates:
Example 272, Table 1

Method 31

Synthesis of 1-(3-{1-[4-(2-Amino-pyrimidin-5-yl)-phenyl]-1,2-dimethyl-propyl}-[1,2,4]oxadiazol-5-yl)-3-methyl-azetidin-3-ol (Example 203, Table 1)

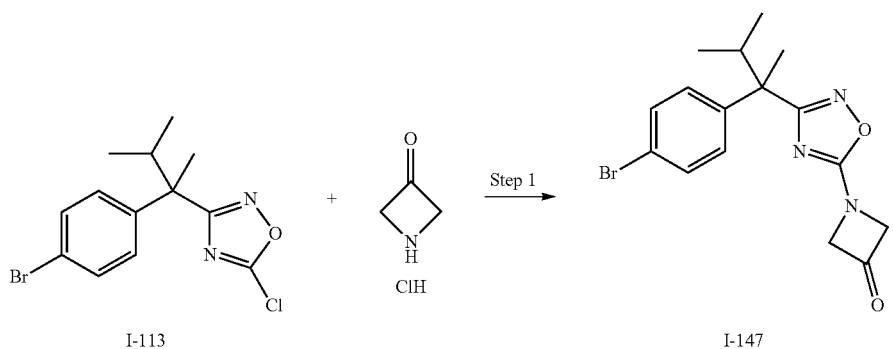

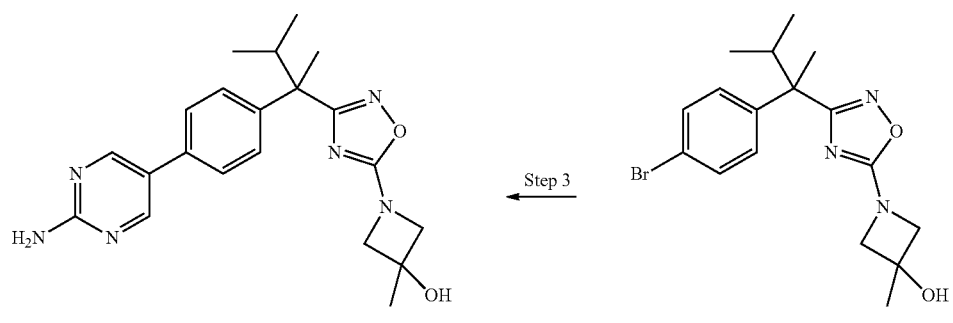

Synthesis of 1-{3-[1-(4-Bromo-phenyl)-1,2-dimethyl-propyl]-[1,2,4]oxadiazol-5-yl}-azetidin-3-one Synthesis is performed in similar conditions used in Method 21 Step 3 using the appropriate reagents; m/z 364 [M+H].

The following intermediates are synthesized in similar fashion from the appropriate reagents:

| Intermediate | Structure | m/z [M/M + 2H] |
|---|---|---|
| I-147bis | 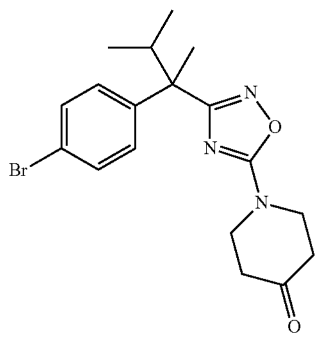 [SMILES: CC(C)C(C)(c1ccc(Br)cc1)c1noc(N2CCC(=O)CC2)n1] | 392.2/394.2 |
| I-147tris | 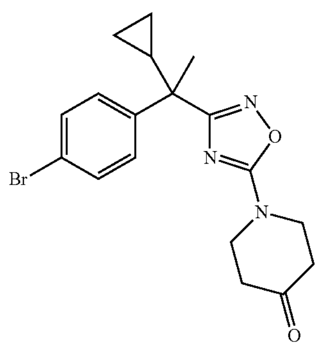 [SMILES: CC(c1ccc(Br)cc1)(c1noc(N2CCC(=O)CC2)n1)C1CC1] | 390.1/392.1 |
| I-147quadris | 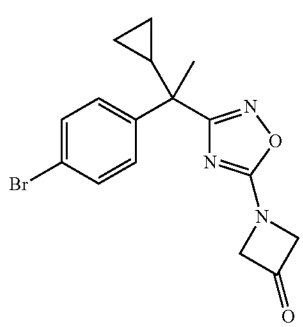 [SMILES: CC(c1ccc(Br)cc1)(c1noc(N2CC(=O)C2)n1)C1CC1] | 362.2/364.0 |

Synthesis of 1-{3-[1-(4-Bromo-phenyl)-1,2-dimethyl-propyl]-[1,2,4]oxadiazol-5-yl}-3-methyl-azetidin-3-ol To a cooled solution of I-147 (132.6 mg, 0.364 mmol) in THF (1 mL) at −78° C. is added 3M methyl magnesium chloride in THF (0.485 mL, 1.456 mmol). The reaction mixture is stirred at −78° C. for 10 minutes then at room temperature for 20 minutes. After this time, the reaction mixture is quenched with water and extracted with EtOAc twice. The organics are combined and washed with brine, dried over $Na_2SO_4$, filtered and concentrated in vacuo to afford the title compound (122 mg); m/z 380 [M+H].

The following intermediates are synthesized in similar fashion from the appropriate reagents:

| Intermediate | Structure | m/z [M/M + 2H] |
|---|---|---|
| I-148bis | 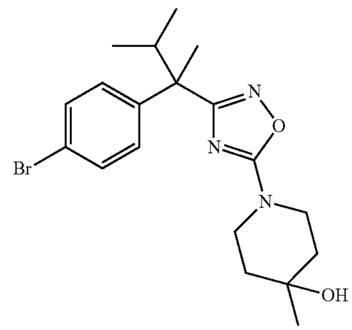 [SMILES: CC(C)C(C)(c1ccc(Br)cc1)c1noc(N2CCC(C)(O)CC2)n1] | 408.4/410.4 |
| I-148tris | 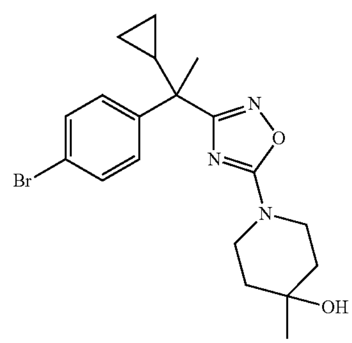 [SMILES: CC1(O)CCN(c2nc(C(C)(c3ccc(Br)cc3)C3CC3)no2)CC1] | 406.1/408.1 |
| I-148quadris | 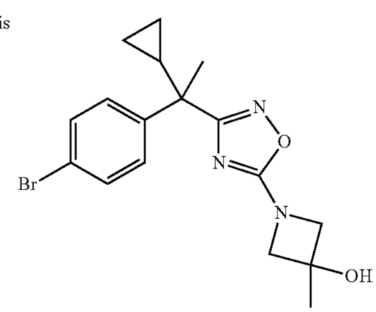 | 378.2/380.2 |

Synthesis of 1-(3-{1-[4-(2-Amino-pyrimidin-5-yl)-phenyl]-1,2-dimethyl-propyl}-[1,2,4]oxadiazol-5-yl)-3-methyl-azetidin-3-ol Synthesis is performed in similar conditions used in Method 21 Step 4 using the appropriate reagents.

The following compounds are synthesized in a similar fashion from the appropriate intermediates:

Example 216, Table 1

Example 238, Table 1

Example 276, Table 1

Method 32

Synthesis of 2-[4-(3-{1-[4-(2-Amino-pyrimidin-5-yl)-phenyl]-1-cyclopropyl-ethyl}-[1,2,4]oxadiazol-5-yl)-piperazin-1-yl]-ethanol (Example 252, Table 1)

Synthesis of 2-(4-{3-[1-(4-Bromo-phenyl)-1-cyclopropyl-ethyl]-[1,2,4]oxadiazol-5-yl}-piperazin-1-yl)-ethanol Synthesis is similar to conditions used in Method 21, Step 3 using the appropriate reagents; m/z 421/423[M/M+2H].

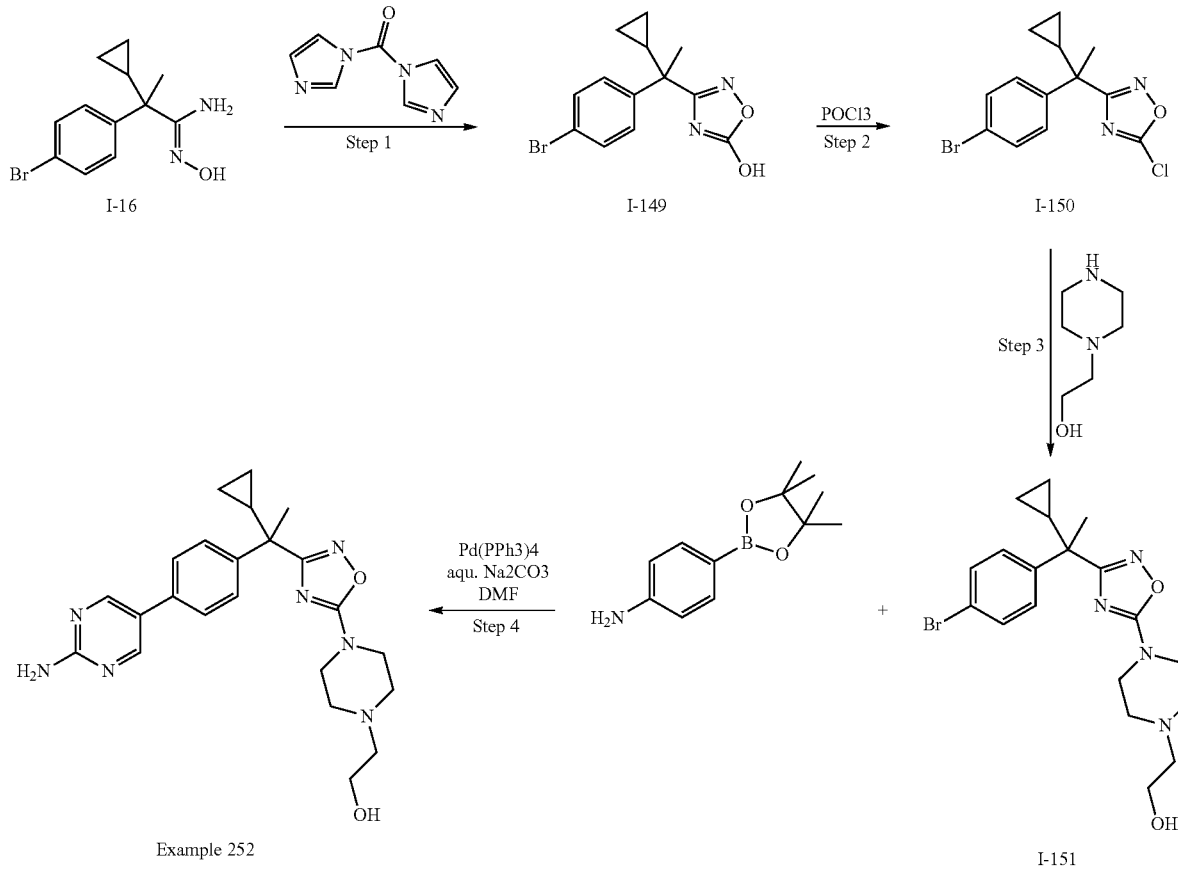

Synthesis of 3-[1-(4-Bromo-phenyl)-1-cyclopropyl-ethyl]-[1,2,4]oxadiazol-5-ol Synthesis is performed in similar conditions used in Method 21, Step 1 using the appropriate reagents; m/z 307 [M+H].

Synthesis of 3-[1-(4-Bromo-phenyl)-1-cyclopropyl-ethyl]-5-chloro-[1,2,4]oxadiazole To a solution of I-149 (847 mg, 2.74 mmol) in DCM (8 mL) in a microwave vial is added $POCl_3$ (0.401 mL, 4.384 mmol) and pyridine (1.107 mL, 13.7 mmol). The reaction mixture is heated in microwave oven at 120° C. for 1 hour. After this time, the reaction mixture is quenched with water and extracted with $CH_2Cl_2$ twice. The organics are combined and washed with brine, dried over $Na_2SO_4$, filtered and concentrated in vacuo. The crude is purified by flash chromatography ($SiO_2$, 6-50% EA/Hep) to afford the title intermediate (694 mg). 1H-NMR: (DMSO-d6) δ ppm 7.5 (2H, d), 7.3 (1H, d), 1.5 (1H, m), 1.4 (3H, s), 0.6 (1H, m), 0.5 (1H, m), 0.4 (1H, m), 0.3 (1H, m).

Synthesis of 2-[4-(3-{1-[4-(2-Amino-pyrimidin-5-yl)-phenyl]-1-cyclopropyl-ethyl}-[1,2,4]oxadiazol-5-yl)-piperazin-1-yl]-ethanol To a mixture of I-151 (193 mg, 0.458 mmol) and $Pd(PPh_3)_4$ (53 mg, 0.046 mmol) in a microwave vial is added the DMF (5 mL) solution of 2-aminopyrimidine-5-boronic acid pinacol ester (121.6 mg, 0.55 mmol) and 2M $Na_2CO_3$ aqueous solution (0.92 mL). The reaction mixture is purged with Ar and then heated in microwave oven at 110° C. for 45 minutes. After this time, the reaction mixture is quenched with water and extracted with EtOAc twice. The organics are combined and washed with brine, dried over $Na_2SO_4$, filtered and concentrated in vacuo. The crude is purified by flash chromatography ($SiO_2$, 1.2-10% MeOH/DCM) to afford the title compound (83 mg).

The following compounds are synthesized in a similar fashion from the appropriate intermediates:
Example 204-205, Table 1
Example 248, Table 1
Example 252, Table 1
Example 259, Table 1
Example 274, Table 1
Example 287-288, Table 1
Example 297, table 1

Method 33

Synthesis of 1-(3-{(R)-1-[4-(2-Amino-pyrimidin-5-yl)-phenyl]-1,2-dimethyl-propyl}-[1,2,4]oxadiazol-5-yl)-piperidin-4-ol (Example 223, Table 1) and 1-(3-{(S)-1-[4-(2-Amino-pyrimidin-5-yl)-phenyl]-1,2-dimethyl-propyl}-[1,2,4]oxadiazol-5-yl)-piperidin-4-ol (Example 224, Table 1)

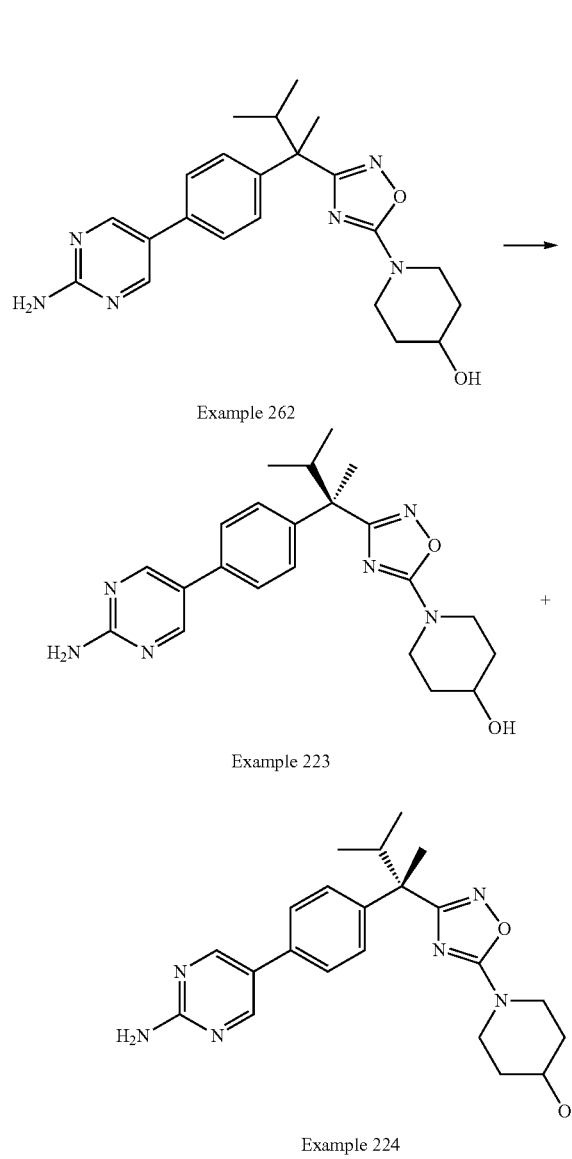

Example 223 and Example 224 are prepared by resolution of Example 262 (90.3 mg) on a RegisPak (available from Regis Technologies, Morton Grove, Ill.) semi-preparative (30×250 mm) HPLC column (eluting with 35% 1:1 MeOH in Isopropanol containing 0.1% isopropylamine in CO2) at 100 bar. The faster eluting enantiomer Example 223 having a retention time of 2.07 min (RegisPack 4.6×100 mm, available from Regis Technologies, Morton Grove, Ill.) and the slower eluting enantiomer Example 224 having a retention time of 2.68 min. The eluents are concentrated to provide Example 223 (36 mg) and Example 224 (34 mg).

Method 34

Synthesis of 5-[4-((R)-1-Cyclopropyl-1-{5-[1-(2-dimethylamino-ethyl)-1H-pyrazol-4-yl]-[1,2,4]oxadiazol-yl}-ethyl)-phenyl]-pyrimidin-2-ylamine (Example 182, Table 1)

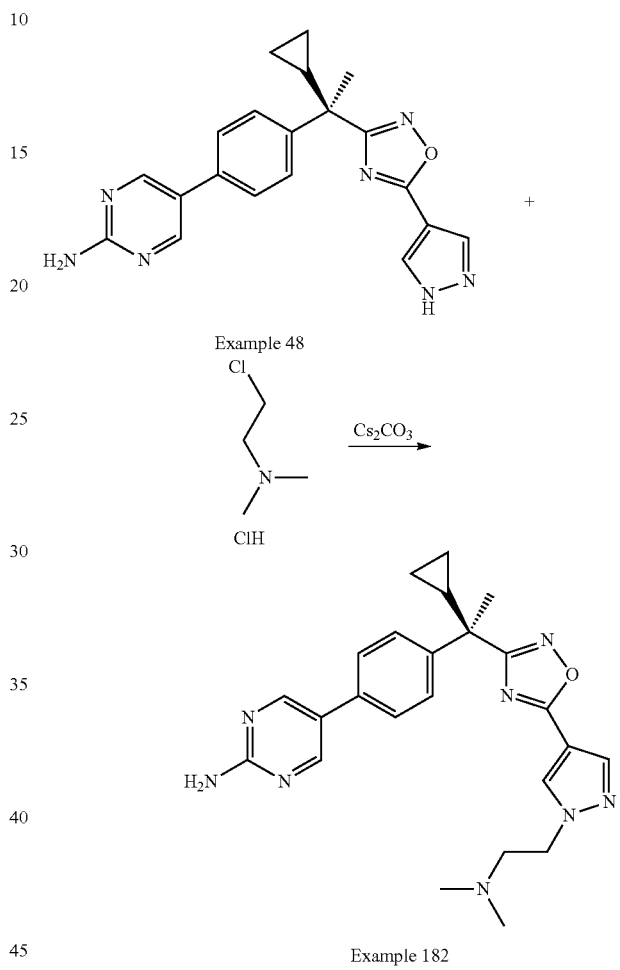

Example 48 (75.0 mg, 0.201 mmol) is treated with (2-Chloro-ethyl)-dimethyl-amine hydrochloride (43.4 mg, 0.301 mmol), $Cs_2CO_3$ (147 mg, 0.452 mmol), and DMF (1.5 mL) and the resulting mixture is stirred at 60° C. for 1 hour. At this time the mixture is treated with (2-Chloro-ethyl)-dimethyl-amine hydrochloride (14.5 mg, 0.100 mmol), $Cs_2CO_3$ (32.7 mg, 0.100 mmol) and stirred for 1 hour longer. The reaction is then purified directly by flash chromatography over C-18 silica eluting 10-60% acetonitrile/water/0.1% trifluoroacetic acid. The resulting semi-pure material is treated with $CH_2Cl_2$ and saturated aqueous $NaHCO_3$ and the phases are separated. The resulting aqueous phase is extracted 5 additional times with $CH_2Cl_2$ and the combined organic phases are dried over $Na_2SO_4$, filtered, and concentrated in vacuo to give a residue that is further purified by preparative TLC eluting 8% methanol/$CH_2Cl_2$ to give the title compound (35.0 mg).

The following compound is synthesized in a similar fashion from the appropriate intermediates:

Example 215, table 1

Method 35

Synthesis of 2-[4-(3-{(R)-1-[4-(2-Amino-pyrimidin-5-yl)-phenyl]-1-cyclopropyl-ethyl}-[1,2,4]oxadiazol-5-yl)-pyrazol-1-yl]-1-((R)-3-methoxy-pyrrolidin-1-yl)-ethanone (Example 220, Table 1)

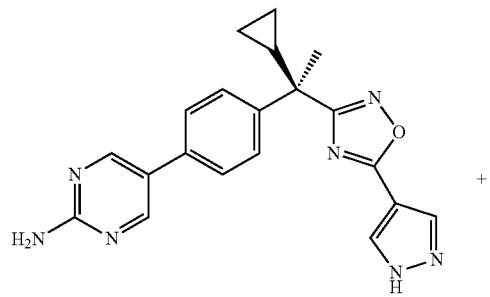

Example 48

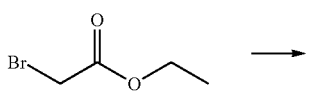

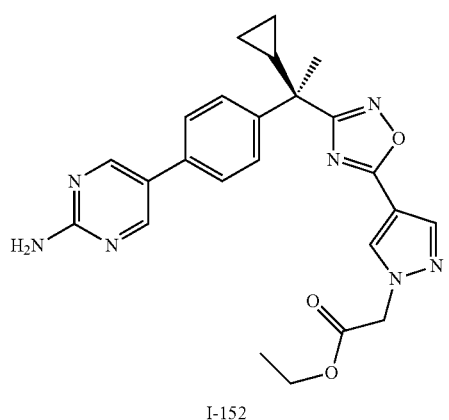

I-152

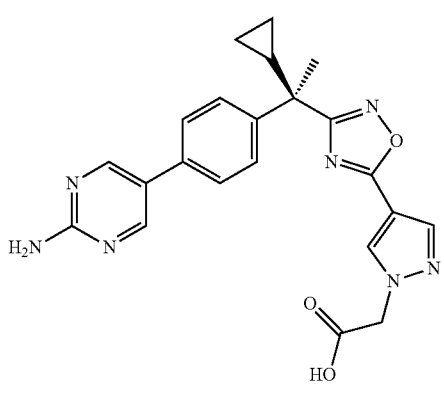

I-153

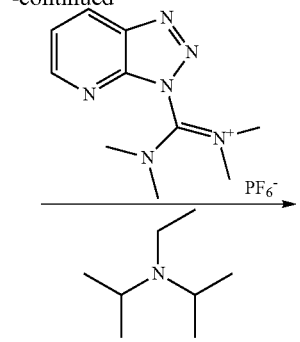

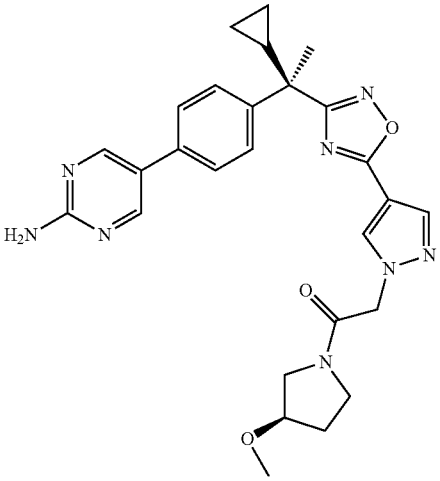

Example 220

Synthesis of [4-(3-{(R)-1-[4-(2-Amino-pyrimidin-5-yl)-phenyl]-1-cyclopropyl-ethyl}-[1,2,4]oxadiazol-5-yl)-pyrazol-1-yl]-acetic Acid Ethyl Ester Example 48 is alkylated according to Method 9; m/z 460 [M+H].

Synthesis of [4-(3-{(R)-1-[4-(2-Amino-pyrimidin-5-yl)-phenyl]-1-cyclopropyl-ethyl}-[1,2,4]oxadiazol-5-yl)-pyrazol-1-yl]-acetic Acid I-152 is hydrolyzed according to the final step of Method 16; m/z 432 [M+H].

I-153 (94.0 mg, 0.218 mmol) is treated with (R)-3-methoxy-pyrrolidine (33.1 mg, 0.327 mmol), HATU (125 mg, 0.327 mmol), DIEA (114 μL, 0.654 mmol), and DMF (1.50 mL) and the resulting mixture is stirred for 1 hour. The reaction is purified directly by reverse phase preparative HPLC eluting 30-70% acetonitrile/water/0.1% formic acid to give the title compound (16.0 mg).

The following compounds are synthesized in a similar fashion from the appropriate intermediates:

Example 194, table 1

Example 221, table 1

Method 36

Synthesis of 2-[4-(3-{(R)-1-[4-(2-amino-6-oxo-1,6-dihydro-pyrimidin-5-yl)-phenyl]-1-cyclopropyl-ethyl}-[1,2,4]oxadiazol-5-yl)-pyrazol-1-yl]-N,N-dimethyl-acetamide (Example 197, Table 1)

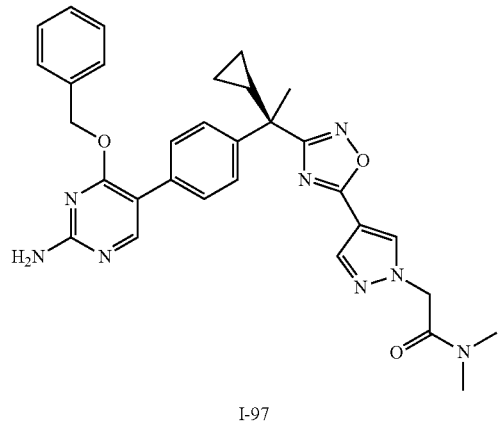

I-97

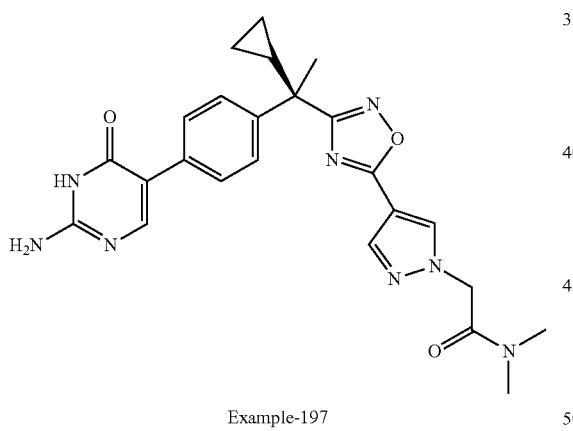

Example-197

I-97 (170 mg, 0.30 mmol) is dissolved in ethanol (10 ml) and treated with Pearlman's catalyst (Palladium hydroxide, 35 mg, 50% wet, 0.12 mmol). The vessel is degassed and placed under hydrogen (balloon). Upon complete conversion, the reaction is filtered through a pad of celite and the solids are washed with methanol. The combined filtrates are concentrated and the remaining crude is purified via flash column chromatography (0-10% MeOH/DCM) to give the title compound (100 mg).

Method 37

Preparation of 5-[4-((R)-1-{5-[1-(2-Amino-ethyl)-1H-pyrazol-4-yl]-[1,2,4]oxadiazol-3-yl}-1-cyclopropyl-ethyl)-phenyl]-pyrimidin-2-ylamine (Example 190, Table 1)

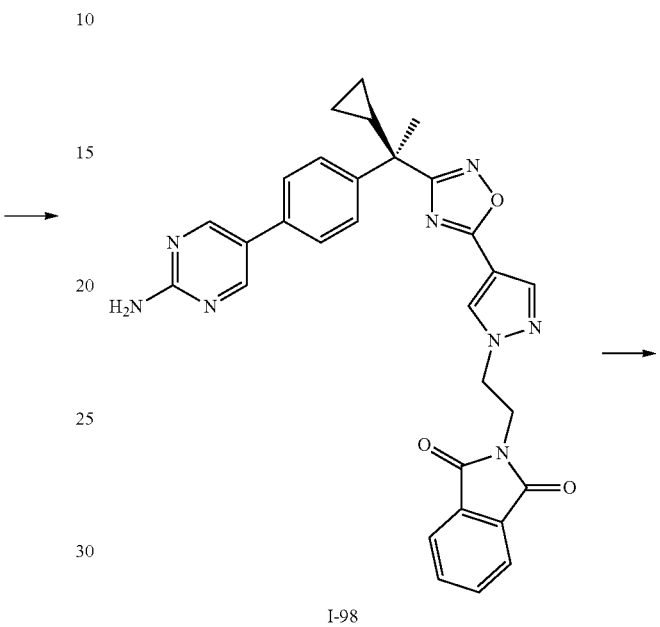

I-98

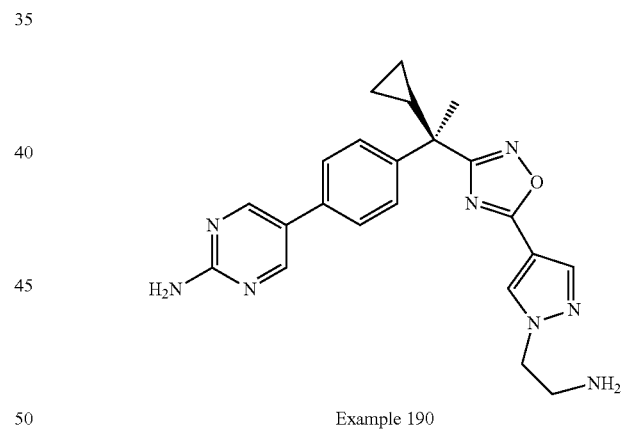

Example 190

Intermediate I-98 (120 mg, 0.22 mmol) is treated with ethanol (2.7 mL) and THF (0.5 mL) and hydrazine (97 mg, 1.93 mmol) is then added. The resulting mixture is stirred at 50° C. for 2 hours. The resulting mixture is filtered, rinsing with ethanol, diluted with ethyl acetate and water, and the phases separated. The organic phase is washed with brine dried over $Na_2SO_4$, filtered, and concentrated in vacuo. The residue is purified by reverse-phase preparative HPLC eluting 10-80% acetonitrile/water/trifluoroacetic acid to give the title compound (33.0 mg).

Method 38

Syntheses of 2-[4-(3-{1-[4-(2-Amino-6-fluoro-pyridin-3-yl)-phenyl]-1-cyclopropyl-ethyl}-[1,2,4]oxadiazol-5-yl)-pyrazol-1-yl]-N,N-dimethyl-acetamide (Example 277, Table 1) and 2-[4-(3-{1-[4-(6-Amino-2-fluoro-pyridin-3-yl)-phenyl]-1-cyclopropyl-ethyl}-[1,2,4]oxadiazol-5-yl)-pyrazol-1-yl]-N,N-dimethyl-acetamide (Example 278, Table 1)

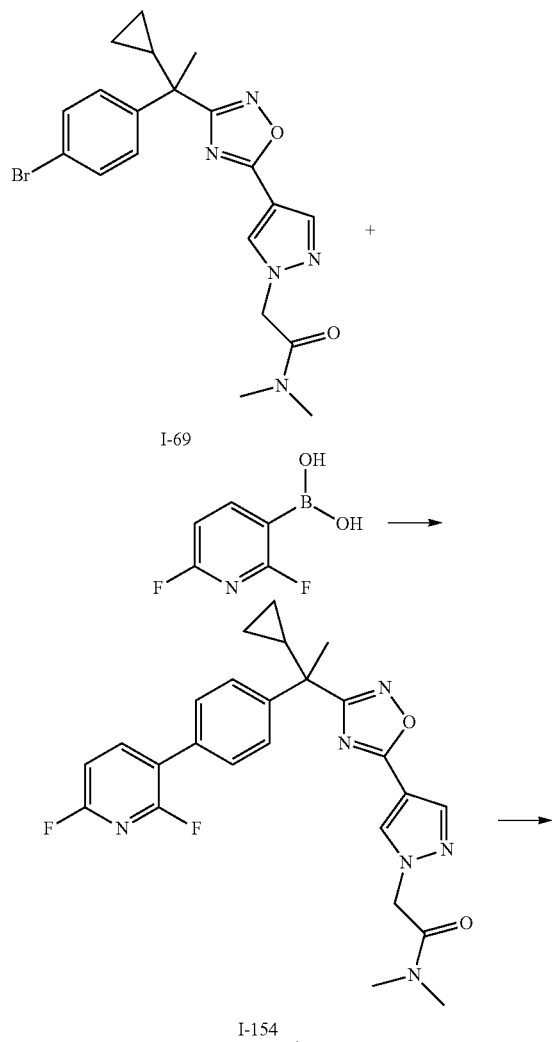

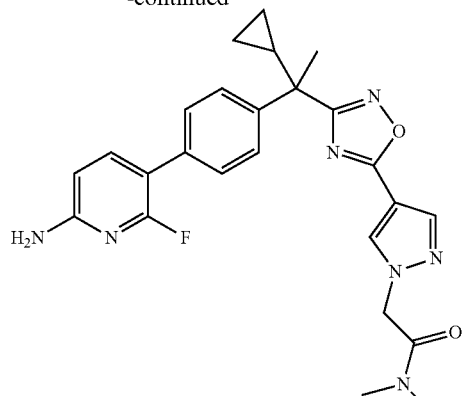

Example 278

To a mixture of I-69 (300 mg, 0.68 mmol) in 1,4-dioxane (10 mL) are added 2,6-difluoropyridin-3-boronic acid (128 mg, 0.81 mmol), PdCl$_2$(PPh$_3$)$_2$ (47 mg, 0.068 mmol) and 2 M Na$_2$CO$_3$ solution (2M aqueous solution) (1 mL, 02 mmol). The mixture is heated to 100° C. for 1 hour in a microwave reactor. The solution is cooled down and is extracted with H$_2$O and EtOAc. The combined organic layer is dried with Mg$_2$SO$_4$ and is filtered. The filtrate is concentrated and the residue is purified by silica gel flash column chromatography with 10% MeOH in CH$_2$Cl$_2$ as the eluent to afford I-154 (200 mg) (m/z: 479.2 [M$^+$+H]).

I-154 (150 mg, 0.31 mmol) is dissolved in NH$_3$ in MeOH (2M solution) (10 mL) and the solution is heated to 100° C. for 72 hours. The solution is cooled down and is concentrated. The residue is purified by preparative silica gel TLC to obtain the title compounds (example 277: 10 mg; example 278: 14 mg)

Method 39

Synthesis of 2-[4-(3-{1-[4-(5-Amino-3-cyano-pyrazin-2-yl)-phenyl]-1-cyclopropyl-ethyl}-[1,2,4]oxadiazol-5-yl)-pyrazol-1-yl]-N,N-dimethyl-acetamide (Example 295, Table 1)

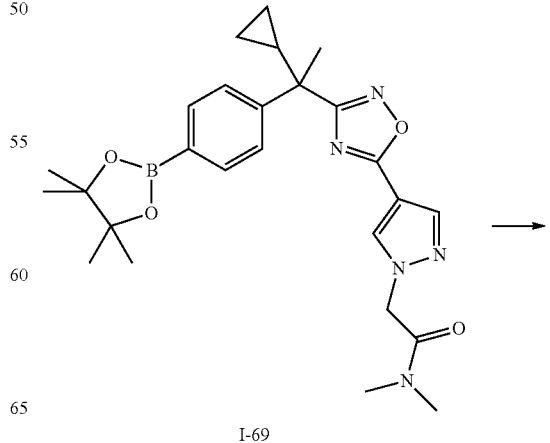

I-69

269

-continued

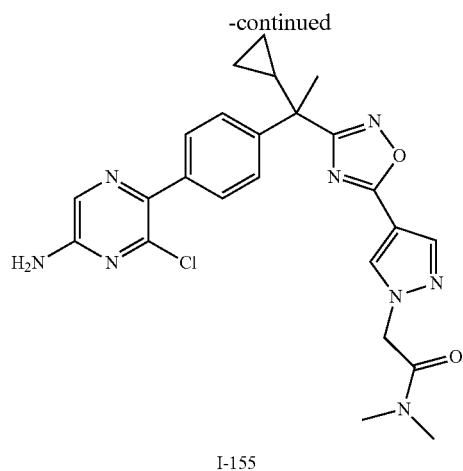

I-155

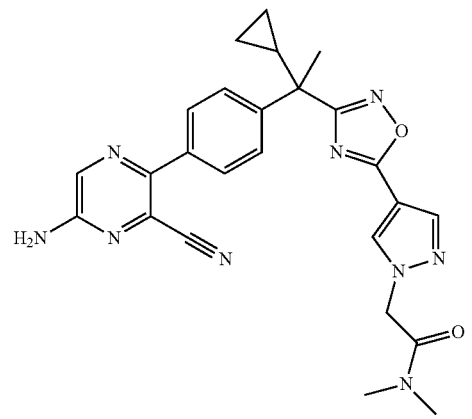

Example 295

To a solution of I-69 (100 mg, 0.2 mmol) in DMF are added 2-amino-5-bromo-6-chloropyrazine (51 mg, 0.24 mmol), Tetrakis(triphenylphosphine)palladium (0) (24 mg, 0.02 mmol) and 2M Na₂CO₃ solution (2M aqueous) (0.5 mL, 1 mmol). The mixture is heated to 100° C. for 1 hour in a microwave reactor. The mixture is cooled down and is extracted with H₂O and EtOAc. The combined organic layer is dried with MgSO₄ and is filtered. The filtrate is concentrated and the residue is purified by silica gel flash column chromatography with 10% MeOH in CH₂Cl₂ as the eluent to afford I-155 (86 mg) (m/z: 493.2 [M⁺+H]).

In a microwave reaction vessel is dissolved I-155 (80 mg, 0.16 mmol) in DMF (8 mL). Zinc cyanide (23 mg, 0.19 mmol) and Pd(PPh₃)₄ (18 mg, 0.016 mmol) are added and the solution is heated to 120° C. in a microwave for 2 hours. The solution is cooled down and is poured into water and extracted the product into EtOAc. The combined organics are dried with MgSO₄, filtered and concentrated. The residue is purified by silica gel flash column chromatography with 10% MeOH in CH₂Cl₂ as the eluent to afford the title compound (38 mg).

270

Method 40

Synthesis of 2-[4-(3-{1-[4-(6-Amino-2-cyano-pyridin-3-yl)-phenyl]-1-cyclopropyl-ethyl}-1,2,4]oxadiazol-5-yl)-pyrazol-1-yl]-N,N-dimethyl-acetamide (Example 296, Table 1)

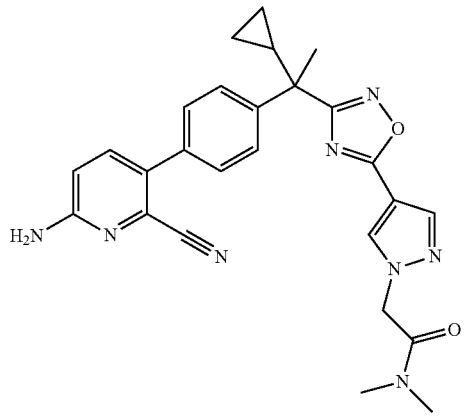

Example 296

To a solution of 2-bromo-6-aminopyridine (200 mg, 1.2 mmol) in DMF (10 mL) are added Zn(CN)₂ (163 mg, 1.4 mmol) and Pd(PPh₃)₄ (134 mg, 0.12 mmol) at room temperature. The solution is heated at 120° C. in a microwave reactor for 2 hours. The solution is cooled down and water is added. The solution is extracted with EtOAc and the combined organic layer was dried with MgSO₄ and is filtered. The filtrate is concentrated and the residue is purified by silica gel flash column chromatography with 10% MeOH in CH₂Cl₂ as the eluent to afford I-156 (54 mg) (m/z: 119.9 [M⁺]).

To a solution of I-156 (54 mg, 0.46 mmol) in CH₃CN (10 mL) is added NBS (162 mg, 0.9 mmol) at room temperature. The solution is stirred at the same temperature for 12 hours. The solution is concentrated and the residue is purified by silica gel flash column chromatography with 10% MeOH in CH₂Cl₂ as the eluent to afford I-157 (35 mg) (m/z: 197.9 [M⁺]).

To a solution of I-69 (50 mg, 0.1 mmol) in DMF (8 mL) are added I-157 (24 mg, 0.12 mmol), Tetrakis(triphenylphosphine)palladium (0) (11 mg, 0.01 mmol) and 2M Na₂CO₃ (0.25 mL, 0.51 mmol). The mixture is heated to 100° C. for 1 hour in a microwave reactor. The mixture is cooled down and is extracted with H₂O and EtOAc. The combined organic layer is dried with MgSO₄ and is filtered. The filtrate is concentrated and the residue is purified by silica gel flash column chromatography with 10% MeOH in CH$_2$Cl$_2$ as the eluent to afford the title compound (26 mg).

Method 41

Synthesis of 3-{1-[4-(2-Amino-pyrimidin-5-yl)-phenyl]-1,2-dimethyl-propyl}-[1,2,4]oxadiazol-5-ol (Example 88, Table 1)

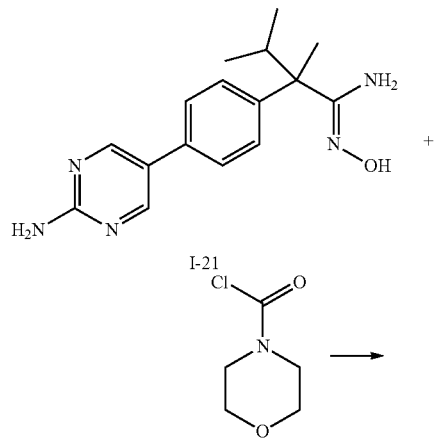

-continued

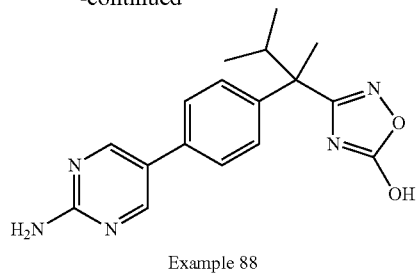

Example 88

To a suspension of morpholine-4-carbonyl chloride (32.907 mg, 0.220 mmol) in DMF (1 ml) is added I-21 (60.000 mg, 0.200 mmol). The reaction mixture is stirred at room temperature for 20 mins then Hunig's base (0.038 mL, 0.22 mmol) is added and the reaction mixture is heated at 55° C. for 1 hour then heated in microwave oven at 150° C. for 30 mins. After this time, the reaction mixture is concentrated in vacuo. Purification of the crude by flash chromatography (SiO2, 0-10% MeOH in DCM) then pre-TLC (10% MeOH in DCM) yields Example 88 (23 mg) as a white solid; m/z 326.0 [M+H].

TABLE 3

| Example | Structure | Method | Retention time (min) | m/z [M + H]$^+$ | LC-MS method |
|---|---|---|---|---|---|
| 1 | 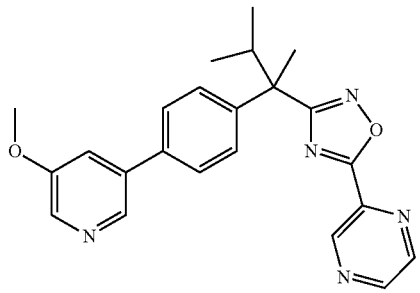 [SMILES: COc1cncc(-c2ccc(C(C)(c3noc(-c4cnccn4)n3)C(C)C)cc2)c1] | 1 | 7.4 | 402.6 | A |
| 2 | 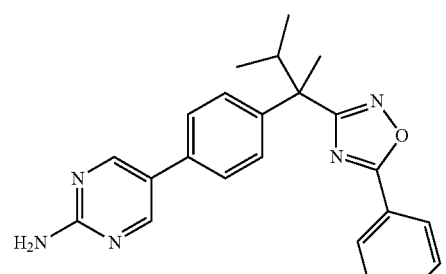 | 1 | 8.23 | 386.6 | A |

TABLE 3-continued

Final Compounds;

| Example | Structure | Method | Retention time (min) | m/z [M + H]+ | LC-MS method |
|---|---|---|---|---|---|
| 3 | 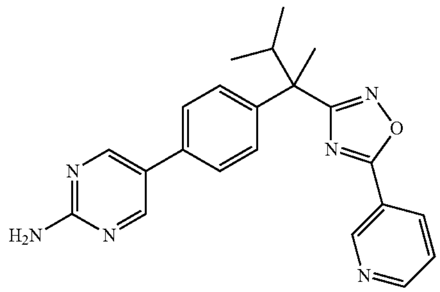 [SMILES: CC(C)C(C)(c1ccc(-c2cnc(N)nc2)cc1)c1noc(-c2cccnc2)n1] | 1 | 7.32 | 387.6 | A |
| 4 | 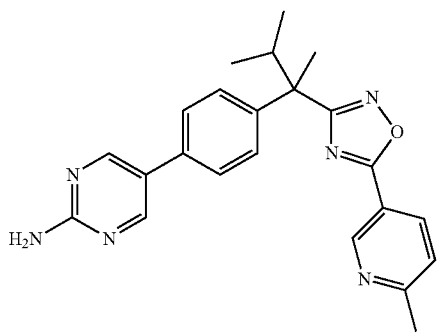 [SMILES: Cc1ccc(-c2nc(C(C)(c3ccc(-c4cnc(N)nc4)cc3)C(C)C)no2)cn1] | 1 | 7.66 | 401.2 | A |
| 5 | 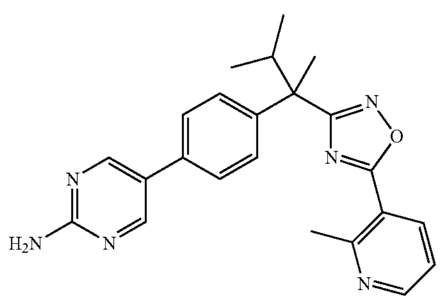 [SMILES: Cc1ncccc1-c1nc(C(C)(c2ccc(-c3cnc(N)nc3)cc2)C(C)C)no1] | 1 | 7.51 | 401.6 | A |
| 6 | 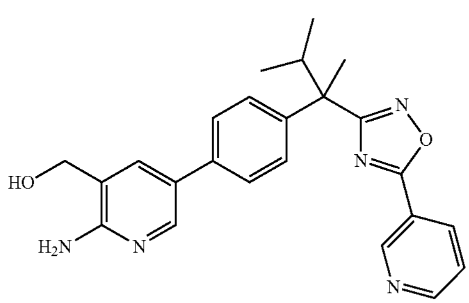 [SMILES: CC(C)C(C)(c1ccc(-c2cnc(N)c(CO)c2)cc1)c1noc(-c2cccnc2)n1] | 2 | 6 | 416.6 | A |

TABLE 3-continued
Final Compounds;
| Example | Structure | Method | Retention time (min) | m/z [M + H]+ | LC-MS method |
|---|---|---|---|---|---|
| 7 | 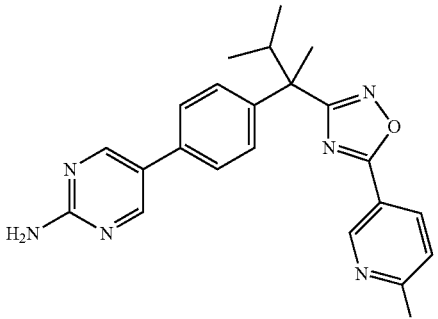 | 1 | 7.98 | 421.5 | A |
| 8 | 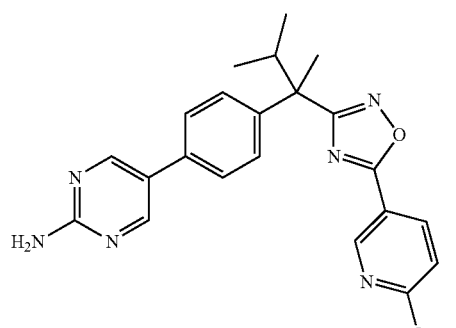 | 3 | 8.04 | 417.6 | A |
| 9 | 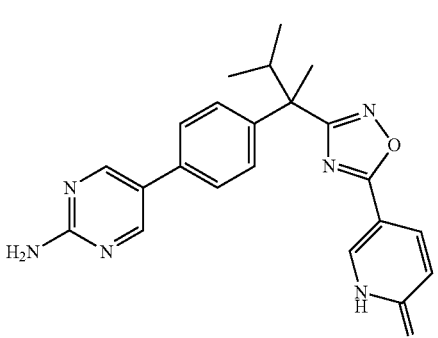 | 3 | 6.55 | 403.5 | A |
| 10 | 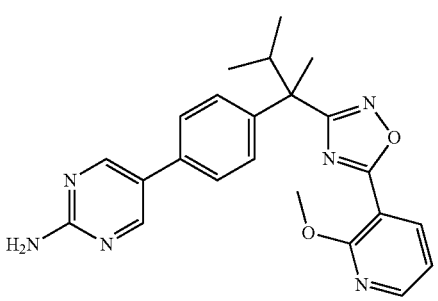 [SMILES: COc1ncccc1-c1nc(C(C)(c2ccc(-c3cnc(N)nc3)cc2)C(C)C)no1] | 4 | 7.82 | 417.6 | A |

TABLE 3-continued

Final Compounds;

| Example | Structure | Method | Retention time (min) | m/z [M + H]+ | LC-MS method |
|---|---|---|---|---|---|
| 11 | 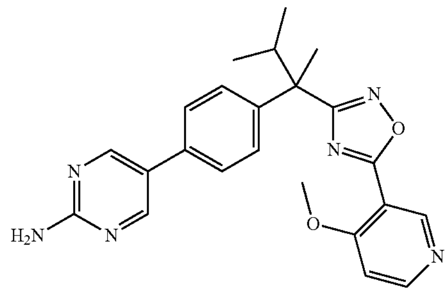 [SMILES: COc1ccncc1-c1nc(C(C)(c2ccc(-c3cnc(N)nc3)cc2)C(C)C)no1] | 5 | 6.75 | 417.6 | A |
| 12 | 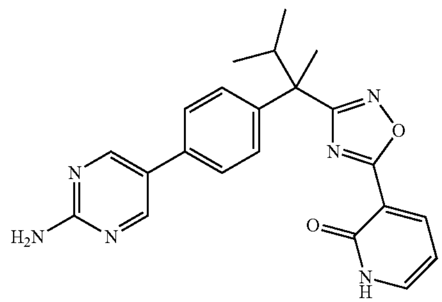 [SMILES: CC(C)C(C)(c1ccc(-c2cnc(N)nc2)cc1)c1noc(-c2ccc[nH]c2=O)n1] | 4 | 6.37 | 403.5 | A |
| 13 | 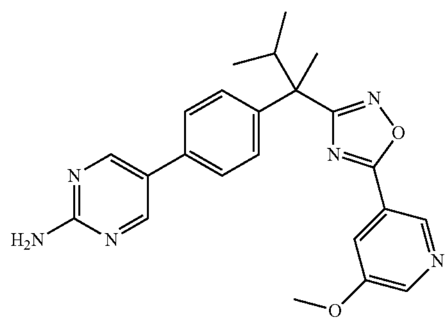 [SMILES: COc1cncc(-c2nc(C(C)(c3ccc(-c4cnc(N)nc4)cc3)C(C)C)no2)c1] | 5 | 7.55 | 417.5 | A |
| 14 | 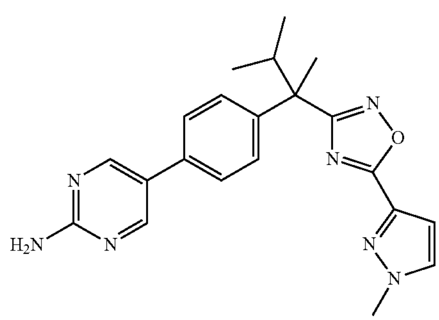 [SMILES: CC(C)C(C)(c1ccc(-c2cnc(N)nc2)cc1)c1noc(-c2ccn(C)n2)n1] | 5 | 5.87 | 390.6 | A |
| 15 | 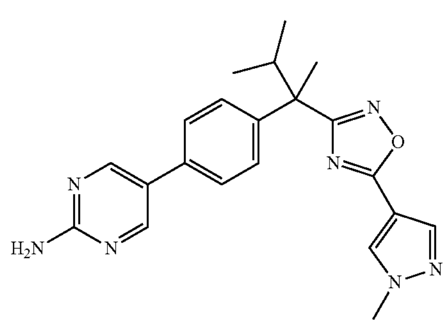 [SMILES: CC(C)C(C)(c1ccc(-c2cnc(N)nc2)cc1)c1noc(-c2cnn(C)c2)n1] | 5 | 5.74 | 390.6 | A |

TABLE 3-continued

Final Compounds;

| Example | Structure | Method | Retention time (min) | m/z [M + H]+ | LC-MS method |
|---|---|---|---|---|---|
| 16 | 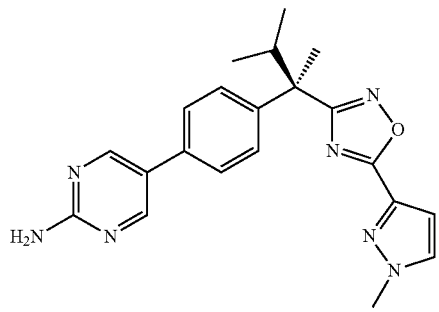 [SMILES: CC(C)[C@](C)(c1ccc(-c2cnc(N)nc2)cc1)c1noc(-c2ccn(C)n2)n1] | 19 | 1.6 | 390.7 | B |
| 17 | 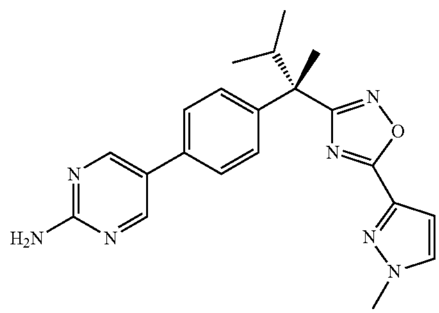 [SMILES: CC(C)[C@@](C)(c1ccc(-c2cnc(N)nc2)cc1)c1noc(-c2ccn(C)n2)n1] | 19 | 1.6 | 390.7 | B |
| 18 | 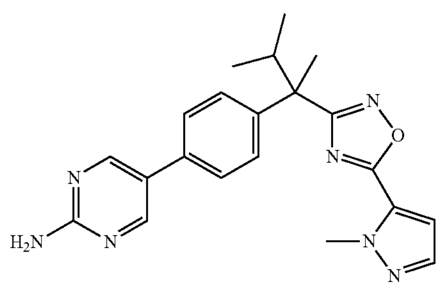 [SMILES: CC(C)C(C)(c1ccc(-c2cnc(N)nc2)cc1)c1noc(-c2ccnn2C)n1] | 5 | 6.36 | 390.6 | A |
| 19 | 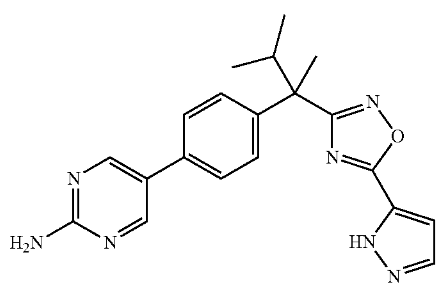 [SMILES: CC(C)C(C)(c1ccc(-c2cnc(N)nc2)cc1)c1noc(-c2ccn[nH]2)n1] | 5 | 5.46 | 376.6 | A |
| 20 | 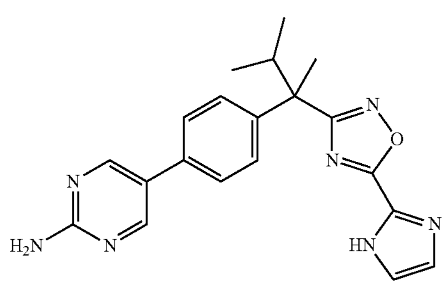 [SMILES: CC(C)C(C)(c1ccc(-c2cnc(N)nc2)cc1)c1noc(-c2ncc[nH]2)n1] | 5 | 4.82 | 376.6 | A |

TABLE 3-continued

Final Compounds;

| Example | Structure | Method | Retention time (min) | m/z [M + H]+ | LC-MS method |
|---|---|---|---|---|---|
| 21 | 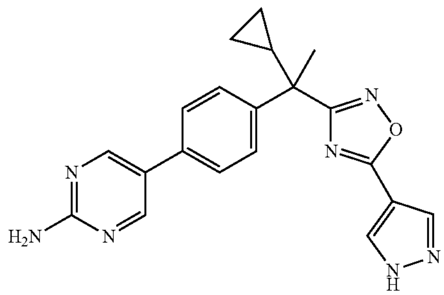 [SMILES: CC(c1ccc(-c2cnc(N)nc2)cc1)(c1noc(-c2cn[nH]c2)n1)C1CC1] | 5 | 5.03 | 374.6 | A |
| 22 | 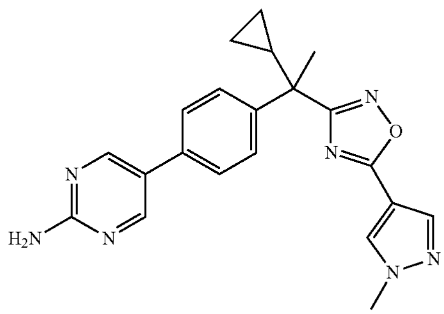 [SMILES: Cn1cc(-c2nc(C(C)(c3ccc(-c4cnc(N)nc4)cc3)C3CC3)no2)cn1] | 5 | 5.37 | 388.6 | A |
| 23 | 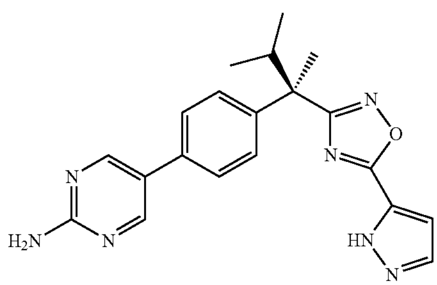 [SMILES: CC(C)[C@](C)(c1ccc(-c2cnc(N)nc2)cc1)c1noc(-c2ccn[nH]2)n1] | 18 | 5.48 | 376.6 | A |
| 24 | 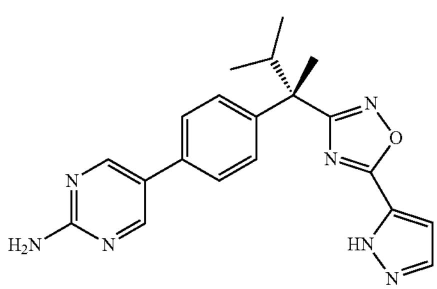 [SMILES: CC(C)[C@@](C)(c1ccc(-c2cnc(N)nc2)cc1)c1noc(-c2ccn[nH]2)n1] | 18 | 5.48 | 376.6 | A |
| 25 | 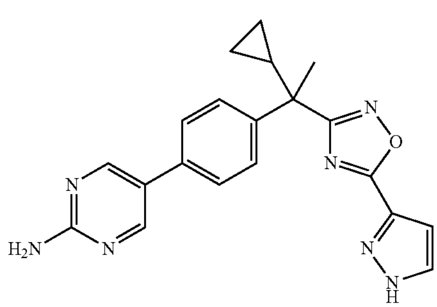 [SMILES: CC(c1ccc(-c2cnc(N)nc2)cc1)(c1noc(-c2cc[nH]n2)n1)C1CC1] | 5 | 5.13 | 374.6 | A |

TABLE 3-continued

Final Compounds;

| Example | Structure | Method | Retention time (min) | m/z [M + H]+ | LC-MS method |
|---------|-----------|--------|----------------------|--------------|--------------|
| 26 | 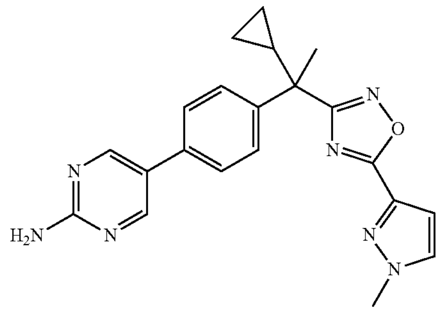 [SMILES: Cn1ccc(-c2nc(C(C)(c3ccc(-c4cnc(N)nc4)cc3)C3CC3)no2)n1] | 5 | 5.5 | 388.6 | A |
| 27 | 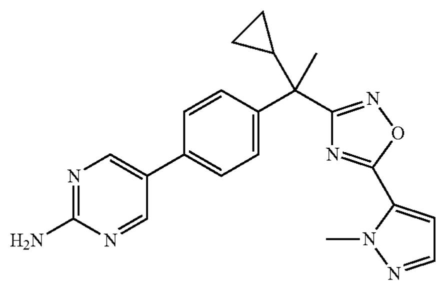 [SMILES: Cn1nccc1-c1nc(C(C)(c2ccc(-c3cnc(N)nc3)cc2)C2CC2)no1] | 5 | 5.98 | 388.6 | A |
| 28 | 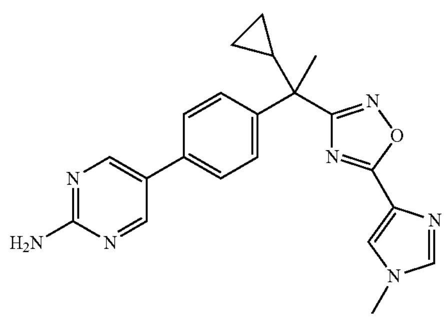 [SMILES: Cn1cnc(-c2nc(C(C)(c3ccc(-c4cnc(N)nc4)cc3)C3CC3)no2)c1] | 5 | 4.8 | 388.6 | A |
| 29 | 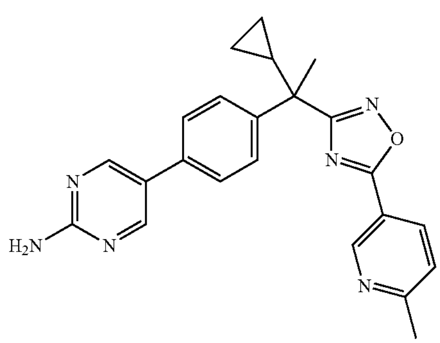 [SMILES: Cc1ccc(-c2nc(C(C)(c3ccc(-c4cnc(N)nc4)cc3)C3CC3)no2)cn1] | 5 | 5.78 | 399.6 | A |

TABLE 3-continued

Final Compounds:

| Example | Structure | Method | Retention time (min) | m/z [M + H]+ | LC-MS method |
|---|---|---|---|---|---|
| 30 | 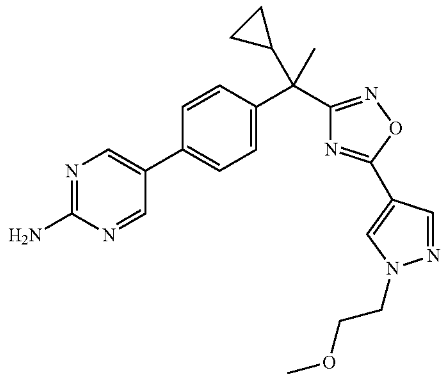 [SMILES: COCCn1cc(-c2nc(C(C)(c3ccc(-c4cnc(N)nc4)cc3)C3CC3)no2)cn1] | 9 | 2.32 | 432.2 | B |
| 31 | 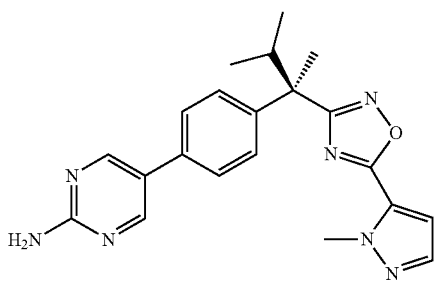 [SMILES: CC(C)[C@](C)(c1ccc(-c2cnc(N)nc2)cc1)c1noc(-c2ccnn2C)n1] | 18 | 6.39 | 390.4 | A |
| 32 | 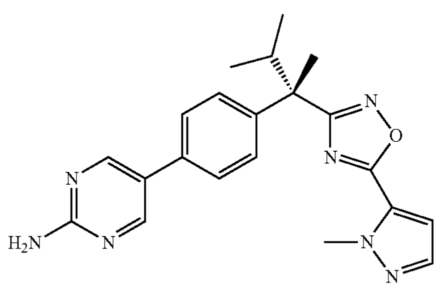 [SMILES: CC(C)[C@@](C)(c1ccc(-c2cnc(N)nc2)cc1)c1noc(-c2ccnn2C)n1] | 18 | 6.39 | 390.4 | A |
| 33 | 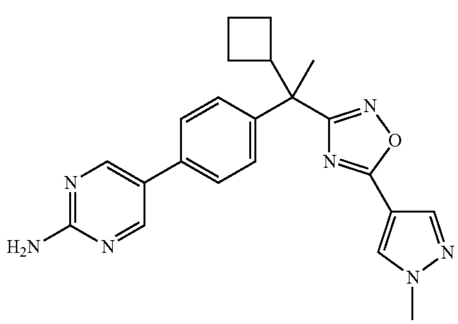 [SMILES: Cn1cc(-c2nc(C(C)(c3ccc(-c4cnc(N)nc4)cc3)C3CCC3)no2)cn1] | 5 | 2.51 | 402.4 | C |

TABLE 3-continued

Final Compounds;

| Example | Structure | Method | Retention time (min) | m/z [M + H]+ | LC-MS method |
|---------|-----------|--------|----------------------|--------------|--------------|
| 34 | 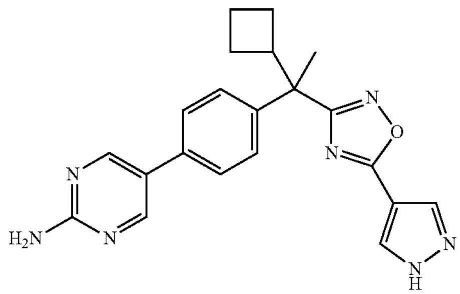 [SMILES: CC(c1ccc(-c2cnc(N)nc2)cc1)(c1noc(-c2cn[nH]c2)n1)C1CCC1] | 5 | 1.74 | 388.3 | C |
| 35 | 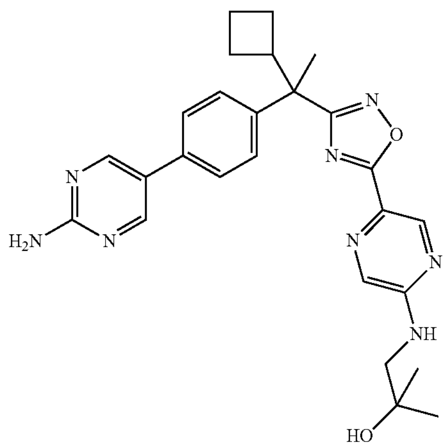 [SMILES: CC(C)(O)CNc1cnc(-c2nc(C(C)(c3ccc(-c4cnc(N)nc4)cc3)C3CCC3)no2)cn1] | 11 | 2.52 | 487.4 | C |
| 36 | 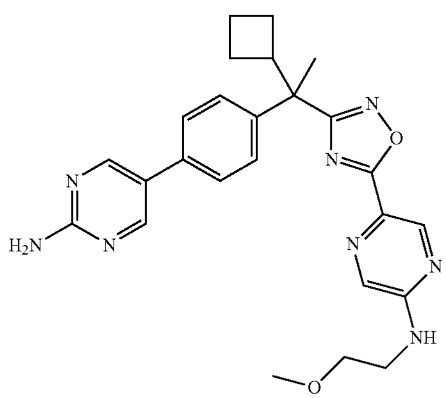 [SMILES: COCCNc1cnc(-c2nc(C(C)(c3ccc(-c4cnc(N)nc4)cc3)C3CCC3)no2)cn1] | 11 | 2.61 | 473.4 | C |
| 37 | 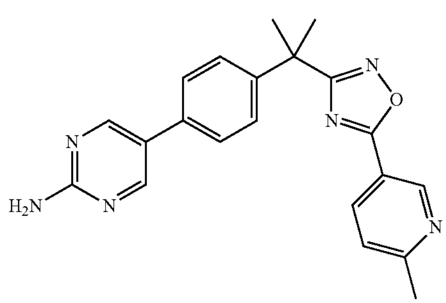 [SMILES: Cc1ccc(-c2nc(C(C)(C)c3ccc(-c4cnc(N)nc4)cc3)no2)cn1] | 5 | 2.31 | 373.2 | C |

TABLE 3-continued
Final Compounds;
| Example | Structure | Method | Retention time (min) | m/z [M + H]+ | LC-MS method |
|---|---|---|---|---|---|
| 38 | 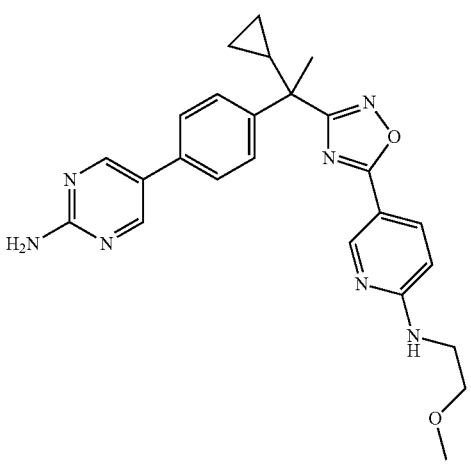 [SMILES: COCCNc1ccc(-c2nc(C(C)(c3ccc(-c4cnc(N)nc4)cc3)C3CC3)no2)cn1] | 12 | 5.42 | 458.4 | A |
| 39 | 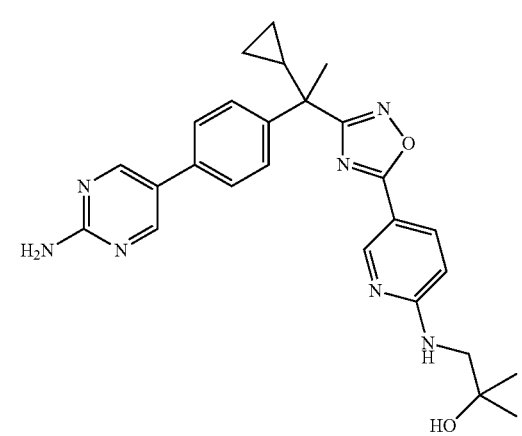 [SMILES: CC(C)(O)CNc1ccc(-c2nc(C(C)(c3ccc(-c4cnc(N)nc4)cc3)C3CC3)no2)cn1] | 12 | 2.29 | 472.2 | C |
| 40 | 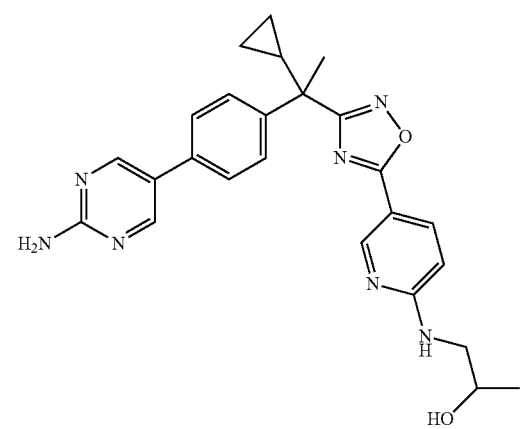 [SMILES: CC(O)CNc1ccc(-c2nc(C(C)(c3ccc(-c4cnc(N)nc4)cc3)C3CC3)no2)cn1] | 12 | 2.15 | 458.2 | C |

TABLE 3-continued
Final Compounds;
| Example | Structure | Method | Retention time (min) | m/z [M + H]+ | LC-MS method |
|---------|-----------|--------|----------------------|--------------|--------------|
| 41 | 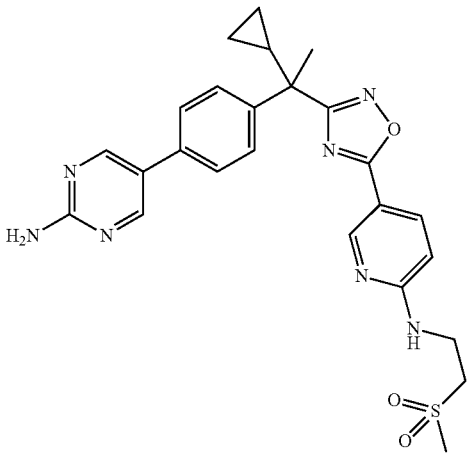 [SMILES: CC(c1ccc(-c2cnc(N)nc2)cc1)(c1noc(-c2ccc(NCCS(C)(=O)=O)nc2)n1)C1CC1] | 12 | 5.34 | 506.4 | A |
| 42 | 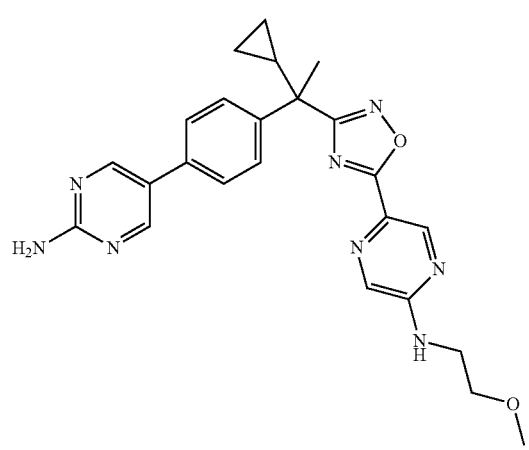 [SMILES: COCCNc1cnc(-c2nc(C(C)(c3ccc(-c4cnc(N)nc4)cc3)C3CC3)no2)cn1] | 11 | 2.33 | 459.4 | C |
| 43 | 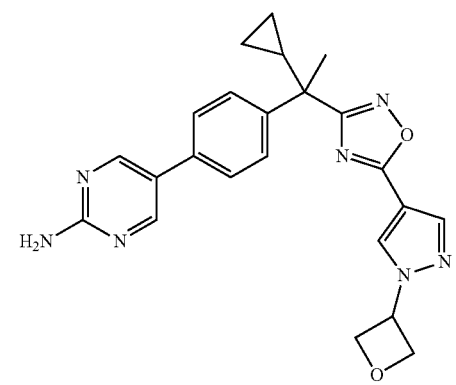 [SMILES: CC(c1ccc(-c2cnc(N)nc2)cc1)(c1noc(-c2cnn(C3COC3)c2)n1)C1CC1] | 9 | 5.32 | 430.4 | A |

TABLE 3-continued

Final Compounds;

| Example | Structure | Method | Retention time (min) | m/z [M + H]+ | LC-MS method |
|---------|-----------|--------|----------------------|--------------|--------------|
| 44 | 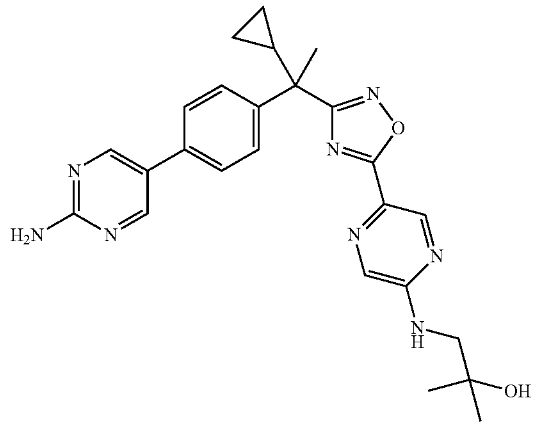 [SMILES: CC(C)(O)CNc1cnc(-c2nc(C(C)(c3ccc(-c4cnc(N)nc4)cc3)C3CC3)no2)cn1] | 11 | 5.26 | 473.4 | A |
| 45 | 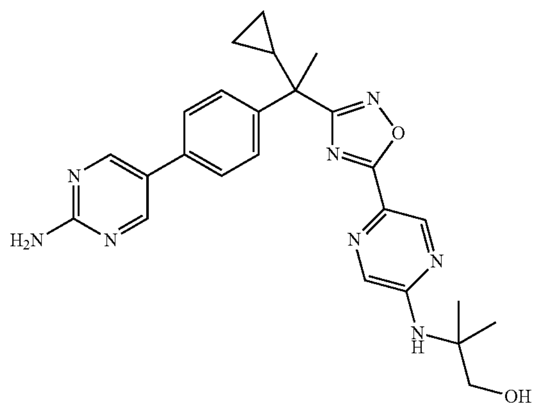 [SMILES: CC(C)(CO)Nc1cnc(-c2nc(C(C)(c3ccc(-c4cnc(N)nc4)cc3)C3CC3)no2)cn1] | 11 | 5.57 | 473.4 | A |
| 46 | 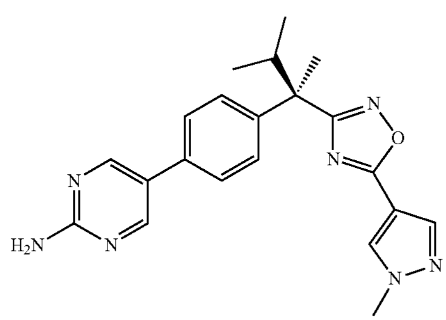 [SMILES: CC(C)[C@](C)(c1ccc(-c2cnc(N)nc2)cc1)c1noc(-c2cnn(C)c2)n1] | 19 | 2.45 | 390.4 | C |
| 47 | 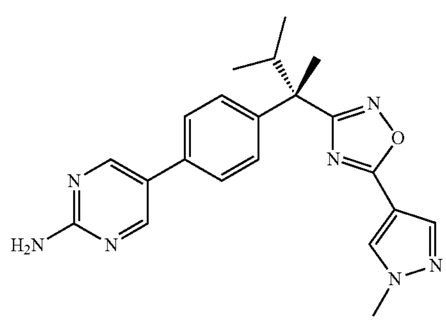 [SMILES: CC(C)[C@@](C)(c1ccc(-c2cnc(N)nc2)cc1)c1noc(-c2cnn(C)c2)n1] | 19 | 2.45 | 390.4 | C |

TABLE 3-continued

Final Compounds;

| Example | Structure | Method | Retention time (min) | m/z [M + H]+ | LC-MS method |
|---|---|---|---|---|---|
| 48 | 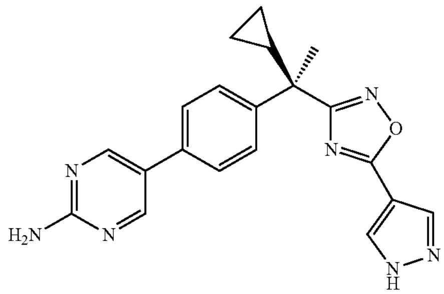 [SMILES: C[C@@](c1ccc(-c2cnc(N)nc2)cc1)(c1noc(-c2cn[nH]c2)n1)C1CC1] | 19 | 2.01 | 374.4 | C |
| 49 | 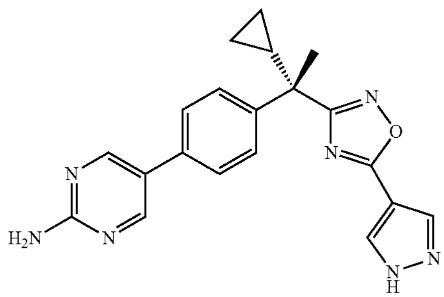 [SMILES: C[C@](c1ccc(-c2cnc(N)nc2)cc1)(c1noc(-c2cn[nH]c2)n1)C1CC1] | 19 | 2.01 | 374.4 | C |
| 50 | 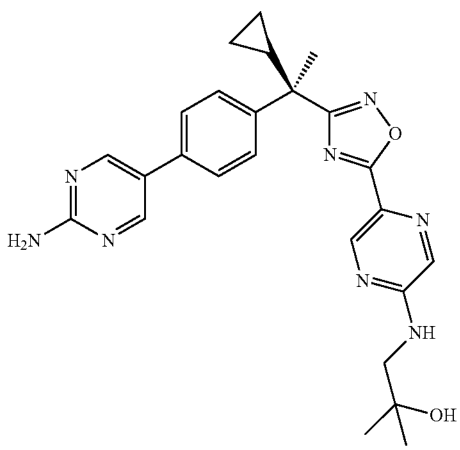 [SMILES: CC(C)(O)CNc1cnc(-c2nc([C@@](C)(c3ccc(-c4cnc(N)nc4)cc3)C3CC3)no2)cn1] | 20 | 5.26 | 473.4 | A |
| 51 | 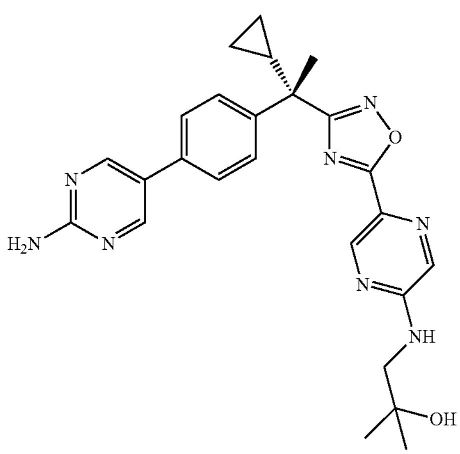 [SMILES: CC(C)(O)CNc1cnc(-c2nc([C@](C)(c3ccc(-c4cnc(N)nc4)cc3)C3CC3)no2)cn1] | 20 | 5.26 | 473.4 | A |

TABLE 3-continued

Final Compounds;

| Example | Structure | Method | Retention time (min) | m/z [M + H]+ | LC-MS method |
|---|---|---|---|---|---|
| 52 | 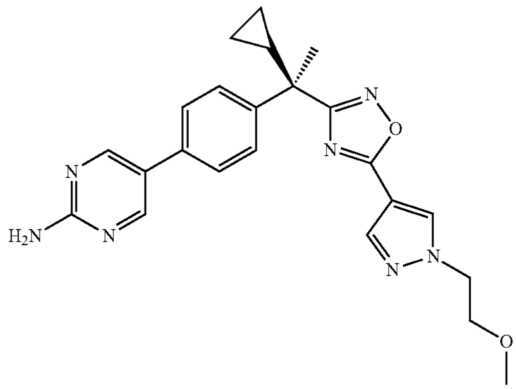 [SMILES: COCCn1cc(-c2nc([C@@](C)(c3ccc(-c4cnc(N)nc4)cc3)C3CC3)no2)cn1] | 20 | 5.55 | 432.4 | A |
| 53 | 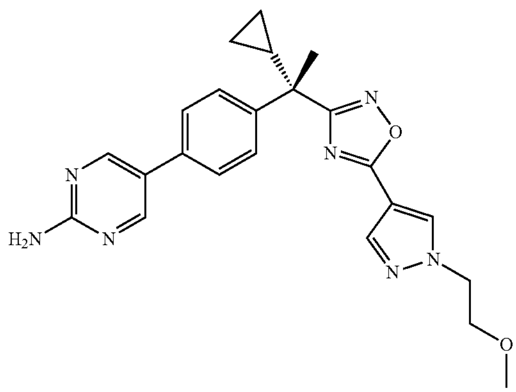 [SMILES: COCCn1cc(-c2nc([C@](C)(c3ccc(-c4cnc(N)nc4)cc3)C3CC3)no2)cn1] | 20 | 5.55 | 432.4 | A |
| 54 | 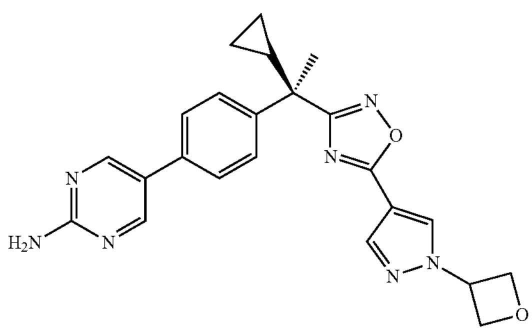 [SMILES: C[C@@](c1ccc(-c2cnc(N)nc2)cc1)(c1noc(-c2cnn(C3COC3)c2)n1)C1CC1] | 20 | 5.32 | 430.4 | A |
| 55 | 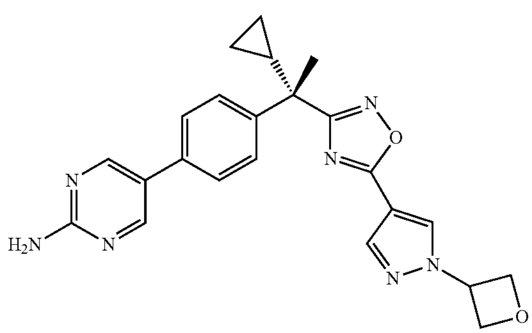 [SMILES: C[C@](c1ccc(-c2cnc(N)nc2)cc1)(c1noc(-c2cnn(C3COC3)c2)n1)C1CC1] | 20 | 5.32 | 430.4 | A |

TABLE 3-continued
Final Compounds;
| Example | Structure | Method | Retention time (min) | m/z [M + H]+ | LC-MS method |
|---|---|---|---|---|---|
| 56 | 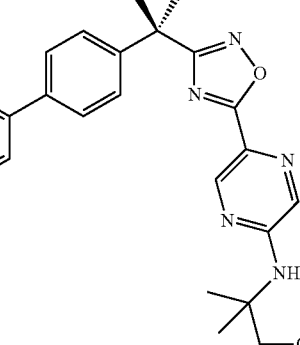 | 20 | 5.57 | 473.5 | A |
| 57 | 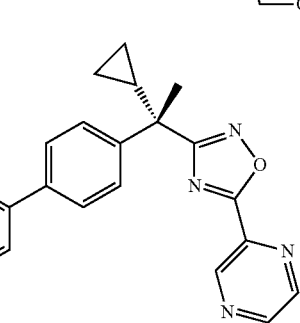 | 20 | 5.57 | 473.5 | A |
| 58 | 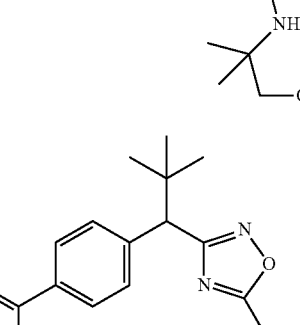 | 5 | 5.9 | 390.3 | A |
| 59 | 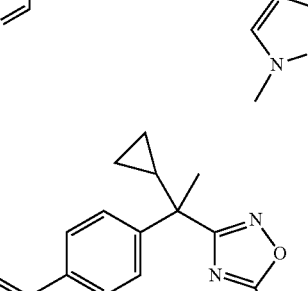 | 9 | 4.97 | 459.6 | A |

TABLE 3-continued

Final Compounds;

| Example | Structure | Method | Retention time (min) | m/z [M + H]+ | LC-MS method |
|---------|-----------|--------|----------------------|--------------|--------------|
| 60 | 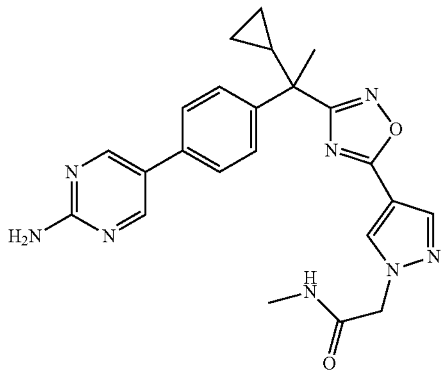 [SMILES: CNC(=O)Cn1cc(-c2nc(C(C)(c3ccc(-c4cnc(N)nc4)cc3)C3CC3)no2)cn1] | 9 | 4.74 | 445.5 | A |
| 61 | 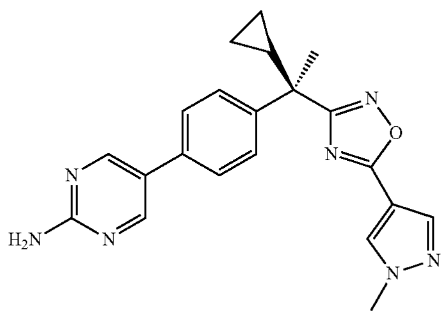 [SMILES: Cn1cc(-c2nc([C@@](C)(c3ccc(-c4cnc(N)nc4)cc3)C3CC3)no2)cn1] | 18 | 5.36 | 388.3 | A |
| 62 | 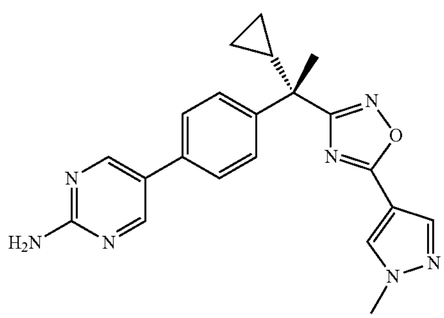 [SMILES: Cn1cc(-c2nc([C@](C)(c3ccc(-c4cnc(N)nc4)cc3)C3CC3)no2)cn1] | 18 | 5.36 | 388.3 | A |
| 63 | 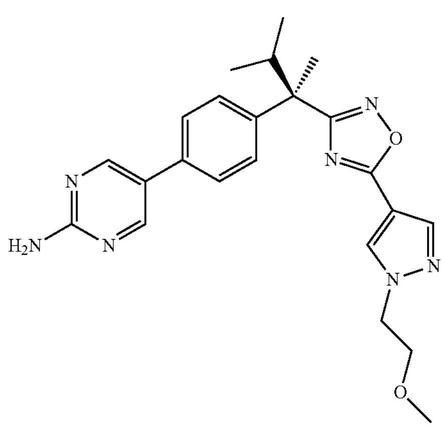 [SMILES: COCCn1cc(-c2nc([C@@](C)(c3ccc(-c4cnc(N)nc4)cc3)C(C)C)no2)cn1] | 20 | 5.91 | 434.4 | A |

TABLE 3-continued

Final Compounds;

| Example | Structure | Method | Retention time (min) | m/z [M + H]+ | LC-MS method |
|---|---|---|---|---|---|
| 64 | 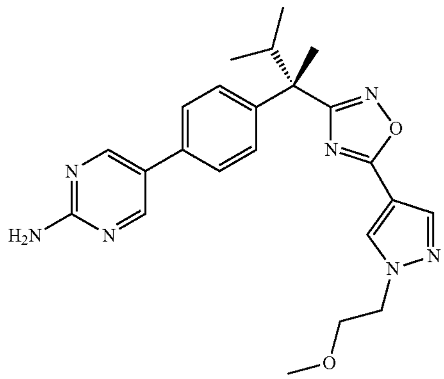 [SMILES: COCCn1cc(-c2nc([C@](C)(c3ccc(-c4cnc(N)nc4)cc3)C(C)C)no2)cn1] | 20 | 5.91 | 434.4 | A |
| 65 | 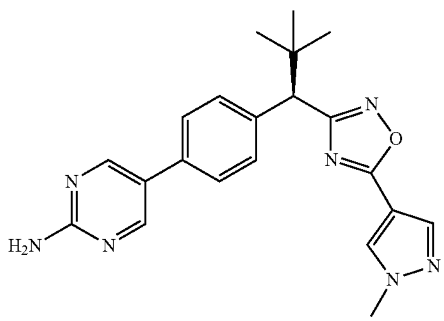 [SMILES: Cn1cc(-c2nc([C@@H](c3ccc(-c4cnc(N)nc4)cc3)C(C)(C)C)no2)cn1] | 18 | 5.89 | 390.3 | A |
| 66 | 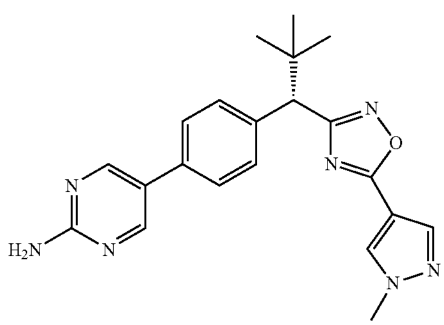 [SMILES: Cn1cc(-c2nc([C@H](c3ccc(-c4cnc(N)nc4)cc3)C(C)(C)C)no2)cn1] | 18 | 5.89 | 390.3 | A |
| 67 | 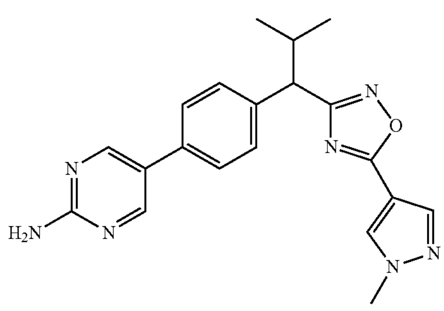 [SMILES: CC(C)C(c1ccc(-c2cnc(N)nc2)cc1)c1noc(-c2cnn(C)c2)n1] | 5 | 2.27 | 376.4 | C |

TABLE 3-continued
Final Compounds;
| Example | Structure | Method | Retention time (min) | m/z [M + H]+ | LC-MS method |
|---|---|---|---|---|---|
| 68 | 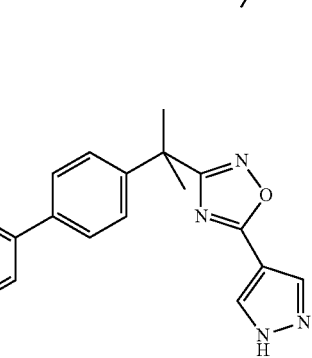 | 5 | 1.16 | 362.4 | D |
| 69 | 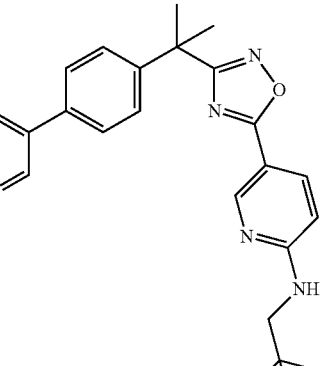 | 5 | 1.08 | 346.4 | D |
| 70 | 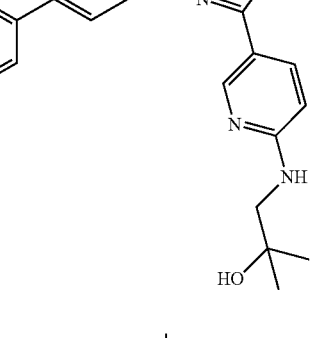 | 12 | 1.19 | 446.4 | D |
| 71 | 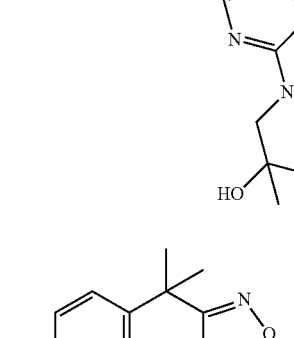 | 12 | 1.15 | 480.4 | D |

TABLE 3-continued

Final Compounds;

| Example | Structure | Method | Retention time (min) | m/z [M + H]+ | LC-MS method |
|---|---|---|---|---|---|
| 72 | 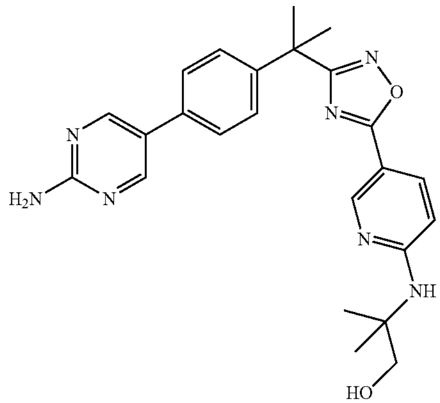 [SMILES: CC(C)(CO)Nc1ccc(-c2nc(C(C)(C)c3ccc(-c4cnc(N)nc4)cc3)no2)cn1] | 12 | 1.24 | 446.4 | D |
| 73 | 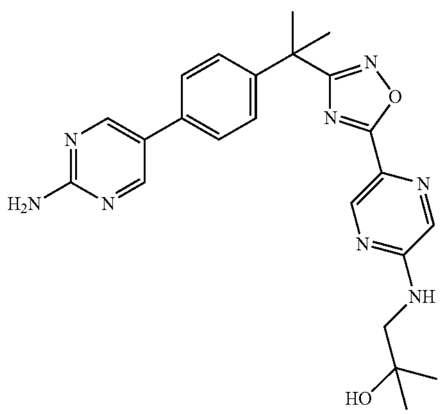 [SMILES: CC(C)(O)CNc1cnc(-c2nc(C(C)(C)c3ccc(-c4cnc(N)nc4)cc3)no2)cn1] | 11 | 1.18 | 447.4 | D |
| 74 | 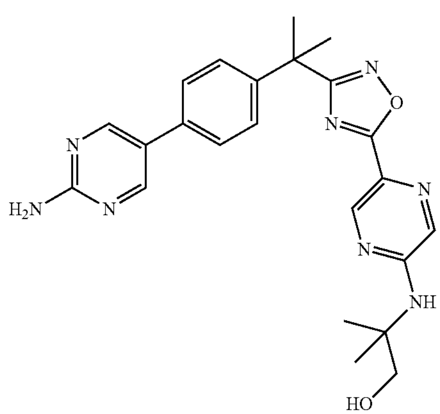 [SMILES: CC(C)(CO)Nc1cnc(-c2nc(C(C)(C)c3ccc(-c4cnc(N)nc4)cc3)no2)cn1] | 11 | 1.22 | 447.4 | D |

TABLE 3-continued

Final Compounds;

| Example | Structure | Method | Retention time (min) | m/z [M + H]+ | LC-MS method |
|---------|-----------|--------|----------------------|--------------|--------------|
| 75 | 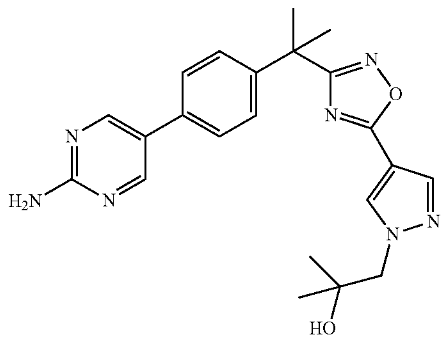 [SMILES: CC(C)(O)Cn1cc(-c2nc(C(C)(C)c3ccc(-c4cnc(N)nc4)cc3)no2)cn1] | 9 | 1.17 | 420.4 | D |
| 76 | 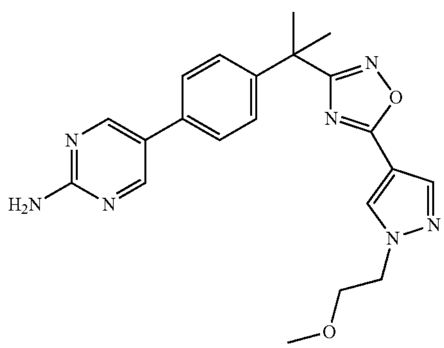 [SMILES: COCCn1cc(-c2nc(C(C)(C)c3ccc(-c4cnc(N)nc4)cc3)no2)cn1] | 9 | 1.19 | 406.4 | D |
| 77 | 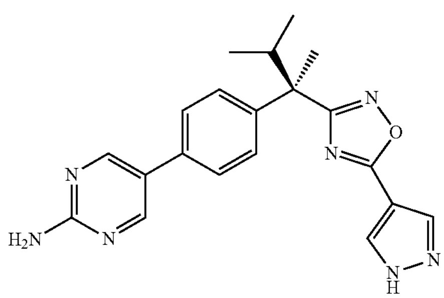 [SMILES: CC(C)[C@](C)(c1ccc(-c2cnc(N)nc2)cc1)c1noc(-c2cn[nH]c2)n1] | 18 | 1.21 | 376.4 | D |
| 78 | 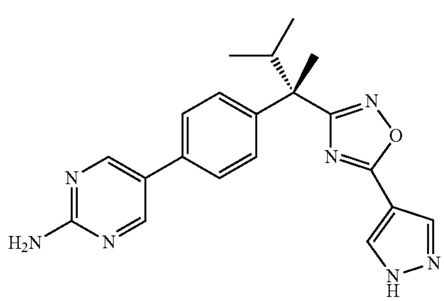 [SMILES: CC(C)[C@@](C)(c1ccc(-c2cnc(N)nc2)cc1)c1noc(-c2cn[nH]c2)n1] | 18 | 1.21 | 376.4 | D |

TABLE 3-continued

Final Compounds;

| Example | Structure | Method | Retention time (min) | m/z [M + H]+ | LC-MS method |
|---|---|---|---|---|---|
| 79 | 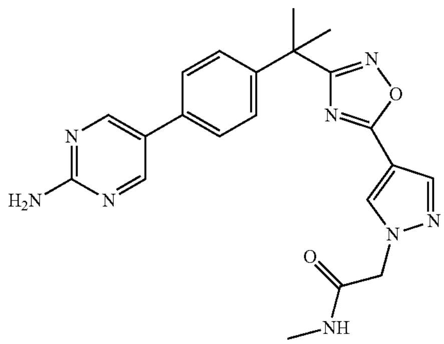 [SMILES: CNC(=O)Cn1cc(-c2nc(C(C)(C)c3ccc(-c4cnc(N)nc4)cc3)no2)cn1] | 9 | 1.06 | 419.4 | D |
| 80 | 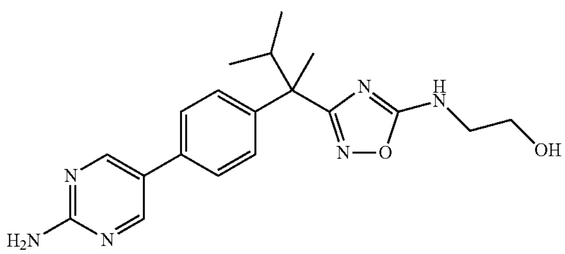 [SMILES: CC(C)C(C)(c1ccc(-c2cnc(N)nc2)cc1)c1noc(NCCO)n1] | 10 | 1.28 | 369.4 | D |
| 81 | 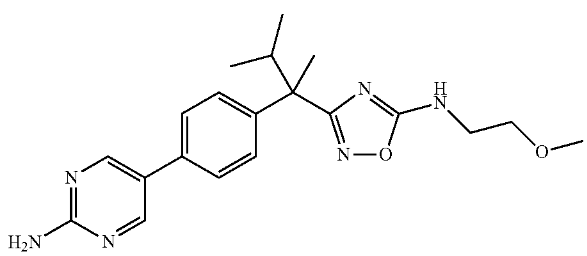 [SMILES: COCCNc1nc(C(C)(c2ccc(-c3cnc(N)nc3)cc2)C(C)C)no1] | 10 | 1.4 | 383.4 | D |
| 82 | 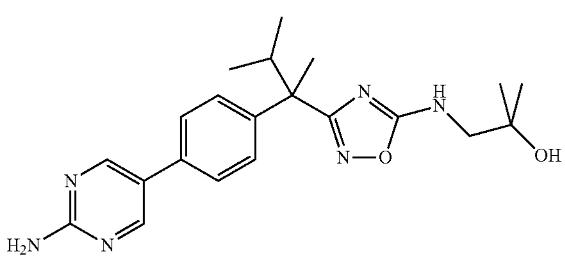 [SMILES: CC(C)C(C)(c1ccc(-c2cnc(N)nc2)cc1)c1noc(NCC(C)(C)O)n1] | 10 | 1.37 | 397.4 | D |
| 83 | 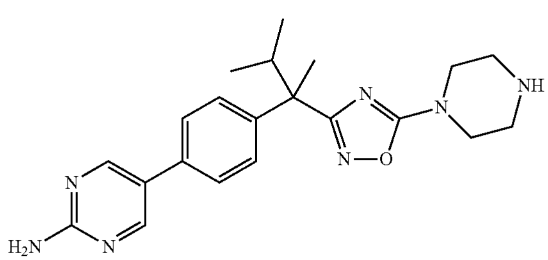 [SMILES: CC(C)C(C)(c1ccc(-c2cnc(N)nc2)cc1)c1noc(N2CCNCC2)n1] | 10 | 1.11 | 394.4 | D |

TABLE 3-continued

Final Compounds;

| Example | Structure | Method | Retention time (min) | m/z [M + H]+ | LC-MS method |
|---------|-----------|--------|----------------------|--------------|--------------|
| 84 | 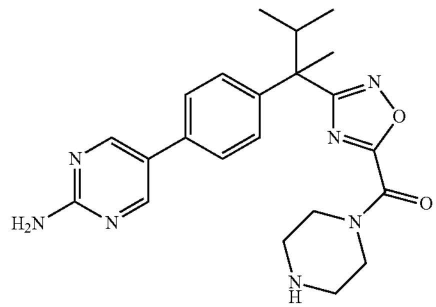 [SMILES: CC(C)C(C)(c1ccc(-c2cnc(N)nc2)cc1)c1noc(C(=O)N2CCNCC2)n1] | 10 | 1.12 | 422.4 | D |
| 85 | 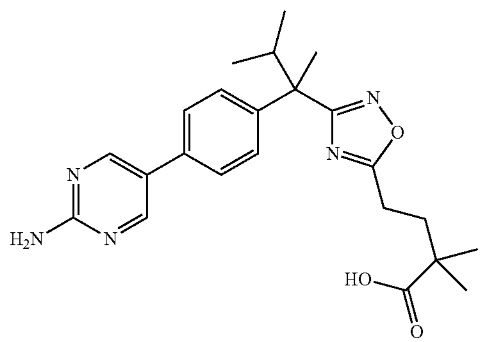 [SMILES: CC(C)C(C)(c1ccc(-c2cnc(N)nc2)cc1)c1noc(CCC(C)(C)C(=O)O)n1] | 22 | 1.46 | 424.4 | D |
| 86 | 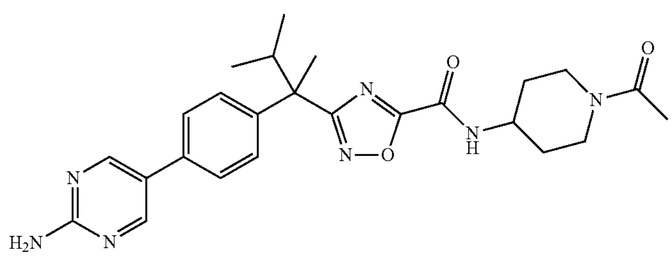 [SMILES: CC(=O)N1CCC(NC(=O)c2nc(C(C)(c3ccc(-c4cnc(N)nc4)cc3)C(C)C)no2)CC1] | 10 | 1.37 | 478.5 | D |
| 87 | 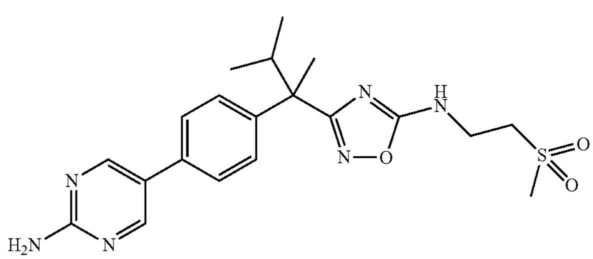 [SMILES: CC(C)C(C)(c1ccc(-c2cnc(N)nc2)cc1)c1noc(NCCS(C)(=O)=O)n1] | 10 | 1.29 | 431.4 | D |
| 88 | 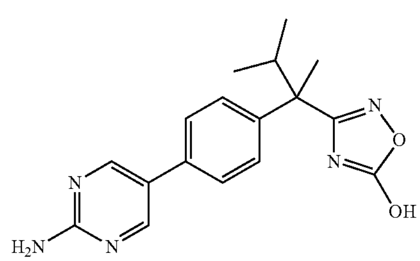 [SMILES: CC(C)C(C)(c1ccc(-c2cnc(N)nc2)cc1)c1noc(O)n1] | 41 | 1.26 | 326.4 | D |

TABLE 3-continued
Final Compounds;
| Example | Structure | Method | Retention time (min) | m/z [M + H]+ | LC-MS method |
|---|---|---|---|---|---|
| 89 | 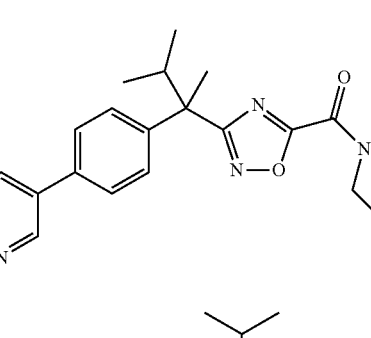 | 10 | 1.59 | 395.4 | D |
| 90 | 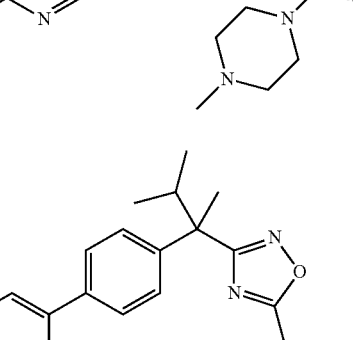 | 10 | 1.43 | 423.4 | D |
| 91 | 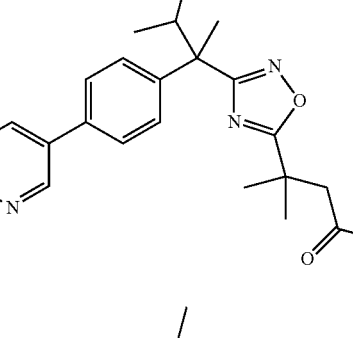 | 10 | 1.12 | 436.4 | D |
| 92 | 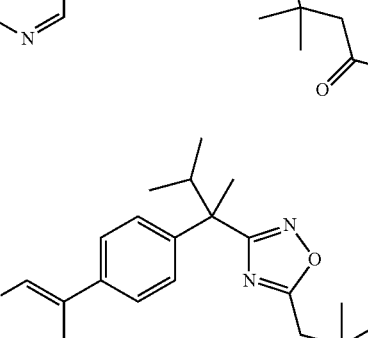 | 22 | 1.43 | 410.4 | D |
| 93 | 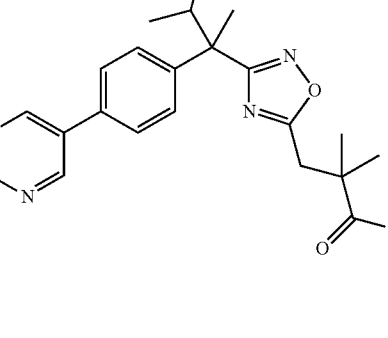 | 22 | 1.43 | 410.4 | D |

TABLE 3-continued

Final Compounds;

| Example | Structure | Method | Retention time (min) | m/z [M + H]+ | LC-MS method |
|---|---|---|---|---|---|
| 94 | 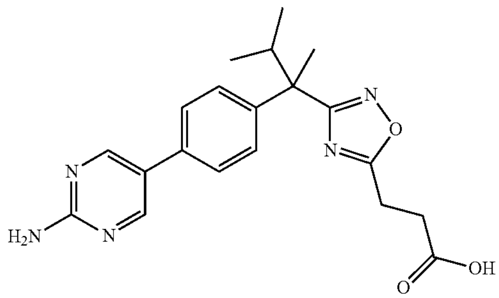 [SMILES: CC(C)C(C)(c1ccc(-c2cnc(N)nc2)cc1)c1noc(CCC(=O)O)n1] | 22 | 1.32 | 382.4 | D |
| 95 | 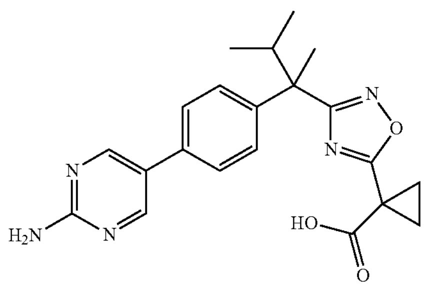 [SMILES: CC(C)C(C)(c1ccc(-c2cnc(N)nc2)cc1)c1noc(C2(C(=O)O)CC2)n1] | 14 | 1.39 | 394.4 | D |
| 96 | 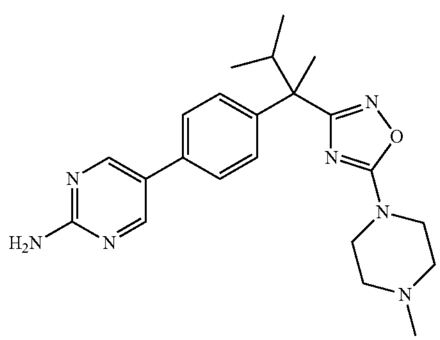 [SMILES: CC(C)C(C)(c1ccc(-c2cnc(N)nc2)cc1)c1noc(N2CCN(C)CC2)n1] | 21 | 0.64 | 408.4 | D |
| 97 | 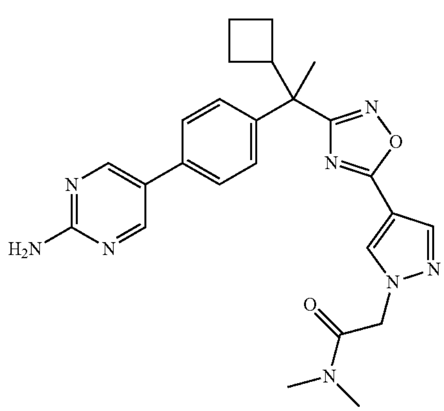 [SMILES: CN(C)C(=O)Cn1cc(-c2nc(C(C)(c3ccc(-c4cnc(N)nc4)cc3)C3CCC3)no2)cn1] | 9 | 2.3 | 473.4 | C |

TABLE 3-continued

Final Compounds;

| Example | Structure | Method | Retention time (min) | m/z [M + H]+ | LC-MS method |
|---|---|---|---|---|---|
| 98 | 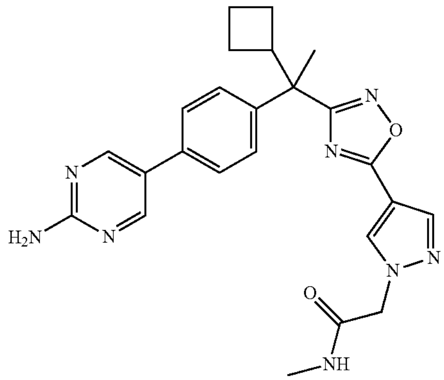 [SMILES: CNC(=O)Cn1cc(-c2nc(C(C)(c3ccc(-c4cnc(N)nc4)cc3)C3CCC3)no2)cn1] | 9 | 2.24 | 459.4 | C |
| 99 | 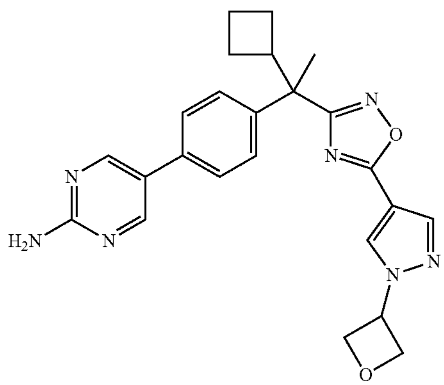 [SMILES: CC(c1ccc(-c2cnc(N)nc2)cc1)(c1noc(-c2cnn(C3COC3)c2)n1)C1CCC1] | 9 | 1.58 | 444.4 | B |
| 100 | 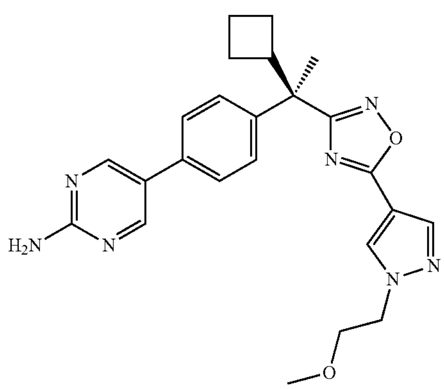 [SMILES: COCCn1cc(-c2nc([C@@](C)(c3ccc(-c4cnc(N)nc4)cc3)C3CCC3)no2)cn1] | 20 | 2.61 | 446.4 | C |
| 101 | 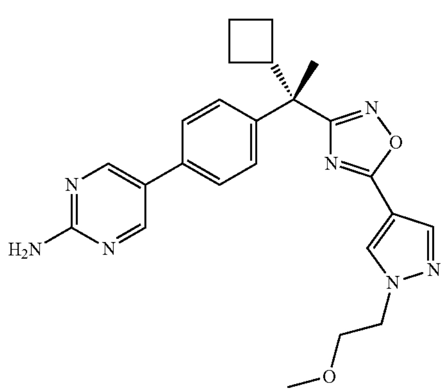 [SMILES: COCCn1cc(-c2nc([C@](C)(c3ccc(-c4cnc(N)nc4)cc3)C3CCC3)no2)cn1] | 20 | 2.61 | 446.4 | C |

TABLE 3-continued

Final Compounds;

| Example | Structure | Method | Retention time (min) | m/z [M + H]+ | LC-MS method |
|---|---|---|---|---|---|
| 102 | 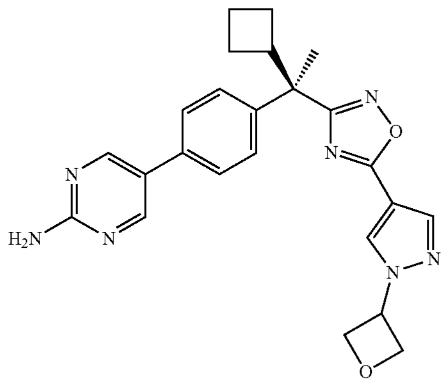 [SMILES: C[C@@](c1ccc(-c2cnc(N)nc2)cc1)(c1noc(-c2cnn(C3COC3)c2)n1)C1CCC1] | 18 | 1.07 | 444.4 | C |
| 103 | 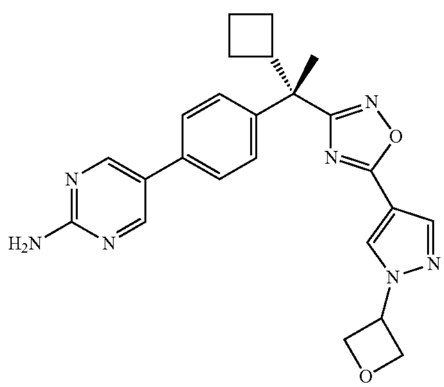 [SMILES: C[C@](c1ccc(-c2cnc(N)nc2)cc1)(c1noc(-c2cnn(C3COC3)c2)n1)C1CCC1] | 18 | 1.07 | 444.4 | C |
| 104 | 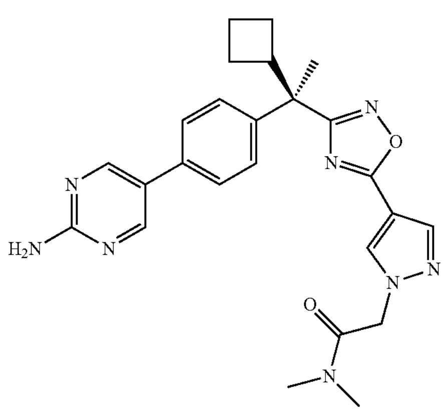 [SMILES: CN(C)C(=O)Cn1cc(-c2nc([C@@](C)(c3ccc(-c4cnc(N)nc4)cc3)C3CCC3)no2)cn1] | 18 | 2.3 | 473.4 | C |

TABLE 3-continued

Final Compounds;

| Example | Structure | Method | Retention time (min) | m/z [M + H]+ | LC-MS method |
|---|---|---|---|---|---|
| 105 | 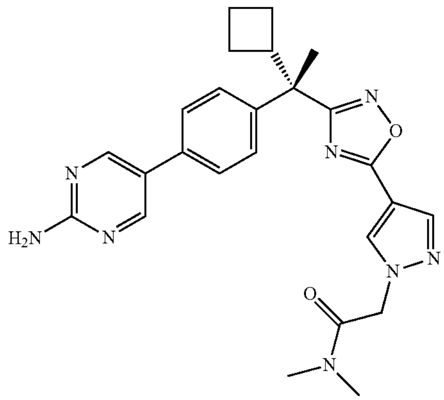 [SMILES: CN(C)C(=O)Cn1cc(-c2nc([C@](C)(c3ccc(-c4cnc(N)nc4)cc3)C3CCC3)no2)cn1] | 18 | 2.3 | 473.4 | C |
| 106 | 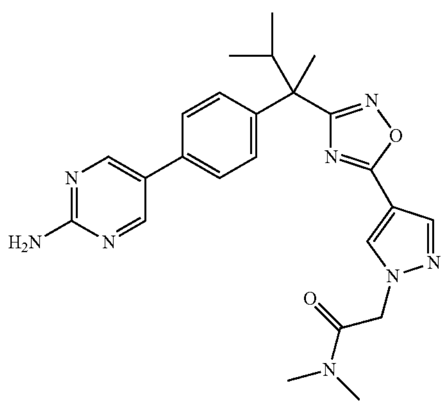 [SMILES: CC(C)C(C)(c1ccc(-c2cnc(N)nc2)cc1)c1noc(-c2cnn(CC(=O)N(C)C)c2)n1] | 9 | 2.24 | 461.4 | C |
| 107 | 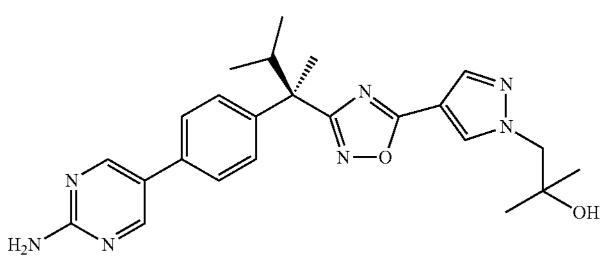 [SMILES: CC(C)[C@](C)(c1ccc(-c2cnc(N)nc2)cc1)c1noc(-c2cnn(CC(C)(C)O)c2)n1] | 18 | 1.29 | 448.4 | D |
| 108 | 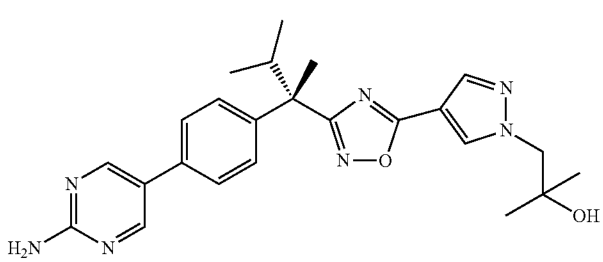 [SMILES: CC(C)[C@@](C)(c1ccc(-c2cnc(N)nc2)cc1)c1noc(-c2cnn(CC(C)(C)O)c2)n1] | 18 | 1.29 | 448.4 | D |

TABLE 3-continued

Final Compounds;

| Example | Structure | Method | Retention time (min) | m/z [M + H]+ | LC-MS method |
|---|---|---|---|---|---|
| 109 | 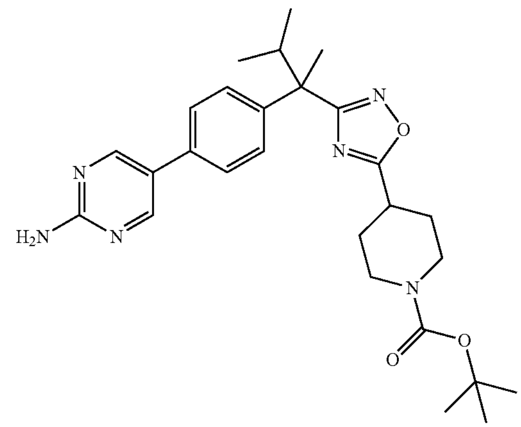 [SMILES: CC(C)C(C)(c1ccc(-c2cnc(N)nc2)cc1)c1noc(C2CCN(C(=O)OC(C)(C)C)CC2)n1] | 6 | 1.67 | 493.4 | E |
| 110 | 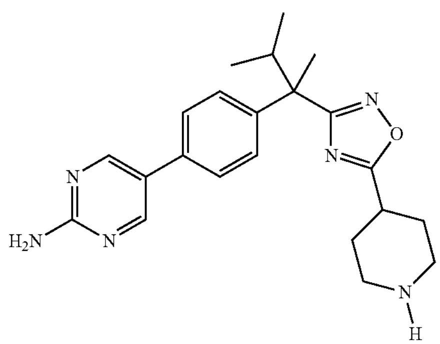 [SMILES: CC(C)C(C)(c1ccc(-c2cnc(N)nc2)cc1)c1noc(C2CCNCC2)n1] | 6 | 1.09 | 393.4 | E |
| 111 | 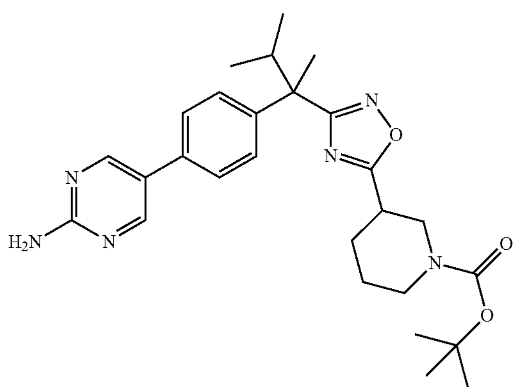 [SMILES: CC(C)C(C)(c1ccc(-c2cnc(N)nc2)cc1)c1noc(C2CCCN(C(=O)OC(C)(C)C)C2)n1] | 6 | 1.68 | 493.4 | E |
| 112 | 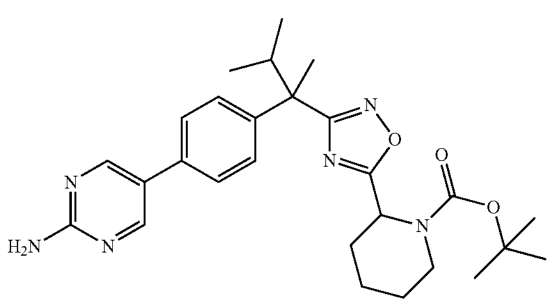 [SMILES: CC(C)C(C)(c1ccc(-c2cnc(N)nc2)cc1)c1noc(C2CCCCN2C(=O)OC(C)(C)C)n1] | 6 | 1.72 | 493.4 | E |

TABLE 3-continued

Final Compounds;

| Example | Structure | Method | Retention time (min) | m/z [M + H]+ | LC-MS method |
|---|---|---|---|---|---|
| 113 | 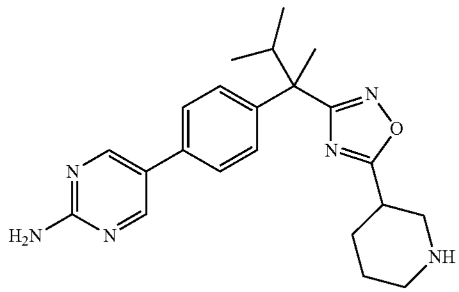 [SMILES: CC(C)C(C)(c1ccc(-c2cnc(N)nc2)cc1)c1noc(C2CCCNC2)n1] | 6 | 1.13 | 393.4 | E |
| 114 | 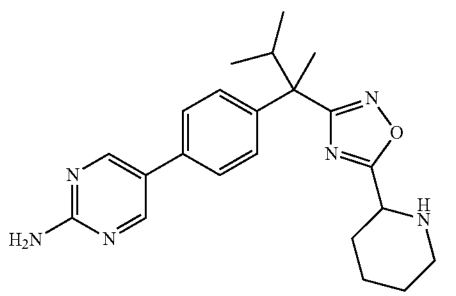 [SMILES: CC(C)C(C)(c1ccc(-c2cnc(N)nc2)cc1)c1noc(C2CCCCN2)n1] | 6 | 1.13 | 393.4 | E |
| 115 | 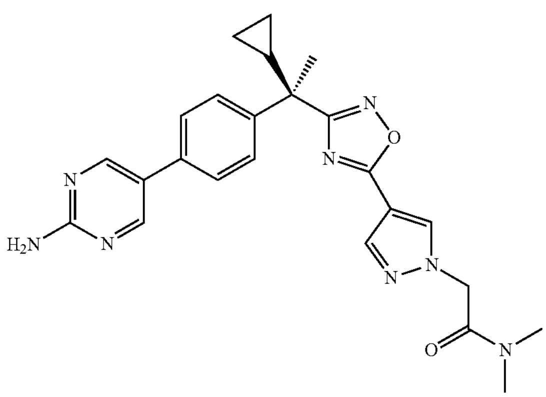 [SMILES: CN(C)C(=O)Cn1cc(-c2nc([C@@](C)(c3ccc(-c4cnc(N)nc4)cc3)C3CC3)no2)cn1] | 18 | 4.97 | 459.4 | A |
| 116 | 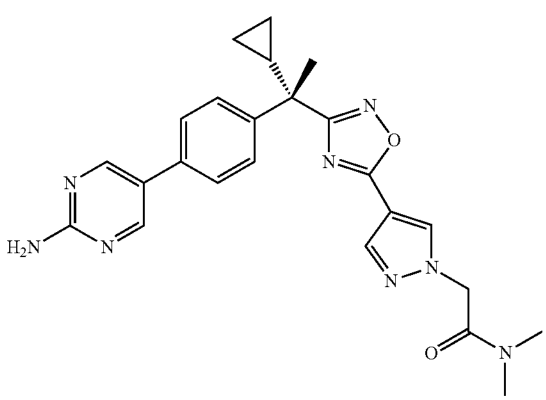 [SMILES: CN(C)C(=O)Cn1cc(-c2nc([C@](C)(c3ccc(-c4cnc(N)nc4)cc3)C3CC3)no2)cn1] | 18 | 4.97 | 459.4 | A |

TABLE 3-continued

Final Compounds;

| Example | Structure | Method | Retention time (min) | m/z [M + H]+ | LC-MS method |
|---|---|---|---|---|---|
| 117 | 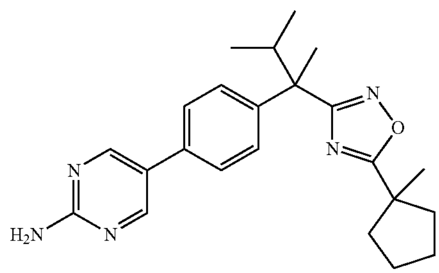 [SMILES: CC(C)C(C)(c1ccc(-c2cnc(N)nc2)cc1)c1noc(C2(C)CCCC2)n1] | 1 | 1.69 | 392.4 | D |
| 118 | 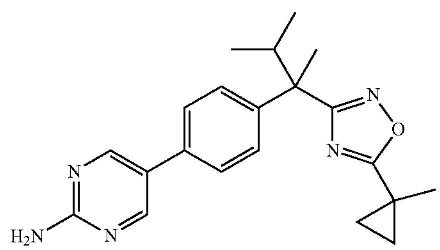 [SMILES: CC(C)C(C)(c1ccc(-c2cnc(N)nc2)cc1)c1noc(C2(C)CC2)n1] | 1 | 1.58 | 364.4 | D |
| 119 | 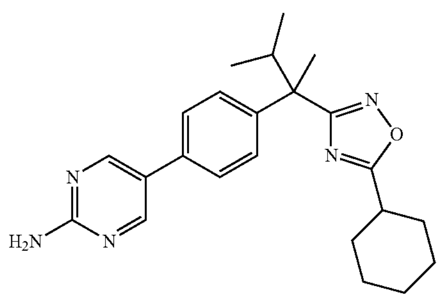 [SMILES: CC(C)C(C)(c1ccc(-c2cnc(N)nc2)cc1)c1noc(C2CCCCC2)n1] | 5 | 1.68 | 392.4 | D |
| 120 | 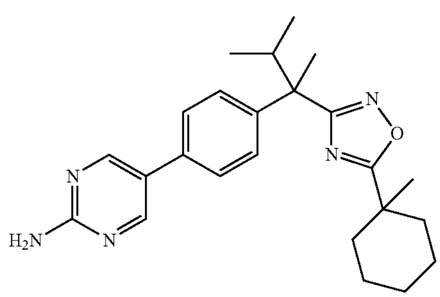 [SMILES: CC(C)C(C)(c1ccc(-c2cnc(N)nc2)cc1)c1noc(C2(C)CCCCC2)n1] | 1 | 1.73 | 406.4 | D |
| 121 | 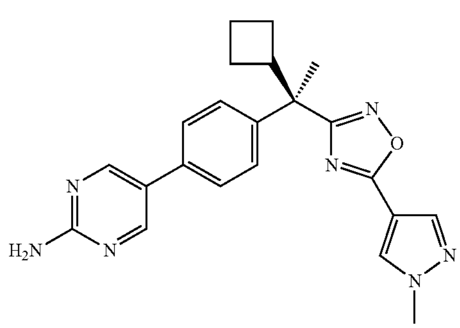 [SMILES: Cn1cc(-c2nc([C@@](C)(c3ccc(-c4cnc(N)nc4)cc3)C3CCC3)no2)cn1] | 18 | 2.5 | 402.4 | C |

TABLE 3-continued

Final Compounds;

| Example | Structure | Method | Retention time (min) | m/z [M + H]+ | LC-MS method |
|---------|-----------|--------|----------------------|--------------|--------------|
| 122 | 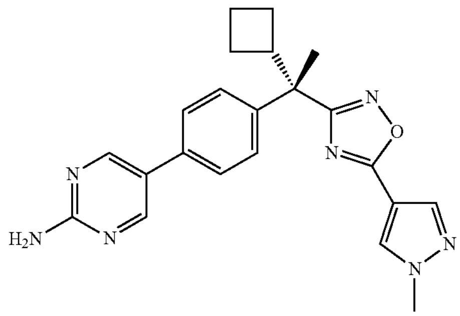 [SMILES: Cn1cc(-c2nc([C@](C)(c3ccc(-c4cnc(N)nc4)cc3)C3CCC3)no2)cn1] | 18 | 2.5 | 402.4 | C |
| 123 | 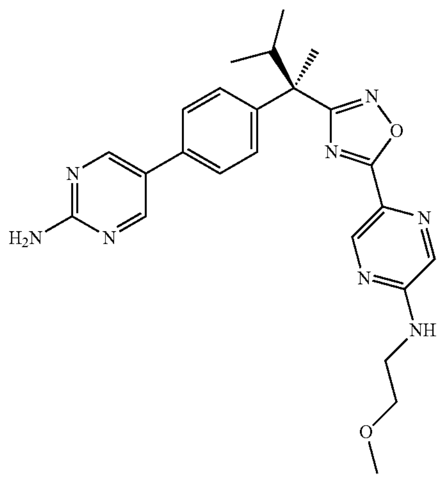 [SMILES: COCCNc1cnc(-c2nc([C@@](C)(c3ccc(-c4cnc(N)nc4)cc3)C(C)C)no2)cn1] | 18 | 1.33 | 461.4 | D |
| 124 | 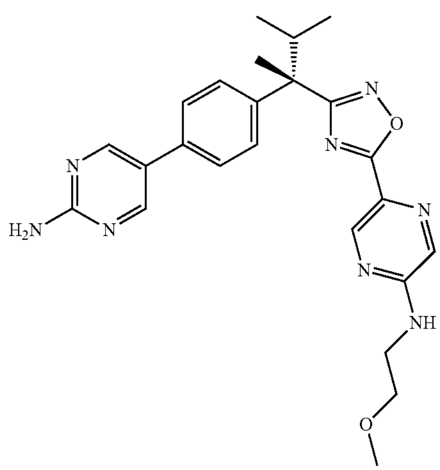 [SMILES: COCCNc1cnc(-c2nc([C@](C)(c3ccc(-c4cnc(N)nc4)cc3)C(C)C)no2)cn1] | 18 | 1.33 | 461.4 | D |
| 125 | 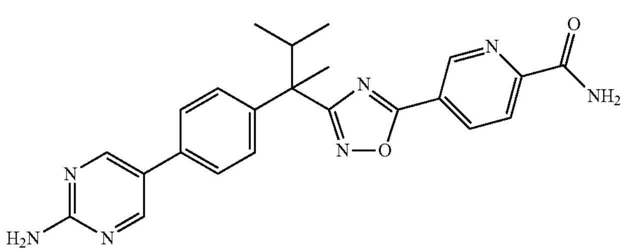 [SMILES: CC(C)C(C)(c1ccc(-c2cnc(N)nc2)cc1)c1noc(-c2ccc(C(N)=O)nc2)n1] | 7 | 4.03 | 430.1 | F |

TABLE 3-continued

Final Compounds;

| Example | Structure | Method | Retention time (min) | m/z [M + H]+ | LC-MS method |
|---|---|---|---|---|---|
| 126 | 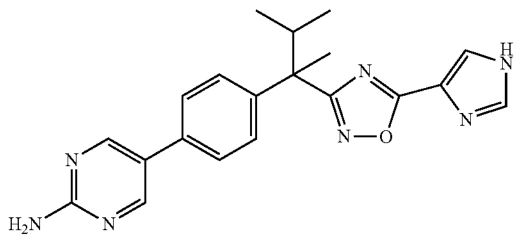 [SMILES: CC(C)C(C)(c1ccc(-c2cnc(N)nc2)cc1)c1noc(-c2c[nH]cn2)n1] | 7 | 3.47 | 376.1 | F |
| 127 | 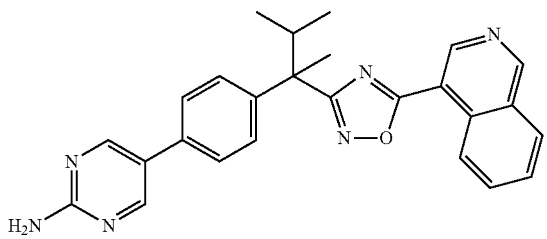 [SMILES: CC(C)C(C)(c1ccc(-c2cnc(N)nc2)cc1)c1noc(-c2cncc3ccccc23)n1] | 7 | 4.92 | 437.1 | F |
| 128 | 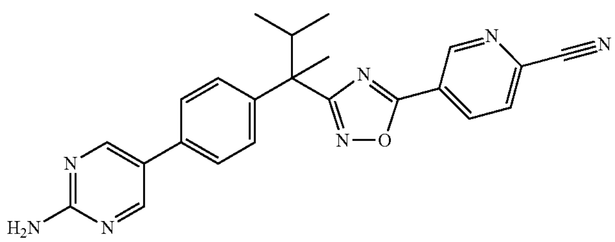 [SMILES: CC(C)C(C)(c1ccc(-c2cnc(N)nc2)cc1)c1noc(-c2ccc(C#N)nc2)n1] | 7 | 4.54 | 412.1 | F |
| 129 | 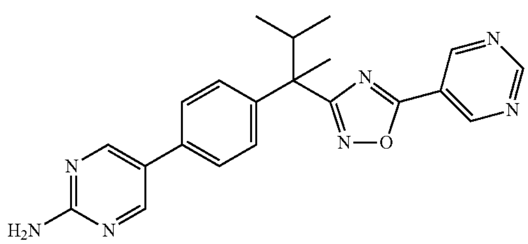 [SMILES: CC(C)C(C)(c1ccc(-c2cnc(N)nc2)cc1)c1noc(-c2cncnc2)n1] | 7 | 4.02 | 388.1 | F |
| 130 | 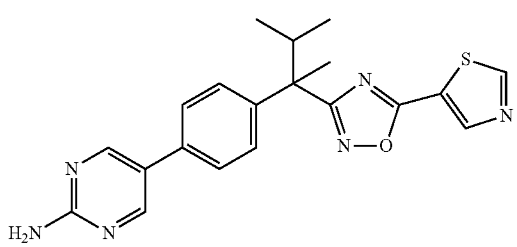 [SMILES: CC(C)C(C)(c1ccc(-c2cnc(N)nc2)cc1)c1noc(-c2cncs2)n1] | 7 | 4.92 | 393.1 | F |
| 131 | 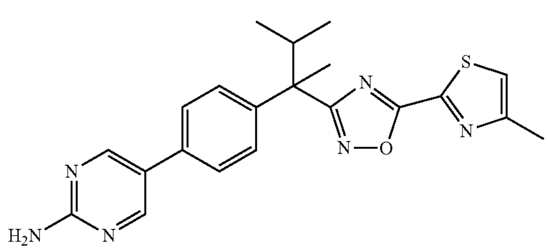 [SMILES: Cc1csc(-c2nc(C(C)(c3ccc(-c4cnc(N)nc4)cc3)C(C)C)no2)n1] | 7 | 4.6 | 407.1 | F |

TABLE 3-continued

Final Compounds;

| Example | Structure | Method | Retention time (min) | m/z [M + H]+ | LC-MS method |
|---------|-----------|--------|----------------------|--------------|--------------|
| 132 | 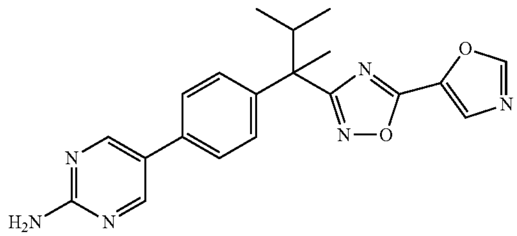 [SMILES: CC(C)C(C)(c1ccc(-c2cnc(N)nc2)cc1)c1noc(-c2cnco2)n1] | 7 | 4.07 | 377.1 | F |
| 133 | 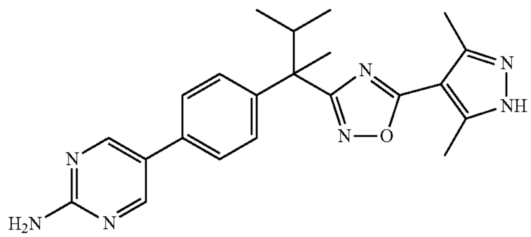 [SMILES: Cc1n[nH]c(C)c1-c1nc(C(C)(c2ccc(-c3cnc(N)nc3)cc2)C(C)C)no1] | 7 | 4.13 | 404.2 | F |
| 134 | 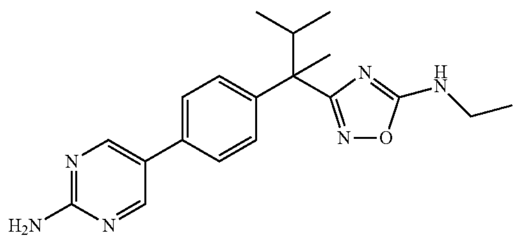 [SMILES: CCNc1nc(C(C)(c2ccc(-c3cnc(N)nc3)cc2)C(C)C)no1] | 10 | 3.94 | 353.2 | F |
| 135 | 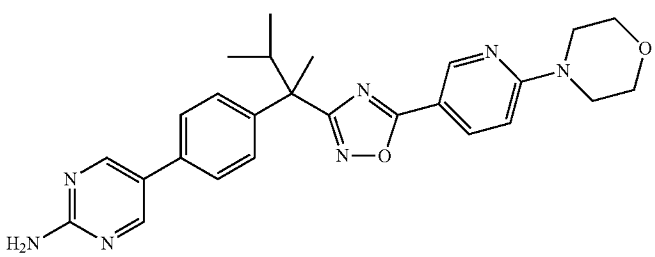 [SMILES: CC(C)C(C)(c1ccc(-c2cnc(N)nc2)cc1)c1noc(-c2ccc(N3CCOCC3)nc2)n1] | 8 | 4.65 | 472.1 | F |
| 136 | 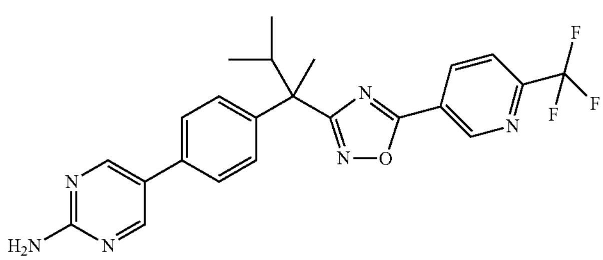 [SMILES: CC(C)C(C)(c1ccc(-c2cnc(N)nc2)cc1)c1noc(-c2ccc(C(F)(F)F)nc2)n1] | 8 | 4.87 | 455 | F |
| 137 | 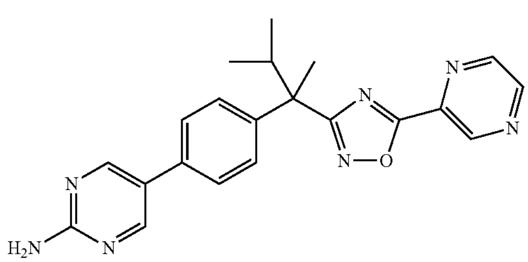 [SMILES: CC(C)C(C)(c1ccc(-c2cnc(N)nc2)cc1)c1noc(-c2cnccn2)n1] | 8 | 3.74 | 388.1 | F |

TABLE 3-continued

Final Compounds;

| Example | Structure | Method | Retention time (min) | m/z [M + H]+ | LC-MS method |
|---------|-----------|--------|----------------------|--------------|--------------|
| 138 | 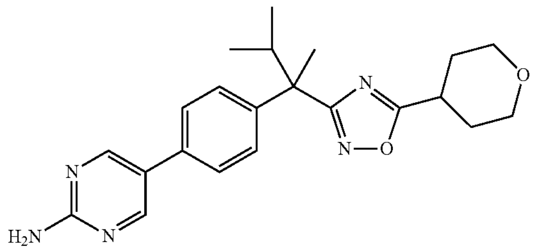 [SMILES: CC(C)C(C)(c1ccc(-c2cnc(N)nc2)cc1)c1noc(C2CCOCC2)n1] | 8 | 4.26 | 394.1 | F |
| 139 | 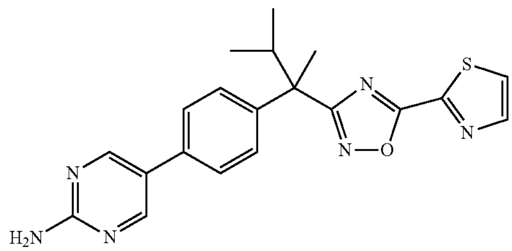 [SMILES: CC(C)C(C)(c1ccc(-c2cnc(N)nc2)cc1)c1noc(-c2nccs2)n1] | 7 | 4.36 | 393.1 | F |
| 140 | 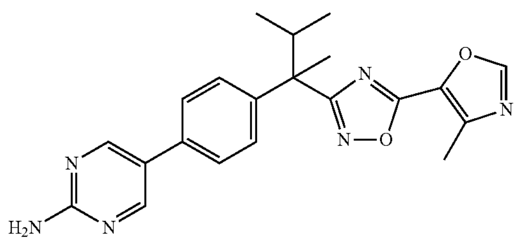 [SMILES: Cc1ncoc1-c1nc(C(C)(c2ccc(-c3cnc(N)nc3)cc2)C(C)C)no1] | 8 | 4.3 | 391.1 | F |
| 141 | 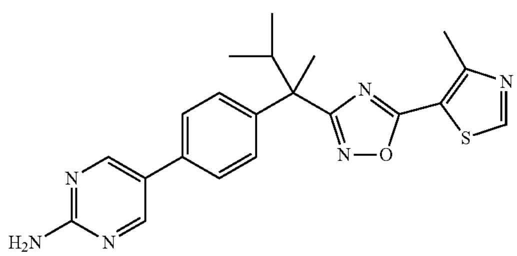 [SMILES: Cc1ncsc1-c1nc(C(C)(c2ccc(-c3cnc(N)nc3)cc2)C(C)C)no1] | 8 | 4.59 | 407.1 | F |
| 142 | 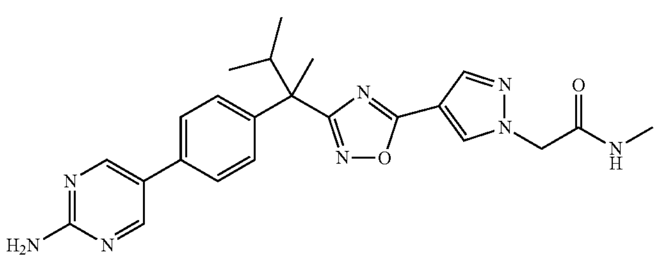 [SMILES: CNC(=O)Cn1cc(-c2nc(C(C)(c3ccc(-c4cnc(N)nc4)cc3)C(C)C)no2)cn1] | 13 | 3.62 | 447.1 | F |
| 143 | 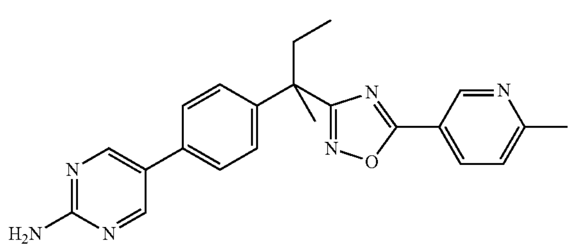 [SMILES: CCC(C)(c1ccc(-c2cnc(N)nc2)cc1)c1noc(-c2ccc(C)nc2)n1] | 7 | 4.85 | 387.1 | F |

TABLE 3-continued

Final Compounds;

| Example | Structure | Method | Retention time (min) | m/z [M + H]+ | LC-MS method |
|---|---|---|---|---|---|
| 144 | 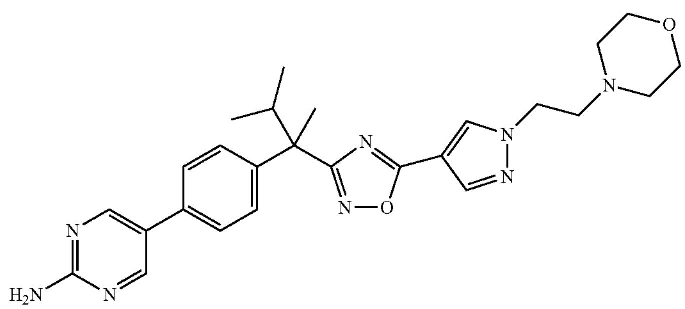 [SMILES: CC(C)C(C)(c1ccc(-c2cnc(N)nc2)cc1)c1noc(-c2cnn(CCN3CCOCC3)c2)n1] | 13 | 3.06 | 489.3 | F |
| 145 | 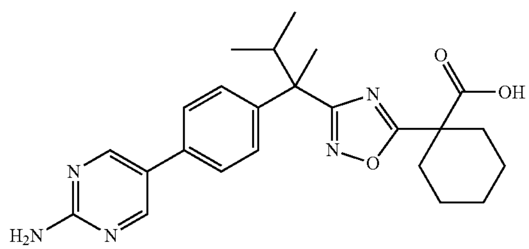 [SMILES: CC(C)C(C)(c1ccc(-c2cnc(N)nc2)cc1)c1noc(C2(C(=O)O)CCCCC2)n1] | 15 | 4.35 | 436.2 | F |
| 146 | 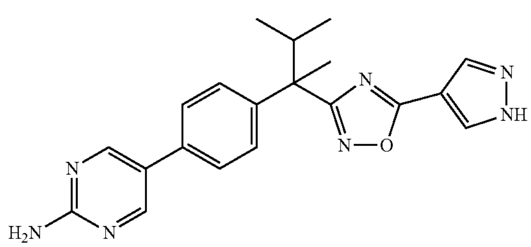 [SMILES: CC(C)C(C)(c1ccc(-c2cnc(N)nc2)cc1)c1noc(-c2cn[nH]c2)n1] | 7 | 3.73 | 376.1 | F |
| 147 | 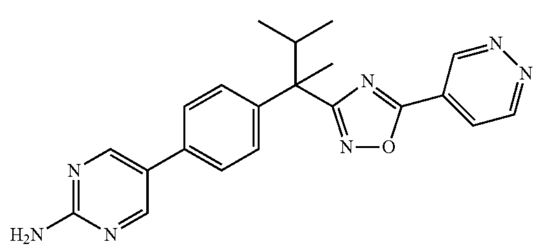 [SMILES: CC(C)C(C)(c1ccc(-c2cnc(N)nc2)cc1)c1noc(-c2ccnnc2)n1] | 7 | 3.87 | 388.1 | F |
| 148 | 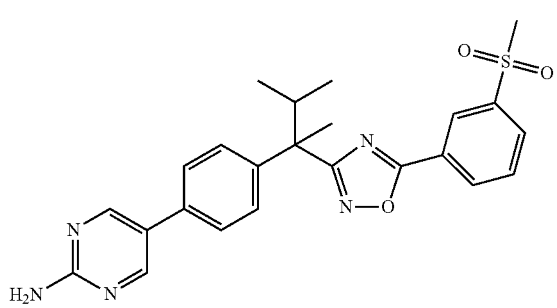 [SMILES: CC(C)C(C)(c1ccc(-c2cnc(N)nc2)cc1)c1noc(-c2cccc(S(C)(=O)=O)c2)n1] | 7 | 4.37 | 464.1 | F |

TABLE 3-continued

Final Compounds;

| Example | Structure | Method | Retention time (min) | m/z [M + H]+ | LC-MS method |
|---|---|---|---|---|---|
| 149 | 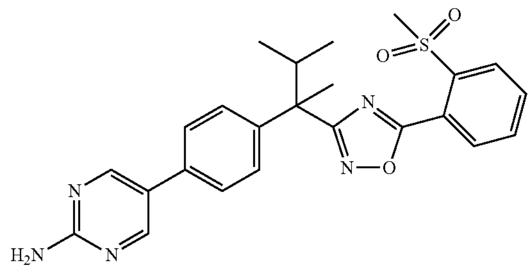 [SMILES: CC(C)C(C)(c1ccc(-c2cnc(N)nc2)cc1)c1noc(-c2ccccc2S(C)(=O)=O)n1] | 7 | 4.28 | 464.1 | F |
| 150 | 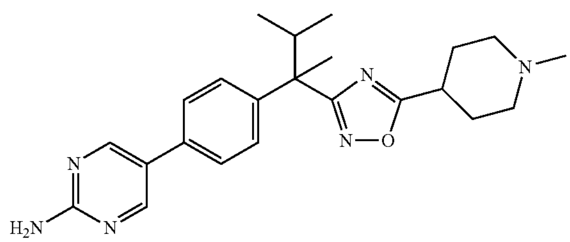 [SMILES: CC(C)C(C)(c1ccc(-c2cnc(N)nc2)cc1)c1noc(C2CCN(C)CC2)n1] | 7 | 2.92 | 407.2 | F |
| 151 | 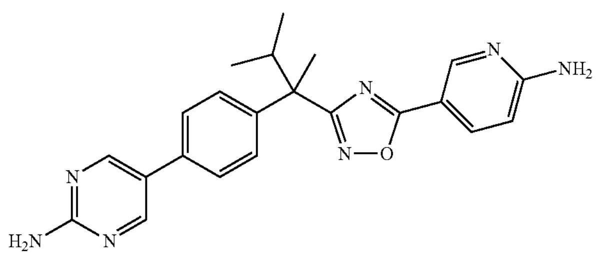 [SMILES: CC(C)C(C)(c1ccc(-c2cnc(N)nc2)cc1)c1noc(-c2ccc(N)nc2)n1] | 7 | 3.57 | 402.2 | F |
| 152 | 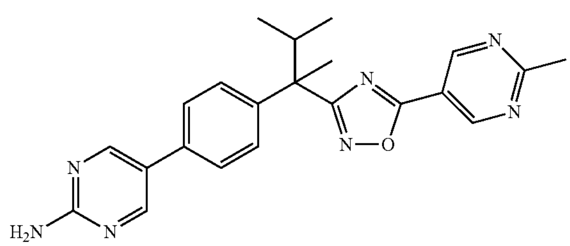 [SMILES: Cc1ncc(-c2nc(C(C)(c3ccc(-c4cnc(N)nc4)cc3)C(C)C)no2)cn1] | 7 | 4.23 | 402.2 | F |
| 153 | 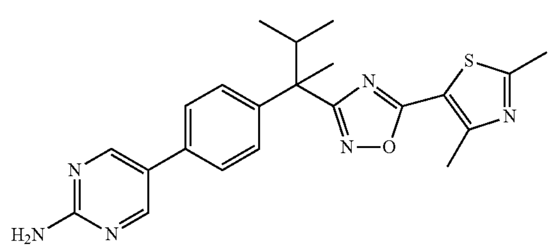 [SMILES: Cc1nc(C)c(-c2nc(C(C)(c3ccc(-c4cnc(N)nc4)cc3)C(C)C)no2)s1] | 7 | 4.72 | 421.1 | F |
| 154 | 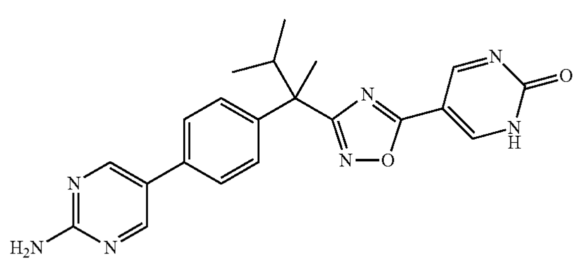 [SMILES: CC(C)C(C)(c1ccc(-c2cnc(N)nc2)cc1)c1noc(-c2cnc(=O)[nH]c2)n1] | 7 | 3.02 | 404.1 | F |

TABLE 3-continued

Final Compounds;

| Example | Structure | Method | Retention time (min) | m/z [M + H]+ | LC-MS method |
|---|---|---|---|---|---|
| 155 | 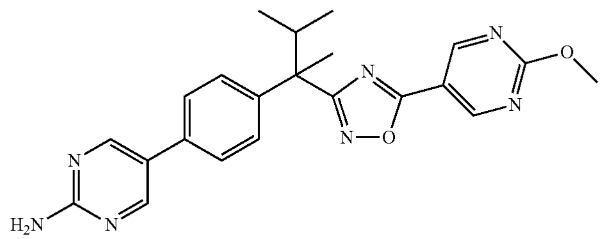 [SMILES: COc1ncc(-c2nc(C(C)(c3ccc(-c4cnc(N)nc4)cc3)C(C)C)no2)cn1] | 7 | 4.33 | 418.1 | F |
| 156 | 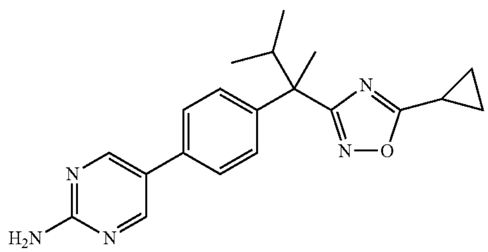 [SMILES: CC(C)C(C)(c1ccc(-c2cnc(N)nc2)cc1)c1noc(C2CC2)n1] | 7 | 4.41 | 350.2 | F |
| 157 | 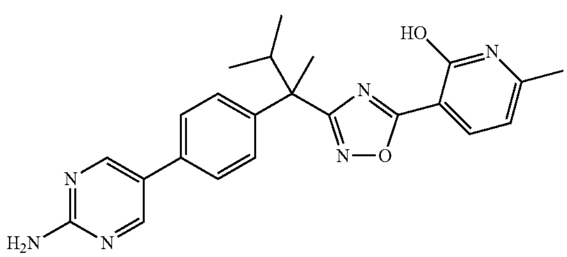 [SMILES: Cc1ccc(-c2nc(C(C)(c3ccc(-c4cnc(N)nc4)cc3)C(C)C)no2)c(O)n1] | 7 | 3.65 | 417.2 | F |
| 158 | 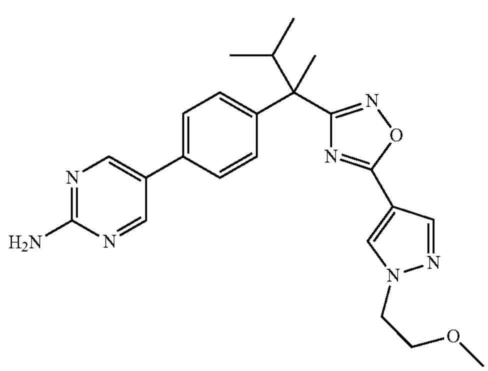 [SMILES: COCCn1cc(-c2nc(C(C)(c3ccc(-c4cnc(N)nc4)cc3)C(C)C)no2)cn1] | 13 | 5.91 | 434.4 | A |
| 159 | 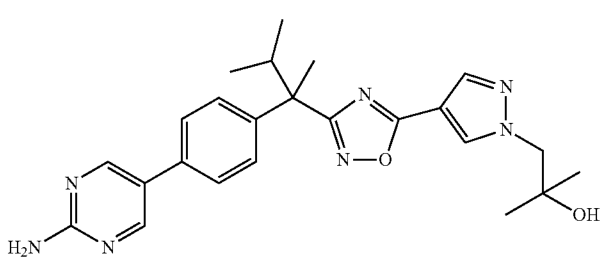 [SMILES: CC(C)C(C)(c1ccc(-c2cnc(N)nc2)cc1)c1noc(-c2cnn(CC(C)(C)O)c2)n1] | 13 | 4.06 | 448.3 | F |

TABLE 3-continued

Final Compounds;

| Example | Structure | Method | Retention time (min) | m/z [M + H]+ | LC-MS method |
|---|---|---|---|---|---|
| 160 | 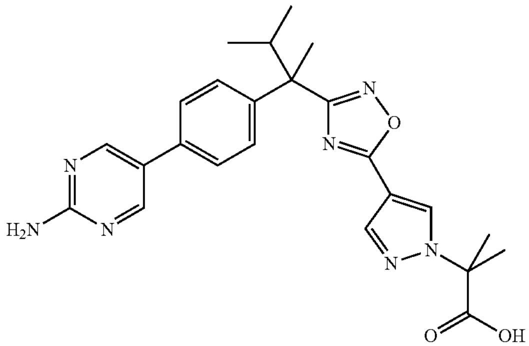 [SMILES: CC(C)C(C)(c1ccc(-c2cnc(N)nc2)cc1)c1noc(-c2cnn(C(C)(C)C(=O)O)c2)n1] | 16 | 3.93 | 462.2 | F |
| 161 | 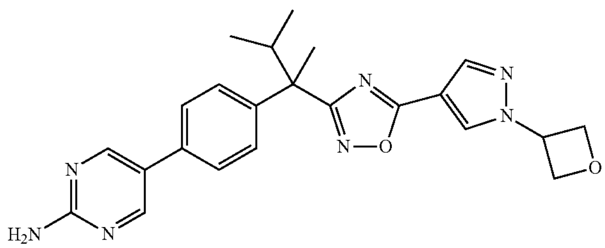 [SMILES: CC(C)C(C)(c1ccc(-c2cnc(N)nc2)cc1)c1noc(-c2cnn(C3COC3)c2)n1] | 13 | 3.91 | 432.2 | F |
| 162 | 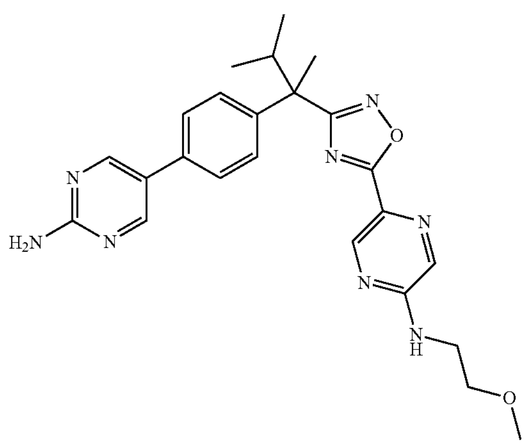 [SMILES: COCCNc1cnc(-c2nc(C(C)(c3ccc(-c4cnc(N)nc4)cc3)C(C)C)no2)cn1] | 11 | 4.06 | 461.3 | F |
| 163 | 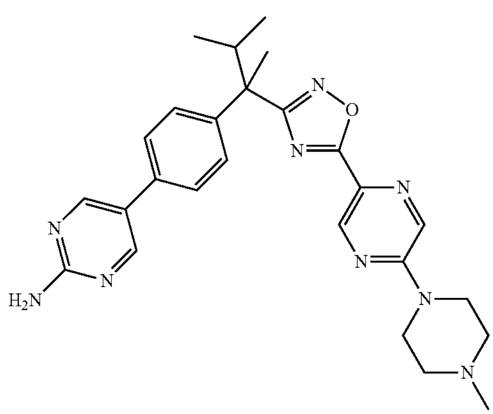 [SMILES: CC(C)C(C)(c1ccc(-c2cnc(N)nc2)cc1)c1noc(-c2cnc(N3CCN(C)CC3)cn2)n1] | 11 | 3.12 | 486.3 | F |

TABLE 3-continued

Final Compounds;

| Example | Structure | Method | Retention time (min) | m/z [M + H]+ | LC-MS method |
|---|---|---|---|---|---|
| 164 | 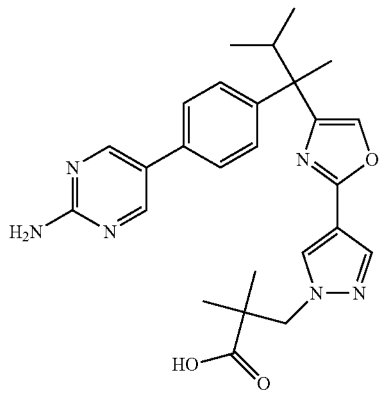 [SMILES: CC(C)C(C)(c1ccc(-c2cnc(N)nc2)cc1)c1coc(-c2cnn(CC(C)(C)C(=O)O)c2)n1] | 16 | 4.04 | 476.2 | F |
| 165 | 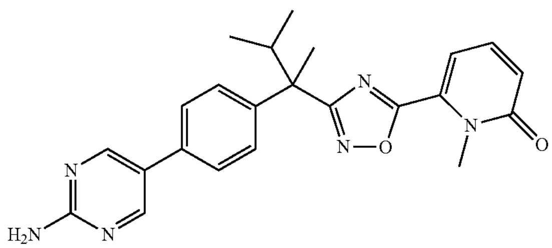 [SMILES: CC(C)C(C)(c1ccc(-c2cnc(N)nc2)cc1)c1noc(-c2cccc(=O)n2C)n1] | 17 | 3.97 | 417.2 | F |
| 166 | 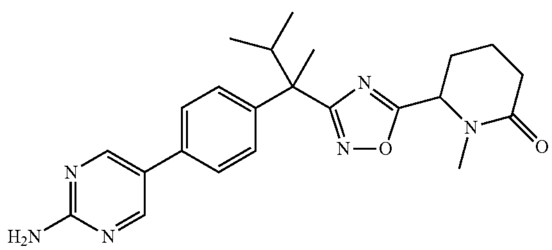 [SMILES: CC(C)C(C)(c1ccc(-c2cnc(N)nc2)cc1)c1noc(C2CCCC(=O)N2C)n1] | 17 | 3.79 | 421.1 | F |
| 167 | 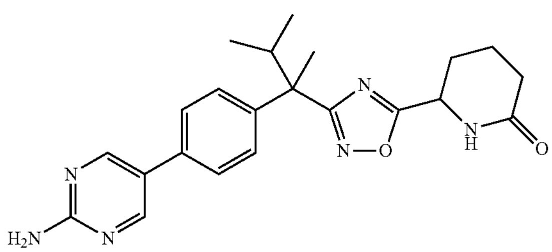 [SMILES: CC(C)C(C)(c1ccc(-c2cnc(N)nc2)cc1)c1noc(C2CCCC(=O)N2)n1] | 17 | 3.6 | 407.1 | F |
| 168 | 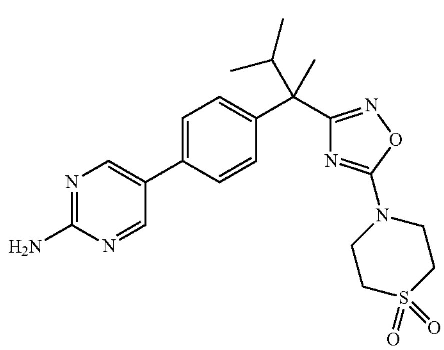 [SMILES: CC(C)C(C)(c1ccc(-c2cnc(N)nc2)cc1)c1noc(N2CCS(=O)(=O)CC2)n1] | 21 | 1.37 | 443.4 | E |

TABLE 3-continued

Final Compounds;

| Example | Structure | Method | Retention time (min) | m/z [M + H]+ | LC-MS method |
|---------|-----------|--------|----------------------|--------------|--------------|
| 169 | 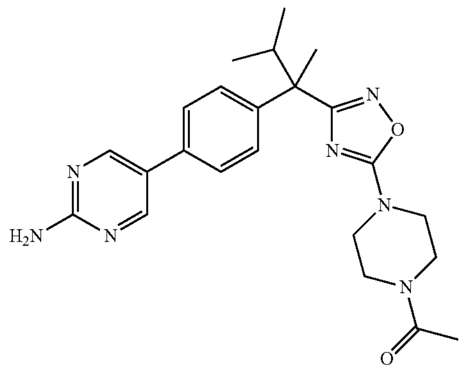 [SMILES: CC(=O)N1CCN(c2nc(C(C)(c3ccc(-c4cnc(N)nc4)cc3)C(C)C)no2)CC1] | 21 | 1.39 | 436.4 | E |
| 170 | 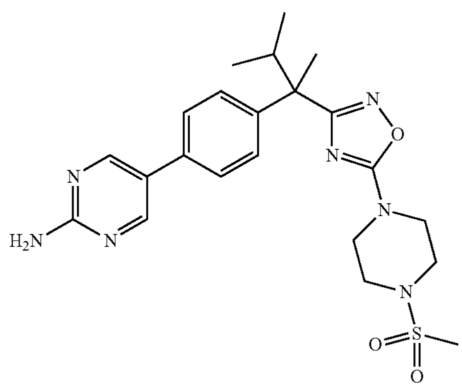 [SMILES: CC(C)C(C)(c1ccc(-c2cnc(N)nc2)cc1)c1noc(N2CCN(S(C)(=O)=O)CC2)n1] | 21 | 1.42 | 472.4 | E |
| 171 | 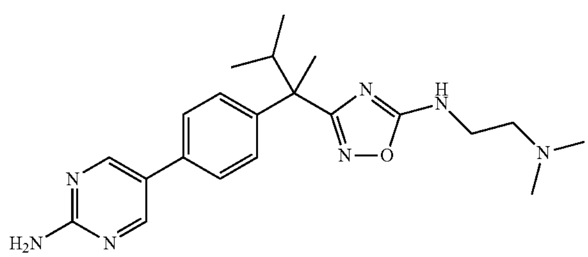 | 10 | 1.1 | 396.4 | E |
| 172 | 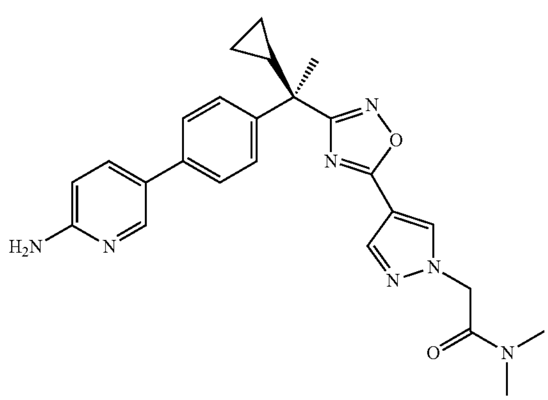 [SMILES: CN(C)C(=O)Cn1cc(-c2nc([C@@](C)(c3ccc(-c4ccc(N)nc4)cc3)C3CC3)no2)cn1] | 27 | 1.06 | 458.4 | H |

TABLE 3-continued

Final Compounds;

| Example | Structure | Method | Retention time (min) | m/z [M + H]+ | LC-MS method |
|---------|-----------|--------|----------------------|--------------|--------------|
| 173 | 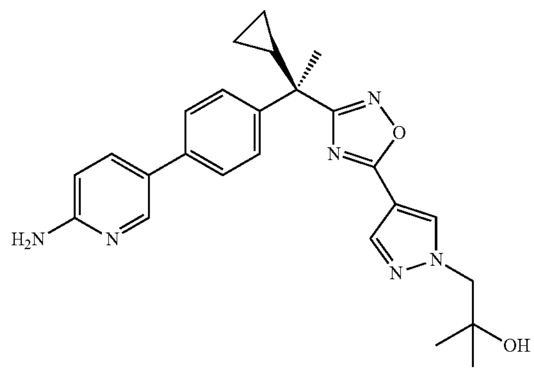 [SMILES: CC(C)(O)Cn1cc(-c2nc([C@@](C)(c3ccc(-c4ccc(N)nc4)cc3)C3CC3)no2)cn1] | 27 | 0.66 | 445.3 | G |
| 174 | 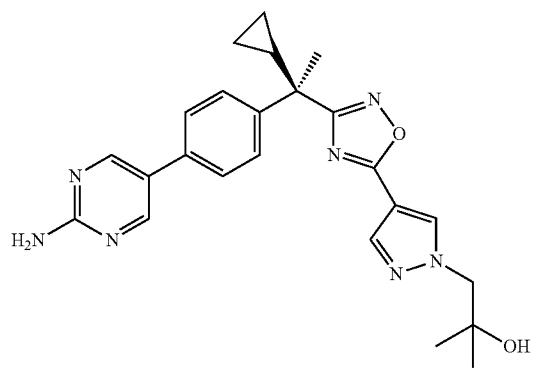 [SMILES: CC(C)(O)Cn1cc(-c2nc([C@@](C)(c3ccc(-c4cnc(N)nc4)cc3)C3CC3)no2)cn1] | 27 | 0.82 | 446.4 | G |
| 175 | 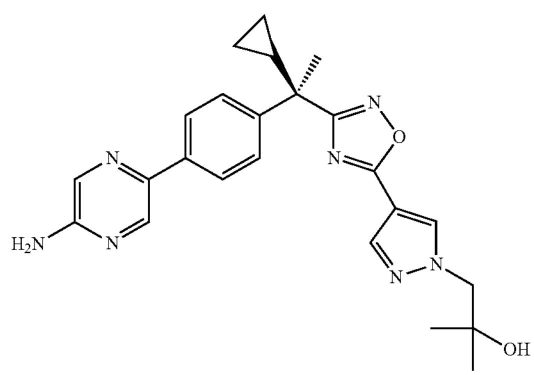 [SMILES: CC(C)(O)Cn1cc(-c2nc([C@@](C)(c3ccc(-c4cnc(N)cn4)cc3)C3CC3)no2)cn1] | 26 | 0.86 | 446.4 | G |
| 176 | 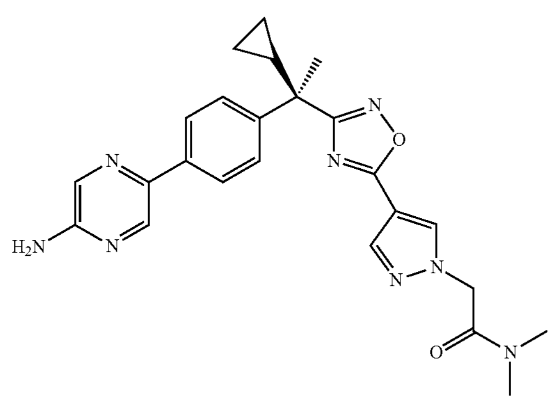 [SMILES: CN(C)C(=O)Cn1cc(-c2nc([C@@](C)(c3ccc(-c4cnc(N)cn4)cc3)C3CC3)no2)cn1] | 26 | 0.78 | 459.4 | G |

TABLE 3-continued

Final Compounds;

| Example | Structure | Method | Retention time (min) | m/z [M + H]+ | LC-MS method |
|---|---|---|---|---|---|
| 177 | 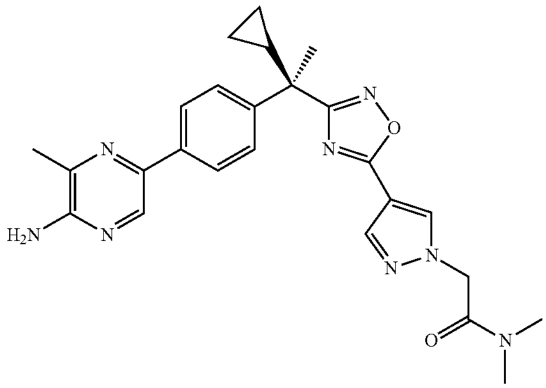 [SMILES: Cc1nc(-c2ccc([C@](C)(c3noc(-c4cnn(CC(=O)N(C)C)c4)n3)C3CC3)cc2)cnc1N] | 26 | 0.82 | 473.4 | G |
| 178 | 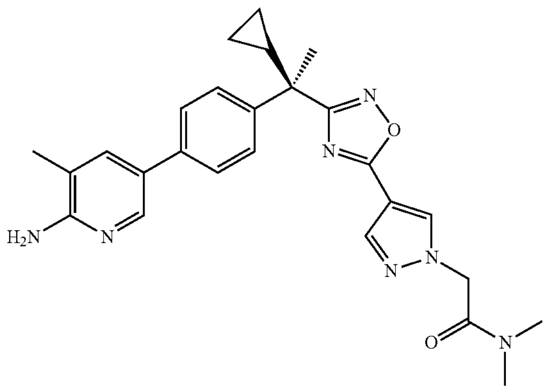 [SMILES: Cc1cc(-c2ccc([C@](C)(c3noc(-c4cnn(CC(=O)N(C)C)c4)n3)C3CC3)cc2)cnc1N] | 26 | 0.66 | 472.4 | G |
| 179 | 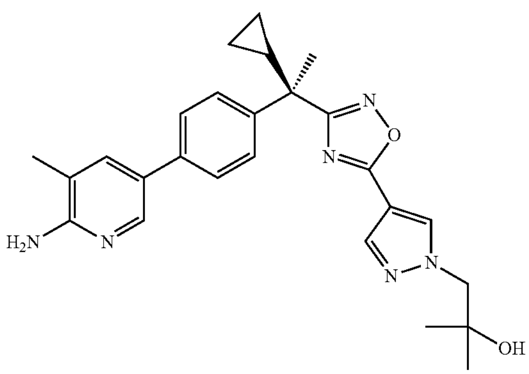 [SMILES: Cc1cc(-c2ccc([C@](C)(c3noc(-c4cnn(CC(C)(C)O)c4)n3)C3CC3)cc2)cnc1N] | 26 | 0.71 | 459.4 | G |
| 180 | 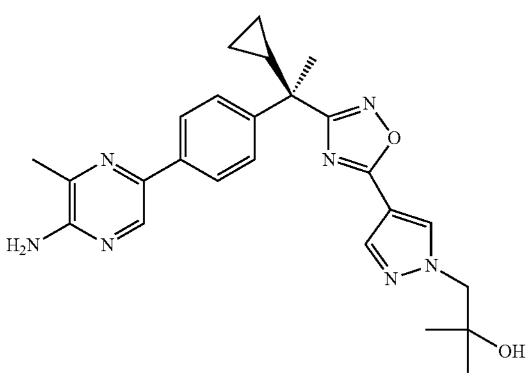 [SMILES: Cc1nc(-c2ccc([C@](C)(c3noc(-c4cnn(CC(C)(C)O)c4)n3)C3CC3)cc2)cnc1N] | 26 | 0.9 | 460.4 | G |

TABLE 3-continued
Final Compounds;
| Example | Structure | Method | Retention time (min) | m/z [M + H]+ | LC-MS method |
|---|---|---|---|---|---|
| 181 | 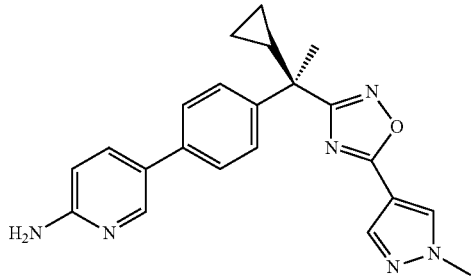 [SMILES: Cn1cc(-c2nc([C@@](C)(c3ccc(-c4ccc(N)nc4)cc3)C3CC3)no2)cn1] | 27 | 0.65 | 388.3 | G |
| 182 | 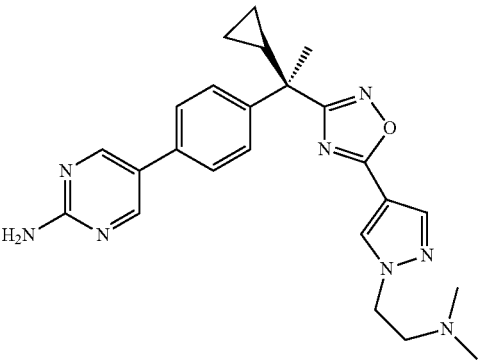 [SMILES: CN(C)CCn1cc(-c2nc([C@@](C)(c3ccc(-c4cnc(N)nc4)cc3)C3CC3)no2)cn1] | 34 | 1 | 445.4 | H |
| 183 | 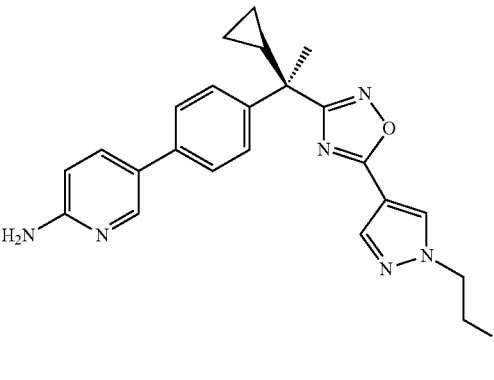 | 27 | 0.68 | 432.4 | G |
| 184 | 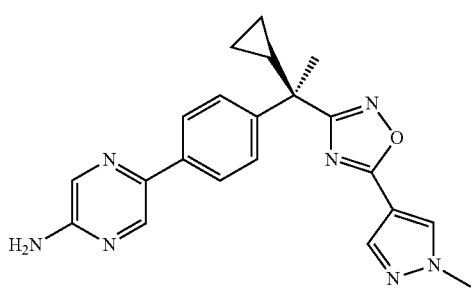 [SMILES: Cn1cc(-c2nc([C@@](C)(c3ccc(-c4cnc(N)cn4)cc3)C3CC3)no2)cn1] | 26 | 0.85 | 389.5 | G |

TABLE 3-continued

Final Compounds;

| Example | Structure | Method | Retention time (min) | m/z [M + H]+ | LC-MS method |
|---|---|---|---|---|---|
| 185 | 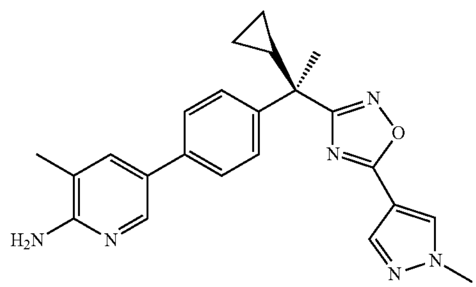 [SMILES: Cc1cc(-c2ccc([C@](C)(c3noc(-c4cnn(C)c4)n3)C3CC3)cc2)cnc1N] | 26 | 0.69 | 401.6 | G |
| 186 | 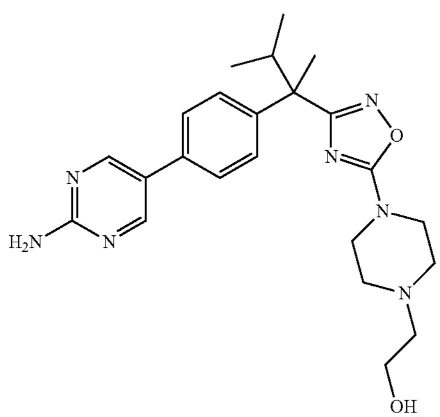 [SMILES: CC(C)C(C)(c1ccc(-c2cnc(N)nc2)cc1)c1noc(N2CCN(CCO)CC2)n1] | 21 | 1.1 | 438.4 | E |
| 187 | 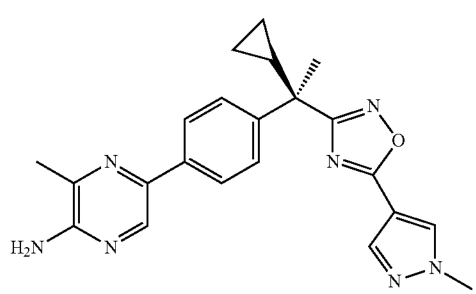 [SMILES: Cc1nc(-c2ccc([C@](C)(c3noc(-c4cnn(C)c4)n3)C3CC3)cc2)cnc1N] | 26 | 0.9 | 403.4 | G |
| 188 | 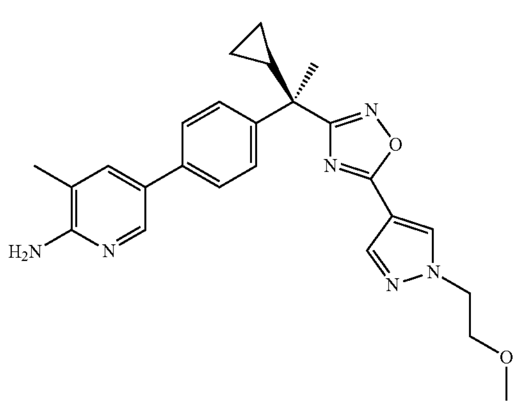 [SMILES: COCCn1cc(-c2nc([C@@](C)(c3ccc(-c4cnc(N)c(C)c4)cc3)C3CC3)no2)cn1] | 26 | 0.74 | 445.1 | G |

TABLE 3-continued

Final Compounds;

| Example | Structure | Method | Retention time (min) | m/z [M + H]+ | LC-MS method |
|---|---|---|---|---|---|
| 189 | 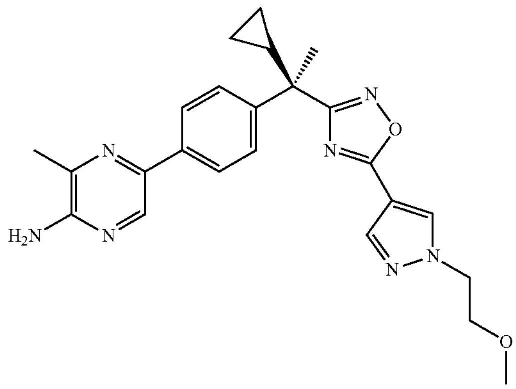 [SMILES: COCCn1cc(-c2nc([C@@](C)(c3ccc(-c4cnc(N)c(C)n4)cc3)C3CC3)no2)cn1] | 26 | 0.94 | 446.1 | G |
| 190 | 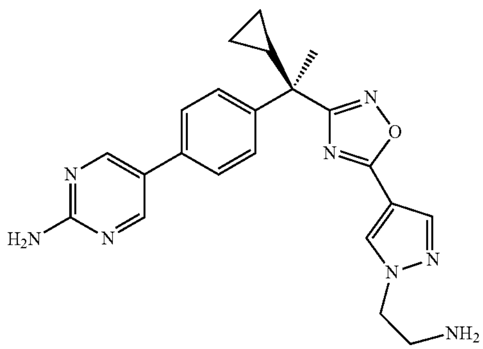 [SMILES: C[C@@](c1ccc(-c2cnc(N)nc2)cc1)(c1noc(-c2cnn(CCN)c2)n1)C1CC1] | 37 | 0.98 | 417.4 | H |
| 191 | 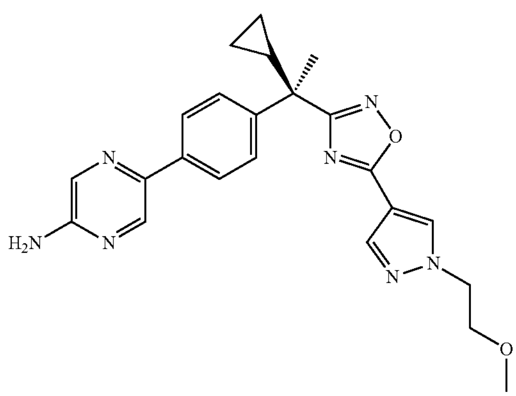 [SMILES: COCCn1cc(-c2nc([C@@](C)(c3ccc(-c4cnc(N)cn4)cc3)C3CC3)no2)cn1] | 26 | 0.9 | 433.3 | G |
| 192 | 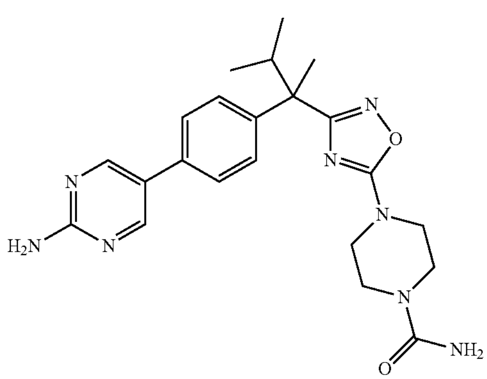 [SMILES: CC(C)C(C)(c1ccc(-c2cnc(N)nc2)cc1)c1noc(N2CCN(C(N)=O)CC2)n1] | 21 | 1.31 | 437.4 | E |

TABLE 3-continued
Final Compounds;
| Example | Structure | Method | Retention time (min) | m/z [M + H]+ | LC-MS method |
|---|---|---|---|---|---|
| 193 | 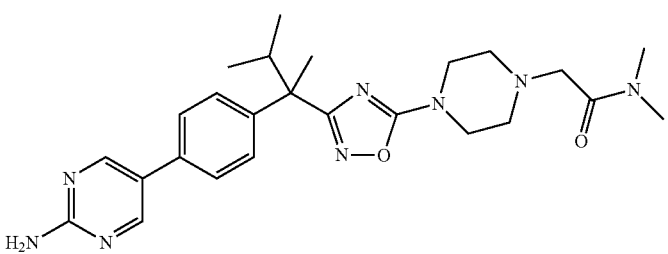 [SMILES: CC(C)C(C)(c1ccc(-c2cnc(N)nc2)cc1)c1noc(N2CCN(CC(=O)N(C)C)CC2)n1] | 29 | 1.15 | 479.4 | E |
| 194 | 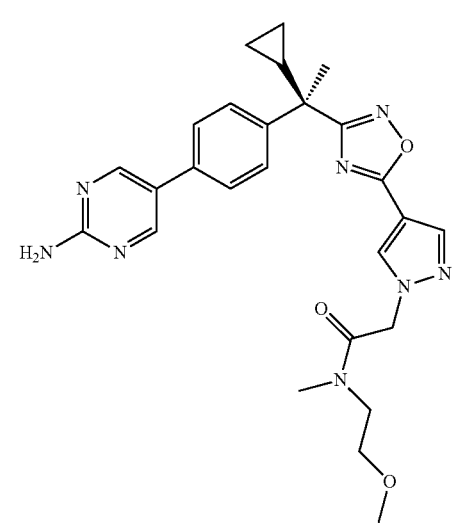 [SMILES: COCCN(C)C(=O)Cn1cc(-c2nc([C@@](C)(c3ccc(-c4cnc(N)nc4)cc3)C3CC3)no2)cn1] | 35 | 1.19 | 503.4 | H |
| 195 | 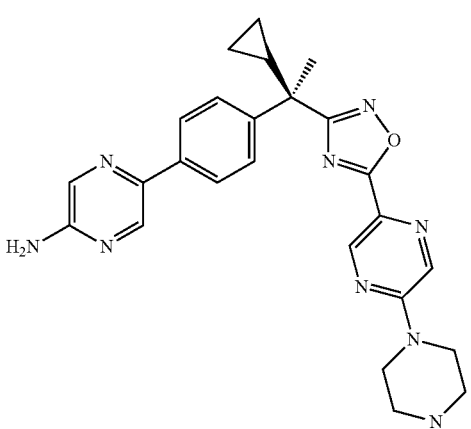 | 23 | 0.59 | 470.3 | G |

TABLE 3-continued

Final Compounds;

| Example | Structure | Method | Retention time (min) | m/z [M + H]+ | LC-MS method |
|---------|-----------|--------|----------------------|--------------|--------------|
| 196 | 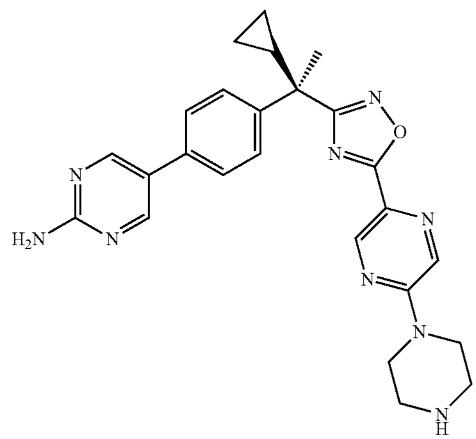 [SMILES: C[C@@](c1ccc(-c2cnc(N)nc2)cc1)(c1noc(-c2cnc(N3CCNCC3)cn2)n1)C1CC1] | 23 | 1 | 470.4 | D |
| 197 | 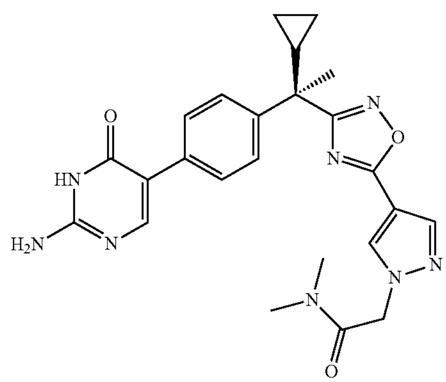 [SMILES: CN(C)C(=O)Cn1cc(-c2nc([C@@](C)(c3ccc(-c4cnc(N)[nH]c4=O)cc3)C3CC3)no2)cn1] | 36 | 0.59 | 475.3 | G |
| 198 | 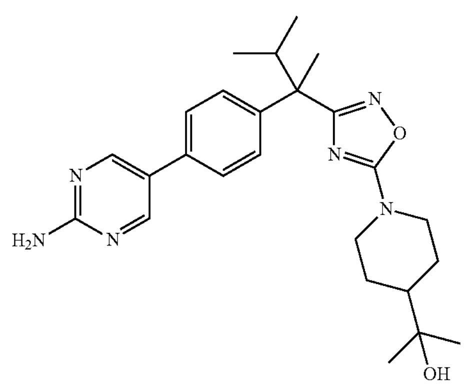 [SMILES: CC(C)C(C)(c1ccc(-c2cnc(N)nc2)cc1)c1noc(N2CCC(C(C)(C)O)CC2)n1] | 21 | 1.49 | 451.4 | E |
| 199 | 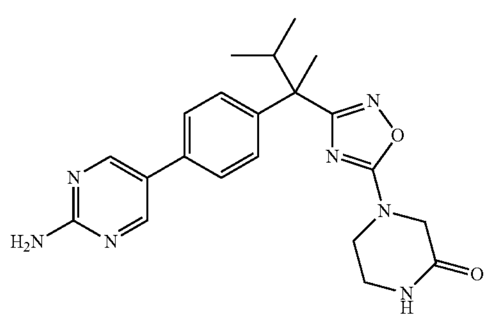 [SMILES: CC(C)C(C)(c1ccc(-c2cnc(N)nc2)cc1)c1noc(N2CCNC(=O)C2)n1] | 21 | 1.29 | 408.4 | E |

TABLE 3-continued

Final Compounds;

| Example | Structure | Method | Retention time (min) | m/z [M + H]+ | LC-MS method |
|---------|-----------|--------|----------------------|--------------|--------------|
| 200 | 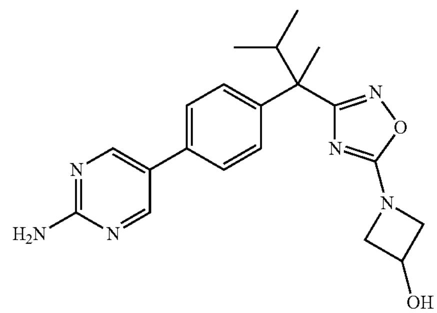 [SMILES: CC(C)C(C)(c1ccc(-c2cnc(N)nc2)cc1)c1noc(N2CC(O)C2)n1] | 21 | 1.29 | 391.4 | E |
| 201 | 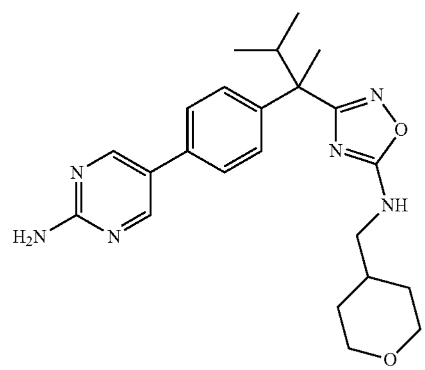 [SMILES: CC(C)C(C)(c1ccc(-c2cnc(N)nc2)cc1)c1noc(NCC2CCOCC2)n1] | 21 | 1.42 | 423.4 | E |
| 202 | 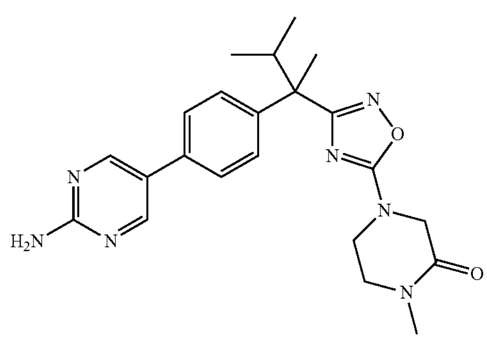 [SMILES: CC(C)C(C)(c1ccc(-c2cnc(N)nc2)cc1)c1noc(N2CCN(C)C(=O)C2)n1] | 21 | 1.36 | 422.4 | E |
| 203 | 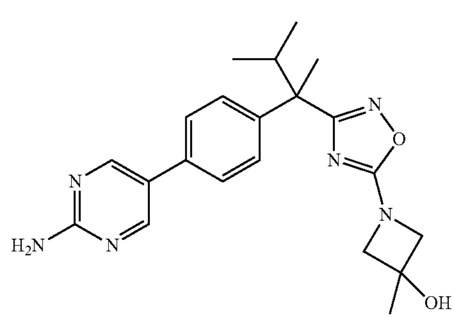 [SMILES: CC(C)C(C)(c1ccc(-c2cnc(N)nc2)cc1)c1noc(N2CC(C)(O)C2)n1] | 31 | 1.34 | 395.4 | E |

TABLE 3-continued

Final Compounds;

| Example | Structure | Method | Retention time (min) | m/z [M + H]+ | LC-MS method |
|---|---|---|---|---|---|
| 204 | 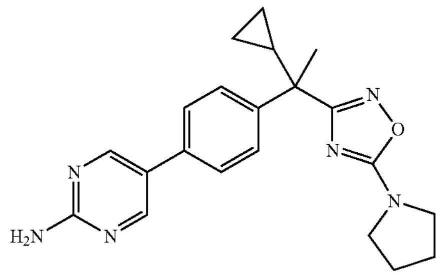 [SMILES: CC(c1ccc(-c2cnc(N)nc2)cc1)(c1noc(N2CCCC2)n1)C1CC1] | 32 | 1.43 | 377.4 | E |
| 205 | 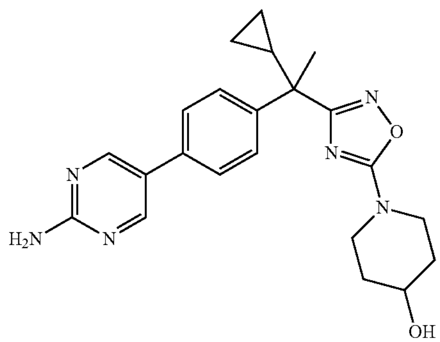 [SMILES: CC(c1ccc(-c2cnc(N)nc2)cc1)(c1noc(N2CCC(O)CC2)n1)C1CC1] | 32 | 1.3 | 407.4 | E |
| 206 | 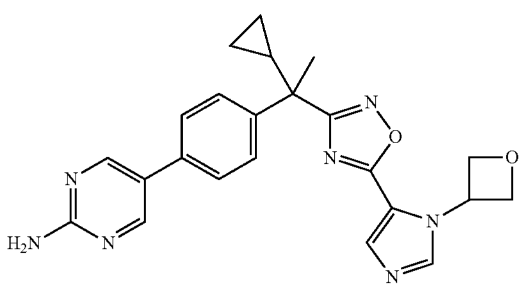 [SMILES: CC(c1ccc(-c2cnc(N)nc2)cc1)(c1noc(-c2cncn2C2COC2)n1)C1CC1] | 25 | 1.4 | 430.4 | D |
| 207 | 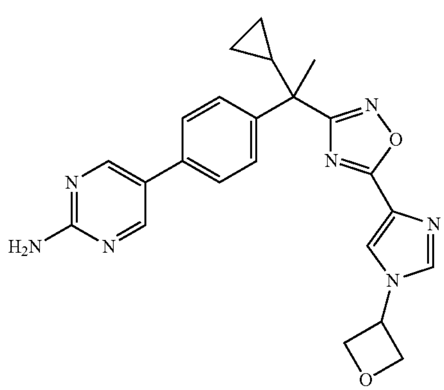 [SMILES: CC(c1ccc(-c2cnc(N)nc2)cc1)(c1noc(-c2cn(C3COC3)cn2)n1)C1CC1] | 25 | 1.3 | 430.2 | D |

TABLE 3-continued

Final Compounds;

| Example | Structure | Method | Retention time (min) | m/z [M + H]⁺ | LC-MS method |
|---|---|---|---|---|---|
| 208 | 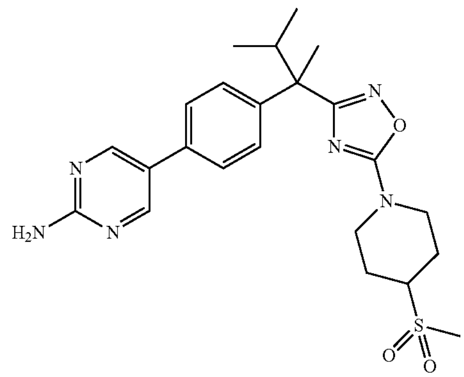 [SMILES: CC(C)C(C)(c1ccc(-c2cnc(N)nc2)cc1)c1noc(N2CCC(S(C)(=O)=O)CC2)n1] | 21 | 0.8 | 471.3 | G |
| 209 | 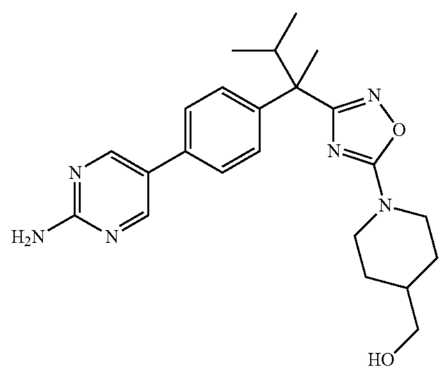 [SMILES: CC(C)C(C)(c1ccc(-c2cnc(N)nc2)cc1)c1noc(N2CCC(CO)CC2)n1] | 21 | 0.82 | 423.3 | G |
| 210 | 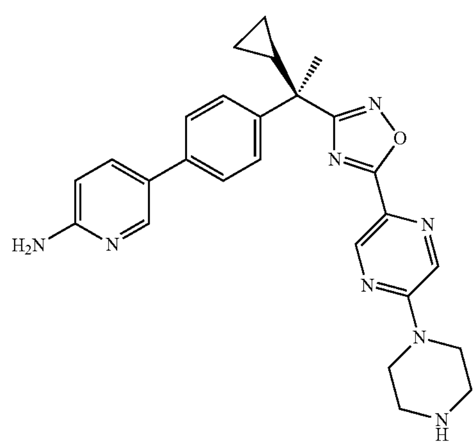 [SMILES: C[C@@](c1ccc(-c2ccc(N)nc2)cc1)(c1noc(-c2cnc(N3CCNCC3)cn2)n1)C1CC1] | 23 | 0.85 | 469.4 | H |
| 211 | 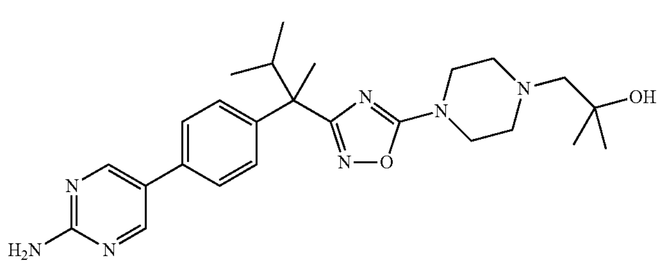 [SMILES: CC(C)C(C)(c1ccc(-c2cnc(N)nc2)cc1)c1noc(N2CCN(CC(C)(C)O)CC2)n1] | 29 | 0.63 | 466.4 | G |

TABLE 3-continued

Final Compounds;

| Example | Structure | Method | Retention time (min) | m/z [M + H]+ | LC-MS method |
|---|---|---|---|---|---|
| 212 | 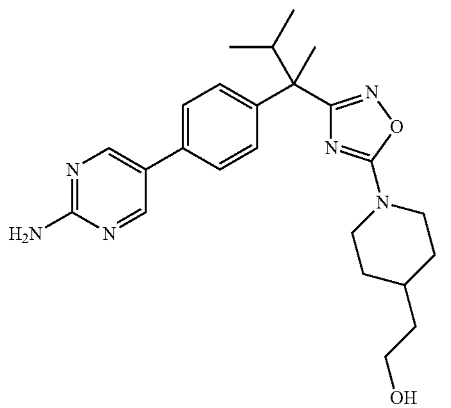 [SMILES: CC(C)C(C)(c1ccc(-c2cnc(N)nc2)cc1)c1noc(N2CCC(CCO)CC2)n1] | 21 | 0.87 | 437.4 | G |
| 213 | 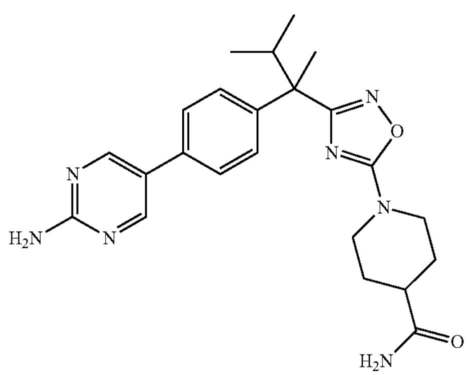 [SMILES: CC(C)C(C)(c1ccc(-c2cnc(N)nc2)cc1)c1noc(N2CCC(C(N)=O)CC2)n1] | 21 | 0.75 | 436.3 | G |
| 214 | 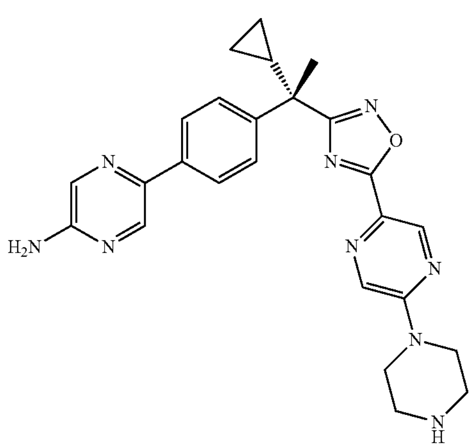 [SMILES: C[C@](c1ccc(-c2cnc(N)cn2)cc1)(c1noc(-c2cnc(N3CCNCC3)cn2)n1)C1CC1] | 23 | 0.68 | 470.3 | G |

TABLE 3-continued

Final Compounds;

| Example | Structure | Method | Retention time (min) | m/z [M + H]+ | LC-MS method |
|---|---|---|---|---|---|
| 215 | 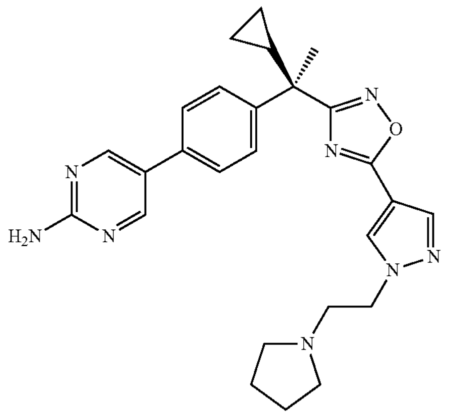 [SMILES: C[C@@](c1ccc(-c2cnc(N)nc2)cc1)(c1noc(-c2cnn(CCN3CCCC3)c2)n1)C1CC1] | 34 | 0.7 | 471.4 | J |
| 216 | 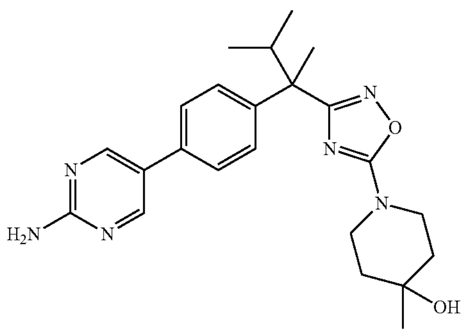 [SMILES: CC(C)C(C)(c1ccc(-c2cnc(N)nc2)cc1)c1noc(N2CCC(C)(O)CC2)n1] | 31 | 0.89 | 423.3 | G |
| 217 | 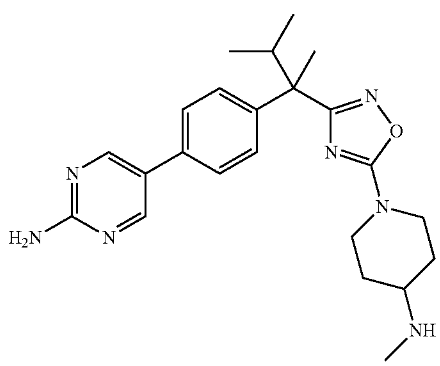 [SMILES: CNC1CCN(c2nc(C(C)(c3ccc(-c4cnc(N)nc4)cc3)C(C)C)no2)CC1] | 28 | 0.7 | 422.4 | G |
| 218 | 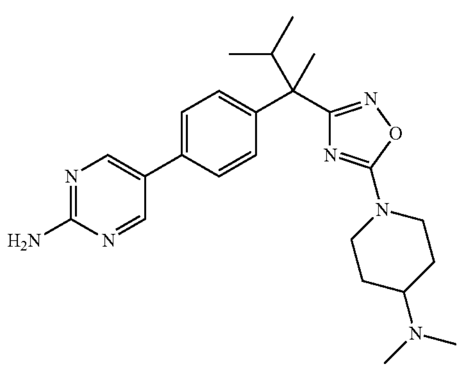 [SMILES: CC(C)C(C)(c1ccc(-c2cnc(N)nc2)cc1)c1noc(N2CCC(N(C)C)CC2)n1] | 21 | 1.14 | 436.4 | E |

TABLE 3-continued
Final Compounds;
| Example | Structure | Method | Retention time (min) | m/z [M + H]+ | LC-MS method |
|---------|-----------|--------|----------------------|--------------|--------------|
| 219 | 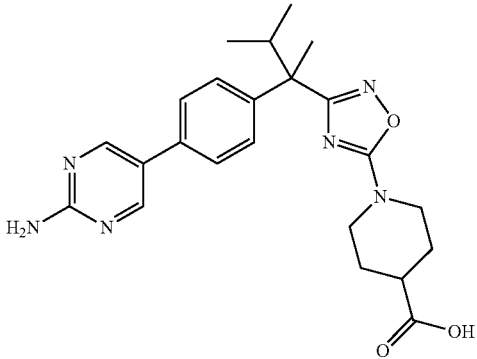 [SMILES: CC(C)C(C)(c1ccc(-c2cnc(N)nc2)cc1)c1noc(N2CCC(C(=O)O)CC2)n1] | 30 | 1.39 | 437.4 | E |
| 220 | 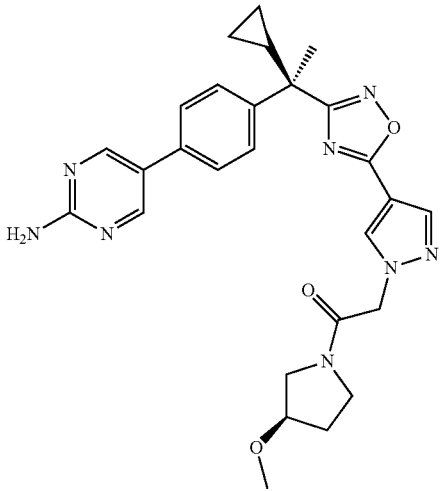 [SMILES: CO[C@@H]1CCN(C(=O)Cn2cc(-c3nc([C@@](C)(c4ccc(-c5cnc(N)nc5)cc4)C4CC4)no3)cn2)C1] | 35 | 1.17 | 515.4 | F |
| 221 | 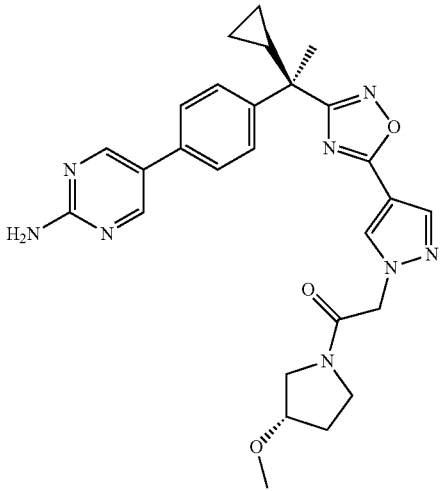 [SMILES: CO[C@H]1CCN(C(=O)Cn2cc(-c3nc([C@@](C)(c4ccc(-c5cnc(N)nc5)cc4)C4CC4)no3)cn2)C1] | 35 | 1.17 | 515.4 | F |

TABLE 3-continued

Final Compounds;

| Example | Structure | Method | Retention time (min) | m/z [M + H]⁺ | LC-MS method |
|---|---|---|---|---|---|
| 222 | 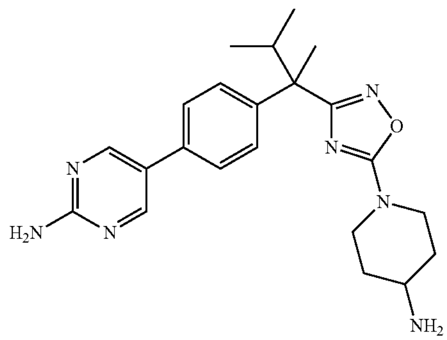 [SMILES: CC(C)C(C)(c1ccc(-c2cnc(N)nc2)cc1)c1noc(N2CCC(N)CC2)n1] | 28 | 0.69 | 408.4 | G |
| 223 | 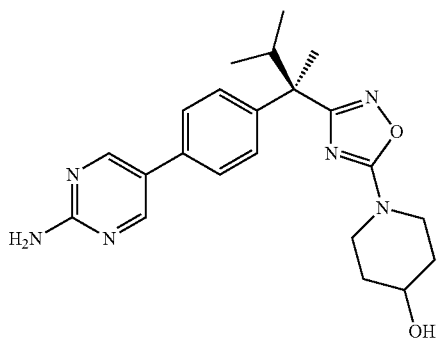 [SMILES: CC(C)[C@](C)(c1ccc(-c2cnc(N)nc2)cc1)c1noc(N2CCC(O)CC2)n1] | 33 | 1.36 | 409.4 | E |
| 224 | 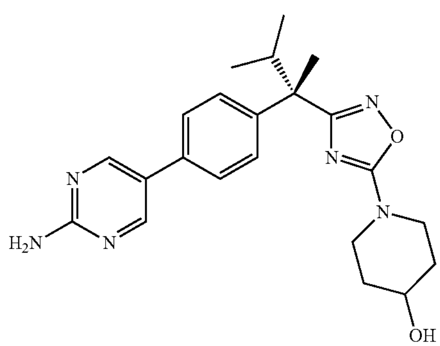 [SMILES: CC(C)[C@@](C)(c1ccc(-c2cnc(N)nc2)cc1)c1noc(N2CCC(O)CC2)n1] | 33 | 1.36 | 409.4 | E |
| 225 | 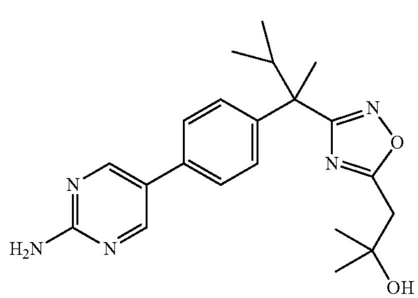 [SMILES: CC(C)C(C)(c1ccc(-c2cnc(N)nc2)cc1)c1noc(CC(C)(C)O)n1] | 24 | 1.26 | 382.4 | D |

TABLE 3-continued

Final Compounds;

| Example | Structure | Method | Retention time (min) | m/z [M + H]+ | LC-MS method |
|---------|-----------|--------|----------------------|--------------|--------------|
| 226 | 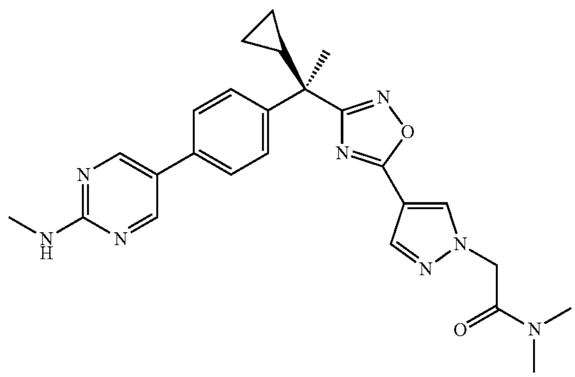 | 9 | 0.8 | 473.3 | G |
| 227 | 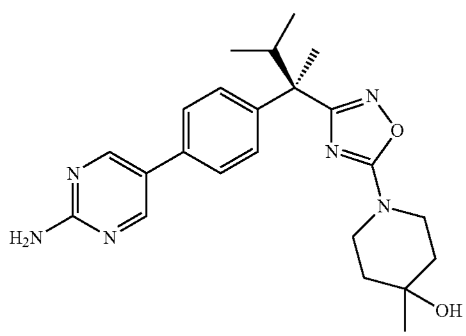 [SMILES: CC(C)[C@](C)(c1ccc(-c2cnc(N)nc2)cc1)c1noc(N2CCC(C)(O)CC2)n1] | 18 | 1.44 | 423.4 | E |
| 228 | 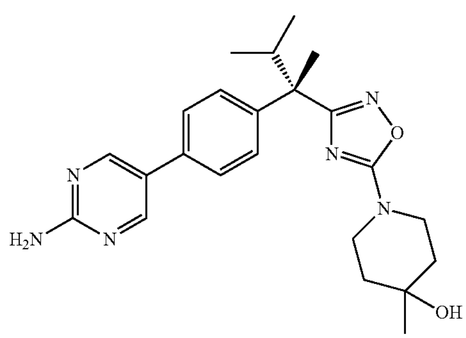 [SMILES: CC(C)[C@@](C)(c1ccc(-c2cnc(N)nc2)cc1)c1noc(N2CCC(C)(O)CC2)n1] | 18 | 1.44 | 423.4 | E |
| 229 | 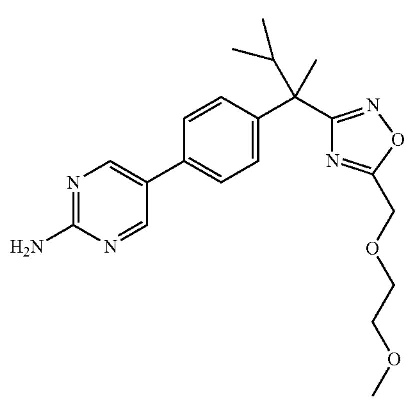 [SMILES: COCCOCc1nc(C(C)(c2ccc(-c3cnc(N)nc3)cc2)C(C)C)no1] | 24 | 1.32 | 398.4 | D |

TABLE 3-continued

Final Compounds;

| Example | Structure | Method | Retention time (min) | m/z [M + H]+ | LC-MS method |
|---|---|---|---|---|---|
| 230 | 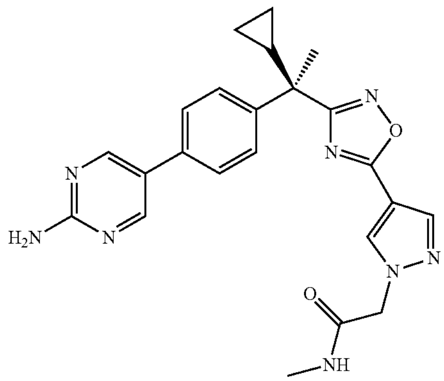 [SMILES: CNC(=O)Cn1cc(-c2nc([C@@](C)(c3ccc(-c4cnc(N)nc4)cc3)C3CC3)no2)cn1] | 18 | 1.29 | 445.4 | D |
| 231 | 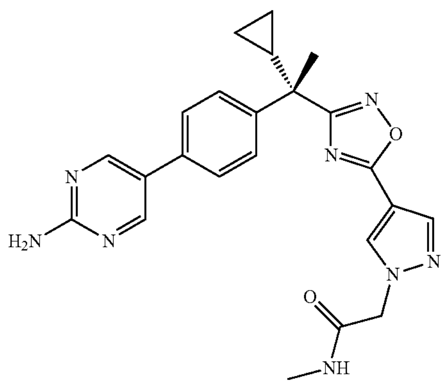 [SMILES: CNC(=O)Cn1cc(-c2nc([C@](C)(c3ccc(-c4cnc(N)nc4)cc3)C3CC3)no2)cn1] | 18 | 1.29 | 445.4 | D |
| 232 | 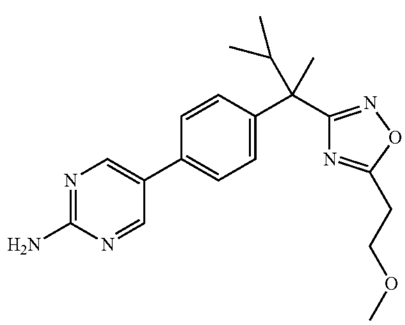 [SMILES: COCCc1nc(C(C)(c2ccc(-c3cnc(N)nc3)cc2)C(C)C)no1] | 24 | 1.3 | 368.4 | D |
| 233 | 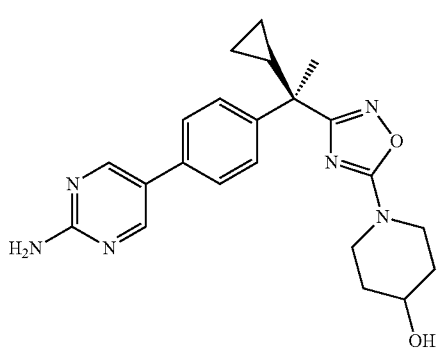 [SMILES: C[C@@](c1ccc(-c2cnc(N)nc2)cc1)(c1noc(N2CCC(O)CC2)n1)C1CC1] | 18 | 1.3 | 407.4 | E |

TABLE 3-continued

Final Compounds;

| Example | Structure | Method | Retention time (min) | m/z [M + H]+ | LC-MS method |
|---------|-----------|--------|----------------------|--------------|--------------|
| 234 | 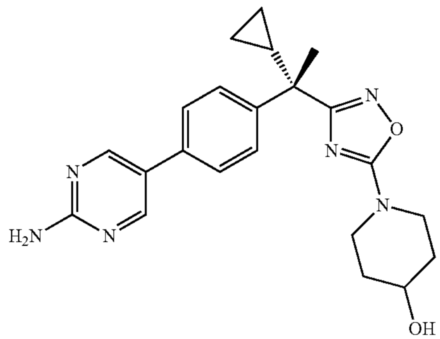 [SMILES: C[C@](c1ccc(-c2cnc(N)nc2)cc1)(c1noc(N2CCC(O)CC2)n1)C1CC1] | 18 | 1.3 | 407.4 | E |
| 235 | 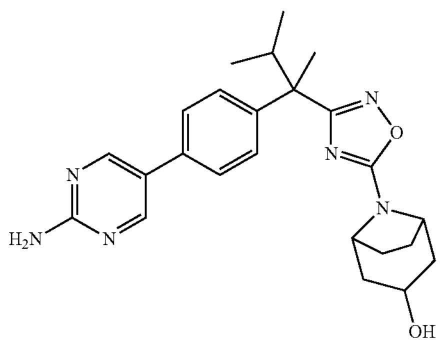 [SMILES: CC(C)C(C)(c1ccc(-c2cnc(N)nc2)cc1)c1noc(N2C3CCC2CC(O)C3)n1] | 21 | 0.87 | 435.3 | G |
| 236 | 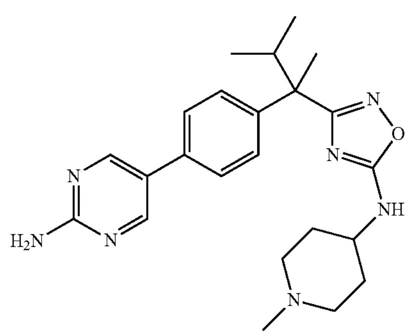 [SMILES: CC(C)C(C)(c1ccc(-c2cnc(N)nc2)cc1)c1noc(NC2CCN(C)CC2)n1] | 21 | 1.11 | 422.4 | E |
| 237 | 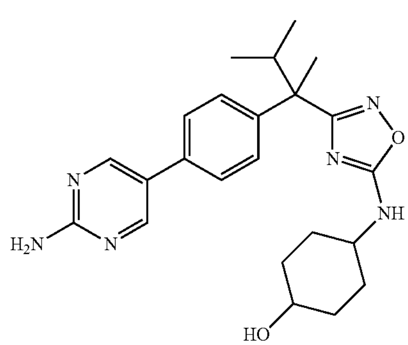 [SMILES: CC(C)C(C)(c1ccc(-c2cnc(N)nc2)cc1)c1noc(NC2CCC(O)CC2)n1] | 21 | 1.33 | 423.4 | E |

TABLE 3-continued

Final Compounds;

| Example | Structure | Method | Retention time (min) | m/z [M + H]+ | LC-MS method |
|---|---|---|---|---|---|
| 238 | 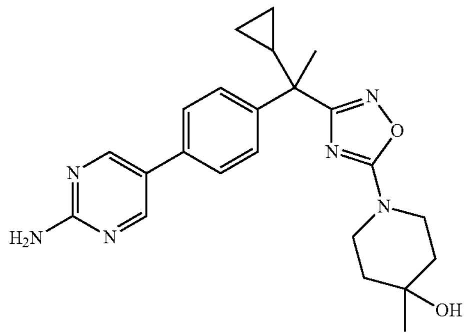 [SMILES: CC1(O)CCN(c2nc(C(C)(c3ccc(-c4cnc(N)nc4)cc3)C3CC3)no2)CC1] | 31 | 1.35 | 421.2 | E |
| 239 | 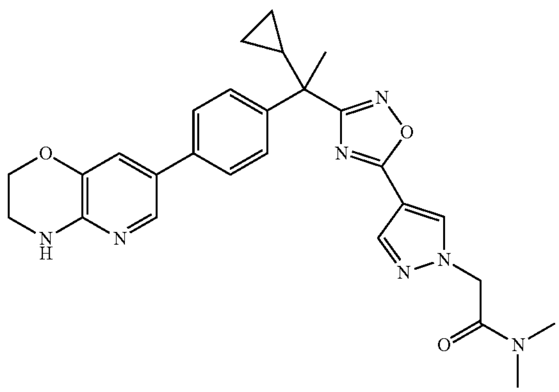 [SMILES: CN(C)C(=O)Cn1cc(-c2nc(C(C)(c3ccc(-c4cnc5c(c4)OCCN5)cc3)C3CC3)no2)cn1] | 26 | 0.67 | 500.3 | G |
| 240 | 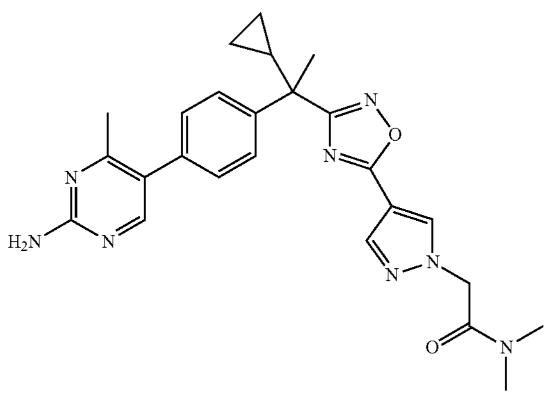 [SMILES: Cc1nc(N)ncc1-c1ccc(C(C)(c2noc(-c3cnn(CC(=O)N(C)C)c3)n2)C2CC2)cc1] | 26 | 0.72 | 473.3 | G |
| 241 | 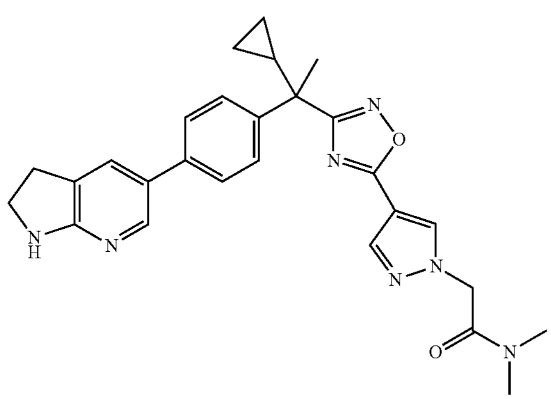 [SMILES: CN(C)C(=O)Cn1cc(-c2nc(C(C)(c3ccc(-c4cnc5c(c4)CCN5)cc3)C3CC3)no2)cn1] | 26 | 1.15 | 484 | H |

TABLE 3-continued

Final Compounds;

| Example | Structure | Method | Retention time (min) | m/z [M + H]+ | LC-MS method |
|---|---|---|---|---|---|
| 242 | 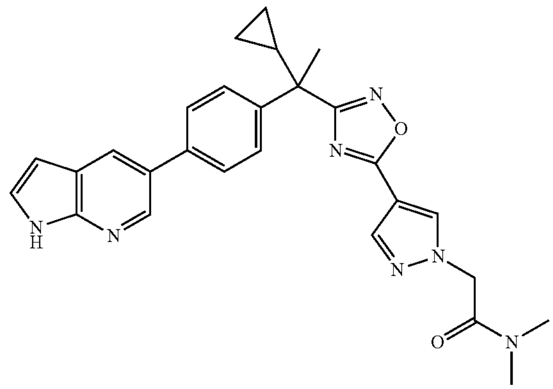 [SMILES: CN(C)C(=O)Cn1cc(-c2nc(C(C)(c3ccc(-c4cnc5[nH]ccc5c4)cc3)C3CC3)no2)cn1] | 26 | 1.98 | 482.3 | H |
| 243 | 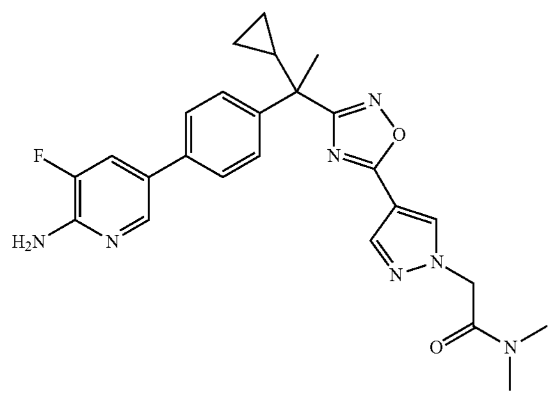 [SMILES: CN(C)C(=O)Cn1cc(-c2nc(C(C)(c3ccc(-c4cnc(N)c(F)c4)cc3)C3CC3)no2)cn1] | 26 | 0.81 | 476.3 | G |
| 244 | 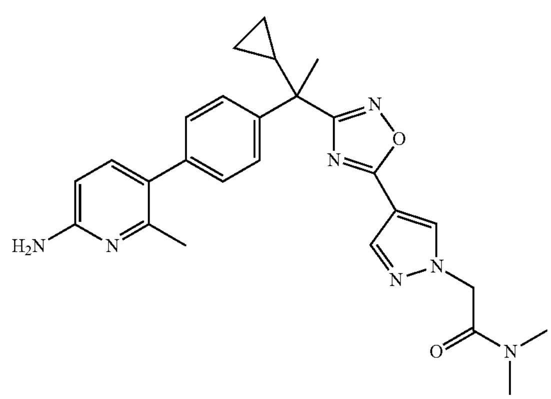 [SMILES: Cc1nc(N)ccc1-c1ccc(C(C)(c2noc(-c3cnn(CC(=O)N(C)C)c3)n2)C2CC2)cc1] | 26 | 1.01 | 472.2 | D |

TABLE 3-continued

Final Compounds;

| Example | Structure | Method | Retention time (min) | m/z [M + H]+ | LC-MS method |
|---------|-----------|--------|----------------------|--------------|--------------|
| 245 | 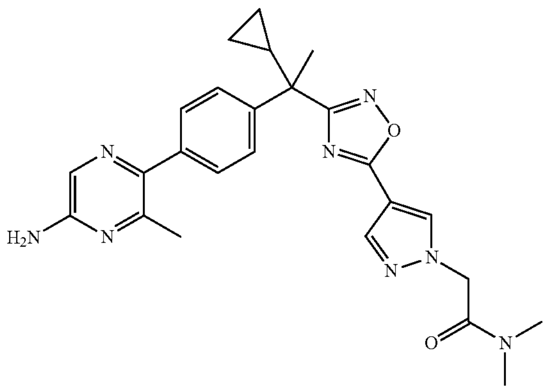 [SMILES: Cc1nc(N)cnc1-c1ccc(C(C)(c2noc(-c3cnn(CC(=O)N(C)C)c3)n2)C2CC2)cc1] | 26 | 1.16 | 473.4 | D |
| 246 | 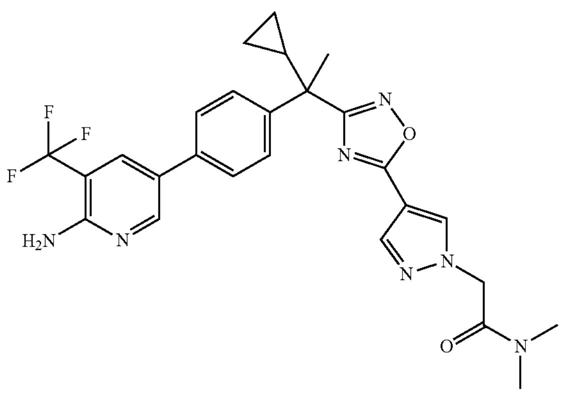 [SMILES: CN(C)C(=O)Cn1cc(-c2nc(C(C)(c3ccc(-c4cnc(N)c(C(F)(F)F)c4)cc3)C3CC3)no2)cn1] | 26 | 1.38 | 526.2 | D |
| 247 | 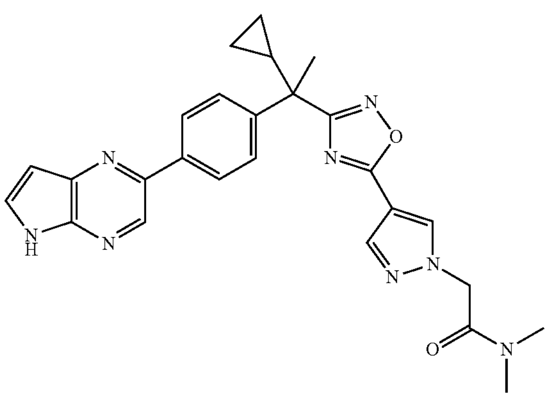 [SMILES: CN(C)C(=O)Cn1cc(-c2nc(C(C)(c3ccc(-c4cnc5[nH]ccc5n4)cc3)C3CC3)no2)cn1] | 26 | 0.85 | 483.3 | G |
| 248 | 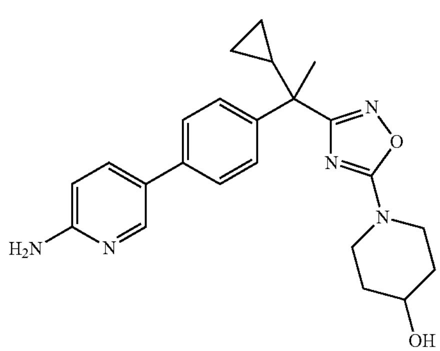 | 32 | 0.59 | 406.3 | G |

TABLE 3-continued

Final Compounds;

| Example | Structure | Method | Retention time (min) | m/z [M + H]⁺ | LC-MS method |
|---|---|---|---|---|---|
| 249 | 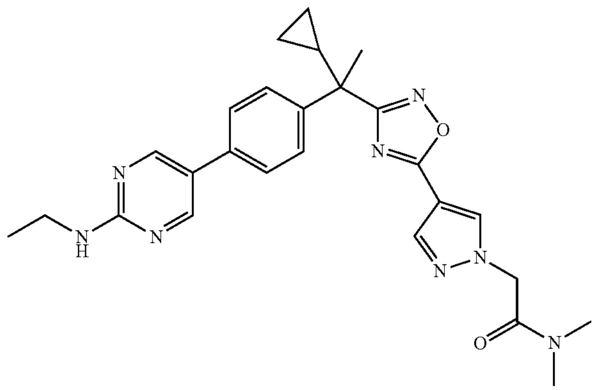 [SMILES: CCNc1ncc(-c2ccc(C(C)(c3noc(-c4cnn(CC(=O)N(C)C)c4)n3)C3CC3)cc2)cn1] | 26 | 0.89 | 487.3 | G |
| 250 | 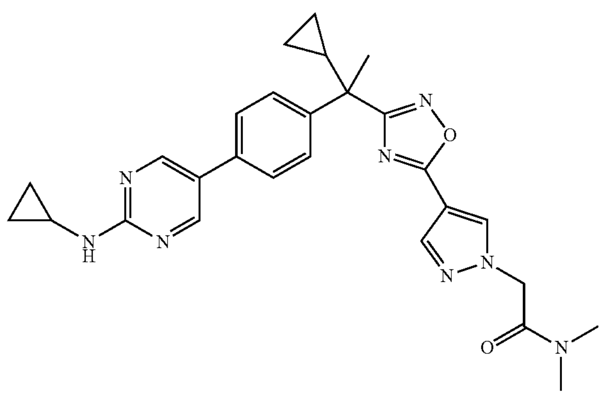 [SMILES: CN(C)C(=O)Cn1cc(-c2nc(C(C)(c3ccc(-c4cnc(NC5CC5)nc4)cc3)C3CC3)no2)cn1] | 26 | 0.87 | 499.3 | G |
| 251 | 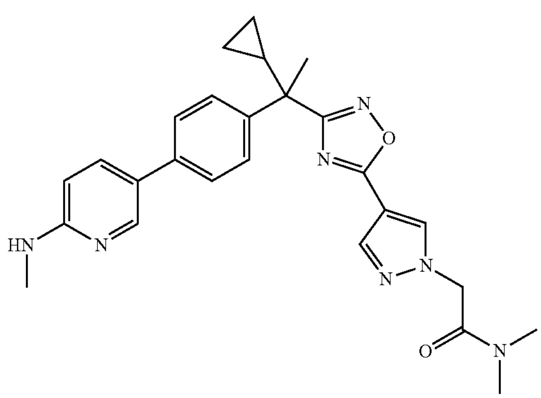 [SMILES: CNc1ccc(-c2ccc(C(C)(c3noc(-c4cnn(CC(=O)N(C)C)c4)n3)C3CC3)cc2)cn1] | 26 | 0.62 | 472.3 | D |

TABLE 3-continued
Final Compounds;
| Example | Structure | Method | Retention time (min) | m/z [M + H]+ | LC-MS method |
|---------|-----------|--------|---------------------|--------------|--------------|
| 252 | 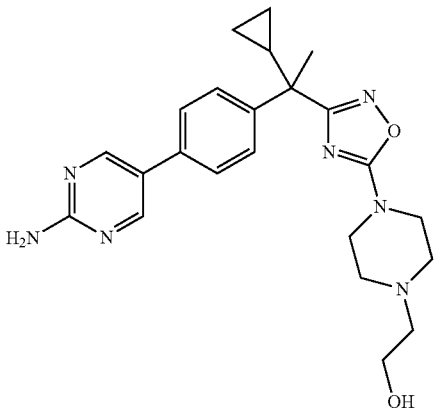 [SMILES: CC(c1ccc(-c2cnc(N)nc2)cc1)(c1noc(N2CCN(CCO)CC2)n1)C1CC1] | 32 | 1.08 | 436.2 | E |
| 253 | 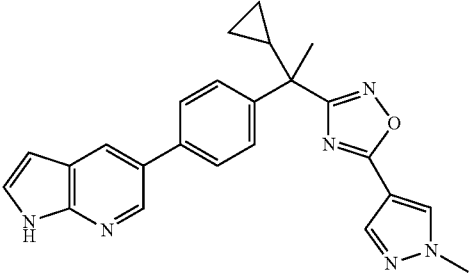 [SMILES: Cn1cc(-c2nc(C(C)(c3ccc(-c4cnc5[nH]ccc5c4)cc3)C3CC3)no2)cn1] | 26 | 1.32 | 413.3 | H |
| 254 | 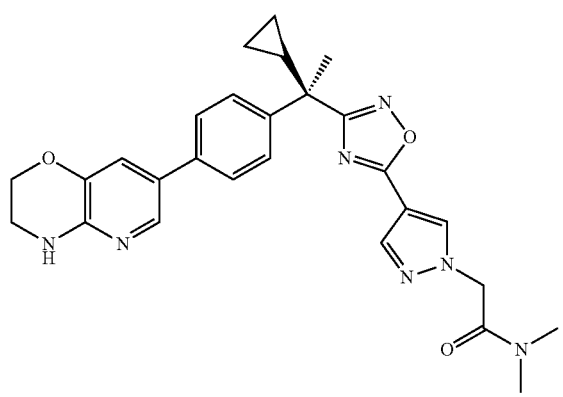 [SMILES: CN(C)C(=O)Cn1cc(-c2nc([C@@](C)(c3ccc(-c4cnc5c(c4)OCCN5)cc3)C3CC3)no2)cn1] | 18 | 0.66 | 500.1 | G |
| 255 | 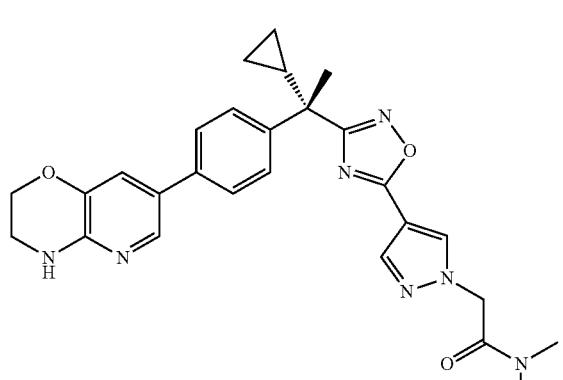 | 18 | 0.66 | 500.3 | G |

TABLE 3-continued

Final Compounds;

| Example | Structure | Method | Retention time (min) | m/z [M + H]+ | LC-MS method |
|---------|-----------|--------|----------------------|--------------|--------------|
| 256 | 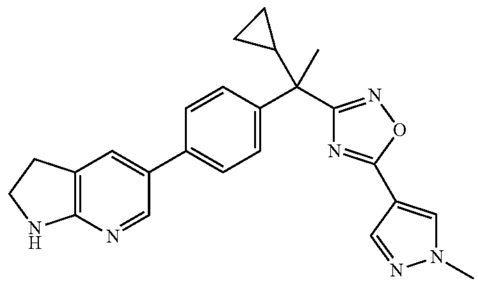 [SMILES: Cn1cc(-c2nc(C(C)(c3ccc(-c4cnc5c(c4)CCN5)cc3)C3CC3)no2)cn1] | 26 | 1.32 | 413.3 | H |
| 257 | 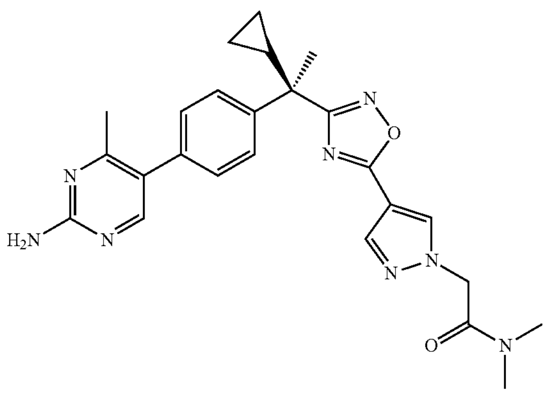 | 18 | 0.72 | 473.3 | G |
| 258 | 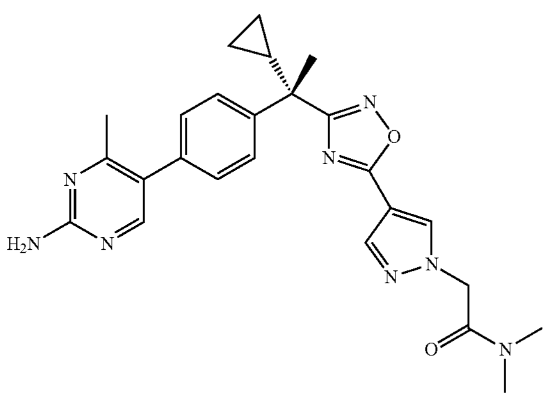 [SMILES: Cc1nc(N)ncc1-c1ccc([C@@](C)(c2noc(-c3cnn(CC(=O)N(C)C)c3)n2)C2CC2)cc1] | 18 | 0.72 | 473.3 | G |
| 259 | 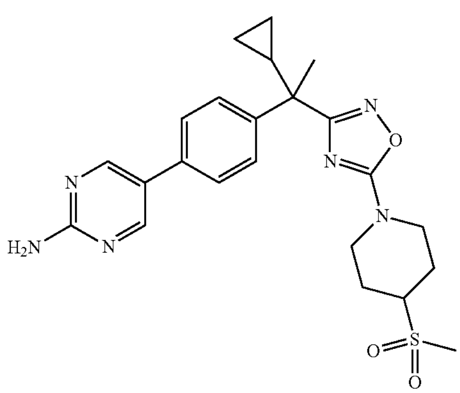 [SMILES: CC(c1ccc(-c2cnc(N)nc2)cc1)(c1noc(N2CCC(S(C)(=O)=O)CC2)n1)C1CC1] | 32 | 1.32 | 469.2 | E |

TABLE 3-continued
Final Compounds;
| Example | Structure | Method | Retention time (min) | m/z [M + H]+ | LC-MS method |
|---|---|---|---|---|---|
| 260 | 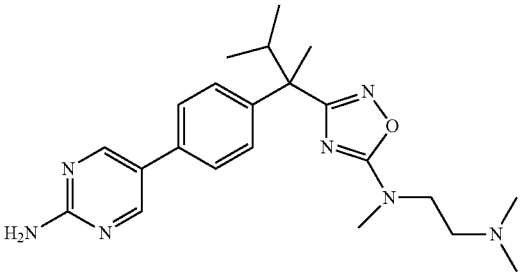 [SMILES: CC(C)C(C)(c1ccc(-c2cnc(N)nc2)cc1)c1noc(N(C)CCN(C)C)n1] | 21 | 1.14 | 410.4 | E |
| 261 | 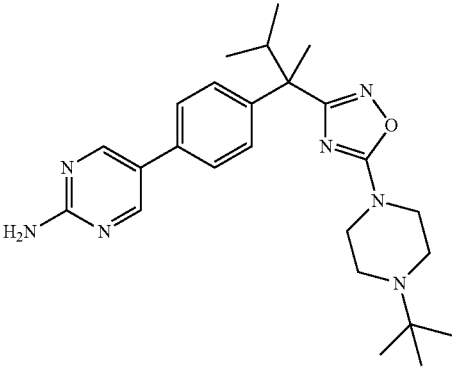 [SMILES: CC(C)C(C)(c1ccc(-c2cnc(N)nc2)cc1)c1noc(N2CCN(C(C)(C)C)CC2)n1] | 21 | 1.16 | 450.4 | E |
| 262 | 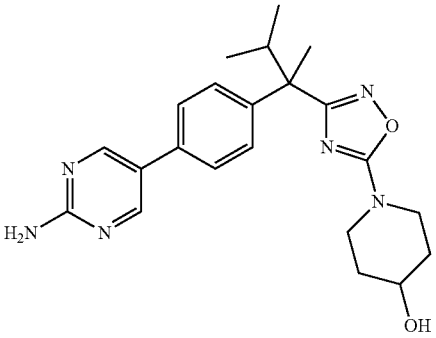 [SMILES: CC(C)C(C)(c1ccc(-c2cnc(N)nc2)cc1)c1noc(N2CCC(O)CC2)n1] | 21 | 1.37 | 409.4 | E |
| 263 | 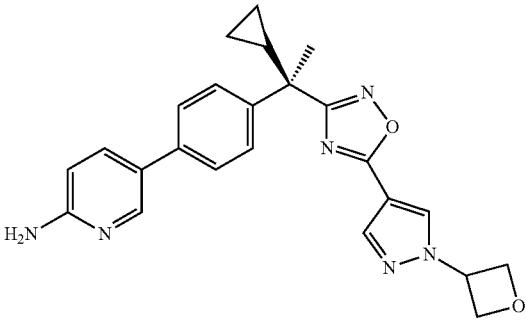 [SMILES: C[C@@](c1ccc(-c2ccc(N)nc2)cc1)(c1noc(-c2cnn(C3COC3)c2)n1)C1CC1] | 27 | 1.34 | 429.3 | H |

TABLE 3-continued

Final Compounds;

| Example | Structure | Method | Retention time (min) | m/z [M + H]+ | LC-MS method |
|---------|-----------|--------|----------------------|--------------|--------------|
| 264 | 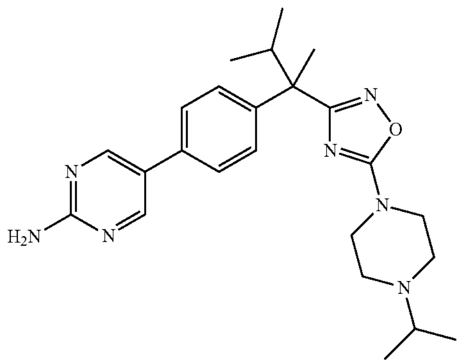 [SMILES: CC(C)N1CCN(c2nc(C(C)(c3ccc(-c4cnc(N)nc4)cc3)C(C)C)no2)CC1] | 21 | 1.16 | 436.4 | E |
| 265 | 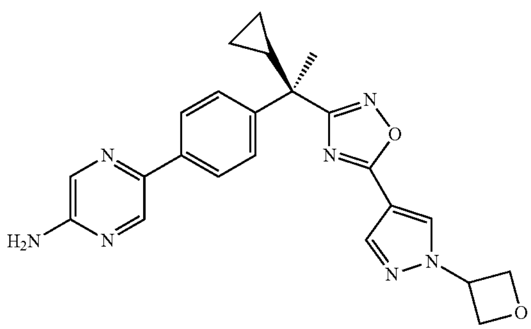 [SMILES: C[C@@](c1ccc(-c2cnc(N)cn2)cc1)(c1noc(-c2cnn(C3COC3)c2)n1)C1CC1] | 26 | 0.8 | 430.3 | G |
| 266 | 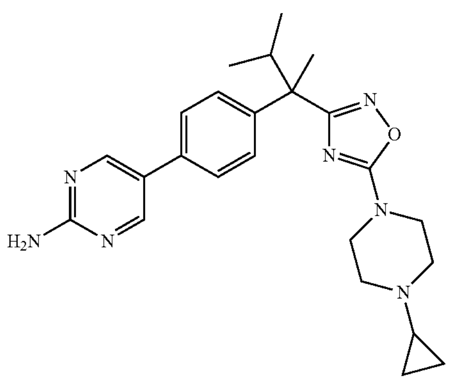 [SMILES: CC(C)C(C)(c1ccc(-c2cnc(N)nc2)cc1)c1noc(N2CCN(C3CC3)CC2)n1] | 21 | 0.63 | 434.4 | G |
| 267 | 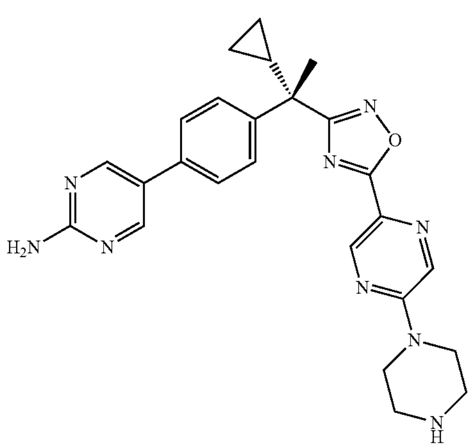 [SMILES: C[C@](c1ccc(-c2cnc(N)nc2)cc1)(c1noc(-c2cnc(N3CCNCC3)cn2)n1)C1CC1] | 23 | 0.61 | 470.4 | G |

TABLE 3-continued

Final Compounds;

| Example | Structure | Method | Retention time (min) | m/z [M + H]+ | LC-MS method |
|---|---|---|---|---|---|
| 268 | 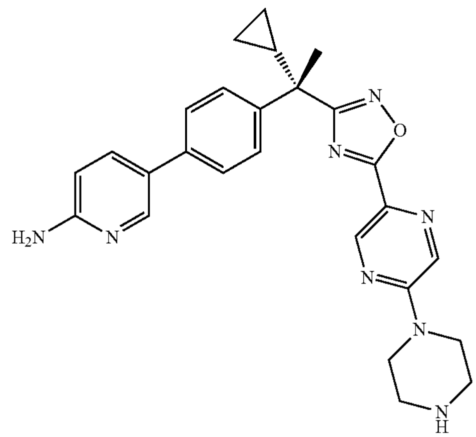 [SMILES: C[C@](c1ccc(-c2ccc(N)nc2)cc1)(c1noc(-c2cnc(N3CCNCC3)cn2)n1)C1CC1] | 23 | 0.53 | 469.4 | G |
| 269 | 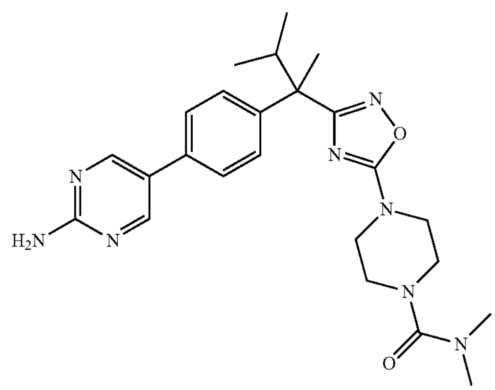 [SMILES: CC(C)C(C)(c1ccc(-c2cnc(N)nc2)cc1)c1noc(N2CCN(C(=O)N(C)C)CC2)n1] | 21 | 0.82 | 465.4 | G |
| 270 | 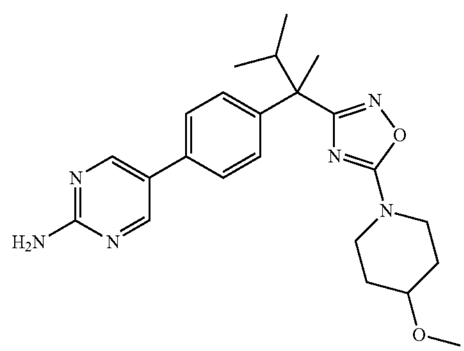 [SMILES: COC1CCN(c2nc(C(C)(c3ccc(-c4cnc(N)nc4)cc3)C(C)C)no2)CC1] | 21 | 0.93 | 423.3 | G |
| 271 | 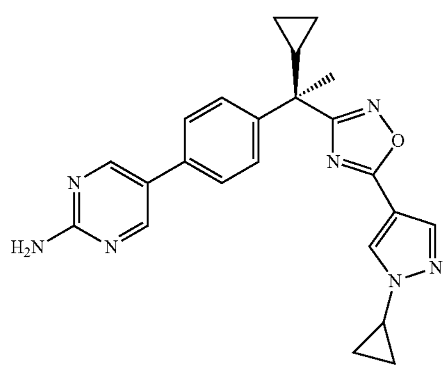 [SMILES: C[C@@](c1ccc(-c2cnc(N)nc2)cc1)(c1noc(-c2cnn(C3CC3)c2)n1)C1CC1] | 9 | 0.87 | 414.4 | D |

TABLE 3-continued

Final Compounds;

| Example | Structure | Method | Retention time (min) | m/z [M + H]+ | LC-MS method |
|---------|-----------|--------|---------------------|--------------|--------------|
| 272 | 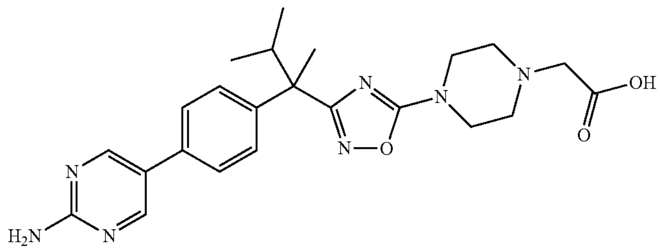 [SMILES: CC(C)C(C)(c1ccc(-c2cnc(N)nc2)cc1)c1noc(N2CCN(CC(=O)O)CC2)n1] | 30 | 0.61 | 452.3 | G |
| 273 | 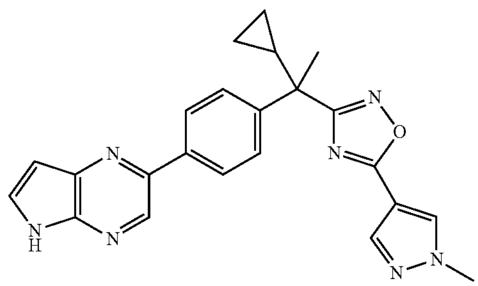 [SMILES: Cn1cc(-c2nc(C(C)(c3ccc(-c4cnc5[nH]ccc5n4)cc3)C3CC3)no2)cn1] | 26 | 2.02 | 412.3 | H |
| 274 | 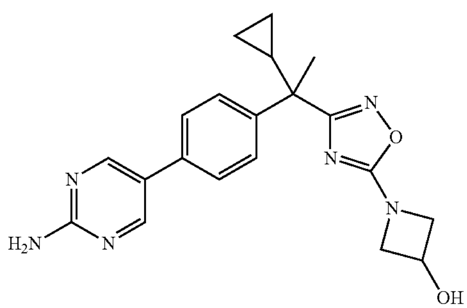 [SMILES: CC(c1ccc(-c2cnc(N)nc2)cc1)(c1noc(N2CC(O)C2)n1)C1CC1] | 32 | 1.23 | 379.4 | E |
| 275 | 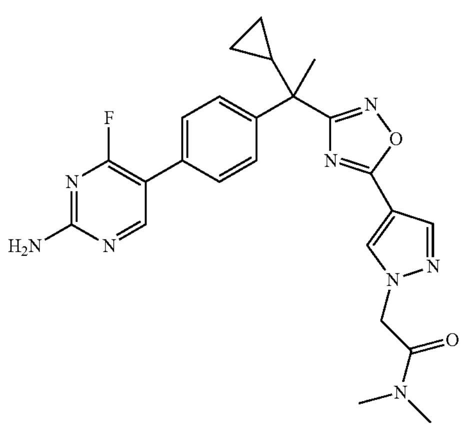 [SMILES: CN(C)C(=O)Cn1cc(-c2nc(C(C)(c3ccc(-c4cnc(N)nc4F)cc3)C3CC3)no2)cn1] | 26 | 1.38 | 477.4 | D |

TABLE 3-continued

Final Compounds;

| Example | Structure | Method | Retention time (min) | m/z [M + H]+ | LC-MS method |
|---|---|---|---|---|---|
| 276 | 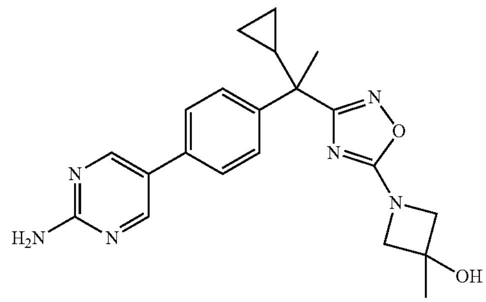 [SMILES: CC1(O)CN(c2nc(C(C)(c3ccc(-c4cnc(N)nc4)cc3)C3CC3)no2)C1] | 31 | 0.71 | 393.2 | G |
| 277 | 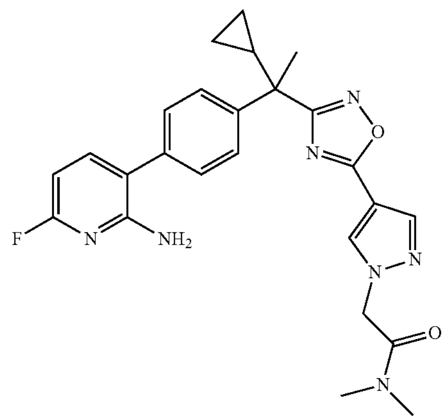 [SMILES: CN(C)C(=O)Cn1cc(-c2nc(C(C)(c3ccc(-c4ccc(F)nc4N)cc3)C3CC3)no2)cn1] | 38 | 0.93 | 476.3 | D |
| 278 | 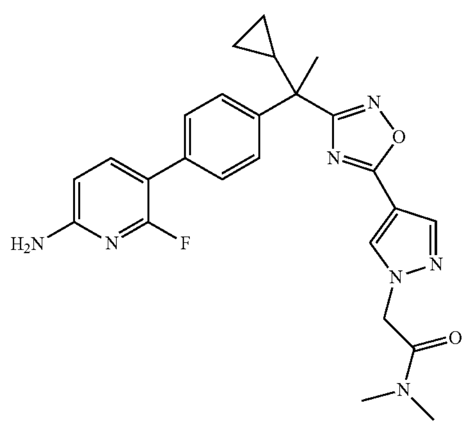 [SMILES: CN(C)C(=O)Cn1cc(-c2nc(C(C)(c3ccc(-c4ccc(N)nc4F)cc3)C3CC3)no2)cn1] | 38 | 0.88 | 476.3 | D |
| 279 | 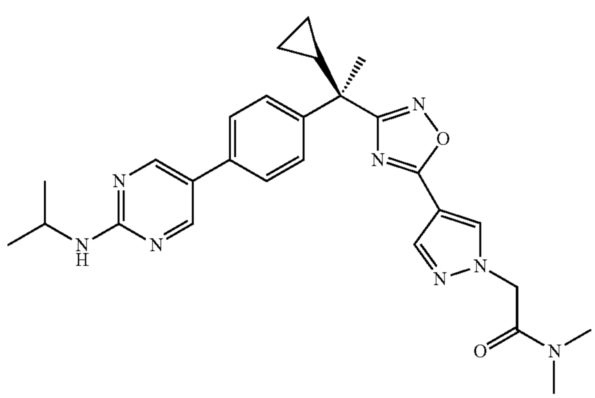 [SMILES: CC(C)Nc1ncc(-c2ccc([C@](C)(c3noc(-c4cnn(CC(=O)N(C)C)c4)n3)C3CC3)cc2)cn1] | 26 | 0.97 | 501.3 | G |

TABLE 3-continued

Final Compounds;

| Example | Structure | Method | Retention time (min) | m/z [M + H]+ | LC-MS method |
|---------|-----------|--------|----------------------|--------------|--------------|
| 280 | 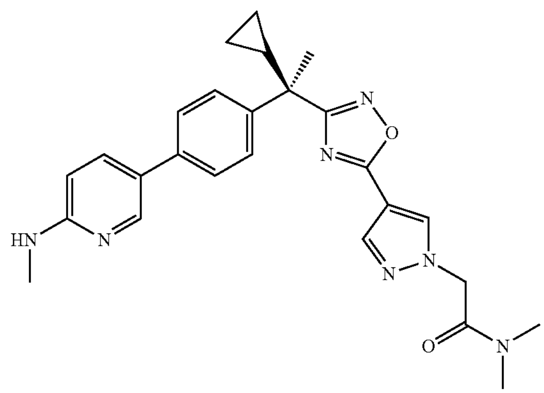 [SMILES: CNc1ccc(-c2ccc([C@](C)(c3noc(-c4cnn(CC(=O)N(C)C)c4)n3)C3CC3)cc2)cn1] | 26 | 0.63 | 472.3 | D |
| 281 | 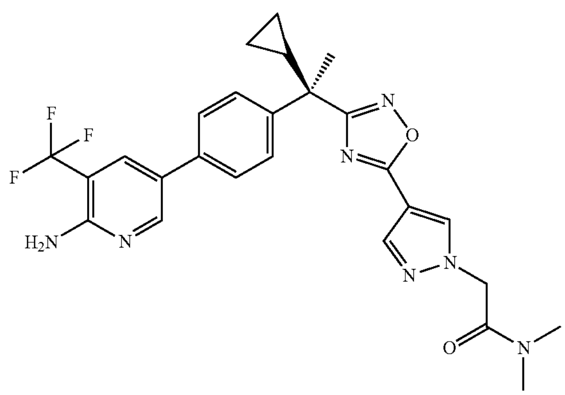 [SMILES: CN(C)C(=O)Cn1cc(-c2nc([C@@](C)(c3ccc(-c4cnc(N)c(C(F)(F)F)c4)cc3)C3CC3)no2)cn1] | 26 | 0.97 | 526.6 | D |
| 282 | 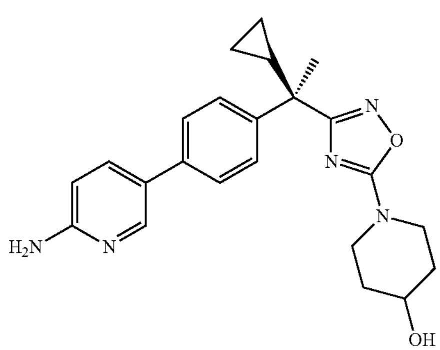 [SMILES: C[C@@](c1ccc(-c2ccc(N)nc2)cc1)(c1noc(N2CCC(O)CC2)n1)C1CC1] | 18 | 0.62 | 406.3 | G |
| 283 | 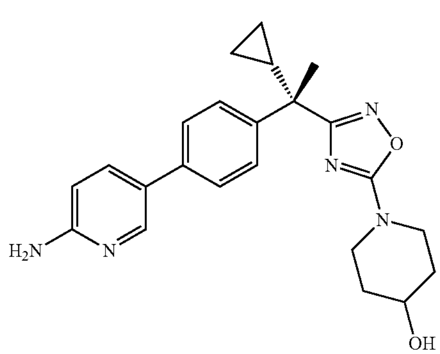 [SMILES: C[C@](c1ccc(-c2ccc(N)nc2)cc1)(c1noc(N2CCC(O)CC2)n1)C1CC1] | 18 | 0.62 | 406.3 | G |

TABLE 3-continued

Final Compounds;

| Example | Structure | Method | Retention time (min) | m/z [M + H]+ | LC-MS method |
|---|---|---|---|---|---|
| 284 | 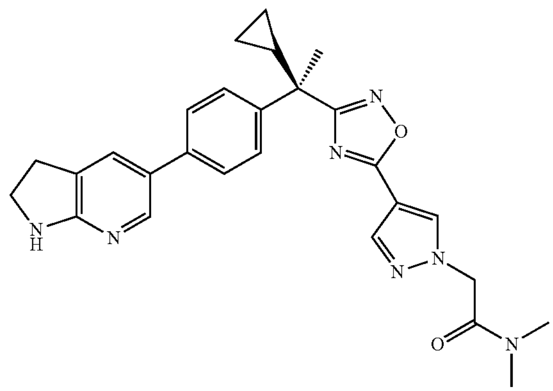 [SMILES: CN(C)C(=O)Cn1cc(-c2nc([C@@](C)(c3ccc(-c4cnc5c(c4)CCN5)cc3)C3CC3)no2)cn1] | 26 | 1.28 | 484.3 | H |
| 285 | 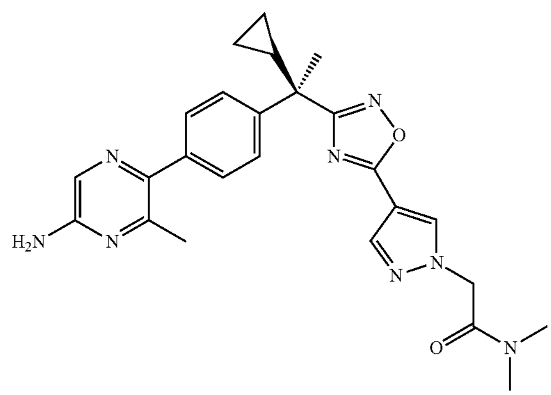 [SMILES: Cc1nc(N)cnc1-c1ccc([C@](C)(c2noc(-c3cnn(CC(=O)N(C)C)c3)n2)C2CC2)cc1] | 26 | 0.76 | 473.3 | D |
| 286 | 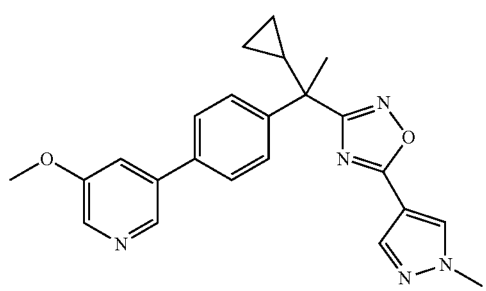 | 26 | 0.89 | 402.2 | G |
| 287 | 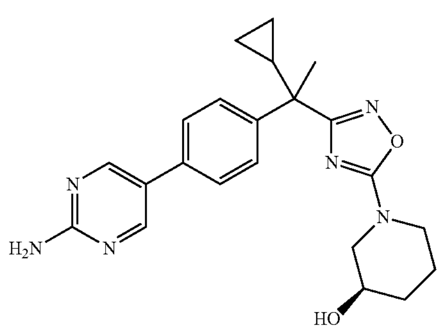 [SMILES: CC(c1ccc(-c2cnc(N)nc2)cc1)(c1noc(N2CCC[C@@H](O)C2)n1)C1CC1] | 32 | 1.31 | 407.2 | E |

TABLE 3-continued

Final Compounds;

| Example | Structure | Method | Retention time (min) | m/z [M + H]+ | LC-MS method |
|---|---|---|---|---|---|
| 288 | 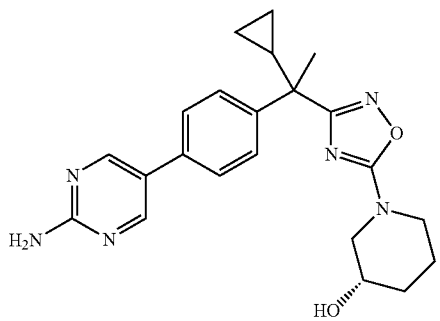 [SMILES: CC(c1ccc(-c2cnc(N)nc2)cc1)(c1noc(N2CCC[C@H](O)C2)n1)C1CC1] | 32 | 1.31 | 407.2 | E |
| 289 | 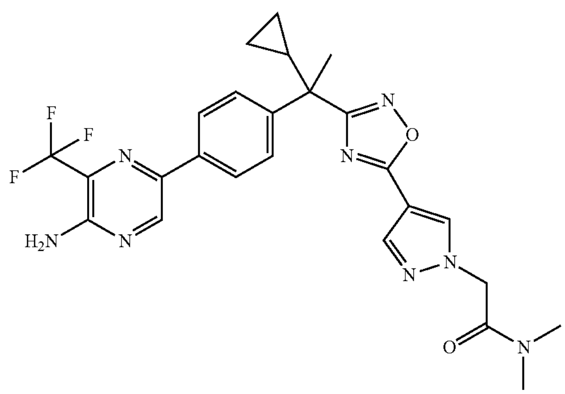 [SMILES: CN(C)C(=O)Cn1cc(-c2nc(C(C)(c3ccc(-c4cnc(N)c(C(F)(F)F)n4)cc3)C3CC3)no2)cn1] | 26 | 2.35 | 527.2 | H |
| 290 | 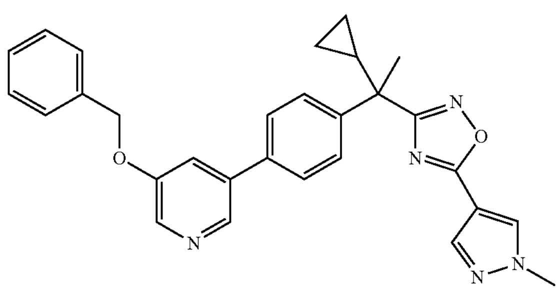 [SMILES: Cn1cc(-c2nc(C(C)(c3ccc(-c4cncc(OCc5ccccc5)c4)cc3)C3CC3)no2)cn1] | 26 | 1.1 | 478.3 | G |
| 291 | 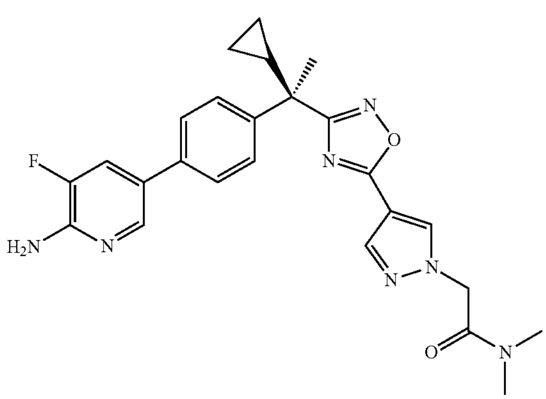 [SMILES: CN(C)C(=O)Cn1cc(-c2nc([C@@](C)(c3ccc(-c4cnc(N)c(F)c4)cc3)C3CC3)no2)cn1] | 26 | 0.79 | 476.3 | G |

TABLE 3-continued

Final Compounds;

| Example | Structure | Method | Retention time (min) | m/z [M + H]⁺ | LC-MS method |
|---------|-----------|--------|----------------------|--------------|--------------|
| 292 | 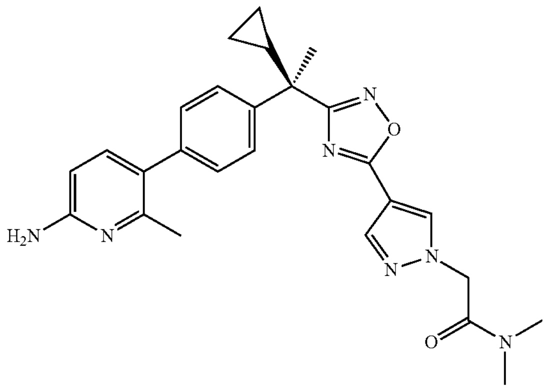 [SMILES: Cc1nc(N)ccc1-c1ccc([C@](C)(c2noc(-c3cnn(CC(=O)N(C)C)c3)n2)C2CC2)cc1] | 26 | 0.64 | 472.3 | D |
| 293 | 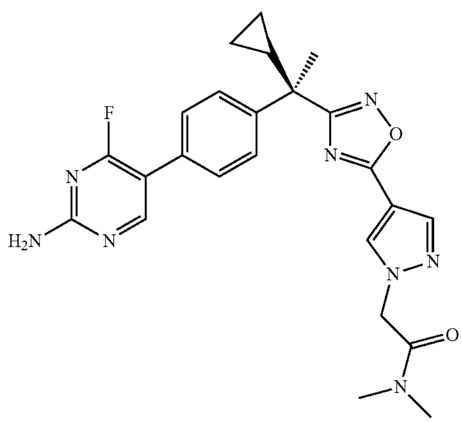 [SMILES: CN(C)C(=O)Cn1cc(-c2nc([C@@](C)(c3ccc(-c4cnc(N)nc4F)cc3)C3CC3)no2)cn1] | 26 | 0.83 | 477.3 | D |
| 294 | 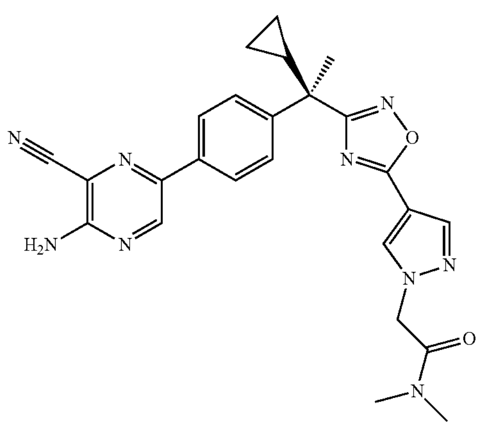 [SMILES: CN(C)C(=O)Cn1cc(-c2nc([C@@](C)(c3ccc(-c4cnc(N)c(C#N)n4)cc3)C3CC3)no2)cn1] | 26 | 0.88 | 484.2 | D |

TABLE 3-continued

Final Compounds;

| Example | Structure | Method | Retention time (min) | m/z [M + H]+ | LC-MS method |
|---------|-----------|--------|----------------------|--------------|--------------|
| 295 | 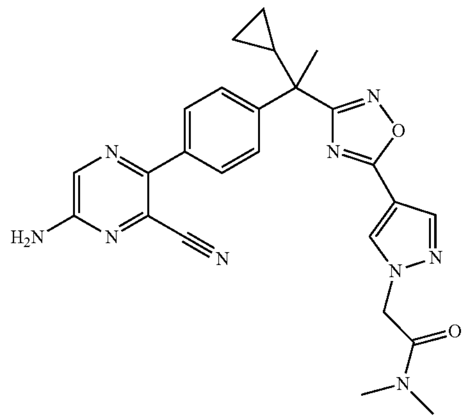 [SMILES: CN(C)C(=O)Cn1cc(-c2nc(C(C)(c3ccc(-c4ncc(N)nc4C#N)cc3)C3CC3)no2)cn1] | 39 | 0.83 | 484.2 | D |
| 296 | 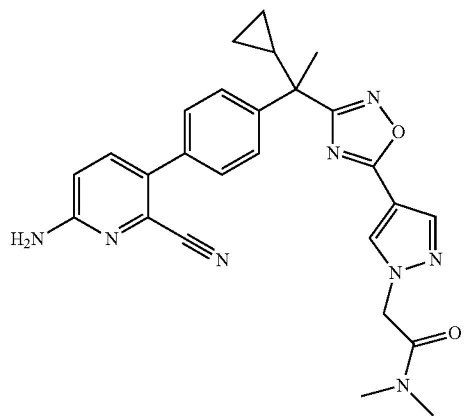 [SMILES: CN(C)C(=O)Cn1cc(-c2nc(C(C)(c3ccc(-c4ccc(N)nc4C#N)cc3)C3CC3)no2)cn1] | 40 | 0.85 | 483.3 | D |
| 297 | 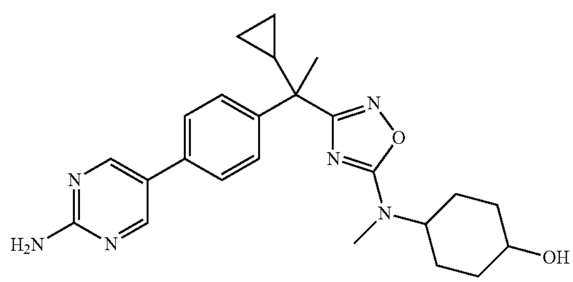 [SMILES: CN(c1nc(C(C)(c2ccc(-c3cnc(N)nc3)cc2)C2CC2)no1)C1CCC(O)CC1] | 32 | 0.82 | 435.3 | G |
| 298 | 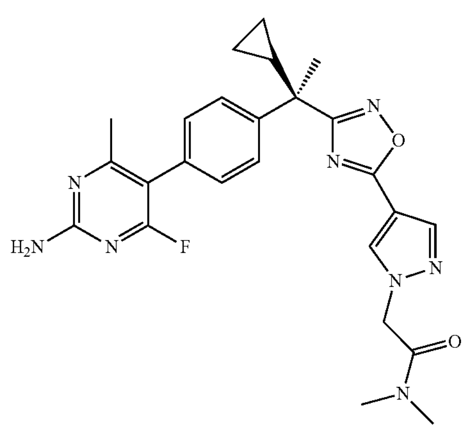 [SMILES: Cc1nc(N)nc(F)c1-c1ccc([C@](C)(c2noc(-c3cnn(CC(=O)N(C)C)c3)n2)C2CC2)cc1] | 26 | 0.85 | 491.3 | D |

Assessment of Biological Properties
1. Binding Assay

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM $MgCl_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 µl, 5 µg) is mixed with WGA SPA beads (Amersham) and stirred for 1 h. To an assay plate (Perkin Elmer FlexiPlate) is added 25 µl of test compound prepared in Binding buffer [100 mM Tris (pH 7.5), 140 mM NaCl, 5% glycerol, 2 mM EDTA, 0.5 mM TCEP, 0.05% Tween 20], 25 µl of [$^{125}$I]L-691,831 (an iodinated analog of MK-591, Charleson et al. Mol. Pharmacol., 41, 873-879, 1992) and finally 50 µl of the bead/protein mixture. (final concentrations: beads, 200 µg/well; protein, 5 µg/well; [$^{125}$I] probe, 0 08 nM/well (17 nCi/well). The plates are shaken for 2 h before reading on a Microbeta plate reader. Non-specific binding is determined by the addition of 10 µM cold L-691,831 compound.

In general, the preferred potency range ($IC_{50}$) of compounds in the above assay is between 0.1 nM to 10 µM, the more preferred potency range is 0.1 nM to 1 µM, and the most preferred potency range is 0.1 nM to 100 nM.

2. Whole Blood Assay:

Compounds are additionally tested in a human whole blood assay to determine their ability to inhibit the synthesis of $LTB_4$ in a cellular system. Compounds are combined with heparinized human whole blood and incubated for 15 minutes at 37° C. Calcimycin (20 µM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma $LTB_4$ concentrations are then measured using an antibody-based homogenous time-resolved fluorescence method (CisBio, Bedford, Mass.).

The additional effect of an exemplary compound of Formula I, i.e. compound 115, Table I, in combination with a statin, is exemplified by Example A and FIG. 1.

3. In Vivo Studies:

The objective of the study is to determine if the compounds of Formula I provide additional reduction in atherosclerosis development in high fat/high cholesterol (HF/HC) fed rabbits on top of simvastatin compared to simvastatin alone.

Treatment with a statin is considered the standard of care for atherosclerosis clinically. In order to determine if the anti-atherosclerotic effect observed in rabbits is effective on top of statin treatment, rabbits were treated with compound 115 (Table 1) in combination with simvastatin and the effects on atherosclerosis reduction with both control and statin treatment alone were compared.

Compound 115 was tested for its ability to reduce atherosclerosis on top of treatment with simvastatin in a 13 week rabbit model of disease induced by feeding the rabbits a HF/HC diet. Compound 115 was tested at doses of 0.05 and 2.5 mg/kg combined with 2.5 mg/kg of simvastatin and compared to control untreated rabbits and rabbits treated with simvastatin alone at 2.5 mg/kg. Compound 115 plus simvastatin significantly reduced atherosclerotic plaque area in the descending aorta in a dose dependent fashion by 37% and 50% at 0.05 mg/kg and 2.5 mg/kg doses, respectively, compared to control rabbits. In addition, the combination of compound 115 at 2.5 mg/kg and simvastatin at 2.5 mg/kg showed a 32% further reduction in plaque area compared to simvastatin alone (p=0.05). Simvastatin alone at 2.5 mg/kg did not significantly inhibit plaque area compared to control.

Example A

Materials and Method

Animals:

The in-life portion of this study was conducted at Covance Labs (Greenfield, Ind.). NZW rabbits were placed on a HF/HC diet manufactured by Research Diets Inc. (C30355) containing 0.25% cholesterol, 3% peanut oil, and 3% coconut oil for 3 weeks before randomization into treatment groups of 23 animals based on cholesterol levels and $LTB_4$ production. Rabbits with cholesterol levels below 250 mg/dL at the start of treatment were removed from further analysis. The rabbits were fed 125 g of rabbit chow each day and both food consumption and body weights were measured throughout the study period. After 3 weeks the rabbits were either continued on this same diet for 10 weeks (control) or treated with the test article Compound 115 in the same food formulation at a dose of 0.05 and 2.5 mg/kg in combination with 2.5 mg/kg of simvastatin. Another group of rabbits were treated with simvastatin alone at a dose of 2.5 mg/kg. During this time, plasma samples were taken for cholesterol, compound exposure, ALT and AST activity, and ex vivo $LTB_4$ production at treatment week 0, 2, 4 and 10. Plasma samples for HDL and LDL levels were taken at week 2, 4 and 10. The animals were sacrificed after ten weeks of treatment, perfused with 10% formalin, and their descending aortas dissected out and placed in 100% formalin for transport to Boehringer Ingelheim Pharmaceuticals Inc. for processing.

Evaluation of Atherosclerosis in Rabbits

The extent of atherosclerosis development was measured in the descending aorta after the vessels were pinned out on the silicone surface of metal trays and stained with Sunan IV stain. The stained vessels were photographed using NIS Elements version BR 3.1 analysis software. The percentage of plaque area of the descending aorta was determined. Histological evaluation of the brachiocephalic artery was done after fixation in formalin, paraffin embedding, and evaluation of lesion formation in cross sections starting from the aortic arch using a rotary microtome at 5 µm thickness. These sections were affixed to a slide and stained with Hematoxylin and Eosin and photographed using a digital camera with Spot-Advance software. Atherosclerotic lesion formation was quantified by image analysis software using ImagePro Plus software. The mean of thee different sections 100 µm apart was determined.

Statistical Analysis

The mean value of each parameter was calculated for each different treatment group and compared to the control value. A one way ANOVA was used to compare treatment groups to the control group using a Dunnett's test for multiplicity of measures using Excell Stat software. As a pre-planned measurement the mean value of Compound 115 treatment groups were individually compared to the simvastatin alone group by a Student's T test. Statistical significance was considered at the p<0.05 level.

Atherosclerosis Development

Atherosclerosis progression was significantly inhibited in the descending aorta in a dose dependent manner with Compound 115 combination treatment (FIG. 1). The reduction was significantly different from control in both the 0.05 mg/kg and 2.5 mg/kg dose groups. The inhibition observed was −37% and −50% in the 0.05 and 2.5 mg/kg dose groups respectively compared to control. Simvastatin alone showed a 26% reduction in plaque area which was not statistically significant from control. However, the high dose combination treatment group of compound 115 at 2.5 mg/kg and simvastatin showed a further decrease of 34% compared to simvastatin alone (p=0.05).

The development of atherosclerosis was significantly inhibited by treatment of Compound 115 in combination with simvastatin in a NZW rabbit model of atherosclerosis as measured by plaque reduction in the descending aorta. The reduction in plaque area observed was greater than simvastatin treatment alone.

Method of Use

The compounds of the invention are effective inhibitors of 5-lipoxygenase activating protein (FLAP) and thus suggest they inhibit leukotriene production. Therefore, in one embodiment of the invention, there is provided methods of treating leukotriene-mediated disorders using compounds of the invention or their pharmaceutically acceptable salts thereof. In another embodiment, there is provided methods of treating cardiovascular, inflammatory, allergic, pulmonary and fibrotic diseases, renal diseases and cancer using compounds of the invention or their pharmaceutically acceptable salts thereof.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:

Cardiovascular diseases including atherosclerosis and all related disorders, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease, inflammatory pain, multiple sclerosis, systemic lupus erythematosus, transplant rejection, inflammatory and allergic ocular diseases;

Cancer including solid tumors, leukemias and lymphomas; and

Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

Combination Therapy

The compounds of the invention may be administered alone or in combination with at least one additional active agent. Thus, in one embodiment, the invention relates to a pharmaceutical composition comprising one or more compounds of the invention in combination with at least one additional agent. In another embodiment, the invention relates a method of treating diseases mediated by $LTB_4$, the method comprising administering a therapeutically effective amount of one or more compounds of the invention in combination with at least one additional agent.

Nonlimiting examples of additional active agents include statins (or HMG-CoA reductase inhibitors); cholesterol ester transfer protein (CETP) inhibitors (or antagonists); fibrates, niacin derivatives, Lp-PLA2-inhibitors (e.g., darapladib, varespladib), antiplatelets and anticoagulants.

In one embodiment, the additional active agent is a statin. In another embodiment, the additional active agent is a statin selected from the group consisting of atorvastatin, fluvastatin, lovastatin, pitavastatin, pravastatin, rosuvastatin, and simvastatin.

In one embodiment, the invention relates to a pharmaceutical composition comprising compound 115 of the invention in combination with a statin, particularly in combination with atorvastatin, fluvastatin, lovastatin, pitavastatin, pravastatin, rosuvastatin, or simvastatin, more particularly in combination with simvastatin.

In one embodiment, the additional active agent is a CETP inhibitor. In another embodiment, the additional active agent is a CETP inhibitor selected from the group consisting of anacetrapib, dalcetrapib, evacetrapib, TA-8995 (Mitsubishi Tanabe Pharma), ATH-03 (Affris), DRL-17822 (Dr. Reddy's). In yet another embodiment, the additional active is selected from dalcetrapib and anacetrapib.

In one embodiment, the additional active agent is a PCSK9 inhibitor. A preferred example for a PCSK9 inhibitor is alirocumab. In another embodiment the said PCSK9 inhibitor is, most likely, but not limited to, being administered subcutaneously every 2 or 4 weeks.

In one embodiment, the additional active agent is an IL1-beta antibody. In another embodiment the said IL1-beta antibody is, most likely, but not limited to, being administered subcutaneously every three months.

In one embodiment the additional active agent would have overlapping biological activity, such as antiatherosclerotic effect.

In one embodiment, the additional active agent is Apo A-1 or HDL. In another embodiment Apo A-1 or HDL are, most likely, but not limited to, being administered intravenously.

What is claimed is:

1. A method of treating atherosclerosis comprising administering to a patient a combination of a compound of formula (I) or a pharmaceutically acceptable salt thereof:

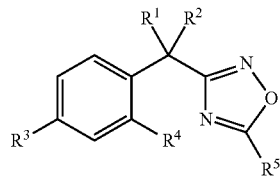

I wherein:
$R^1$ and $R^2$ are each independently hydrogen, $C_{1-7}$ alkyl or $C_{3-10}$ carbocycle, with the proviso that both $R^1$ and $R^2$ are not hydrogen;
$R^3$ is a 5-11 membered heteroaryl ring containing one to three heteroatoms selected from nitrogen, oxygen and sulfur, wherein the heteroaryl ring is optionally independently substituted with one to three groups selected from $C_{1-5}$ alkyl optionally substituted with one to three halogen atoms, $C_{1-5}$ alkoxy, $C_{1-3}$ hydroxy, halogen, hydroxy, —O-benzyl, oxo, cyano, amino, —NH—$C_{3-6}$ carbocycle, $C_{1-6}$ alkylamino and $C_{1-3}$ dialkylamino;
$R^4$ is hydrogen, $C_{1-3}$ alkyl, halogen or nitrile;

$R^5$ is $C_{1-6}$ alkyl, $C_{3-10}$ carbocycle, 3-11 membered heterocycle, aryl, 5-11 membered heteroaryl, —C(O)—$R^6$, hydroxy or —$NR^7R^8$, wherein each $R^5$ is optionally independently substituted with one to three groups selected from $R^9$, $R^{10}$ and $R^{11}$;
$R^6$ is $C_{3-8}$ heterocycle or —NH-5-6 membered heterocycle, each optionally independently substituted with one to three groups selected from $R^9$, $R^{10}$ and $R^{11}$;
$R^7$ and $R^8$ are each independently hydrogen, 5-6 membered heterocycle optionally substituted with $C_{1-6}$ alkyl, $C_{3-10}$ carbocycle optionally substituted with hydroxy or $C_{1-6}$ alkyl;
$R^9$, $R^{10}$ and $R^{11}$ are independently selected from
 (a) —H,
 (b) —OH,
 (c) halogen,
 (d) —CN,
 (e) —$CF_3$,
 (f) $C_{1-6}$alkyl optionally substituted with one to three —OH, —$N(R^{12})(R^{13})$, 3-6 membered heterocycle, $C_{1-6}$alkoxy, $C_{1-6}$alkoxy-O—$C_{1-6}$alkyl, —$CO_2R^{12}$, —$C(O)N(R^{12})(R^{13})$ or —$S(O)_nC_{1-6}$alkyl,
 (g) $C_{1-6}$alkoxy,
 (h) —$N(R^{12})(R^{13})$,
 (i) —$S(O)_nC_{1-6}$alkyl,
 (j) —$CO_2R^{12}$,
 (k) —$C(O)N(R^{12})(R^{13})$,
 (l) —$S(O)_2N(R^{12})(R^{13})$,
 (m) a 3-10 membered heterocyclic group optionally substituted with one to three $C_{1-6}$ alkyl groups,
 (n') oxo,
 (o) —$C(O)$—$C_{1-3}$ alkyl;
$R^{12}$ and $R^{13}$ are each independently selected from —H, —$C_{1-6}$alkyl, $C(O)C_{1-6}$alkyl, and a 3-6 membered heterocyclic group, each of which is optionally independently substituted with one to three $C_{1-6}$alkyl groups, —OH, $C_{1-6}$alkoxy, —$C(O)N(R^{14})(R^{15})$, —$S(O)_nC_{1-6}$alkyl, CN, a 3-6 membered heterocyclic group, —$OC_{1-6}$alkyl, $CF_3$, or;
$R^{12}$ and $R^{13}$ taken together with the nitrogen ring to which they are attached form a heterocyclyl ring optionally substituted with one to three —OH, CN, —$OC_{1-6}$alkyl or oxo;
$R^{14}$ and $R^{15}$ are each independently selected from —H and —$C_{1-6}$alkyl;
n is 0, 1 or 2; and
an additional pharmaceutically active agent for separate, sequential or simultaneous therapeutic use of the active components.

2. The method of claim 1 wherein the additional pharmaceutically active agent is selected from a group consisting of statins, HMG-CoA reductase inhibitors, cholesterol ester transfer protein (CETP) inhibitors or antagonists, fibrates, niacin derivatives, Lp-PLA2-inhibitors, antiplatelets and anticoagulants.

3. The method of claim 2, wherein the additional pharmaceutically active agent is a statin.

4. The method of claim 3, wherein the statin is selected from a group consisting of atorvastatin, fluvastatin, lovastatin, pitavastatin, pravastatin, rosuvastatin, and simvastatin.

5. The method of claim 2, wherein the additional pharmaceutically active agent is a cholesterol ester transfer protein (CETP) inhibitor or antagonist.

6. The method of claim 5, wherein the CETP inhibitor is selected from anacetrapib, dalcetrapib, evacetrapib, TA-8995 (Mitsubishi Tanabe Pharma), ATH-03 (Affris), DRL-17822 (Dr. Reddy's).

7. The method of claim 6, wherein the CETP inhibitor is further selected from anacetrapib and dalcetrapib.

8. The method of claim 1, wherein the additonal pharmaceutically active agent is a PCSK9 inhibitor.

9. The method of claim 8, wherein the PCSK9 inhibitor is alirocumab.

10. The method of claim 1, wherein the compound of formula I and the additional pharmaceutically active agent are present in separate dosage forms.

11. The method of claim 1, wherein the compound of formula I and the additional pharmaceutically active agent are present in the same dosage form.

12. The method of claim 1, wherein the compound of formula I is administered orally.

13. The method of claim 1, the combination of the compound of formula I and the additional pharmaceutically active agent are for oral administration.

14. The method of claim 1 further comprising more than one pharmaceutically active agent selected from a group consisting of statins, HMG-CoA reductase inhibitors, cholesterol ester transfer protein (CETP) inhibitors or antagonists, fibrates, niacin derivatives, Lp-PLA2-inhibitors, antiplatelets and anticoagulants.

15. The method according to claim 1, wherein the cardiovascular disease is selected from atherosclerosis, myocardial infarction, stroke, aortic aneurysm, sickle cell crisis, ischemia-reperfusion injury, pulmonary arterial hypertension and sepsis.

16. The method according to claim 1, wherein the cardiovascular disease is atherosclerosis.

17. A method of treating atherosclerosis comprising administering to a patient a combination comprising a pharmaceutical composition of a compound of formula (I) or a pharmaceutically acceptable salt thereof:

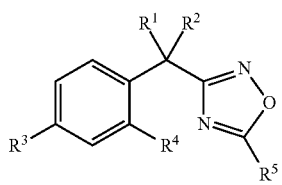

I wherein:
- $R^1$ and $R^2$ are each independently hydrogen, $C_{1-7}$ alkyl or $C_{3-10}$ carbocycle, with the proviso that both $R^1$ and $R^2$ are not hydrogen;
- $R^3$ is a 5-11 membered heteroaryl ring containing one to three heteroatoms selected from nitrogen, oxygen and sulfur, wherein the heteroaryl ring is optionally independently substituted with one to three groups selected from $C_{1-5}$ alkyl optionally substituted with one to three halogen atoms, $C_{1-5}$ alkoxy, $C_{1-3}$ hydroxy, halogen, hydroxy, —O-benzyl, oxo, cyano, amino, —NH—$C_{3-6}$ carbocycle, $C_{1-6}$ alkylamino and $C_{1-3}$ dialkylamino;
- $R^4$ is hydrogen, $C_{1-3}$ alkyl, halogen or nitrile;
- $R^5$ is $C_{1-6}$ alkyl, $C_{3-10}$ carbocycle, 3-11 membered heterocycle, aryl, 5-11 membered heteroaryl, —C(O)—$R^6$, hydroxy or —$NR^7R^8$, wherein each $R^5$ is optionally independently substituted with one to three groups selected from $R^9$, $R^{10}$ and $R^{11}$;
- $R^6$ is $C_{3-8}$ heterocycle or —NH-5-6 membered heterocycle, each optionally independently substituted with one to three groups selected from $R^9$, $R^{10}$ and $R^{11}$;
- $R^7$ and $R^8$ are each independently hydrogen, 5-6 membered heterocycle optionally substituted with $C_{1-6}$ alkyl, $C_{3-10}$ carbocycle optionally substituted with hydroxy or $C_{1-6}$ alkyl;
- $R^9$, $R^{10}$ and $R^{11}$ are independently selected from
  - (a) —H,
  - (b) —OH,
  - (c) halogen,
  - (d) —CN,
  - (e) —$CF_3$,
  - (f) $C_{1-6}$alkyl optionally substituted with one to three —OH, —$N(R^{12})(R^{13})$, 3-6 membered heterocycle, $C_{1-6}$alkoxy, $C_{1-6}$alkoxy-O—$C_{1-6}$alkyl, —$CO_2R^{12}$, —$C(O)N(R^{12})(R^{13})$ or —$S(O)_nC_{1-6}$alkyl,
  - (g) $C_{1-6}$alkoxy,
  - (h) —$N(R^{12})(R^{13})$,
  - (i) —$S(O)_nC_{1-6}$alkyl,
  - (j) —$CO_2R^{12}$,
  - (k) —$C(O)N(R^{12})(R^{13})$,
  - (l) —$S(O)_2N(R^{12})(R^{13})$,
  - (m) a 3-10 membered heterocyclic group optionally substituted with one to three $C_{1-6}$ alkyl groups,
  - (n') oxo,
  - (o) —C(O)—$C_{1-3}$ alkyl;
- $R^{12}$ and $R^{13}$ are each independently selected from —H, —$C_{1-6}$alkyl, $C(O)C_{1-6}$alkyl, and a 3-6 membered heterocyclic group, each of which is optionally independently substituted with one to three $C_{1-6}$alkyl groups, —OH, $C_{1-6}$alkoxy, —$C(O)N(R^{14})(R^{15})$, —$S(O)_nC_{1-6}$alkyl, CN, a 3-6 membered heterocyclic group, —$OC_{1-6}$ alkyl, $CF_3$, or;
- $R^{12}$ and $R^{13}$ taken together with the nitrogen ring to which they are attached form a heterocyclyl ring optionally substituted with one to three —OH, CN, —$OC_{1-6}$alkyl or oxo;
- $R^{14}$ and $R^{15}$ are each independently selected from —H and —$C_{1-6}$alkyl;
- n is 0, 1 or 2; and
- an additional pharmaceutically active agent optionally combined with one or more pharmaceutically acceptable carrier, for separate, sequential or simultaneous therapeutic use of the active components.

* * * * *